(12) United States Patent
Arnold et al.

(10) Patent No.: US 10,273,228 B2
(45) Date of Patent: Apr. 30, 2019

(54) HEPATITIS B VIRAL ASSEMBLY EFFECTORS

(71) Applicant: Indiana University Research and Technology Corporation, Indianapolis, IN (US)

(72) Inventors: Lee Daniel Arnold, Bloomington, IN (US); Hans Maag, Kleines Wiesental (DE); William W. Turner, Jr., Bloomington, IN (US)

(73) Assignees: Indiana University Research and Technology Corporation, Indianapolis, IN (US); Assembly Biosciences, Inc., Carmel, IN (US)

( * ) Notice: Subject to any disclaimer, the term of this patent is extended or adjusted under 35 U.S.C. 154(b) by 0 days.

(21) Appl. No.: 15/566,633

(22) PCT Filed: Apr. 15, 2016

(86) PCT No.: PCT/US2016/027780
§ 371 (c)(1),
(2) Date: Oct. 13, 2017

(87) PCT Pub. No.: WO2016/168619
PCT Pub. Date: Oct. 20, 2016

(65) Prior Publication Data
US 2018/0099952 A1    Apr. 12, 2018

Related U.S. Application Data

(60) Provisional application No. 62/148,994, filed on Apr. 17, 2015.

(51) Int. Cl.
| | | |
|---|---|---|
| *C07D 403/14* | (2006.01) | |
| *C07D 401/04* | (2006.01) | |
| *C07D 403/12* | (2006.01) | |
| *C07D 401/12* | (2006.01) | |
| *C07D 403/04* | (2006.01) | |
| *C07D 239/42* | (2006.01) | |
| *C07D 239/48* | (2006.01) | |
| *C07D 409/12* | (2006.01) | |
| *C07D 417/04* | (2006.01) | |
| *C07D 417/12* | (2006.01) | |
| *C07D 401/14* | (2006.01) | |
| *C07D 417/14* | (2006.01) | |
| *C07D 213/74* | (2006.01) | |
| *C07D 239/47* | (2006.01) | |
| *C07D 413/04* | (2006.01) | |
| *A61K 31/496* | (2006.01) | |
| *A61K 31/506* | (2006.01) | |
| *A61P 31/20* | (2006.01) | |

(52) U.S. Cl.
CPC .......... *C07D 403/14* (2013.01); *A61K 31/496* (2013.01); *A61K 31/506* (2013.01); *A61P 31/20* (2018.01); *C07D 213/74* (2013.01); *C07D 239/42* (2013.01); *C07D 239/47* (2013.01); *C07D 239/48* (2013.01); *C07D 401/04* (2013.01); *C07D 401/12* (2013.01); *C07D 401/14* (2013.01); *C07D 403/04* (2013.01); *C07D 403/12* (2013.01); *C07D 409/12* (2013.01); *C07D 413/04* (2013.01); *C07D 417/04* (2013.01); *C07D 417/12* (2013.01); *C07D 417/14* (2013.01)

(58) Field of Classification Search
CPC .. C07D 403/14; C07D 213/74; C07D 239/42; C07D 239/47; C07D 239/48; C07D 401/04; C07D 401/12; C07D 401/14; C07D 403/04; C07D 403/12; C07D 409/12; C07D 413/04; C07D 417/04; C07D 417/12; C07D 417/14; A61P 31/20; A61K 31/496; A61K 31/506
USPC ........................................................ 514/218
See application file for complete search history.

(56) References Cited

U.S. PATENT DOCUMENTS

| | | | |
|---|---|---|---|
| 7,482,351 | B2 | 1/2009 | Singh et al. |
| 7,816,351 | B2 | 10/2010 | Han et al. |
| 2006/0293343 | A1 | 12/2006 | Naganuma et al. |
| 2008/0293711 | A1 | 11/2008 | Clark et al. |
| 2011/0288082 | A1 | 11/2011 | Deshaies et al. |
| 2012/0329780 | A1 | 12/2012 | Thormann et al. |
| 2015/0087673 | A1 | 3/2015 | Hitoshi et al. |
| 2016/0271130 | A1 | 9/2016 | Zlotnick et al. |

FOREIGN PATENT DOCUMENTS

| | | |
|---|---|---|
| CN | 101268081 A | 9/2008 |
| JP | 2006022073 A * | 1/2006 |
| WO | WO 99/58526 A1 | 11/1999 |
| WO | WO 2010/118367 A2 | 10/2010 |
| WO | WO 2013/006394 A1 | 1/2013 |
| WO | WO 2013/019967 A1 | 2/2013 |
| WO | WO 2014/060112 A1 | 4/2014 |
| WO | WO2014/074906 A1 | 5/2014 |
| WO | WO 2015/057945 A1 | 4/2015 |

OTHER PUBLICATIONS

Machine translation of JP2006022073A (Year: 2006).*

(Continued)

*Primary Examiner* — Yevgeny Valendrod
(74) *Attorney, Agent, or Firm* — Faegre Baker Daniels LLP

(57) ABSTRACT

Novel assembly effector compounds having a therapeutic effect against hepatitis B viral (HBV) infection are disclosed. Assembly effector molecules described herein can lead to defective viral assembly and also may affect other viral activities associated with chronic HBV infection. Also disclosed is a process to synthesize disclosed compounds, method of treatment of HBV by administration of disclosed compounds, and use of these compounds in the manufacture of medicaments against HBV.

15 Claims, No Drawings

(56) References Cited

OTHER PUBLICATIONS

International Preliminary Report on Patentability issued by The International Bureau of WIPO, dated Oct. 17, 2017, for International Application No. PCT/US2016/027780; 10 pages.
International Search Report and Written Opinion issued by the ISA/US, Commissioner for Patents, dated Jul. 15, 2016, for International Application No. PCT/US2016/027780; 12 pages.
Martyn, D.C. et al., "Antiplasmodial activity of piperazine sulfonamides", Bioorganic & Medicinal Chemistry Letters, Pergamon, Amsterdam, NL, vol. 20, No. 1, Jan. 1, 2010; 4 pages.
Marugan, Juan J. et al., "Evaluation of Quinazoline Analogues as Glucocerebrosidase Inhibitors with Chaperone Activity", Journal of Medicinal Chemistry, vol. 54, No. 4, Feb. 24, 2011; 26 pages.
Extended European Search Report issued by European Patent Office, dated Aug. 21, 2018, for European Patent Application No. EP 16 78 0846.8; 11 pages.
RN 946314-38-1. Electronic Resource. Sep. 7, 2007.

\* cited by examiner

HEPATITIS B VIRAL ASSEMBLY EFFECTORS

RELATED APPLICATIONS

This application is a U.S. National Stage Application of International Patent Application No. PCT/2016/027780, filed Apr. 15, 2016, which claims the benefit of U.S. Provisional Patent Application No. 62/148,994, filed Apr. 17, 2015, each of which is incorporated herein by reference in its entirety.

GOVERNMENT RIGHTS

This invention was made with government support under AI067417 awarded by the National Institutes of Health. The Government has certain rights in the invention.

BACKGROUND

Hepatitis B (HBV) causes viral hepatitis that can further lead to chronic liver disease and increase the risk of liver cirrhosis and liver cancer (hepatocellular carcinoma). Worldwide, more than 2 billion people have been infected with HBV. Around 360 million people are chronically infected and every year HBV infection causes more than one million deaths. HBV can be spread by body fluids: from mother to child, by sex, and via blood products. Children born to HBV-positive mothers may also be infected, unless vaccinated at birth.

At present, chronic HBV is primarily treated with nucleosides/nucleotides (e.g. entecavir) that suppress the virus while the patient remains on treatment, but they do not eliminate the infection, even after many years of treatment. Once a patient starts taking nucleotide analogs most must continue taking them or risk the possibility of a life threatening immune response to viral rebound. Further, antiviral nucleoside therapy may lead to the emergence of antiviral drug resistance.

The only FDA approved alternative to antiviral nucleoside/nucleotide analogs is treatment with interferon α or pegylated interferon α. Unfortunately, the adverse event incidence and profile of interferon-α can result in poor tolerability, and many patients are unable to complete therapy. Moreover, only a small percentage of patients are considered appropriate for interferon therapy, as only a small subset of patients who present with low viral loads and transaminitis greater than 2× the upper limit of normal are likely to have a sustained clinical response to a year-long course of interferon therapy. As a result, interferon-based therapies are used in only a small percentage of all diagnosed patients who elect for treatment.

Thus, current HBV treatments can range from palliative to benign neglect. Nucleoside analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

The present disclosure is directed in part to compounds having activity against hepatitis B virus, for example, by affecting assembly of viral capsid proteins. For example, disclosed compounds may be considered CpAMs—core protein allosteric modifiers—which can lead to defective viral capsid assembly. Without being bound by any theory, such CpAMs may affect steps "upstream" of capsid assembly by altering the concentrations of Cp (core protein) available as dimers as compared to capsid or other multimeric forms. Disclosed compounds or CpAMs may noticeably affect functions upstream of viral assembly, such as interfering with cccDNA transcription, RNA stability and/or protein-protein interactions.

In one aspect, the present disclosure provides a pharmaceutical composition comprising: (i) a compound of Formula 1 having the structure:

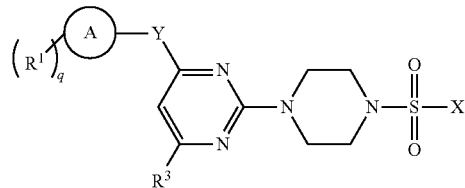

Formula 1 or a pharmaceutically acceptable salt or stereoisomer thereof, wherein:

is selected from the group consisting of phenyl, naphthyl, and heteroaryl;

Y is selected from the group consisting of a bond, —O—, —S(O)$_w$—, and —N(R')—;

X is selected from the group consisting of phenyl, naphthyl, and heteroaryl; wherein X is optionally substituted with one, two, three, or four R$^2$ groups;

provided that at least one of

or X is a heteroaryl;

R$^1$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, cyano, —OH, —C(O)H, —CO$_2$R', —C(O)N(R')(R''), —C(O)C$_1$-C$_6$alkyl, —N(R')(R''), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R'');

q is 0, 1, 2, 3 or 4;

w is 0, 1 or 2;

R' is independently for each occurrence selected from the group consisting of —H and —C$_1$-C$_6$alkyl;

R'' is independently for each occurrence selected from the group consisting of —H and —C$_1$-C$_6$alkyl; or R' and R'' are taken together with the nitrogen atom to which they are attached to form a 4-7 membered heterocyclic or heteroaryl ring, each of which is optionally substituted with an oxo group;

R$^2$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, oxo, cyano, —OH, —C(O)H, —CO₂R', —C(O)N(R')(R''), —C(O)C₁-C₆alkyl, —N(R')(R''), —NO₂, —N(R')C(O)C₁-C₆alkyl, —S(O)_w—C₁-C₆alkyl, —N(R')S(O)_w—C₁-C₆alkyl, and —S(O)_w—N(R')(R''); and R³ is selected from the group consisting of —H, —C₁-C₆alkyl, —N(R')(R''), —N(R')C₁-C₆alkyl-N(R')(R''), —N(R')—C₁-C₆alkyl-OR', —OH, —C₁-C₆alkoxy, —O—C₁-C₆alkyl-OR', —O-heterocyclyl, —O-heteroaryl, —O—C₁-C₆alkyl-heteroaryl, —C₁-C₆alkyl-heteroaryl, heterocyclyl, and heteroaryl, wherein heterocyclyl and heteroaryl are optionally substituted with one or two C₁-C₆alkyl or halogen;

wherein C₁-C₆alkyl or C₁-C₆alkoxy may be independently for each occurrence optionally substituted with one, two, or three halogens; and (ii) optionally, a pharmaceutically acceptable excipient.

In another aspect, the present disclosure provides a pharmaceutical composition comprising: (i) a compound of Formula 2 having the structure:

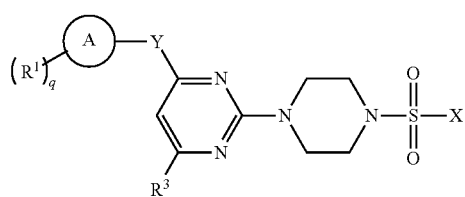

Formula 2 or a pharmaceutically acceptable salt or stereoisomer thereof, wherein:

is selected from the group consisting of phenyl, naphthyl, and heteroaryl;

Y is selected from the group consisting of a bond, —O—, and —S(O)_w—;

X is selected from the group consisting of phenyl, naphthyl, and heteroaryl; wherein X is optionally substituted with one, two, three, or four R² groups;

R¹ is independently for each occurrence selected from the group consisting of —H, —C₁-C₆alkyl, —C₁-C₆alkoxy, —C₁-C₆alkyl-O—C₁-C₆alkyl, halogen, cyano, —OH, —C(O)H, —CO₂R', —C(O)N(R')(R''), —C(O)C₁-C₆alkyl, —N(R')(R''), —NO₂, —N(R')C(O)C₁-C₆alkyl, —S(O)_w—C₁-C₆alkyl, —N(R')S(O)_w—C₁-C₆alkyl, and —S(O)_w—N(R')(R'');

q is 0, 1, 2, 3 or 4;
w is 0, 1 or 2;

R' is independently for each occurrence selected from the group consisting of —H and —C₁-C₆alkyl;

R'' is independently for each occurrence selected from the group consisting of —H and —C₁-C₆alkyl; or R' and R'' are taken together with the nitrogen atom to which they are attached to form a 4-7 membered heterocyclic or heteroaryl ring, each of which is optionally substituted with an oxo group;

R² is independently for each occurrence selected from the group consisting of —H, —C₁-C₆alkyl, —C₁-C₆alkoxy, —C₁-C₆alkyl-O—C₁-C₆alkyl, halogen, oxo, cyano, —OH, —C(O)H, —CO₂R', —C(O)N(R')(R''), —C(O)C₁-C₆alkyl, —N(R')(R''), —NO₂, —N(R')C(O)C₁-C₆alkyl, —S(O)_w—C₁-C₆alkyl, —N(R')S(O)_w—C₁-C₆alkyl, and —S(O)_w—N(R')(R''); and R³ is selected from the group consisting of —H, —C₁-C₆alkyl, —N(R')(R''), —N(R')C₁-C₆alkyl-N(R')(R''), —N(R')—C₁-C₆alkyl-OR', —OH, —C₁-C₆alkoxy, —O—C₁-C₆alkyl-OR', —O-heterocyclyl, —O-heteroaryl, —O—C₁-C₆alkyl-heteroaryl, —C₁-C₆alkyl-heteroaryl, heterocyclyl, and heteroaryl, wherein heterocyclyl and heteroaryl are optionally substituted with one or two C₁-C₆alkyl or halogen;

wherein C₁-C₆alkyl or C₁-C₆alkoxy may be independently for each occurrence optionally substituted with one, two, or three halogens; and (ii) optionally, a pharmaceutically acceptable excipient.

In another aspect, the present disclosure provides a pharmaceutical composition comprising: (i) a compound of Formula 3 having the structure:

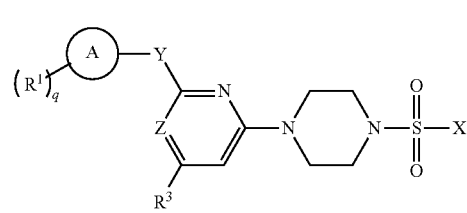

Formula 3 or a pharmaceutically acceptable salt or stereoisomer thereof, wherein:

is selected from the group consisting of phenyl, naphthyl, and heteroaryl;

Y is selected from the group consisting of a bond, —O—, —S(O)_w—, and —N(R')—;

Z is CH or N;

X is selected from the group consisting of phenyl, naphthyl, and heteroaryl; wherein X is optionally substituted with one, two, three, or four R² groups;

R¹ is independently for each occurrence selected from the group consisting of —H, —C₁-C₆alkyl, —C₁-C₆alkoxy, —C₁-C₆alkyl-O—C₁-C₆alkyl, halogen, cyano, —OH, —C(O)H, —CO₂R', —C(O)N(R')(R''), —C(O)C₁-C₆alkyl, —N(R')(R''), —NO₂, —N(R')C(O)C₁-C₆alkyl, —S(O)_w—C₁-C₆alkyl, —N(R')S(O)_w—C₁-C₆alkyl, and —S(O)_w—N(R')(R'');

q is 0, 1, 2, 3 or 4;
w is 0, 1 or 2;

R' is independently for each occurrence selected from the group consisting of —H and —C₁-C₆alkyl;

R'' is independently for each occurrence selected from the group consisting of —H and —C₁-C₆alkyl; or R' and R'' are taken together with the nitrogen atom to which they are attached to form a 4-7 membered heterocyclic or heteroaryl ring, each of which is optionally substituted with an oxo group;

R² is independently for each occurrence selected from the group consisting of —H, —C₁-C₆alkyl, —C₁-C₆alkoxy, —C₁-C₆alkyl-O—C₁-C₆alkyl, halogen, oxo, cyano, —OH, —C(O)H, —CO₂R', —C(O)N(R')(R''), —C(O)C₁-C₆alkyl, —N(R')(R''), —NO₂, —N(R')C(O)

$C_1$-$C_6$alkyl, —S(O)$_w$—$C_1$-$C_6$alkyl, —N(R')S(O)$_w$—$C_1$-$C_6$alkyl, and —S(O)$_w$—N(R')(R"); and $R^3$ is selected from the group consisting of —H, —$C_1$-$C_6$alkyl, —N(R')(R"), —N(R')$C_1$-$C_6$alkyl-N(R')(R"), —N(R')—$C_1$-$C_6$alkyl-OR', —OH, —$C_1$-$C_6$alkoxy, —O—$C_1$-$C_6$alkyl-OR', —O-heterocyclyl, —O-heteroaryl, —O—$C_1$-$C_6$alkyl-heteroaryl, —$C_1$-$C_6$alkyl-heteroaryl, heterocyclyl, and heteroaryl, wherein heterocyclyl and heteroaryl are optionally substituted with one or two $C_1$-$C_6$alkyl or halogen;

wherein $C_1$-$C_6$alkyl or $C_1$-$C_6$alkoxy may be independently for each occurrence optionally substituted with one, two, or three halogens; and (ii) optionally, a pharmaceutically acceptable excipient.

In another aspect, the present disclosure provides a pharmaceutical composition comprising: (i) a compound of Formula 4 having the structure:

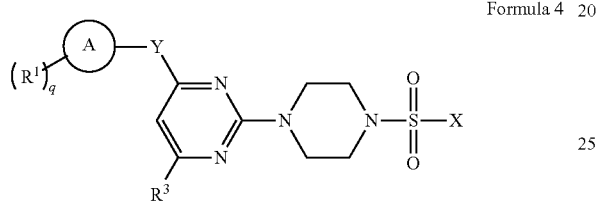

Formula 4 or a pharmaceutically acceptable salt or stereoisomer thereof, wherein:

is selected from the group consisting of phenyl, naphthyl, and heteroaryl;

Y is selected from the group consisting of a bond, —O—, —S(O)$_w$—, and —N(R')—;

X is selected from the group consisting of phenyl, naphthyl, and heteroaryl; wherein X is optionally substituted with one, two, three, or four $R^2$ groups;

$R^1$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R");

q is 0, 1, 2, 3 or 4;

w is 0, 1 or 2;

R' is independently for each occurrence selected from the group consisting of —H and —$C_1$-$C_6$alkyl;

R" is independently for each occurrence selected from the group consisting of —H and —$C_1$-$C_6$alkyl; or R' and R" are taken together with the nitrogen atom to which they are attached to form a 4-7 membered heterocyclic or heteroaryl ring, each of which is optionally substituted with an oxo group;

$R^2$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, oxo, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R"); and $R^3$ is selected from the group consisting of —N(R')(R"), —N(R')$C_1$-$C_6$alkyl-N(R')(R"), —N(R')—$C_1$-$C_6$alkyl-OR', —OH, —$C_1$-$C_6$alkoxy, —O—$C_1$-$C_6$alkyl-OR', —O-heterocyclyl, —O-heteroaryl, —O—$C_1$-$C_6$alkyl-heteroaryl, —$C_1$-$C_6$alkyl-heteroaryl, heterocyclyl, and heteroaryl, wherein heterocyclyl and heteroaryl are optionally substituted with one or two $C_1$-$C_6$alkyl or halogen;

wherein $C_1$-$C_6$alkyl or $C_1$-$C_6$alkoxy may be independently for each occurrence optionally substituted with one, two, or three halogens; and (ii) optionally, a pharmaceutically acceptable excipient.

In another aspect, the present disclosure provides a compound selected from the group consisting of:

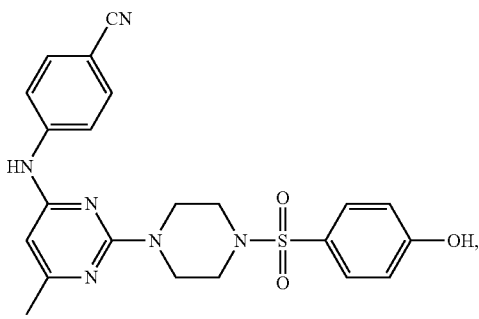

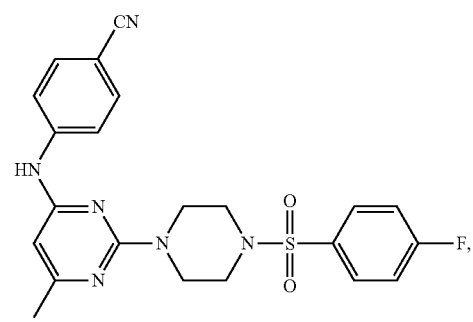

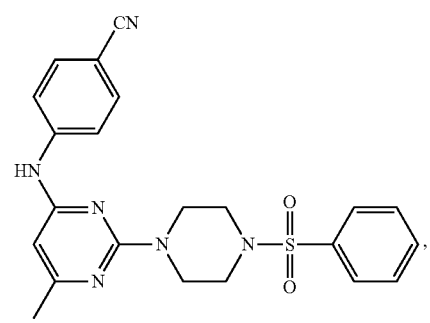

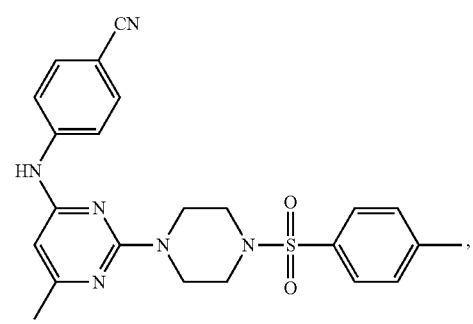

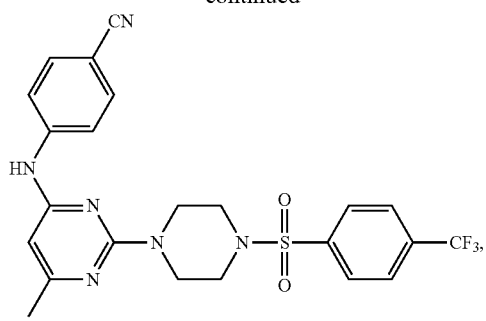
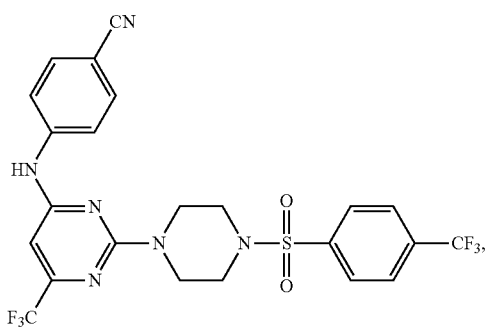
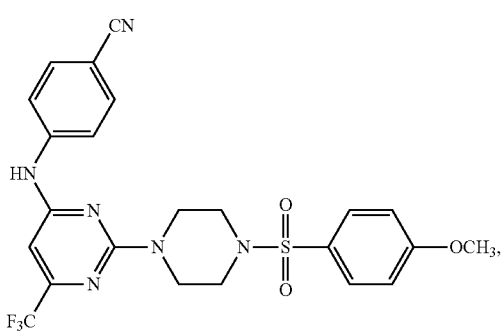
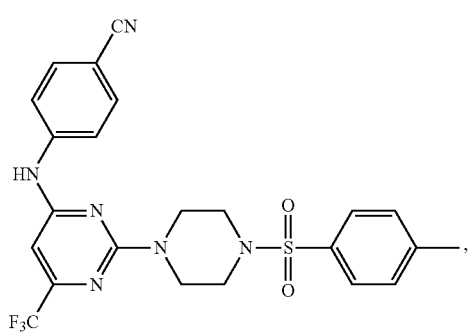
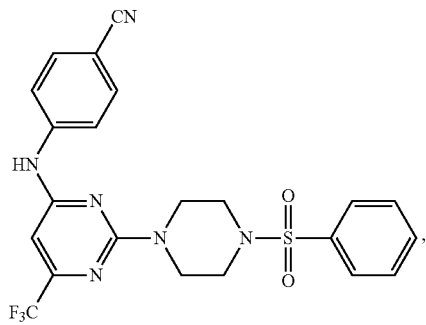
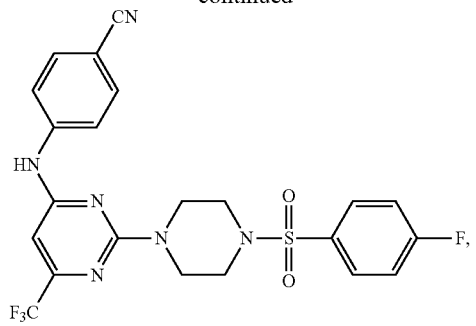
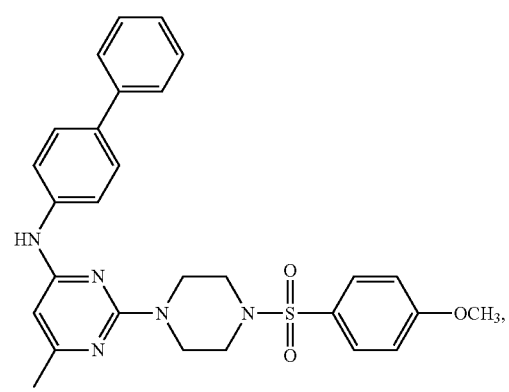
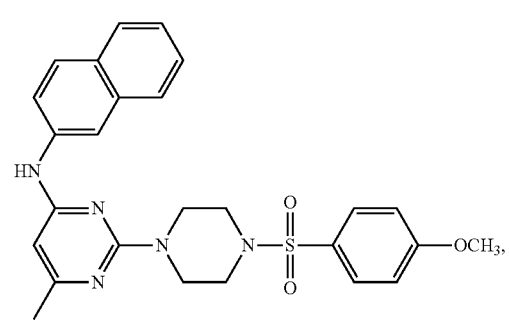
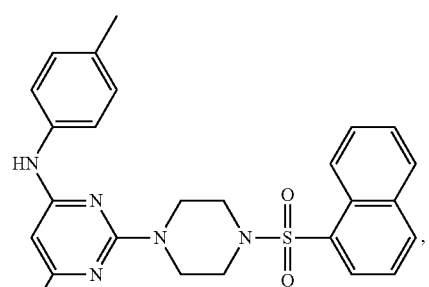
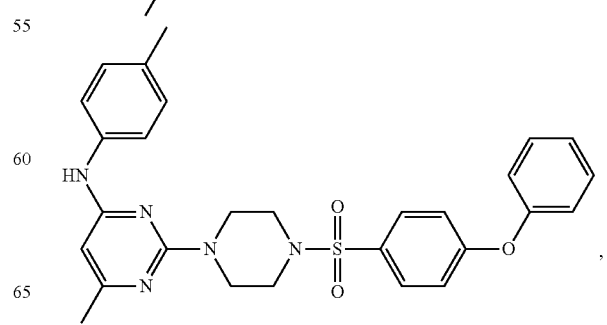

-continued

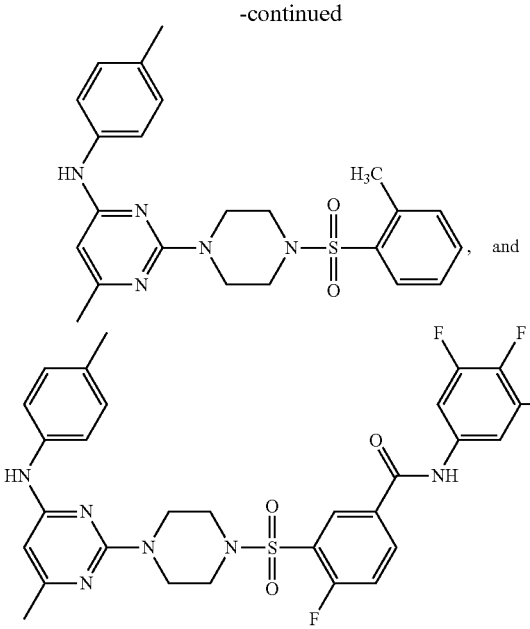

or a pharmaceutically acceptable salt or stereoisomer thereof.

In another aspect, the present disclosure provides a compound selected from the group consisting of compounds according to Table 1, Table 2, Table 3, Table 4, Table 5, Table 6, Table 7, Table 8, and Table 9; or a pharmaceutically acceptable salt or stereoisomer thereof.

In another aspect, the present disclosure provides a pharmaceutical composition comprising: (i) a compound of Formula 5 having the structure:

Formula 5

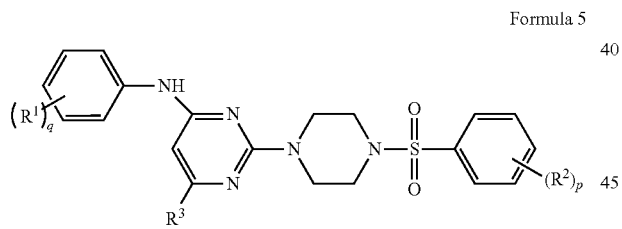

or a pharmaceutically acceptable salt or stereoisomer thereof, wherein:
or a pharmaceutically acceptable salt or stereoisomer thereof, wherein:
$R^1$ is independently for each occurrence selected from the group consisting of —H, —$C_1$-$C_6$alkyl, —$C_1$-$C_6$alkoxy, halogen, cyano, —OH, —C(O)H, —$CO_2R'$, —C(O)N(R')(R''), and —C(O)$C_1$-$C_6$alkyl;
q is 0, 1, 2, 3 4 or 5;
$R^3$ is $C_1$-$C_6$alkyl optionally substituted with halogen or heteroaryl optionally substituted with one, two, or three $C_1$-$C_6$alkyl or halogen;
p is 0, 1, 2, 3, 4 or 5;
$R^2$ is independently for each occurrence selected from the group consisting of —H; —$C_1$-$C_6$alkyl; —$C_1$-$C_6$alkoxy; —O—$C_1$-$C_6$alkyl-$CO_2R'$; —$C_1$-$C_6$alkyl-$CO_2R'$; halogen; —$CO_2R'$; —O—$C_1$-$C_6$alkyl-N(R')(R''); $C_1$-$C_6$alkoxy substituted with a heterocycle; and $C_1$-$C_8$alkylene, wherein at least one carbon of $C_1$-$C_8$alkylene is optionally substituted with O; wherein —$C_1$-$C_6$alkyl and —$C_1$-$C_6$alkoxy are optionally substituted with $C_1$-$C_6$alkyl or halogen;
R' and R'' are independently selected from the group consisting of —H, —$C_1$-$C_6$alkoxy, and —$C_1$-$C_6$alkyl; and
(ii) optionally, a pharmaceutically acceptable excipient.

In another aspect, the present disclosure provides a pharmaceutical composition comprising: (i) a compound of Formula 6 having the structure:

Formula 6

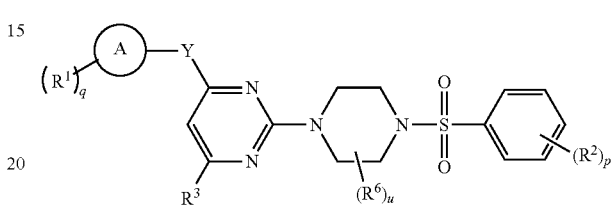

or a pharmaceutically acceptable salt or stereoisomer thereof, wherein:

A is selected from the group consisting of phenyl, naphthyl, and heteroaryl;
$R^1$ is independently for each occurrence selected from the group consisting of —H, —$C_1$-$C_6$alkyl, —$C_1$-$C_6$alkoxy, halogen, cyano, —OH, —C(O)H, —$CO_2R'$, —C(O)N(R')(R''), and —C(O)$C_1$-$C_6$alkyl;
q is 0, 1, 2, 3, 4 or 5;
Y is selected from the group consisting of a —O—, —S(O)$_w$—, and —N(R')— where w is 0, 1 or 2;
$R^3$ is selected from the group consisting of —$C_1$-$C_6$alkyl, —$C_1$-$C_6$alkoxy, —$C_1$-$C_6$alkyl-heteroaryl, heterocyclyl, and heteroaryl, wherein —$C_1$-$C_6$alkyl and heterocyclyl are optionally substituted with one, two, or three $C_1$-$C_6$alkyl or halogen;
p is 0, 1, 2 or 3;
$R^2$ is independently for each occurrence selected from the group consisting of —H; —$C_1$-$C_6$alkyl optionally substituted with halogen; and —O—$C_1$-$C_6$alkyl optionally substituted with halogen;
R' and R'' are independently selected from the group consisting of —H, —$C_1$-$C_6$alkoxy, and —$C_1$-$C_6$alkyl;
$R^6$ is independently for each occurrence selected from the group consisting of —$C_1$-$C_6$alkyl and —O—$C_1$-$C_6$alkyl; or two $R^6$ groups are on the same carbon atom, or alternatively, two $R^6$ groups are on the same carbon atom and when taken together form oxo; wherein —$C_1$-$C_6$alkyl or —O—$C_1$-$C_6$alkyl are optionally substituted with halogen;
u is 0, 1, 2, 3, 4, 5, 6, 7, or 8; and
(ii) optionally, a pharmaceutically acceptable excipient.

In another aspect, the present disclosure provides a pharmaceutical composition comprising: (i) a compound of Formula 7 having the structure:

Formula 7

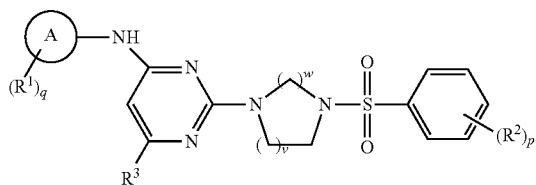

or a pharmaceutically acceptable salt or stereoisomer thereof, wherein:

is selected from the group consisting of phenyl, naphthyl, and heteroaryl;
$R^1$ is independently for each occurrence selected from the group consisting of —H, —$C_1$-$C_6$alkyl, —$C_1$-$C_6$alkoxy, halogen, cyano, —OH, —C(O)H, —$CO_2R'$, —C(O)N(R')(R"), and —C(O)$C_1$-$C_6$alkyl;
q is 0, 1, 2, 3 or 4;
$R^3$ is selected from the group consisting of —$C_1$-$C_6$alkyl, —$C_1$-$C_6$alkoxy, —$C_1$-$C_6$alkyl-heteroaryl, heterocyclyl, and heteroaryl, wherein —$C_1$-$C_6$alkyl and heterocyclyl are optionally substituted with one, two, or three $C_1$-$C_6$alkyl or halogen;
w is 1 or 2;
v is 1 or 2.
p is 0, 1, 2 or 3;
$R^2$ is independently for each occurrence selected from the group consisting of —H; —$C_1$-$C_6$alkyl; —$C_1$-$C_6$alkoxy; or —O—$C_1$-$C_6$alkyl-$CO_2R'$; wherein —$C_1$-$C_6$alkyl, —$C_1$-$C_6$alkoxy, and —O—$C_1$-$C_6$alkyl-$CO_2R'$ are optionally substituted with halogen or $C_1$-$C_6$alkyl;
R' and R" are independently selected from the group consisting of —H, —$C_1$-$C_6$alkoxy, and —$C_1$-$C_6$alkyl; and
(ii) optionally, a pharmaceutically acceptable excipient.

DETAILED DESCRIPTION

Definitions

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As intended herein, the terms "a" and "an" include singular as well as plural references unless the context clearly dictates otherwise. For example, the term "an assembly effector" can include one or more such effectors.

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_2$-$C_6$ alkenyl, and $C_3$-$C_4$ alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as $C_1$-$C_6$ alkoxy, and $C_2$-$C_6$ alkoxy, respectively. Exemplary alkoxy groups include, but are not limited to methoxy, ethoxy, isopropoxy, etc.

The term "alkyl" as used herein refers to a saturated straight or branched hydrocarbon, such as a straight or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$ alkynyl and $C_3$-$C_6$ alkynyl, respectively. Exemplary alkynyl groups include, but are not limited to, ethynyl, propynyl, butynyl, pentynyl, hexynyl, methylpropynyl, etc.

The term "cycloalkoxy" as used herein refers to a cycloalkyl group attached to an oxygen (cycloalkyl-O—).

The term "cycloalkyl" as used herein refers to a monocyclic or bicyclic saturated or partially unsaturated hydrocarbon group of, for example 3-6, or 4-6, or 3-8, or 3-12 carbons, referred to herein, e.g., as $C_3$-$C_6$cycloalkyl, $C_4$-$C_6$cycloalkyl, $C_3$-$C_8$cycloalkyl, or $C_3$-$C_{12}$cycloalkyl. Exemplary cycloalkyl groups include, but are not limited to, cyclohexane, cyclohexene, cyclopentane, cyclobutane, or cyclopropane.

The term "heteroaryl" as used herein includes monocyclic aromatic 5-6 membered ring systems containing one or more heteroatoms, for example one to three heteroatoms, such as nitrogen, oxygen, and sulfur. The term "heteroaryl" also includes 7-12 membered fused bicyclic ring systems containing one or more heteroatoms, for example one to six heteroatoms, such as nitrogen, oxygen, and sulfur. Where chemically possible, said heteroaryl groups may be linked to the adjacent radical though carbon or nitrogen. Examples of heteroaryl rings include but are not limited to furan, thiophene, pyrrole, thiazole, oxazole, isothiazole, isoxazole, imidazole, pyrazole, 1,2,3-triazole, 1,2,4-triazole, pyridine, pyrimidine, pyrazine, benzimidazole, 2,3-dihydro-1H-benzo[d]imidazole, 1,3-dihydro-2H-benzo[d]imidazol-2-one, benzimidazole, etc.

The terms "heterocyclyl" and "heterocyclic group" are art-recognized and include saturated or partially unsaturated monocyclic 4-7 membered ring structures, whose ring structures include one to three heteroatoms, such as nitrogen, oxygen, and sulfur, as well as 7-12 membered bicyclic ring structures, whose ring structures include one to six heteroatoms, such as nitrogen, oxygen, and sulfur. Where chemically possible, heterocyclyl rings may be linked to the adjacent radical through carbon or nitrogen. Examples of heterocyclyl groups include, but are not limited to, oxetane, pyrrolidine, 2-pyrrolidinone, piperidine, 2-piperidinone, morpholine, thiomorpholine, piperazine, N-methylpiperazine, oxetane, azetidine, tetrahydrofuran or dihydrofuran etc.

The terms "halo" or "halogen" as used herein refer to F, Cl, Br, or I.

The terms "hydroxy" and "hydroxyl" as used herein refers to the radical —OH.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety, and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of hepatitis B is desired. "Modulation" includes antagonism (e.g., inhibition), agonism, partial antagonism and/or partial agonism.

In the present disclosure, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. Mixtures of enantiomers or diastereomers may be designated "(±)" in nomenclature.

Geometric isomers, resulting from the arrangement of substituents around a carbon-carbon double bond or arrangement of substituents around a cycloalkyl or heterocyclic ring, can exist in the compounds of the present invention. The symbol ═ denotes a bond that may be a single, double or triple bond as described herein. Substituents around a carbon-carbon double bond are designated as being in the "Z" or "F" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diasteriomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically-labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and/or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group, for example with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-$((C_{1-6})$alkanoyloxy)ethyl, 1-methyl-1-$((C_1-C_6)$alkanoyloxy)ethyl $(C_1-C_6)$alkoxycarbonyloxymethyl, N—$(C_1-C_6)$ alkoxycarbonyl aminomethyl, succinoyl, $(C_1-C_6)$alkanoyl, α-amino$(C_1-C_4)$alkanoyl, arylacyl and α-aminoacyl, or α-aminoacyl-α-aminoacyl, wherein each α-aminoacyl group is independently selected from the naturally occurring L-amino acids; or $P(O)(OH)_2$, —$P(O)(O(C_1-C_6)$alkyl$)_2$, or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

The present invention is based in part on the discovery of that certain classes of compounds such as those described herein may activate assembly of the viral capsid independent of the normal nucleating signals, e.g. act as core protein allosteric modulators having an effect against HBV. For example, disclosed compounds may activate assembly of the viral capsid independent of the normal nucleating signals.

Hepatitis B virus, for example, consists of an envelope, a nucleocapsid core, viral DNA, and reverse transcriptase (RT). Infection starts when the virus enters the host. The viral core enclosing the viral DNA and the RT are then transferred to cytoplasm of the host and to the host's nucleus, a process in which the circular and partially double stranded viral DNA is released from the viral core.

Inside the nucleus, the viral DNA is converted into a covalently-closed circular DNA (cccDNA), which codes for a pregenomic RNA (pg RNA) and other mRNAs. The pregenomic RNA, exported to the cytoplasm, codes for core protein and the reverse transcriptase. Encapsidation of the pregenomic RNA and the reverse transcriptase by core protein results in the formation of immature HBV cores which maturate as the pregenomic RNA is reverse transcribed to the circular and partially double stranded DNA, completing the cycle.

Central to HBV infection is the assembly of the viral core. The capsid itself is a complex of 120 copies of core protein homodimers that spontaneously self-assemble. In the presence of assembly effectors (AE) capsid assembly begins with an CpAM•Cp (Assembly effector•Core protein) complex instead of waiting for the biological RT•pgRNA nucleating complex; the resulting capsid is thus defective. CpAMs can leverage consumption of a few molecules needed for nucleation to consume for example up to 117 Cp dimers. To nucleate assembly, in some embodiments, CpAMs may have one or both of activities such as substantially interacting with or e.g., binding to Cp dimers, activating assembly, and/or substantially binding or interacting with capsids at e.g., a higher affinity as compared to binding to the Cp dimer.

Core proteins also have roles upstream of capsid assembly and are associated with nuclear cccDNA and affect their stability and transcription; they are involved in export of the pregenomic RNA from the nucleus.

For example, the compounds provided herein may affect virus assembly by interacting with core protein dimers as well as capsids, and/or may affect core protein activity upstream of capsid assembly. Defective assembly can immediately suppress virus production. Suppressed Cp activity upstream of assembly can also interfere with activities of the virus required for stability of the infection itself. For example, provided compounds may successfully treat HBV with a finite course of therapy (as opposed to the potentially life-long therapy necessary with current antiviral nucleosides/nucleotides), e.g. such finite therapy would result from a loss of new viral proteins and mRNA resulting from epigenetic modification of the viral cccDNA, as well as a reduction in new infectious virions. In other words, disclosed compounds may activate viral capsid assembly independent of the normal nucleating signals leading to defective assembly: capsid assembly begins with an AE•Cp complex instead of waiting for the biological RT•pgRNA nucleating complex; the resulting capsid or aberrant complex, e.g., cannot support production of a new virion. In some embodiments, disclosed compounds may leverage consumption of a few molecules needed for nucleation to consume up to 120 Cp dimers. Without being bound by theory, disclosed compounds may, for example, alter the concentration of Cp (core protein), likely required for activities upstream of capsid assembly. Suppressing Cp activity upstream of assembly interferes with the Cp interactions with the viral reservoir (cccDNA). This may lead to clearance of the infection by reduction of viral proteins and cccDNA activity.

In one aspect, the present disclosure provides a pharmaceutical composition comprising: (i) a compound of Formula 1 having the structure:

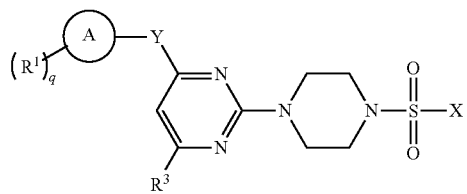

Formula 1 or a pharmaceutically acceptable salt or stereoisomer thereof, wherein:

is selected from the group consisting of phenyl, naphthyl, and heteroaryl;

Y is selected from the group consisting of a bond, —O—, —S(O)$_w$—, and —N(R')—;

X is selected from the group consisting of phenyl, naphthyl, and heteroaryl; wherein X is optionally substituted with one, two, three, or four R$^2$ groups;

provided that at least one of

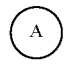

or X is a heteroaryl;

R$^1$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R");

q is 0, 1, 2, 3 or 4;

w is 0, 1 or 2;

R' is independently for each occurrence selected from the group consisting of —H and —C$_1$-C$_6$alkyl;

R" is independently for each occurrence selected from the group consisting of —H and —C$_1$-C$_6$alkyl; or R' and R" are taken together with the nitrogen atom to which they are attached to form a 4-7 membered heterocyclic or heteroaryl ring, each of which is optionally substituted with an oxo group;

R$^2$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, oxo, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R"); and R$^3$ is selected from the group consisting of —H, —C$_1$-C$_6$alkyl, —N(R')(R"), —N(R')C$_1$-C$_6$alkyl-N(R')(R"), —N(R')—C$_1$-C$_6$alkyl-OR', —OH, —C$_1$-C$_6$alkoxy, —O—C$_1$-C$_6$alkyl-OR', —O-heterocyclyl, —O-heteroaryl, —O—C$_1$-C$_6$alkyl-heteroaryl, —C$_1$-C$_6$alkyl-heteroaryl, heterocyclyl, and heteroaryl, wherein heterocyclyl and heteroaryl are optionally substituted with one or two C$_1$-C$_6$alkyl or halogen;

wherein C$_1$-C$_6$alkyl or C$_1$-C$_6$alkoxy may be independently for each occurrence optionally substituted with one, two, or three halogens; and (ii) optionally, a pharmaceutically acceptable excipient.

In certain embodiments,

is selected from the group consisting of

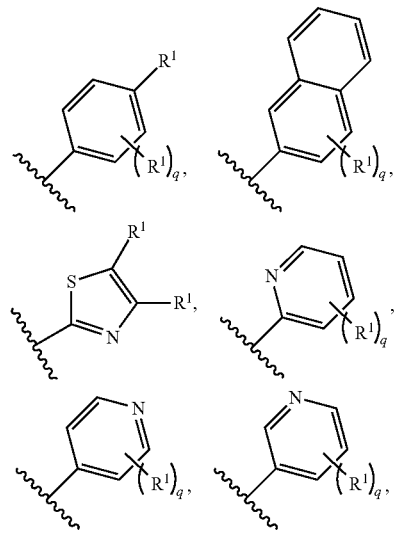

-continued

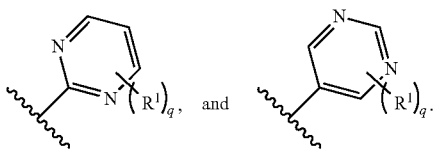

In certain embodiments,

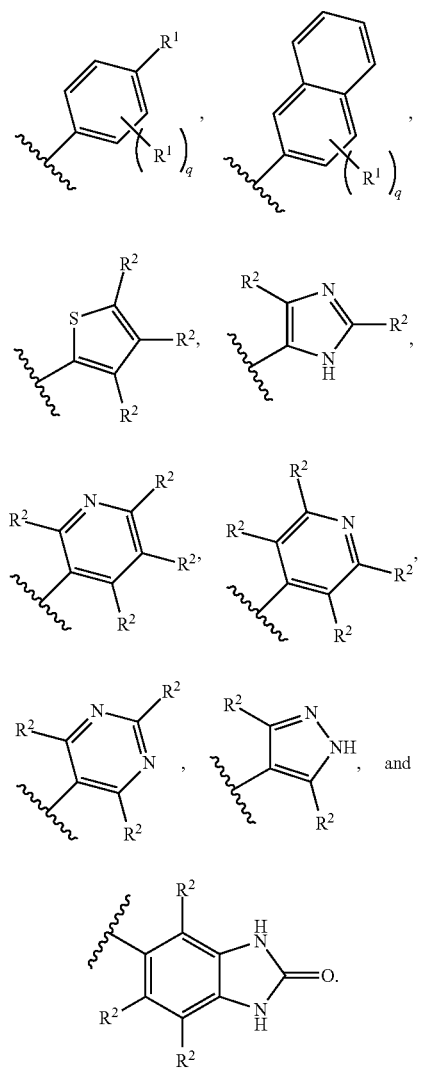

is phenyl.

In certain embodiments, X is selected from the group consisting of

In certain embodiments, X is phenyl.

In certain embodiments, $R^1$ is independently for each occurrence selected from the group consisting of —$C_1$-$C_6$alkyl, —$C_1$-$C_6$alkoxy, halogen, cyano, —OH, —$CO_2R'$, and —N(R')(R").

In certain embodiments, $R^1$ is independently for each occurrence selected from the group consisting of —$CH_3$, -Et, i-Pr, —$CF_3$, —OMe, —$OCF_3$, F, Cl, Br, —$NH_2$, —NHMe, and —$NMe_2$.

In certain embodiments, q is 1, 2, or 3.

In certain embodiments, $R^2$ is independently for each occurrence selected from the group consisting of —$C_1$-$C_6$alkyl, —$C_1$-$C_6$alkoxy, halogen, oxo, cyano, —OH, —$CO_2R'$, and —N(R')(R").

In certain embodiments, $R^2$ is independently for each occurrence selected from the group consisting of —$CH_3$, -Et, i-Pr, —$CF_3$, oxo, —OMe, —$OCF_3$, F, Cl, Br, —$NH_2$, —NHMe, and —$NMe_2$.

In certain embodiments, X is optionally substituted with one, two, or three $R^2$ groups.

In certain embodiments, $R^3$ is independently for each occurrence selected from the group consisting of —H, —$C_1$-$C_6$alkyl, —N(R')(R"), —NH—$C_1$-$C_6$alkyl-N($C_1$-$C_6$alkyl)$_2$, —NH—$C_1$-$C_6$-alkyl-OR', —OH, —$C_1$-$C_6$alkoxy, —O—$C_1$-$C_6$alkyl-OR', heterocyclyl, and heteroaryl, wherein heterocyclyl and heteroaryl are optionally substituted with one or two $C_1$-$C_6$alkyl or halogen.

In certain embodiments, $R^3$ is independently for each occurrence selected from the group consisting of —H, —$CH_3$, -Et, i-Pr, —N($CH_3$)$_2$, —NH(i-Pr), —NH(t-Bu), —N($CH_3$)(t-Bu), —NH($CH_3$), —NH($CH_2CH_2OH$), —NH—$CH_2CH_2$—N($CH_3$)$_2$, —OMe, —$OCH_2CH_2OH$,

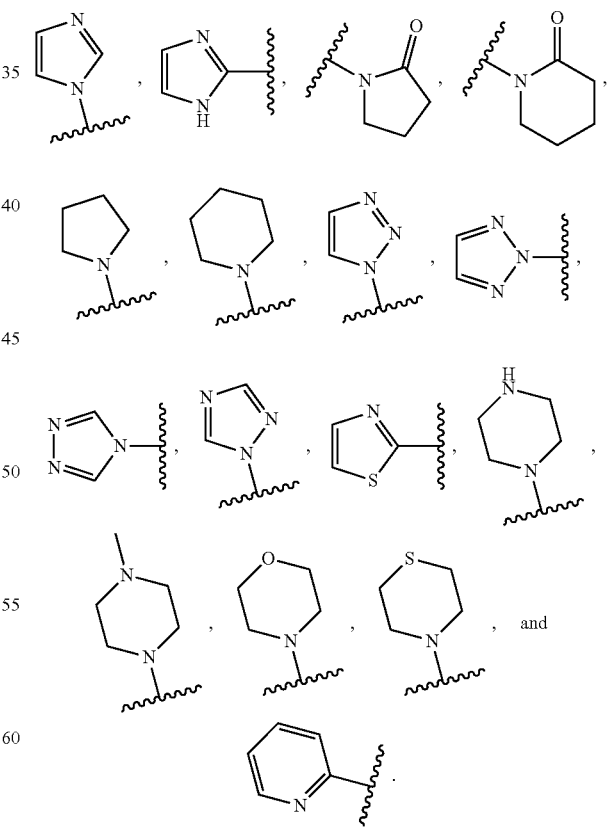

In certain embodiments, the compound is represented by Formula 1-A:

Formula 1-A

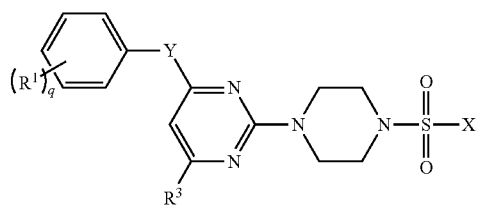

wherein X is heteroaryl.

In certain embodiments, the compound is represented by Formula 1-B:

Formula 1-B

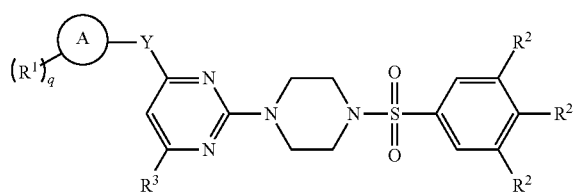

wherein

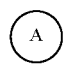

is heteroaryl.

In certain embodiments, Y is —NH—.

In another aspect, the present disclosure provides a pharmaceutical composition comprising: (i) a compound of Formula 2 having the structure:

Formula 2

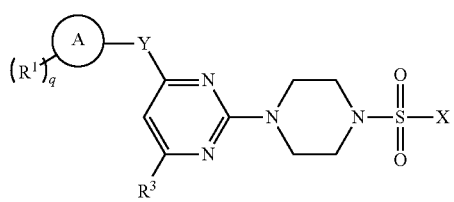

or a pharmaceutically acceptable salt or stereoisomer thereof, wherein:

is selected from the group consisting of phenyl, naphthyl, and heteroaryl;
Y is selected from the group consisting of a bond, —O—, and —S(O)$_w$—;
X is selected from the group consisting of phenyl, naphthyl, and heteroaryl; wherein X is optionally substituted with one, two, three, or four R$^2$ groups;
R$^1$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R");
q is 0, 1, 2, 3 or 4;
w is 0, 1 or 2;
R' is independently for each occurrence selected from the group consisting of —H and —C$_1$-C$_6$alkyl;
R" is independently for each occurrence selected from the group consisting of —H and —C$_1$-C$_6$alkyl; or R' and R" are taken together with the nitrogen atom to which they are attached to form a 4-7 membered heterocyclic or heteroaryl ring, each of which is optionally substituted with an oxo group;
R$^2$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, oxo, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R"); and
R$^3$ is selected from the group consisting of —H, —C$_1$-C$_6$alkyl, —N(R')(R"), —N(R')C$_1$-C$_6$alkyl-N(R')(R"), —N(R')—C$_1$-C$_6$alkyl-OR', —OH, —C$_1$-C$_6$alkoxy, —O—C$_1$-C$_6$alkyl-OR', —O-heterocyclyl, —O-heteroaryl, —O—C$_1$-C$_6$alkyl-heteroaryl, —C$_1$-C$_6$alkyl-heteroaryl, heterocyclyl, and heteroaryl, wherein heterocyclyl and heteroaryl are optionally substituted with one or two C$_1$-C$_6$alkyl or halogen;
wherein C$_1$-C$_6$alkyl or C$_1$-C$_6$alkoxy may be independently for each occurrence optionally substituted with one, two, or three halogens; and
(ii) optionally, a pharmaceutically acceptable excipient.

In certain embodiments,

is selected from the group consisting of

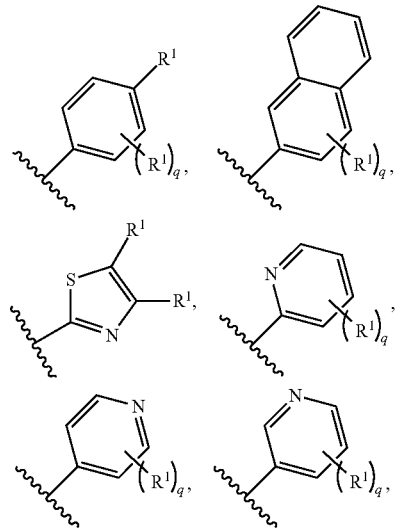

-continued

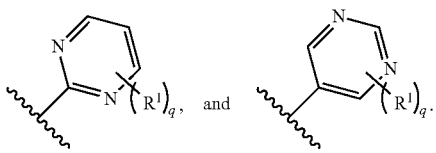

In certain embodiments,

is phenyl.

In certain embodiments, X is selected from the group consisting of

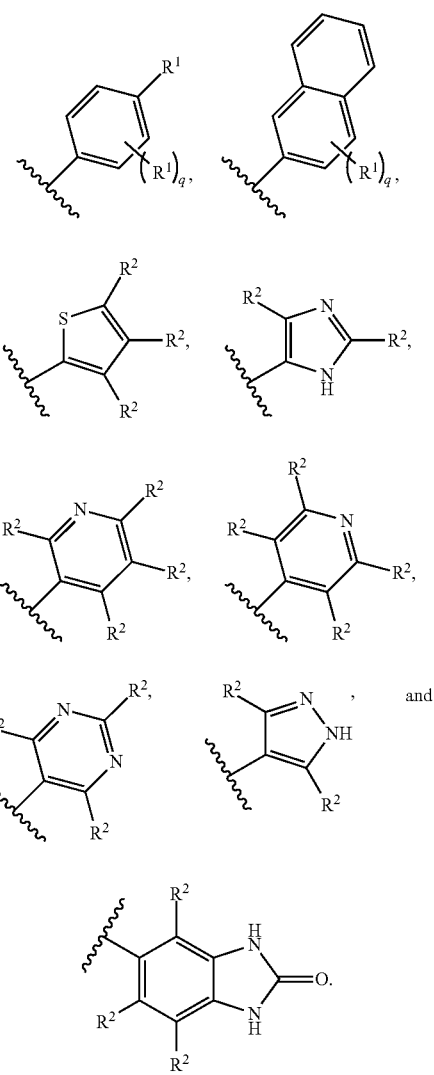

In certain embodiments, X is phenyl.

In certain embodiments, $R^1$ is independently for each occurrence selected from the group consisting of —$C_1$-$C_6$alkyl, —$C_1$-$C_6$alkoxy, halogen, cyano, —OH, —$CO_2R'$, and —N(R')(R").

In certain embodiments, $R^1$ is independently for each occurrence selected from the group consisting of —$CH_3$, -Et, i-Pr, —$CF_3$, —OMe, —$OCF_3$, F, Cl, Br, —$NH_2$, —NHMe, and —$NMe_2$.

In certain embodiments, q is 1, 2, or 3.

In certain embodiments, $R^2$ is independently for each occurrence selected from the group consisting of —$C_1$-$C_6$alkyl, —$C_1$-$C_6$alkoxy, halogen, oxo, cyano, —OH, —$CO_2R'$, and —N(R')(R").

In certain embodiments, $R^2$ is independently for each occurrence selected from the group consisting of —$CH_3$, -Et, i-Pr, —$CF_3$, oxo, —OMe, —$OCF_3$, F, Cl, Br, —$NH_2$, —NHMe, and —$NMe_2$.

In certain embodiments, X is optionally substituted with one, two, or three $R^2$ groups.

In certain embodiments, $R^3$ is independently for each occurrence selected from the group consisting of —H, —$C_1$-$C_6$alkyl, —N(R')(R"), —NH—$C_1$-$C_6$alkyl-N($C_1$-$C_6$alkyl)$_2$, —NH—$C_1$-$C_6$-alkyl-OR', —OH, —$C_1$-$C_6$alkoxy, —O—$C_1$-$C_6$alkyl-OR', heterocyclyl, and heteroaryl, wherein heterocyclyl and heteroaryl are optionally substituted with one or two $C_1$-$C_6$alkyl or halogen.

In certain embodiments, $R^3$ is independently for each occurrence selected from the group consisting of —H, —$CH_3$, -Et, i-Pr, —N($CH_3$)$_2$, —NH(i-Pr), —NH(t-Bu), —N($CH_3$)(t-Bu), —NH($CH_3$), —NH($CH_2CH_2$OH), —NH—$CH_2CH_2$—N($CH_3$)$_2$, —OMe, —$OCH_2CH_2$OH,

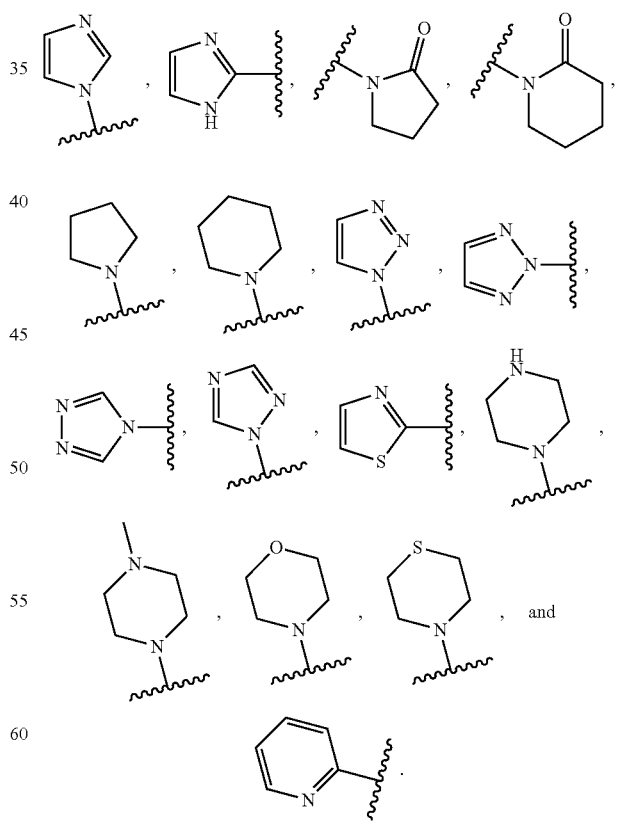

In certain embodiments, the compound is represented by Formula 2-A:

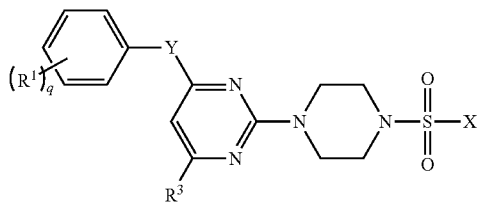

Formula 2-A wherein X is heteroaryl.

In certain embodiments, the compound is represented by Formula 2-B:

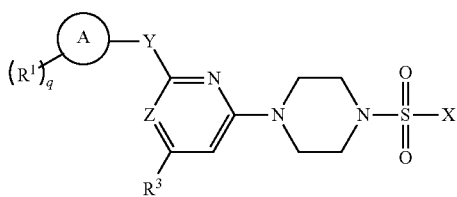

Formula 2-B wherein

is heteroaryl.

In certain embodiments, Y is —O—, —S—, or —SO$_2$—.

In another aspect, the present disclosure provides a pharmaceutical composition comprising: (i) a compound of Formula 3 having the structure:

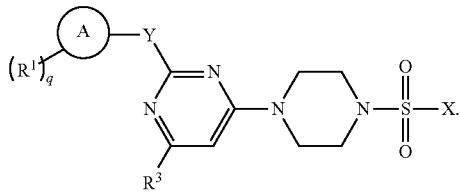

Formula 3 or a pharmaceutically acceptable salt or stereoisomer thereof, wherein:

is selected from the group consisting of phenyl, naphthyl, and heteroaryl;

Y is selected from the group consisting of a bond, —O—, —S(O)$_w$—, and —N(R')—;

Z is CH or N;

X is selected from the group consisting of phenyl, naphthyl, and heteroaryl; wherein X is optionally substituted with one, two, three, or four R$^2$ groups;

R$^1$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, cyano, —OH, —C(O)H, —CO$_2$R', —C(O)N(R')(R''), —C(O)C$_1$-C$_6$alkyl, —N(R')(R''), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R'');

q is 0, 1, 2, 3 or 4;

w is 0, 1 or 2;

R' is independently for each occurrence selected from the group consisting of —H and —C$_1$-C$_6$alkyl;

R'' is independently for each occurrence selected from the group consisting of —H and —C$_1$-C$_6$alkyl; or R' and R'' are taken together with the nitrogen atom to which they are attached to form a 4-7 membered heterocyclic or heteroaryl ring, each of which is optionally substituted with an oxo group;

R$^2$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, oxo, cyano, —OH, —C(O)H, —CO$_2$R', —C(O)N(R')(R''), —C(O)C$_1$-C$_6$alkyl, —N(R')(R''), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R''); and R$^3$ is selected from the group consisting of —H, —C$_1$-C$_6$alkyl, —N(R')(R''), —N(R')C$_1$-C$_6$alkyl-N(R')(R''), —N(R')—C$_1$-C$_6$alkyl-OR', —OH, —C$_1$-C$_6$alkoxy, —O—C$_1$-C$_6$alkyl-OR', —O-heterocyclyl, —O-heteroaryl, —O—C$_1$-C$_6$alkyl-heteroaryl, —C$_1$-C$_6$alkyl-heteroaryl, heterocyclyl, and heteroaryl, wherein heterocyclyl and heteroaryl are optionally substituted with one or two C$_1$-C$_6$alkyl or halogen;

wherein C$_1$-C$_6$alkyl or C$_1$-C$_6$alkoxy may be independently for each occurrence optionally substituted with one, two, or three halogens; and (ii) optionally, a pharmaceutically acceptable excipient.

In certain embodiments, the compound is represented by Formula 3-A:

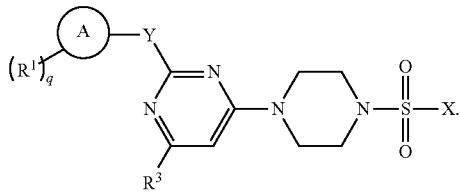

Formula 3-A

In certain embodiments, the compound is represented by Formula 3-B:

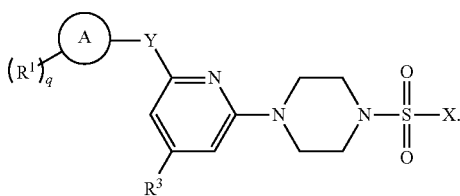

Formula 3-B

In certain embodiments,

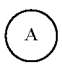

is selected from the group consisting of

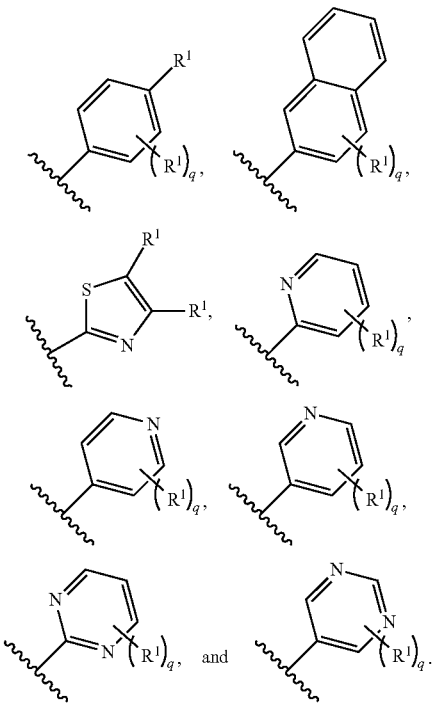

In certain embodiments,

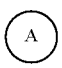

is phenyl.

In certain embodiments, X is selected from the group consisting of

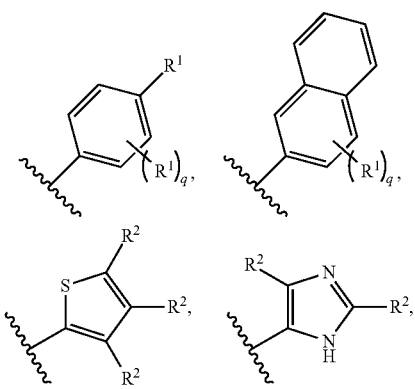

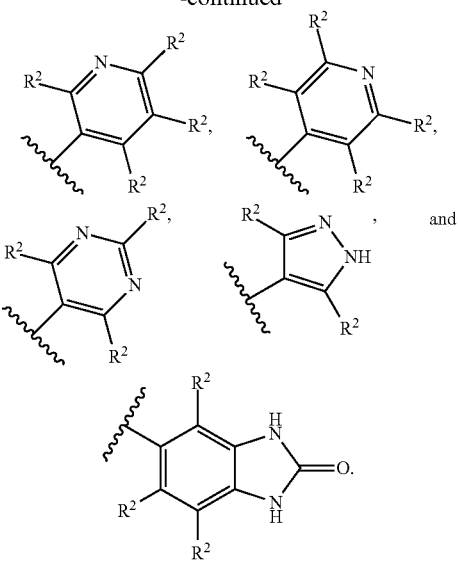

In certain embodiments, X is phenyl.

In certain embodiments, $R^1$ is independently for each occurrence selected from the group consisting of —$C_1$-$C_6$alkyl, —$C_1$-$C_6$alkoxy, halogen, cyano, —OH, —$CO_2$R', and —N(R')(R").

In certain embodiments, $R^1$ is independently for each occurrence selected from the group consisting of —$CH_3$, -Et, i-Pr, —$CF_3$, —OMe, —$OCF_3$, F, Cl, Br, —$NH_2$, —NHMe, and —$NMe_2$.

In certain embodiments, q is 1, 2, or 3.

In certain embodiments, $R^2$ is independently for each occurrence selected from the group consisting of —$C_1$-$C_6$alkyl, —$C_1$-$C_6$alkoxy, halogen, oxo, cyano, —OH, —$CO_2$R', and —N(R')(R").

In certain embodiments, $R^2$ is independently for each occurrence selected from the group consisting of —$CH_3$, -Et, i-Pr, —$CF_3$, oxo, —OMe, —$OCF_3$, F, Cl, Br, —$NH_2$, —NHMe, and —$NMe_2$.

In certain embodiments, X is optionally substituted with one, two, or three $R^2$ groups.

In certain embodiments, $R^3$ is independently for each occurrence selected from the group consisting of —H, —$C_1$-$C_6$alkyl, —N(R')(R"), —NH—$C_1$-$C_6$alkyl-N($C_1$-$C_6$alkyl)$_2$, —NH—$C_1$-$C_6$-alkyl-OR', —OH, —$C_1$-$C_6$alkoxy, —O—$C_1$-$C_6$alkyl-OR', heterocyclyl, and heteroaryl, wherein heterocyclyl and heteroaryl are optionally substituted with one or two $C_1$-$C_6$alkyl or halogen.

In certain embodiments, $R^3$ is independently for each occurrence selected from the group consisting of —H, —$CH_3$, -Et, i-Pr, —N($CH_3$)$_2$, —NH(i-Pr), —NH(t-Bu), —N($CH_3$)(t-Bu), —NH($CH_3$), —NH($CH_2CH_2OH$), —NH—$CH_2CH_2$—N($CH_3$)$_2$, —OMe, —$OCH_2CH_2OH$,

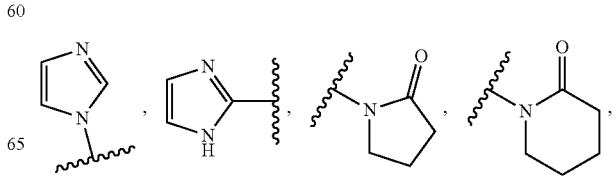

-continued

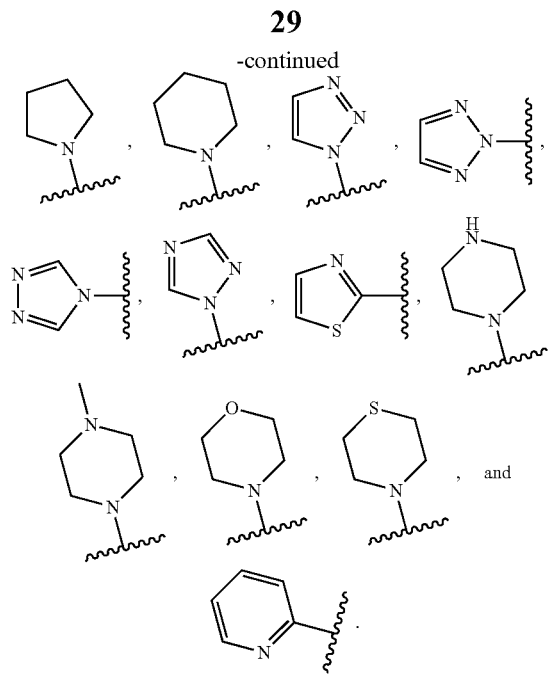

In certain embodiments, the compound is represented by Formula 3-C:

Formula 3-C

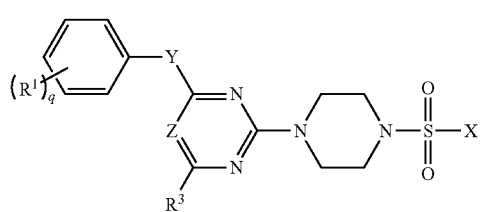

wherein X is heteroaryl.

In certain embodiments, the compound is represented by Formula 3-D:

Formula 3-D

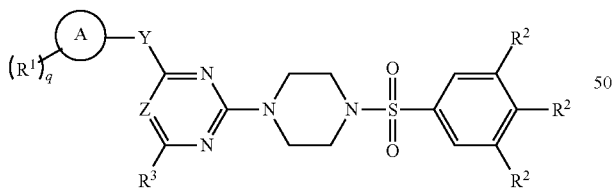

wherein

is heteroaryl.

In certain embodiments, Y is —NH—.

In another aspect, the present disclosure provides a pharmaceutical composition comprising: (i) a compound of Formula 4 having the structure:

Formula 4

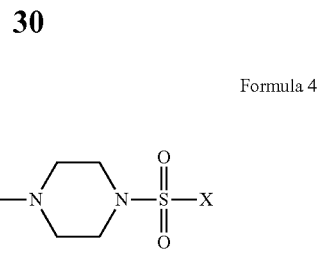

or a pharmaceutically acceptable salt or stereoisomer thereof, wherein:

is selected from the group consisting of phenyl, naphthyl, and heteroaryl;

Y is selected from the group consisting of a bond, —O—, —S(O)$_w$—, and —N(R')—;

X is selected from the group consisting of phenyl, naphthyl, and heteroaryl; wherein X is optionally substituted with one, two, three, or four R$^2$ groups;

R$^1$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R");

q is 0, 1, 2, 3 or 4;

w is 0, 1 or 2;

R' is independently for each occurrence selected from the group consisting of —H and —C$_1$-C$_6$alkyl;

R" is independently for each occurrence selected from the group consisting of —H and —C$_1$-C$_6$alkyl; or R' and R" are taken together with the nitrogen atom to which they are attached to form a 4-7 membered heterocyclic or heteroaryl ring, each of which is optionally substituted with an oxo group;

R$^2$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, oxo, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R"); and R$^3$ is selected from the group consisting of —N(R')(R"), —N(R')C$_1$-C$_6$alkyl-N(R')(R"), —N(')—C$_1$-C$_6$alkyl-OR', —OH, —C$_1$-C$_6$alkoxy, —O—C$_1$-C$_6$alkyl-OR', —O-heterocyclyl, —O-heteroaryl, —O—C$_1$-C$_6$alkyl-heteroaryl, —C$_1$-C$_6$alkyl-heteroaryl, heterocyclyl, and heteroaryl, wherein heterocyclyl and heteroaryl are optionally substituted with one or two C$_1$-C$_6$alkyl or halogen;

wherein C$_1$-C$_6$alkyl or C$_1$-C$_6$alkoxy may be independently for each occurrence optionally substituted with one, two, or three halogens; and (ii) optionally, a pharmaceutically acceptable excipient.

In certain embodiments, is selected from the group consisting of

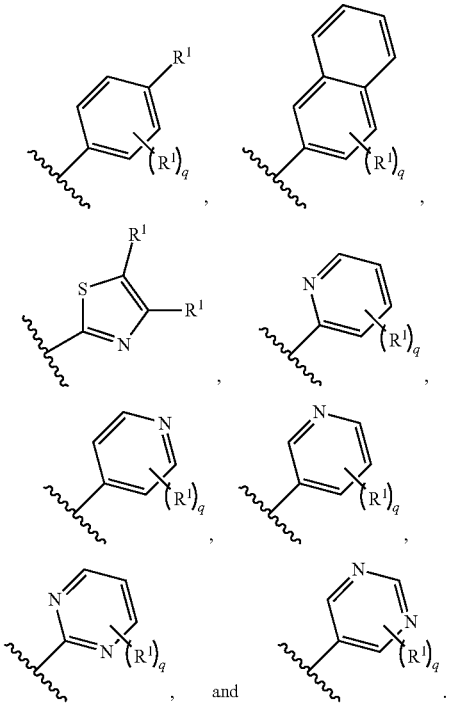

In certain embodiments

Ⓐ is phenyl.

In certain embodiments, X is selected from the group consisting of

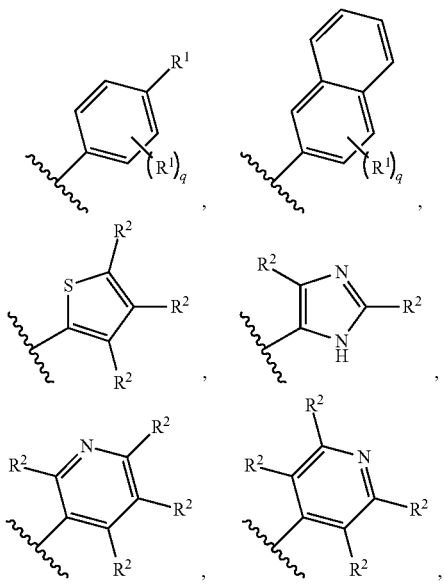

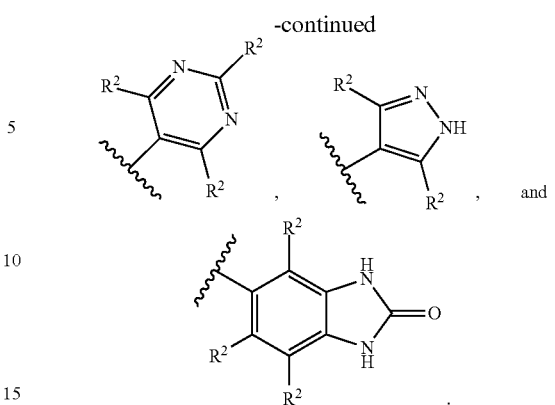

In certain embodiments, X is phenyl.

In certain embodiments, $R^1$ is independently for each occurrence selected from the group consisting of —$C_1$-$C_6$alkyl, —$C_1$-$C_6$alkoxy, halogen, cyano, —OH, —$CO_2R'$, and —N(R')(R").

In certain embodiments, $R^1$ is independently for each occurrence selected from the group consisting of —$CH_3$, -Et, i-Pr, —$CF_3$, —OMe, —$OCF_3$, F, Cl, Br, —$NH_2$, —NHMe, and —$NMe_2$.

In certain embodiments, q is 1, 2, or 3.

In certain embodiments, $R^2$ is independently for each occurrence selected from the group consisting of —$C_1$-$C_6$alkyl, —$C_1$-$C_6$alkoxy, halogen, oxo, cyano, —OH, —$CO_2R'$, and —N(R')(R").

In certain embodiments, $R^2$ is independently for each occurrence selected from the group consisting of —$CH_3$, -Et, i-Pr, —$CF_3$, oxo, —OMe, —$OCF_3$, F, Cl, Br, —$NH_2$, —NHMe, and —$NMe_2$.

In certain embodiments, X is optionally substituted with one, two, or three $R^2$ groups.

In certain embodiments, $R^3$ is independently for each occurrence selected from the group consisting of —N(R') (R"), —NH—$C_1$-$C_6$alkyl-N($C_1$-$C_6$alkyl)$_2$, —NH—$C_1$-$C_6$-alkyl-OR', —OH, —$C_1$-$C_6$alkoxy, —O—$C_1$-$C_6$alkyl-OR', heterocyclyl, and heteroaryl, wherein heterocyclyl and heteroaryl are optionally substituted with one or two $C_1$-$C_6$alkyl or halogen.

In certain embodiments, $R^3$ is independently for each occurrence selected from the group consisting of —N($CH_3$)$_2$, —NH(i-Pr), —NH(t-Bu), —N($CH_3$)(t-Bu), —NH($CH_3$), —NH($CH_2CH_2OH$), —NH—$CH_2CH_2$—N($CH_3$)$_2$, —OMe, —$OCH_2CH_2OH$,

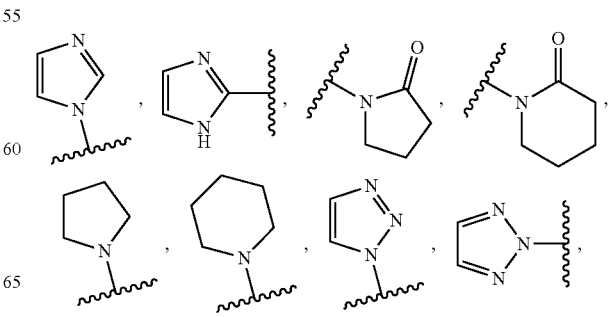

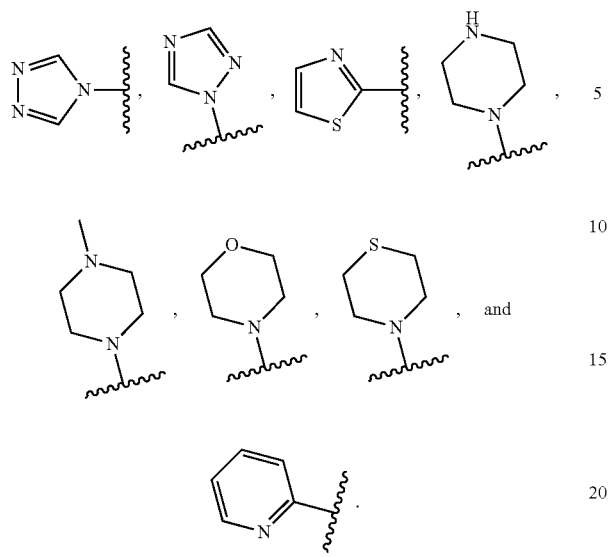
In certain embodiments, the compound is represented by Formula 3-C:
Formula 3-C
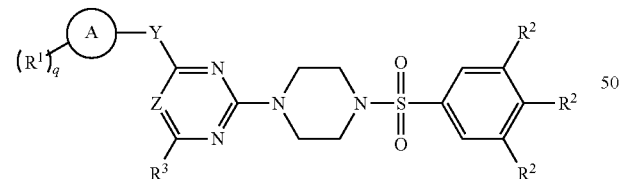
wherein X is heteroaryl.
In certain embodiments, the compound is represented by Formula 3-D:
Formula 3-D
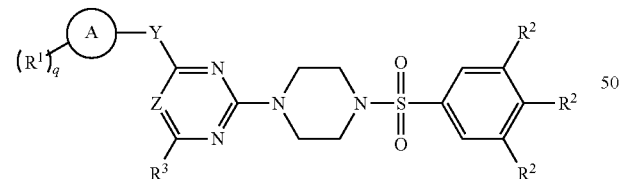
wherein
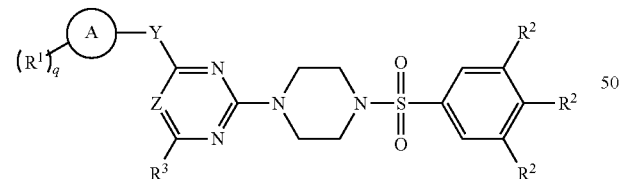
is heteroaryl.
In certain embodiments, Y is —NH—.
In another aspect, the present disclosure provides a compound selected from the group consisting of:
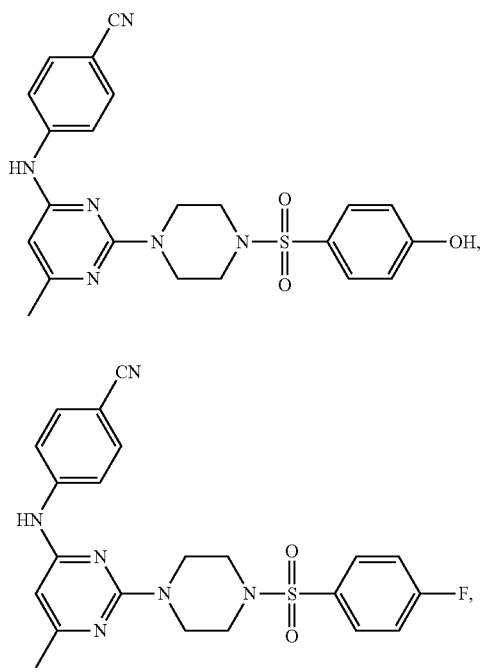
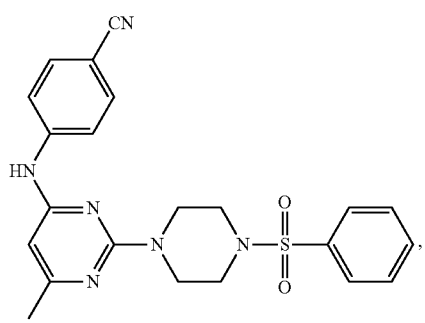
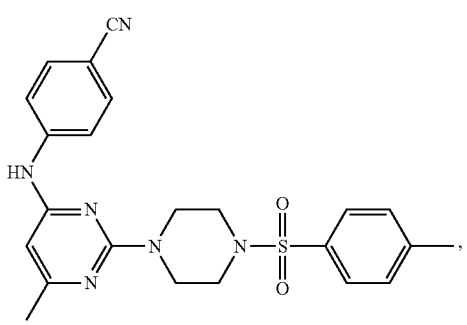
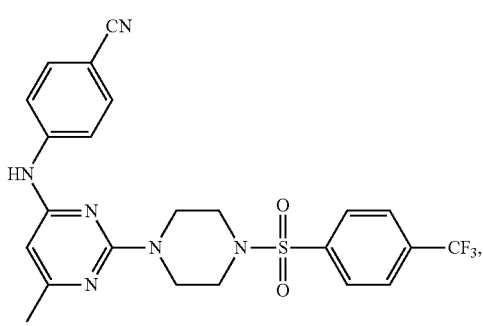

-continued
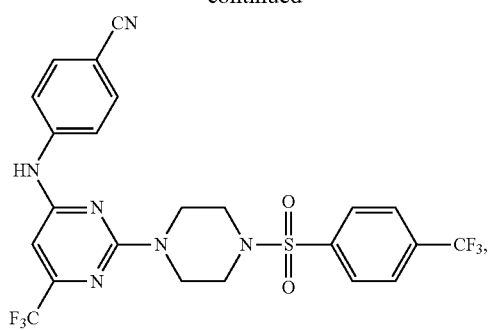
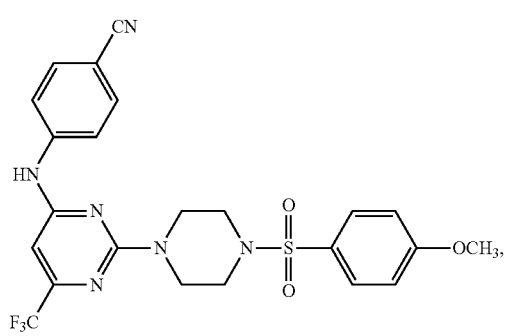
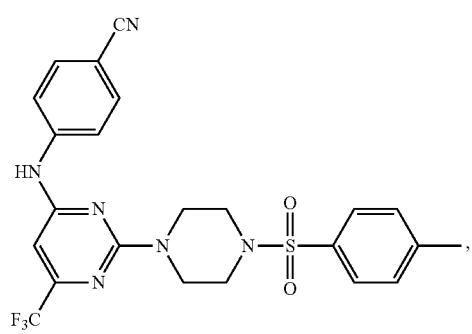
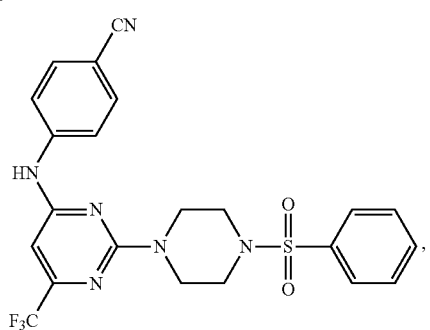
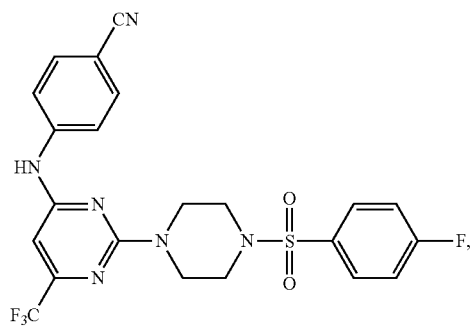
-continued
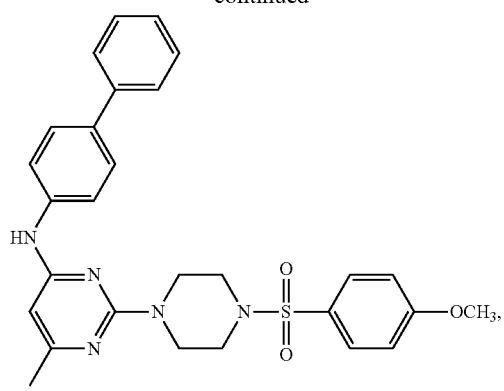
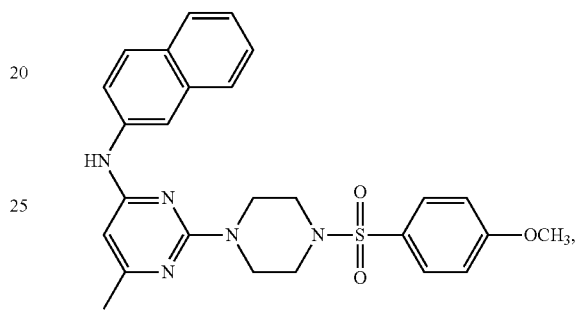
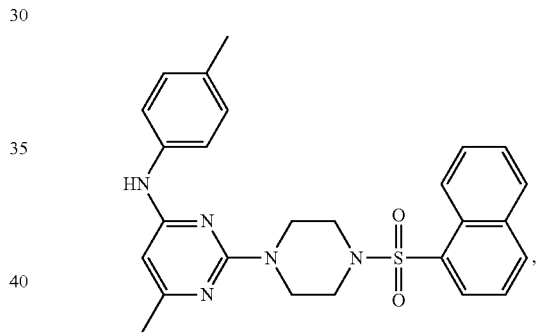
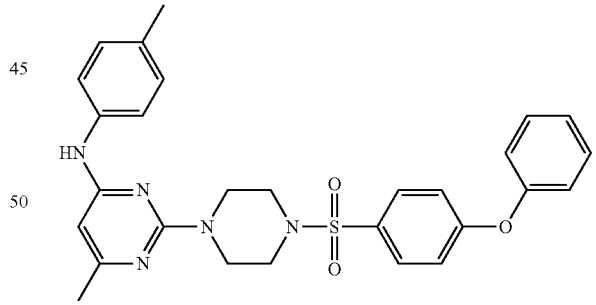
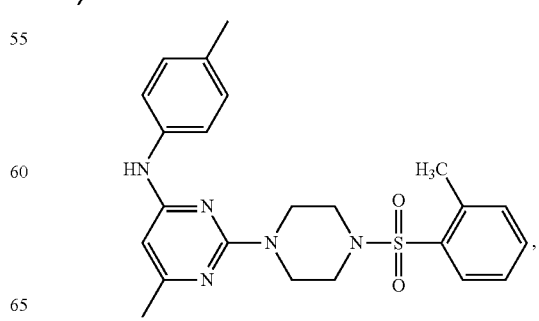

37
-continued
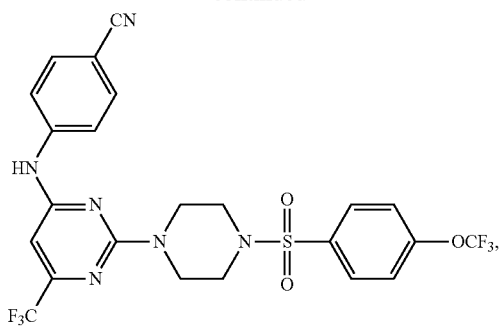
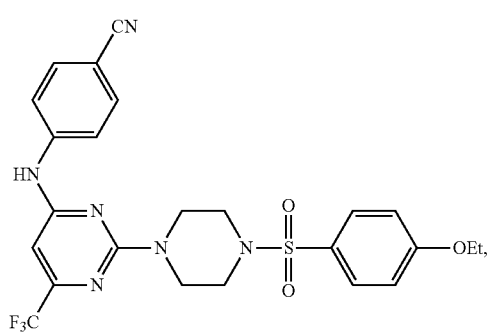
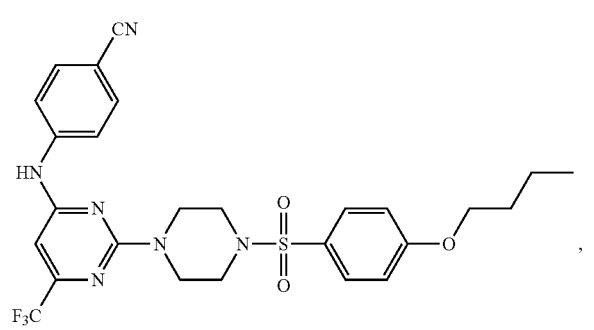
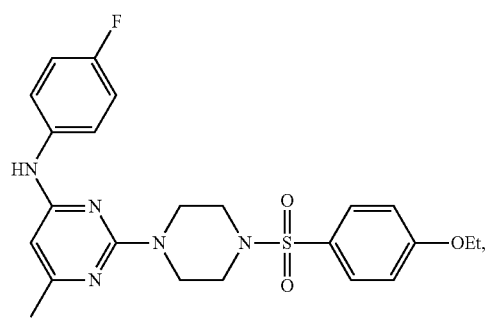
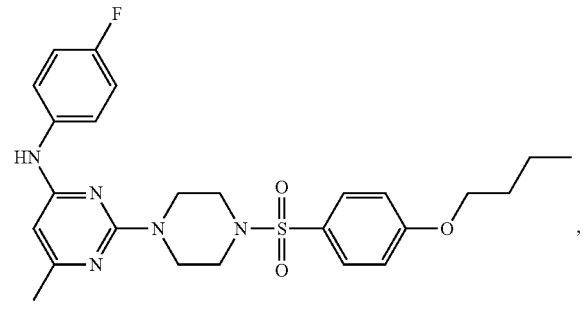
38
-continued
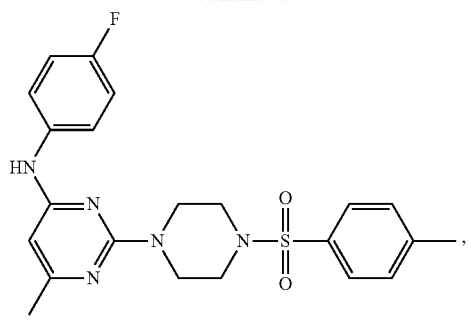
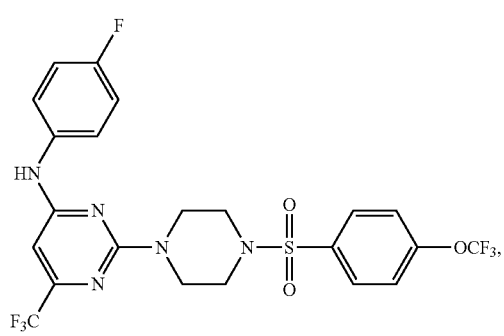
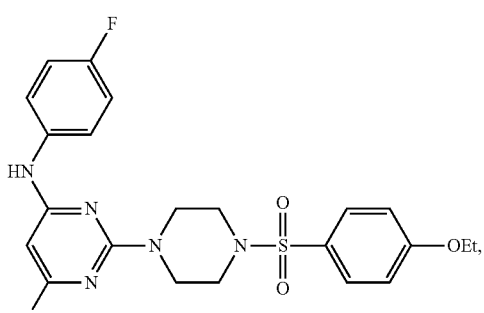
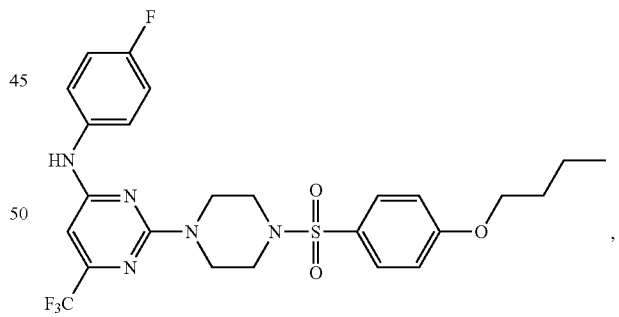
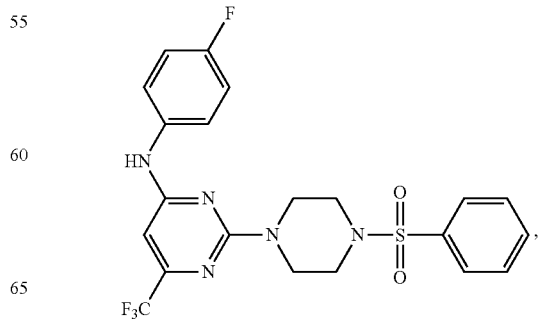

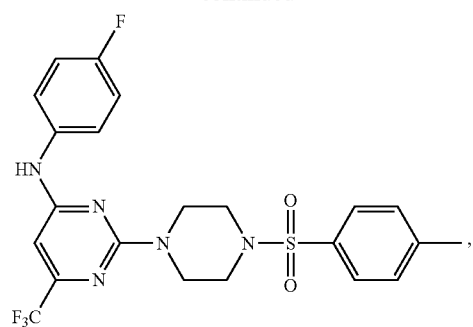
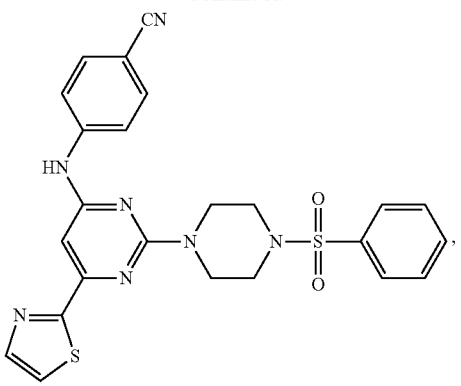
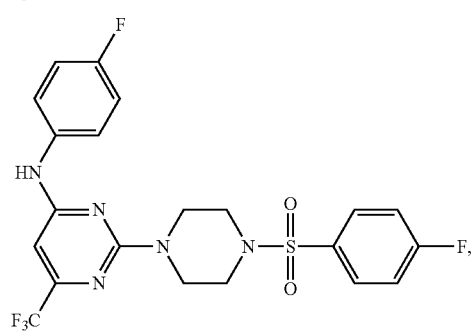
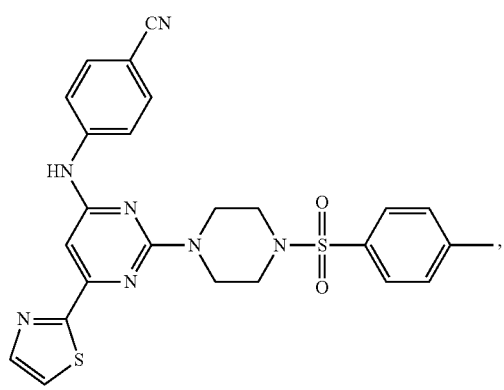
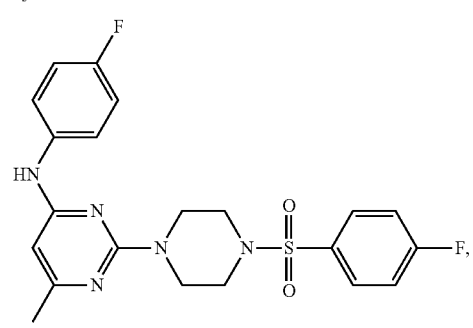
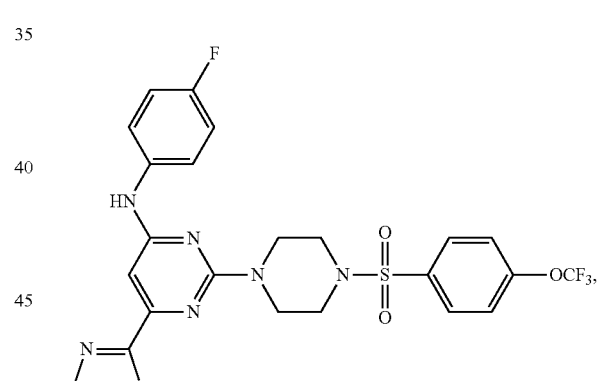
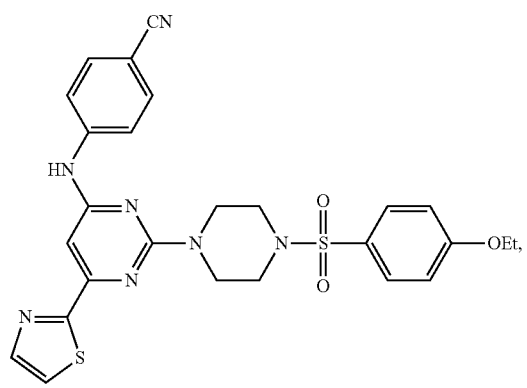
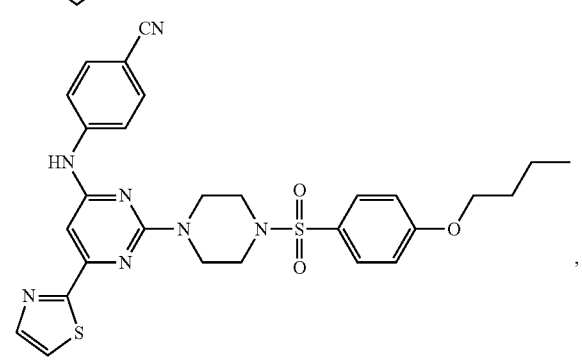
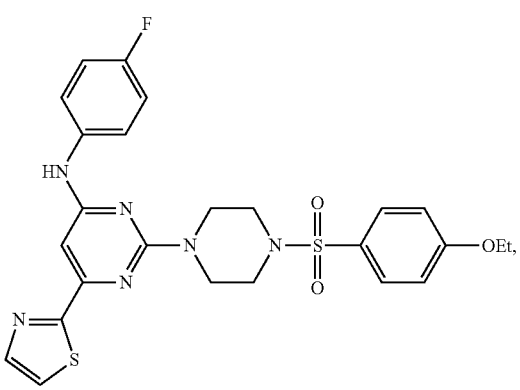

41
-continued
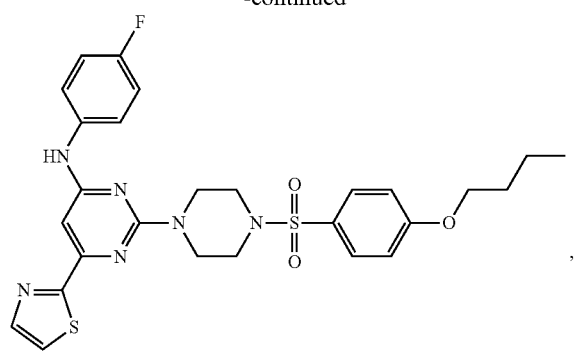
,
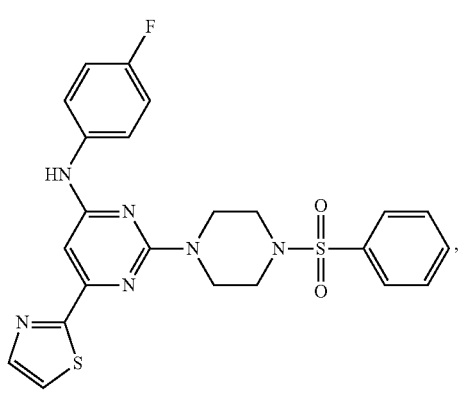
,
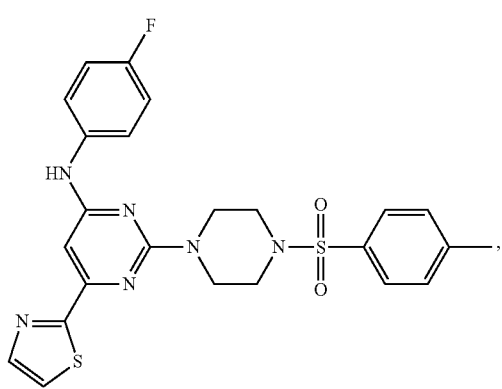
,
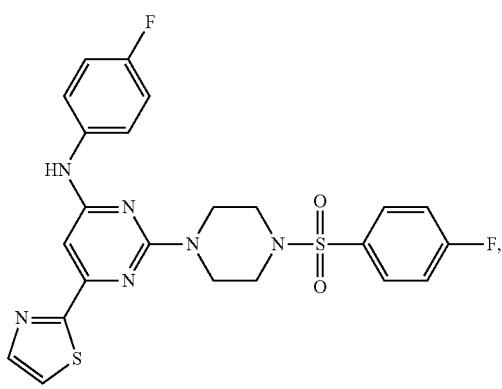
,
42
-continued
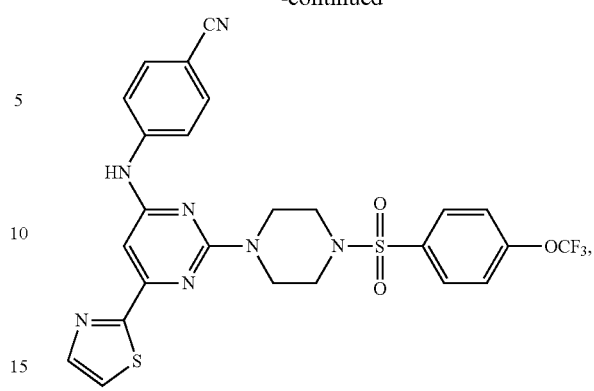
,
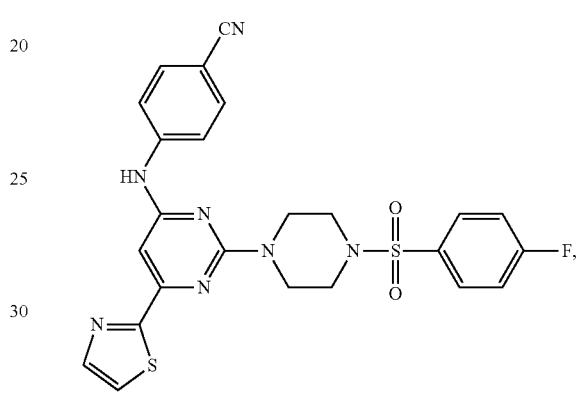
,
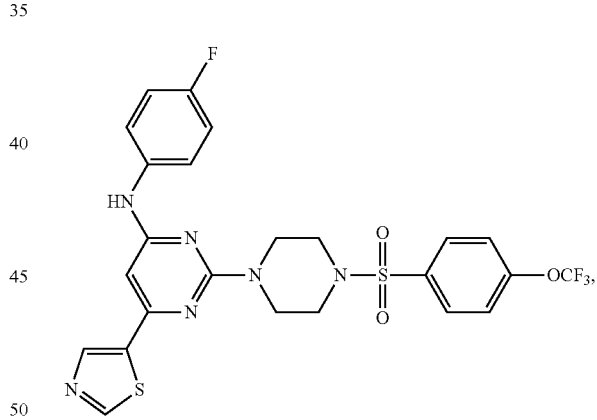
,
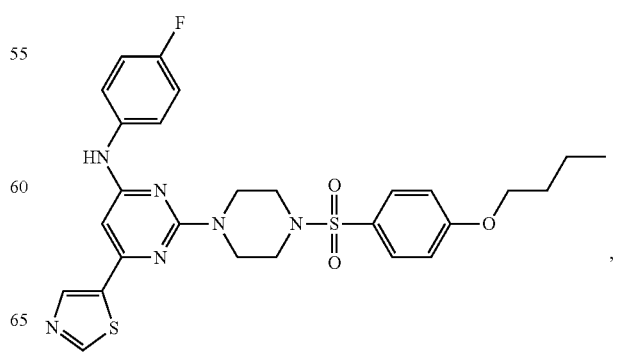
, 43
-continued
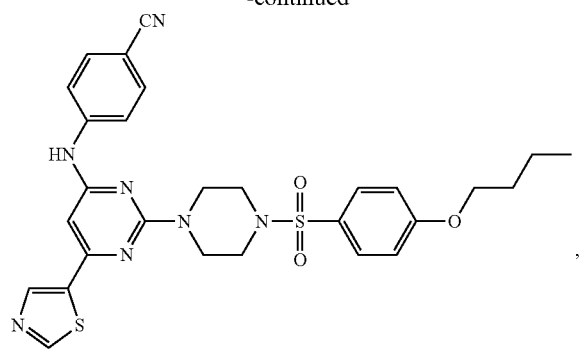
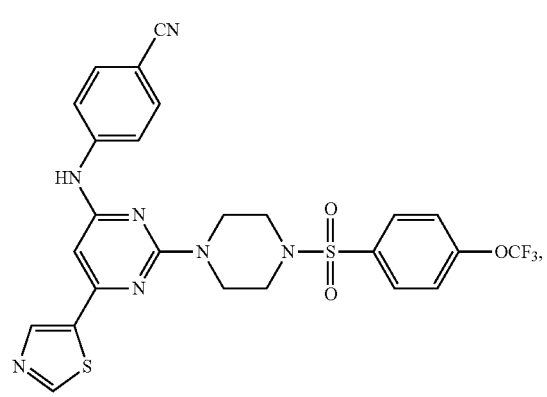
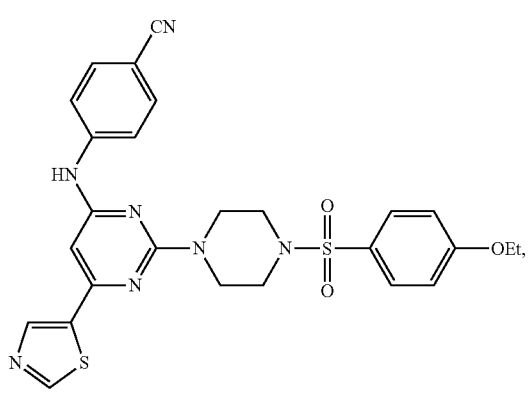
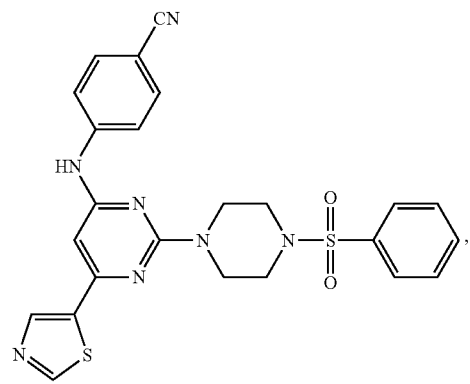
44
-continued
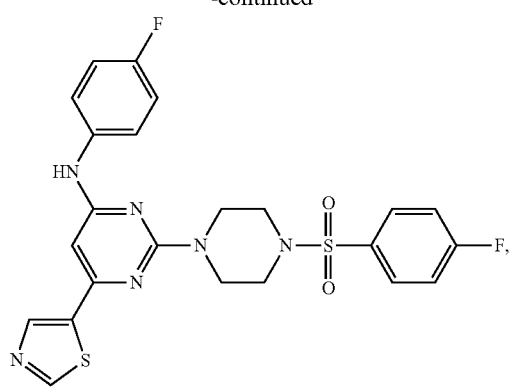

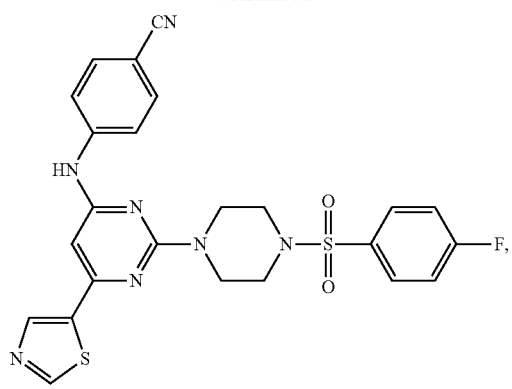
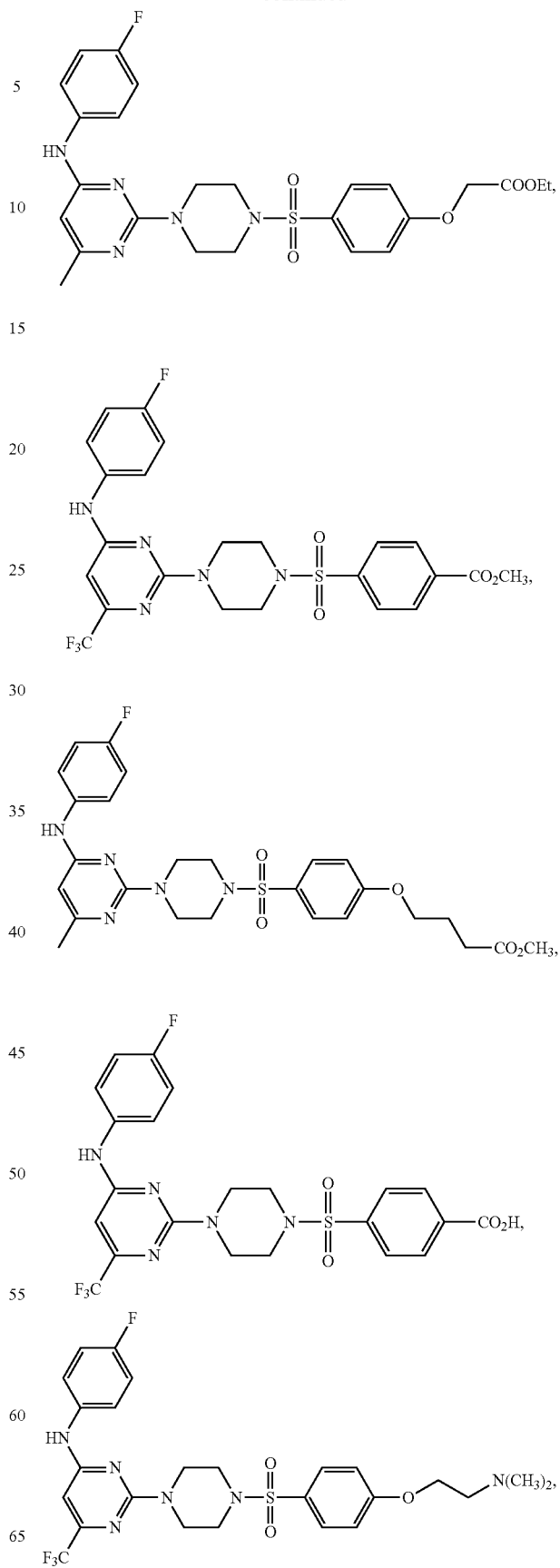

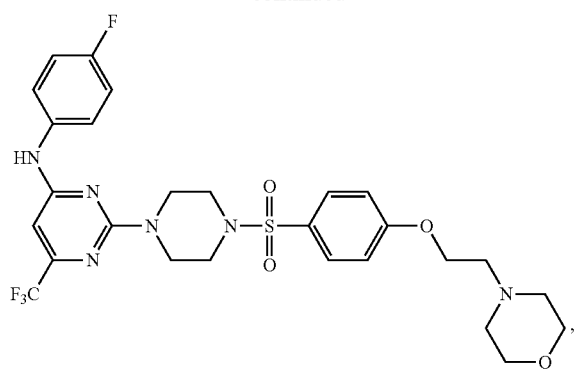
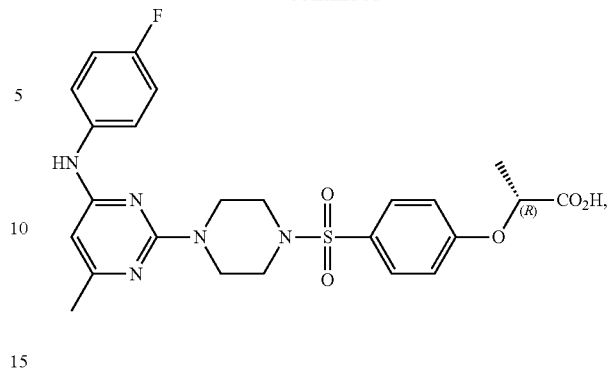
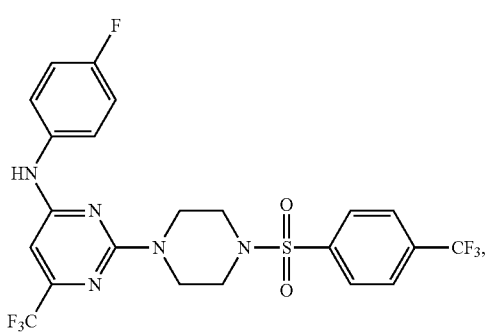
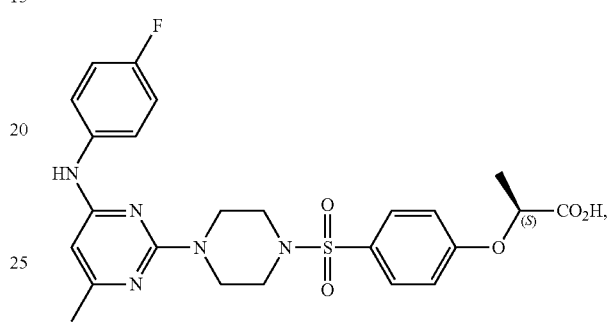
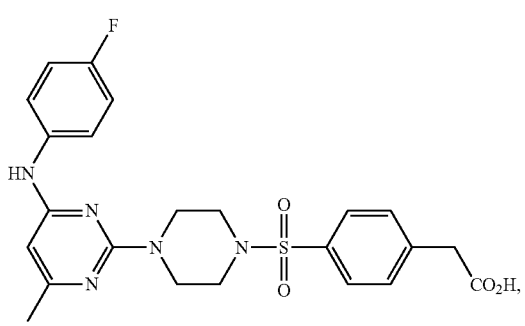
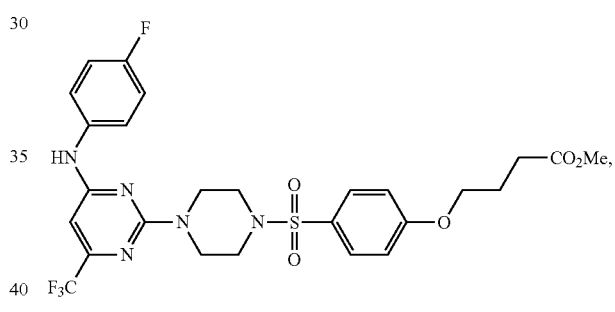
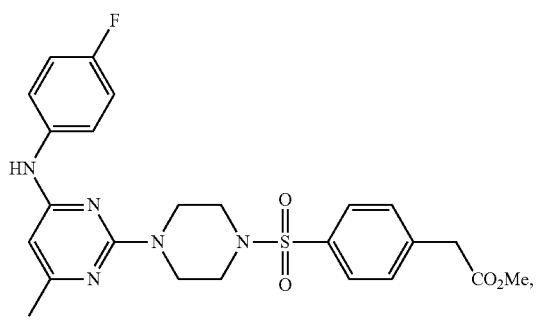
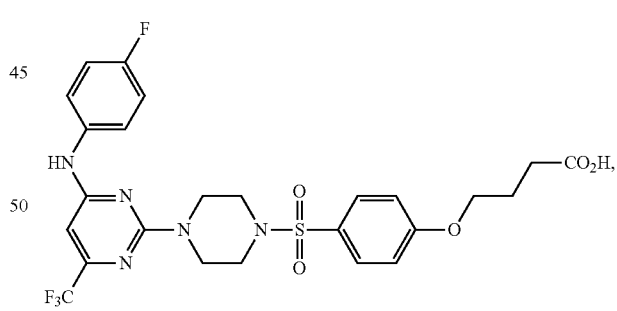
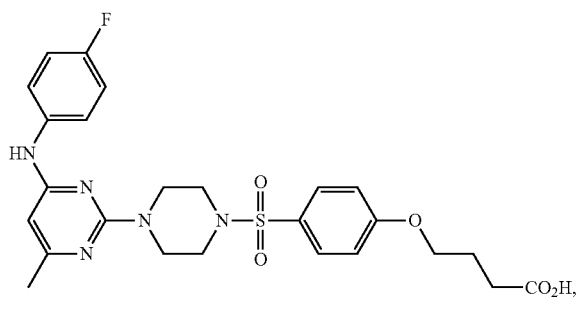
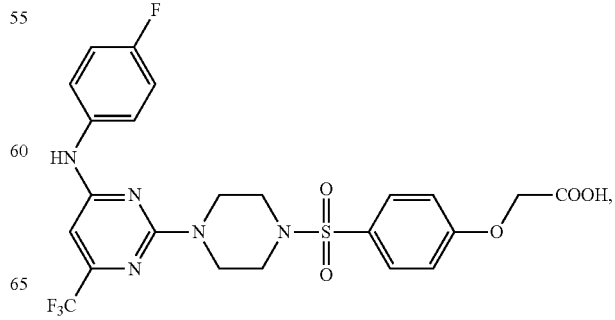

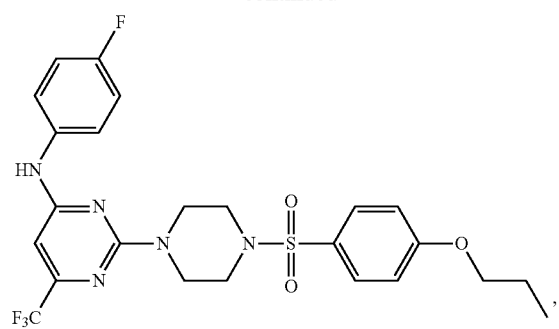
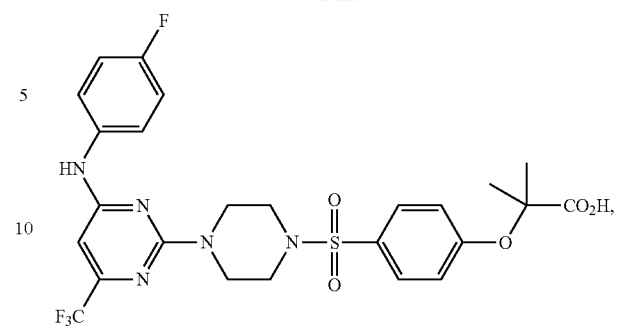
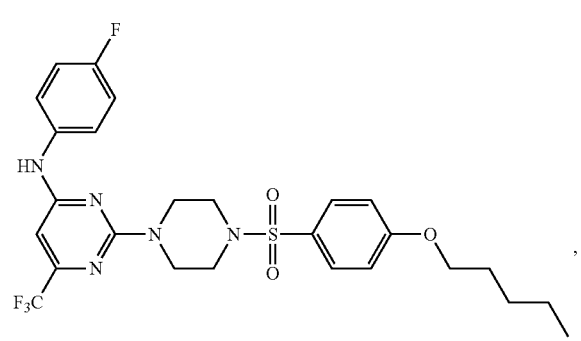
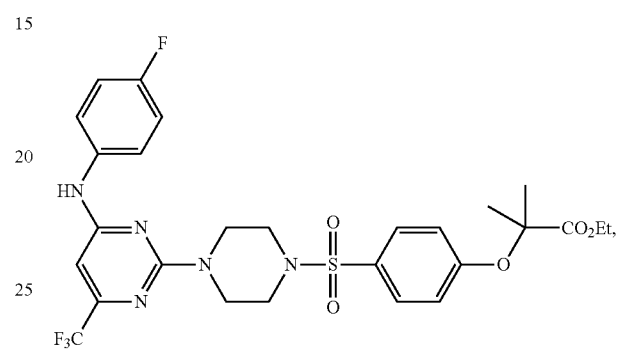
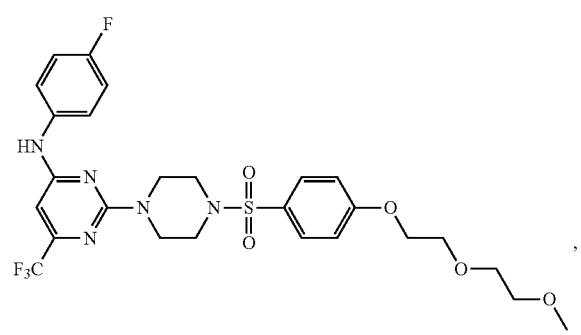
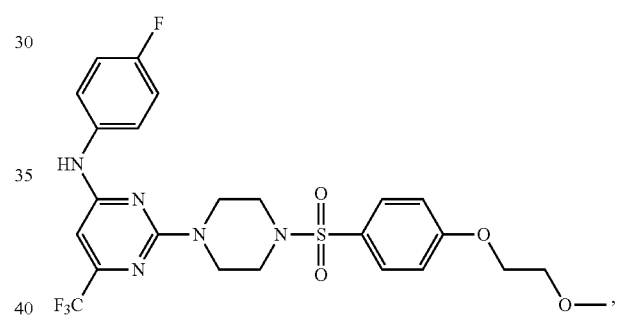
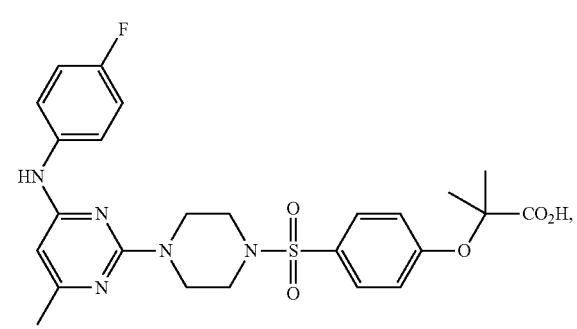
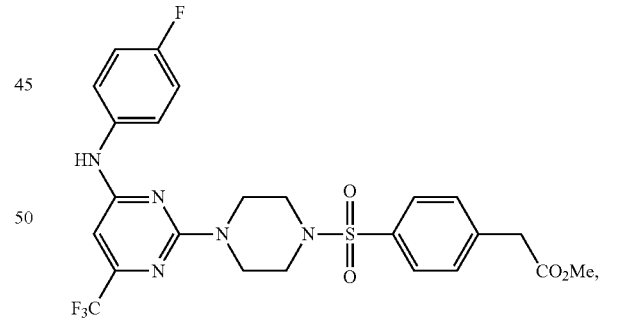
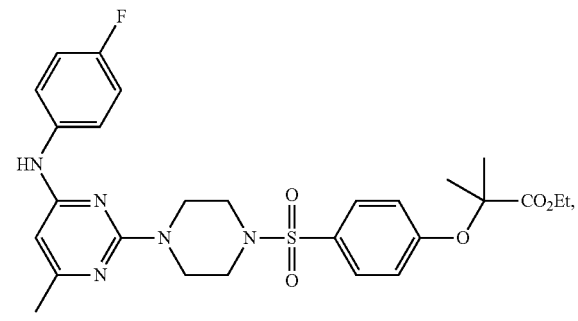
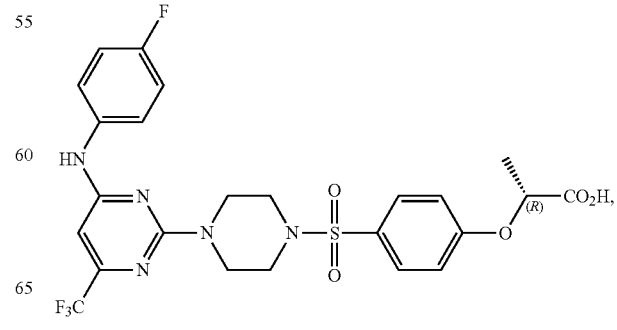

-continued

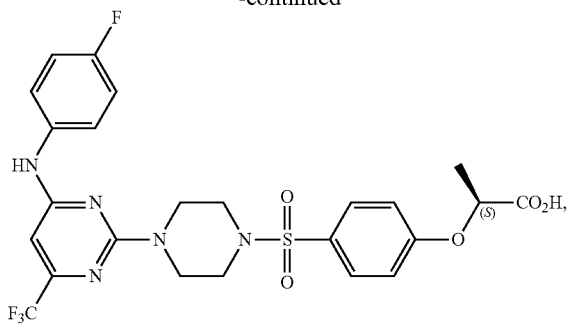

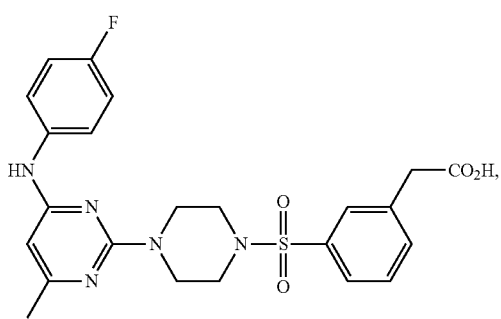

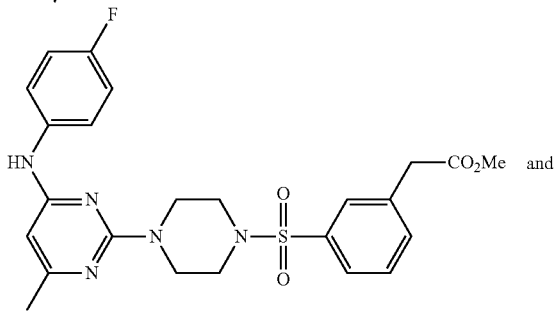

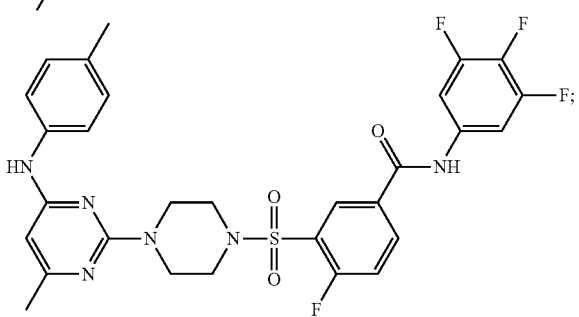

and a pharmaceutically acceptable salt or stereoisomer thereof.

In another aspect, the present disclosure provides a pharmaceutical composition comprising: (i) a compound of Formula 5 having the structure:

Formula 5

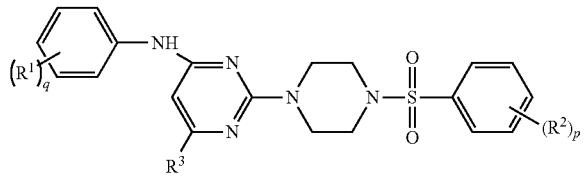

or a pharmaceutically acceptable salt or stereoisomer thereof, wherein:

or a pharmaceutically acceptable salt or stereoisomer thereof, wherein:

$R^1$ is independently for each occurrence selected from the group consisting of —H, —$C_1$-$C_6$alkyl, —$C_1$-$C_6$alkoxy, halogen, cyano, —OH, —C(O)H, —$CO_2R'$, —C(O)N(R')(R''), and —C(O)$C_1$-$C_6$alkyl;

q is 0, 1, 2, 3 4 or 5;

$R^3$ is $C_1$-$C_6$alkyl optionally substituted with halogen or heteroaryl optionally substituted with one, two, or three $C_1$-$C_6$alkyl or halogen;

p is 0, 1, 2, 3, 4 or 5;

$R^2$ is independently for each occurrence selected from the group consisting of —H; —$C_1$-$C_6$alkyl; —$C_1$-$C_6$alkoxy; —O—$C_1$-$C_6$alkyl-$CO_2R'$; —$C_1$-$C_6$alkyl-$CO_2R'$; halogen; —$CO_2R'$; —O—$C_1$-$C_6$alkyl-N(R')(R''); $C_1$-$C_6$alkoxy substituted with a heterocycle; and $C_1$-$C_8$alkylene, wherein at least one carbon of $C_1$-$C_8$alkylene is optionally substituted with O; wherein —$C_1$-$C_6$alkyl and —$C_1$-$C_6$alkoxy are optionally substituted with $C_1$-$C_6$alkyl or halogen; R' and R'' are independently selected from the group consisting of —H, —$C_1$-$C_6$alkoxy, and —$C_1$-$C_6$alkyl; and (ii) optionally, a pharmaceutically acceptable excipient.

In certain embodiments, $R^3$ is selected from the group consisting of

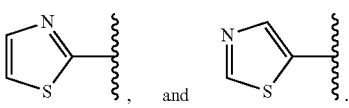

In certain embodiments, $R^1$ is either halogen or cyano.

In certain embodiments, $R^2$ is selected from the group consisting of —H, —$CH_3$, F, —$CF_3$, ethoxy, methoxy,

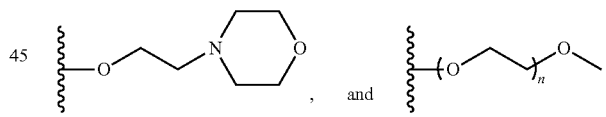

where n is 1, 2, or 3.

In another aspect, the present disclosure provides a pharmaceutical composition comprising: (i) a compound of Formula 6 having the structure:

Formula 6

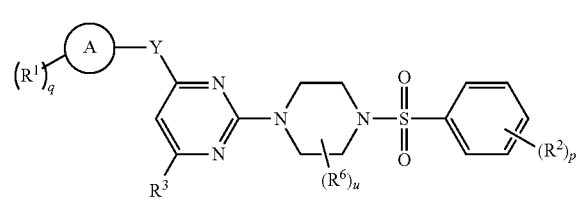

or a pharmaceutically acceptable salt or stereoisomer thereof, wherein:

is selected from the group consisting of phenyl, naphthyl, and heteroaryl;

R¹ is independently for each occurrence selected from the group consisting of —H, —C₁-C₆alkyl, —C₁-C₆alkoxy, halogen, cyano, —OH, —C(O)H, —CO₂R', —C(O)N(R')(R"), and —C(O)C₁-C₆alkyl;

q is 0, 1, 2, 3, 4 or 5;

Y is selected from the group consisting of a —O—, —S(O)$_w$—, and —N(R')— where w is 0, 1 or 2;

R³ is selected from the group consisting of —C₁-C₆alkyl, —C₁-C₆alkoxy, —C₁-C₆alkyl-heteroaryl, heterocyclyl, and heteroaryl, wherein —C₁-C₆alkyl and heterocyclyl are optionally substituted with one, two, or three C₁-C₆alkyl or halogen;

p is 0, 1, 2 or 3;

R² is independently for each occurrence selected from the group consisting of —H; —C₁-C₆alkyl optionally substituted with halogen; and —O—C₁-C₆alkyl optionally substituted with halogen;

R' and R" are independently selected from the group consisting of —H, —C₁-C₆alkoxy, and —C₁-C₆alkyl;

R⁶ is independently for each occurrence selected from the group consisting of —C₁-C₆alkyl and —O—C₁-C₆alkyl; or two R⁶ groups are on the same carbon atom, or alternatively, two R⁶ groups are on the same carbon atom and when taken together form oxo; wherein —C₁-C₆alkyl or —O—C₁-C₆alkyl are optionally substituted with halogen;

u is 0, 1, 2, 3, 4, 5, 6, 7, or 8; and (ii) optionally, a pharmaceutically acceptable excipient.

In certain embodiments, R³ is CH₃.

In certain embodiments, R¹ is either halogen or cyano.

In certain embodiments, u is 1 and R⁶ is CH₃ or u is 2 and two R⁶ groups are taken together to form oxo.

In certain embodiments, the compound is selected from the group consisting of

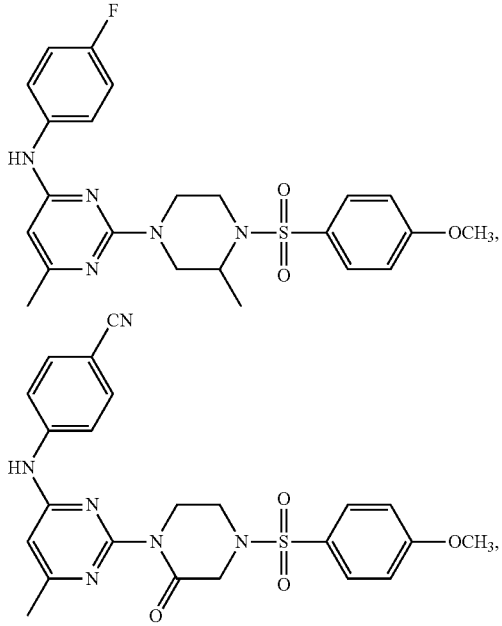

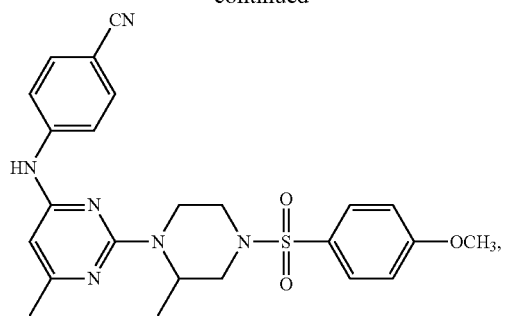

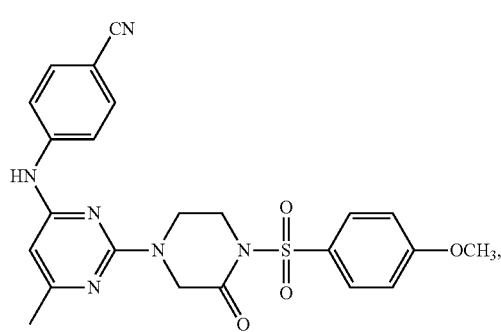

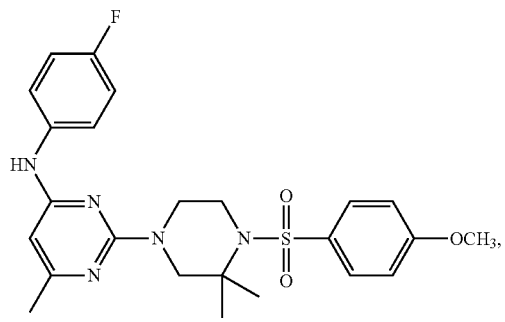

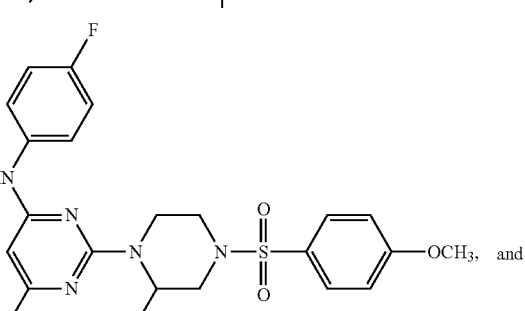

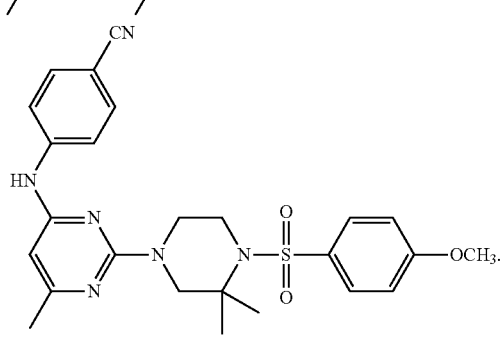

In another aspect, the present disclosure provides a pharmaceutical composition comprising: (i) a compound of Formula 7 having the structure:

Formula 7

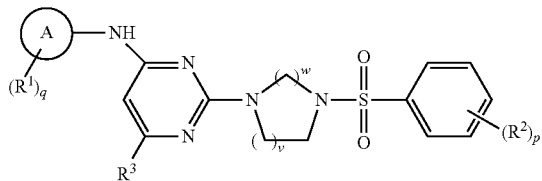

or a pharmaceutically acceptable salt or stereoisomer thereof, wherein:

is selected from the group consisting of phenyl, naphthyl, and heteroaryl;

$R^1$ is independently for each occurrence selected from the group consisting of —H, —$C_1$-$C_6$alkyl, —$C_1$-$C_6$alkoxy, halogen, cyano, —OH, —C(O)H, —$CO_2$R', —C(O)N(R')(R''), and —C(O)$C_1$-$C_6$alkyl;

q is 0, 1, 2, 3 or 4;

$R^3$ is selected from the group consisting of —$C_1$-$C_6$alkyl, —$C_1$-$C_6$alkoxy, —$C_1$-$C_6$alkyl-heteroaryl, heterocyclyl, and heteroaryl, wherein —$C_1$-$C_6$alkyl and heterocyclyl are optionally substituted with one, two, or three $C_1$-$C_6$alkyl or halogen;

w is 1 or 2;

v is 1 or 2.

p is 0, 1, 2 or 3;

$R^2$ is independently for each occurrence selected from the group consisting of —H; —$C_1$-$C_6$alkyl; —$C_1$-$C_6$alkoxy; or —O—$C_1$-$C_6$alkyl-$CO_2$R'; wherein —$C_1$-$C_6$alkyl, —$C_1$-$C_6$alkoxy, and —O—$C_1$-$C_6$alkyl-$CO_2$R' are optionally substituted with halogen or $C_1$-$C_6$alkyl;

R' and R'' are independently selected from the group consisting of —H, —$C_1$-$C_6$alkoxy, and —$C_1$-$C_6$alkyl; and (ii) optionally, a pharmaceutically acceptable excipient.

In certain embodiments, $R^1$ is F.

In certain embodiments, $R^3$ is $CF_3$.

In certain embodiments, the compound is selected from the group consisting of

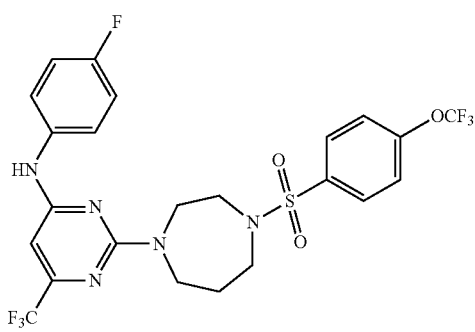

and

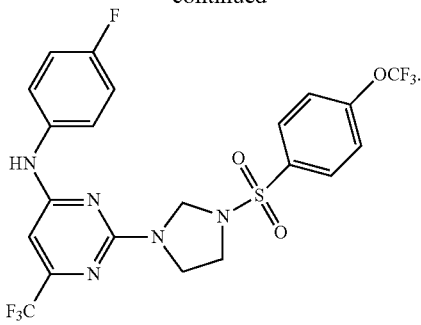

In certain embodiments, a compound is selected from the group consisting of compounds according to Table 1, Table 2, Table 3, Table 4, Table 5, Table 7 and Table 8; or a pharmaceutically acceptable salt or stereoisomer thereof.

In certain embodiments, a method of treating, ameliorating, preventing, or substantially delaying a hepatitis B viral infection in an individual is performed, the method comprising administering to the individual a pharmaceutical composition from Table 1, Table 2, Table 3, Table 4, Table 5, Table 7 or Table 8.

In certain embodiments, a compound from Table 1, Table 2, Table 3, Table 4, Table 5, Table 7 or Table 8 is used in the manufacture of a medicament for the treatment of a hepatitis B viral infection.

Disclosed compounds may be prepared by methods known in the art. Some disclosed compounds may be preparing using a method comprising providing 2,4-dichloro-6-substituted pyrimidine and a R-substituted aniline group together in an organic solvent (wherein R may be selected from $R^1$ above), and then contacting a resultant compound with Z (e.g. piperazine or 4-amino aniline group).

Thereafter, an optionally substituted sulfonyl benzene group is added. In a further aspect, a method for treating HBV infection (e.g. an acute or chronic HBV infection) in a patient in need thereof is provided. The method includes administering to a patient a pharmaceutical composition comprising a therapeutically effective amount of a disclosed compound.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 15 mg/kg body weight. In some cases, the administration dose of the compound may be less than 10 mg/kg body weight. In other cases, the administration dose may be less than 5 mg/kg body weight. In yet other cases, the administration dose may be in the range between about 0.1 to about 1 mg/kg body weight. The dose may be conveniently administered once daily, or in divided doses up to, for example, four times a day or in sustained release form.

A compound or composition may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulfate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, disclosed compounds may be administered as part of a combination therapy in conjunction with one or more antivirals. Exemplary antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate. This may involve administering to a subject a first amount of a disclosed compound in combination with a second amount of an antiviral, wherein the first and second amounts together comprise a pharmaceutically effective amount. The first amount, the second amount, or both may be the same, more, or less than effective amounts of each compound administered as monotherapies. Therapeutically effective amounts of disclosed compound and antiviral may be co-administered to the subject, i.e., administered to the subject simultaneously or separately, in any given order and by the same or different routes of administration. In some instances, it may be advantageous to initiate administration of a disclosed compound or composition first, for example one or more days or weeks prior to initiation of administration of the antiviral. Moreover, additional drugs may be given in conjunction with the above combination therapy.

Also provided are methods of treating, ameliorating, preventing, or substantially delaying a hepatitis B viral infection in an individual, the method comprising administering to the individual a pharmaceutical composition comprising a compound disclosed herein.

In another aspect, the present disclosure provides a method of use of a compound disclosed herein in the manufacture of a medicament for the treatment of a hepatitis B viral infection.

Examples

Example 1: Synthesis of 6-methyl-2-(piperazin-1-yl)-N-(p-tolyl) pyrimidin-4-amine (6)—A Common Intermediate

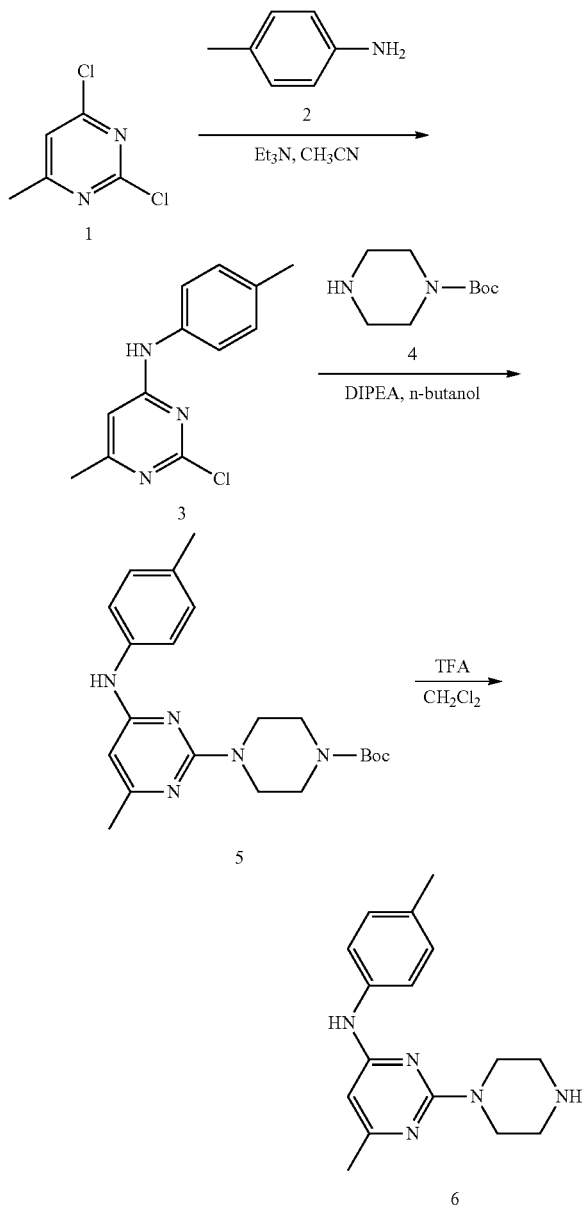

Synthesis of 2-chloro-6-methyl-N-(p-tolyl) pyrimidin-4-amine (3)

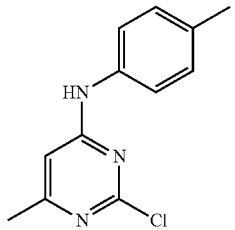

3

To a stirred solution of 2, 4-dichloro-6-methylpyrimidine 1 (600 mg, 3.68 mmol) in CH$_3$CN (5 mL) under argon atmosphere were added p-toluidine 2 (473 mg, 4.41 mmol), triethyl amine (0.77 mL, 5.52 mmol) at RT; heated to 80° C. and stirred for 24 h. The reaction was monitored by TLC; after completion of the reaction, the volatiles were removed in vacuo to obtain the crude. The crude was purified through silica gel column chromatography using 10% EtOAc/hexanes to afford compound 3 (300 mg, 35%) as an off-white solid. TLC: 20% EtOAc/hexanes (R$_f$, 0.4); $^1$H-NMR (DMSO-d$_6$, 400 MHz): δ 9.76 (s, 1H), 7.42 (d, J=8.0 Hz, 2H), 7.16 (d, J=8.4 Hz, 2H), 6.52 (s, 1H), 2.27 (s, 3H), 2.25 (s, 3H).

Synthesis of tert-butyl 4-(4-methyl-6-(p-tolylamino) pyrimidin-2-yl) piperazine-1-carboxylate (5)

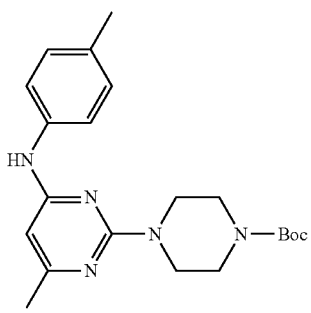

5

To a stirred solution of compound 3 (200 mg, 0.85 mmol) in n-butanol (3 mL) under argon atmosphere were added tert-butyl piperazine-1-carboxylate 4 (238 mg, 1.28 mmol), diisopropylethyl amine (0.30 mL, 1.70 mmol) at RT; heated to 100° C. and stirred for 16 h. The reaction was monitored by TLC; after completion of the reaction, the volatiles were removed in vacuo to obtain crude. The crude was purified through silica gel column chromatography using 20% EtOAc/hexanes to afford compound 5 (220 mg, 67%) as an off-white solid. TLC: 20% EtOAc/hexanes (R$_f$, 0.5); $^1$H-NMR (DMSO-d$_6$, 400 MHz): δ 9.00 (s, 1H), 7.45 (d, J=8.4 Hz, 2H), 7.10 (d, J=8.0 Hz, 2H), 5.89 (s, 1H), 3.66 (t, J=5.6 Hz, 4H), 3.31 (t, J=5.6 Hz, 4H), 2.24 (s, 3H), 2.12 (s, 3H), 1.42 (s, 9H).

Synthesis of 6-methyl-2-(piperazin-1-yl)-N-(p-tolyl) pyrimidin-4-amine (6)

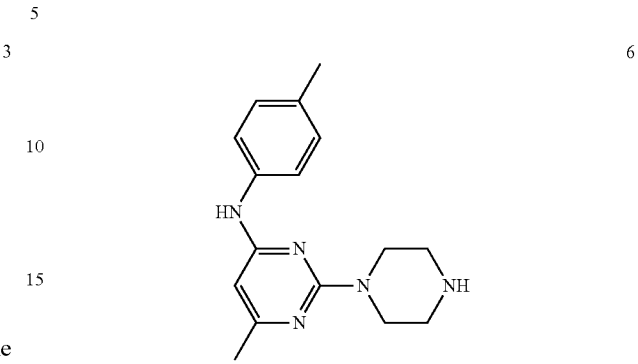

6

To a stirred solution of compound 5 (220 mg, 0.57 mmol) in CH$_2$Cl$_2$ (3 mL) under inert atmosphere was added trifluoroacetic acid (0.25 mL, 2.86 mmol) at 0° C.; warmed to 15° C. and stirred for 30 min. The reaction was monitored by TLC; after completion of the reaction, the volatiles were removed in vacuo. The residue was neutralized with saturated NaHCO$_3$ solution (30 mL) and extracted with EtOAc (2×30 mL). The combined organic extracts were dried over sodium sulfate, filtered and concentrated in vacuo to afford compound 6 (130 mg, 80%) as an off-white solid. TLC: 5% MeOH/CH$_2$Cl$_2$ (R$_f$, 0.2); $^1$H-NMR (DMSO-d$_6$, 400 MHz): δ 8.98 (s, 1H), 7.45 (d, J=8.4 Hz, 2H), 7.09 (d, J=8.4 Hz, 2H), 5.87 (s, 1H), 3.67 (t, J=5.2 Hz, 4H), 2.81 (t, J=4.8 Hz, 4H), 2.24 (s, 3H), 2.12 (s, 3H).

Example 2: Synthesis of 4-methyl-2-(piperazin-1-yl)-6-(p-tolyloxy) pyrimidine (10)—A Common Intermediate

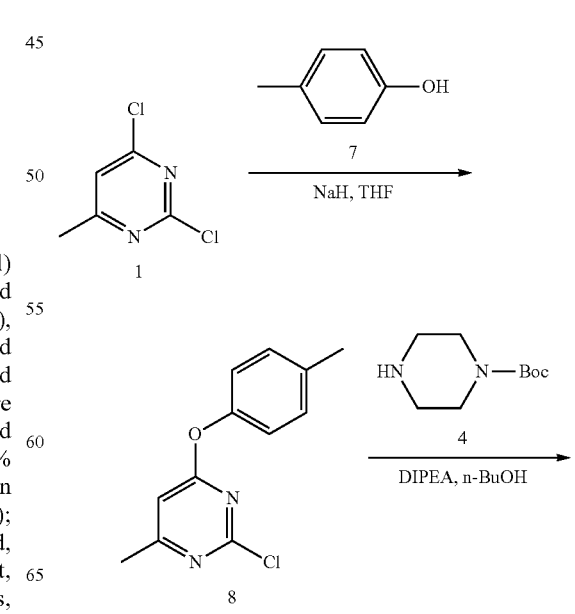

Synthesis of tert-butyl 4-(4-methyl-6-(p-tolyloxy)pyrimidin-2-yl) piperazine-1-carboxylate (9)

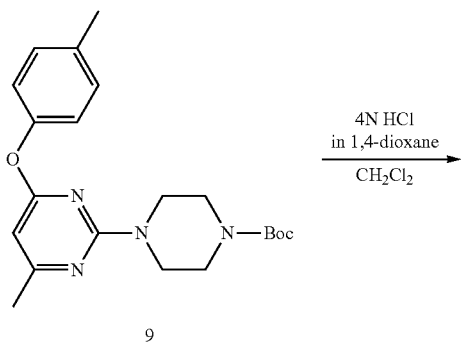

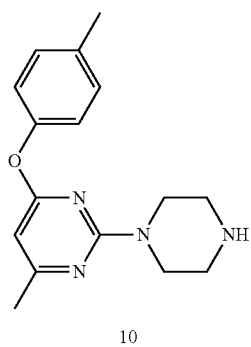

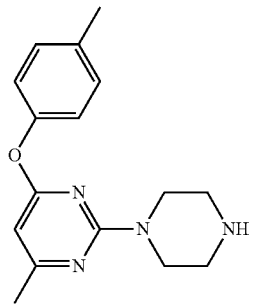

To a stirred solution of compound 8 (150 mg, 0.64 mmol) in n-butanol (6 mL) under argon atmosphere were added tert-butyl piperazine-1-carboxylate 4 (238 mg, 1.28 mmol) and diisopropylethylamine (0.23 mL, 1.28 mmol) in sealed tube at RT; heated to 100° C. and stirred for 16 h. The reaction was monitored by TLC; after completion of the reaction, the volatiles were removed in vacuo to obtain the crude. The crude was purified through silica gel column chromatography using 10% EtOAc/hexanes to afford compound 9 (150 mg, 61%) as white sticky solid. TLC: 10% EtOAc/hexanes ($R_f$ 0.8); $^1$H-NMR (DMSO-$d_6$, 400 MHz): δ 7.23 (d, J=8.0 Hz, 2H), 7.04 (d, J=8.4 Hz, 2H), 5.94 (s, 1H), 3.59-3.56 (m, 4H), 3.33-3.31 (m, 4H), 2.32 (s, 3H), 2.22 (s, 3H), 1.40 (s, 9H).

Synthesis of 4-methyl-2-(piperazin-1-yl)-6-(p-tolyloxy) pyrimidine (10)

Synthesis of 2-chloro-4-methyl-6-(p-tolyloxy) pyrimidine (8)

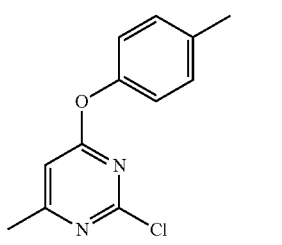

To a stirred solution of p-cresol 7 (145 mg, 1.34 mmol) in anhydrous THF (2 mL) under argon atmosphere was added sodium hydride (73.6 mg, 1.84 mmol) at 0° C.; warmed to RT and stirred for 30 min. To this was added 2, 4-dichloro-6-methylpyrimidine 1 (200 mg, 1.22 mmol) in anhydrous THF (2 mL) at 0° C.; warmed to RT and stirred for 2 h. The reaction was monitored by TLC; after completion of the reaction, the reaction mixture was diluted with ice cold water (20 mL) and extracted with EtOAc (2×30 mL). The combined organic extracts were dried over sodium sulfate, filtered and concentrated in vacuo to afford crude compound 8 (200 mg, 70%) as brown syrup. TLC: 10% EtOAc/hexanes ($R_f$ 0.6); $^1$H-NMR (CDCl$_3$, 500 MHz): δ 7.23 (d, J=7.5 Hz, 2H), 7.04-7.02 (m, 2H), 6.55 (s, 1H), 2.32 (s, 3H), 2.21 (s, 3H).

To a stirred solution of compound 9 (150 mg, 0.39 mmol) in CH$_2$Cl$_2$ (6 mL) under argon atmosphere was added 4 N HCl in 1, 4-dioxane (0.48 mL, 1.90 mmol) at 0° C.; warmed to RT and stirred for 2 h. The reaction was monitored by TLC; after completion of the reaction, the reaction mixture was diluted with CH$_2$Cl$_2$ (20 mL), washed with water (2×15 mL), neutralized with 10% NaHCO$_3$ solution (15 mL) and extracted with 5% MeOH/CH$_2$Cl$_2$ (2×30 mL). The combined organic extracts were dried over sodium sulfate, filtered and concentrated in vacuo to obtain the crude, which was triturated with 20% EtOAc/hexanes to afford compound 10 (50 mg, 45%) as colorless sticky solid. TLC: 10% MeOH/CH$_2$Cl$_2$ ($R_f$ 0.2); $^1$H-NMR (DMSO-$d_6$, 500 MHz): δ 7.22 (d, J=8.5 Hz, 2H), 7.04 (d, J=8.5 Hz, 2H), 5.90 (s, 1H), 3.51-3.49 (m, 4H), 2.65-2.63 (m, 4H), 2.31 (s, 3H), 2.20 (s, 3H).

Example 3: Synthesis of 4-methyl-2-(piperazin-1-yl)-6-(p-tolylthio) pyrimidine (14)—A Common Intermediate

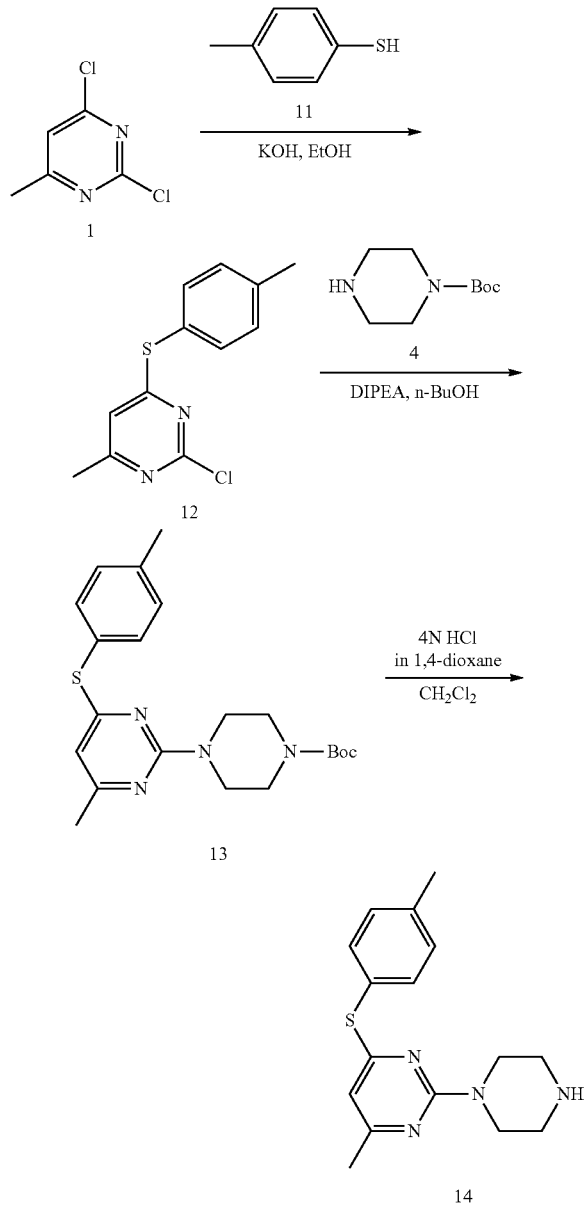

Synthesis of 2-chloro-4-methyl-6-(p-tolylthio) pyrimidine (12)

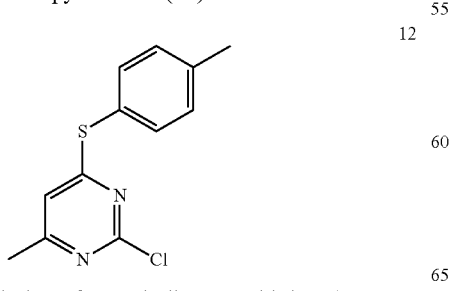

To a stirred solution of 4-methylbenzenethiol 11 (380 mg, 3.06 mmol) in ethanolic KOH (171 mg, 3.06 mmol of KOH in 25 mL of ethanol) under argon atmosphere was added 2,4-dichloro-6-methylpyrimidine 1 (500 mg, 3.06 mmol) at 0° C.; warmed to RT and stirred for 2 h. The reaction was monitored by TLC; after completion of the reaction, the volatiles were removed in vacuo, the residue was diluted with water (50 mL) and extracted with EtOAc (2×30 mL). The combined organic extracts were dried over sodium sulfate, filtered and concentrated in vacuo to obtain the crude. The crude was purified through silica gel column chromatography using 3% EtOAc/hexanes to afford compound 12 (580 mg, 75%) as an off-white solid. TLC: 20% EtOAc/hexanes ($R_f$ 0.3); $^1$H-NMR (DMSO-$d_6$, 400 MHz): δ 7.52 (d, J=8.0 Hz, 2H), 7.37 (d, J=8.0 Hz, 2H), 6.79 (s, 1H), 2.39 (s, 3H), 2.30 (s, 3H).

Synthesis of tert-butyl 4-(4-methyl-6-(p-tolylthio) pyrimidin-2-yl) piperazine-1-carboxylate (13)

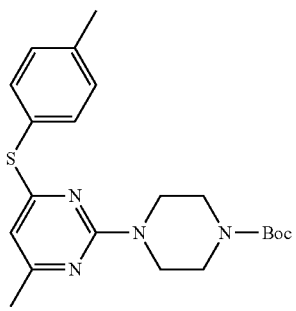

To a stirred solution of compound 12 (130 mg, 0.52 mmol) in n-butanol (7 mL) under argon atmosphere were added tert-butyl piperazine-1-carboxylate 4 (290 mg, 1.56 mmol) and diisopropylethylamine (0.18 mL, 1.04 mmol) in a sealed tube at RT; heated to 100° C. and stirred for 16 h. The reaction was monitored by TLC; after completion of the reaction, the volatiles were removed in vacuo to obtain the crude. The crude was purified through silica gel column chromatography using 30% EtOAc/hexanes to afford compound 13 (175 mg, 84%) as white solid. TLC: 20% EtOAc/hexanes ($R_f$ 0.4); $^1$H-NMR (DMSO-$d_6$, 400 MHz): δ 7.47 (d, J=8.0 Hz, 2H), 7.32 (d, J=8.0 Hz, 2H), 5.93 (s, 1H), 3.61 (t, J=4.8 Hz, 4H), 3.35-3.32 (m, 4H), 2.37 (s, 3H), 2.11 (s, 3H), 1.41 (s, 9H).

Synthesis of 4-methyl-2-(piperazin-1-yl)-6-(p-tolylthio) pyrimidine (14)

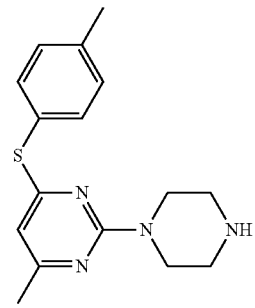

To a stirred solution of compound 13 (175 mg, 0.44 mmol) in CH$_2$Cl$_2$ (10 mL) under argon atmosphere was added 4 N HCl in 1, 4-dioxane (0.54 mL, 2.18 mmol) at 0° C.; warmed to RT and stirred for 4 h. The reaction was monitored by TLC; after completion of the reaction, the reaction mixture was diluted with water (30 mL) and extracted with CH$_2$Cl$_2$ (10 mL). The aqueous layer was neutralized with 10% NaHCO$_3$ solution (15 mL) to pH ~7 and extracted with 5% MeOH/CH$_2$Cl$_2$ (2×30 mL). The combined organic extracts were dried over sodium sulfate, filtered and concentrated in vacuo to obtain the crude compound 14 (110 mg, 83%) as white solid. TLC: 20% EtOAc/hexanes (R$_f$ 0.1); $^1$H-NMR (DMSO-d$_6$, 500 MHz): δ 7.47 (d, J=7.5 Hz, 2H), 7.32 (d, J=8.0 Hz, 2H), 5.87 (s, 1H), 3.55 (t, J=5.0 Hz, 4H), 2.66 (t, J=5.0 Hz, 4H), 2.37 (s, 3H), 2.09 (s, 3H).

Example 4: Synthesis of 4-((6-methyl-2-(piperazin-1-yl) pyrimidin-4-yl) amino) benzonitrile (18)—A Common Intermediate

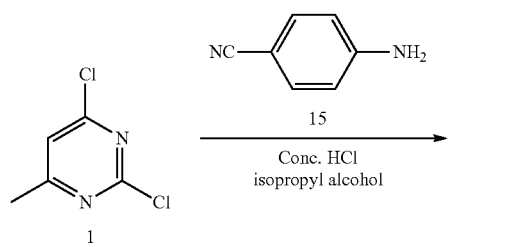

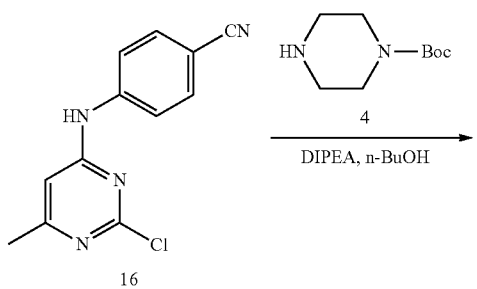

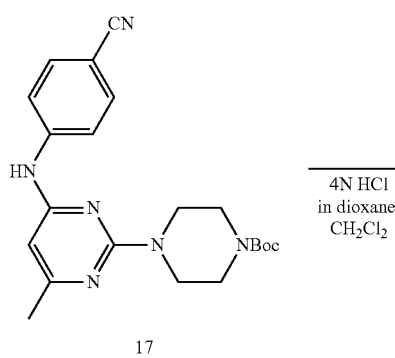

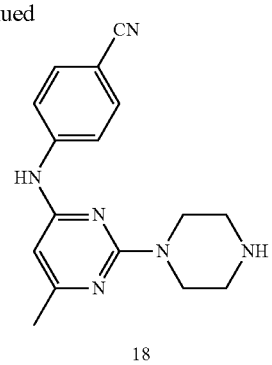

18

Synthesis of 4-((2-chloro-6-methylpyrimidin-4-yl) amino) benzonitrile (16)

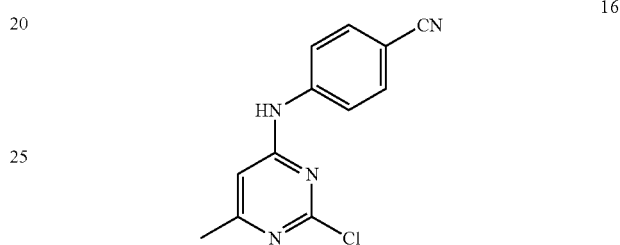

To a stirred solution of 2, 4-dichloro-6-methylpyrimidine 1 (5 g, 30.67 mmol) in isopropyl alcohol (60 mL) under argon atmosphere were added 4-aminobenzonitrile 15 (3.62 g, 30.67 mmol) and concentrated HCl (3 mL, 30.67 mmol) in sealed tube at 0° C.; warmed to RT and stirred for 120 h. The reaction was monitored by TLC; after completion of the reaction, the volatiles were removed in vacuo. The residue was diluted with water (100 mL) and pH was adjusted to ~8 with saturated NaHCO$_3$ solution (30 mL), extracted with EtOAc (3×100 mL) and washed with brine (100 mL). The organic extract was dried over sodium sulfate, filtered and concentrated in vacuo to obtain the crude. The crude was purified through combiflash chromatography (80 g column with 40-60 μm silica gel) using 30-40% EtOAc/hexanes to afford compound 16 (2.5 g, 33%) as white solid. TLC: 30% EtOAc/hexanes (R$_f$ 0.5); $^1$H NMR (DMSO-d$_6$, 400 MHz): δ 10.33 (s, 1H), 7.82-7.79 (m, 4H), 6.71 (s, 1H), 2.34 (s, 3H).

Synthesis of tert-butyl 4-(4-((4-cyanophenyl) amino)-6-methylpyrimidin-2-yl) piperazine-1-carboxylate (17)

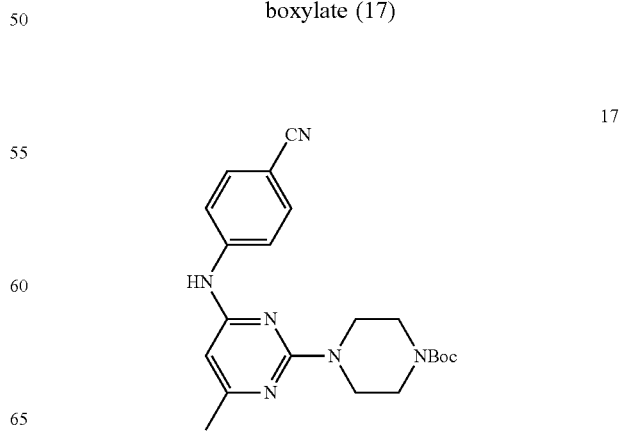

To a stirred solution of compound 16 (2 g, 8.19 mmol) in n-butanol (20 mL) under argon atmosphere were added tert-butyl piperazine-1-carboxylate 4 (2.29 g, 12.29 mmol) and diisopropylethylamine (DIPEA) (2.8 mL, 16.39 mmol) at RT; heated to 100° C. and stirred for 30 h. The reaction was monitored by TLC; after completion of the reaction, the volatiles were removed in vacuo to obtain the crude. The crude was purified through flash column chromatography using 20-25% EtOAc/hexanes to afford compound 17 (2.45 g, 76%) as white solid. TLC: 50% EtOAc/hexanes ($R_f$, 0.8); $^1$H NMR (DMSO-$d_6$, 400 MHz): δ 9.65 (s, 1H), 7.81 (d, J=8.8 Hz, 2H), 7.72 (d, J=9.0 Hz, 2H), 6.01 (s, 1H), 3.72-3.67 (m, 4H), 3.40-3.38 (m, 4H), 2.19 (s, 3H), 1.43 (s, 9H).

Synthesis of 4-((6-methyl-2-(piperazin-1-yl) pyrimidin-4-yl) amino) benzonitrile (18)

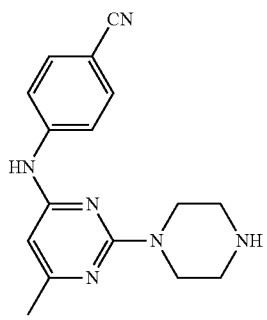

To a stirred solution of compound 17 (2.8 g, 7.10 mmol) in CH$_2$Cl$_2$ (60 mL) was added 4 N HCl in 1, 4-dioxane (2.8 mL) under argon atmosphere at 0° C.; warmed to RT and stirred for 6 h. The reaction was monitored by TLC; after completion of the reaction, the volatiles were removed in vacuo. The residue was diluted with water (50 mL) and neutralized with 10% aqueous NaHCO$_3$ solution (50 mL) and extracted with EtOAc (3×200 mL). The combined organic extracts were dried over sodium sulfate, filtered and concentrated in vacuo to afford compound 18 (2.08 g, quantitative yield) as an off-white solid. TLC: 40% EtOAc/hexanes ($R_f$, 0.2); $^1$H NMR (DMSO-$d_6$, 400 MHz): δ 9.60 (s, 1H), 7.81 (d, J=8.7 Hz, 2H), 7.71 (d, J=8.7 Hz, 2H), 5.97 (s, 1H), 3.67-3.59 (m, 4H), 2.75-2.71 (m, 4H), 2.40 (br s, 1H), 2.17 (s, 3H).

Example 5: Synthesis of 4-(4-fluorophenoxy)-6-isopropyl-2-(piperazin-1-yl) pyrimidine (24)—A Common Intermediate

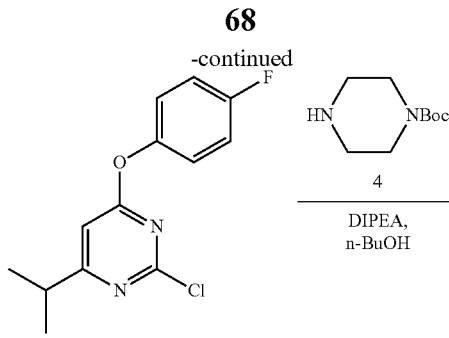

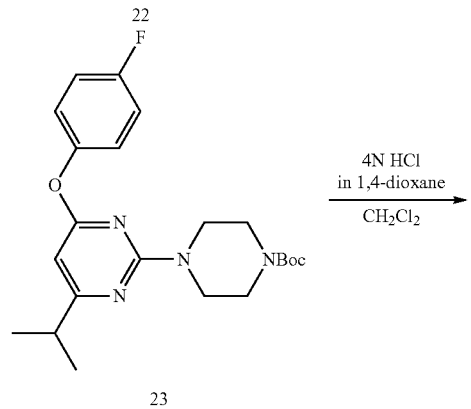

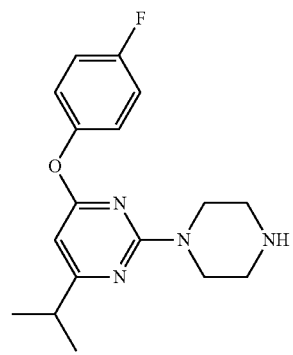

Synthesis of 2, 4-dichloro-6-isopropylpyrimidine (20)

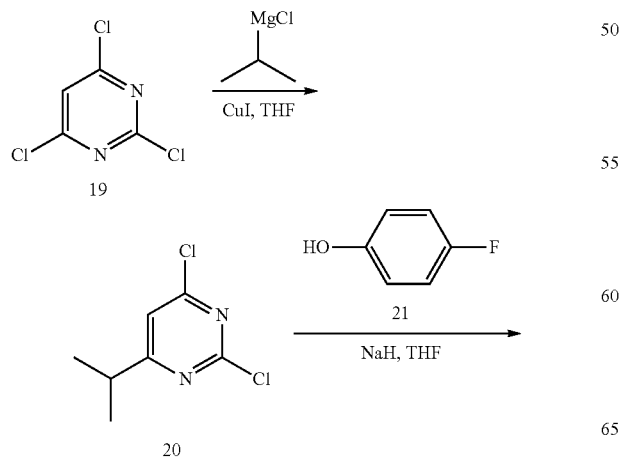

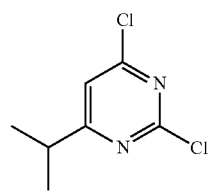

To a stirred solution of 2, 4, 6-trichloropyrimidine 19 (10 g, 54.49 mmol) in anhydrous THF (200 mL) were added isopropyl magnesium chloride (2 M sol. in THF, 54.5 mL, 109.0 mmol) and copper iodide (520 mg, 2.72 mmol) at −20° C. under argon atmosphere; stirred at 0° C. for 2 h. The reaction was monitored by TLC; after completion of the reaction, the reaction mixture was quenched with aqueous saturated ammonium chloride solution (150 mL) and extracted with EtOAc (2×150 mL). The combined organic extracts were dried over sodium sulfate, filtered and concentrated in vacuo to obtain the crude. The crude was purified through silica gel column chromatography using 2% EtOAc/hexanes to afford compound 20 (6 g, 58%) as colorless liquid. TLC: 7% EtOAc/hexanes ($R_f$ 0.8); $^1$H-NMR (CDCl$_3$, 400 MHz): δ 7.16 (s, 1H), 3.04-2.97 (m, 1H), 1.31 (d, J=6.8 Hz, 6H).

Synthesis of
2-chloro-4-(4-fluorophenoxy)-6-isopropylpyrimidine (22)

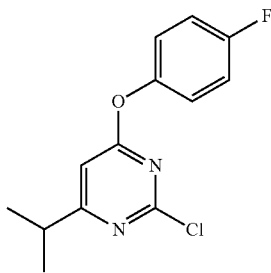

22

To a stirred solution of 4-fluorophenol 21 (387 mg, 3.45 mmol) in anhydrous THF (5 mL) was added sodium hydride (60% in mineral oil, 188 mg, 4.71 mmol) at 0° C. under argon atmosphere; warmed to RT and stirred for 30 min. To this was added compound 20 (600 mg, 3.14 mmol) in anhydrous THF (5 mL) at 0° C. and stirred at 0° C. for 1 h. The reaction was monitored by TLC; after completion of the reaction, the reaction mixture was quenched with ice cold water (30 mL) and extracted with EtOAc (2×40 mL). The combined organic extracts were dried over sodium sulfate, filtered and concentrated in vacuo to obtain the crude. The crude was purified through silica gel column chromatography using 2% EtOAc/hexanes to afford compound 22 (500 mg, 60%) as white low melting solid. TLC: 10% EtOAc/hexanes ($R_f$ 0.4); $^1$H-NMR (CDCl$_3$, 400 MHz): δ 7.12-7.10 (m, 4H), 6.62 (s, 1H), 3.02-2.91 (m, 1H), 1.29 (d, J=6.8 Hz, 6H).

Synthesis of tert-butyl 4-(4-(4-fluorophenoxy)-6-isopropylpyrimidin-2-yl) piperazine-1-carboxylate (23)

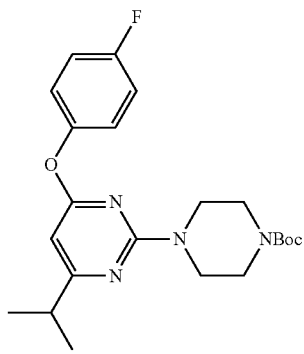

23

To a stirred solution of compound 22 (480 mg, 1.80 mmol) in n-butanol (15 mL) were added tert-butyl piperazine-1-carboxylate 4 (668 mg, 3.61 mmol) and diisopropylethylamine (0.31 mL, 1.80 mmol) in sealed tube at RT under argon atmosphere; heated to 110° C. and stirred for 16 h. The reaction was monitored by TLC; after completion of the reaction, the volatiles were removed in vacuo to obtain the crude. The crude was purified through silica gel column chromatography using 5% EtOAc/hexanes to afford compound 23 (500 mg, 66%) as white solid. TLC: 10% EtOAc/hexanes ($R_f$ 0.6); $^1$H-NMR (CDCl$_3$, 400 MHz): δ 7.09-7.07 (m, 4H), 5.91 (s, 1H), 3.68-3.66 (m, 4H), 3.44-3.41 (m, 4H), 2.80-2.73 (m, 1H), 1.48 (s, 9H), 1.22 (d, J=6.8 Hz, 6H).

Synthesis of 4-(4-fluorophenoxy)-6-isopropyl-2-(piperazin-1-yl) pyrimidine (24)

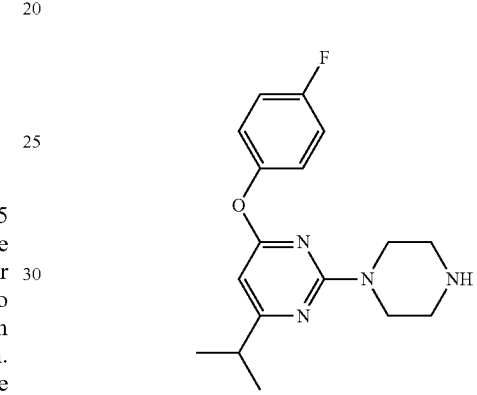

24

To a stirred solution of compound 23 (500 mg, 1.2 mmol) in CH$_2$Cl$_2$ (10 mL) was added 4 N HCl in 1, 4-dioxane (4 mL) at 0° C. under argon atmosphere; warmed to RT and stirred for 2 h. The reaction was monitored by TLC; after completion of the reaction, the volatiles were removed in vacuo. The residue was neutralized with 10% NaHCO$_3$ solution (15 mL) and extracted with CH$_2$Cl$_2$ (2×40 mL). The combined organic extracts were dried over sodium sulfate, filtered and concentrated in vacuo to afford 24 (340 mg, 90%) as thick syrup. TLC: 10% MeOH/CH$_2$Cl$_2$ ($R_f$ 0.1); $^1$H-NMR (DMSO-d$_6$, 400 MHz): δ 7.27-7.18 (m, 4H), 6.02 (s, 1H), 3.48-3.46 (m, 4H), 2.77-2.70 (m, 1H), 2.63 (t, J=4.8 Hz, 4H), 1.16 (d, J=6.8 Hz, 6H).

Example 6: Synthesis of 4-((2-(piperazin-1-yl)-6-(trifluoromethyl) pyrimidin-4-yl) amino) benzonitrile (28)—A Common Intermediate

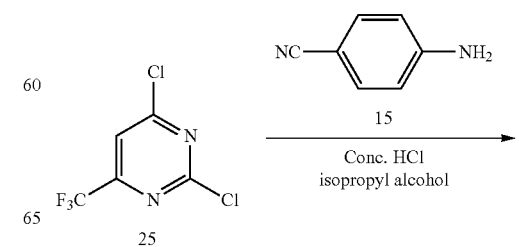

25

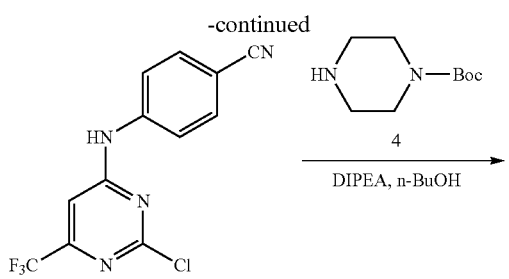

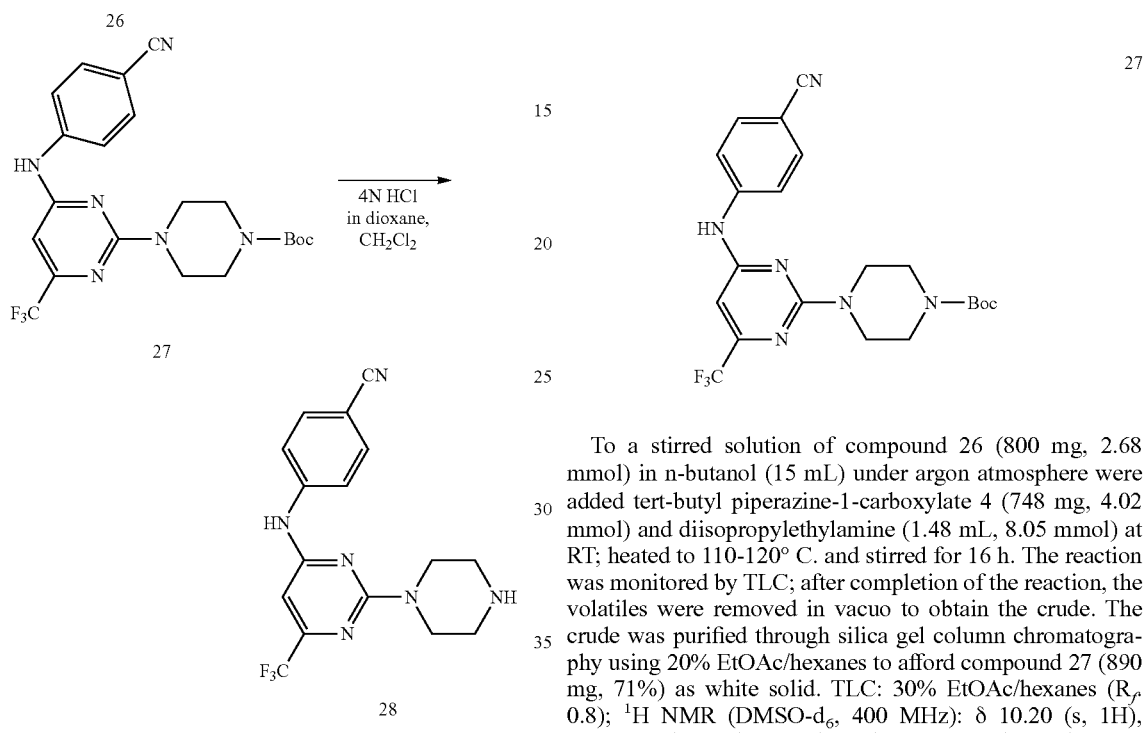

Synthesis of 4-((2-chloro-6-(trifluoromethyl) pyrimidin-4-yl) amino) benzonitrile (26)

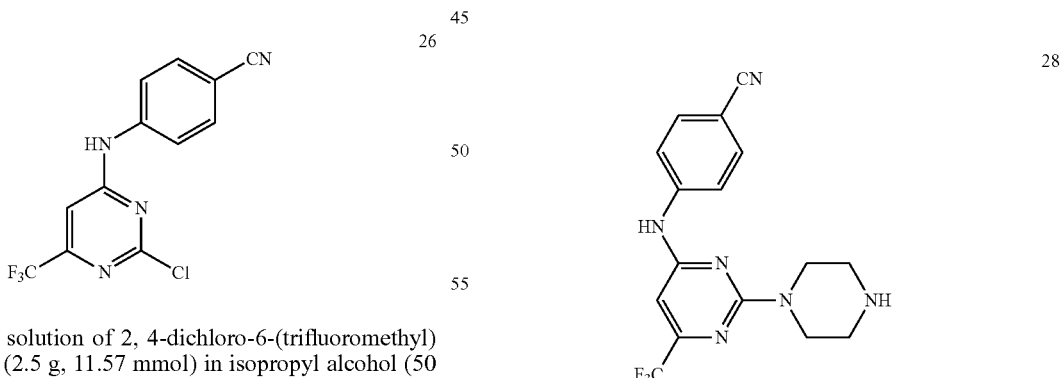

To a stirred solution of 2, 4-dichloro-6-(trifluoromethyl) pyrimidine 25 (2.5 g, 11.57 mmol) in isopropyl alcohol (50 mL) under argon atmosphere were added 4-aminobenzonitrile 15 (1.36 g, 11.57 mmol) and concentrated HCl (1.17 mL, 11.57 mmol) in sealed tube at RT; heated to 80-90° C. and stirred for 24 h. The reaction was monitored by TLC; after completion of the reaction, the volatiles were removed in vacuo, the residue was diluted with EtOAc (200 mL), washed with 10% aqueous NaHCO$_3$ solution (150 mL). The organic extract was dried over sodium sulfate, filtered and concentrated in vacuo to obtain the crude, which was purified through silica gel column chromatography using 15% EtOAc/hexanes to afford compound 26 (800 mg, 23%) as white solid. TLC: 30% EtOAc/hexanes (R$_f$ 0.5); $^1$H NMR (DMSO-d$_6$, 400 MHz): δ 10.93 (s, 1H), 7.91-7.83 (m, 4H), 7.21 (s, 1H).

Synthesis of tert-butyl 4-(4-((4-cyanophenyl) amino)-6-(trifluoromethyl) pyrimidin-2-yl) piperazine-1-carboxylate (27)

To a stirred solution of compound 26 (800 mg, 2.68 mmol) in n-butanol (15 mL) under argon atmosphere were added tert-butyl piperazine-1-carboxylate 4 (748 mg, 4.02 mmol) and diisopropylethylamine (1.48 mL, 8.05 mmol) at RT; heated to 110-120° C. and stirred for 16 h. The reaction was monitored by TLC; after completion of the reaction, the volatiles were removed in vacuo to obtain the crude. The crude was purified through silica gel column chromatography using 20% EtOAc/hexanes to afford compound 27 (890 mg, 71%) as white solid. TLC: 30% EtOAc/hexanes (R$_f$ 0.8); $^1$H NMR (DMSO-d$_6$, 400 MHz): δ 10.20 (s, 1H), 7.87-7.76 (m, 4H), 6.47 (s, 1H), 3.74-3.72 (m, 4H), 3.47-3.41 (m, 4H), 1.43 (s, 9H).

Synthesis of 4-((2-(piperazin-1-yl)-6-(trifluoromethyl) pyrimidin-4-yl) amino) benzonitrile (28)

To a stirred solution of compound 27 (850 mg, 1.89 mmol) in CH$_2$Cl$_2$ (10 mL) was added 4 N HCl in 1, 4-dioxane (5 mL) under argon atmosphere at 0° C.; warmed to RT and stirred for 2 h. The reaction was monitored by TLC; after completion of the reaction, the pH of the reaction mixture was neutralized with 10% aqueous NaHCO$_3$ solution and extracted with 5% MeOH/CH$_2$Cl$_2$ (2×100 mL). The combined organic extracts were dried over sodium sulfate, filtered and concentrated in vacuo to afford compound 28 (500 mg, 76%) as white solid. TLC: 7% MeOH/CH$_2$Cl$_2$ (R$_f$. 0.2); $^1$H NMR (DMSO-d$_6$, 400 MHz): δ 10.52 (br s, 1H), 7.89-7.84 (m, 2H), 7.81-7.75 (m, 2H), 6.50 (s, 1H), 3.68-3.59 (m, 4H), 2.78-2.72 (m, 4H).

Example 7: Synthesis of 6-methoxy-2-(piperazin-1-yl)-N-(p-tolyl) pyrimidin-4-amine (33)—A Common Intermediate

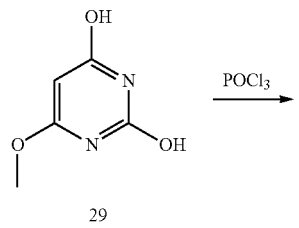

29

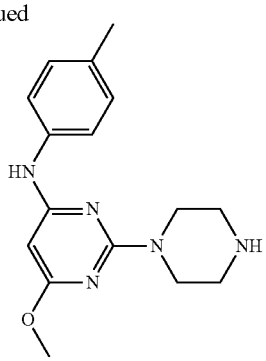

33

Synthesis of 2, 4-dichloro-6-methoxypyrimidine (30)

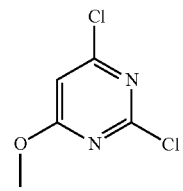

30

A stirred solution of 6-methoxypyrimidine-2, 4-diol 29 (7 g, 49.30 mmol) in phosphoryl chloride (150 mL) under argon atmosphere was heated to reflux for 4 h. The reaction was monitored by TLC; after completion of the reaction, the excess phosphoryl chloride was removed in vacuo. The residue was diluted with ice-cold water (100 mL) and extracted with EtOAc (2×100 mL). The combined organic extracts were washed with aqueous saturated NaHCO$_3$ solution (50 mL) followed by water (50 mL), dried over sodium sulfate, filtered and concentrated in vacuo to obtain the crude compound 30 (3 g, 34%) as colorless oily liquid. TLC: 10% EtOAc/hexanes (R$_f$. 0.7); $^1$H-NMR (CDCl$_3$, 500 MHz): δ 6.72 (s, 1H), 4.03 (s, 3H).

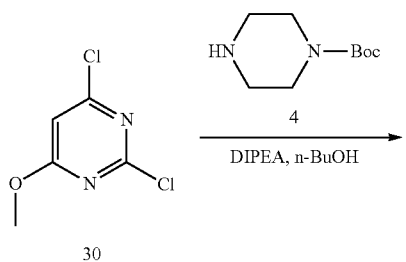

30

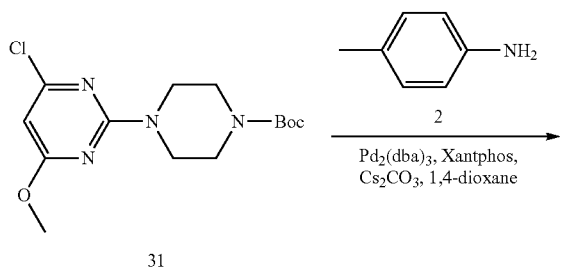

31

Synthesis of tert-butyl 4-(4-chloro-6-methoxypyrimidin-2-yl) piperazine-1-carboxylate (31)

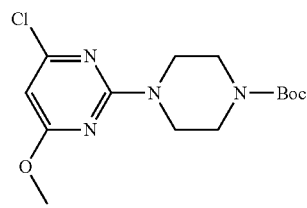

31

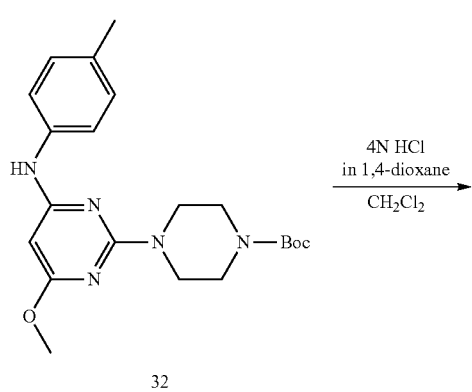

32

To a stirred solution of compound 30 (500 mg, 2.79 mmol) in n-butanol (5 mL) under argon atmosphere were added tert-butyl piperazine-1-carboxylate 4 (572 mg, 3.07 mmol) and diisopropylethylamine (0.77 mL, 4.18 mmol) in sealed tube at RT; heated to 80° C. for 16 h. The reaction was monitored by TLC; after completion of the reaction, the volatiles were removed in vacuo, the residue was diluted with water (20 mL) and extracted with EtOAc (2×40 mL). The combined organic extracts were dried over sodium sulfate, filtered and concentrated in vacuo to obtain the crude. The crude was purified through silica gel column chromatography using 10% EtOAc/hexanes to afford compound 31 (620 mg, 67%) as white solid. TLC: 20% EtOAc/hexanes ($R_f$ 0.4); $^1$H-NMR (CDCl$_3$, 400 MHz): δ 6.01 (s, 1H), 3.89 (s, 3H), 3.80-3.77 (m, 4H), 3.49-3.46 (m, 4H), 1.48 (s, 9H).

Synthesis of tert-butyl 4-(4-methoxy-6-(p-toyly-lamino) pyrimidin-2-yl) piperazine-1-carboxylate (32)

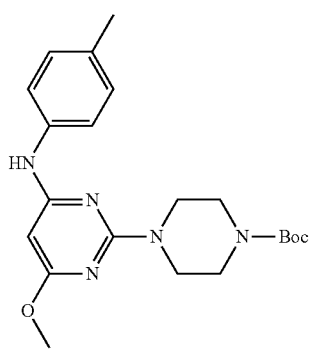

32

To a stirred solution of compound 31 (300 mg, 0.91 mmol) in 1, 4-dioxane (5 mL) under argon atmosphere were added p-toluidine 2 (117 mg, 1.09 mmol) and cesium carbonate (444 mg, 1.36 mmol) in sealed tube at RT and degassed under argon for 20 min. To this were added Pd$_2$(dba)$_3$ (41 mg, 0.04 mmol) and Xantphos (37 mg, 0.06 mmol) at RT and degassed under argon for 15 min; heated to 100° C. and stirred for 16 h. The reaction was monitored by TLC; after completion of the reaction, the reaction mixture was diluted with water (20 mL) and extracted with EtOAc (2×40 mL). The combined organic extracts were dried over sodium sulfate, filtered and concentrated in vacuo to obtain the crude. The crude was purified through silica gel column chromatography using 10% EtOAc/hexanes to afford compound 32 (260 mg, 71%) as white solid. TLC: 20% EtOAc/hexanes ($R_f$ 0.5); $^1$H-NMR (CDCl$_3$, 400 MHz): δ 7.19-7.09 (m, 4H), 6.33 (br s, 1H), 5.42 (s, 1H), 3.84 (s, 3H), 3.79-3.68 (m, 4H), 3.52-3.39 (m, 4H), 2.33 (s, 3H), 1.48 (s, 9H).

Synthesis of 6-methoxy-2-(piperazin-1-yl)-N-(p-tolyl) pyrimidin-4-amine (33)

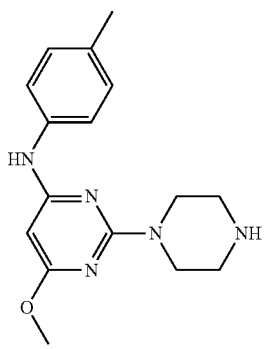

33

To a stirred solution of compound 32 (150 mg, 0.37 mmol) in CH$_2$Cl$_2$ (5 mL) under argon atmosphere was added 4 N HCl in 1, 4-dioxane (2 mL) at 0° C.; warmed to RT and stirred for 4 h. The reaction was monitored by TLC; after completion of the reaction, the reaction mixture was diluted with water (20 mL), pH was adjusted to ~8 with aqueous saturated NaHCO$_3$ solution (30 mL) and extracted with CH$_2$Cl$_2$ (2×30 mL). The combined organic extracts were washed with water (20 mL), dried over sodium sulfate, filtered and concentrated in vacuo to obtain the crude compound 33 (89 mg, 79%) as white solid. TLC: 30% EtOAc/hexanes ($R_f$ 0.1); $^1$H-NMR (DMSO-d$_6$, 400 MHz): δ 8.85 (s, 1H), 7.40 (d, J=8.4 Hz, 2H), 7.07 (d, J=8.0 Hz, 2H), 5.33 (s, 1H), 3.75 (s, 3H), 3.60 (t, J=4.8 Hz, 4H), 2.71 (t, J=4.8 Hz, 4H), 2.23 (s, 3H).

Example 8: Synthesis of 4-methyl-6-(piperazin-1-yl)-N-(p-tolyl) pyrimidin-2-amine (36)—A Common Intermediate

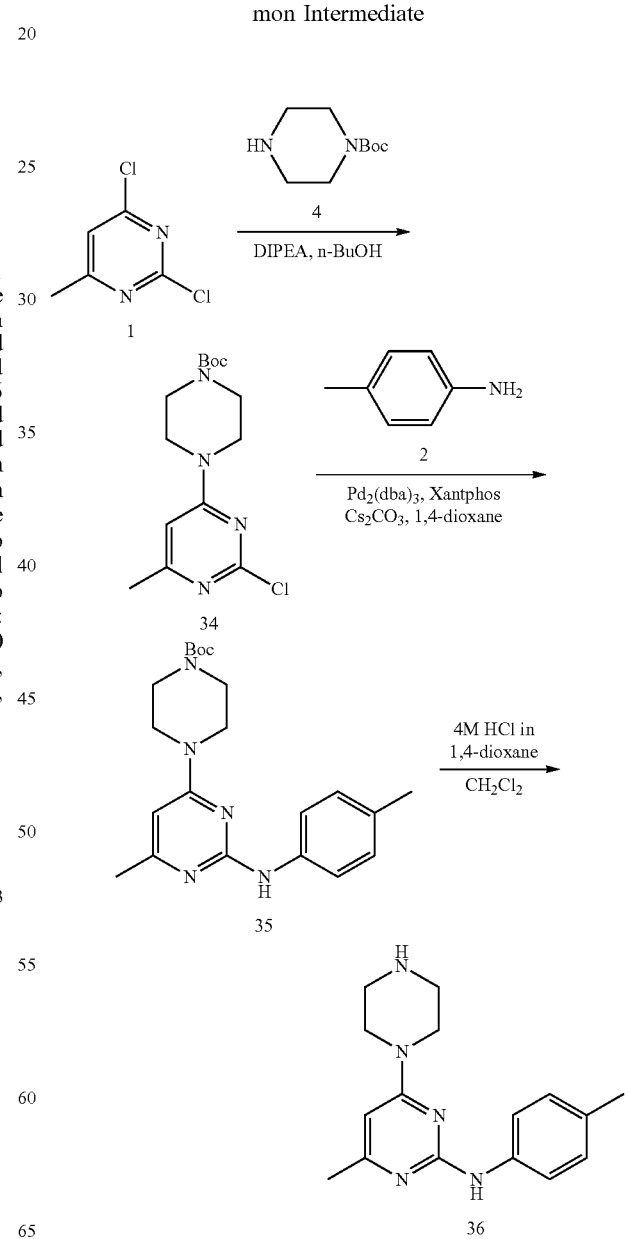

Synthesis of tert-butyl 4-(2-chloro-6-methylpyrimidin-4-yl) piperazine-1-carboxylate (34)

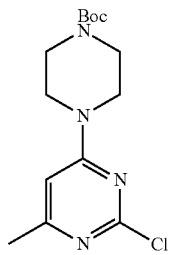

34

To a stirred solution of 2, 4-dichloro-6-methylpyrimidine 1 (200 mg, 1.23 mmol) in n-butanol (5 mL) were added tert-butyl piperazine-1-carboxylate 4 (251 mg, 1.35 mmol) and diisopropylethylamine (0.32 mL, 1.84 mmol) in sealed tube at RT under argon atmosphere; heated to 70° C. and stirred for 16 h. The reaction was monitored by TLC; after completion of the reaction, the volatiles were removed in vacuo, the residue was diluted with water (20 mL) and extracted with EtOAc (2×30 mL). The combined organic extracts were dried over sodium sulfate, filtered and concentrated in vacuo to obtain the crude. The crude was purified through silica gel column chromatography using 10% EtOAc/hexanes to afford compound 34 (100 mg, 26%) as colorless syrup. TLC: 20% EtOAc/hexanes ($R_f$ 0.6); $^1$H-NMR (DMSO-$d_6$, 400 MHz): δ 6.67 (s, 1H), 3.69 (t, J=4.8 Hz, 4H), 3.86 (t, J=5.2 Hz, 4H), 2.28 (s, 3H), 1.42 (s, 9H).

Synthesis of tert-butyl 4-(6-methyl-2-(p-tolylamino) pyrimidin-4-yl) piperazine-1-carboxylate (35)

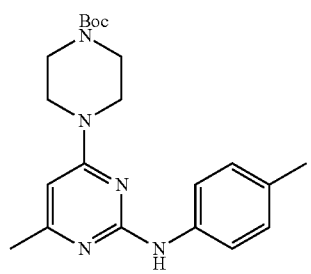

35

To a stirred solution of compound 34 (100 mg, 0.32 mmol) in 1, 4-dioxane (5 mL) under argon atmosphere was added p-toluidine 2 (41 mg, 0.38 mmol) in sealed tube at RT and degassed under argon for 20 min. To this were added cesium carbonate (125 mg, 0.38 mmol), Pd$_2$(dba)$_3$ (15 mg, 0.02 mmol) followed by Xantphos (13 mg, 0.02 mmol) and degassed under argon for 20 min; heated to 80° C. and stirred for 16 h. The reaction was monitored by TLC; after completion of the reaction, the volatiles were removed in vacuo, the residue was diluted with water (25 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 25% EtOAc/hexanes to afford compound 35 (100 mg, 82%) as an off-white solid. TLC: 50% EtOAc/hexanes ($R_f$ 0.2); $^1$H-NMR (DMSO-$d_6$, 500 MHz): δ 8.91 (s, 1H), 7.58 (d, J=8.5 Hz, 2H), 7.04 (d, J=8.0 Hz, 2H), 6.12 (s, 1H), 3.58-3.56 (m, 4H), 3.41-3.39 (m, 4H), 2.22 (s, 3H), 2.18 (s, 3H), 1.42 (s, 9H).

Synthesis of 4-methyl-6-(piperazin-1-yl)-N-(p-tolyl) pyrimidin-2-amine (36)

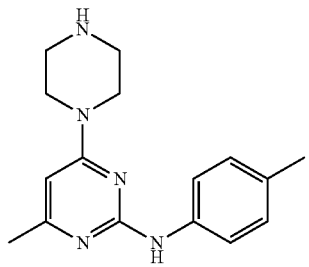

36

To a stirred solution of compound 35 (150 mg, 0.39 mmol) in CH$_2$Cl$_2$ (5 mL) under argon atmosphere was added 4 N HCl in 1, 4-dioxane (1 mL) at 5° C.; warmed to RT and stirred for 6 h. The reaction was monitored by TLC; after completion of the reaction, the reaction mixture was diluted with water (20 mL) and washed with EtOAc (10 mL). The aqueous layer was neutralized with 10% aqueous NaHCO$_3$ solution (20 mL) and extracted with EtOAc (2×30 mL). The combined organic extracts were dried over sodium sulfate, filtered and concentrated in vacuo to obtain the crude compound 36 (90 mg, 82%) as an off-white solid. TLC: 5% MeOH/CH$_2$Cl$_2$ ($R_f$ 0.1); $^1$H-NMR (DMSO-$d_6$, 500 MHz): δ 8.84 (s, 1H), 7.58 (d, J=8.0 Hz, 2H), 7.02 (d, J=8.0 Hz, 2H), 6.08 (s, 1H), 3.49-3.47 (m, 4H), 2.73-2.71 (m, 4H), 2.21 (s, 3H), 2.16 (s, 3H).

Example 9: Synthesis of 4-methyl-6-(piperazin-1-yl)-N-(p-tolyl) pyridin-2-amine (40)—A Common Intermediate

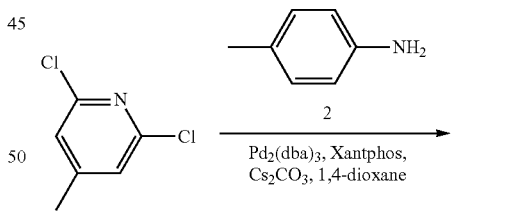

37

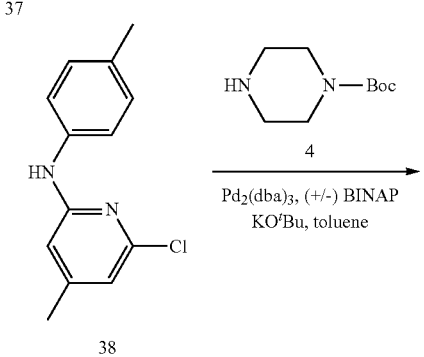

38

-continued

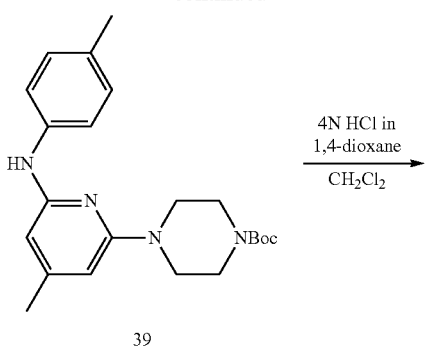

39

→ 4N HCl in 1,4-dioxane / CH₂Cl₂

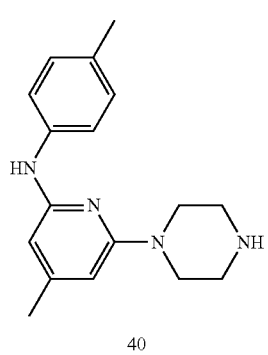

40

Synthesis of 6-chloro-4-methyl-N-(p-tolyl) pyridin-2-amine (38)

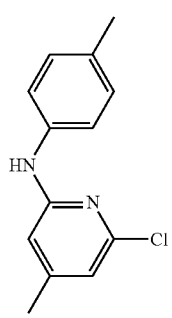

38

To a stirred solution of 2, 6-dichloro-4-methylpyridine 37 (500 mg, 3.08 mmol) in 1, 4-dioxane (8 mL) under argon atmosphere were added p-toluidine 2 (363 mg, 3.39 mmol), cesium carbonate (1.2 g, 3.70 mmol), Pd$_2$(dba)$_3$ (141 mg, 0.15 mmol) and Xantphos (178 mg, 0.31 mmol) in a sealed tube at RT and purged under argon for 20 min; heated to 120° C. and stirred for 16 h. The reaction was monitored by TLC; after completion of the reaction, the reaction mixture was filtered through a pad of celite and the filtrate was concentrated in vacuo to obtain the crude, which was purified through flash column chromatography using 5% EtOAc/hexanes to afford compound 38 (310 mg, 38%) as brown semi solid. TLC: 10% EtOAc/hexanes (R$_f$ 0.4); $^1$H-NMR (DMSO-d$_6$, 500 MHz): δ 9.10 (s, 1H), 7.48-7.42 (m, 4H), 6.62 (s, 1H), 6.54 (s, 1H), 2.24 (s, 3H), 2.20 (s, 3H).

Synthesis of tert-butyl 4-(4-(methyl)-6-(p-tolylamino) pyridin-2-yl) piperazine-1-carboxylate (39)

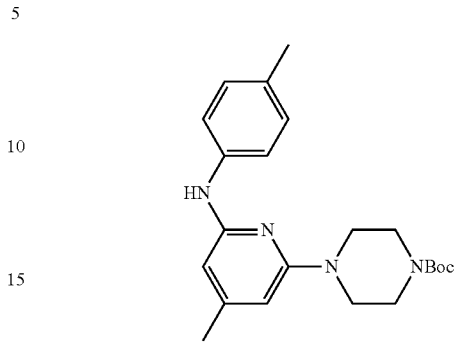

39

To a stirred solution of compound 38 (1 g, 4.31 mmol) in toluene (12 mL) under argon atmosphere were added tert-butyl piperazine-1-carboxylate 4 (1.2 g, 6.46 mmol), Pd$_2$(dba)$_3$ (98.6 mg, 0.11 mmol), (+/−) BINAP (134 mg, 0.21 mmol), potassium tert-butoxide (1 M in THF, 6.4 mL, 6.45 mmol) in sealed tube at RT and purged under argon for 20 min; heated to 120° C. and stirred for 16 h. The reaction was monitored by TLC; after completion of the reaction, the reaction mixture was filtered through a pad of celite and the filtrate was concentrated in vacuo to obtain the crude, which was purified through silica gel column chromatography using 25% EtOAc/hexanes to afford compound 39 (700 mg, 42%) as yellow solid. TLC: 50% EtOAc/hexanes (R$_f$ 0.4); $^1$H-NMR (DMSO-d$_6$, 400 MHz): δ 8.50 (s, 1H), 7.41 (d, J=8.4 Hz, 2H), 7.03 (d, J=8.4 Hz, 2H), 5.97 (s, 1H), 5.95 (s, 1H), 3.44-3.39 (m, 8H), 2.21 (s, 3H), 2.12 (s, 3H), 1.42 (s, 9H).

Synthesis of 4-methyl-6-(piperazin-1-yl)-N-(p-tolyl) pyridin-2-amine (40)

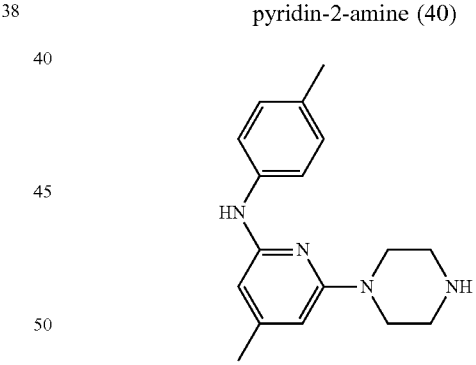

40

To a stirred solution of compound 39 (700 mg, 1.83 mmol) in CH$_2$Cl$_2$ (5 mL) under argon atmosphere was added 4 N HCl in 1, 4-dioxane (2.29 mL, 9.16 mmol) at RT and stirred for 16 h. The reaction was monitored by TLC; after completion of the reaction, the volatiles were removed in vacuo, the residue was diluted with 1 N HCl (10 mL) and extracted with diethyl ether (2×15 mL). The aqueous layer was neutralized with aqueous saturated NaHCO$_3$ solution (20 mL) and extracted with CH$_2$Cl$_2$ (2×40 mL). The combined organic extracts were dried over sodium sulfate, filtered and concentrated in vacuo to obtain the crude compound 40 (300 mg, 58%) as an off-white solid. TLC: 5% MeOH/CH$_2$Cl$_2$ (R$_f$ 0.2); $^1$H-NMR (DMSO-d$_6$, 400 MHz): δ 8.44 (s, 1H), 7.43 (d, J=8.4 Hz, 2H), 7.01 (d, J=8.0 Hz, 2H), 5.92 (s, 2H), 3.31 (t, J=4.8 Hz, 4H), 2.76 (t, J=4.8 Hz, 4H), 2.21 (s, 3H), 2.11 (s, 3H).

Example 10: Synthesis of 6-(piperazin-1-yl)-N-(p-tolyl) pyridin-2-amine (44)—A Common Intermediate

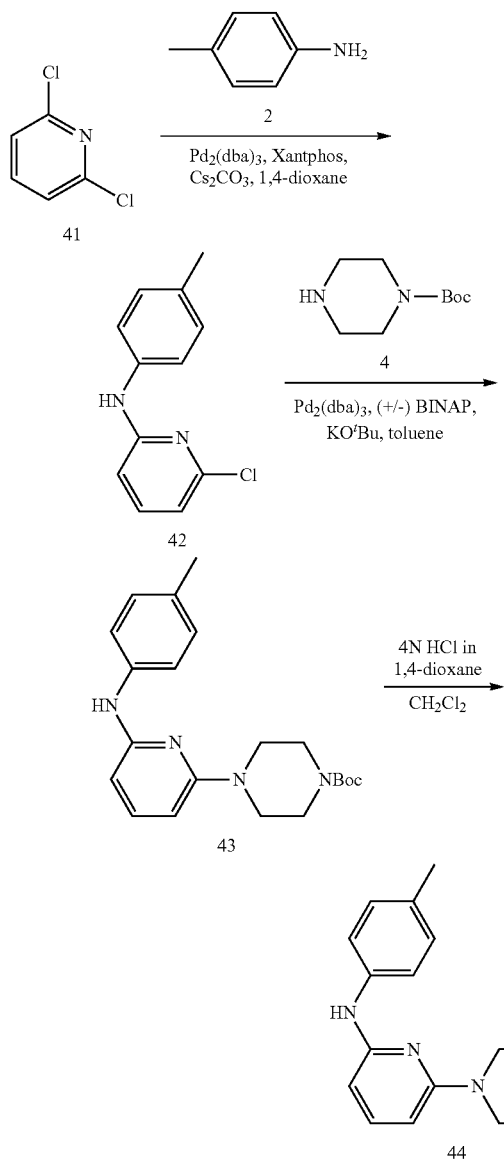

Synthesis of 6-chloro-N-(p-tolyl) pyridin-2-amine (42)

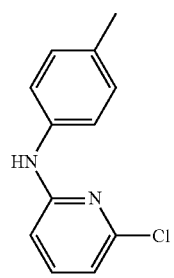

To a stirred solution of 2, 6-dichloropyridine 41 (3 g, 23.44 mmol) in 1, 4-dioxane (60 mL) under argon atmosphere were added p-toluidine 2 (2.63 g, 24.61 mmol), cesium carbonate (9.14 g, 28.12 mmol), Pd$_2$(dba)$_3$ (536 mg, 0.58 mmol) followed by Xantphos (677 mg, 1.17 mmol) in sealed tube at RT and degassed under argon for 20 min; heated to 120° C. and stirred for 36 h. The reaction was monitored by TLC; after completion of the reaction, the volatiles were removed in vacuo, the residue was diluted with water (25 mL) and extracted with EtOAc (2×60 mL). The combined organic extracts were dried over sodium sulfate, filtered and concentrated in vacuo to obtain the crude, which was purified through silica gel column chromatography using 10% EtOAc/hexanes to afford compound 42 (1.2 g, 24%) as brown syrup. TLC: 10% EtOAc/hexanes (R$_f$, 0.6); $^1$H-NMR (DMSO-d$_6$, 400 MHz): δ 9.21 (s, 1H), 7.54 (t, J=8.0 Hz, 1H), 7.46 (d, J=8.4 Hz, 2H), 7.10 (d, J=8.4 Hz, 2H), 6.73 (d, J=7.2 Hz, 2H), 2.24 (s, 3H).

Synthesis of tert-butyl 4-(6-(p-tolylamino) pyridin-2-yl) piperazine-1-carboxylate (43)

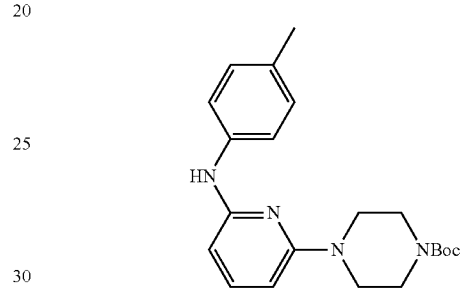

To a stirred solution of compound 42 (50 mg, 0.23 mmol) in toluene (6 mL) under argon atmosphere were added tert-butyl piperazine-1-carboxylate 4 (63 mg, 0.34 mmol), Pd$_2$(dba)$_3$ (10.5 mg, 0.01 mmol), (+/−) BINAP (15 mg, 0.02 mmol) and potassium tert-butoxide (1 M in THF, 0.3 mL, 0.27 mmol) in sealed tube at RT and degassed under argon for 20 min; heated to 120° C. and stirred for 16 h. The reaction was monitored by TLC; after completion of the reaction, the reaction mixture was filtered through a pad of celite and the filtrate was concentrated in vacuo to obtain the crude. The crude was purified through silica gel column chromatography using 12% EtOAc/hexanes to afford compound 43 (30 mg, 35%) as brown syrup. TLC: 10% EtOAc/hexanes (R$_f$, 0.3); $^1$H-NMR (DMSO-d$_6$, 400 MHz): δ 8.60 (s, 1H), 7.43 (d, J=8.4 Hz, 2H), 7.32 (t, J=8.0 Hz, 1H), 7.05 (d, J=8.0 Hz, 2H), 6.12-6.09 (m, 2H), 3.44-3.39 (m, 8H), 2.22 (s, 3H), 1.42 (s, 9H).

Synthesis of 6-(piperazin-1-yl)-N-(p-tolyl) pyridin-2-amine (44)

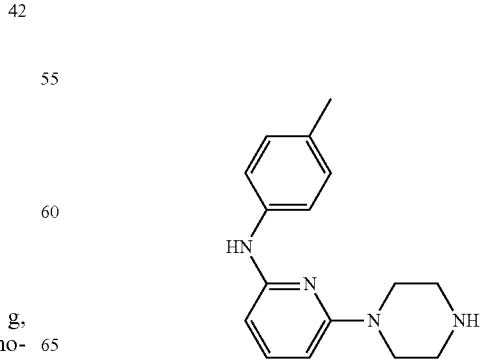

To a stirred solution of compound 43 (400 mg, 1.09 mmol) in $CH_2Cl_2$ (10 mL) under argon atmosphere was added 4 N HCl in 1, 4-dioxane (1.4 mL, 5.43 mmol) at RT and stirred for 16 h. The reaction was monitored by TLC; after completion of the reaction, the volatiles were removed in vacuo, the residue was diluted with 1 N HCl (10 mL) and washed with water (20 mL). The aqueous layer was neutralized with aqueous saturated $NaHCO_3$ solution (20 mL) and extracted with $CH_2Cl_2$ (2×30 mL). The combined organic extracts were dried over sodium sulfate, filtered and concentrated in vacuo to obtain the crude. The crude was purified through silica gel column chromatography using 2% $MeOH/CH_2Cl_2$ to afford compound 44 (150 mg, 50%) as pale yellow solid. TLC: 10% $MeOH/CH_2Cl_2$ ($R_f$ 0.2); $^1$H-NMR (DMSO-$d_6$, 400 MHz): δ 8.97 (br s, 1H), 8.73 (br s, 1H), 7.47-7.38 (m, 4H), 7.05 (d, J=8.4 Hz, 2H), 6.18 (t, J=6.8 Hz, 1H), 3.67-3.64 (m, 4H), 3.21-3.16 (m, 4H), 2.23 (s, 3H).

Example 11: Synthesis of Test Compounds From Various Common Intermediates and Sulfonyl Chlorides Amines similar to compound 6, 10, 14, 18, 24, 28, 33, 36, 40 and 44 were synthesized as described herein and converted to final products using commercially available sulfonyl chlorides employing Procedure A and the results are captured in Table 1 below.

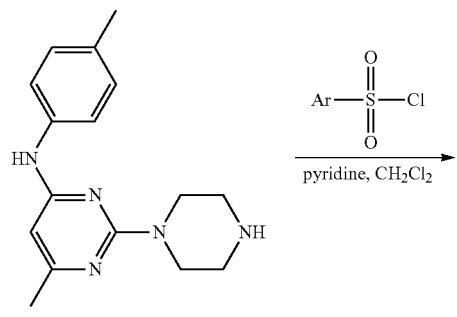

6

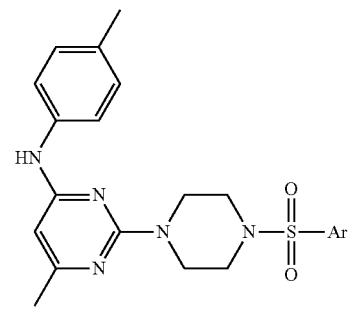

Procedure A: To a stirred solution of compound 6 (40 mg, 0.14 mmol) in $CH_2Cl_2$ (5 mL) under argon atmosphere were added pyridine (0.06 mL, 0.70 mmol), thiophene-2-sulfonyl chloride 45 (29.5 mg, 0.15 mmol) at 0° C.; warmed to RT and stirred for 6 h. The reaction was monitored by TLC; after completion the reaction, the reaction mixture was diluted with water (20 mL) extracted with $CH_2Cl_2$ (2×30 mL), washed with 1 N HCl (20 mL), 10% $NaHCO_3$ solution (30 mL), brine (30 mL), dried over sodium sulfate, filtered and concentrated in vacuo to obtain crude. The precipitated material was either directly dried in vacuo or triturated or purified by column chromatography to afford the desired compound.

Commercially Available Sulfonyl Chlorides Used for Test Compounds:

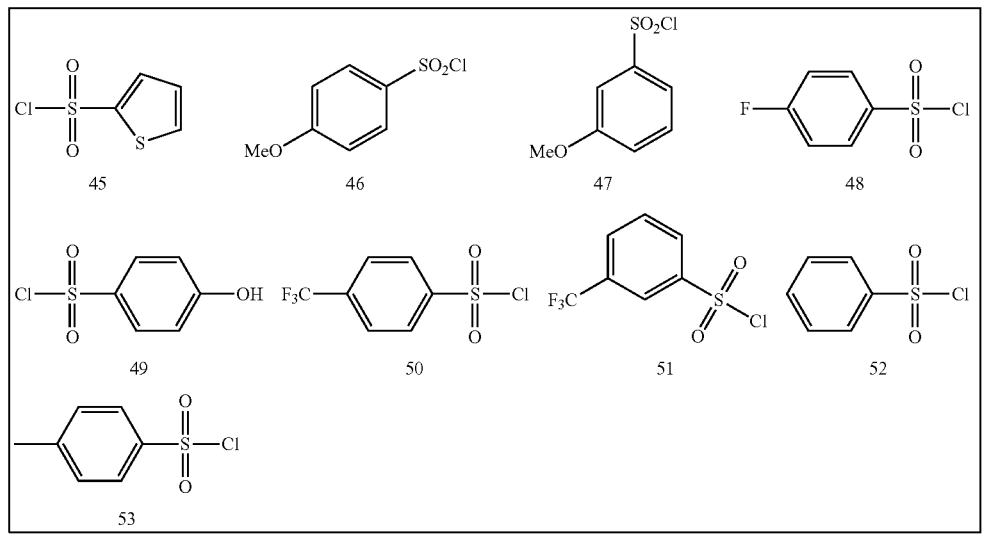

TABLE 1

Synthesis of test compounds from compounds 6, 10, 14, 18, 24, 28, 33, 36, 40, 44 and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1146 | 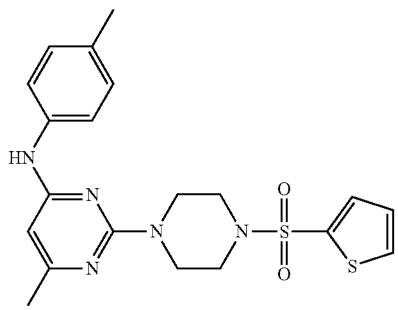 [SMILES: Cc1ccc(Nc2cc(C)nc(N3CCN(S(=O)(=O)c4cccs4)CC3)n2)cc1] | A, 6, 45 | 25% | 430.5 | 429.13 for (M$^+$ + 1) $C_{20}H_{23}N_5O_2S_2$ | $^1$H-NMR (DMSO-d$_6$, 400 MHz): δ 9.02 (s, 1H), 8.03 (d, J = 6.4 Hz, 1H), 7.65 (d, J = 4.8 Hz, 1H), 7.40 (d, J = 8.4 Hz, 2H), 7.27-7.26 (m, 1H), 7.09 (d, J = 8.4 Hz, 2H), 5.88 (s, 1H), 3.81 (t, J = 5.2 Hz, 4H), 2.97 (t, J = 4.8 Hz, 4H), 2.24 (s, 3H), 2.10 (s, 3H) |
| 1152 | 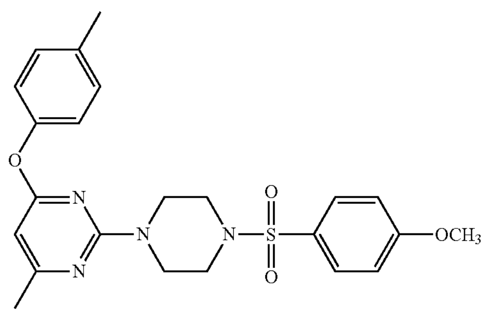 [SMILES: COc1ccc(S(=O)(=O)N2CCN(c3nc(C)cc(Oc4ccc(C)cc4)n3)CC2)cc1] | A$^a$, 10, 46 | 50% | 455.0 | 454.17 for (M$^+$ + 1) $C_{23}H_{26}N_4O_4S$ | $^1$H-NMR (DMSO-d$_6$, 400 MHz): δ 7.66 (d, J = 8.8 Hz, 2H), 7.21 (d, J = 8.4 Hz, 2H), 7.13 (d, J = 8.8 Hz, 2H), 7.01 (d, J = 8.4 Hz, 2H), 5.91 (s, 1H), 3.83 (s, 3H), 3.69-3.67 (m, 4H), 2.84 (t, J = 4.8 Hz, 4H), 2.31 (s, 3H), 2.17 (s, 3H) |
| 1159 | 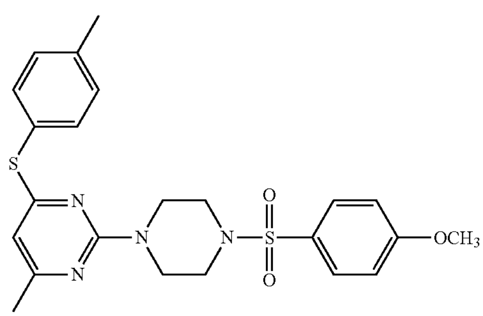 [SMILES: COc1ccc(S(=O)(=O)N2CCN(c3nc(C)cc(Sc4ccc(C)cc4)n3)CC2)cc1] | A$^a$, 14, 46 | 81% | 471.0 | 470.14 for (M$^+$ + 1) $C_{23}H_{26}N_4O_3S_2$ | $^1$H-NMR (DMSO-d$_6$, 400 MHz): δ 7.67 (d, J = 8.8 Hz, 2H), 7.44 (d, J = 8.0 Hz, 2H), 7.31 (d, J = 8.0 Hz, 2H), 7.14 (d, J = 9.2 Hz, 2H), 5.89 (s, 1H), 3.84 (s, 3H), 3.73 (t, J = 4.8 Hz, 4H), 2.85 (t, J = 4.8 Hz, 4H), 2.36 (s, 3H), 2.07 (s, 3H) |
| 1328 | 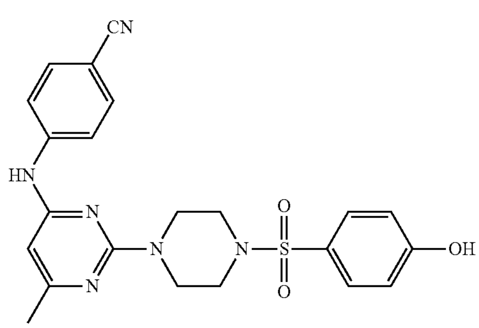 [SMILES: Cc1cc(Nc2ccc(C#N)cc2)nc(N2CCN(S(=O)(=O)c3ccc(O)cc3)CC2)n1] | A$^b$, 18, 49 | 23% | 451.0 | 450.15 for (M$^+$ + 1) $C_{22}H_{22}N_6O_3S$ | $^1$H NMR (DMSO-d$_6$, 400 MHz): δ 10.53 (s, 1H), 9.65 (s, 1H), 7.78-7.74 (m, 2H), 7.73-7.68 (m, 2H), 7.57 (d, J = 8.8 Hz, 2H), 6.93 (d, J = 8.8 Hz, 2H), 5.99 (s, 1H), 3.79 (t, J = 4.4 Hz, 4H), 2.90 (t, J = 4.7 Hz, 4H), 2.15 (s, 3H) |

TABLE 1-continued

Synthesis of test compounds from compounds 6, 10, 14, 18, 24, 28, 33, 36, 40, 44 and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1319 | 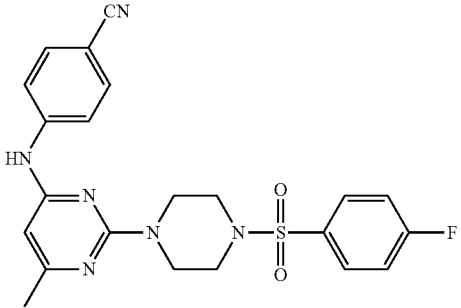 [SMILES: Cc1cc(Nc2ccc(C#N)cc2)nc(N2CCN(S(=O)(=O)c3ccc(F)cc3)CC2)n1] | $A^b$, 18, 48 | 33% | 453.0 (M$^+$ + 1) | 452.14 for $C_{22}H_{21}FN_6O_2S$ | $^1$H NMR (DMSO-d$_6$, 400 MHz): δ 9.66 (s, 1H), 7.86-7.79 (m, 2H), 7.78-7.68 (m, 4H), 7.47 (t, J = 8.8 Hz, 2H), 5.99 (s, 1H), 3.81 (t, J = 4.6 Hz, 4H), 2.97 (t, J = 4.8 Hz, 4H), 2.15 (s, 3H); |
| 1327 | 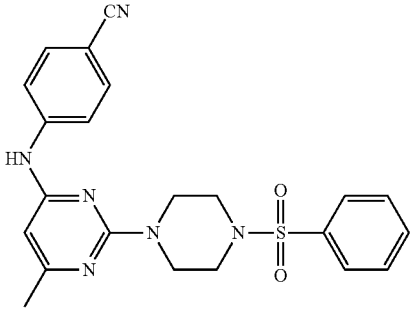 [SMILES: Cc1cc(Nc2ccc(C#N)cc2)nc(N2CCN(S(=O)(=O)c3ccccc3)CC2)n1] | $A^b$, 18, 52 | 48% | 435.0 (M$^+$ + 1) | 434.15 for $C_{22}H_{22}N_6O_2S$ | $^1$H NMR (DMSO-d$_6$, 400 MHz): δ 9.65 (s, 1H), 7.80-7.59 (m, 9H), 5.99 (s, 1H), 3.80 (t, J = 4.6 Hz, 4H), 2.96 (t, J = 4.8 Hz, 4H), 2.15 (s, 3H) |
| 1321 | 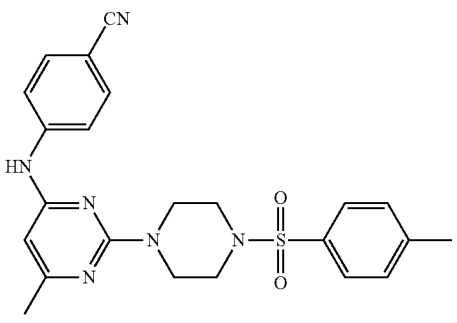 | $A^b$, 18, 53 | 72% | 449.0 (M$^+$ + 1) | 448.17 for $C_{23}H_{24}N_6O_2S$ | $^1$H NMR (DMSO-d$_6$, 400 MHz): δ 9.65 (s, 1H), 7.78-7.68 (m, 4H), 7.63 (d, J = 8.3 Hz, 2H), 7.44 (d, J = 7.9 Hz, 2H), 5.99 (s, 1H), 3.80 (t, J = 4.5 Hz, 4H), 2.93 (t, J = 4.8 Hz, 4H), 2.38 (s, 3H), 2.15 (s, 3H) |
| 1322 | 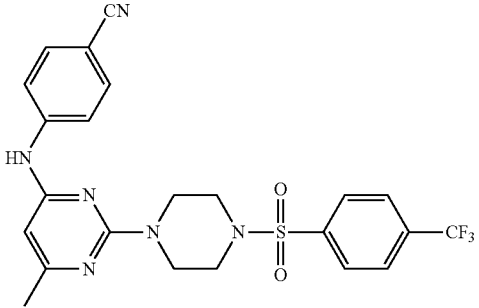 | $A^b$, 18, 50 | 29% | 503.1 (M$^+$ + 1) | 502.14 for $C_{23}H_{21}F_3N_6O_2S$ | $^1$H NMR (DMSO-d$_6$, 400 MHz): δ 9.66 (s, 1H), 8.02-7.96 (m, 4H), 7.76 (d, J = 9.0 Hz, 2H), 7.70 (d, J = 9.0 Hz, 2H), 5.99 (s, 1H), 3.82 (t, J = 4.5 Hz, 4H), 3.03 (t, J = 4.7 Hz, 4H), 2.15 (s, 3H) |

TABLE 1-continued

Synthesis of test compounds from compounds 6, 10, 14, 18, 24, 28, 33, 36, 40, 44 and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1295 | (structure) | A, 24, 48 | 72% | 475.0 (M$^+$ + 1) | 474.15 for $C_{23}H_{24}F_2N_4O_3S$ | $^1$H-NMR (DMSO-d$_6$, 400 MHz): δ 7.82-7.79 (m, 2H), 7.46 (t, J = 8.8 Hz, 2H), 7.26-7.16 (m, 4H), 6.06 (s, 1H), 3.67-3.65 (m, 4H), 2.89 (t, J = 4.8 Hz, 4H), 2.76-2.62 (m, 1H), 1.12 (d, J = 6.8 Hz, 6H) |
| 1296 | (structure) | A, 24, 50 | 46% | 525.0 (M$^+$ + 1) | 524.15 for $C_{24}H_{24}F_4N_4O_3S$ | $^1$H-NMR (DMSO-d$_6$, 400 MHz): δ 8.01-7.94 (m, 4H), 7.26-7.16 (m, 4H), 6.06 (s, 1H), 3.68-3.66 (m, 4H), 2.96 (t, J = 4.8 Hz, 4H), 2.75-2.69 (m, 1H), 1.12 (d, J = 6.8 Hz, 6H) |
| 1287 | (structure) | A, 24, 51 | 58% | 525.0 (M$^+$ + 1) | 524.15 for $C_{24}H_{24}F_4N_4O_3S$ | $^1$H-NMR (DMSO-d$_6$, 400 MHz): δ 8.11 (d, J = 8.0 Hz, 1H), 8.06 (d, J = 7.6 Hz, 1H), 7.96 (s, 1H), 7.88 (t, J = 8.0 Hz, 1H), 7.26-7.16 (m, 4H), 6.06 (s, 1H), 3.67-3.65 (m, 4H), 2.97 (t, J = 4.8 Hz, 4H), 2.76-2.69 (m, 1H), 1.12 (d, J = 6.8 Hz, 6H) |
| 1301 | (structure) | A, 24, 52 | 53% | 457.1 (M$^+$ + 1) | 456.16 for $C_{23}H_{25}FN_4O_3S$ | $^1$H-NMR (DMSO-d$_6$, 400 MHz): δ 7.74-7.69 (m, 3H), 7.65-7.61 (m, 2H), 7.26-7.16 (m, 4H), 6.05 (s, 1H), 3.66-3.64 (m, 4H), 2.88 (t, J = 4.8 Hz, 4H), 2.75-2.68 (m, 1H), 1.12 (d, J = 7.2 Hz, 6H) |

TABLE 1-continued

Synthesis of test compounds from compounds 6, 10, 14, 18, 24, 28, 33, 36, 40, 44 and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1288 | 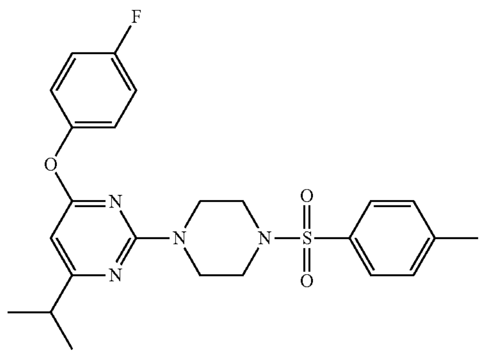 | A, 24, 53 | 59% | 471.1 (M$^+$ + 1) | 470.18 for $C_{24}H_{27}FN_4O_3S$ | $^1$H-NMR (DMSO-d$_6$, 400 MHz): δ 7.61 (d, J = 8.4 Hz, 2H), 7.42 (d, J = 8.0 Hz, 2H), 7.26-7.16 (m, 4H), 6.05 (s, 1H), 3.66-3.64 (m, 4H), 2.85 (t, J = 4.8 Hz, 4H), 2.75-2.68 (m, 1H), 2.38 (s, 3H), 1.12 (d, J = 6.8 Hz, 6H) |
| 1320 | 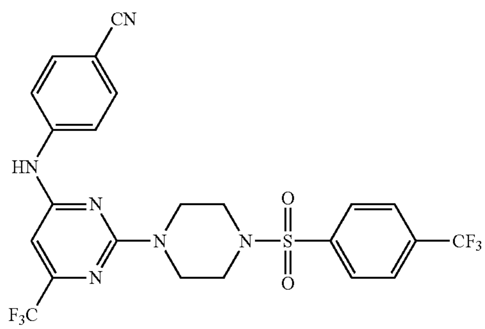 | A$^b$, 28, 50 | 52% | 556.9 (M$^+$ + 1) | 556.11 for $C_{23}H_{18}F_6N_6O_2S$ | $^1$H NMR (DMSO-d$_6$, 400 MHz): δ 10.19 (s, 1H), 8.04-7.95 (m, 4H), 7.79-7.77 (m 4H) 6.44 (s, 1H), 3.85 (t, J = 4.6 Hz, 4H), 3.08 (t, J = 4.6 Hz, 4H) |
| 1329 | 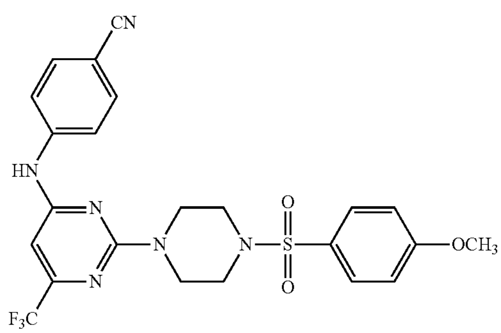 [SMILES: COc1ccc(S(=O)(=O)N2CCN(c3nc(Nc4ccc(C#N)cc4)cc(C(F)(F)F)n3)CC2)cc1] | A$^b$, 28, 46 | 42% | 519.0 (M$^+$ + 1) | 518.13 for $C_{23}H_{21}F_3N_6O_3S$ | $^1$H NMR (DMSO-d$_6$, 400 MHz): δ 10.19 (s, 1H), 7.79-7.77 (m, 4H), 7.69 (d, J = 9.0 Hz, 2H), 7.14 (d, J = 9.0 Hz, 2H), 6.44 (s, 1H), 3.85-3.81 (m, 7H), 2.96 (t, J = 4.7 Hz, 4H) |
| 1324 | 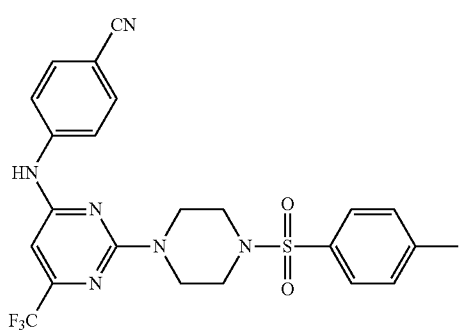 [SMILES: Cc1ccc(S(=O)(=O)N2CCN(c3nc(Nc4ccc(C#N)cc4)cc(C(F)(F)F)n3)CC2)cc1] | A$^b$, 28, 53 | 35 | 503.0 (M$^+$ + 1) | 502.14 for $C_{23}H_{21}F_3N_6O_2S$ | $^1$H NMR (DMSO-d$_6$, 400 MHz): δ 10.19 (s, 1H), 7.79-7.77 (m, 4H), 7.64 (d, J = 8.3 Hz, 2H), 7.44 (d, J = 8.0 Hz, 2H), 6.44 (s, 1H), 3.83 (t, J = 4.4 Hz, 4H), 2.97 (t, J = 4.8 Hz, 4H), 2.38 (s, 3H) |

TABLE 1-continued

Synthesis of test compounds from compounds 6, 10, 14, 18, 24, 28, 33, 36, 40, 44 and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1325 | 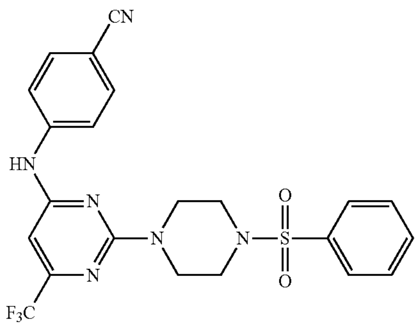 | A$^b$, 28, 52 | 34 | 489.0 (M$^+$ + 1) | 488.12 for $C_{22}H_{19}F_3N_6O_2S$ | $^1$H NMR (DMSO-d$_6$, 400 MHz): δ 10.19 (s, 1H), 7.80-7.69 (m, 7H), 7.68-7.61 (m 2H) 6.44 (s, 1H), 3.83 (t, J = 4.5 Hz, 4H), 3.00 (t, J = 4.7 Hz, 4H) |
| 1326 | 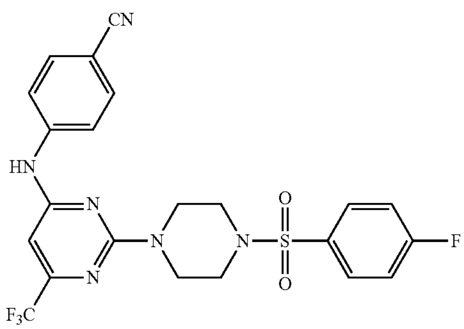 [SMILES: N#Cc1ccc(Nc2cc(C(F)(F)F)nc(N3CCN(S(=O)(=O)c4ccc(F)cc4)CC3)n2)cc1] | A$^b$, 28, 48 | 41 | 507.1 (M$^+$ + 1) | 506.11 for $C_{22}H_{18}F_4N_6O_2S$ | $^1$H NMR (DMSO-d$_6$, 400 MHz): δ 10.20 (s, 1H), 7.86-7.80 (m, 2H), 7.79-7.77 (m 4H) 7.48 (t, J = 8.9 Hz, 2H), 6.45 (s, 1H), 3.86-3.82 (m, 4H), 3.02 (t, J = 4.8 Hz, 4H) |
| 1157 | 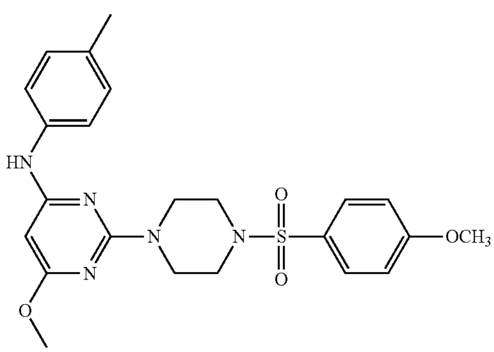 [SMILES: COc1ccc(S(=O)(=O)N2CCN(c3nc(Nc4ccc(C)cc4)cc(OC)n3)CC2)cc1] | A$^c$, 33, 46 | 69 | 470.4 (M$^+$ + 1) | 469.18 for $C_{23}H_{27}N_5O_4S$ | $^1$H-NMR (DMSO-d$_6$, 400 MHz): δ 8.92 (s, 1H), 7.68 (d, J = 8.8 Hz, 2H), 7.33 (d, J = 8.4 Hz, 2H), 7.13 (d, J = 8.8 Hz, 2H), 7.07 (d, J = 8.0 Hz, 2H), 5.34 (s, 1H), 3.83 (s, 3H), 3.78 (t, J = 4.8 Hz, 4H), 3.72 (s, 3H), 2.89 (t, J = 4.8 Hz, 4H), 2.23 (s, 3H) |
| 1150 | 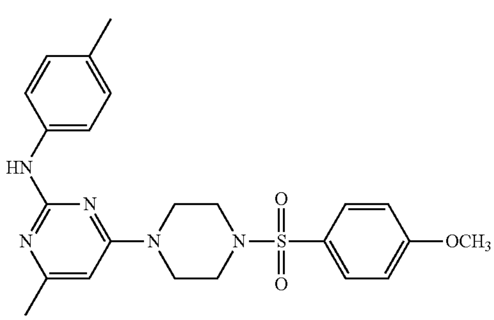 [SMILES: COc1ccc(S(=O)(=O)N2CCN(c3cc(C)nc(Nc4ccc(C)cc4)n3)CC2)cc1] | A, 36, 46 | 39 | 454.0 (M$^+$ + 1) | 453.18 for $C_{23}H_{27}N_5O_3S$ | $^1$H-NMR (DMSO-d$_6$, 400 MHz): δ 8.97 (br s, 1H), 7.68 (d, J = 8.8 Hz, 2H), 7.50 (d, J = 8.4 Hz, 2H), 7.13 (d, J = 8.8 Hz, 2H), 7.03 (d, J = 8.4 Hz, 2H), 6.12 (s, 1H), 3.82 (s, 3H), 3.69 (t, J = 4.4 Hz, 4H), 2.91 (t, J = 4.4 Hz, 4H), 2.22 (s, 3H), 2.15 (s, 3H) |

TABLE 1-continued

Synthesis of test compounds from compounds 6, 10, 14, 18, 24, 28, 33, 36, 40, 44 and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1151 | 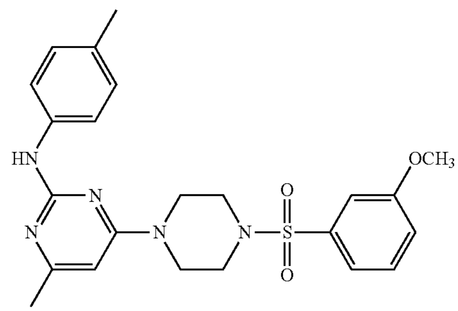 [SMILES: COc1cccc(S(=O)(=O)N2CCN(c3cc(C)nc(Nc4ccc(C)cc4)n3)CC2)c1] | A, 36, 47 | 44% | 454.1 | 453.18 for (M$^+$ + 1) $C_{23}H_{27}N_5O_3S$ | $^1$H-NMR (DMSO-d$_6$, 400 MHz): δ 8.90 (s, 1H), 7.57-7.52 (m, 3H), 7.32-7.26 (m, 2H), 7.20-7.19 (m, 1H), 7.02 (d, J = 8.0 Hz, 2H), 6.08 (s, 1H), 3.83 (s, 3H), 3.68 (t, J = 4.8 Hz, 4H), 2.97 (t, J = 4.8 Hz, 4H), 2.21 (s, 3H), 2.14 (s, 3H) |
| 1172 | 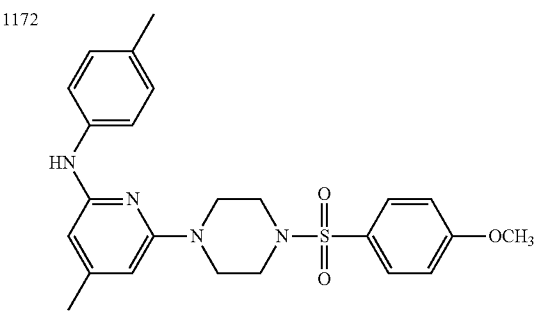 | A$^b$, 40, 46 | 40% | 453.0 | 452.19 for (M$^+$ + 1) $C_{24}H_{28}N_4O_3S$ | $^1$H-NMR (DMSO-d$_6$, 400 MHz): δ 8.48 (s, 1H), 7.69 (d, J = 8.8 Hz, 2H), 7.36 (d, J = 8.4 Hz, 2H), 7.14 (d, J = 9.2 Hz, 2H), 7.02 (d, J = 8.0 Hz, 2H), 5.93 (s, 2H), 3.83 (s, 3H), 3.53 (t, J = 4.8 Hz, 4H), 2.92 (t, J = 4.8 Hz, 4H), 2.21 (s, 3H), 2.08 (s, 3H) |
| 1173 | 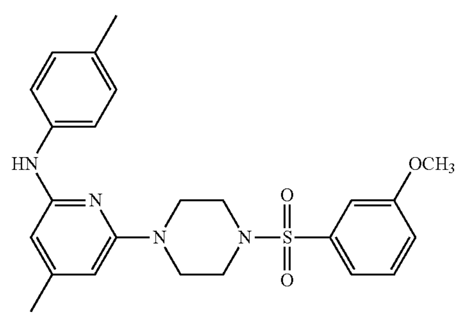 [SMILES: COc1cccc(S(=O)(=O)N2CCN(c3cc(C)cc(Nc4ccc(C)cc4)n3)CC2)c1] | A$^b$, 40, 47 | 48% | 453.0 | 452.19 for (M$^+$ + 1) $C_{24}H_{28}N_4O_3S$ | $^1$H-NMR (DMSO-d$_6$, 400 MHz): δ 8.48 (s, 1H), 7.56 (t, J = 8.0 Hz, 1H), 7.36 (d, J = 8.4 Hz, 2H), 7.33-7.26 (m, 2H), 7.20-7.19 (m, 1H), 7.02 (d, J = 8.4 Hz, 2H), 5.93 (s, 2H), 3.83 (s, 3H), 3.52 (t, J = 4.8 Hz, 4H), 2.98 (t, J = 4.8 Hz, 4H), 2.21 (s, 3H), 2.09 (s, 3H) |
| 1158 | 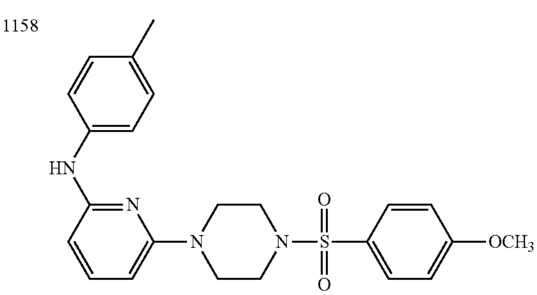 | A, 44, 46 | 32% | 439.4 | 438.17 for (M$^+$ + 1) $C_{23}H_{26}N_4O_3S$ | $^1$H-NMR (DMSO-d$_6$, 400 MHz): δ 8.59 (s, 1H), 7.69 (d, J = 8.8 Hz, 2H), 7.38 (d, J = 8.4 Hz, 2H), 7.28 (t, J = 8.0 Hz, 1H), 7.14 (d, J = 8.8 Hz, 2H), 7.03 (d, J = 8.4 Hz, 2H), 6.09-6.06 (m, 2H), 3.83 (s, 3H), 3.53 (t, J = 4.4 Hz, 4H), 2.93 (t, J = 4.4 Hz, 4H), 2.22 (s, 3H) |

TABLE 1-continued

Synthesis of test compounds from compounds 6, 10, 14, 18, 24, 28, 33, 36, 40, 44 and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1168 | 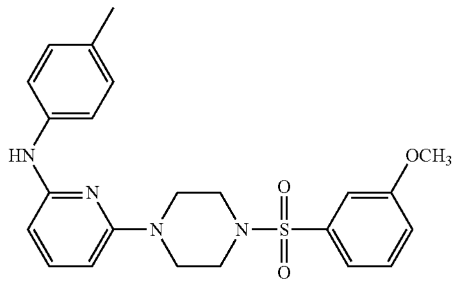 [SMILES: COc1cccc(S(=O)(=O)N2CCN(c3cccc(Nc4ccc(C)cc4)n3)CC2)c1] | A$^c$, 44, 47 | 49% | 439.3 (M$^+$ + 1) | 438.17 for $C_{23}H_{26}N_4O_3S$ | $^1$H-NMR (DMSO-d$_6$, 400 MHz): δ 8.59 (s, 1H), 7.56 (t, J = 8.0 Hz, 1H), 7.38 (d, J = 8.4 Hz, 2H), 7.33-7.27 (m, 3H), 7.21-7.20 (m, 1H), 7.04 (d, J = 8.0 Hz, 2H), 6.08 (d, J = 8.0 Hz, 2H), 3.83 (s, 3H), 3.53 (t, J = 4.8 Hz, 4H), 2.99 (t, J = 4.8 Hz, 4H), 2.22 (s, 3H) |

$^a$3 h, RT;
$^b$16 h, RT;
$^c$4 h, RT.

Example 12: Synthesis of 1160

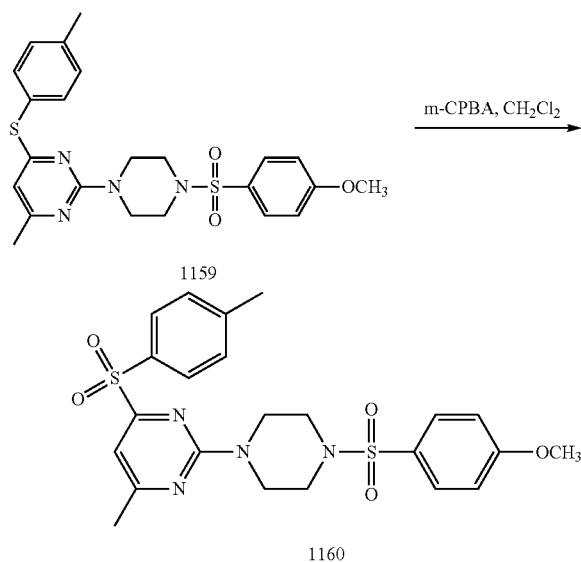

Synthesis of 2-(4-((4-methoxyphenyl) sulfonyl) piperazin-1-yl)-4-methyl-6-tosylpyrimidine (1160)

To a stirred solution of 1159 (100 mg, 0.21 mmol) in CH$_2$Cl$_2$ (10 mL) under argon atmosphere was added m-chloroperoxybenzoic acid (73 mg, 0.42 mmol) at 0° C.; warmed to RT and stirred for 3 h. The reaction was monitored by TLC; after completion of the reaction, the reaction mixture was diluted with CH$_2$Cl$_2$ (15 mL), washed with 1 N NaOH solution (2×10 mL). The organic layer was dried over sodium sulfate, filtered and concentrated in vacuo to obtain the crude. The crude was purified through silica gel column chromatography using 70% EtOAc/hexanes to afford 1160 (60 mg, 56%) as an off-white solid. TLC: 50% EtOAc/hexanes (R$_f$, 0.2); $^1$H-NMR (DMSO-d$_6$, 400 MHz): δ 7.81 (d, J=8.4 Hz, 2H), 7.65 (d, J=9.2 Hz, 2H), 7.45 (d, J=8.0 Hz, 2H), 7.13-7.11 (m, 3H), 3.82 (s, 3H), 3.75-3.74 (m, 4H), 2.87 (t, J=4.8 Hz, 4H), 2.40 (s, 3H), 2.37 (s, 3H); LC-MS: 97.60%; 503.5 (M$^-$+1); (column; X-Select CSH C-18 (50× 3.0 mm, 3.5 μm); RT 4.17 min. 5.0 mM NH$_4$OAc:ACN; 0.8 mL/min); UPLC (purity): 97.70%; (column: Acquity BEH C-18 (50×2.1 mm, 1.7μ); RT 2.76 min. ACN: 0.025% TFA (Aq); 0.5 mL/min).

Example 13: Synthesis of 2-(4-((4-methoxyphenyl) sulfonyl) piperazin-1-yl)-4-methyl-6-(methylsulfonyl) pyrimidine (58)—A Common Intermediate

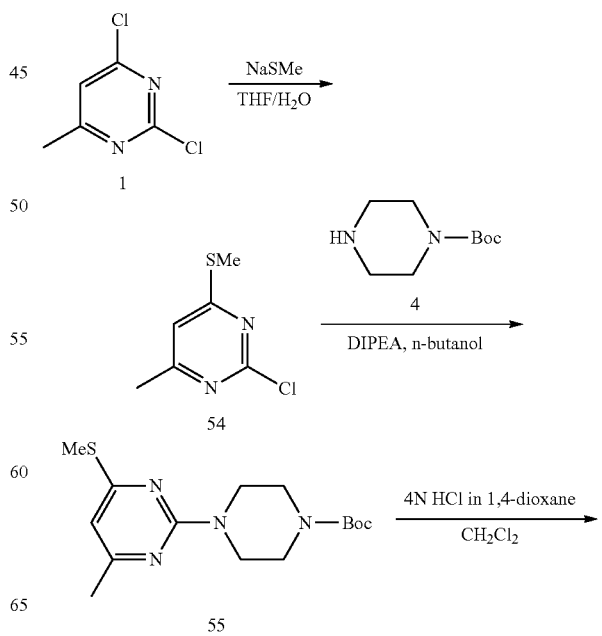

-continued

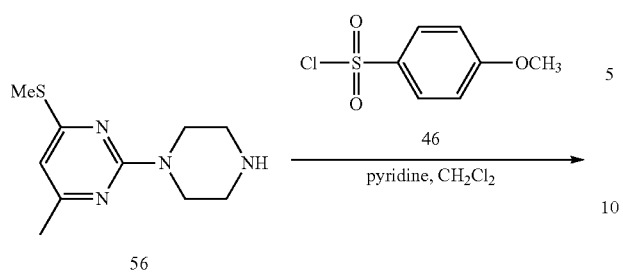

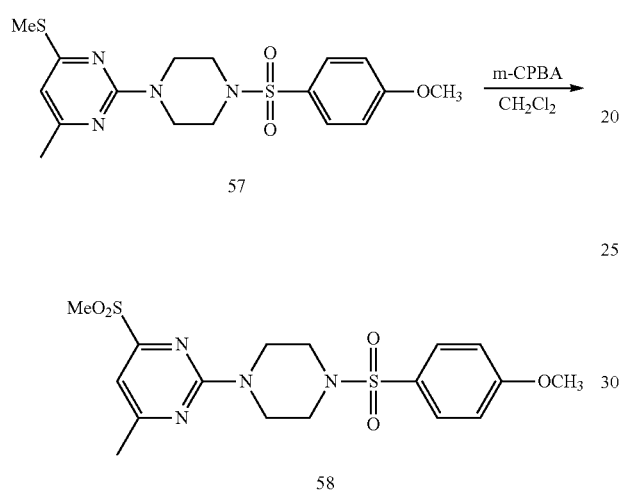

Synthesis of 2-chloro-4-methyl-6-(methylthio) pyrimidine (54)

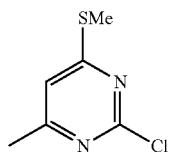

To a stirred solution of 2, 4-dichloro-6-methylpyrimidine 1 (200 mg, 1.22 mmol) under argon atmosphere in THF (10 mL) was added sodium methanethiolate (103 mg, 1.47 mmol in 4 mL of water) at −10° C. and stirred for 2 h. The reaction was monitored by TLC; after completion of the reaction, the reaction mixture was diluted with water (20 mL) and extracted with EtOAc (2×30 mL). The combined organic extracts were dried over sodium sulfate, filtered and concentrated in vacuo to obtain the crude. The crude was purified through silica gel column chromatography using 3% EtOAc/hexanes to afford compound 54 (130 mg, 61%) as white solid. TLC: 5% EtOAc/Toluene ($R_f$ 0.8); $^1$H-NMR (DMSO-$d_6$, 400 MHz): δ 7.38 (s, 1H), 2.53 (s, 3H), 2.37 (s, 3H).

Synthesis of tert-butyl 4-(4-methyl-6-(methylthio) pyrimidin-2-yl) piperazine-1-carboxylate (55)

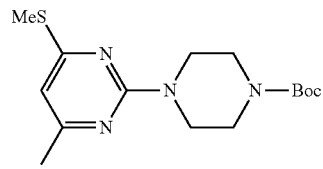

To a stirred solution of compound 54 (100 mg, 0.57 mmol) in n-butanol (5 mL) under argon atmosphere were added tert-butyl piperazine-1-carboxylate 4 (160 mg, 0.86 mmol), diisopropylethyl amine (0.16 mL, 0.86 mmol) at RT; heated to 100° C. and stirred for 24 h in a sealed tube. The reaction was monitored by TLC; after completion of the reaction, the volatiles were removed in vacuo to obtain crude. The crude was purified through silica gel column chromatography using 10% EtOAc/hexanes to afford compound 55 (120 mg, 65%) as sticky white solid. TLC: 15% EtOAc/hexanes ($R_f$ 0.7); $^1$H-NMR (DMSO-$d_6$, 400 MHz): δ 6.48 (s, 1H), 3.70 (t, J=4.8 Hz, 4H), 3.78 (t, J=4.8 Hz, 4H), 2.45 (s, 3H), 2.20 (s, 3H), 1.42 (s, 9H).

Synthesis of 4-methyl-6-(methylthio)-2-(piperazin-1-yl) pyrimidine (56)

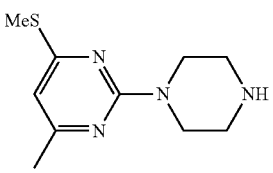

To a stirred solution of compound 55 (2 g, 6.17 mmol) in CH$_2$Cl$_2$ (40 mL) under inert atmosphere was added 4 N HCl in 1,4-dioxane (10 mL) at 0° C.; warmed to RT and stirred for 3 h. The reaction was monitored by TLC; after completion of the reaction, the volatiles were removed in vacuo. The residue was neutralized with saturated NaHCO$_3$ solution (30 mL) and extracted with CH$_2$Cl$_2$ (2×30 mL). The combined organic extracts were dried over sodium sulfate, filtered and concentrated in vacuo to afford crude compound 56 (1.2 g) as white solid. TLC: 10% MeOH/CH$_2$Cl$_2$ ($R_f$ 0.2); $^1$H-NMR (DMSO-$d_6$, 400 MHz): δ 6.41 (s, 1H), 3.63 (t, J=5.2 Hz, 4H), 2.70 (t, J=5.2 Hz, 4H), 2.43 (s, 3H), 2.17 (s, 3H).

Synthesis of 2-(4-((4-methoxyphenyl) sulfonyl) piperazin-1-yl)-4-methyl-6-methylthio) pyrimidine (57)

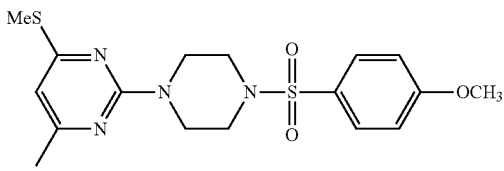

To a stirred solution of 56 (1.2 g, crude) in CH$_2$Cl$_2$ (30 mL) under argon atmosphere were added pyridine (2.18 mL, 26.75 mmol), 4-methoxybenzenesulfonyl chloride 35 (1.21 g, 5.87 mmol) at 0° C.; warmed to RT, stirred for 4 h. The reaction was monitored by TLC; after completion of the reaction, the reaction mixture was diluted with water (20 mL) and extracted with CH$_2$Cl$_2$ (2×30 mL). The combined organic extracts were washed with 1 N HCl (2×50 mL), 10% NaHCO$_3$ solution (2×50 mL), brine (30 mL), dried over sodium sulfate, filtered and concentrated in vacuo to obtain the crude. The crude was triturated with pentane (2×5 mL) to afford compound 57 (1.2 g, 57%) as white solid. TLC: 50% EtOAc/hexanes (R$_f$: 0.8); $^1$H-NMR (DMSO-d$_6$, 400 MHz): δ 7.67 (d, J=8.8 Hz, 2H), 7.13 (d, J=9.2 Hz, 2H), 6.46 (s, 1H), 3.83 (s, 3H), 3.81 (t, J=5.2 Hz, 4H), 2.89 (t, J=4.8 Hz, 4H), 2.41 (s, 3H), 2.16 (s, 3H).

Synthesis of 2-(4-((4-methoxyphenyl) sulfonyl) piperazin-1-yl)-4-methyl-6-(methylsulfonyl) pyrimidine (58)

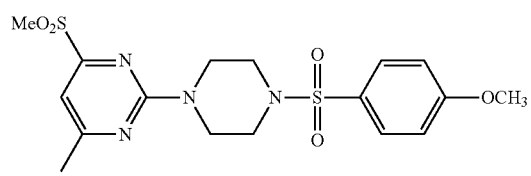

58

To a stirred solution of 57 (1.2 g, 3.04 mmol) in CH$_2$Cl$_2$ (48 mL) under argon atmosphere were added m-chloroperoxybenzoic acid (1.4 g, 8.11 mmol) at 0° C.; warmed to RT, stirred for 24 h. The reaction was monitored by TLC; after completion of the reaction, the reaction mixture was diluted with water (50 mL) and extracted with CH$_2$Cl$_2$ (2×150 mL). The combined organic extracts were washed with 10% NaHCO$_3$ solution (100 mL), dried over sodium sulfate, filtered and concentrated in vacuo to obtain the crude. The crude was purified through silica gel column chromatography using 40% EtOAc/hexanes to afford compound 58 (1 g, 77%) as an off-white solid. TLC: 60% EtOAc/hexanes (R$_f$: 0.5); $^1$H-NMR (DMSO-d$_6$, 400 MHz): δ 7.68 (d, J=9.2 Hz, 2H), 7.14 (d, J=9.2 Hz, 2H), 7.03 (s, 1H), 3.88 (t, J=4.8 Hz, 4H), 3.83 (s, 3H), 3.21 (s, 3H), 2.94 (t, J=4.8 Hz, 4H), 2.39 (s, 3H).

Example 14: Synthesis of 4-chloro-2-(4-((4-methoxyphenyl) sulfonyl) piperazin-1-yl)-6-methyl-pyrimidine (67)—A Common Intermediate

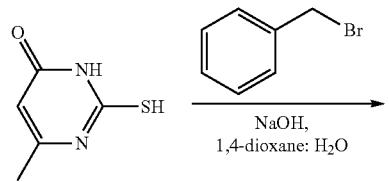

59

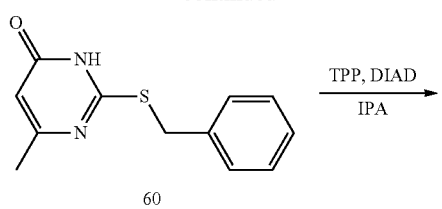

60

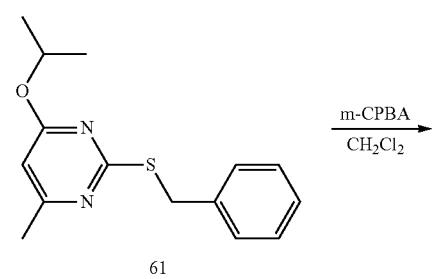

61

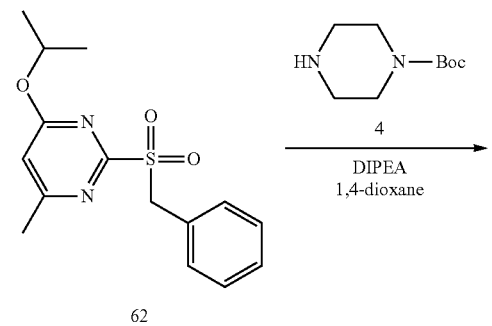

62

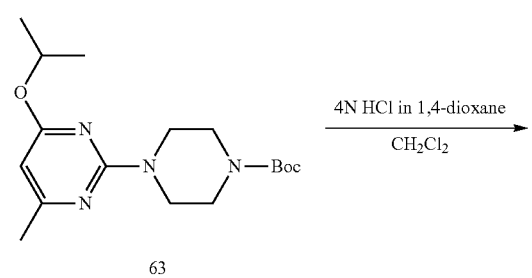

63

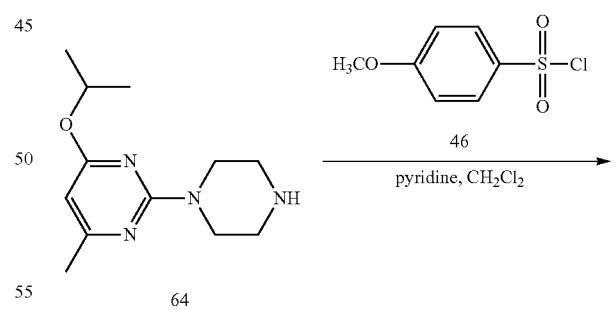

64

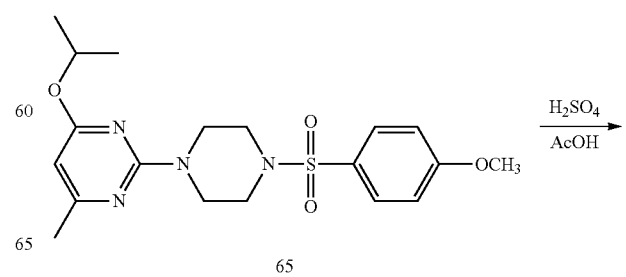

65

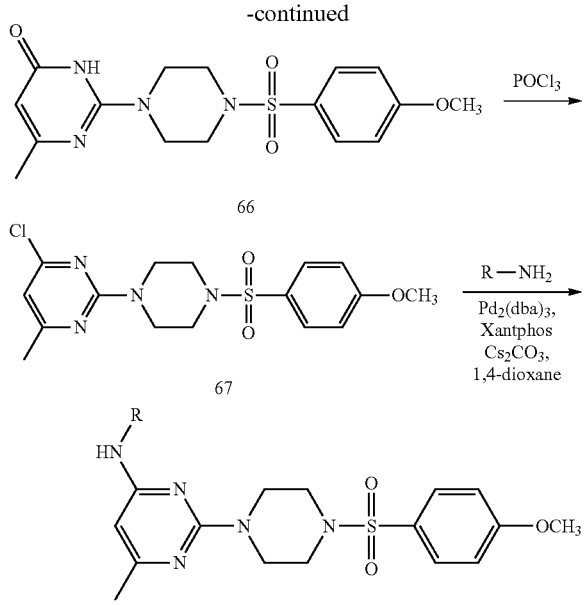

Synthesis of 2-(benzylthio)-6-methylpyrimidin-4 (3H)-one (60)

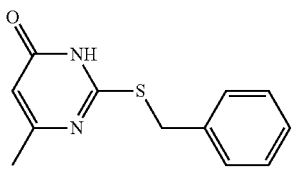

To a stirred solution of 2-mercapto-6-methylpyrimidin-4 (3H)-one 59 (1 g, 7.04 mmol) in 1, 4-dioxane (10 mL) was added sodium hydroxide (563 mg, 14.07 mmol in 10 mL of water) and benzyl bromide (1.3 g, 7.74 mmol) at 0° C.; heated to 50° C. and stirred for 1 h. The reaction was monitored by TLC; after completion of the reaction, the reaction mixture was diluted with ice cold water (20 mL) and the pH was neutralized with 6 N HCl. The precipitated solid was filtered, washed with EtOAc (2×5 mL), water (2×10 mL) and dried in vacuo to afford compound 60 (1 g, 62%) as yellow syrup. TLC: 40% EtOAc/hexane ($R_f$ 0.5); $^1$H-NMR (DMSO-$d_6$, 400 MHz): δ 12.50-12.23 (m, 1H), 7.42-7.39 (m, 2H), 7.33-7.22 (m, 3H), 5.99 (br s, 1H), 4.37 (s, 2H), 2.20 (s, 3H).

Synthesis of 2-(benzylthio)-4-isopropoxy-6-methylpyrimidine (61)

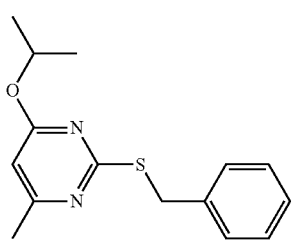

To a stirred solution of diisopropyl azodicarboxylate (1.3 g, 6.46 mmol) in ether (10 mL) under argon atmosphere were added triphenyl phosphine (1.6 g, 6.46 mmol) and compound 60 (500 mg, 2.15 mmol) at RT and stirred for 15 min. To this was added isopropyl alcohol (0.4 mL, 5.38 mmol) at RT; stirred for 72 h. The reaction was monitored by TLC; after completion of the reaction, the volatiles were removed in vacuo to obtain the crude. The crude was purified through silica gel column chromatography using 5% EtOAc/hexanes to afford compound 61 (350 mg, 59%) as yellow syrup. TLC: 40% EtOAc/hexanes ($R_f$ 0.7); $^1$H-NMR (DMSO-$d_6$, 400 MHz): δ 7.41 (d, J=8.4 Hz, 2H), 7.32-7.28 (m, 2H), 7.25-7.21 (m, 1H), 6.40 (s, 1H), 5.30-5.29 (m, 1H), 4.36 (s, 2H), 2.29 (s, 3H), 1.25 (d, J=6.4 Hz, 6H).

Synthesis of 2-(benzylsulfonyl)-4-isopropoxy-6-methylpyrimidine (62)

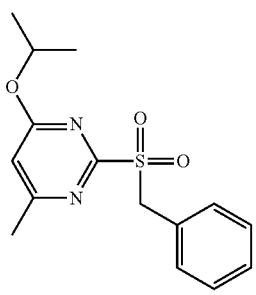

To a stirred solution of compound 61 (650 mg, 2.37 mmol) in CH$_2$Cl$_2$ (10 mL) under argon atmosphere were added m-chloroperoxybenzoic acid (818 mg, 4.74 mmol) at 0° C.; warmed to RT and stirred for 4 h. The reaction was monitored by TLC; after completion of the reaction, the reaction mixture was diluted with water (20 mL) and extracted with CH$_2$Cl$_2$ (2×30 mL). The combined organic extracts were washed with 10% NaHCO$_3$ solution (30 mL) dried over sodium sulfate, filtered and concentrated in vacuo to obtain the crude. The crude was purified through silica gel column chromatography using 40% EtOAc/hexanes to afford compound 62 (530 mg, 73%) as white solid. TLC: 30% EtOAc/hexanes ($R_f$ 0.4); $^1$H-NMR (DMSO-$d_6$, 400 MHz): δ 7.39-7.29 (m, 5H), 7.02 (s, 1H), 5.36-5.30 (m, 1H), 4.90 (s, 2H), 2.49 (d, J=4.8 Hz, 3H), 1.31 (d, J=6.0 Hz, 6H).

Synthesis of tert-butyl 4-(4-isopropoxy-6-methylpyrimidin-2-yl) piperazine-1-carboxylate (63)

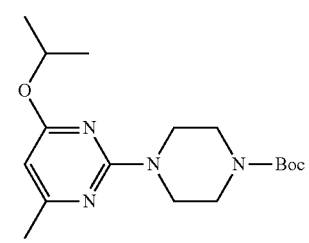

To a stirred solution of compound 62 (200 mg, 0.65 mmol) in 1, 4-dioxane (10 mL) under argon atmosphere were added tert-butyl piperazine-1-carboxylate 4 (364 mg, 1.96 mmol), diisopropylethyl amine (0.28 mL, 1.96 mmol) at RT; heated to 90° C. and stirred for 48 h. The reaction was monitored by TLC; after completion of the reaction, the volatiles were removed in vacuo to obtain crude. The crude was purified through silica gel column chromatography using 20% EtOAc/hexanes to afford compound 63 (150 mg, 64%) as yellow syrup. TLC: 40% EtOAc/hexanes ($R_f$ 0.6); $^1$H-NMR (DMSO-$d_6$, 400 MHz): δ 5.89 (s, 1H), 5.24-5.18 (m, 1H), 3.68-3.65 (m, 4H), 3.38-3.58 (m, 4H), 2.17 (s, 3H), 1.48 (s, 9H), 1.26 (d, J=6.0 Hz, 6H).

Synthesis of 4-isopropoxy-6-methyl-2-(piperazin-1-yl) pyrimidine (64)

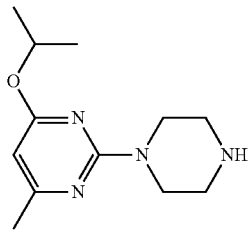

64

To a stirred solution of compound 63 (150 mg, 0.44 mmol) in CH$_2$Cl$_2$ (5 mL) under inert atmosphere was added 4 N HCl in 1,4-dioxane (0.6 mL) at 0° C.; warmed to RT and stirred for 4 h. The reaction was monitored by TLC; after completion of the reaction, the volatiles were removed in vacuo. The pH of the residue was neutralized with saturated NaHCO$_3$ solution (30 mL) and extracted with CH$_2$Cl$_2$ (2×30 mL). The combined organic extracts were dried over sodium sulfate, filtered and concentrated in vacuo to afford compound 64 (80 mg, 80%) as white solid. TLC: 40% EtOAc/ hexanes ($R_f$ 0.2); $^1$H-NMR (DMSO-$d_6$, 400 MHz): δ 5.81 (s, 1H), 5.22-5.12 (m, 1H), 3.62-3.58 (m, 4H), 2.72-2.65 (m, 4H), 2.12 (s, 3H), 1.25 (d, J=6.0 Hz, 6H).

Synthesis of 4-isopropoxy-2-(4-((4-methoxyphenyl) sulfonyl) piperazin-1-yl)-6-methylpyrimidine (65)

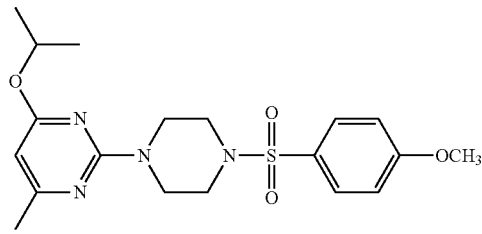

65

To a stirred solution of 64 (80 mg, 0.35 mmol) in CH$_2$Cl$_2$ (5 mL) under argon atmosphere were added pyridine (0.14 mL, 2.2 mmol), 4-methoxybenzenesulfonyl chloride 46 (100 mg, 0.48 mmol) at 0° C.; warmed to RT, stirred for 4 h. The reaction was monitored by TLC; after completion of the reaction, the reaction mixture was diluted with water (20 mL) and extracted with CH$_2$Cl$_2$ (2×30 mL). The combined organic extracts were washed with 1 N HCl (20 mL), 10% NaHCO$_3$ solution (30 mL), brine (30 mL), dried over sodium sulfate, filtered and concentrated in vacuo to afford crude compound 65 (100 mg) as an off-white solid. TLC: 5% MeOH/CH$_2$Cl$_2$ ($R_f$ 0.8); $^1$H-NMR (DMSO-$d_6$, 400 MHz): δ 7.67 (d, J=7.2 Hz, 2H), 7.13 (d, J=7.2 Hz, 2H), 5.87 (s, 1H), 5.18-5.12 (m, 1H), 3.83 (s, 3H), 3.78 (t, J=4.8 Hz, 4H), 2.88 (t, J=4.8 Hz, 4H), 2.13 (s, 3H), 1.22 (d, J=6.0 Hz, 6H).

Synthesis of 2-(4-((4-methoxyphenyl) sulfonyl) piperazin-1-yl)-6-methylpyrimidin-4 (3H)-one (66)

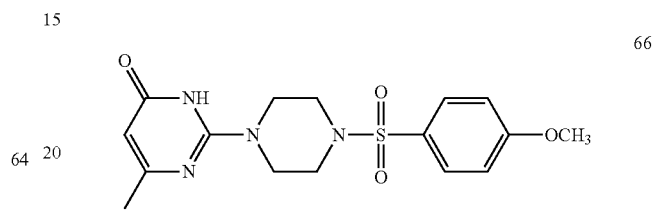

66

To a stirred solution of compound 65 (100 mg, 0.24 mmol) in acetic acid (5 mL) was added 10% aqueous H$_2$SO$_4$ (5 mL) at 0° C. and heated to 90° C. for 2 h. The reaction was monitored by TLC; after completion of the reaction, the volatiles were removed in vacuo. The pH of the residue was neutralized with 4 N aqueous NaOH solution (30 mL) and extracted with 10% MeOH/CH$_2$Cl$_2$ (2×30 mL). The combined organic extracts were dried over sodium sulfate, filtered and concentrated in vacuo to afford compound 66 (70 mg, 78%) as off-white solid. TLC: 5% MeOH/CH$_2$Cl$_2$ ($R_f$ 0.2); $^1$H-NMR (DMSO-$d_6$, 400 MHz): δ 7.67 (d, J=7.2 Hz, 2H), 7.14 (d, J=7.2 Hz, 2H), 5.57 (s, 1H), 3.84 (s, 3H), 3.69 (t, J=4.8 Hz, 4H), 2.86 (t, J=4.8 Hz, 4H), 2.02 (s, 3H).

Synthesis of 4-chloro-2-(4-((4-methoxyphenyl) sulfonyl) piperazin-1-yl)-6-methylpyrimidine (67)

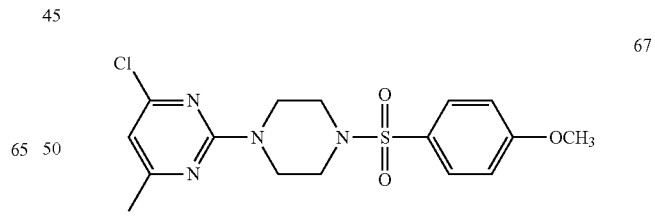

67

To compound 66 (70 mg, 0.19 mmol) was added phosphorous oxychloride (3 mL) under argon atmosphere at 0° C.; heated to 90° C. for 3 h. The reaction was monitored by TLC; after completion of the reaction, the volatiles were removed in vacuo. The pH of the residue was neutralized with aqueous NaHCO$_3$ solution (30 mL) and extracted with EtOAc (2×30 mL). The combined organic extracts were dried over sodium sulfate, filtered and concentrated in vacuo to afford compound 67 (50 mg, 68%) as off-white solid. TLC: 5% MeOH/CH$_2$Cl$_2$ ($R_f$ 0.7); $^1$H-NMR (DMSO-$d_6$, 400 MHz): δ 7.66 (d, J=7.2 Hz, 2H), 7.13 (d, J=6.8 Hz, 2H), 6.65 (s, 1H), 3.83 (s, 3H), 3.80 (t, J=4.8 Hz, 4H), 2.91 (t, J=4.8 Hz, 4H), 2.24 (s, 3H).

Example 15: Preparation of Additional Test Compounds

Test compounds were prepared using compounds 58 or 67 and suggested amines employing the following Procedures B or C and the results are captured in Table 2 below.

Synthesis of Test Compounds

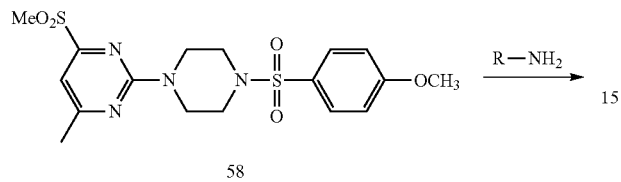

58

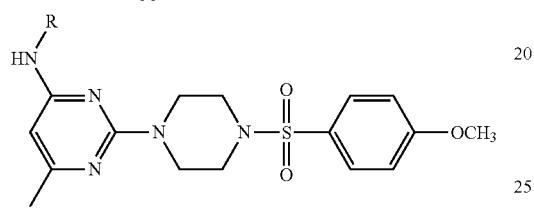

Procedure B: A mixture of compound 58 (75 mg, 0.17 mmol) and [1,1'-biphenyl]-4-amine 68 (1 g) was heated at 120-130° C. in a sealed tube for 5 h. The reaction was monitored by TLC; after completion the reaction, the reaction mixture was diluted with water (20 mL) and extracted with CH$_2$Cl$_2$ (3×50 mL). The combined organic extracts were dried over sodium sulfate, filtered and concentrated in vacuo to obtain the crude. The crude was either directly dried in vacuo or triturated or purified by column chromatography or preparative HPLC to afford the desired compound.

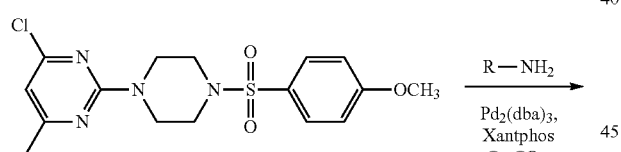

67

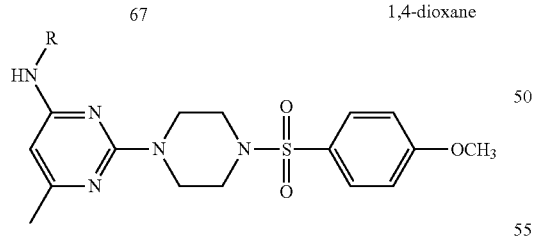

Procedure C: To a stirred solution of compound 67 (70 mg, 0.18 mmol) in 1,4-dioxane (3 mL) under argon atmosphere were added 4-amino pyridine 69 (32.4 mg, 0.20 mmol), Cs$_2$CO$_3$ (71 mg, 0.21 mmol) at RT, purged under argon for 30 min. To this were added Pd$_2$(dba)$_3$ (4 mg, 0.004 mmol), xantphos (5.2 mg, 0.009 mmol), heated to 110-120° C. and stirred for 16 h. The reaction was monitored by TLC; after completion of the reaction, the volatiles were removed in vacuo to obtain the crude. The residue was diluted with water extracted with EtOAc (2×20 mL). The combined organic extracts were dried over sodium sulfate, filtered and dried in vacuo to obtain the crude. The crude was directly dried in vacuo, triturated or purified by column chromatography or preparative HPLC to afford the desired compound.

Commercially Available Amines Used for the Synthesis of Test Compounds

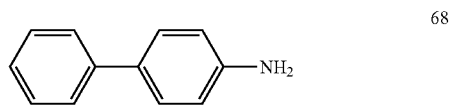

68

69

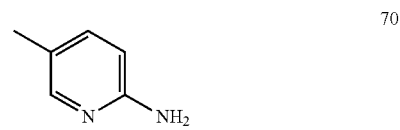

70

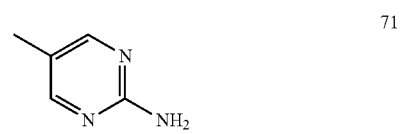

71

72

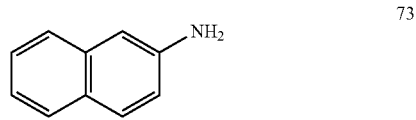

73

74

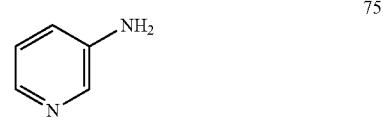

75

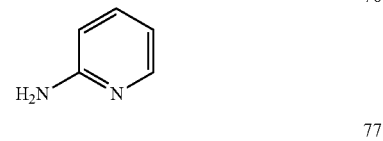

76

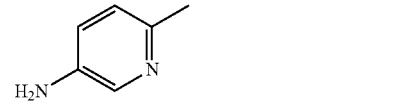

77

TABLE 2

Synthesis of test compounds from compounds 58, 67 and various amines

| No. | Structure | Procedure, Intermediate, amine | Rx. Yield (%) | Mass Spec. Found | Mass Spec. Calculated | $^1$H-NMR |
|---|---|---|---|---|---|---|
| 1201 | 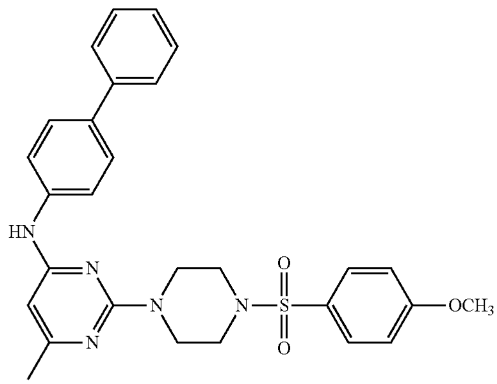 [SMILES: COc1ccc(S(=O)(=O)N2CCN(c3nc(C)cc(Nc4ccc(-c5ccccc5)cc4)n3)CC2)cc1] | B, 58, 68 | 36% | 516.0 (M$^+$ + 1) | 515.20 for $C_{28}H_{29}N_5O_3S$ | $^1$H-NMR (DMSO-d$_6$, 400 MHz): δ 9.25 (s, 1H), 7.70-7.60 (m, 8H), 7.44 (t, J = 7.6 Hz, 2H), 7.31 (d, J = 7.2 Hz, 1H), 7.13 (t, J = 8.8 Hz, 2H), 5.94 (s, 1H), 3.82-3.80 (m, 7H), 2.91 (t, J = 5.2 Hz, 4H), 2.12 (s, 3H) |
| 1240 | 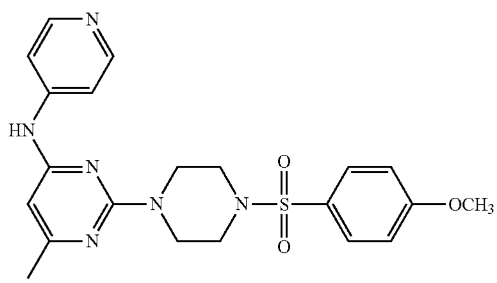 [SMILES: COc1ccc(S(=O)(=O)N2CCN(c3nc(C)cc(Nc4ccncc4)n3)CC2)cc1] | C$^a$, 67, 69 | 45% | 441.3 (M$^+$ + 1) | 440.16 for $C_{21}H_{24}N_6O_3S$ | $^1$H-NMR (DMSO-d$_6$, 400 MHz): δ 9.57 (s, 1H), 8.34-8.33 (m, 2H), 7.68 (d, J = 8.8 Hz, 2H), 7.55-7.53 (m, 2H), 7.13 (d, J = 8.8 Hz, 2H), 6.00 (s, 1H), 3.82-3.80 (m, 7H), 2.92 (t, J = 5.2 Hz, 4H), 2.15 (s, 3H) |
| 1200 | 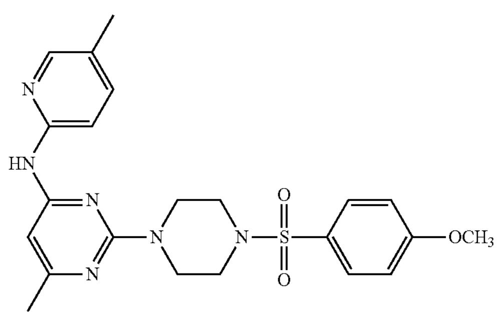 [SMILES: COc1ccc(S(=O)(=O)N2CCN(c3nc(C)cc(Nc4ccc(C)cn4)n3)CC2)cc1] | C, 67, 70 | 36% | 455.0 (M$^+$ + 1) | 454.18 for $C_{22}H_{26}N_6O_3S$ | $^1$H-NMR (DMSO-d$_6$, 400 MHz): δ 9.56 (s, 1H), 8.07 (s, 1H), 7.69-7.64 (m, 3H), 7.65 (d, J = 8.8 Hz, 1H), 7.52 (d, J = 8.4 Hz, 2H), 6.59 (s, 1H), 3.82 (s, 3H), 3.80 (t, J = 5.2 Hz, 4H), 2.90 (t, J = 4.8 Hz, 4H), 2.21 (s, 3H), 2.13 (s, 3H) |
| 1261 | 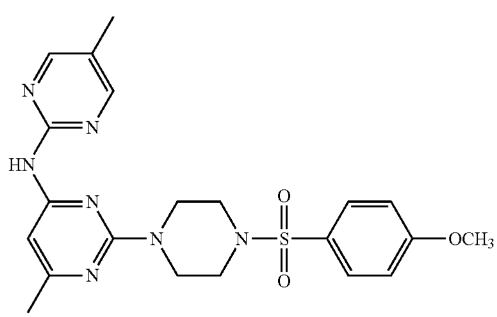 | C, 67, 71 | 50% | 456.5 (M$^+$ + 1) | 455.17 for $C_{21}H_{25}N_7O_3S$ | $^1$H-NMR (DMSO-d$_6$, 400 MHz): δ 9.54 (s, 1H), 8.44 (s, 2H), 7.67 (d, J = 8.8 Hz, 2H), 7.37 (s, 1H), 7.13 (d, J = 9.2 Hz, 2H), 3.82 (s, 3H), 3.80 (t, J = 5.2 Hz, 4H), 2.89 (t, J = 4.8 Hz, 4H), 2.20 (s, 3H), 2.17 (s, 3H) |

TABLE 2-continued

Synthesis of test compounds from compounds 58, 67 and various amines

| No. | Structure | Procedure, Intermediate, amine | Rx. Yield (%) | Mass Spec. Found | Mass Spec. Calculated | $^1$H-NMR |
|---|---|---|---|---|---|---|
| 1186 | 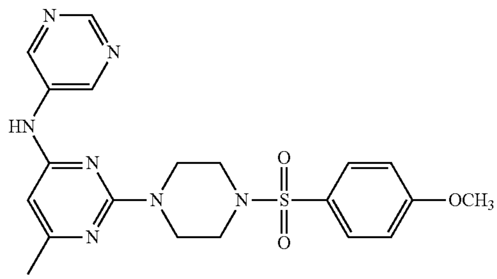 [SMILES: COc1ccc(S(=O)(=O)N2CCN(c3nc(C)cc(Nc4cncnc4)n3)CC2)cc1] | C, 67, 72 | 43% | 441.9 (M$^+$ + 1) | 441.16 for $C_{20}H_{23}N_7O_3S$ | $^1$H-NMR (DMSO-d$_6$, 400 MHz): δ 9.51 (s, 1H), 8.98 (s, 2H), 8.77 (s, 1H), 7.68 (d, J = 6.8 Hz, 2H), 7.12 (d, J = 7.2 Hz, 2H), 5.96 (s, 1H), 3.82 (s, 3H), 3.78 (t, J = 5.2 Hz, 4H), 2.91 (t, J = 4.8 Hz, 4H), 2.15 (s, 3H) |
| 1188 | 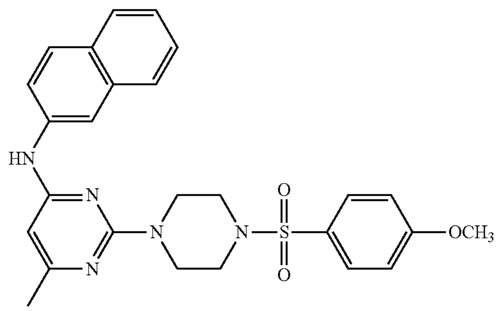 [SMILES: COc1ccc(S(=O)(=O)N2CCN(c3nc(C)cc(Nc4ccc5ccccc5c4)n3)CC2)cc1] | C, 67, 73 | 39% | 489.9 (M$^+$ + 1) | 489.18 for $C_{26}H_{27}N_5O_3S$ | $^1$H-NMR (DMSO-d$_6$, 400 MHz): δ 9.37 (s, 1H), 8.27 (s, 1H), 7.83 (s, 1H), 7.79 (d, J = 8.0 Hz, 2H), 7.70 (d, J = 7.2 Hz, 2H), 7.54 (d, J = 8.8 Hz, 1H), 7.45 (t, J = 8.0 Hz, 1H), 7.35 (t, J = 8.0 Hz, 1H), 7.12 (t, J = 6.8 Hz, 2H), 6.00 (s, 1H), 3.85 (t, J = 5.2 Hz, 4H), 3.81 (s, 3H), 2.94 (t, J = 4.8 Hz, 4H), 2.13 (s, 3H) |
| 1233 | 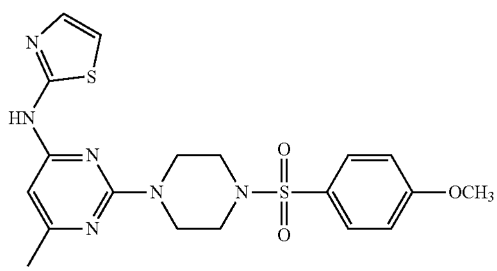 [SMILES: COc1ccc(S(=O)(=O)N2CCN(c3nc(C)cc(Nc4nccs4)n3)CC2)cc1] | C, 67, 74 | 22% | 447.5 (M$^+$ + 1) | 446.12 for $C_{19}H_{22}N_6O_3S_2$ | $^1$H-NMR (DMSO-d$_6$, 400 MHz): δ 11.32 (s, 1H), 7.68 (dd, J = 7.2, 2.0 Hz, 2H), 7.40 (s, 1H), 7.12 (dd, J = 9.2, 2.0 Hz, 3H), 6.09 (s, 1H), 3.92 (t, J = 4.8 Hz, 4H), 3.82 (s, 3H), 2.93 (t, J = 4.8 Hz, 4H), 2.15 (s, 3H) |
| 1234 | 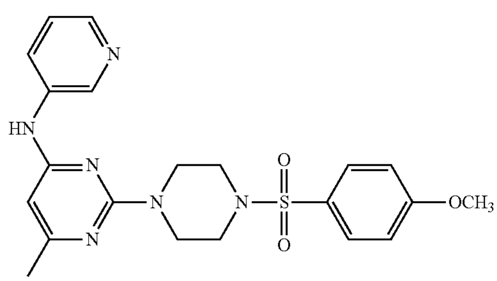 [SMILES: COc1ccc(S(=O)(=O)N2CCN(c3nc(C)cc(Nc4cccnc4)n3)CC2)cc1] | C, 67, 75 | 42% | 441.3 (M$^+$ + 1) | 440.16 for $C_{21}H_{24}N_6O_3S$ | $^1$H-NMR (DMSO-d$_6$, 400 MHz): δ 9.32 (s, 1H), 8.70-8.69 (m, 1H), 8.15 (d, J = 4.8 Hz, 1H), 8.00 (dd, J = 6.0, 1.6 Hz, 1H), 7.67 (d, J = 6.8 Hz, 2H), 7.32-7.29 (m, 1H), 7.12 (d, J = 7.2 Hz, 2H), 5.93 (s, 1H), 3.82 (s, 3H), 3.78 (t, J = 5.2 Hz, 4H), 2.90 (t, J = 4.8 Hz, 4H), 2.12 (s, 3H) |
| 1215 | 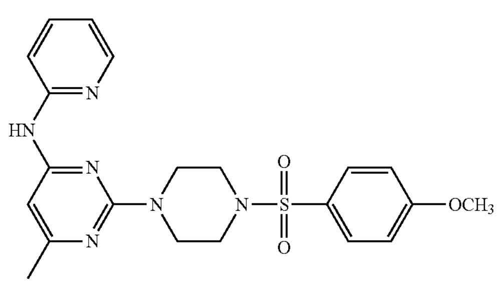 [SMILES: COc1ccc(S(=O)(=O)N2CCN(c3nc(C)cc(Nc4ccccn4)n3)CC2)cc1] | C, 67, 76 | 34% | 441.5 (M$^+$ + 1) | 440.16 for $C_{21}H_{24}N_6O_3S$ | $^1$H-NMR (DMSO-d$_6$, 400 MHz): δ 9.66 (s, 1H), 8.24-8.23 (m, 1H), 7.74-7.66 (m, 4H), 7.13 (d, J = 7.2 Hz, 2H), 6.95-6.92 (m, 1H), 6.67 (s, 1H), 3.82 (s, 3H), 3.79 (t, J = 5.2 Hz, 4H), 2.90 (t, J = 5.2 Hz, 4H), 2.14 (s, 3H) |

TABLE 2-continued

Synthesis of test compounds from compounds 58, 67 and various amines

| No. | Structure | Procedure, Intermediate, amine | Rx. Yield (%) | Mass Spec. Found | Mass Spec. Calculated | $^1$H-NMR |
|---|---|---|---|---|---|---|
| 1194 | 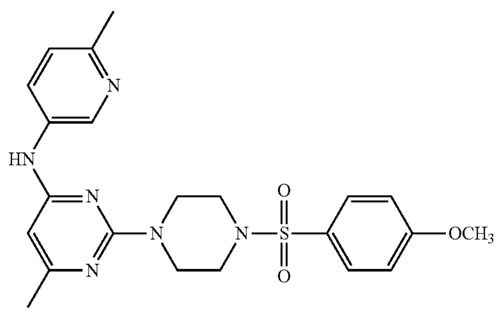 [SMILES: COc1ccc(S(=O)(=O)N2CCN(c3nc(C)cc(Nc4ccc(C)nc4)n3)CC2)cc1] | C, 67, 77 | 38, % | 455.5 (M$^+$ + 1) | 454.18 for $C_{22}H_{26}N_6O_3S$ | $^1$H-NMR (DMSO-d$_6$, 400 MHz): δ 9.20 (s, 1H), 8.59 (s, 1H), 7.83 (dd, J = 8.4, 2.4 Hz, 1H), 7.68 (d, J = 8.8 Hz, 2H), 7.17-7.12 (m, 3H), 5.89 (s, 1H), 3.82 (s, 3H), 3.77 (t, J = 4.8 Hz, 4H), 2.89 (t, J = 4.8 Hz, 4H), 2.40 (s, 3H), 2.11 (s, 3H) |

$^a$reaction temperature 80° C.

Example 16: Synthesis of N$^4$-(4-fluorophenyl)-N$^6$, N$^6$-dimethyl-2-(piperazin-1-yl) pyrimidine-4, 6-diamine hydrochloride (81)—A Common Intermediate

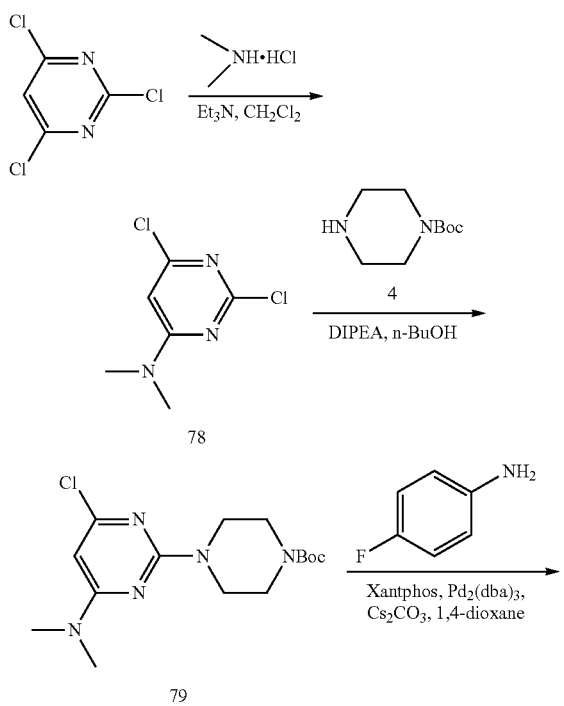

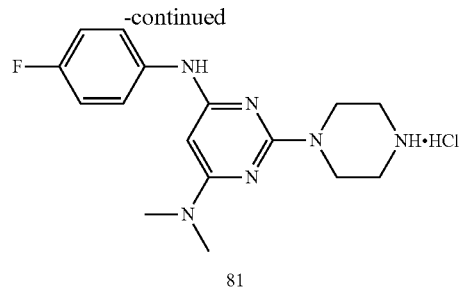

Synthesis of 2, 6-dichloro-N, N-dimethylpyrimidin-4-amine (78)

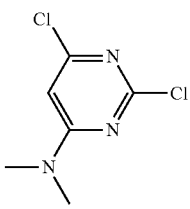

To a stirred solution of 2, 4, 6-trichloropyrimidine (10 g, 54.64 mmol) in CH$_2$Cl$_2$ (300 mL) was added dimethylamine hydrochloride (4.45 g, 54.64 mmol) at −78° C. under argon atmosphere. To this was added triethylamine (15.22 mL, 109.29 mmol) drop wise and stirred for 2 h at −78° C. and gradually warmed to 0° C. over a period of 2 h. The reaction was monitored by TLC; after completion of the reaction, the reaction mixture was diluted with water (150 mL) and extracted with CH$_2$Cl$_2$ (2×100 mL). The combined organic extracts were dried over sodium sulfate, filtered and concentrated in vacuo to obtain the crude. The crude was purified through silica gel column chromatography using 20% EtOAc/hexanes to afford compound 78 (8.1 g, 77%) as white solid. TLC: 10% EtOAc/hexanes (R$_f$ 0.4); $^1$H-NMR (DMSO-d$_6$, 500 MHz): δ 6.82 (s, 1H), 3.09 (s, 6H).

115

Synthesis of tert-butyl 4-(4-chloro-6-(dimethyl-amino) pyrimidin-2-yl) piperazine-1-carboxylate (79)

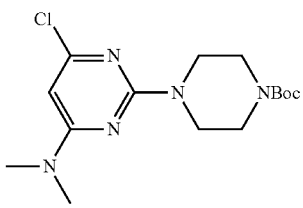

To a stirred solution of compound 78 (7 g, 36.46 mmol) in n-butanol (70 mL) were added tert-butyl piperazine-1-carboxylate 4 (7.5 g, 40.10 mmol) and N, N-diisopropyl-ethylamine (10 mL, 54.69 mmol) in sealed tube at RT under argon atmosphere; heated to 80° C. and stirred for 16 h. The reaction was monitored by TLC; after completion of the reaction, the reaction mixture was diluted with water (100 mL) and extracted with $CH_2Cl_2$ (2×80 mL). The combined organic extracts were dried over sodium sulfate, filtered and concentrated in vacuo to obtain the crude. The crude was purified through silica gel column chromatography using 10% EtOAc/hexanes to afford compound 79 (9 g, 72%) as white solid. TLC: 20% EtOAc/hexanes ($R_f$, 0.5); $^1$H-NMR (CDCl$_3$, 500 MHz): δ 5.81 (s, 1H), 3.75-3.73 (m, 4H), 3.45 (t, J=4.5 Hz, 4H), 3.03 (s, 6H), 1.47 (s, 9H).

Synthesis of tert-butyl 4-(4-(dimethylamino)-6-((4-fluorophenyl) amino) pyrimidin-2-yl) piperazine-1-carboxylate (80)

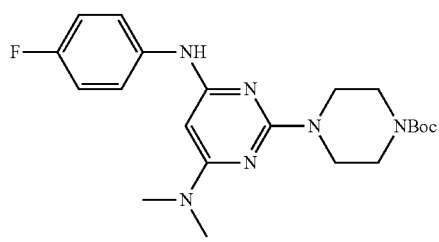

To a stirred solution of compound 79 (5 g, 14.66 mmol) in 1, 4-dioxane (50 mL) under argon atmosphere were added 4-fluoroaniline (1.95 g, 17.59 mmol) and cesium carbonate (7.15 g, 21.99 mmol) in sealed tube at RT and degassed under argon for 30 min. To this were added Pd$_2$(dba)$_3$ (671 mg, 0.73 mmol) and Xantphos (593 mg, 1.03 mmol) at RT and degassed under argon for 10 min; heated to 90° C. and stirred for 16 h. The reaction was monitored by TLC; after completion of the reaction, the reaction mixture was filtered through a pad of celite and washed with ethyl acetate (2×60 mL). The combined organic extracts were dried over sodium sulfate, filtered and concentrated in vacuo to obtain the crude. The crude was purified through silica gel column chromatography using 15% EtOAc/hexanes to afford compound 80 (4 g, 65%) as an off-white solid. TLC: 20% EtOAc/hexanes ($R_f$, 0.2); $^1$H-NMR (DMSO-d$_6$, 500 MHz): δ 8.76 (s, 1H), 7.56-7.53 (m, 2H), 7.07 (t, J=8.5 Hz, 2H), 5.22 (s, 1H), 3.63 (t, J=4.5 Hz, 4H), 3.37-3.35 (m, 4H), 2.94 (s, 6H), 1.42 (s, 9H).

116

Synthesis of $N^4$-(4-fluorophenyl)-$N^6$, $N^6$-dimethyl-2-(piperazin-1-yl) pyrimidine-4, 6-diamine hydrochloride (81)

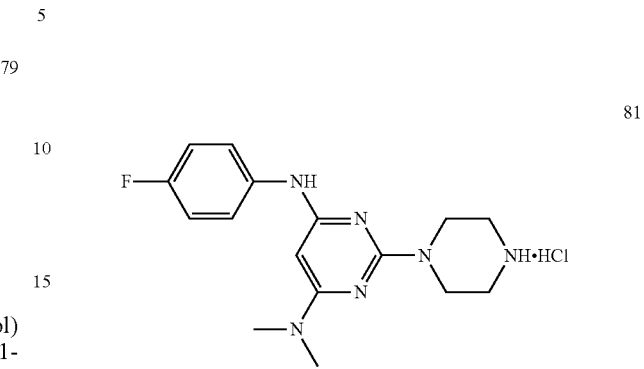

To a stirred solution of compound 80 (500 mg, 1.25 mmol) in $CH_2Cl_2$ (5 mL) was added 4 N HCl in 1, 4-dioxane (5 mL) at 0° C. under argon atmosphere; warmed to RT and stirred for 4 h. The reaction was monitored by TLC; after completion of the reaction, the volatiles were removed in vacuo. The residue was basified with aqueous NaHCO$_3$ solution (20 mL) and extracted with EtOAc (2×30 mL). The combined organic extracts were dried over sodium sulfate, filtered and concentrated in vacuo to obtain the crude, which was triturated with diethylether/n-pentane (1; 1, 10 mL) to afford compound 81 (280 mg, 75%) as an off-white solid. TLC: 50% EtOAc/hexanes ($R_f$, 0.2); $^1$H-NMR (DMSO-d$_6$, 400 MHz): δ 8.70 (s, 1H), 7.57-7.53 (m, 2H), 7.06 (t, J=8.8 Hz, 2H), 5.19 (s, 1H), 3.56 (t, J=4.8 Hz, 4H), 2.93 (s, 6H), 2.70 (t, J=4.8 Hz, 4H).

Example 17: Synthesis of 4-methyl-6-(piperazin-1-yl)-N-(p-tolyl) pyridin-2-amine (84)—A Common Intermediate

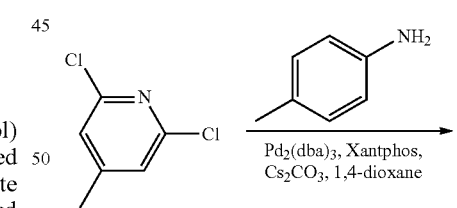

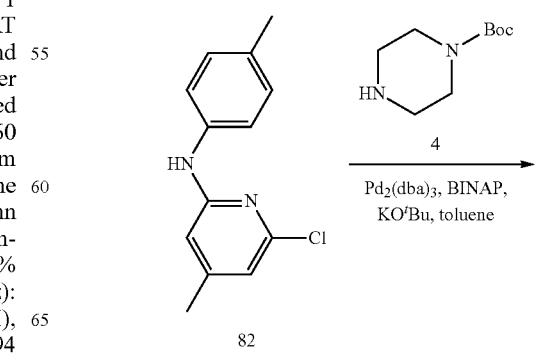

117

-continued

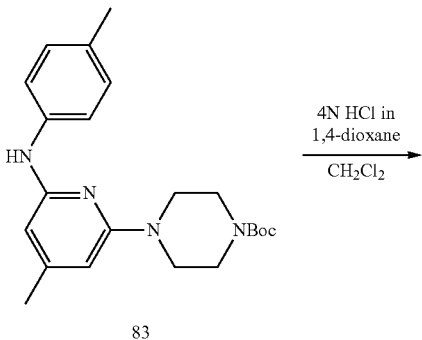

83

→ (4N HCl in 1,4-dioxane / CH$_2$Cl$_2$)

Synthesis of 6-chloro-4-methyl-N-(p-tolyl) pyridin-2-amine (82)

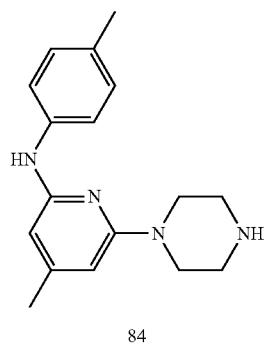

84

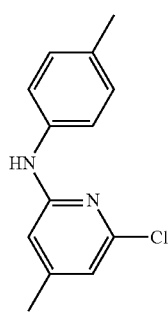

82

To a stirred solution of 2, 6-dichloro-4-methylpyridine (500 mg, 3.08 mmol) in 1, 4-dioxane (8 mL) under argon atmosphere were added p-toluidine (363 mg, 3.39 mmol), cesium carbonate (1.2 g, 3.70 mmol), Pd$_2$(dba)$_3$ (141 mg, 0.15 mmol) and Xantphos (178 mg, 0.31 mmol) in sealed tube at RT and degassed under argon for 20 min; heated to 120° C. and stirred for 16 h. The reaction was monitored by TLC; after completion of the reaction, the reaction mixture was filtered through a pad of Celite and the filtrate was concentrated in vacuo to obtain the crude, which was purified through flash column chromatography using 5% EtOAc/hexanes to afford compound 82 (310 mg, 38%) as brown semi solid. TLC: 10% EtOAc/hexanes (R$_f$ 0.4); $^1$H-NMR (DMSO-d$_6$, 500 MHz): δ 9.10 (s, 1H), 7.48-7.42 (m, 4H), 6.62 (s, 1H), 6.54 (s, 1H), 2.24 (s, 3H), 2.20 (s, 3H).

118

Synthesis of tert-butyl 4-(4-(methyl)-6-(p-tolylamino) pyridin-2-yl) piperazine-1-carboxylate (83)

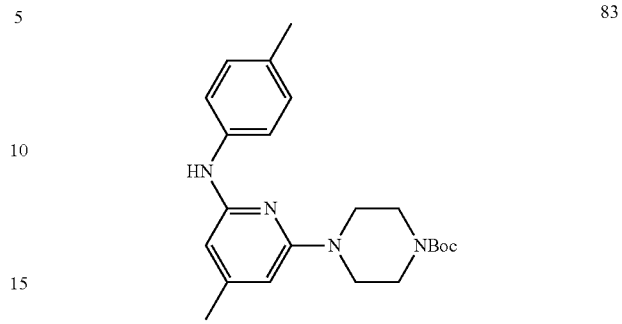

83

To a stirred solution of compound 20 (1 g, 4.31 mmol) in toluene (12 mL) under argon atmosphere were added tert-butyl piperazine-1-carboxylate 4 (1.2 g, 6.46 mmol), Pd$_2$(dba)$_3$ (98.5 mg, 0.11 mmol), BINAP (134 mg, 0.21 mmol), potassium tert-butoxide (1 M in THF, 6.4 mL, 6.45 mmol) in sealed tube at RT and degassed under argon for 20 min; heated to 120° C. and stirred for 16 h. The reaction was monitored by TLC; after completion of the reaction, the reaction mixture was filtered through a pad of celite and the filtrate was concentrated in vacuo to obtain the crude, which was purified through silica gel column chromatography using 25% EtOAc/hexanes to afford compound 83 (700 mg, 42%) as yellow solid. TLC: 50% EtOAc/hexanes (R$_f$ 0.4); $^1$H-NMR (DMSO-d$_6$, 400 MHz): δ 8.50 (s, 1H), 7.41 (d, J=8.4 Hz, 2H), 7.03 (d, J=8.4 Hz, 2H), 5.97 (s, 1H), 5.95 (s, 1H), 3.44-3.39 (m, 8H), 2.21 (s, 3H), 2.12 (s, 3H), 1.42 (s, 9H).

Synthesis of 4-methyl-6-(piperazin-1-yl)-N-(p-tolyl) pyridin-2-amine (84)

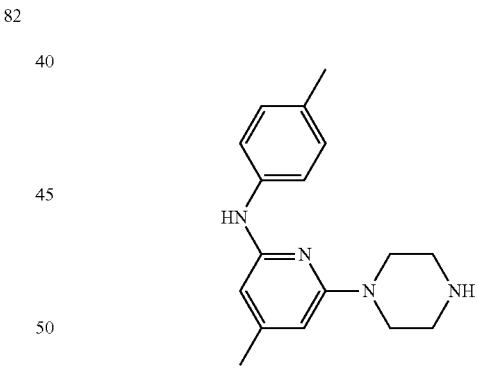

84

To a stirred solution of compound 83 (700 mg, 1.83 mmol) in CH$_2$Cl$_2$ (5 mL) under argon atmosphere was added 4 N HCl in 1, 4-dioxane (2.29 mL, 9.16 mmol) at RT and stirred for 16 h. The reaction was monitored by TLC; after completion of the reaction, the volatiles were removed in vacuo, the residue was diluted with 1 N HCl (10 mL) and extracted with diethyl ether (2×15 mL). The aqueous layer was neutralized with aqueous saturated NaHCO$_3$ solution (20 mL) and extracted with CH$_2$Cl$_2$ (2×40 mL). The combined organic extracts were dried over sodium sulfate, filtered and concentrated in vacuo to obtain the crude compound 84 (300 mg, 58%) as an off-white solid. TLC: 5% CH$_3$OH/CH$_2$Cl$_2$ (R$_f$ 0.2); $^1$H-NMR (DMSO-d$_6$, 400 MHz): δ 8.44 (s, 1H), 7.43 (d, J=8.4 Hz, 2H), 7.01 (d, J=8.0 Hz, 2H), 5.92 (s, 2H), 3.31 (t, J=4.8 Hz, 4H), 2.76 (t, J=4.8 Hz, 4H), 2.21 (s, 3H), 2.11 (s, 3H).

Example 18: Synthesis of 4-methyl-6-(piperazin-1-yl)-N-(p-tolyl) pyrimidin-2-amine (87)—A Common Intermediate

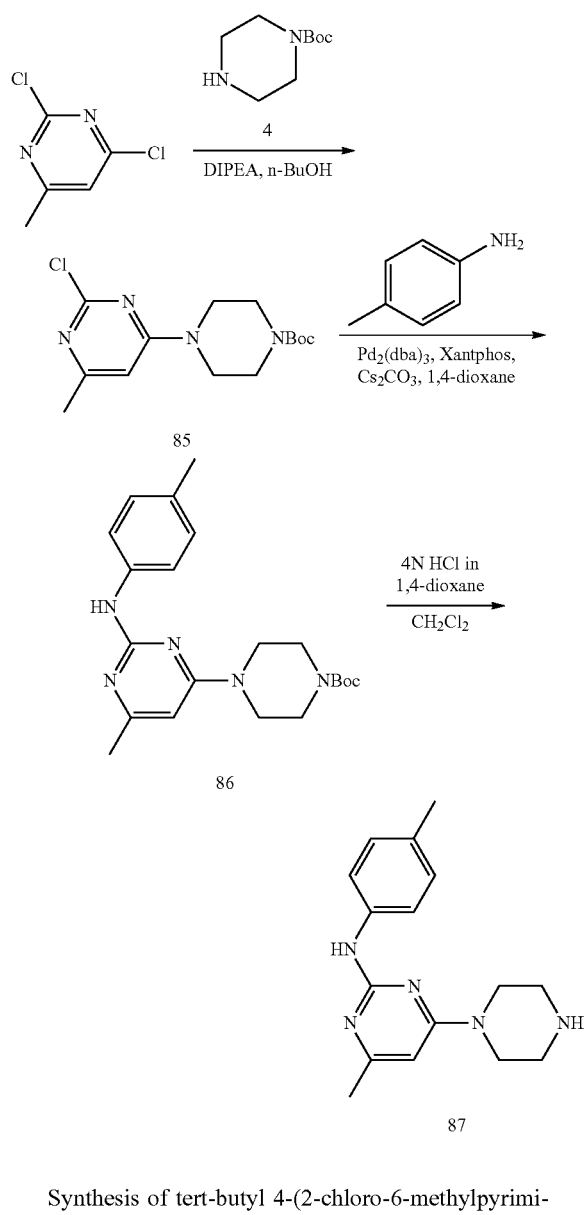

Synthesis of tert-butyl 4-(2-chloro-6-methylpyrimidin-4-yl) piperazine-1-carboxylate (85)

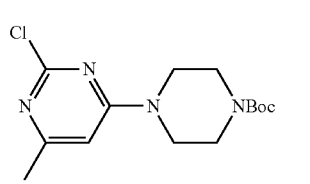

To a stirred solution of 2, 4-dichloro-6-methylpyrimidine (200 mg, 1.22 mmol) in n-butanol (5 mL) under argon atmosphere were added tert-butyl piperazine-1-carboxylate 4 (251 mg, 1.35 mmol) and N, N-diisopropylethylamine (0.32 mL, 1.84 mmol) at RT; heated to 70° C. and stirred for 16 h. The reaction was monitored by TLC; after completion of the reaction, the volatiles were removed in vacuo, the residue was diluted with water (20 mL) and extracted with EtOAc (2×30 mL). The combined organic extracts were dried over sodium sulfate, filtered and concentrated in vacuo to obtain the crude. The crude was purified through silica gel column chromatography using 10% EtOAc/hexanes to afford compound 85 (100 mg, 26%) as colorless syrup. TLC: 20% EtOAc/hexanes ($R_f$ 0.6); $^1$H-NMR (DMSO-$d_6$, 400 MHz): δ 6.67 (s, 1H), 3.69 (t, J=4.8 Hz, 4H), 3.86 (t, J=5.2 Hz, 4H), 2.28 (s, 3H), 1.42 (s, 9H).

Synthesis of tert-butyl 4-(6-methyl-2-(p-tolylamino) pyrimidin-4-yl) piperazine-1-carboxylate (86)

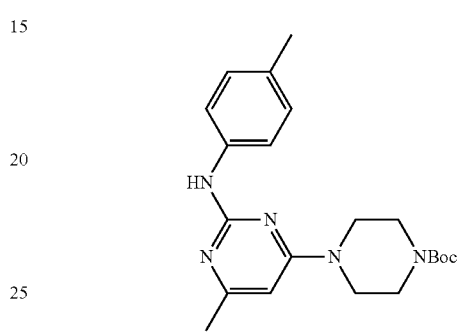

To a stirred solution of compound 85 (100 mg, 0.32 mmol) in 1, 4-dioxane (5 mL) under argon atmosphere was added p-toluidine (41 mg, 0.38 mmol) in sealed tube at RT and degassed under argon for 20 min. To this were added cesium carbonate (125 mg, 0.38 mmol), Pd$_2$(dba)$_3$ (15 mg, 0.02 mmol) followed by Xantphos (13 mg, 0.02 mmol) and degassed under argon for 20 min; heated to 80° C. and stirred for 16 h. The reaction was monitored by TLC; after completion of the reaction, the volatiles were removed in vacuo, the residue was diluted with water (25 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 25% EtOAc/hexanes to afford compound 86 (100 mg, 82%) as an off-white solid. TLC: 50% EtOAc/hexanes ($R_f$ 0.2); $^1$H-NMR (DMSO-$d_6$, 500 MHz): δ 8.91 (s, 1H), 7.58 (d, J=8.5 Hz, 2H), 7.04 (d, J=8.0 Hz, 2H), 6.12 (s, 1H), 3.58-3.56 (m, 4H), 3.41-3.39 (m, 4H), 2.22 (s, 3H), 2.18 (s, 3H), 1.42 (s, 9H).

Synthesis of 4-methyl-6-(piperazin-1-yl)-N-(p-tolyl) pyrimidin-2-amine (87)

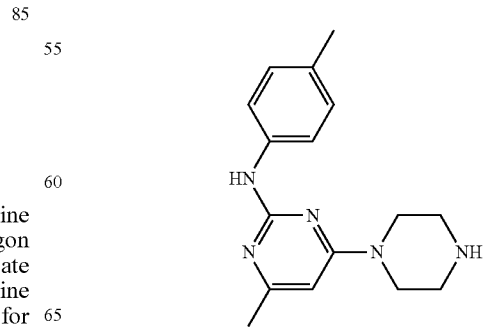

To a stirred solution of compound 86 (150 mg, 0.39 mmol) in CH$_2$Cl$_2$ (5 mL) under argon atmosphere was added 4 N HCl in 1, 4-dioxane (1 mL) at 5° C.; warmed to RT and stirred for 6 h. The reaction was monitored by TLC; after completion of the reaction, the reaction mixture was diluted with water (20 mL) and washed with EtOAc (1×10 mL). The aqueous layer was neutralized with 10% aqueous NaHCO$_3$ solution (20 mL) and extracted with EtOAc (2×30 mL). The combined organic extracts were dried over sodium sulfate, filtered and concentrated in vacuo to obtain the crude compound 87 (90 mg, 82%) as an off-white solid. TLC: 5% CH$_3$OH/CH$_2$Cl$_2$ (R$_f$ 0.1); $^1$H-NMR (DMSO-d$_6$, 500 MHz): δ 8.84 (s, 1H), 7.58 (d, J=8.0 Hz, 2H), 7.02 (d, J=8.0 Hz, 2H), 6.08 (s, 1H), 3.49-3.47 (m, 4H), 2.73-2.71 (m, 4H), 2.21 (s, 3H), 2.16 (s, 3H).

Example 19: Preparation of Additional Test Compounds

Amines similar to 6 (compounds 81, 84, 87) were synthesized as described herein and converted to final products either by using commercially available sulfonyl chlorides or by using prepared sulfonyl chlorides employing Procedure A and the results are captured in Table 3 below.

Procedure A: To a stirred solution of compound 6 (40 mg, 0.14 mmol) in CH$_2$Cl$_2$ (5 mL) under argon atmosphere were added pyridine (0.06 mL, 0.70 mmol), and sulfonyl chloride (29.5 mg, 0.15 mmol) at 0° C.; warmed to RT and stirred for 4 h. The reaction was monitored by TLC; after completion the reaction, the reaction mixture was diluted with CH$_2$Cl$_2$ (30 mL), washed with water (15 mL), 1 N HCl (10 mL), 10% NaHCO$_3$ solution (15 mL), brine (15 mL), dried over sodium sulfate, filtered and concentrated in vacuo to obtain crude. The precipitated material was either directly dried in vacuo or triturated or purified by column chromatography to afford the desired test compounds.

Commercially Available Sulfonyl Chlorides Used for Preparation of Test Compounds:

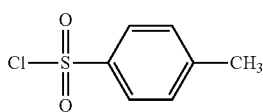

88

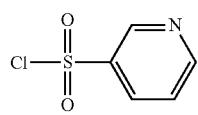

89

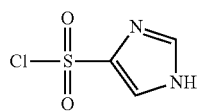

90

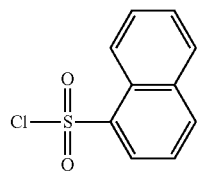

91

-continued

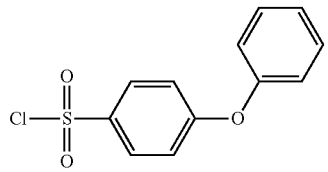

92

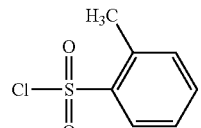

93

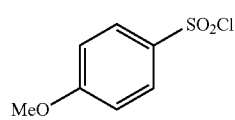

94

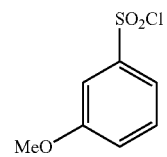

95

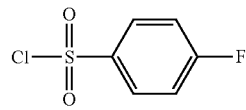

96

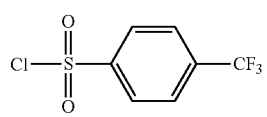

97

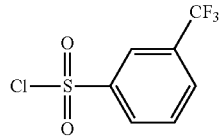

98

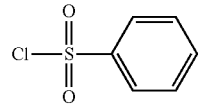

99

Synthesis of Sulfonyl Chlorides for Preparation of Test Compounds

Synthesis of 4-hydroxybenzenesulfonyl chloride (101)

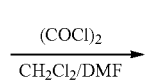

100

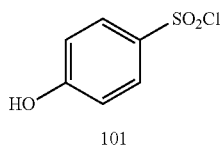

To a stirred solution of 4-hydroxybenzenesulfinic acid 100 (2 g, 9.52 mmol) in CH$_2$Cl$_2$ (30 mL) were added oxalyl chloride (5.45 mL, 57.14 mmol), DMF (10 mL) under argon atmosphere at −30° C.; warmed to RT and stirred for 18 h. The reaction was monitored by TLC; after completion the reaction, the reaction mixture was diluted with ice cold water (30 mL) and extracted with CH$_2$Cl$_2$ (2×50 mL). The combined organic extracts were dried over sodium sulfate, filtered and concentrated in vacuo to obtain the crude compound 101 (2.8 g) as light brown syrup. The crude was carried to the next step without further purification. TLC: 5% MeOH/CH$_2$Cl$_2$ (R$_f$: 0.8); $^1$H-NMR (DMSO-d$_6$, 400 MHz): δ 10.88 (br s, 1H), 7.43 (d, J=8.4 Hz, 2H), 6.70 (d, J=8.4 Hz, 2H).

Synthesis of 6-aminopyridine-3-sulfonyl chloride (103)

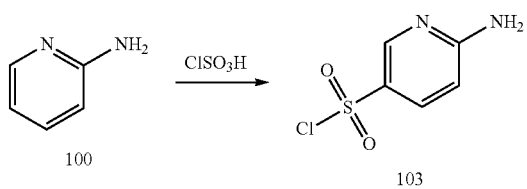

Pyridin-2-amine 102 (2 g, 21.25 mmol) was added cautiously portion wise over a period of 15 min to an ice cold chlorosulfonic acid (12 mL, 212.49 mmol) under argon atmosphere at 0° C.; heated to 150° C. and stirred for 2 h. The reaction was monitored by TLC; after completion of the reaction, the reaction mixture was cooled to RT and poured into an ice cold water (100 mL) and extracted with CH$_2$Cl$_2$ (2×50 mL). The combined organic extracts were dried over sodium sulfate and concentrated in vacuo to obtain the crude compound 103 (60 mg) as yellow sticky solid. TLC: 70% EtOAc/hexanes (R$_f$: 0.9).

Synthesis of pyridine-4-sulfonyl chloride (105)

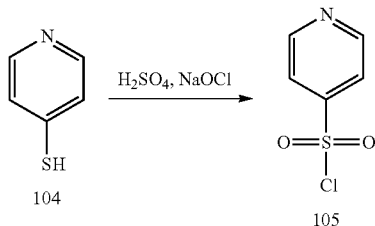

To a stirred solution of pyridine-4-thiol 104 (500 mg, 3.96 mmol) in sulfuric acid (5 mL) under argon atmosphere was added 10-15% sodium hypochlorite solution (60 mL) at −78° C.; warmed to 0° C. and stirred for 4 h at 0° C. The reaction was monitored by TLC; after completion of the reaction, the reaction mixture was diluted with ice cold water (40 mL) and extracted with ice cold CH$_2$Cl$_2$ (2×30 mL). The combined organic extracts were dried over sodium sulfate and concentrated in vacuo to obtain the crude compound 105 (200 mg) as yellow oil. TLC: 10% CH$_3$OH/CH$_2$Cl$_2$ (R$_f$: 0.1).

Synthesis of 6-methylpyridine-3-sulfonyl chloride (108)

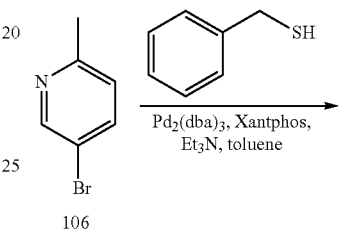

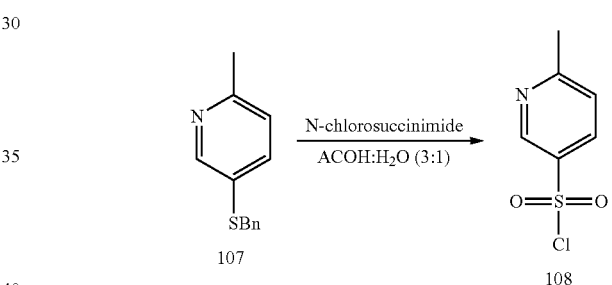

Synthesis of 5-(benzylthio)-2-methylpyridine (107)

To a stirred solution of 5-bromo-2-methylpyridine 106 (1 g, 5.81 mmol) in toluene (20 mL) under argon atmosphere were added phenylmethanethiol (790 mg, 6.39 mmol), Pd$_2$(dba)$_3$ (132 mg, 0.14 mmol), Xantphos (168 mg, 0.29 mmol) and triethylamine (1.2 mL, 8.72 mmol) in sealed tube at RT and degassed under argon for 15 min; heated to 100° C. and stirred for 16 h. The reaction was monitored by TLC; after completion of the reaction, the volatiles were removed in vacuo to obtain the crude, which was purified through silica gel column chromatography using 15% EtOAc/hexanes to afford compound 107 (1.2 g, 95%) as yellow oil. TLC: 20% EtOAc/hexane (R$_f$: 0.4); $^1$H-NMR (CDCl$_3$, 500 MHz): δ 8.41 (s, 1H), 7.44 (d, J=8.5 Hz, 1H), 7.28-7.20 (m, 5H), 7.01 (d, J=7.5 Hz, 1H), 4.03 (s, 2H), 2.50 (s, 3H).

Synthesis of 6-methylpyridine-3-sulfonyl chloride (108)

To a stirred solution of compound 107 (250 mg, 1.16 mmol) in AcOH/H$_2$O (3:1, 16 mL) was added N-chlorosuccinimide (1.38 g, 11.60 mmol) at RT; stirred for 2 h. The reaction was monitored by TLC; after completion of the reaction, the volatiles were removed in vacuo, the residue was neutralized with aqueous saturated NaHCO₃ solution (30 mL) and extracted with CH₂Cl₂ (2×40 mL). The combined organic extracts were dried over sodium sulfate and concentrated in vacuo to obtain the crude. The crude was purified through silica gel column chromatography using 20% EtOAc/hexanes to afford compound 108 (100 mg, 45%) as yellow oil. TLC: 20% EtOAc/hexanes ($R_f$ 0.3); ¹H-NMR (CDCl₃, 400 MHz): δ 9.12 (s, 1H), 8.18 (d, J=8.0 Hz, 1H), 7.41 (d, J=8.4 Hz, 1H), 2.72 (s, 3H).

Synthesis of 2-aminopyrimidine-5-sulfonyl chloride (110)

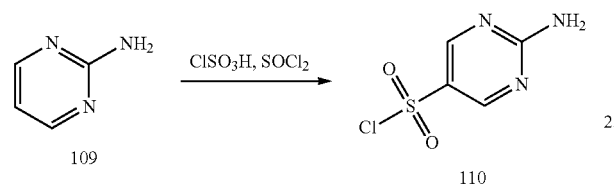

To ice cold chlorosulfuric acid (12 mL, 212.49 mmol) under argon atmosphere at 0° C. was added pyrimidin-2-amine 109 (2 g, 21.24 mmol) very cautiously; stirred at 0° C. for 10 min. To this was added thionyl chloride (9.7 g, 84.99 mmol) and heated to 150° C.; stirred for 70 h. The reaction was monitored by TLC; after completion of the reaction, the reaction mixture was cooled to RT and poured into an ice cold water (100 mL) and extracted with CH₂Cl₂ (2×50 mL). The combined organic extracts were dried over sodium sulfate, filtered and concentrated in vacuo to obtain the crude compound 110 (100 mg) as yellow solid. TLC: 10% CH₃OH/CH₂Cl₂ ($R_f$ 0.2); ¹H-NMR (CDCl₃, 400 MHz): δ 8.81 (s, 2H), 5.85 (br s, 2H).

Synthesis of 1H-pyrazole-4-sulfonyl chloride (112)

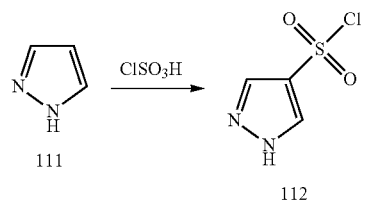

1H-pyrazole 111 (1 g, 14.70 mmol) was added to an ice cold chlorosulfuric acid (5 mL, 73.53 mmol) cautiously over a period of 15 min under argon atmosphere at 0° C.; warmed to RT, heated to reflux and stirred for 24 h. The reaction was monitored by TLC; after completion of the reaction, the reaction mixture was cooled to 0° C. and poured into an ice cold water (100 mL) cautiously and extracted with CH₂Cl₂ (2×50 mL). The combined organic extracts were dried over sodium sulfate, filtered and concentrated in vacuo to obtain the crude compound 112 (100 mg) as yellow sticky solid. TLC: 70% EtOAc/hexanes ($R_f$ 0.1); ¹H-NMR (CDCl₃, 400 MHz): δ 8.18 (s, 2H).

Synthesis of 2-oxo-2, 3-dihydro-1H-benzo [d] imidazole-5-sulfonyl chloride (115)

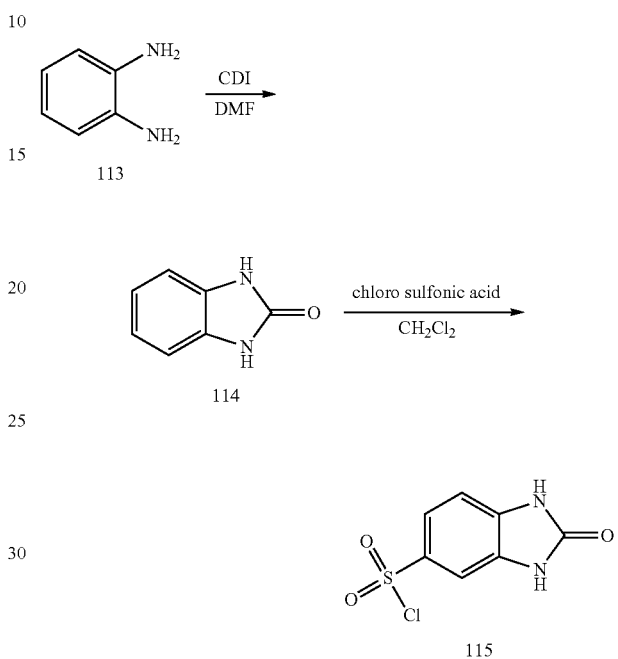

Synthesis of 1, 3-dihydro-2H-benzo[d] imidazol-2-one (114)

To a stirred solution of benzene-1, 2-diamine 113 (2 g, 18.51 mmol) in DMF (3 mL) under argon atmosphere was added 1,1'-carbonyldiimidazole (CDI) (3 g, 18.51 mmol) at 0° C.; and warmed to RT, stirred for 24 h. The reaction was monitored by TLC; after completion of the reaction, the volatiles were removed in vacuo and the residue diluted with EtOAc (10 mL); the precipitated solid was filtered, washed with EtOAc (2×5 mL) and dried in vacuo to afford compound 114 (2 g, 81%) as white solid. TLC: 5% MeOH/CH₂Cl₂ ($R_f$ 0.3); ¹H-NMR (DMSO-d₆, 400 MHz): δ 10.55 (s, 2H), 6.91 (s, 4H).

Synthesis of 2-oxo-2, 3-dihydro-1H-benzo[d]imidazole-5-sulfonyl chloride (115)

To a stirred solution of compound 114 (1 g, 7.46 mmol) in CH₂Cl₂ (10 mL) under argon atmosphere was added chlorosulfonic acid (1 mL, 14.92 mmol) at 0° C.; heated to reflux and stirred for 16 h. The reaction was monitored by TLC; after completion of the reaction, the volatiles were removed in vacuo and the residue diluted with water (10 mL); neutralized with aqueous NaOH solution and extracted with EtOAc (3×20 mL). The combined organic extracts were dried over sodium sulfate, filtered and concentrated in vacuo to afford compound 115 (980 mg, 58%) as an off-white solid. TLC: 10% MeOH/CH₂Cl₂ ($R_f$ 0.5); ¹H-NMR (DMSO-d₆, 400 MHz): δ 10.66 (s, 1H), 10.61 (s, 1H), 7.24 (d, J=6.4 Hz, 1H), 7.18 (s, 1H), 6.85 (d, J=8.4 Hz, 1H).

TABLE 3

Synthesis of test compounds from compound 6, 81, 84, and 87, and various sulfonyl chlorides

| No. | Structure | Procedure, Intermediate, sulfonyl chloride | Rx. Yield (%) | Mass Spec. Found | Mass Spec. Calculated | 1H-NMR |
|---|---|---|---|---|---|---|
| 1133 | 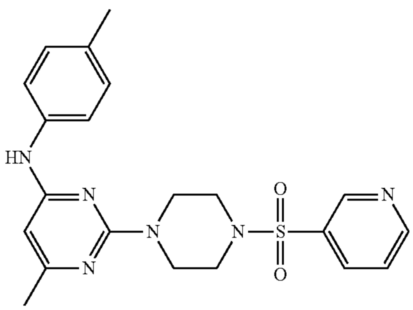 [SMILES: Cc1ccc(Nc2cc(C)nc(N3CCN(S(=O)(=O)c4cccnc4)CC3)n2)cc1] | A, 6, 89 | 68% | 425.5 (M+ + 1) | 424.17 for $C_{21}H_{24}N_6O_2S$ | 1H-NMR (DMSO-$d_6$, 400 MHz): δ 9.01 (s, 1H), 8.92 (s, 1H), 8.87 (d, J = 8.0 Hz, 1H), 8.17 (d, J = 8.0 Hz, 1H), 7.69-7.65 (m, 1H), 7.39 (d, J = 8.4 Hz, 2H), 7.08 (d, J = 8.4 Hz, 2H), 5.87 (s, 1H), 3.78 (t, J = 4.8 Hz, 4H), 3.01 (t, J = 4.8 Hz, 4H), 2.24 (s, 3H), 2.09 (s, 3H) |
| 1245[a] | 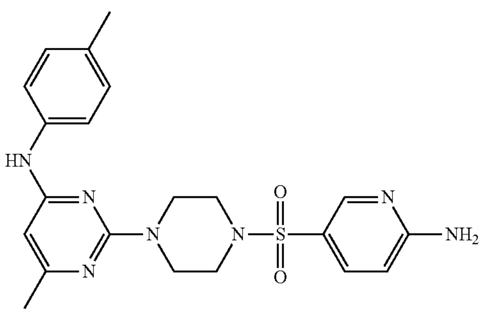 | A, 6, 103 | 9% | 440.4 (M+ + 1) | 439.18 for $C_{21}H_{25}N_7O_2S$ | 1H-NMR (DMSO-$d_6$, 500 MHz): δ 9.01 (s, 1H), 8.21 (s, 1H), 7.62 (d, J = 9.0 Hz, 1H), 7.41 (d, J = 8.5 Hz, 2H), 7.09 (d, J = 8.0 Hz, 2H), 6.96 (s, 2H), 6.50 (d, J = 9.0 Hz, 1H), 5.88 (s, 1H), 3.81-3.76 (m, 4H), 2.94-2.88 (m, 4H), 2.25 (s, 3H), 2.10 (s, 3H) |
| 1258[b] | 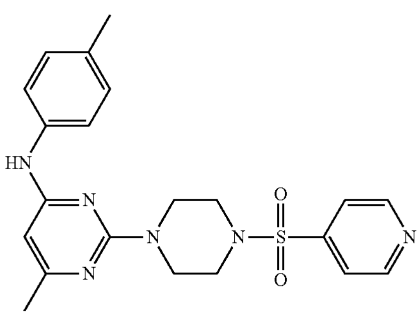 [SMILES: Cc1ccc(Nc2cc(C)nc(N3CCN(S(=O)(=O)c4ccncc4)CC3)n2)cc1] | A, 6, 105 | 11% | 425.4 (M+ + 1) | 424.17 for $C_{21}H_{24}N_6O_2S$ | 1H-NMR (DMSO-$d_6$, 400 MHz): δ 9.01 (s, 1H), 8.88 (d, J = 6.0 Hz, 2H), 7.70 (d, J = 6.0 Hz, 2H), 7.39 (d, J = 8.4 Hz, 2H), 7.08 (d, J = 8.4 Hz, 2H), 5.87 (s, 1H), 3.78 (t, J = 4.8 Hz, 4H), 3.02 (t, J = 4.8 Hz, 4H), 2.24 (s, 3H), 2.08 (s, 3H) |
| 1330[a] | 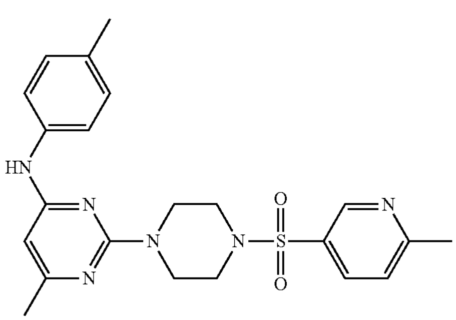 [SMILES: Cc1ccc(Nc2cc(C)nc(N3CCN(S(=O)(=O)c4ccc(C)nc4)CC3)n2)cc1] | A, 6, 108 | 33% | 439.4 (M+ + 1) | 438.18 for $C_{22}H_{26}N_6O_2S$ | 1H-NMR (DMSO-$d_6$, 500 MHz): δ 9.01 (s, 1H), 8.78 (s, 1H), 8.03 (d, J = 8.0 Hz, 1H), 7.52 (d, J = 8.0 Hz, 1H), 7.40 (d, J = 8.0 Hz, 2H), 7.09 (d, J = 8.5 Hz, 2H), 5.87 (s, 1H), 3.81-3.77 (m, 4H), 3.01-2.96 (m, 4H), 2.56 (s, 3H), 2.25 (s, 3H), 2.09 (s, 3H) |

TABLE 3-continued

Synthesis of test compounds from compound 6, 81, 84, and 87, and various sulfonyl chlorides

| No. | Structure | Procedure, Intermediate, sulfonyl chloride | Rx. Yield (%) | Mass Spec. Found | Mass Spec. Calculated | 1H-NMR |
|-----|-----------|--------------------------------------------|---------------|------------------|-----------------------|--------|
| 1260 | 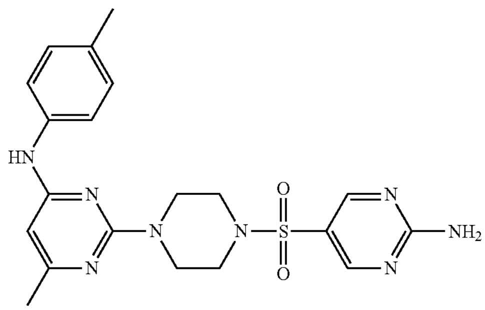 [SMILES: Cc1ccc(Nc2cc(C)nc(N3CCN(S(=O)(=O)c4cnc(N)nc4)CC3)n2)cc1] | A, 6, 110 | 16% | 441.4 (M+ + 1) | 440.17 for $C_{20}H_{24}N_8O_2S$ | 1H-NMR (DMSO-$d_6$, 400 MHz): δ 9.01 (s, 1H), 8.48 (s, 2H), 7.71 (s, 2H), 7.41 (d, J = 8.4 Hz, 2H), 7.09 (d, J = 8.4 Hz, 2H), 5.88 (s, 1H), 3.79 (t, J = 4.8 Hz, 4H), 2.96 (t, J = 4.8 Hz, 4H), 2.24 (s, 3H), 2.10 (s, 3H) |
| 1238 | 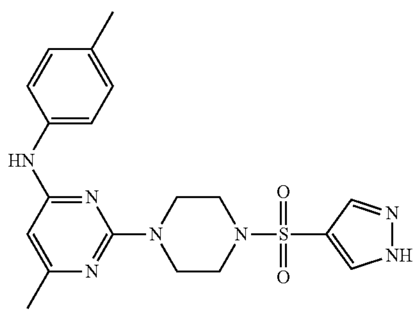 [SMILES: Cc1ccc(Nc2cc(C)nc(N3CCN(S(=O)(=O)c4cn[nH]c4)CC3)n2)cc1] | A, 6, 112 | 50% | 414.3 (M+ + 1) | 413.16 for $C_{19}H_{23}N_7O_2S$ | 1H-NMR (DMSO-$d_6$, 500 MHz): δ 13.75 (s, 1H), 9.01 (s, 1H), 8.36 (br s, 1H), 7.83 (br s, 1H), 7.41 (d, J = 8.0 Hz, 2H), 7.09 (d, J = 8.0 Hz, 2H), 5.88 (s, 1H), 3.82-3.78 (m, 4H), 2.88-2.85 (m, 4H), 2.25 (s, 3H), 2.10 (s, 3H) |
| 1134 | 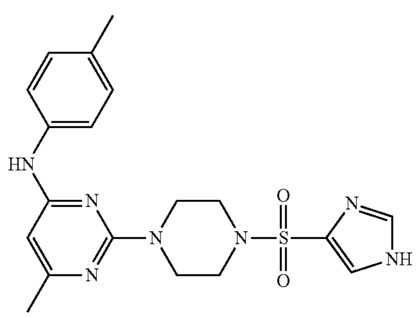 [SMILES: Cc1ccc(Nc2cc(C)nc(N3CCN(S(=O)(=O)c4c[nH]cn4)CC3)n2)cc1] | A, 6, 90 | 34% | 414.5 (M+ + 1) | 413.16 for $C_{19}H_{23}N_7O_2S$ | 1H-NMR (DMSO-$d_6$, 400 MHz): δ 12.80 (br s, 1H), 9.01 (s, 1H), 7.84 (s, 1H), 7.79 (s, 1H), 7.41 (d, J = 8.4 Hz, 2H), 7.09 (d, J = 8.0 Hz, 2H), 5.88 (s, 1H), 3.76 (t, J = 5.2 Hz, 4H), 3.03 (t, J = 4.8 Hz, 4H), 2.24 (s, 3H), 2.10 (s, 3H) |
| 1167[a] | 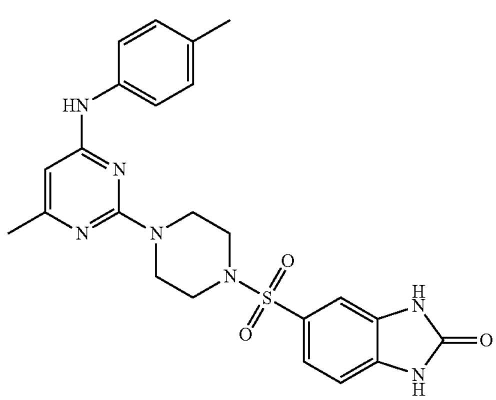 [SMILES: Cc1ccc(Nc2cc(C)nc(N3CCN(S(=O)(=O)c4ccc5[nH]c(=O)[nH]c5c4)CC3)n2)cc1] | A, 6, 115 | 83% | 480.0 (M+ + 1) | 479.17 for $C_{23}H_{25}N_7O_3S$ | 1H-NMR (DMSO-$d_6$, 400 MHz): δ 11.15 (s, 1H), 10.98 (s, 1H), 9.01 (br s, 1H), 7.40-7.33 (m, 3H), 7.20 (s, 1H), 7.10 (d, J = 8.0 Hz, 3H), 5.88 (br s, 1H), 3.78 (t, J = 4.8 Hz, 4H), 2.98-2.85 (m, 4H), 2.25 (s, 3H), 2.10 (s, 3H) |

TABLE 3-continued

Synthesis of test compounds from compound 6, 81, 84, and 87, and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1135 | 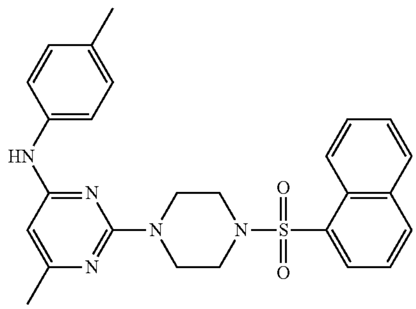 [SMILES: Cc1ccc(Nc2cc(C)nc(N3CCN(S(=O)(=O)c4cccc5ccccc45)CC3)n2)cc1] | A, 6, 91 | 45% | 474.7 (M$^+$ + 1) | 473.19 for $C_{26}H_{27}N_5O_2S$ | $^1$H-NMR (DMSO-d$_6$, 400 MHz): δ 8.98 (s, 1H), 8.70 (d, J = 8.8 Hz, 1H), 8.28 (d, J = 8.4 Hz, 1H), 8.16 (d, J = 7.2 Hz, 1H), 8.10 (d, J = 7.6 Hz, 1H), 7.74-7.66 (m, 3H), 7.37 (d, J = 8.4 Hz, 2H), 7.07 (d, J = 8.0 Hz, 2H), 5.85 (s, 1H), 3.72 (t, J = 5.2 Hz, 4H), 3.14 (t, J = 4.8 Hz, 4H), 2.24 (s, 3H), 2.07 (s, 3H) |
| 1136 | 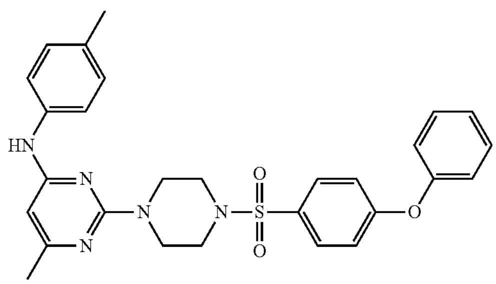 [SMILES: Cc1ccc(Nc2cc(C)nc(N3CCN(S(=O)(=O)c4ccc(Oc5ccccc5)cc4)CC3)n2)cc1] | A, 6, 92 | 67% | 516.7 (M$^+$ + 1) | 515.20 for $C_{28}H_{29}N_5O_3S$ | $^1$H-NMR (DMSO-d$_6$, 400 MHz): δ 9.01 (s, 1H), 7.73 (d, J = 7.6 Hz, 2H), 7.47-7.41 (m, 4H), 7.25 (t, J = 8.4 Hz, 1H), 7.16-7.07 (m, 6H), 5.87 (s, 1H), 3.78 (t, J = 4.8 Hz, 4H), 2.92 (t, J = 4.8 Hz, 4H), 2.24 (s, 3H), 2.09 (s, 3H) |
| 1153 | 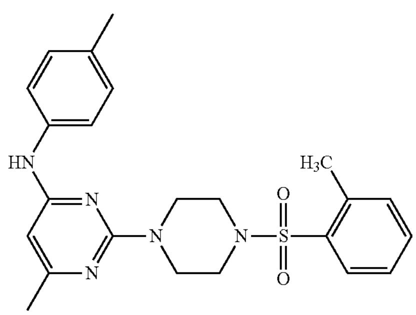 [SMILES: Cc1ccc(Nc2cc(C)nc(N3CCN(S(=O)(=O)c4ccccc4C)CC3)n2)cc1] | A, 6, 93 | 39% | 438.6 (M$^+$ + 1) | 437.19 for $C_{23}H_{27}N_5O_2S$ | $^1$H-NMR (DMSO-d$_6$, 400 MHz): δ 9.02 (s, 1H), 7.81 (d, J = 7.6 Hz, 1H), 7.57 (d, J = 7.2 Hz, 1H), 7.45-7.40 (m, 4H), 7.08 (d, J = 8.4 Hz, 2H), 5.89 (s, 1H), 3.76 (t, J = 4.8 Hz, 4H), 3.09 (t, J = 4.8 Hz, 4H), 2.59 (s, 3H), 2.23 (s, 3H), 2.10 (s, 3H) |
| 1302[b] | 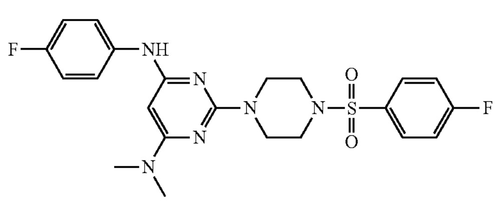 [SMILES: CN(C)c1cc(Nc2ccc(F)cc2)nc(N2CCN(S(=O)(=O)c3ccc(F)cc3)CC2)n1] | A, 81, 96 | 46% | 475.5 (M$^+$ + 1) | 474.16 for $C_{22}H_{24}F_2N_6O_2S$ | $^1$H-NMR (DMSO-d$_6$, 400 MHz): δ 8.74 (s, 1H), 7.84-7.80 (m, 2H), 7.50-7.44 (m, 4H), 7.05 (t, J = 8.8 Hz, 2H), 5.19 (s, 1H), 3.75 (t, J = 4.8 Hz, 4H), 2.93-2.91 (m, 10H) |
| 1303[b] | 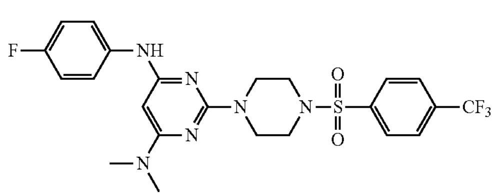 [SMILES: CN(C)c1cc(Nc2ccc(F)cc2)nc(N2CCN(S(=O)(=O)c3ccc(C(F)(F)F)cc3)CC2)n1] | A, 81, 97 | 48% | 525.1 (M$^+$ + 1) | 524.16 for $C_{23}H_{24}F_4N_6O_2S$ | $^1$H-NMR (DMSO-d$_6$, 400 MHz): δ 8.74 (s, 1H), 8.02-7.96 (m, 4H), 7.50-7.47 (m, 2H), 7.05 (t, J = 8.8 Hz, 2H), 5.19 (s, 1H), 3.76 (t, J = 4.8 Hz, 4H), 2.98 (t, J = 4.8 Hz, 4H), 2.91 (s, 6H) |

TABLE 3-continued

Synthesis of test compounds from compound 6, 81, 84, and 87, and various sulfonyl chlorides

| No. | Structure | Procedure, Intermediate, sulfonyl chloride | Rx. Yield (%) | Mass Spec. Found | Mass Spec. Calculated | $^1$H-NMR |
|---|---|---|---|---|---|---|
| 1304[b] | 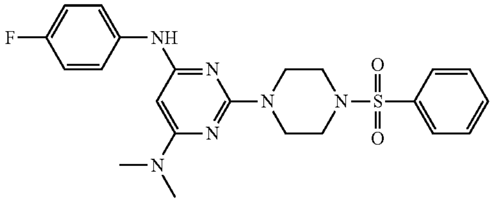 [SMILES: CN(C)c1cc(Nc2ccc(F)cc2)nc(N2CCN(S(=O)(=O)c3ccccc3)CC2)n1] | A, 81, 99 | 20% | 457.1 (M$^+$ + 1) | 456.17 for $C_{22}H_{25}FN_6O_2S$ | $^1$H-NMR (DMSO-$d_6$, 400 MHz): δ 8.74 (s, 1H), 7.76-7.69 (m, 3H), 7.63 (t, J = 8.0 Hz, 2H), 7.50-7.46 (m, 2H), 7.05 (t, J = 8.8 Hz, 2H), 5.18 (s, 1H), 3.75-3.73 (m, 4H), 2.92-2.90 (m, 10H) |
| 1306[b] | 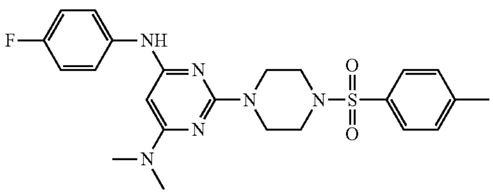 [SMILES: Cc1ccc(S(=O)(=O)N2CCN(c3nc(Nc4ccc(F)cc4)cc(N(C)C)n3)CC2)cc1] | A, 81, 88 | 20% | 471.1 (M$^+$ + 1) | 470.19 for $C_{23}H_{27}FN_6O_2S$ | $^1$H-NMR (DMSO-$d_6$, 400 MHz): δ 8.74 (s, 1H), 7.63 (d, J = 8.0 Hz, 2H), 7.50-7.46 (m, 2H), 7.43 (d, J = 8.0 Hz, 2H), 7.05 (t, J = 8.8 Hz, 2H), 5.18 (s, 1H), 3.74 (t, J = 4.8 Hz, 4H), 2.90 (s, 6H), 2.87 (t, J = 4.8 Hz, 4H), 2.38 (s, 3H) |

[a]6 h was the reaction time;
[b]16 h was the reaction time;
[c]4 h was the reaction time.

Example 20: Synthesis of 1286

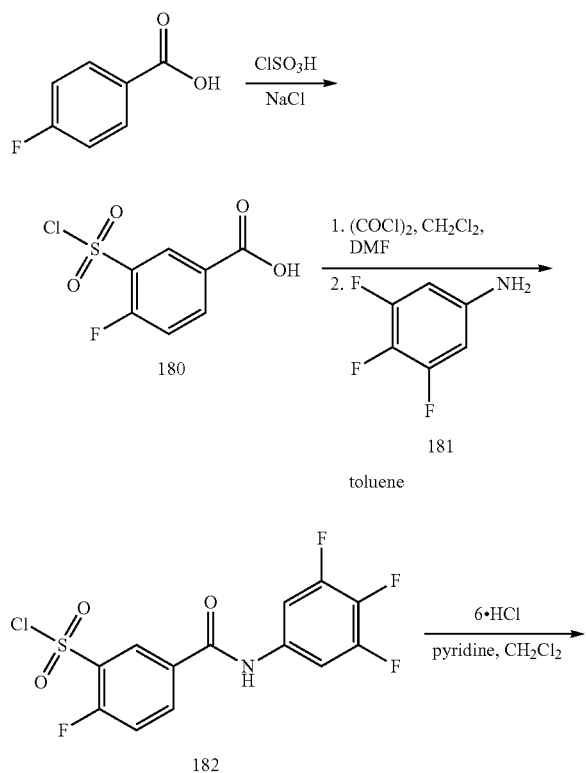

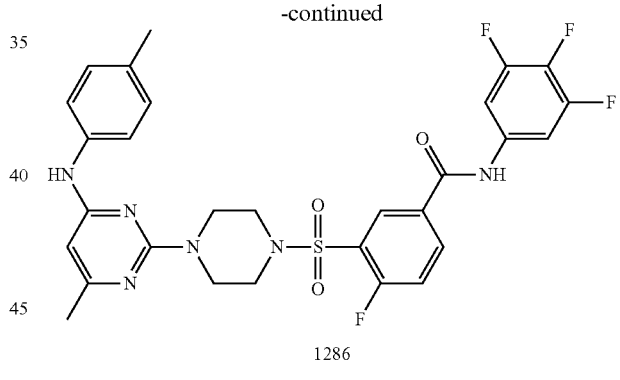

Synthesis of 3-(chlorosulfonyl)-4-fluorobenzoic acid (180)

To a stirred solution of chlorosulfonic acid (8.22 mL, 124.28 mmol) was added 4-fluorobenzoic acid (2 g, 14.28 mmol) very cautiously portion wise over a period of 10 min at 0° C. under argon atmosphere. To this was added sodium chloride (2.51 g, 42.85 mmol) portion wise at 0° C.; warmed to RT and the reaction mixture was heated to 160° C. and stirred for 5 h. The reaction was monitored by TLC; after completion of the reaction, the reaction mixture was cooled to RT and poured into an ice cold water (100 mL) and the obtained solid was filtered, washed with water (15 mL) and dried under vacuum to obtain compound 180 (3 g, crude) as white solid. TLC: 10% $CH_3OH/CH_2Cl_2$ ($R_f$ 0.3). $^1$H-NMR (CDCl$_3$, 400 MHz): δ 8.74 (dd, J=6.8, 2.4 Hz, 1H), 8.51-8.48 (m, 1H), 7.47 (t, J=8.8 Hz, 1H).

Synthesis of 2-fluoro-5-((3, 4, 5-trifluorophenyl) carbamoyl) benzenesulfonyl chloride (182)

To a stirred solution of compound 180 (500 mg, crude) in CH$_2$Cl$_2$ (5 mL) were added oxalyl chloride (0.2 mL, 2.31 mmol) and DMF (5 mL) at 0° C. under argon atmosphere; warmed to RT and stirred for 3 h. The reaction was monitored by TLC; after completion of the reaction, the volatiles were removed in vacuo to obtain the crude.

To this crude material in toluene (15 mL) was added 3, 4, 5-trifluoroaniline 181 (308 mg, 2.10 mmol) in toluene (5 mL) drop wise at 0° C. under argon atmosphere; heated to reflux and stirred for 24 h. The reaction was monitored by TLC; after completion of the reaction, the volatiles were removed in vacuo to afford compound 182 (550 mg, crude) as white solid. This crude material was used in the next step without further purification. TLC: 30% EtOAc/hexanes (R$_f$ 0.7).

Synthesis of 4-fluoro-3-((4-(4-methyl-6-(p-tolylamino) pyrimidin-2-yl) piperazin-1-yl) sulfonyl)-N-(3, 4, 5-trifluorophenyl) benzamide (1286)

To a stirred solution of compound 6. HCl salt (100 mg, 0.35 mmol) in CH$_2$Cl$_2$ (5 mL) were added compound 182 (259 mg, crude) and pyridine (0.28 mL, 3.53 mmol) at 0° C. under argon atmosphere; warmed to RT and stirred for 16 h. The reaction was monitored by TLC; after completion of the reaction, the reaction mixture was quenched with water (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 2% CH$_3$OH/CH$_2$Cl$_2$ to afford 1286 (30 mg, 14%) as an off-white solid. TLC: 5% CH$_3$OH/CH$_2$Cl$_2$ (R$_f$ 0.6); $^1$H-NMR (DMSO-d$_6$, 400 MHz): δ 10.78 (s, 1H), 9.03 (s, 1H), 8.38-8.31 (m, 2H), 7.74-7.69 (m, 3H), 7.41 (d, J=8.4 Hz, 2H), 7.10 (d, J=8.4 Hz, 2H), 5.91 (s, 1H), 3.82 (t, J=4.8 Hz, 4H), 3.21-3.19 (m, 4H), 2.25 (s, 3H), 2.12 (s, 3H); LC-MS: 99.66%; 615.1 (M$^+$+1); (column; X select CSH C-18 (50× 3.0 mm, 3.5 μm); RT 3.44 min. 0.05% TFA (Aq): ACN; 0.8 mL/min); UPLC (purity): 99.23%; (column: Acquity BEH C-18 (50×2.1 mm, 1.7μ); RT 2.61 min. ACN: 0.025% TFA (Aq); 0.5 mL/min) (IP14060390).

Example 21: Synthesis of 6-chloro-2-(4-((4-methoxyphenyl) sulfonyl) piperazin-1-yl)-N-(p-tolyl) pyrimidin-4-amine (1111)—A Common Intermediate

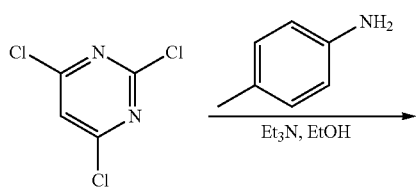

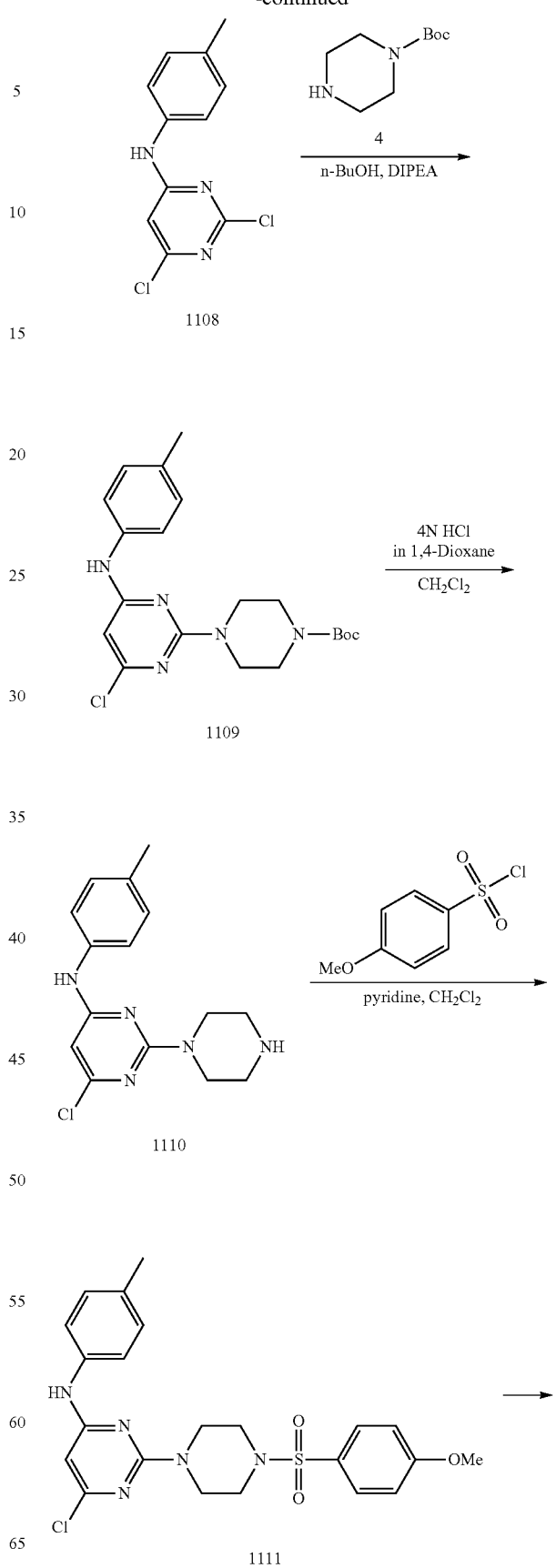

-continued

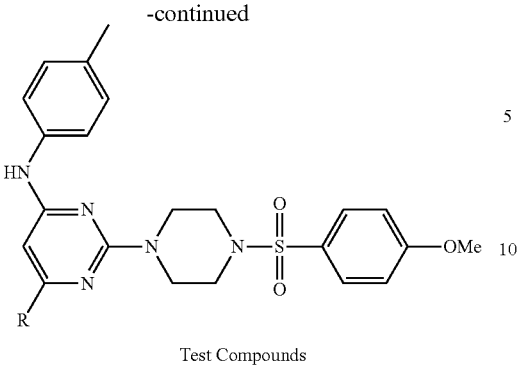

Test Compounds

Synthesis 2, 6-dichloro-N-(p-tolyl) pyrimidin-4-amine (1108)

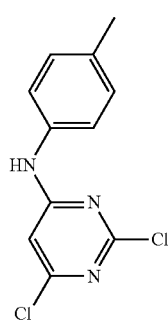

1108

To a stirred solution of 2, 4, 6-trichloropyrimidine (5 g, 27.25 mmol) in ethanol (20 mL) under argon atmosphere were added p-toluidine (2.93 g, 27.25 mmol) and triethylamine (3.39 mL, 32.70 mmol) at −5° C.; stirred at 5-10° C. for 1 h. The reaction was monitored by TLC; after completion of the reaction, the volatiles were removed in vacuo, the residue was diluted with water (60 mL) and extracted with EtOAc (2×100 mL). The combined organic extracts were dried over sodium sulfate, filtered and concentrated in vacuo to obtain the crude. The crude was purified through silica gel column chromatography using 10% EtOAc/hexanes to afford compound 1108 (4 g, 58%) as white solid. TLC: 10% EtOAc/hexanes ($R_f$ 0.2); $^1$H-NMR (DMSO-$d_6$, 400 MHz): δ 10.17 (s, 1H), 7.43-7.36 (m, 2H), 7.19 (d, J=8.0 Hz, 2H), 6.69 (s, 1H), 2.28 (s, 3H).

Synthesis of tert-butyl 4-(4-chloro-6-(p-tolylamino) pyrimidin-2-yl) piperazine-1-carboxylate (1109)

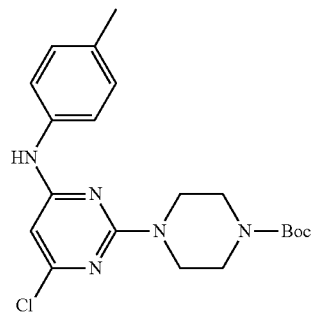

1109

To a stirred solution of compound 1108 (4 g, 15.74 mmol) in n-butanol (20 mL) under argon atmosphere were added tert-butyl piperazine-1-carboxylate 4 (4.39 g, 23.62 mmol) and N, N-diisopropylethylamine (5.4 mL, 31.49 mmol) in sealed tube at RT; heated to 100° C. and stirred for 24 h. The reaction was monitored by TLC; after completion of the reaction, the volatiles were removed in vacuo to obtain the crude. The crude was purified through silica gel column chromatography using 12% EtOAc/hexanes to afford compound 1109 (5 g, 79%) as white solid. TLC: 30% EtOAc/hexanes ($R_f$ 0.6); $^1$H-NMR (DMSO-$d_6$, 500 MHz): δ 9.38 (s, 1H), 7.43 (d, J=8.5 Hz, 2H), 7.14 (d, J=8.0 Hz, 2H), 6.02 (s, 1H), 3.67-3.65 (m, 4H), 3.41-3.36 (m, 4H), 2.26 (s, 3H), 1.43 (s, 9H).

Synthesis of 6-chloro-2-(piperazin-1-yl)-N-(p-tolyl) pyrimidin-4-amine (1110)

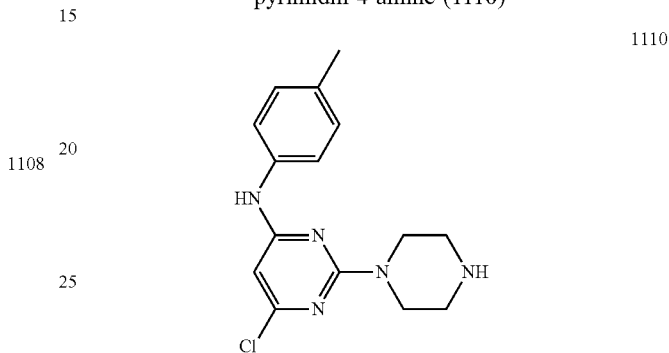

1110

To a stirred solution of compound 1109 (5 g, 12.37 mmol) in $CH_2Cl_2$ (30 mL) under argon atmosphere was added 4 N HCl in 1, 4-dioxane (10 mL) at 0° C.; warmed to RT and stirred for 4 h. The reaction was monitored by TLC; after completion of the reaction, the volatiles were removed in vacuo, the residue was diluted with water (100 mL) and basified with 10% aqueous $NaHCO_3$ solution (10 mL) and extracted with 10% $CH_3OH/CH_2Cl_2$ (2×100 mL). The combined organic extracts were dried over sodium sulfate, filtered and concentrated in vacuo to obtain the crude compound 1110 (3 g, 80%) as white solid. TLC: 30% EtOAc/hexanes ($R_f$ 0.1); $^1$H-NMR (DMSO-$d_6$, 400 MHz): δ 9.57 (s, 1H), 8.93 (br s, 1H), 7.43 (d, J=8.4 Hz, 2H), 7.13 (d, J=8.4 Hz, 2H), 6.10 (s, 1H), 3.86 (t, J=4.8 Hz, 4H), 3.12 (t, J=4.8 Hz, 4H), 2.26 (s, 3H).

Synthesis of 6-chloro-2-(4-((4-methoxyphenyl) sulfonyl) piperazin-1-yl)-N-(p-tolyl) pyrimidin-4-amine (1111)

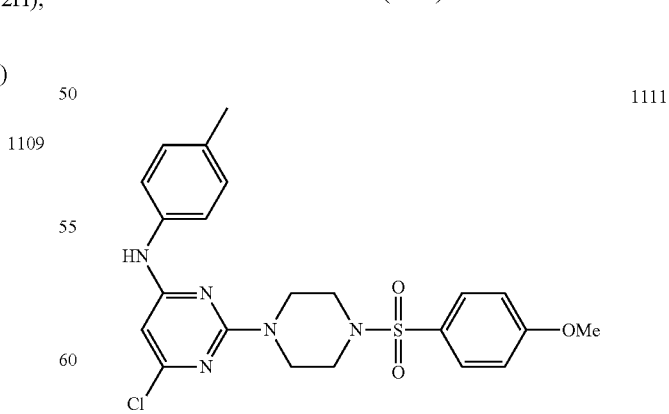

1111

To a stirred solution of compound 1110 (2.5 g, 8.22 mmol) in $CH_2Cl_2$ (50 mL) under argon atmosphere were added 4-methoxybenzenesulfonyl chloride (1.86 g, 9.04 mmol) and pyridine (3.3 mL, 41.10 mmol) at 0° C.; stirred at RT for 6 h. The reaction was monitored by TLC; after completion of the reaction, the reaction mixture was diluted with water (50 mL) and extracted with 5% CH$_3$OH/CH$_2$Cl$_2$ (2×100 mL). The combined organic extracts were dried over sodium sulfate, filtered and concentrated in vacuo to obtain the crude. The crude was purified through silica gel column chromatography using 2% CH$_3$OH/CH$_2$Cl$_2$ to afford compound 1111 (1.9 g, 49%) as white solid. TLC: 40% EtOAc/hexanes (R$_f$, 0.6); $^1$H-NMR (DMSO-d$_6$, 400 MHz): δ 9.37 (s, 1H), 7.67 (d, J=8.8 Hz, 2H), 7.37 (d, J=8.0 Hz, 2H), 7.14-7.11 (m, 4H), 5.98 (s, 1H), 3.83 (s, 3H), 3.76 (t, J=4.8 Hz, 4H), 2.90 (t, J=4.8 Hz, 4H), 2.25 (s, 3H).

Example 22: Synthesis of Additional Test Compounds From 1111

Common intermediate 1111 was converted into the final products by the following procedures (B, C, D, E, or F) and the results are captured in Table 4 below.

Procedure B: To a stirred solution of compound 1111 (70 mg, 0.15 mmol) in 1, 4-dioxane (6 mL) under argon atmosphere were added 1H-imidazole (11 mg, 0.16 mmol), cesium carbonate (58 mg, 0.18 mmol), Pd$_2$(dba)$_3$ (3.4 mg, 0.004 mmol) followed by Xantphos (4.3 mg, 0.007 mmol) in sealed tube at RT and degassed under argon for 30 min; heated to 100-120° C. and stirred for 16 h. The reaction was monitored by TLC; after completion of the reaction, the volatiles were removed in vacuo to obtain the crude. The crude was purified through silica gel column chromatography to afford the desired product.

Procedure C: To a stirred solution of compound 1111 (80 mg, 0.16 mmol) in n-butanol (2 mL) under argon atmosphere were added N, N-diisopropylethylamine (0.15 mL, 0.84 mmol) and isopropylamine (2 mL) in sealed tube at RT; heated to 100° C. and stirred for 16 h. The reaction was monitored by TLC; after completion of the reaction, the volatiles were removed in vacuo to obtain the crude. The crude was purified through silica gel column chromatography to afford the desired product.

Procedure D: To a stirred solution of compound 1111 (100 mg, 0.21 mmol) in N-methyl-2-pyrrolidone (3 mL) under argon atmosphere were added N, N-diisopropylethylamine (0.73 mL, 0.42 mmol) and 2-methylpropan-2-amine 1122 (31 mg, 0.42 mmol) in sealed tube at RT; heated to 180° C. and stirred for 36 h. The reaction was monitored by TLC; after completion of the reaction, the reaction mixture was diluted with EtOAc (50 mL) and washed with water (2×15 mL). The organic layer was separated, dried over sodium sulfate, filtered and concentrated in vacuo to obtain the crude. The crude was purified through silica gel column chromatography followed by preparative HPLC to afford the desired product.

Procedure E: A stirred solution of compound 1111 (70 mg, 0.14 mmol) in methylamine 1123 (2 M sol. in THF, 5 mL) in sealed tube under argon atmosphere was heated to 120° C. and stirred for 24 h. The reaction was monitored by TLC; after completion of the reaction, the volatiles were removed in vacuo to obtain the crude. The crude was purified through silica gel column chromatography to afford the desired product.

Procedure F: To a stirred solution of compound 1111 (70 mg, 0.14 mmol) in THF (2 mL) under argon atmosphere were added thiazol-2-ylzinc (II) bromide 1124 (0.5 M sol. in THF, 0.88 mL, 0.44 mmol) and Pd(PPh$_3$)$_4$ (17 mg, 0.01 mmol) in sealed tube at RT and degassed under argon for 30 min.; heated to 120° C. and stirred for 16 h. The reaction was monitored by TLC; after completion of the reaction, the volatiles were removed in vacuo to obtain the crude. The crude was purified through silica gel column chromatography to afford the desired product.

Commercially available amines used with common intermediate 1111 for preparation of test compounds:

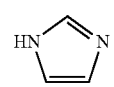

1112

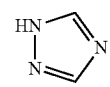

1113

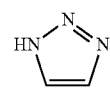

1114

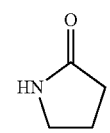

1115

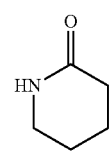

1116

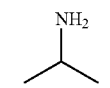

1117

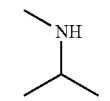

1118

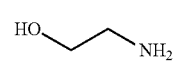

1119

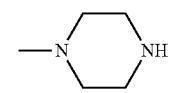

1120

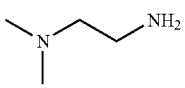

1121

1122

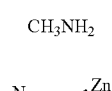

CH$_3$NH$_2$

1123

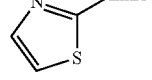

1124

TABLE 4

Synthesis of test compounds from compound 1111 and various amines

| No. | Structure | Procedure, Intermediate, Amine | Rx Yield (%) | Mass Spec. Found | Mass Spec. Calc. | ¹H-NMR |
|---|---|---|---|---|---|---|
| 1229 | 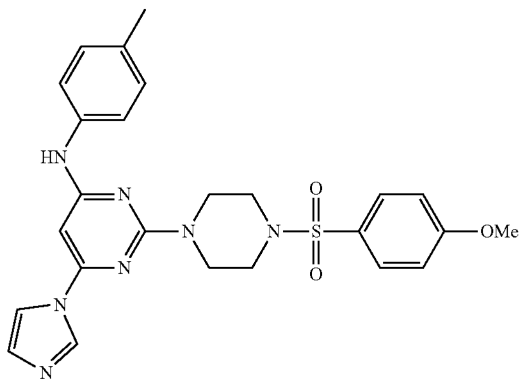 [SMILES: COc1ccc(S(=O)(=O)N2CCN(c3nc(Nc4ccc(C)cc4)cc(-n4ccnc4)n3)CC2)cc1] | B, 1111, 1112 | 40% | 506.5 (M⁺ + 1) | 505.19 for $C_{25}H_{27}N_7O_3S$ | ¹H-NMR (DMSO-$d_6$, 400 MHz): δ 9.41 (s, 1H), 8.42 (br s, 1H), 7.74 (s, 1H), 7.68 (d, J = 8.8 Hz, 2H), 7.42 (d, J = 8.4 Hz, 2H), 7.13 (d, J = 8.8 Hz, 4H), 7.08 (s, 1H), 6.12 (s, 1H), 3.86 (t, J = 5.2 Hz, 4H), 3.82 (s, 3H), 2.92 (t, J = 4.8 Hz, 4H), 2.26 (s, 3H). |
| 1230 | 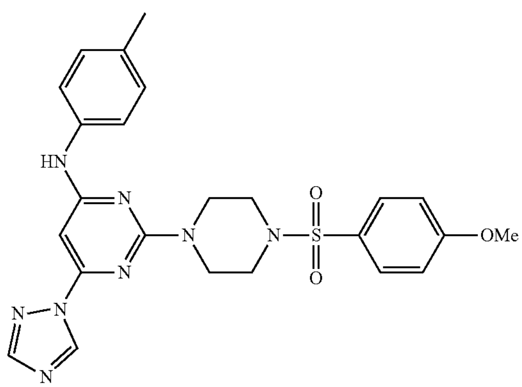 | B, 1111, 1113 | 31% | 507.4 (M⁺ + 1) | 506.18 for $C_{24}H_{26}N_8O_3S$ | ¹H-NMR (DMSO-$d_6$, 400 MHz): δ 9.54 (s, 1H), 9.35 (s, 1H), 8.23 (s, 1H), 7.69 (d, J = 8.8 Hz, 2H), 7.43 (d, J = 8.0 Hz, 2H), 7.15-7.12 (m, 4H), 6.43 (s, 1H), 3.89 (t, J = 4.4 Hz, 4H), 3.81 (s, 3H), 2.93 (t, J = 4.8 Hz, 4H), 2.27 (s, 3H). |
| 1331 and 1247 | 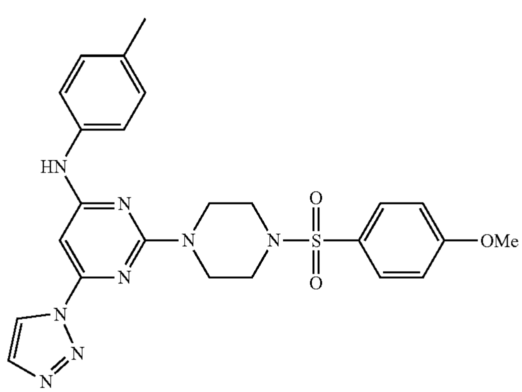 | B, 1111, 1114 | 18% | 507.5 (M⁺ + 1) | 506.18 for $C_{24}H_{26}N_8O_3S$ | ¹H-NMR (DMSO-$d_6$, 400 MHz): δ 9.60 (s, 0.3H), 9.51 (s, 0.6H), 8.79 (s, 0.3H), 8.11 (s, 1H), 7.93 (s, 0.3H), 7.69 (d, J = 8.8 Hz, 2H), 7.45-7.43 (m, 2H), 7.16-7.11 (m, 4H), 6.67 (s, 0.3H), 6.60 (s, 0.7H), 3.89 (t, J = 4.0 Hz, 4H), 3.81 (s, 3H), 2.94 (t, J = 4.8 Hz, 4H), 2.27 (s, 3H). |

TABLE 4-continued

Synthesis of test compounds from compound 1111 and various amines

| No. | Structure | Procedure, Intermediate, Amine | Rx Yield (%) | Mass Spec. Found | Mass Spec. Calc. | ¹H-NMR |
|---|---|---|---|---|---|---|
| 1247 | | | | | | |
| 1212 | 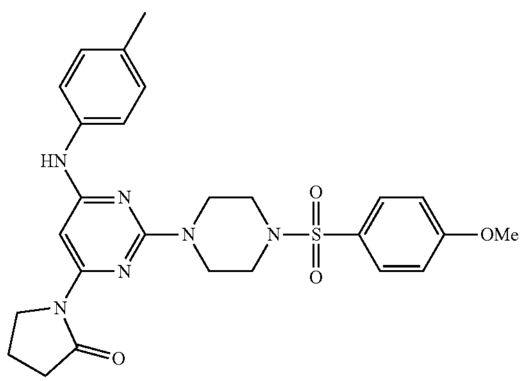 [SMILES: COc1ccc(S(=O)(=O)N2CCN(c3nc(Nc4ccc(C)cc4)cc(N4CCCC4=O)n3)CC2)cc1] | B, 1111, 1115 | 47% | 523.5 (M⁺ + 1) | 522.20 for $C_{26}H_{30}N_6O_4S$ | ¹H-NMR (DMSO-$d_6$, 400 MHz): δ 9.18 (s, 1H), 7.68 (d, J = 8.8 Hz, 2H), 7.41 (d, J = 8.4 Hz, 2H), 7.13 (d, J = 9.2 Hz, 2H), 7.07 (d, J = 8.0 Hz, 2H), 7.03 (s, 1H), 3.87 (t, J = 7.2 Hz, 2H), 3.82 (s, 3H), 3.77 (t, J = 4.4 Hz, 4H), 2.89 (t, J = 4.4 Hz, 4H), 2.50-2.49 (m, 2H), 2.23 (s, 3H), 1.99-1.92 (m, 2H). |
| 1213 | 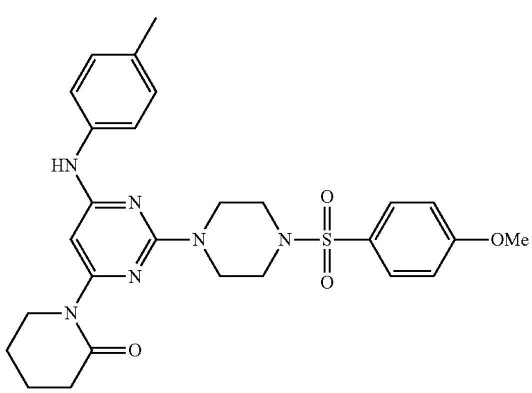 [SMILES: COc1ccc(S(=O)(=O)N2CCN(c3nc(Nc4ccc(C)cc4)cc(N4CCCCC4=O)n3)CC2)cc1] | B, 1111, 1116 | 29% | 537.6 (M⁺ + 1) | 536.22 for $C_{27}H_{32}N_6O_4S$ | ¹H-NMR (DMSO-$d_6$, 400 MHz): δ 9.14 (s, 1H), 7.68 (d, J = 8.8 Hz, 2H), 7.40 (d, J = 8.4 Hz, 2H), 7.13 (d, J = 8.8 Hz, 2H), 7.07 (d, J = 8.4 Hz, 2H), 6.75 (s, 1H), 3.83 (s, 3H), 3.82-3.75 (m, 6H), 2.90 (t, J = 4.8 Hz, 4H), 2.44 (t, J = 6.8 Hz, 2H), 2.24 (s, 3H), 1.79-1.72 (m, 4H). |

TABLE 4-continued

Synthesis of test compounds from compound 1111 and various amines

| No. | Structure | Procedure, Intermediate, Amine | Rx Yield (%) | Mass Spec. Found | Mass Spec. Calc. | ¹H-NMR |
|---|---|---|---|---|---|---|
| 1231 | 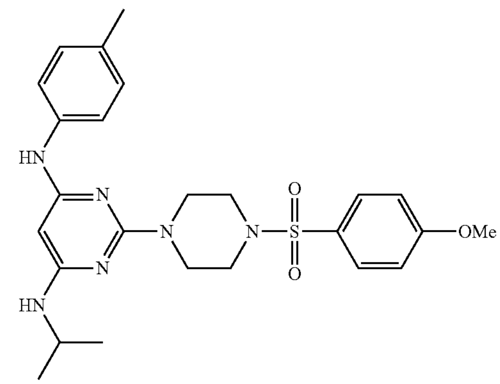 [SMILES: COc1ccc(S(=O)(=O)N2CCN(c3nc(Nc4ccc(C)cc4)cc(NC(C)C)n3)CC2)cc1] | C, 1111, 1117 | 36% | 497.4 (M⁺ + 1) | 496.23 for $C_{25}H_{32}N_6O_3S$ | ¹H-NMR (DMSO-d$_6$, 400 MHz): δ 8.41 (s, 1H), 7.67 (d, J = 8.8 Hz, 2H), 7.28 (d, J = 8.4 Hz, 2H), 7.13 (d, J = 8.8 Hz, 2H), 7.02 (d, J = 8.0 Hz, 2H), 6.27-6.25 (m, 1H), 5.11 (s, 1H), 3.82-3.84 (m, 4H), 3.73 (t, J = 4.8 Hz, 4H), 2.85 (t, J = 4.8 Hz, 4H), 2.21 (s, 3H), 1.07 (d, J = 6.8 Hz, 6H). |
| 1248ᵃ | | C, 1111, 1118 | 29% | 511.5 (M⁺ + 1) | 510.24 for $C_{26}H_{34}N_6O_3S$ | ¹H-NMR (DMSO-d$_6$, 400 MHz): δ 8.57 (s, 1H), 7.67 (d, J = 8.8 Hz, 2H), 7.35 (d, J = 8.4 Hz, 2H), 7.13 (d, J = 8.8 Hz, 2H), 7.03 (d, J = 8.4 Hz, 2H), 5.19 (s, 1H), 4.65-4.61 (m, 1H), 3.82 (s, 3H), 3.75-3.71 (m, 4H), 2.89-2.83 (m, 4H), 2.68 (s, 3H), 2.22 (s, 3H), 1.05 (d, J = 6.4 Hz, 6H). |
| 1249 | 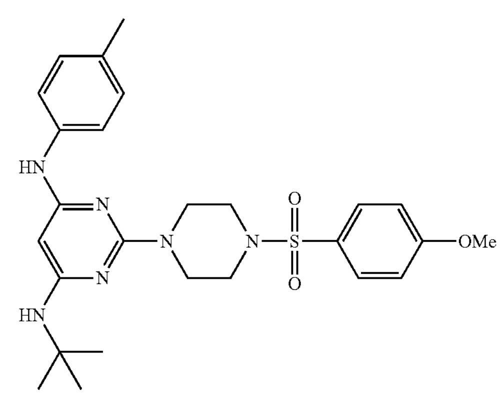 [SMILES: COc1ccc(S(=O)(=O)N2CCN(c3nc(Nc4ccc(C)cc4)cc(NC(C)(C)C)n3)CC2)cc1] | D, 1111, 1122 | 14% | 511.6 (M⁺ + 1) | 510.24 for $C_{26}H_{34}N_6O_3S$ | ¹H-NMR (DMSO-d$_6$, 400 MHz): δ 8.39 (br s, 1H), 7.69 (d, J = 8.8 Hz, 2H), 7.24-7.23 (m, 2H), 7.14 (d, J = 8.8 Hz, 2H), 7.08-7.07 (m, 2H), 6.43 (br s, 1H), 5.27 (s, 1H), 3.83 (s, 3H), 3.73-3.71 (m, 4H), 2.91-2.90 (m, 4H), 2.24 (s, 3H), 1.31 (s, 9H). |

TABLE 4-continued

Synthesis of test compounds from compound 1111 and various amines

| No. | Structure | Procedure, Intermediate, Amine | Rx Yield (%) | Mass Spec. Found | Mass Spec. Calc. | $^1$H-NMR |
|---|---|---|---|---|---|---|
| 1242 | 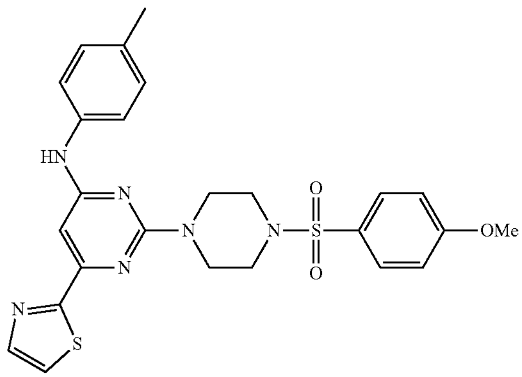 [SMILES: COc1ccc(S(=O)(=O)N2CCN(c3nc(Nc4ccc(C)cc4)cc(-c4nccs4)n3)CC2)cc1] | F, 1111, 1124 | 39% | 523.6 (M$^+$ + 1) | 522.15 for $C_{25}H_{26}N_6O_3S_2$ | $^1$H-NMR (DMSO-d$_6$, 400 MHz): δ 9.46 (s, 1H), 7.97-7.96 (m, 1H), 7.86-7.85 (m, 1H), 7.69 (d, J = 8.8 Hz, 2H), 7.45 (d, J = 8.0 Hz, 2H), 7.15-7.11 (m, 4H), 6.77 (s, 1H), 3.86 (t, J = 5.2 Hz, 4H), 3.82 (s, 3H), 2.95 (t, J = 5.2 Hz, 4H), 2.27 (s, 3H). |
| 1243 | 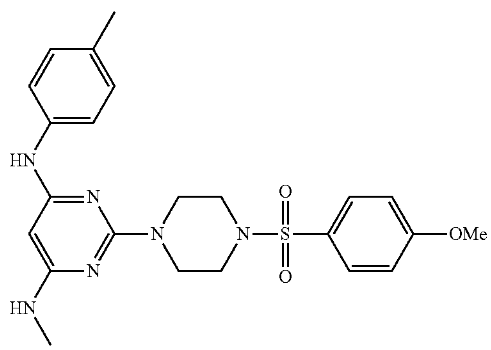 [SMILES: CNc1cc(Nc2ccc(C)cc2)nc(N2CCN(S(=O)(=O)c3ccc(OC)cc3)CC2)n1] | E, 1111, 1123 | 43% | 469.4 (M$^+$ + 1) | 468.19 for $C_{23}H_{28}N_6O_3S$ | $^1$H-NMR (DMSO-d$_6$, 400 MHz): δ 8.47 (s, 1H), 7.67 (d, J = 8.8 Hz, 2H), 7.30 (d, J = 8.4 Hz, 2H), 7.13 (d, J = 8.8 Hz, 2H), 7.03 (d, J = 8.0 Hz, 2H), 6.35 (br s, 1H), 5.09 (s, 1H), 3.83 (s, 3H), 3.74 (t, J = 4.8 Hz, 4H), 2.85 (t, J = 5.2 Hz, 4H), 2.65 (d, J = 4.8 Hz, 3H), 2.22 (s, 3H). |
| 1232[b] | 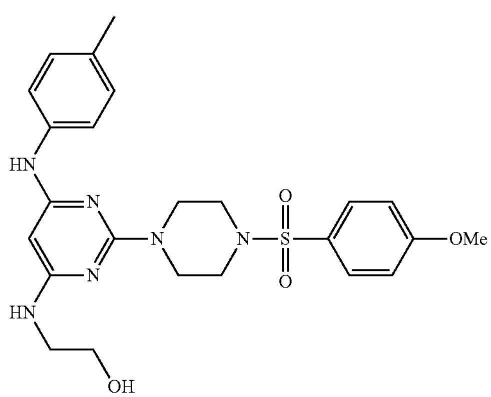 [SMILES: COc1ccc(S(=O)(=O)N2CCN(c3nc(NCCO)cc(Nc4ccc(C)cc4)n3)CC2)cc1] | C, 1111, 1119 | 32% | 499.6 (M$^+$ + 1) | 498.20 for $C_{24}H_{30}N_6O_4S$ | $^1$H-NMR (DMSO-d$_6$, 400 MHz): δ 8.46 (br s, 1H), 7.67 (d, J = 8.8 Hz, 2H), 7.29 (d, J = 8.4 Hz, 2H), 7.13 (d, J = 8.8 Hz, 2H), 7.02 (d, J = 8.0 Hz, 2H), 6.39 (br s, 1H), 5.15 (s, 1H), 4.61 (t, J = 5.2 Hz, 1H), 3.83 (s, 3H), 3.73 (t, J = 5.2 Hz, 4H), 3.46-3.42 (m, 2H), 3.19-3.17 (m, 2H), 2.85 (t, J = 5.2 Hz, 4H), 2.21 (s, 3H). |

TABLE 4-continued

Synthesis of test compounds from compound 1111 and various amines

| No. | Structure | Procedure, Intermediate, Amine | Rx Yield (%) | Mass Spec. Found | Mass Spec. Calc. | $^1$H-NMR |
|---|---|---|---|---|---|---|
| 1207[c] | 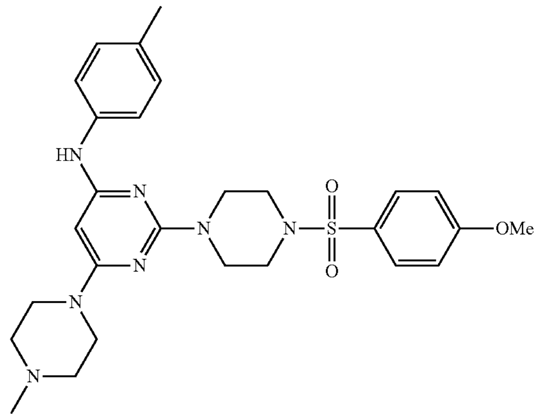 [SMILES: COc1ccc(S(=O)(=O)N2CCN(c3nc(Nc4ccc(C)cc4)cc(N4CCN(C)CC4)n3)CC2)cc1] | C, 1111, 1120 | 37% | 538.4 (M$^+$ + 1) | 537.25 for C$_{27}$H$_{35}$N$_7$O$_3$S | $^1$H-NMR (DMSO-d$_6$, 400 MHz): δ 8.63 (s, 1H), 7.67 (d, J = 8.8 Hz, 2H), 7.34 (d, J = 8.4 Hz, 2H), 7.13 (d, J = 9.2 Hz, 2H), 7.04 (d, J = 8.0 Hz, 2H), 5.30 (s, 1H), 3.82 (s 3H), 3.73 (t, J = 4.8 Hz, 4H), 3.38-3.34 (m, 4H), 2.86 (t, J = 4.8 Hz, 4H), 2.34-2.30 (m, 4H), 2.22 (s, 3H), 2.19 (s, 3H). |
| 1251[d] | 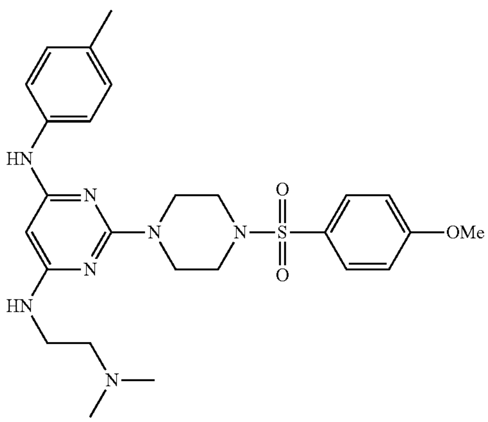 [SMILES: COc1ccc(S(=O)(=O)N2CCN(c3nc(NCCN(C)C)cc(Nc4ccc(C)cc4)n3)CC2)cc1] | C, 1111, 1121 | 39% | 526.5 (M$^+$ + 1) | 525.25 for C$_{26}$H$_{35}$N$_7$O$_3$S | $^1$H-NMR (DMSO-d$_6$, 400 MHz): δ 8.45 (br s, 1H), 7.67 (d, J = 8.8 Hz, 2H), 7.29 (d, J = 8.4 Hz, 2H), 7.13 (d, J = 8.8 Hz, 2H), 7.02 (d, J = 8.4 Hz, 2H), 6.28 (br s, 1H), 5.14 (s, 1H), 3.83 (s, 3H), 3.74-3.72 (m, 4H), 3.21-3.17 (m, 2H), 2.86-2.85 (m, 4H), 2.33-2.30 (m, 2H), 2.22 (s, 3H), 2.13 (s, 6H). |

[a]160° C., 70 h;
[b]140° C., 48 h;
[c]100° C., 24 h;
[d]180° C., 16 h.

Example 23: Synthesis of 1241

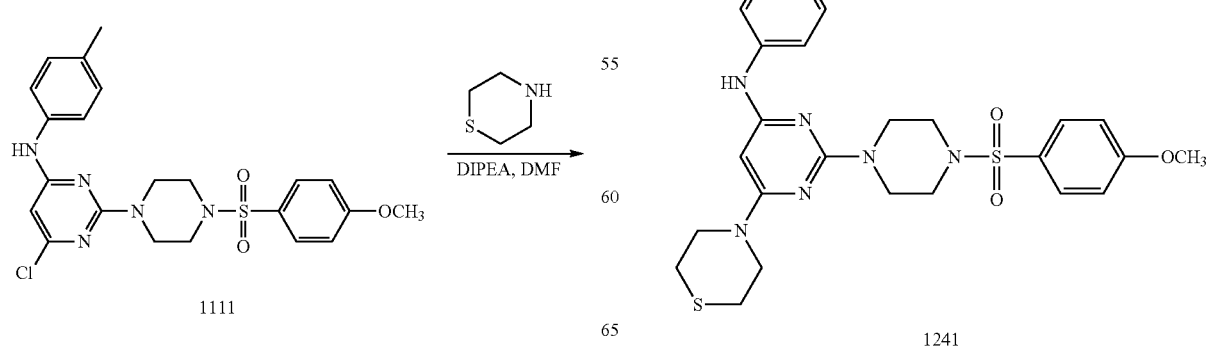

151

Synthesis of 2-(4-((4-methoxyphenyl) sulfonyl) piperazin-1-yl)-6-thiomorpholino-N-(p-tolyl) pyrimidin-4-amine (1241)

To a stirred solution of compound 1111 (60 mg, 0.13 mmol) in DMF (2 mL) under argon atmosphere were added thiomorpholine (20 mg, 0.19 mmol) and diisopropylethylamine (0.04 mL, 0.25 mmol) in a microwave vial at RT. The reaction mixture was irradiated in a microwave reactor at 160° C. for 5 h. The reaction was monitored by TLC; after completion of the reaction, the reaction mixture was diluted with water (20 mL) and extracted with EtOAc (2×30 mL). The combined organic extracts were dried over sodium sulfate, filtered and concentrated in vacuo to obtain the crude. The crude was purified through silica gel column chromatography using 15% EtOAc/hexanes, followed by preparative TLC to afford 1241 (15 mg, 22%) as an off-white solid. TLC: 30% EtOAc/hexanes ($R_f$ 0.5); $^1$H-NMR (DMSO-$d_6$, 400 MHz): δ 8.64 (s, 1H), 7.67 (d, J=9.2 Hz, 2H), 7.34 (d, J=8.4 Hz, 2H), 7.13 (d, J=9.2 Hz, 2H), 7.04 (d, J=8.0 Hz, 2H), 5.30 (s, 1H), 3.83 (s, 3H), 3.76-3.72 (m, 8H), 2.88-2.85 (m, 4H), 2.58-2.54 (m, 4H), 2.22 (s, 3H); LC-MS: 91.01%; 541.5 (M$^+$+1); (column; X-select CSH C-18 (50× 3.0 mm, 3.5 μm); RT 4.02 min. 0.05% TFA (Aq): ACN; 0.8 mL/min); UPLC (purity): 90.74%; (column: Acquity UPLC BEH C-18 {2.1×50 mm, 1.7μ}; RT 2.40 min. ACN: 0.025% TFA (Aq); 0.5 mL/min).

Example 24: Synthesis of 1250

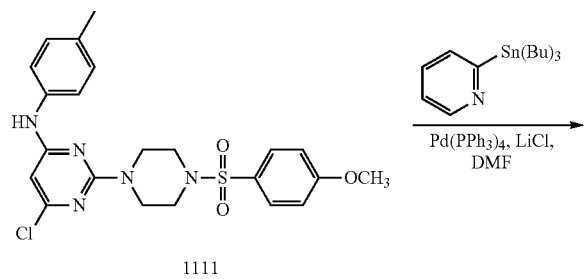

1111

152

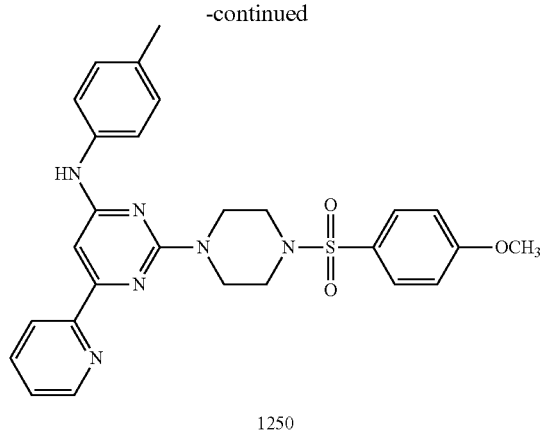

1250

Synthesis of 2-(4-((4-methoxyphenyl) sulfonyl) piperazin-1-yl)-6-(pyridin-2-yl)-N-(p-tolyl) pyrimidin-4-amine (1250)

To a stirred solution of compound 1111 (60 mg, 0.13 mmol) in DMF (3 mL) under argon atmosphere were added 2-(tributylstannyl) pyridine (117 mg, 0.32 mmol) and lithium chloride (12 mg, 0.28 mmol) in sealed tube at RT and purged under argon for 20 min. To this was added Pd(PPh$_3$)$_4$ (15 mg, 0.01 mmol) at RT and purged under argon for 10 min; heated to 120° C. and stirred for 16 h. The reaction was monitored by TLC; after completion of the reaction, the reaction mixture was diluted with water (20 mL) and extracted with EtOAc (2×30 mL). The combined organic extracts were dried over sodium sulfate, filtered and concentrated in vacuo to obtain the crude. The crude was purified through silica gel column chromatography using 20% EtOAc/hexanes to afford 1250 (30 mg, 46%) as an off-white solid. TLC: 30% EtOAc/hexanes ($R_f$ 0.2); $^1$H-NMR (DMSO-$d_6$, 400 MHz): δ 9.36 (s, 1H), 8.63 (d, J=4.0 Hz, 1H), 8.26 (d, J=7.6 Hz, 1H), 7.92 (td, J=9.2, 1.6 Hz, 1H), 7.69 (d, J=8.8 Hz, 2H), 7.48-7.44 (m, 3H), 7.13-7.09 (m, 5H), 3.91 (t, J=5.2 Hz, 4H), 3.81 (s, 3H), 2.95 (t, J=4.8 Hz, 4H), 2.26 (s, 3H); LC-MS: 98.23%; 517.5 (M$^+$+1); (column; X-select CSH C-18 (50×3.0 mm, 3.5 μm); RT 4.05 min. 0.05% TFA (Aq): ACN; 0.8 mL/min); UPLC (purity): 98.05%; (column: Acquity UPLC BEH C-18 {2.1×50 mm, 1.7μ}; RT 2.32 min. ACN: 0.025% TFA (Aq); 0.5 mL/min).

Example 25: Synthesis of 1282

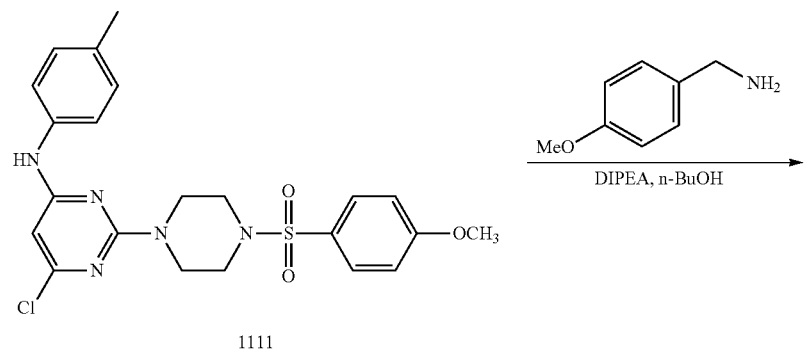

1111

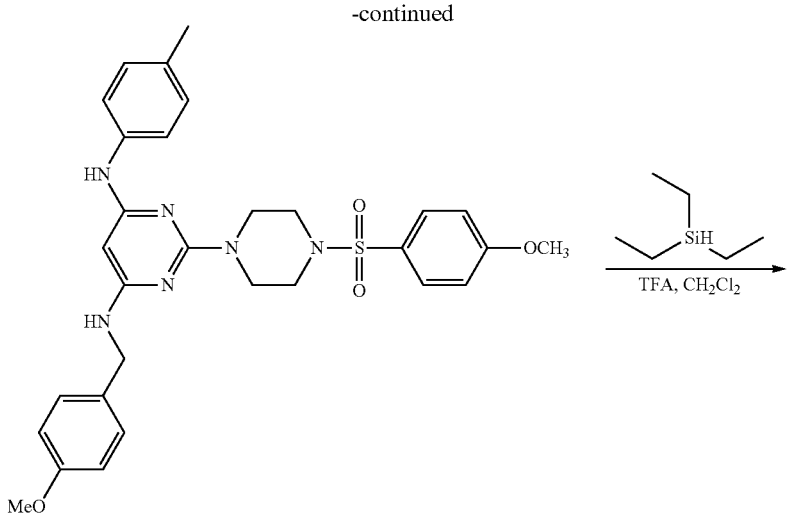

184

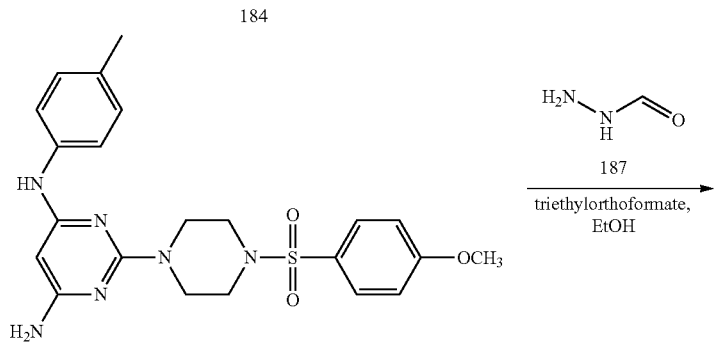

186

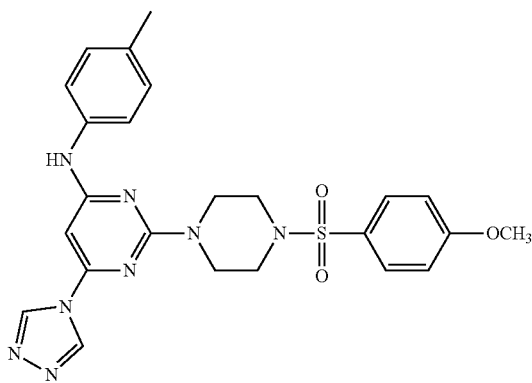

1282

Synthesis of N⁴-(4-methoxybenzyl)-2-(4-((4-methoxyphenyl) sulfonyl) piperazin-1-yl)-N⁶-(p-tolyl) pyrimidine-4, 6-diamine (184)

To a stirred solution of compound 1111 (100 mg, 0.21 mmol) in n-butanol (6 mL) under argon atmosphere were added (4-methoxyphenyl) methanamine (145 mg, 1.06 mmol) and diisopropylethylamine (0.11 mL, 0.63 mmol) in sealed tube at RT; heated to 140° C. and stirred for 72 h. The reaction was monitored by TLC; after completion of the reaction, the volatiles were removed in vacuo to obtain the crude. The crude was purified through silica gel column chromatography using 35% EtOAc/hexanes to afford compound 184 (95 mg, 78%) as an off-white solid. TLC: 40% EtOAc/hexanes ($R_f$ 0.2); ¹H-NMR (DMSO-$d_6$, 500 MHz): δ 8.48 (br s, 1H), 7.66 (d, J=9.0 Hz, 2H), 7.26 (d, J=8.5 Hz, 2H), 7.17 (d, J=8.5 Hz, 2H), 7.13 (d, J=9.0 Hz, 2H), 7.01 (d, J=8.5 Hz, 3H), 6.85 (d, J=8.5 Hz, 2H), 5.13 (br s, 1H), 4.25 (s, 2H), 3.83 (s, 3H), 3.75-3.71 (m, 7H), 2.82-2.78 (m, 4H), 2.21 (s, 3H).

Synthesis of 2-(4-((4-methoxyphenyl) sulfonyl) piperazin-1-yl)-N⁴-(p-tolyl) pyrimidine-4, 6-diamine (186)

To a stirred solution of compound 184 (95 mg, 0.16 mmol) in CH₂Cl₂ (10 mL) under argon atmosphere were added trifluoroacetic acid (0.13 mL, 1.65 mmol) and triethylsilane (0.13 mL, 0.82 mmol) at 0° C.; warmed to RT and stirred for 16 h. The reaction was monitored by TLC; after completion of the reaction, the volatiles were removed in vacuo, the residue was diluted with water (20 mL) and extracted with EtOAc (2×40 mL). The combined organic extracts were dried over sodium sulfate, filtered and concentrated in vacuo to obtain the crude. The crude was purified through silica gel column chromatography using 3% MEOH/CH$_2$Cl$_2$ to afford compound 186 (65 mg, 87%) as an off-white solid. TLC: 5% MEOH/CH$_2$Cl$_2$ (R$_f$, 0.3); $^1$H-NMR (DMSO-d$_6$, 500 MHz): δ 8.47 (s, 1H), 7.68 (d, J=9.0 Hz, 2H), 7.29 (d, J=8.5 Hz, 2H), 7.14 (d, J=9.0 Hz, 2H), 7.04 (d, J=8.0 Hz, 2H), 5.94 (br s, 2H), 5.15 (s, 1H), 3.83 (s, 3H), 3.75-3.70 (m, 4H), 2.86-2.80 (m, 4H), 2.27 (s, 3H).

Synthesis of 2-(4-((4-methoxyphenyl) sulfonyl) piperazin-1-yl)-N-(p-tolyl)-6-(4H-1, 2, 4-triazol-4-yl) pyrimidin-4-amine (1282)

To a stirred solution of N-formylhydrazine 187 (28 mg, 0.46 mmol) in ethanol (5 mL) under argon atmosphere was added triethylorthoformate (114 mg, 0.77 mmol) in sealed tube at RT; heated to 90° C. and stirred for 3 h. The reaction mixture was cooled to RT, to this was added compound 186 (70 mg, 0.15 mmol) at RT; heated to 90° C. and stirred for 72 h. The reaction was monitored by TLC; after completion of the reaction, the volatiles were removed in vacuo, the residue was diluted with water (20 mL) and extracted with EtOAc (2×30 mL). The combined organic extracts were dried over sodium sulfate, filtered and concentrated in vacuo to obtain the crude. The crude was purified through preparative HPLC, followed by preparative TLC to afford 1282 (15 mg, 19%) as an off-white solid. TLC: 5% MeOH/CH$_2$Cl$_2$ (R$_f$, 0.5); $^1$H-NMR (DMSO-d$_6$, 400 MHz): δ 9.53 (s, 1H), 9.18 (s, 2H), 7.68 (d, J=8.8 Hz, 2H), 7.41 (d, J=8.4 Hz, 2H), 7.13 (d, J=8.8 Hz, 4H), 6.18 (s, 1H), 3.87 (t, J=4.8 Hz, 4H), 3.82 (s, 3H), 2.92 (t, J=4.8 Hz, 4H), 2.26 (s, 3H); LC-MS: 99.40%; 507.6 (M$^+$+1); (column; X-select CSH C-18 (50× 3.0 mm, 3.5 µm); RT 3.70 min. 5.0 mM NH$_4$OAc:ACN; 0.8 mL/min); UPLC (purity): 99.62%; (column: Acquity UPLC BEH C-18 {2.1×50 mm, 1.7µ}; RT 2.48 min. ACN: 0.025% TFA (Aq); 0.5 mL/min).

Example 26: Synthesis of 1274

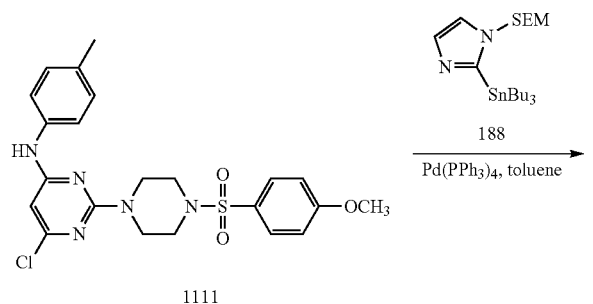

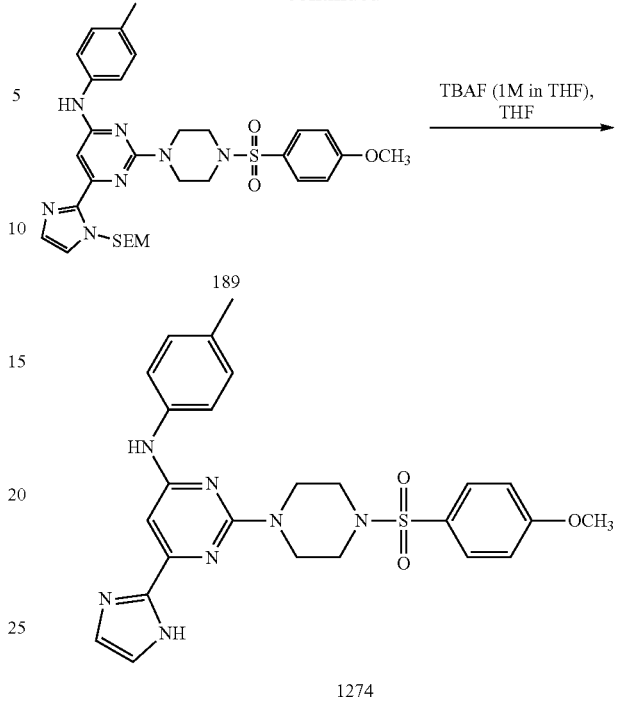

Synthesis of 2-(4-((4-methoxyphenyl) sulfonyl) piperazin-1-yl)-N-(p-tolyl)-6-(1-((2-(trimethylsilyl) ethoxy) methyl)-1H-imidazol-2-yl) pyrimidin-4-amine (189)

To a stirred solution of compound 1111 (100 mg, 0.21 mmol) in toluene (6 mL) under argon atmosphere was added 2-(tributylstannyl)-1-((2-(trimethylsilyl) ethoxy) methyl)-1H-imidazole 188 (258 mg, 0.52 mmol)) in sealed tube at RT and degassed under argon for 20 min. To this was added Pd(PPh$_3$)$_4$ (122 mg, 0.10 mmol) at RT and degassed under argon for 10 min; heated to 120° C. and stirred for 16 h. The reaction was monitored by TLC; after completion of the reaction, the volatiles were removed in vacuo to obtain the crude. The crude was purified through silica gel column chromatography using 45% EtOAc/hexanes to afford compound 189 (110 mg, crude) as light brown syrup. TLC: 40% EtOAc/hexanes (R$_f$, 0.4); LC-MS: 46.40%; 636.1 (M$^+$+1); (column; X-select CSH C-18 (50×3.0 mm, 3.5 µm); RT 3.65 min. 0.05% TFA (Aq): ACN; 0.8 mL/min).

Synthesis of 6-(1H-imidazol-2-yl)-2-(4-((4-methoxyphenyl) sulfonyl) piperazin-1-yl)-N-(p-tolyl) pyrimidin-4-amine (1274)

To a stirred solution of compound 189 (110 mg, crude) in THF (3 mL) was added tetrabutylammonium fluoride (1 M sol. in THF, 0.9 mL, 0.87 mmol) in sealed tube at RT; heated to 80° C. and stirred for 16 h. The reaction was monitored by TLC; after completion of the reaction, the volatiles were removed in vacuo, the residue was diluted with water (20 mL) and extracted with EtOAc (2×30 mL). The combined organic extracts were dried over sodium sulfate, filtered and concentrated in vacuo to obtain the crude. The crude was purified through silica gel column chromatography using 2% MeOH/CH$_2$Cl$_2$ to afford 1274 (25 mg, 29%) as an off-white solid. TLC: 5% MeOH/CH$_2$Cl$_2$ (R$_f$, 0.3); $^1$H-NMR (DMSO-d$_6$, 400 MHz): δ 13.81 (br s, 1H), 9.29 (s, 1H), 8.41 (br s, 1H), 7.91 (s, 1H), 7.69 (d, J=8.8 Hz, 2H), 7.42 (d, J=8.4 Hz, 2H), 7.14-7.11 (m, 4H), 6.48 (s, 1H), 3.91-3.87 (m, 4H), 3.81 (s, 3H), 2.93-2.89 (m, 4H), 2.26 (s, 3H); LC-MS: 99.19%; 506.0 (M$^+$+1); (column; X-select CSH C-18 (50× 3.0 mm, 3.5 μm); RT 3.10 min. 0.05% TFA (Aq): ACN; 0.8 mL/min); UPLC (purity): 98.15%; (column: Acquity UPLC BEH C-18 (2.1×50 mm, 1.7μ); RT 2.21 min. ACN: 0.025% TFA (Aq); 0.5 mL/min).

Example 27: Synthesis of 1265

Synthesis of 6-(2-((tert-butyldimethylsilyl) oxy) ethoxy)-(2-(4-((4-methoxyphenyl) sulfonyl) piperazin-1-yl)-N-(p-tolyl) pyrimidin-4-amine (191)

To a stirred solution of compound 1111 (100 mg, 0.21 mmol) in 1, 4-dioxane (5 mL) under argon atmosphere were added 2-((tert-butyldimethylsilyl) oxy) ethan-1-ol 190 (75 mg, 0.42 mmol) and potassium phosphate tribasic (67 mg, 0.32 mmol) in sealed tube at RT and degassed under argon for 20 min. To this were added Pd$_2$(dba)$_3$ (9.7 mg, 0.01 mmol) and Xantphos (7 mg, 0.01 mmol) at RT and degassed

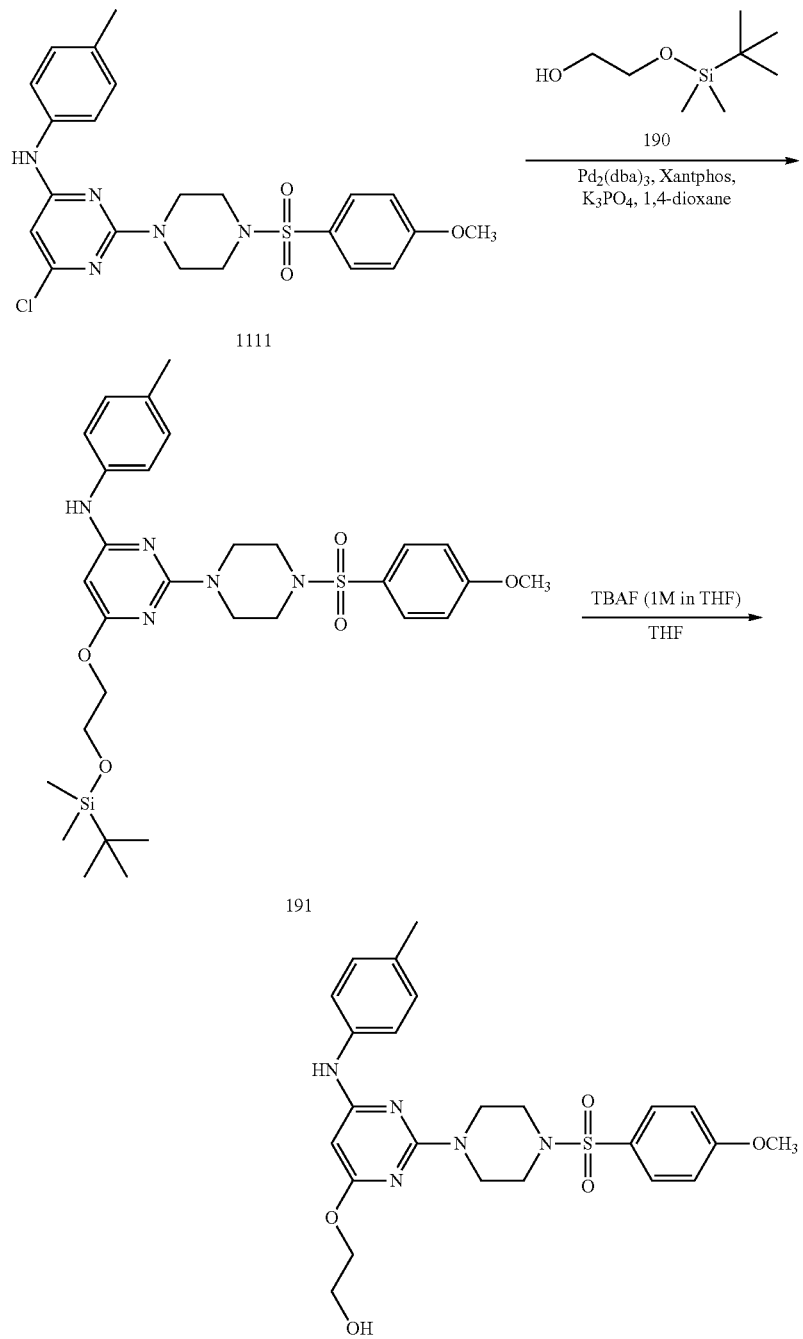

under argon for 10 min; heated to 120° C. and stirred for 16 h. The reaction was monitored by TLC; after completion of the reaction, the volatiles were removed in vacuo, the residue was diluted with water (20 mL) and extracted with EtOAc (2×30 mL). The combined organic extracts were dried over sodium sulfate, filtered and concentrated in vacuo to obtain the crude. The crude was purified through silica gel column chromatography using 10% EtOAc/hexanes to afford compound 191 (60 mg, 46%) as white solid. TLC: 30% EtOAc/hexanes ($R_f$ 0.8); $^1$H-NMR (DMSO-$d_6$, 500 MHz): δ 8.94 (s, 1H), 7.68 (d, J=8.5 Hz, 2H), 7.34 (d, J=8.5 Hz, 2H), 7.13 (d, J=8.5 Hz, 2H), 7.07 (d, J=8.5 Hz, 2H), 5.33 (s, 1H), 4.20 (t, J=4.0 Hz, 2H), 3.82 (s, 3H), 3.80-3.78 (m, 6H), 2.89-2.87 (m, 4H), 2.24 (s, 3H), 0.82 (s, 9H), 0.01 (s, 6H).

Synthesis of 2-((2-(4-((4-methoxyphenyl) sulfonyl) piperazin-1-yl)-6-(p-tolylamino) pyrimidin-4-yl) oxy) ethan-1-ol (1265)

To a stirred solution of compound 191 (40 mg, 0.06 mmol) in THF (5 mL) under argon atmosphere was added tetrabutylammonium fluoride (1 M sol. in THF, 0.13 mL, 0.13 mmol) at 0° C.; warmed to RT and stirred for 2 h. The reaction was monitored by TLC; after completion of the reaction, the reaction mixture was diluted with water (20 mL) and extracted with EtOAc (2×20 mL). The combined organic extracts were dried over sodium sulfate, filtered and concentrated in vacuo to obtain the crude, which was triturated with 10% CH$_2$Cl$_2$/n-pentane to afford 1265 (25 mg, 78%) as an off-white solid. TLC: 5% MEOW CH$_2$Cl$_2$ ($R_f$ 0.3); $^1$H-NMR (DMSO-$d_6$, 400 MHz): δ 8.91 (s, 1H), 7.68 (d, J=9.2 Hz, 2H), 7.33 (d, J=8.4 Hz, 2H), 7.13 (d, J=9.2 Hz, 2H), 7.07 (d, J=8.4 Hz, 2H), 5.34 (s, 1H), 4.75 (t, J=5.6 Hz, 1H), 4.14-4.12 (m, 2H), 3.83 (s, 3H), 3.77 (t, J=4.4 Hz, 4H), 3.63-3.59 (m, 2H), 2.89 (t, J=4.8 Hz, 4H), 2.23 (s, 3H); LC-MS: 99.35%; 500.5 (M$^+$+1); (column; X-select CSH C-18 (50×3.0 mm, 3.5 μm); RT 4.20 min. 0.05% TFA (Aq): ACN; 0.8 mL/min); UPLC (purity): 99.15%; (column: Acquity UPLC BEH C-18 (2.1×50 mm, 1.7μ); RT 2.41 min. ACN: 0.025% TFA (Aq); 0.5 mL/min).

Example 28: Synthesis of N$^4$, N$^4$-dimethyl-2-(piperazin-1-yl)-N$^6$-(p-tolyl) pyrimidine-4, 6-diamine (196)—A Common Intermediate

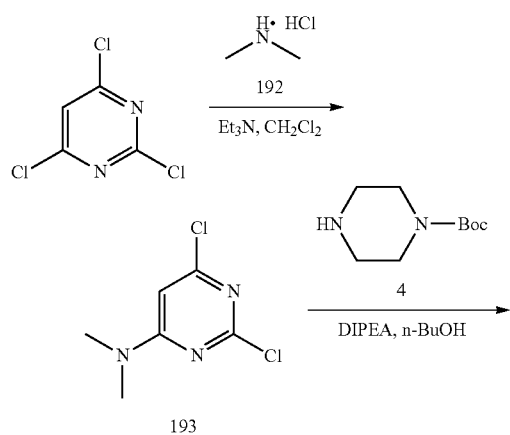

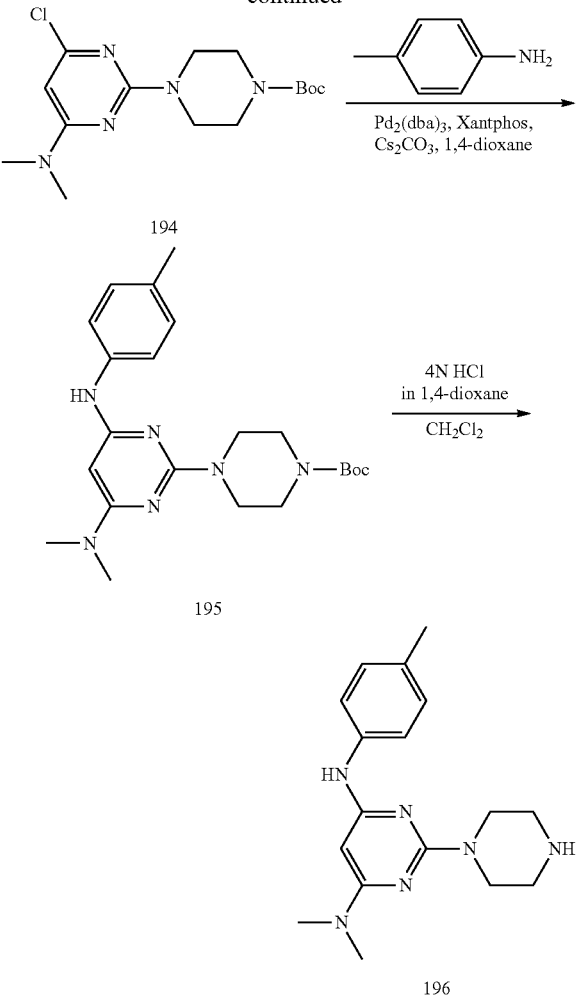

Synthesis of 2, 6-dichloro-N, N-dimethylpyrimidin-4-amine (193)

To a stirred solution of 2, 4, 6-trichloropyrimidine (2 g, 10.92 mmol) in CH$_2$Cl$_2$ (100 mL) under argon atmosphere were added dimethylamine hydrochloride 192 (890 mg, 10.92 mmol) and triethylamine (3.15 mL, 21.85 mmol) at −78° C. and stirred for 2 h; warmed to 0° C. and stirred for 2 h. The reaction was monitored by TLC; after completion of the reaction, the reaction mixture was diluted with ice water (40 mL) and extracted with CH$_2$Cl$_2$ (2×60 mL). The combined organic extracts were dried over sodium sulfate and concentrated in vacuo to obtain the crude, which was purified through silica gel column chromatography using 7% EtOAc/hexanes to afford compound 193 (1.4 g, 70%) as white solid. TLC: 10% EtOAc/hexanes (R$_f$: 0.4); $^1$H-NMR (CDCl$_3$, 500 MHz): δ 6.38 (s, 1H), 3.15 (s, 6H).

Synthesis of tert-butyl 4-(4-chloro-6-(dimethyl-amino) pyrimidin-2-yl) piperazine-1-carboxylate (194)

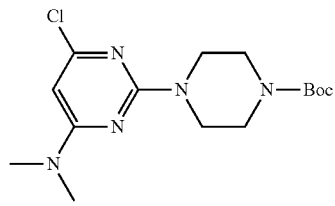

194

To a stirred solution of compound 193 (500 mg, 2.60 mmol) in n-butanol (5 mL) under argon atmosphere were added tert-butyl piperazine-1-carboxylate (533 mg, 2.86 mmol) and diisopropylethylamine (0.7 mL, 3.90 mmol) in sealed tube at RT; heated to 80° C. and stirred for 16 h. The reaction was monitored by TLC; after completion of the reaction, the volatiles were removed in vacuo, the residue was diluted with water (25 mL) and extracted with EtOAc (2×30 mL). The combined organic extracts were dried over sodium sulfate, filtered and concentrated in vacuo to obtain the crude, which was purified through silica gel column chromatography using 10% EtOAc/hexanes to afford compound 194 (690 mg, 78%) as white solid. TLC: 20% EtOAc/hexanes (R$_f$: 0.6); $^1$H-NMR (CDCl$_3$, 400 MHz): δ 5.81 (s, 1H), 3.75-3.73 (m, 4H), 3.46-3.44 (m, 4H), 3.04 (s, 6H), 1.48 (s, 9H).

Synthesis of tert-butyl 4-(4-(dimethylamino)-6-(p-tolylamino) pyrimidin-2-yl) piperazine-1-carboxylate (195)

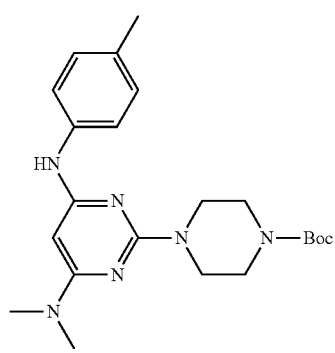

195

To a stirred solution of compound 194 (500 mg, 1.46 mmol) in 1,4-dioxane (6 mL) under argon atmosphere were added p-toluidine (188 mg, 1.75 mmol) and cesium carbonate (713 mg, 2.19 mmol) in sealed tube at RT and degassed under argon for 20 min. To this were added Pd$_2$(dba)$_3$ (67 mg, 0.07 mmol) and Xantphos (59 mg, 0.10 mmol) at RT and degassed under argon for 15 min; heated to 110° C. and stirred for 16 h. The reaction was monitored by TLC; after completion of the reaction, the reaction mixture was diluted with water (25 mL) and extracted with EtOAc (2×40 mL). The combined organic extracts were dried over sodium sulfate, filtered and concentrated in vacuo to obtain the crude, which was purified through silica gel column chromatography using 15% EtOAc/hexanes to afford compound 195 (510 mg, 85%) as white solid. TLC: 20% EtOAc/hexanes (R$_f$: 0.5); $^1$H-NMR (CDCl$_3$, 400 MHz): δ 7.18-7.16 (m, 2H), 7.13-7.11 (m, 2H), 6.21 (br s, 1H), 5.25 (s, 1H), 3.75 (t, J=4.8 Hz, 4H), 3.47 (t, J=4.8 Hz, 4H), 2.98 (s, 6H), 2.32 (s, 3H), 1.48 (s, 9H).

Synthesis of N$^4$, N$^4$-dimethyl-2-(piperazin-1-yl)-N$^6$-(p-tolyl) pyrimidine-4, 6-diamine (196)

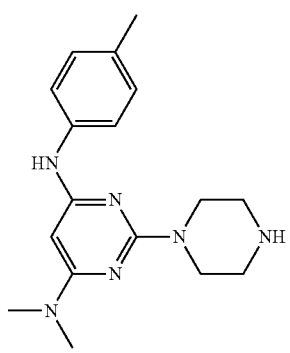

196

To a stirred solution of compound 195 (300 mg, 0.72 mmol) in CH$_2$Cl$_2$ (5 mL) under argon atmosphere was added 4 N HCl in 1, 4-dioxane (1 mL) at 0° C.; warmed to RT and stirred for 2 h. The reaction was monitored by TLC; after completion of the reaction, the reaction mixture was diluted with water (20 mL), pH was adjusted to ~8 with aqueous saturated NaHCO$_3$ solution (25 mL) and extracted with CH$_2$Cl$_2$ (2×30 mL). The combined organic extracts were dried over sodium sulfate, filtered and concentrated in vacuo to obtain the crude compound 196 (170 mg, 75%) as white solid. TLC: 10% MEOH/CH$_2$Cl$_2$ (R$_f$: 0.2); $^1$H-NMR (DMSO-d$_6$, 500 MHz): δ 8.56 (s, 1H), 7.42 (d, J=8.5 Hz, 2H), 7.03 (d, J=8.0 Hz, 2H), 5.75 (s, 1H), 5.21 (s, 1H), 3.58-3.56 (m, 4H), 2.93 (s, 6H), 2.71-2.69 (m, 4H), 2.21 (s, 3H).

Example 29: Synthesis of 6-(4-fluorophenoxy)-N, N-dimethyl-2-(piperazin-1-yl) pyrimidin-4-amine hydrochloride (201)—A Common Intermediate

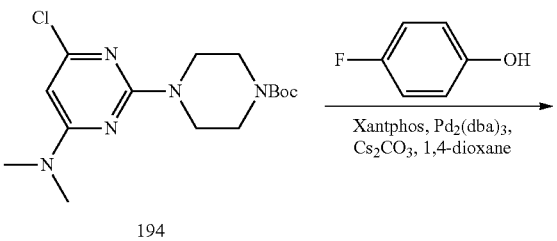

194

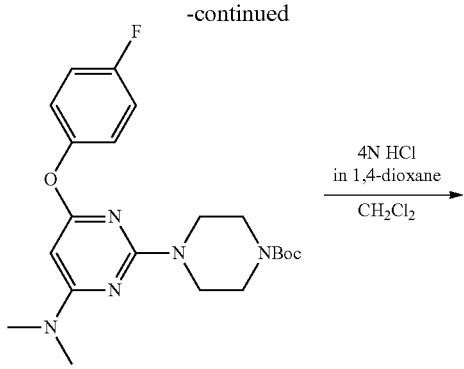

200

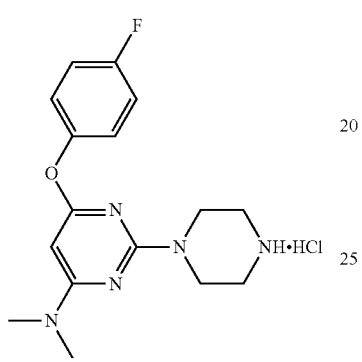

201

Synthesis of tert-butyl 4-(4-(dimethylamino)-6-(4-fluorophenoxy) pyrimidin-2-yl) piperazine-1-carboxylate (200)

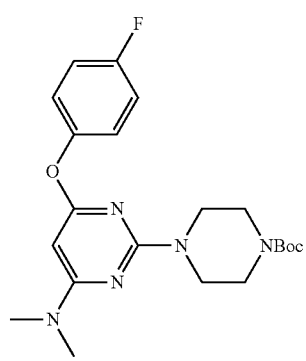

To a stirred solution of compound 194 (5 g, 14.66 mmol) in 1, 4-dioxane (50 mL) under argon atmosphere were added 4-fluorophenol (1.95 g, 17.59 mmol) and cesium carbonate (7.15 g, 21.99 mmol) in sealed tube at RT and degassed under argon for 15 min. To this were added Pd$_2$(dba)$_3$ (671 mg, 0.73 mmol) and Xantphos (593 mg, 1.03 mmol) at RT; heated to 100° C. and stirred for 16 h. The reaction was monitored by TLC; after completion of the reaction, the reaction mixture was filtered through a pad of Celite and washed with ethyl acetate (2×50 mL). The combined organic extracts were dried over sodium sulfate, filtered and concentrated in vacuo to obtain the crude. The crude was purified through silica gel column chromatography using 5% EtOAc/hexanes to afford compound 200 (4 g, 65%) as an off-white solid. TLC: 10% EtOAc/hexanes (R$_f$ 0.4); $^1$H-NMR (DMSO-d$_6$, 500 MHz): δ 7.23-7.13 (m, 4H), 5.34 (s, 1H), 3.51-3.49 (m, 4H), 3.30-3.29 (m, 4H), 2.97 (s, 6H), 1.39 (s, 9H).

Synthesis of 6-(4-fluorophenoxy)-N, N-dimethyl-2-(piperazin-1-yl) pyrimidin-4-amine hydrochloride (201)

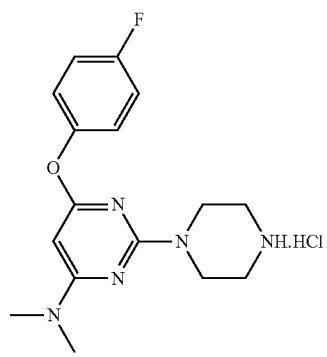

To a stirred solution of compound 200 (500 mg, 1.2 mmol) in CH$_2$Cl$_2$ (5 mL) was added 4 N HCl in 1, 4-dioxane (4 mL) at 0° C. under argon atmosphere; warmed to RT and stirred for 4 h. The reaction was monitored by TLC; after completion of the reaction, the volatiles were removed in vacuo to obtain the crude The crude was triturated with diethyl ether/n-pentane (1:1, 10 mL) to afford compound 201 (400 mg, 94%) as an off-white solid. TLC: 30% EtOAc/hexanes (R$_f$ 0.1); $^1$H-NMR (DMSO-d$_6$, 500 MHz): δ 9.36 (br s, 1H), 7.23-7.14 (m, 4H), 5.41 (s, 1H), 3.75-3.73 (m, 4H), 3.56 (s, 3H), 3.04-3.02 (m, 4H), 2.98 (s, 3H).

Example 30: Synthesis of 2-(piperazin-1-yl)-6-(pyrrolidin-1-yl)-N-(p-tolyl) pyrimidin-4-amine (206)—A Common Intermediate

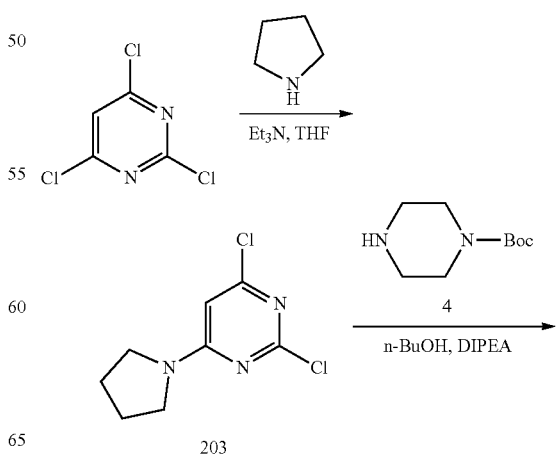

203

-continued

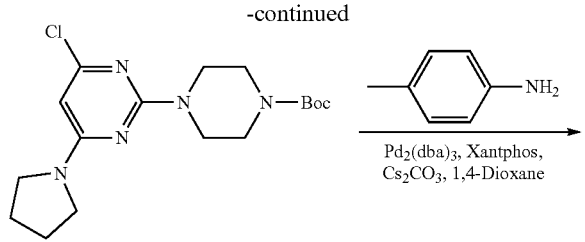

204

205

206

Synthesis of 2, 4-dichloro-6-(pyrrolidin-1-yl) pyrimidine (203)

203

To a stirred solution of 2, 4, 6-trichloropyrimidine (2 g, 10.90 mmol) in THF (20 mL) under argon atmosphere were added pyrrolidine (775 mg, 10.90 mmol) and triethylamine (1.82 mL, 13.08 mmol) at 0° C. and stirred for 30 min at 0° C.; warmed to RT and stirred for 6 h. The reaction was monitored by TLC; after completion of the reaction, the reaction mixture was diluted with water (50 mL) and extracted with EtOAc (2×80 mL). The combined organic extracts were dried over sodium sulfate, filtered and concentrated in vacuo to obtain the crude. The crude was purified through silica gel column chromatography using 8% EtOAc/hexanes to afford compound 203 (1.42 g, 60%) as white solid. TLC: 10% EtOAc/hexanes ($R_f$ 0.3); $^1$H-NMR (DMSO-$d_6$, 400 MHz): δ 6.64 (s, 1H), 3.47 (t, J=6.8 Hz, 2H), 3.36 (t, J=6.8 Hz, 2H), 1.99-1.85 (m, 4H).

Synthesis of tert-butyl 4-(4-chloro-6-(pyrrolidin-1-yl) pyrimidin-2-yl) piperazine-1-carboxylate (204)

204

To a stirred solution of compound 203 (200 mg, 0.92 mmol) in n-butanol (5 mL) under argon atmosphere were added tert-butyl piperazine-1-carboxylate 4 (205 mg, 1.10 mmol) and diisopropylethylamine (0.24 mL, 1.37 mmol) in a sealed tube at RT; heated to 80° C. and stirred for 16 h. The reaction was monitored by TLC; after completion of the reaction, the volatiles were removed in vacuo, the residue was diluted with water (20 mL) and extracted with EtOAc (2×30 mL). The combined organic extracts were dried over sodium sulfate, filtered and concentrated in vacuo to obtain the crude. The crude was purified through silica gel column chromatography using 12% EtOAc/hexanes to afford compound 204 (230 mg, 68%) as an off-white solid. TLC: 20% EtOAc/hexanes ($R_f$ 0.6); $^1$H-NMR (DMSO-$d_6$, 500 MHz): δ 5.83 (s, 1H), 3.64-3.62 (m, 4H), 3.51-3.42 (m, 2H), 3.38-3.34 (m, 4H), 3.29-3.26 (m, 2H), 1.92-1.87 (m, 4H), 1.42 (s, 9H).

Synthesis of tert-butyl 4-(4-(pyrrolidin-1-yl)-6-(p-tolylamino) pyrimidin-2-yl) piperazine-1-carboxylate (205)

205

To a stirred solution of compound 204 (200 mg, 0.54 mmol) in 1, 4-dioxane (5 mL) under argon atmosphere was added p-toluidine 2 (70 mg, 0.65 mmol) in sealed tube at RT and degassed under argon for 20 min. To this were added Pd₂(dba)₃ (25 mg, 0.03 mmol), Xantphos (22 mg, 0.04 mmol) and cesium carbonate (212 mg, 0.65 mmol) at RT and degassed under argon for 10 min; heated to 100° C. and stirred for 16 h. The reaction was monitored by TLC; after completion of the reaction, the volatiles were removed in vacuo, the residue was diluted with water (20 mL) and extracted with EtOAc (2×40 mL). The combined organic extracts were dried over sodium sulfate, filtered and concentrated in vacuo to obtain the crude. The crude was purified through silica gel column chromatography using 10% EtOAc/hexanes to afford compound 205 (120 mg, 50%) as an off-white solid. TLC: 20% EtOAc/hexanes (R$_f$: 0.5); $^1$H-NMR (DMSO-d₆, 400 MHz): δ 8.57 (s, 1H), 7.40 (d, J=8.4 Hz, 2H), 7.04 (d, J=8.4 Hz, 2H), 5.10 (s, 1H), 3.64-3.62 (m, 4H), 3.40-3.31 (m, 4H), 2.53-2.47 (m, 4H), 2.22 (s, 3H), 1.89-1.86 (m, 4H), 1.42 (s, 9H).

Synthesis of 2-(piperazin-1-yl)-6-(pyrrolidin-1-yl)-N-(p-tolyl) pyrimidin-4-amine (206)

206

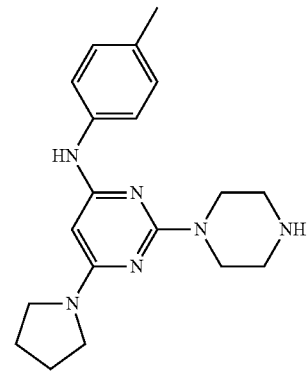

To a stirred solution of compound 205 (120 mg, 0.27 mmol) in CH₂Cl₂ (3 mL) under argon atmosphere was added 4 N HCl in 1, 4-dioxane (0.3 mL) at 0° C.; warmed to RT and stirred for 3 h. The reaction was monitored by TLC; after completion of the reaction, the volatiles were removed in vacuo and the residue was neutralized with 10% aqueous NaHCO₃ solution (10 mL) and extracted with EtOAc (2×30 mL). The combined organic extracts were dried over sodium sulfate, filtered and concentrated in vacuo to obtain the crude compound 206 (50 mg, 54%) as an off-white solid. TLC: 30% EtOAc/hexanes (R$_f$: 0.1); $^1$H-NMR (DMSO-d₆, 400 MHz): δ 8.52 (s, 1H), 7.41 (d, J=8.4 Hz, 2H), 7.02 (d, J=8.4 Hz, 2H), 5.06 (s, 1H), 3.57 (t, J=4.8 Hz, 4H), 3.32-3.29 (m, 4H), 2.69 (t, J=4.8 Hz, 4H), 2.21 (s, 3H), 1.87 (t, J=6.0 Hz, 4H).

Example 31: Synthesis of 6-morpholino-2-(piperazin-1-yl)-N-(p-tolyl) pyrimidin-4-amine (211)—A Common Intermediate

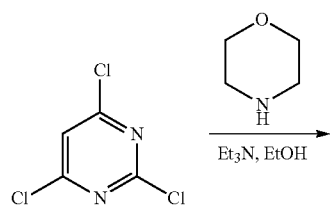

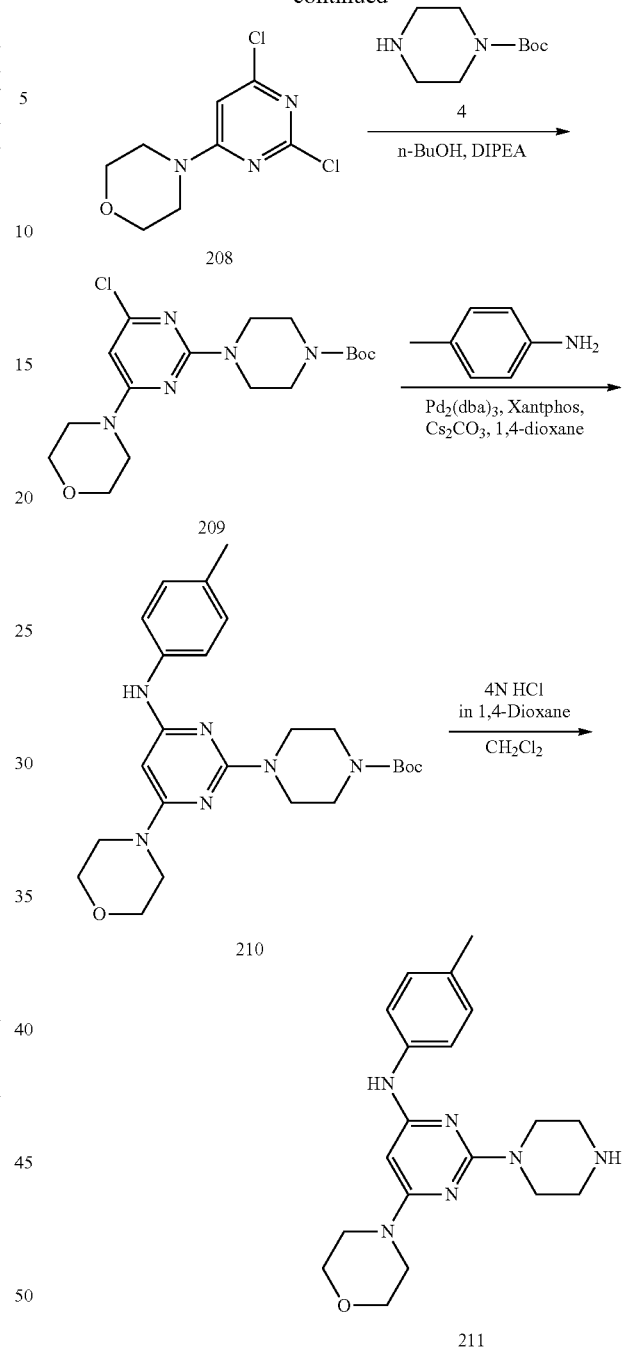

Synthesis of 4-(2, 6-dichloropyrimidin-4-yl) morpholine (208)

208

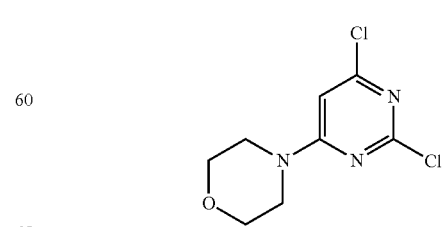

To a stirred solution of 2, 4, 6-trichloropyrimidine (3 g, 16.39 mmol) in ethanol (30 mL) under argon atmosphere were added morpholine 207 (1.42 mL, 16.39 mmol) and triethylamine (1.83 mL, 13.11 mmol) drop wise at −5° C.; warmed to RT and stirred for 10 min. The reaction was monitored by TLC; after completion of the reaction, the reaction mixture was diluted with ice water (40 mL). The precipitated solid was filtered, washed with ice cold EtOH (2×25 mL) and dried in vacuo to obtain the crude, which was purified through flash chromatography to afford compound 208 (2.9 g, 76%) as white solid. TLC: 10% EtOAc/hexanes ($R_f$ 0.2); $^1$H-NMR (CDCl$_3$, 400 MHz): δ 6.40 (s, 1H), 3.78-3.76 (m, 4H), 3.66-3.62 (m, 4H).

Synthesis of tert-butyl 4-(4-chloro-6-morpholinopyrimidin-2-yl) piperazine-1-carboxylate (209)

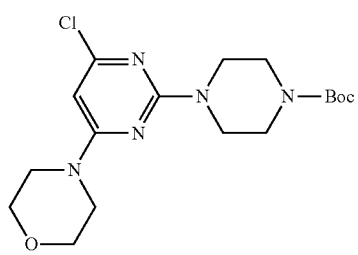

209

To a stirred solution of compound 208 (500 mg, 2.13 mmol) in n-butanol (6 mL) under argon atmosphere were added tert-butyl piperazine-1-carboxylate 4 (437 mg, 2.35 mmol) and diisopropylethylamine (0.6 mL, 3.20 mmol) in sealed tube at RT; heated to 100° C. and stirred for 16 h. The reaction was monitored by TLC; after completion of the reaction, the volatiles were removed in vacuo, the residue was diluted with water (20 mL) and extracted with EtOAc (2×25 mL). The combined organic extracts were dried over sodium sulfate, filtered and concentrated in vacuo to obtain the crude. The crude was purified through silica gel column chromatography using 10% EtOAc/hexanes to afford compound 209 (630 mg, 77%) as white solid. TLC: 20% EtOAc/hexanes ($R_f$ 0.4); $^1$H-NMR (DMSO-d$_6$, 500 MHz): δ 6.19 (s, 1H), 3.64-3.62 (m, 4H), 3.56-3.52 (m, 8H), 3.38-3.32 (m, 4H), 1.42 (s, 9H).

Synthesis of tert-butyl 4-(4-morpholino-6-(p-tolylamino) pyrimidin-2-yl) piperazine-1-carboxylate (210)

210

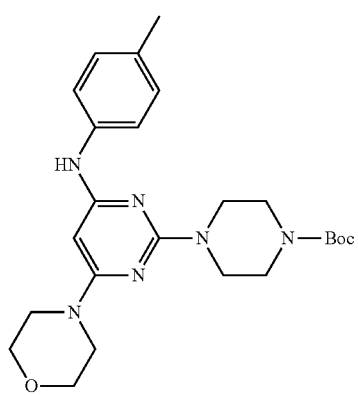

To a stirred solution of compound 209 (500 mg, 1.30 mmol) in 1, 4-dioxane (8 mL) under argon atmosphere were added p-toluidine 2 (167 mg, 1.56 mmol) and cesium carbonate (635 mg, 1.95 mmol) in sealed tube at RT and degassed under argon for 20 min. To this were added Pd$_2$(dba)$_3$ (59.6 mg, 0.06 mmol) and Xantphos (52.7 mg, 0.09 mmol) at RT and degassed under argon for 15 min; heated to 100° C. and stirred for 16 h. The reaction was monitored by TLC; after completion of the reaction, the reaction mixture was diluted with water (25 mL) and extracted with EtOAc (2×30 mL). The combined organic extracts were dried over sodium sulfate, filtered and concentrated in vacuo to obtain the crude, which was purified through silica gel column chromatography using 20% EtOAc/hexanes to afford compound 210 (420 mg, 71%) as white solid. TLC: 40% EtOAc/hexanes ($R_f$ 0.3); $^1$H-NMR (DMSO-d$_6$, 400 MHz): δ 8.69 (s, 1H), 7.40 (d, J=8.4 Hz, 2H), 7.06 (d, J=8.0 Hz, 2H), 5.34 (s, 1H), 3.65-3.61 (m, 8H), 3.38-3.36 (m, 8H), 2.23 (s, 3H), 1.42 (s, 9H).

Synthesis of 6-morpholino-2-(piperazin-1-yl)-N-(p-tolyl) pyrimidin-4-amine (211)

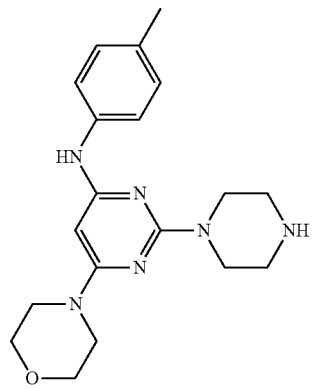

211

To a stirred solution of compound 210 (300 mg, 0.66 mmol) in CH$_2$Cl$_2$ (5 mL) under argon atmosphere was added 4 N HCl in 1, 4-dioxane (3 mL) at 0° C.; warmed to RT and stirred for 4 h. The reaction was monitored by TLC; after completion of the reaction, the reaction mixture was neutralized with aqueous saturated NaHCO$_3$ solution (20 mL) to pH ~8 and extracted with CH$_2$Cl$_2$ (2×25 mL). The combined organic extracts were dried over sodium sulfate, filtered and concentrated in vacuo to obtain the crude compound 211 (190 mg, 82%) as white solid. TLC: 40% EtOAc/hexanes ($R_f$ 0.1); $^1$H-NMR (DMSO-d$_6$, 400 MHz): δ 8.63 (s, 1H), 7.41 (d, J=8.4 Hz, 2H), 7.04 (d, J=8.0 Hz, 2H), 5.30 (s, 1H), 3.64 (t, J=4.8 Hz, 4H), 3.57-3.54 (m, 4H), 3.36 (t, J=4.8 Hz, 4H), 2.69 (t, J=4.8 Hz, 4H), 2.22 (s, 3H).

Example 32: Synthesis of 2-(piperazin-1-yl)-6-(piperidin-1-yl)-N-(p-tolyl) pyrimidin-4-amine (216)—A Common Intermediate

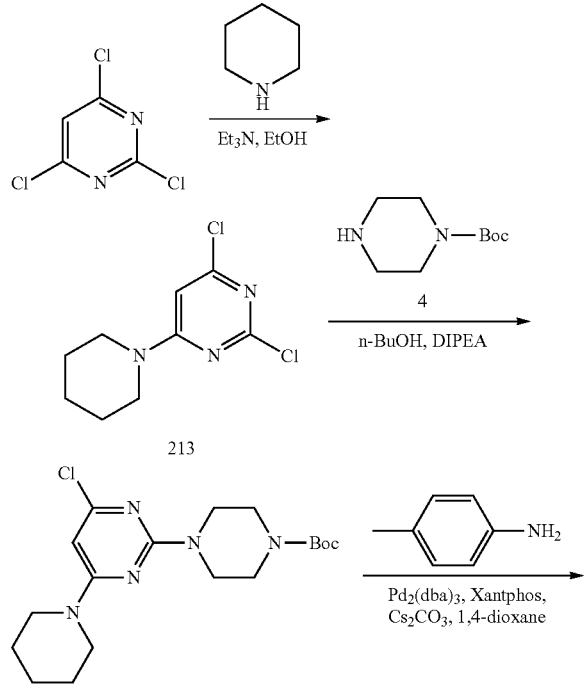

Synthesis of 2, 4-dichloro-6-(piperidin-1-yl) pyrimidine (213)

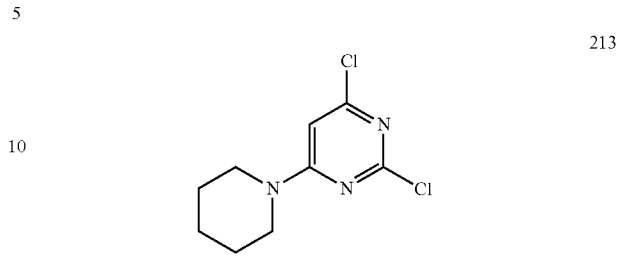

To a stirred solution of 2, 4, 6-trichloropyrimidine (3 g, 16.39 mmol) in ethanol (20 mL) under argon atmosphere were added piperidine 212 (1.61 mL, 16.39 mmol) and triethylamine (1.83 mL, 13.11 mmol) at −5° C.; warmed to RT and stirred for 5 min. The reaction was monitored by TLC; after completion of the reaction, the volatiles were removed in vacuo, the residue was diluted with water (60 mL) and extracted with EtOAc (2×80 mL). The combined organic extracts were dried over sodium sulfate, filtered and concentrated in vacuo to obtain the crude. The crude was purified through silica gel column chromatography using 10% EtOAc/hexanes to afford compound 213 (2.7 g, 71%) as white solid. TLC: 10% EtOAc/hexanes ($R_f$: 0.2); $^1$H-NMR (CDCl$_3$, 500 MHz): δ 6.39 (s, 1H), 3.67-3.54 (m, 4H), 1.71-1.69 (m, 2H), 1.65-1.60 (m, 4H).

Synthesis of tert-butyl 4-(4-chloro-6-(piperidin-1-yl) pyrimidin-2-yl) piperazine-1-carboxylate (214)

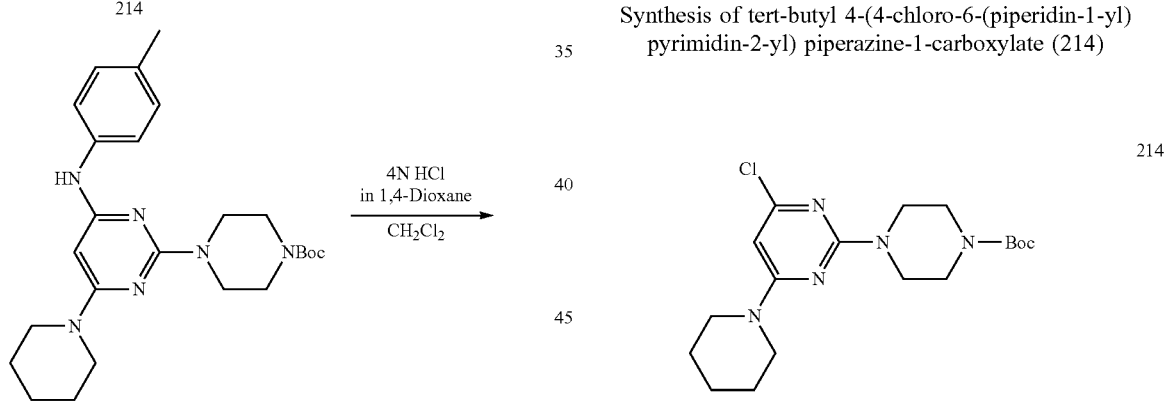

To a stirred solution of compound 213 (500 mg, 2.15 mmol) in n-butanol (6 mL) under argon atmosphere were added tert-butyl piperazine-1-carboxylate 4 (441 mg, 2.37 mmol) and diisopropylethylamine (0.6 mL, 3.23 mmol) in sealed tube at RT; heated to 100° C. and stirred for 16 h. The reaction was monitored by TLC; after completion of the reaction, the volatiles were removed in vacuo, the residue was diluted with water (50 mL) and extracted with EtOAc (2×40 mL). The combined organic extracts were dried over sodium sulfate, filtered and concentrated in vacuo to obtain the crude. The crude was purified through silica gel column chromatography using 20% EtOAc/hexanes to afford compound 214 (558 mg, 68%) as white solid. TLC: 20% EtOAc/hexanes ($R_f$: 0.3); $^1$H-NMR (CDCl$_3$, 500 MHz): δ 5.87 (s, 1H), 3.72 (t, J=5.0 Hz, 4H), 3.55-3.50 (m, 4H), 3.45 (t, J=5.0 Hz, 4H), 1.67-1.66 (m, 2H), 1.61-1.55 (m, 4H), 1.47 (s, 9H).

Synthesis of tert-butyl 4-(4-(piperidin-1-yl)-6-(p-tolylamino) pyrimidin-2-yl) piperazine-1-carboxylate (215)

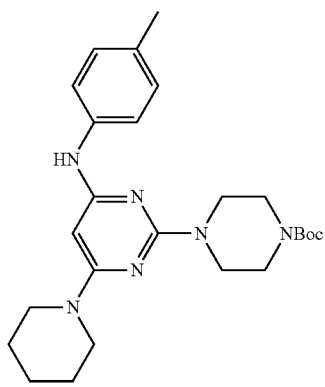

215

To a stirred solution of compound 214 (500 mg, 1.31 mmol) in 1, 4-dioxane (8 mL) under argon atmosphere were added p-toluidine 2 (168 mg, 1.57 mmol) and cesium carbonate (638 mg, 1.96 mmol) in a sealed tube at RT and degassed under argon for 20 min. To this were added Pd$_2$(dba)$_3$ (60 mg, 0.06 mmol), Xantphos (53 mg, 0.09 mmol) at RT and degassed under argon for 15 min; heated to 100° C. and stirred for 16 h. The reaction was monitored by TLC; after completion of the reaction, the reaction mixture was diluted with water (50 mL) and extracted with EtOAc (2×40 mL). The combined organic extracts were dried over sodium sulfate, filtered and concentrated in vacuo to obtain the crude. The crude was purified through silica gel column chromatography using 15% EtOAc/hexanes to afford compound 215 (410 mg, 69%) as an off-white solid. TLC: 30% EtOAc/hexanes (R$_f$ 0.4); $^1$H-NMR (CDCl$_3$, 400 MHz): δ 7.17-7.12 (m, 4H), 6.17 (br s, 1H), 5.33 (s, 1H), 3.74 (t, J=7.6 Hz, 4H), 3.50-3.43 (m, 8H), 2.33 (s, 3H), 1.63-1.62 (m, 3H), 1.60-1.52 (m, 3H), 1.48 (s, 9H).

Synthesis of 2-(piperazin-1-yl)-6-(piperidin-1-yl)-N-(p-tolyl) pyrimidin-4-amine (216)

216

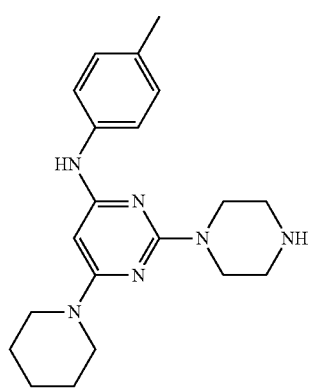

To a stirred solution of compound 215 (300 mg, 0.66 mmol) in CH$_2$Cl$_2$ (5 mL) under argon atmosphere was added 4 N HCl in 1, 4-dioxane (3 mL) at 0° C.; warmed to RT and stirred for 4 h. The reaction was monitored by TLC; after completion of the reaction, the reaction mixture was diluted with water (20 mL) and pH was adjusted to ~8 with aqueous saturated NaHCO$_3$ solution (20 mL) and extracted with CH$_2$Cl$_2$ (2×30 mL). The combined organic extracts were dried over sodium sulfate, filtered and concentrated in vacuo to obtain the crude compound 216 (195 mg, 84%) as white solid. TLC: 40% EtOAc/hexanes (R$_f$ 0.1); $^1$H-NMR (DMSO-d$_6$, 400 MHz): δ 8.54 (s, 1H), 7.41 (d, J=8.8 Hz, 2H), 7.03 (d, J=8.0 Hz, 2H), 5.31 (s, 1H), 3.56-3.54 (m, 4H), 3.42 (t, J=5.2 Hz, 4H), 2.70 (t, J=5.2 Hz, 4H), 2.21 (s, 3H), 1.58-1.57 (m, 2H), 1.49-1.48 (m, 4H).

Example 33: Synthesis of 4-(4-fluorophenoxy)-2-(piperazin-1-yl)-6-(4H-1, 2, 4-triazol-4-yl) pyrimidine (221)—A Common Intermediate

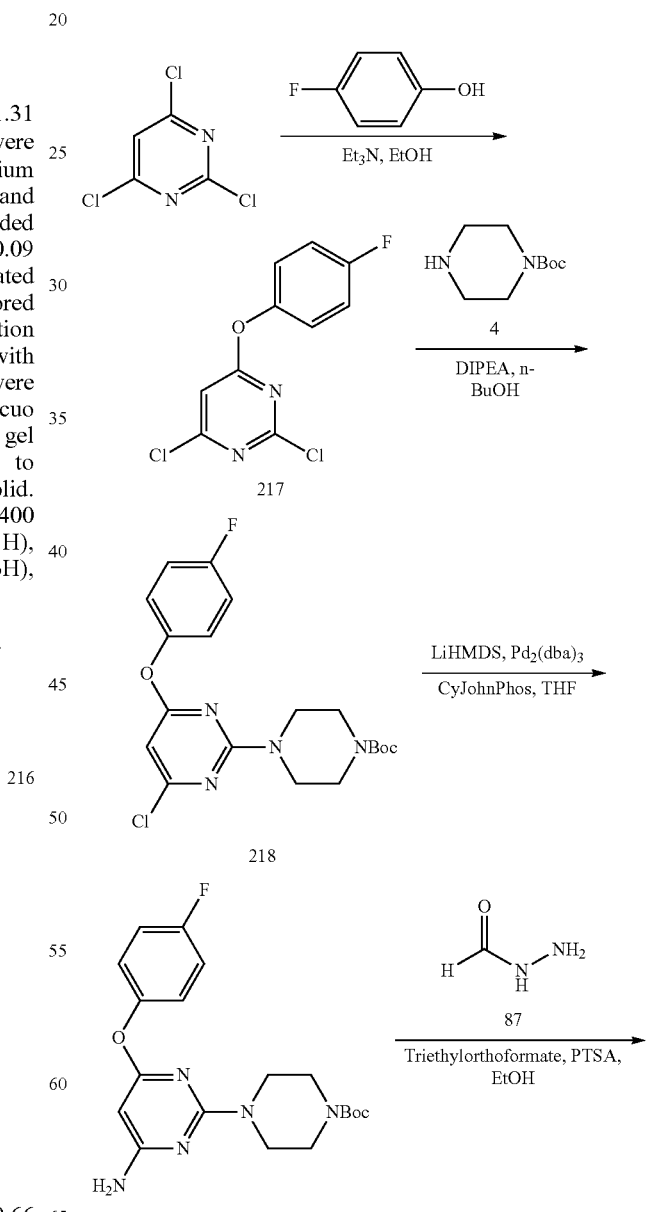

Synthesis of tert-butyl 4-(4-chloro-6-(4-fluorophenoxy) pyrimidin-2-yl) piperazine-1-carboxylate (218)

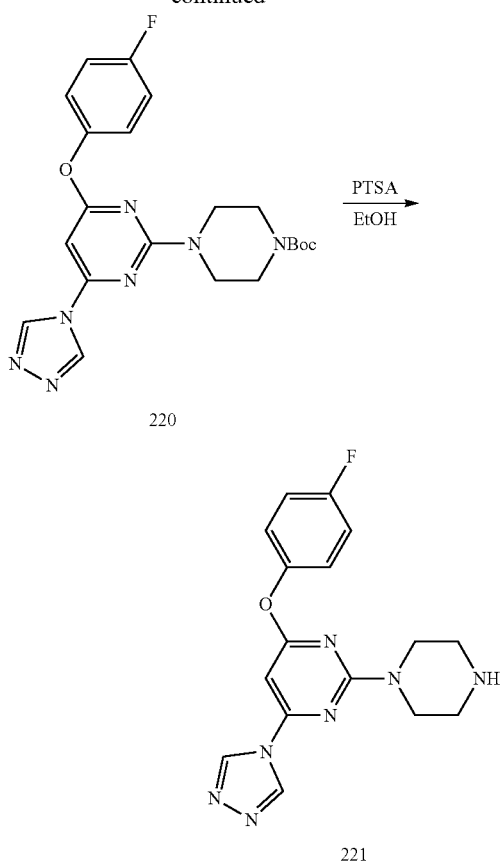

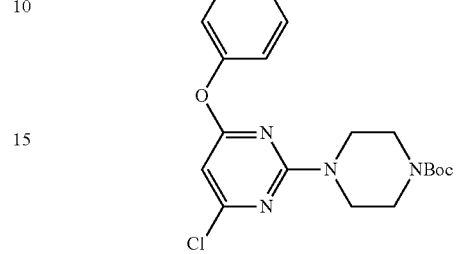

To a stirred solution of compound 217 (5 g, 19.38 mmol) in n-butanol (50 mL) were added tert-butyl piperazine-1-carboxylate 4 (3.6 g, 19.38 mmol) and diisopropylethylamine (4 mL, 23.25 mmol) at 0° C. under argon atmosphere; warmed to RT and stirred for 4 h. The reaction was monitored by TLC; after completion of the reaction, the volatiles were removed in vacuo to obtain the crude. The crude was purified through silica gel column chromatography using 2% EtOAc/hexanes to afford compound 218 (3.5 g, 44%) as white solid. TLC: 10% EtOAc/n-hexane ($R_f$ 0.4); $^1$H-NMR (DMSO-$d_6$, 400 MHz): δ 7.29-7.25 (m, 4H), 6.29 (s, 1H), 3.58-3.50 (m, 4H), 3.35-3.32 (m, 4H), 1.40 (s, 9H).

Synthesis of tert-butyl 4-(4-amino-6-(4-fluorophenoxy) pyrimidin-2-yl) piperazine-1-carboxylate (219)

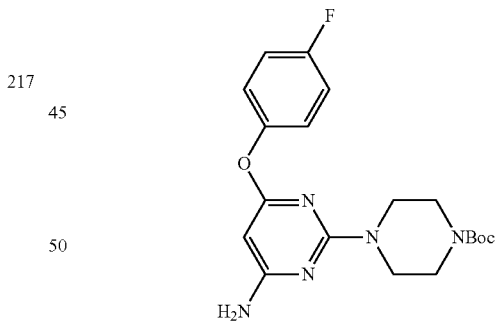

Synthesis of 2, 4-dichloro-6-(4-fluorophenoxy) pyrimidine (217)

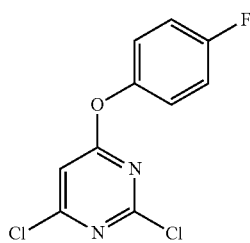

To a stirred solution of 2, 4, 6-trichloropyrimidine (10 g, 54.52 mmol) in ethanol (100 mL) were added triethylamine (11.39 mL, 81.77 mmol) and 4-fluorophenol (6.1 g, 54.52 mmol) at 0° C. under argon atmosphere; warmed to RT and stirred for 16 h. The reaction was monitored by TLC; after completion of the reaction, the volatiles were removed in vacuo to obtain the crude. The crude was purified through silica gel column chromatography using 5% EtOAc/hexanes to afford compound 217 (13 g, 93%) as white solid. TLC: 10% EtOAc/hexanes ($R_f$ 0.4); $^1$H-NMR (DMSO-$d_6$, 500 MHz): δ 7.47 (s, 1H) 7.35-7.31 (m, 4H).

To a stirred solution of compound 218 (1 g, 2.45 mmol) in anhydrous THF (6 mL) were added LiHMDS (1 M in THF, 7.35 mL, 7.35 mmol), Pd$_2$(dba)$_3$ (112 mg, 0.12 mmol) and Cyclohexyl JohnPhos (86 mg, 0.24 mmol) at 0° C. under argon atmosphere. The reaction mixture was stirred in microwave at 100° C. for 45 min. The reaction was monitored by TLC; after completion of the reaction, the reaction mixture was diluted with ethylacetate (80 mL), washed with 1 N HCl solution (20 mL) and water (50 mL). The organic layer was separated, dried over sodium sulfate, filtered and concentrated in vacuo to obtain the crude. The crude was triturated with n-pentane (2×5 mL) to afford compound 219 (700 mg, 73%) as yellow solid. TLC: 5% MeOH/CH$_2$Cl$_2$ ($R_f$ 0.4); $^1$H-NMR (DMSO-$d_6$, 400 MHz): δ 7.28-7.12 (m, 4H), 6.43 (br s, 2H), 5.01 (s, 1H), 3.54-3.50 (m, 4H), 3.32-3.30 (m, 4H), 1.41 (s, 9H).

Synthesis of tert-butyl 4-(4-(4-fluorophenoxy)-6-(4H-1, 2, 4-triazol-4-yl) pyrimidin-2-yl) piperazine-1-carboxylate (220)

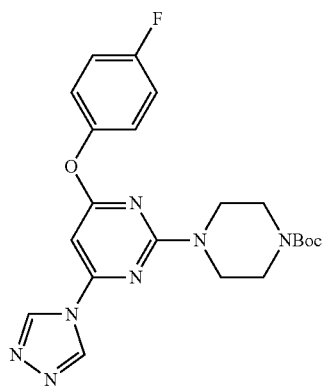

220

To a stirred solution of triethylorthoformate (0.21 mL, 1.28 mmol) in ethanol (3 mL) was added formic acid hydrazide (46 mg, 0.77 mmol) in sealed tube at RT under argon atmosphere; heated to 100° C. and stirred for 2 h. To this were added compound 219 (50 mg, 0.13 mmol) and p-toluenesulfonic acid (25 mg, 0.13 mmol) at RT; heated to 100° C. and stirred for 24 h. The reaction was monitored by TLC; after completion of the reaction, the volatiles were removed in vacuo to obtain the crude. The crude was purified through silica gel column chromatography using 3% MEOH/CH$_2$Cl$_2$ to afford compound 220 (20 mg, 36%) as yellow solid. TLC: 5% MEOW CH$_2$Cl$_2$ ($R_f$ 0.3); $^1$H-NMR (DMSO-$d_6$, 400 MHz): δ 9.40 (s, 2H), 7.29 (d, J=6.6 Hz, 4H), 6.79 (s, 1H), 3.93-3.57 (m, 4H), 3.39-3.31 (m, 4H), 1.40 (s, 9H).

Synthesis of 4-(4-fluorophenoxy)-2-(piperazin-1-yl)-6-(4H-1, 2, 4-triazol-4-yl) pyrimidine (221)

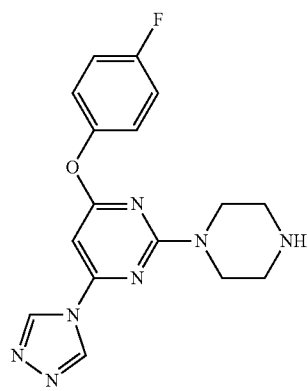

221

To a stirred solution of compound 220 (220 mg, 0.5 mmol) in ethanol (5 mL) was added p-toluenesulfonic acid (PTSA) (91 mg, 0.5 mmol) in a sealed tube at RT under argon atmosphere; heated to 100° C. and stirred for 24 h. The reaction was monitored by TLC; after completion of the reaction, the volatiles were removed in vacuo. The residue was diluted with 10% MeOH/CH$_2$Cl$_2$ (40 mL), basified with triethylamine (0.2 mL) and washed with water (20 mL). The organic layer was separated, dried over sodium sulfate, filtered and concentrated in vacuo to obtain the crude. The crude was purified through silica gel column chromatography using 5% MeOH/CH$_2$Cl$_2$ to afford compound 221 (100 mg, 61%) as yellow solid. TLC: 10% MeOH/CH$_2$Cl$_2$ ($R_f$ 0.4); $^1$H-NMR (DMSO-$d_6$, 400 MHz): δ 9.37 (s, 2H), 7.28 (d, J=6.6 Hz, 4H), 6.73 (s, 1H), 3.69-3.41 (m, 4H), 2.48-2.43 (m, 4H).

Example 34: Synthesis of N-(4-fluorophenyl)-2-(piperazin-1-yl)-6-(4H-1, 2, 4-triazol-4-yl) pyrimidin-4-amine hydrochloride (226)—A Common Intermediate

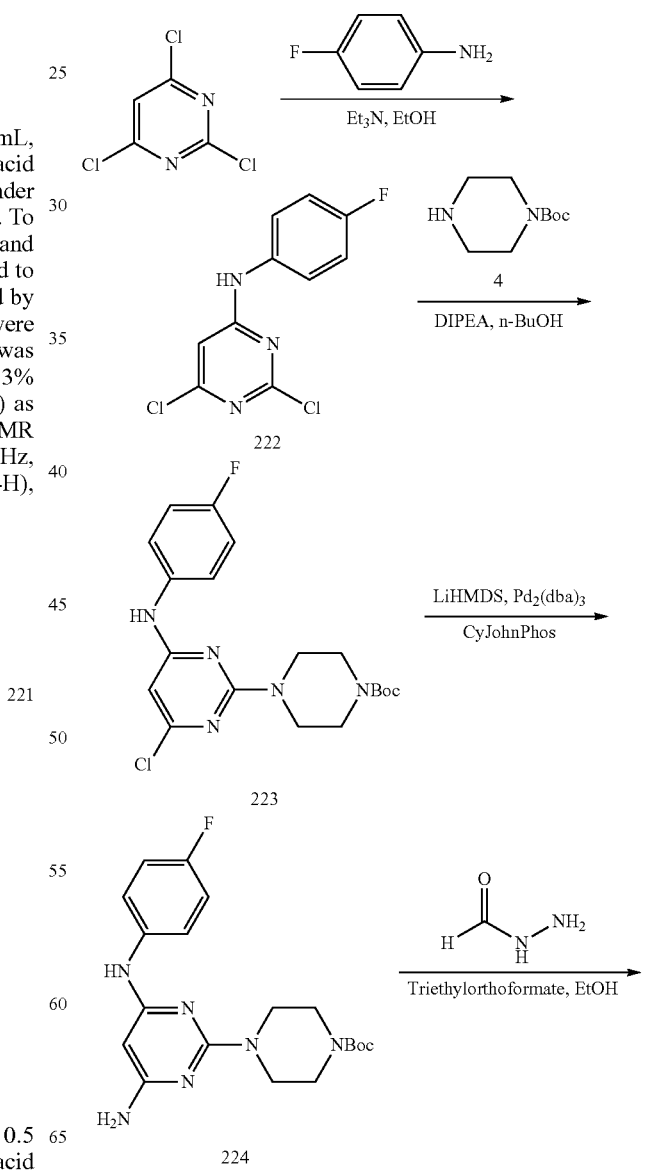

-continued

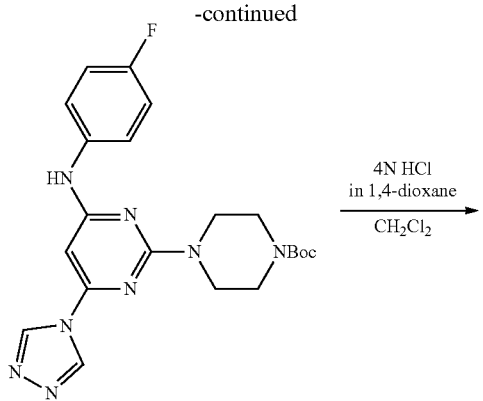

225

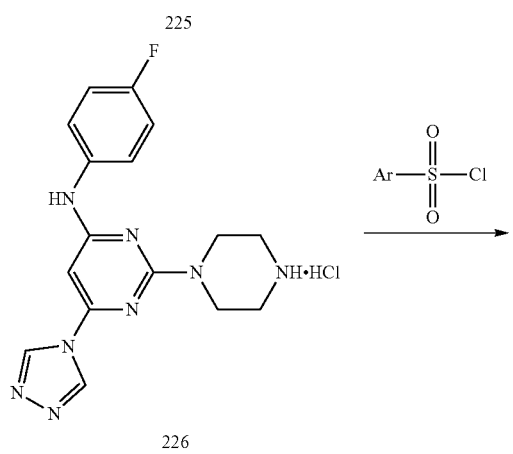

226

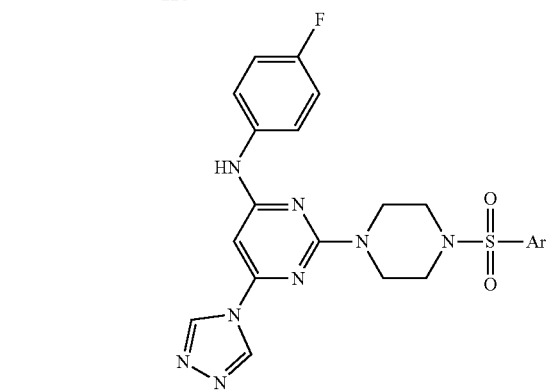

Test Compounds

Synthesis of 2, 6-dichloro-N-(4-fluorophenyl) pyrimidin-4-amine (222)

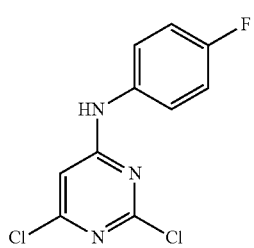

222

To a stirred solution of 2, 4, 6-trichloropyrimidine (10 g, 54.52 mmol) in ethanol (100 mL) were added triethylamine (11.39 mL, 81.77 mmol) and 4-fluoroaniline (6.05 g, 54.52 mmol) at 0° C. under argon atmosphere; warmed to RT and stirred for 16 h. The reaction was monitored by TLC; after completion of the reaction, the volatiles were removed in vacuo to obtain the crude. The crude was purified through silica gel column chromatography using 10% EtOAc/hexanes to afford compound 222 (11 g, 78%) as white solid. TLC: 10% EtOAc/hexanes ($R_f$, 0.1); $^1$H-NMR (DMSO-$d_6$, 500 MHz): δ 10.26 (s, 1H), 7.56-7.52 (m, 2H), 7.23 (br t, J=8.3 Hz, 2H), 6.71 (s, 1H).

Synthesis of tert-butyl 4-(4-chloro-6-((4-fluorophenyl) amino) pyrimidin-2-yl) piperazine-1-carboxylate (223)

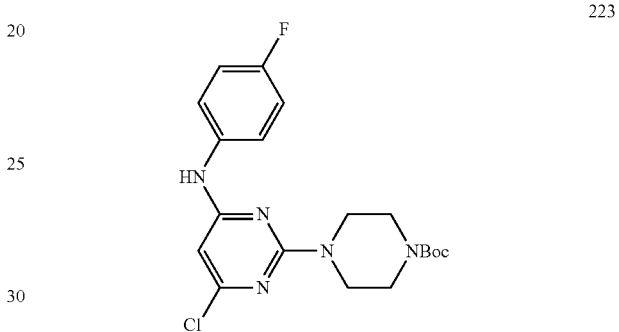

223

To a stirred solution of compound 222 (5.5 g, 21.4 mmol) in n-butanol (20 mL) were added tert-butyl piperazine-1-carboxylate 4 (3.98 g, 21.4 mmol) and diisopropylethylamine (4.47 mL, 25.68 mmol) in sealed tube at RT under argon atmosphere; heated to 80° C. and stirred for 24 h. The reaction was monitored by TLC; after completion of the reaction, the volatiles were removed in vacuo to obtain the crude. The crude was purified through silica gel column chromatography using 10% EtOAc/hexanes to afford compound 223 (3.5 g, 40%) as white solid. TLC: 30% EtOAc/hexanes ($R_f$, 0.6); $^1$H-NMR (DMSO-$d_6$, 500 MHz): δ 9.50 (s, 1H), 7.64-7.53 (m, 2H), 7.17 (br t, J=8.9 Hz, 2H), 6.02 (s, 1H), 3.66-3.64 (m, 4H), 3.40-3.38 (m, 4H), 1.42 (s, 9H).

Synthesis of tert-butyl 4-(4-amino-6-((4-fluorophenyl) amino) pyrimidin-2-yl) piperazine-1-carboxylate (224)

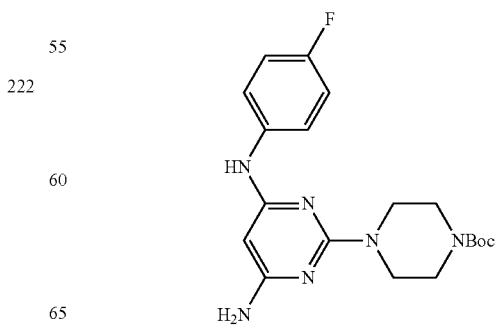

224

To compound 223 (1 g, 2.46 mmol) was added LiHMDS (1 M in THF, 9.82 mL, 9.82 mmol), Pd$_2$(dba)$_3$ (112 mg, 0.12 mmol) and Cyclohexyl JohnPhos (86 mg, 0.24 mmol) at 0° C. under argon atmosphere. The reaction mixture was stirred in microwave at 100° C. for 2 h. The reaction was monitored by TLC; after completion of the reaction, the reaction mixture was quenched with 1 N HCl solution (20 mL) and extracted with ethyl acetate (2×40 mL). The organic layer was separated, dried over sodium sulfate, filtered and concentrated in vacuo to obtain the crude. The crude was triturated with diethyl ether (2×5 mL) and n-pentane (2×5 mL) to afford compound 224 (600 mg, 63%) as yellow solid. TLC: 5% MeOH/CH$_2$Cl$_2$ (R$_f$ 0.1); $^1$H-NMR (DMSO-d$_6$, 500 MHz): δ 9.80 (br s, 1H), 7.48-7.46 (m, 2H), 7.22-7.19 (m, 2H), 5.34 (br s, 1H), 3.69-3.67 (m, 4H), 3.46-3.44 (m, 4H), 1.43 (s, 9H).

Synthesis of tert-butyl 4-(4-((4-fluorophenyl) amino)-6-(4H-1, 2, 4-triazol-4-yl) pyrimidin-2-yl) piperazine-1-carboxylate (225)

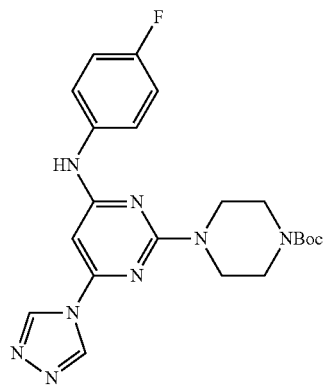

225

To a stirred solution of triethylorthoformate (2.14 mL, 12.89 mmol) in ethanol (8 mL) was added formic acid hydrazide (232 mg, 3.86 mmol) at 0° C. under argon atmosphere. The reaction mixture was stirred in sealed tube at 100° C. for 3 h. To this were added compound 224 (500 mg, 1.29 mmol) at RT; heated to 110° C. and stirred for 48 h. The reaction was monitored by TLC; after completion of the reaction, the volatiles were removed in vacuo to obtain the crude. The crude was purified through silica gel column chromatography using 3% MeOH/CH$_2$Cl$_2$ to afford compound 225 (130 mg, 23%) as yellow solid. TLC: 5% MeOH/CH$_2$Cl$_2$ (R$_f$ 0.4); $^1$H-NMR (DMSO-d$_6$, 400 MHz): δ 9.66 (s, 1H), 9.24 (s, 2H), 7.61 (dd, J=9.0, 5.0 Hz, 2H), 7.19 (t, J=8.9 Hz, 2H), 6.22 (s, 1H), 3.78-3.74 (m, 4H), 3.44-3.40 (m, 4H), 1.43 (s, 9H).

Synthesis of N-(4-fluorophenyl)-2-(piperazin-1-yl)-6-(4H-1, 2, 4-triazol-4-yl) pyrimidin-4-amine hydrochloride (226)

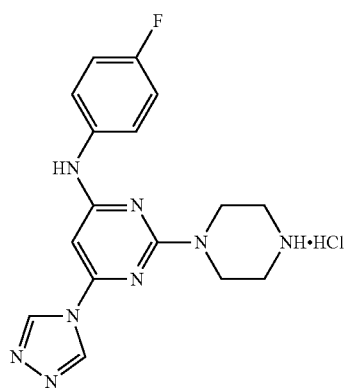

226

To a stirred solution of compound 225 (230 mg, 0.52 mmol) in CH$_2$Cl$_2$ (5 mL) was added 4 N HCl in 1, 4-dioxane (1 mL) at 0° C. under argon atmosphere; warmed to RT and stirred for 3 h. The reaction was monitored by TLC; after completion of the reaction, the volatiles were removed in vacuo to obtain the crude. The crude was triturated with diethyl ether (2×5 mL) to afford compound 226 (200 mg, HCl salt) as yellow solid. TLC: 5% MeOH/CH$_2$Cl$_2$ (R$_f$ 0.1); $^1$H-NMR (DMSO-d$_6$, 400 MHz): δ 9.87 (s, 1H), 9.43 (s, 2H), 7.61 (dd, J=9.0, 4.9 Hz, 2H), 7.18 (t, J=8.9 Hz, 2H), 6.34 (s, 1H), 4.02-3.98 (m, 4H), 3.18-3.14 (m, 4H).

Example 35: Preparation of Additional Test Compounds

Amines similar to compound 196, 81, 201, 206, 211, 216, 221, and 226 were synthesized as described herein and converted to final products using commercially available sulfonyl chlorides employing Procedures A or D and the results are captured in Table 5 below.

Procedure D: To a stirred solution of compound 226 (20 mg, 0.06 mmol) in CH$_2$Cl$_2$ (3 mL) were added diisopropylethylamine (0.03 mL, 0.18 mmol) and 4-fluorobenzenesulfonyl chloride (11 mg, 0.06 mmol) at 0° C. under argon atmosphere; warmed to RT and stirred for 16 h. The reaction was monitored by TLC; after completion of the reaction, the reaction mixture was diluted with water (5 mL) and extracted with CH$_2$Cl$_2$ (2×15 mL). The combined organic extracts were dried over sodium sulfate, filtered and concentrated in vacuo to obtain the crude. The crude was purified through silica gel column chromatography to afford the desired product.

TABLE 5

Synthesis of test compounds from compounds 196, 81, 201, 206, 211, 216, 221, 226 and various sulfonyl chlorides

| No. | Structure | Procedure, Intermediate | Rx. Yield (%) | Mass Spec. Found | Mass Spec. Calculated | $^1$H-NMR |
|---|---|---|---|---|---|---|
| 1143 | 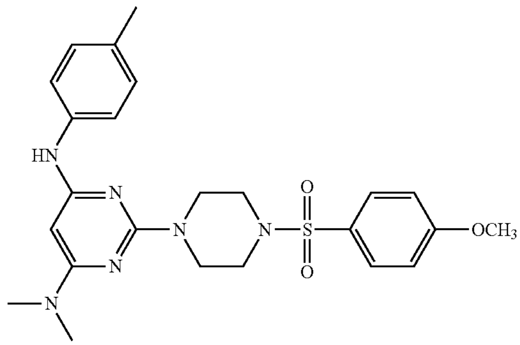 [SMILES: COc1ccc(S(=O)(=O)N2CCN(c3nc(Nc4ccc(C)cc4)cc(N(C)C)n3)CC2)cc1] | A$^a$, 196 | 65% | 483.6 (M$^+$ + 1) | 482.21 for $C_{24}H_{30}N_6O_3S$ | $^1$H-NMR (DMSO-d$_6$, 400 MHz): δ 8.59 (s, 1H), 7.67 (d, J = 8.8 Hz, 2H), 7.35 (d, J = 8.4 Hz, 2H), 7.13 (d, J = 9.2 Hz, 2H), 7.03 (d, J = 8.4 Hz, 2H), 5.20 (s, 1H), 3.82 (s, 3H), 3.75 (t, J = 4.4 Hz, 4H), 2.90 (s, 6H), 2.86 (t, J = 4.8 Hz, 4H), 2.22 (s, 3H) |
| 1305 | 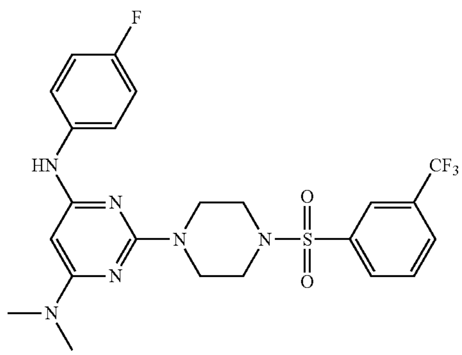 [SMILES: CN(C)c1cc(Nc2ccc(F)cc2)nc(N2CCN(S(=O)(=O)c3cccc(C(F)(F)F)c3)CC2)n1] | A$^b$, 81 | 24% | 525.0 (M$^+$ + 1) | 524.16 for $C_{23}H_{24}F_4N_6O_2S$ | $^1$H-NMR (DMSO-d$_6$, 400 MHz): δ 8.74 (s, 1H), 8.12-8.07 (m, 2H), 7.98 (s, 1H), 7.89 (t, J = 8.0 Hz, 1H), 7.50-7.47 (m, 2H), 7.05 (t, J = 8.8 Hz, 2H), 5.19 (s, 1H), 3.75 (t, J = 4.8 Hz, 4H), 2.99 (t, J = 4.8 Hz, 4H), 2.91 (s, 6H) |
| 1297 | 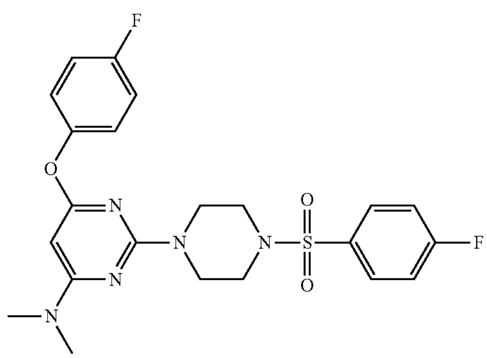 [SMILES: CN(C)c1cc(Oc2ccc(F)cc2)nc(N2CCN(S(=O)(=O)c3ccc(F)cc3)CC2)n1] | A$^b$, 201 | 46% | 476.4 (M$^+$ + 1) | 475.15 for $C_{22}H_{23}F_2N_5O_3S$ | $^1$H-NMR (DMSO-d$_6$, 400 MHz): δ 7.82-7.78 (m, 2H), 7.46 (t, J = 8.8 Hz, 2H), 7.22-7.17 (m, 2H), 7.12-7.09 (m, 2H), 5.31 (s, 1H), 3.63-3.61 (m, 4H), 2.93 (s, 6H), 2.86 (t, J = 4.4 Hz, 4H) |
| 1298 | 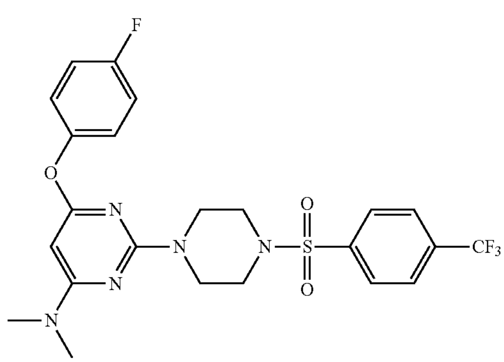 [SMILES: CN(C)c1cc(Oc2ccc(F)cc2)nc(N2CCN(S(=O)(=O)c3ccc(C(F)(F)F)cc3)CC2)n1] | A$^b$, 201 | 27% | 526.1 (M$^+$ + 1) | 525.15 for $C_{23}H_{23}F_4N_5O_3S$ | $^1$H-NMR (DMSO-d$_6$, 400 MHz): δ 8.00 (d, J = 8.4 Hz, 2H), 7.95 (d, J = 8.4 Hz, 2H), 7.19 (t, J = 8.8 Hz, 2H), 7.12-7.08 (m, 2H), 5.31 (s, 1H), 3.64-3.62 (m, 4H), 2.94-2.92 (m, 10H) |

TABLE 5-continued

Synthesis of test compounds from compounds 196, 81, 201, 206, 211, 216, 221, 226 and various sulfonyl chlorides

| No. | Structure | Procedure, Intermediate | Rx. Yield (%) | Mass Spec. Found | Mass Spec. Calculated | $^1$H-NMR |
|---|---|---|---|---|---|---|
| 1289 | 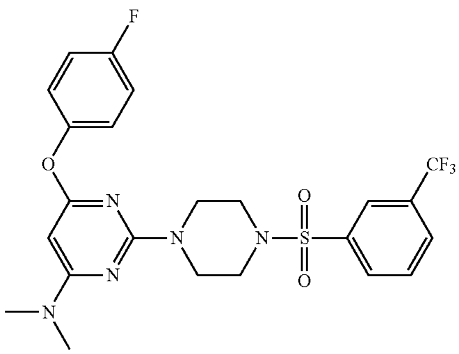 [SMILES: CN(C)c1cc(Oc2ccc(F)cc2)nc(N2CCN(S(=O)(=O)c3cccc(C(F)(F)F)c3)CC2)n1] | A$^b$, 201 | 49% | 526.0 (M$^+$ + 1) | 525.15 for $C_{23}H_{23}F_4N_5O_3S$ | $^1$H-NMR (DMSO-d$_6$, 400 MHz): δ 8.11 (d, J = 8.0 Hz, 1H), 8.06 (d, J = 8.0 Hz, 1H), 7.96 (s, 1H), 7.89 (t, J = 8.0 Hz, 1H), 7.19 (t, J = 8.8 Hz, 2H), 7.12-7.08 (m, 2H), 5.31 (s, 1H), 3.63-3.61 (m, 4H), 2.94-2.92 (m, 10H) |
| 1299 | 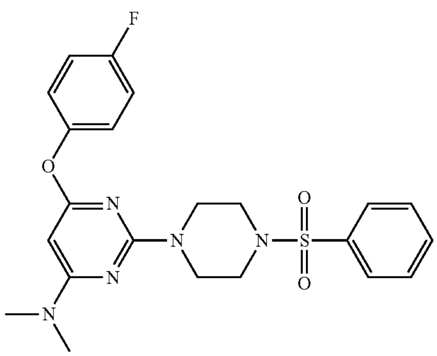 [SMILES: CN(C)c1cc(Oc2ccc(F)cc2)nc(N2CCN(S(=O)(=O)c3ccccc3)CC2)n1] | A$^b$, 201 | 66% | 458.1 (M$^+$ + 1) | 457.16 for $C_{22}H_{24}FN_5O_3S$ | $^1$H-NMR (DMSO-d$_6$, 400 MHz): δ 7.74-7.69 (m, 3H), 7.63 (t, J = 7.6 Hz, 2H), 7.21-7.17 (m, 2H), 7.12-7.08 (m, 2H), 5.30 (s, 1H), 3.63-3.60 (m, 4H), 2.92 (s, 6H), 2.84 (t, J = 4.8 Hz, 4H) |
| 1290 | 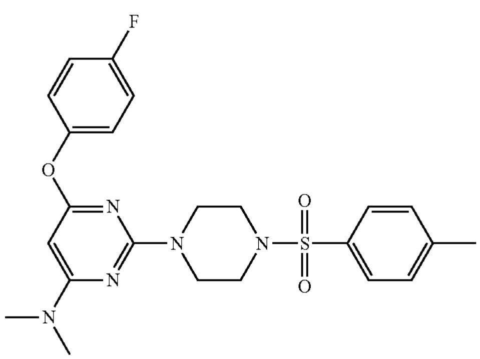 | A$^b$, 201 | 20% | 472.0 (M$^+$ + 1) | 471.17 for $C_{23}H_{26}FN_5O_3S$ | $^1$H-NMR (DMSO-d$_6$, 500 MHz): δ 7.61 (d, J = 8.0 Hz, 2H), 7.43 (d, J = 8.5 Hz, 2H), 7.21-7.18 (m, 2H), 7.12-7.09 (m, 2H), 5.30 (s, 1H), 3.62-3.60 (m, 4H), 2.93 (s, 6H), 2.82-2.80 (m, 4H), 2.39 (s, 3H) |
| 1144 | 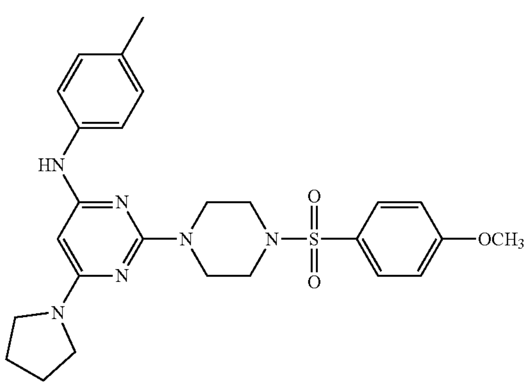 [SMILES: COc1ccc(S(=O)(=O)N2CCN(c3nc(Nc4ccc(C)cc4)cc(N4CCCC4)n3)CC2)cc1] | A, 206 | 47% | 509.7 (M$^+$ + 1); | 508.23 for $C_{26}H_{32}N_6O_3S$ | $^1$H-NMR (DMSO-d$_6$, 400 MHz): δ 8.56 (s, 1H), 7.67 (d, J = 8.8 Hz, 2H), 7.34 (d, J = 8.4 Hz, 2H), 7.12 (d, J = 8.8 Hz, 2H), 7.03 (d, J = 8.4 Hz, 2H), 5.06 (s, 1H). 3.82 (s, 3H), 3.75 (t, J = 4.4 Hz, 4H), 3.30-3.22 (m, 4H), 2.85 (t, J = 4.4 Hz, 4H), 2.22 (s, 3H), 1.85 (t, J = 6.8 Hz, 4H) |

TABLE 5-continued

Synthesis of test compounds from compounds 196, 81, 201, 206, 211, 216, 221, 226 and various sulfonyl chlorides

| No. | Structure | Procedure, Intermediate | Rx. Yield (%) | Mass Spec. Found | Mass Spec. Calculated | $^1$H-NMR |
|---|---|---|---|---|---|---|
| 1179 | 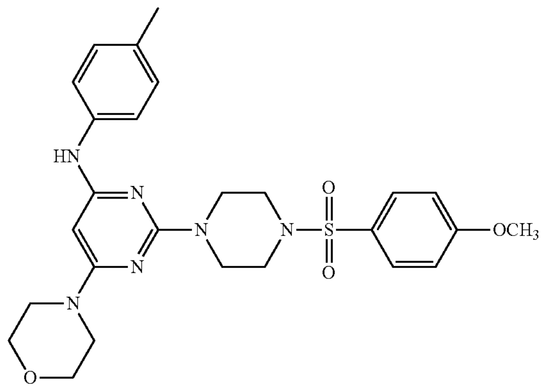 [SMILES: COc1ccc(S(=O)(=O)N2CCN(c3nc(Nc4ccc(C)cc4)cc(N4CCOCC4)n3)CC2)cc1] | A$^c$, 211 | 68% | 525.0 (M$^+$ + 1); | 524.22 for C$_{26}$H$_{32}$N$_6$O$_4$S | $^1$H-NMR (DMSO-d$_6$, 400 MHz): δ 8.68 (s, 1H), 7.67 (d, J = 9.2 Hz, 2H), 7.34 (d, J = 8.4 Hz, 2H), 7.13 (d, J = 8.8 Hz, 2H), 7.04 (d, J = 8.4 Hz, 2H), 5.30 (s, 1H), 3.83 (s, 3H), 3.75-3.73 (m, 4H), 3.62-3.60 (m, 4H), 3.34-3.31 (m, 4H), 2.86 (t, J = 4.8 Hz, 4H), 2.22 (s, 3H) |
| 1190 | 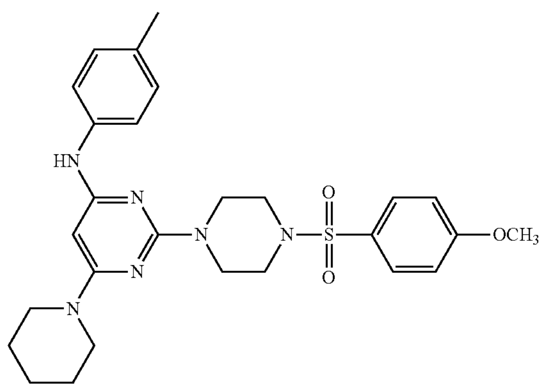 [SMILES: COc1ccc(S(=O)(=O)N2CCN(c3nc(Nc4ccc(C)cc4)cc(N4CCCCC4)n3)CC2)cc1] | A$^c$, 216 | 65% | 523.0 (M$^+$ + 1); | 522.24 for C$_{27}$H$_{34}$N$_6$O$_3$S | $^1$H-NMR (DMSO-d$_6$, 400 MHz): δ 8.58 (s, 1H), 7.67 (d, J = 8.8 Hz, 2H), 7.34 (d, J = 8.4 Hz, 2H), 7.13 (d, J = 9.2 Hz, 2H), 7.03 (d, J = 8.4 Hz, 2H), 5.30 (s, 1H), 3.83 (s, 3H), 3.74-3.72 (m, 4H), 3.40-3.37 (m, 4H), 2.86 (t, J = 4.8 Hz, 4H), 2.22 (s, 3H), 1.57-1.55 (m, 2H), 1.46-1.45 (m, 4H) |
| 1307 | 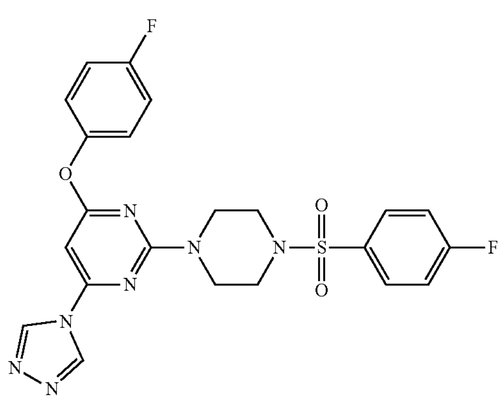 [SMILES: O=S(=O)(c1ccc(F)cc1)N1CCN(c2nc(Oc3ccc(F)cc3)cc(-n3cnnc3)n2)CC1] | A$^b$, 221 | 39% | 500.5 (M$^+$ + 1) | 499.12 for C$_{22}$H$_{19}$F$_2$N$_7$O$_3$S | $^1$H-NMR (DMSO-d$_6$, 400 MHz): δ 9.36 (s, 2H), 7.82 (dd, J = 8.9, 5.1 Hz, 2H), 7.46 (t, J = 8.8 Hz, 2H), 7.28-7.24 (m, 4H), 6.76 (s, 1H), 3.88-3.58 (m, 4H), 2.94-2.90 (m, 4H) |

TABLE 5-continued

Synthesis of test compounds from compounds 196, 81, 201, 206, 211, 216, 221, 226
and various sulfonyl chlorides

| No. | Structure | Procedure, Intermediate | Rx. Yield (%) | Mass Spec. Found | Mass Spec. Calculated | $^1$H-NMR |
|---|---|---|---|---|---|---|
| 1308 | 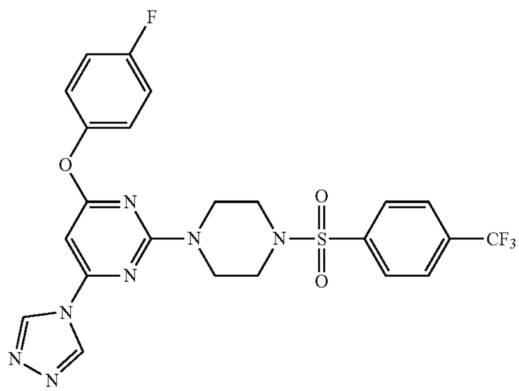 [SMILES: O=S(=O)(c1ccc(C(F)(F)F)cc1)N1CCN(c2nc(Oc3ccc(F)cc3)cc(-n3cnnc3)n2)CC1] | A$^b$, 221 | 18% | 550.0 (M$^+$ + 1) | 549.12 for $C_{23}H_{19}F_4N_7O_3S$ | $^1$H-NMR (DMSO-d$_6$, 400 MHz): δ 9.36 (s, 2H), 8.02-7.94 (m, 4H), 7.29-7.21 (m, 4H), 6.76 (s, 1H), 3.92-3.68 (m, 4H), 3.02-2.96 (m, 4H) |
| 1309 | 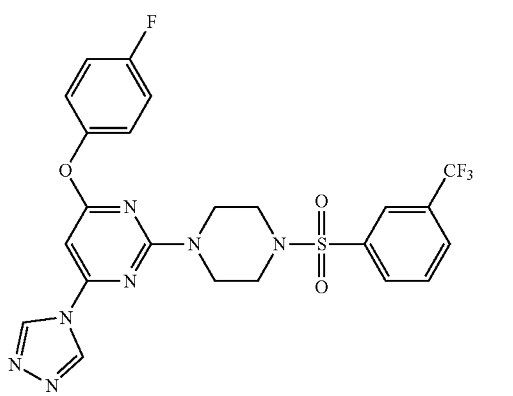 [SMILES: O=S(=O)(c1cccc(C(F)(F)F)c1)N1CCN(c2nc(Oc3ccc(F)cc3)cc(-n3cnnc3)n2)CC1] | A$^b$, 221 | 8% | 550.0 (M$^+$ + 1) | 549.12 for $C_{23}H_{19}F_4N_7O_3S$ | $^1$H-NMR (DMSO-d$_6$, 400 MHz): δ 9.37 (s, 2H), 8.09 (dd, J = 15.7, 7.9 Hz, 2H), 7.98 (s, 1H), 7.89 (t, J = 7.3 Hz, 1H), 7.30-7.22 (m, 4H), 6.76 (s, 1H), 3.81-3.62 (m, 4H), 3.03-2.98 (m, 4H) |
| 1311 | 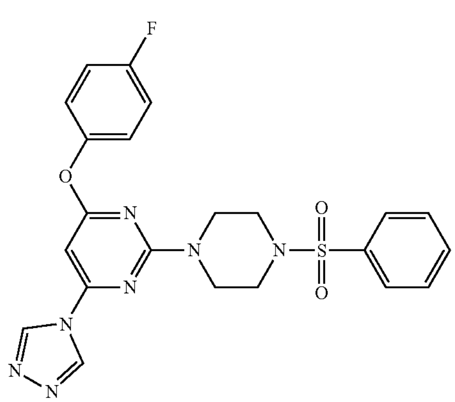 [SMILES: O=S(=O)(c1ccccc1)N1CCN(c2nc(Oc3ccc(F)cc3)cc(-n3cnnc3)n2)CC1] | A$^b$, 221 | 28% | 482.0 (M$^+$ + 1) | 481.13 for $C_{22}H_{20}FN_7O_3S$ | $^1$H-NMR (DMSO-d$_6$, 400 MHz): δ 9.36 (s, 2H), 7.76-7.69 (m, 3H), 7.66-7.60 (m, 2H), 7.28-7.23 (m, 4H), 6.75 (s, 1H), 3.86-3.65 (m, 4H), 2.93-2.89 (m, 4H) |

TABLE 5-continued

Synthesis of test compounds from compounds 196, 81, 201, 206, 211, 216, 221, 226 and various sulfonyl chlorides

| No. | Structure | Procedure, Intermediate | Rx. Yield (%) | Mass Spec. Found | Mass Spec. Calculated | $^1$H-NMR |
|---|---|---|---|---|---|---|
| 1310 | 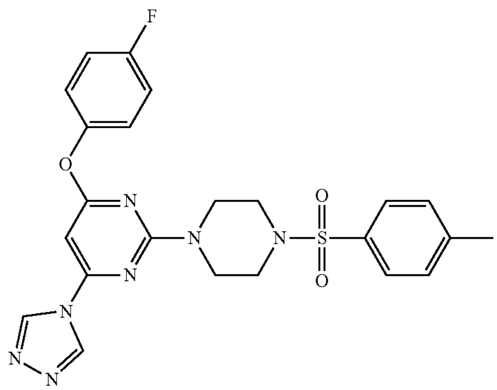 [SMILES: Cc1ccc(S(=O)(=O)N2CCN(c3nc(Oc4ccc(F)cc4)cc(-n4cnnc4)n3)CC2)cc1] | A$^b$, 221 | 17% | 496.0 (M$^+$ + 1) | 495.15 for $C_{23}H_{22}FN_7O_3S$ | $^1$H-NMR (DMSO-d$_6$, 400 MHz): δ 9.36 (s, 2H), 7.62 (d, J = 8.4 Hz, 2H), 7.43 (d, J = 7.9 Hz, 2H), 7.28-7.24 (m, 4H), 6.75 (s, 1H), 3.83-3.61 (m, 4H), 2.90-2.86 (m, 4H), 2.38 (s, 3H) |
| 1312 | 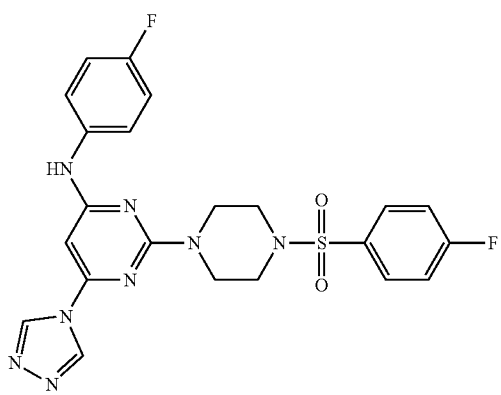 [SMILES: O=S(=O)(c1ccc(F)cc1)N1CCN(c2nc(Nc3ccc(F)cc3)cc(-n3cnnc3)n2)CC1] | D, 226 | 34% | 499.1 (M$^+$ + 1) | 498.14 for $C_{22}H_{20}F_2N_8O_2S$ | $^1$H-NMR (DMSO-d$_6$, 400 MHz): δ 9.68 (s, 1H), 9.20 (s, 2H), 7.84 (dd, J = 8.9, 5.1 Hz, 2H), 7.56 (dd, J = 9.1, 5.0 Hz, 2H), 7.47 (t, J = 8.8 Hz, 2H), 7.16 (t, J = 8.9 Hz, 2H), 6.22 (s, 1H), 3.90-3.86 (m, 4H), 2.99 (br t, J = 4.7 Hz, 4H) |
| 1315 | 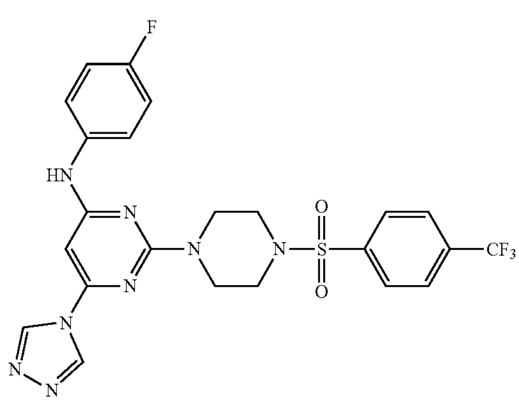 [SMILES: O=S(=O)(c1ccc(C(F)(F)F)cc1)N1CCN(c2nc(Nc3ccc(F)cc3)cc(-n3cnnc3)n2)CC1] | D, 226 | 6% | 549.1 (M$^+$ + 1) | 548.14 for $C_{23}H_{20}F_4N_8O_2S$ | $^1$H-NMR (DMSO-d$_6$, 400 MHz): δ 9.65 (s, 1H), 9.20 (s, 2H), 8.04-7.95 (m, 4H), 7.55 (dd, J = 9.0, 5.0 Hz, 2H), 7.16 (t, J = 8.9 Hz, 2H), 6.19 (s, 1H), 3.90-3.86 (m, 4H), 3.05 (br t, J = 4.6 Hz, 4H) |

TABLE 5-continued

Synthesis of test compounds from compounds 196, 81, 201, 206, 211, 216, 221, 226 and various sulfonyl chlorides

| No. | Structure | Procedure, Intermediate | Rx. Yield (%) | Mass Spec. Found | Mass Spec. Calculated | $^1$H-NMR |
|---|---|---|---|---|---|---|
| 1313 | 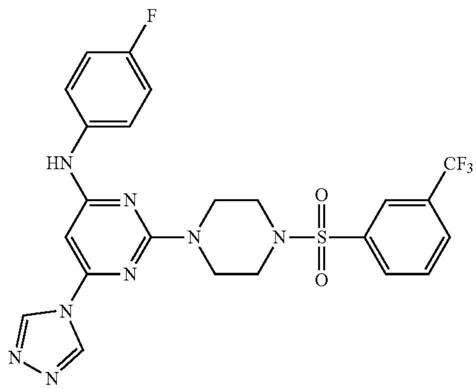 [SMILES: O=S(=O)(c1cccc(C(F)(F)F)c1)N1CCN(c2nc(Nc3ccc(F)cc3)cc(-n3cnnc3)n2)CC1] | D, 226 | 19% | 549.1 (M$^+$ + 1) | 548.14 for $C_{23}H_{20}F_4N_8O_2S$ | $^1$H-NMR (DMSO-d$_6$, 400 MHz): δ 9.68 (s, 1H), 9.18 (s, 2H), 8.08 (t, J = 8.1 Hz, 2H), 7.97 (s, 1H), 7.88 (t, J = 7.5 Hz, 1H), 7.54 (dd, J = 9.0, 4.9 Hz, 2H), 7.14 (t, J = 8.9 Hz, 2H), 6.23 (s, 1H), 3.88-3.84 (m, 4H), 3.04 (br t, J = 4.8 Hz, 4H) |
| 1314 | 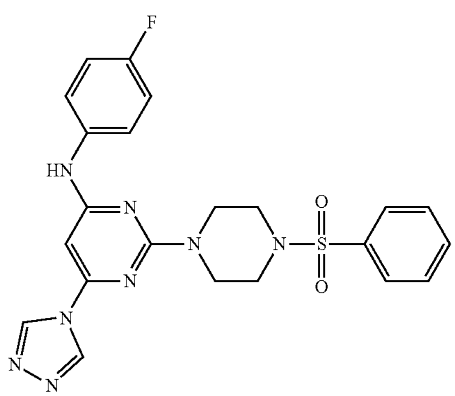 [SMILES: O=S(=O)(c1ccccc1)N1CCN(c2nc(Nc3ccc(F)cc3)cc(-n3cnnc3)n2)CC1] | D, 226 | 11% | 481.1 (M$^+$ + 1) | 480.15 for $C_{22}H_{21}FN_8O_2S$ | $^1$H-NMR (DMSO-d$_6$, 400 MHz): δ 9.68 (s, 1H), 9.20 (s, 2H), 7.79-7.68 (m, 3H), 7.67-7.61 (m, 2H), 7.56 (dd, J = 9.0, 5.0 Hz, 2H), 7.16 (t, J = 8.9 Hz, 2H), 6.22 (s, 1H), 3.89-3.85 (m, 4H), 2.97 (br t, J = 4.8 Hz, 4H) |
| 1316 | 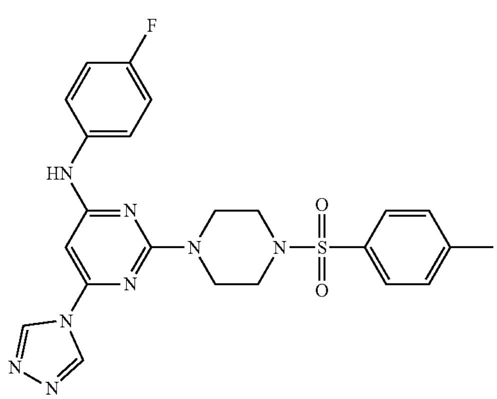 [SMILES: Cc1ccc(S(=O)(=O)N2CCN(c3nc(Nc4ccc(F)cc4)cc(-n4cnnc4)n3)CC2)cc1] | D, 226 | 25% | 495.0 (M$^+$ + 1) | 494.16 for $C_{23}H_{23}FN_8O_2S$ | $^1$H-NMR (DMSO-d$_6$, 400 MHz): δ 9.64 (s, 1H), 9.19 (s, 2H), 7.64 (d, J = 8.3 Hz, 2H), 7.55 (dd, J = 9.0, 4.9 Hz, 2H), 7.43 (d, J = 8.0 Hz, 2H), 7.16 (t, J = 8.8 Hz, 2H), 6.19 (s, 1H), 3.88-3.84 (m, 4H), 2.94 (br t, J = 4.6 Hz, 4H), 2.38 (s, 3H) |

[a] 3 h, RT;
[b] 16 h, RT;
[c] 4 h, RT.

Example 36: Synthesis of 1202
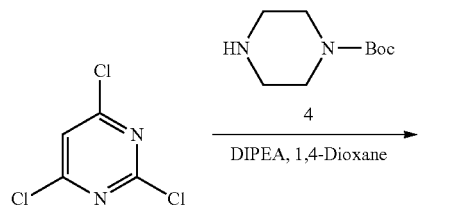
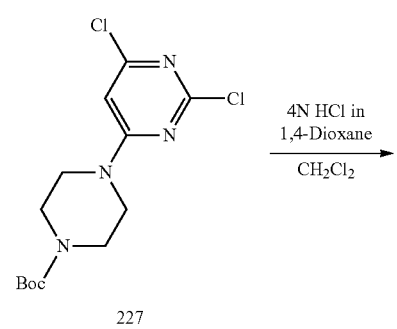
227
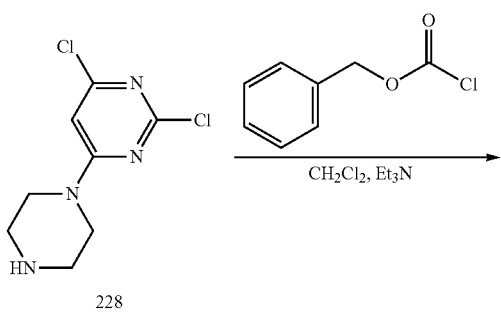
228
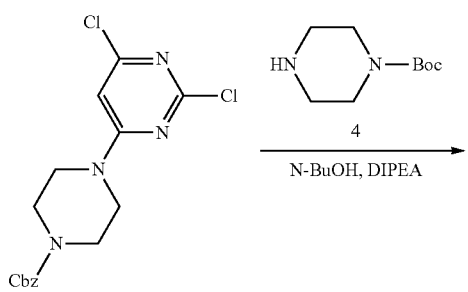
230
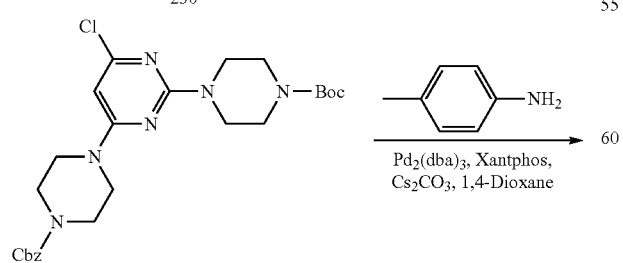
231
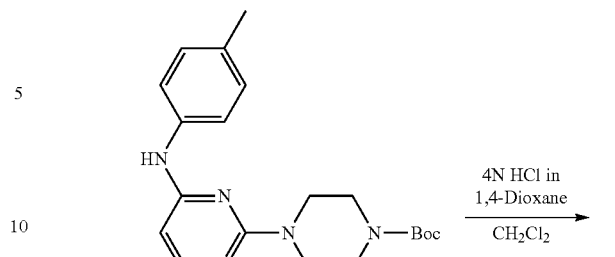
232
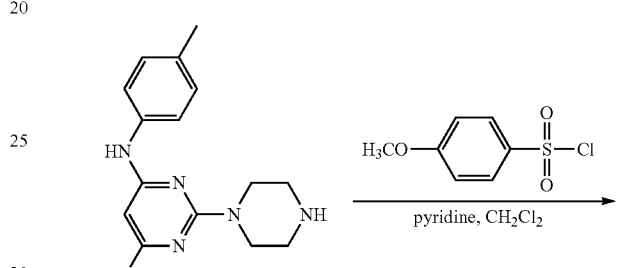
233
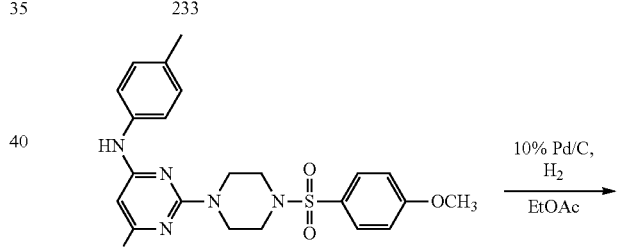
234
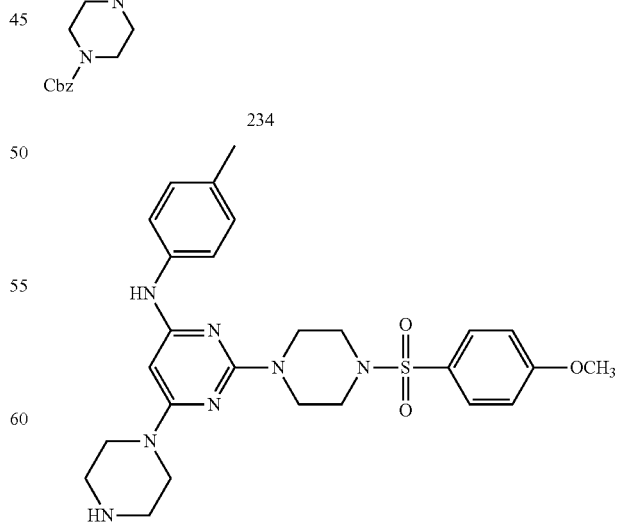
1202

Synthesis of tert-butyl 4-(2, 6-dichloropyrimidin-4-yl) piperazine-1-carboxylate (227)

To a stirred solution of 2, 4, 6-trichloropyrimidine (2 g, 10.90 mmol) in 1, 4-dioxane (20 mL) under argon atmosphere were added tert-butyl piperazine-1-carboxylate 4 (2.04 g, 10.90 mmol) and diisopropylethylamine (3.8 mL, 21.80 mmol) at 0° C.; stirred at RT for 16 h. The reaction was monitored by TLC; after completion of the reaction, the reaction mixture was diluted with water (60 mL) and stirred for 10 min. The precipitate was filtered and dried in vacuo to obtain the crude. The crude was purified through silica gel column chromatography using 20% EtOAc/hexanes to afford compound 227 (2.2 g, 61%) as white solid. TLC: 10% EtOAc/hexanes ($R_f$ 0.2); $^1$H-NMR (DMSO-$d_6$, 400 MHz): δ 7.02 (s, 1H), 3.68-3.62 (m, 4H), 3.41 (t, J=5.2 Hz, 4H), 1.41 (s, 9H).

Synthesis of 2, 4-dichloro-6-(piperazin-1-yl) pyrimidine (228)

To a stirred solution of compound 227 (2.2 g, 6.60 mmol) in $CH_2Cl_2$ (20 mL) under argon atmosphere was added 4 N HCl in 1, 4-dioxane (10 mL) at 0° C.; warmed to RT and stirred for 6 h. The reaction was monitored by TLC; after completion of the reaction, the volatiles were removed in vacuo, the residue was neutralized with 10% aqueous $NaHCO_3$ solution (10 mL) and extracted with EtOAc (2×40 mL). The combined organic extracts were dried over sodium sulfate, filtered and concentrated in vacuo to obtain the crude compound 228 (1.2 g, 78%) as white solid. TLC: 20% EtOAc/hexanes ($R_f$ 0.1); $^1$H-NMR (DMSO-$d_6$, 400 MHz): δ 6.98 (s, 1H), 3.72 (br s, 1H), 3.62-3.50 (m, 4H), 2.76-2.73 (m, 4H).

Synthesis of benzyl 4-(2, 6-dichloropyrimidin-4-yl) piperazine-1-carboxylate (230)

To a stirred solution of compound 228 (1.5 g, 6.43 mmol) in $CH_2Cl_2$ (15 mL) under argon atmosphere were added benzyl chloroformate (50% in toluene, 2.7 mL, 7.72 mmol) and triethylamine (1.8 mL, 12.80 mmol) at 0° C.; warmed to RT and stirred for 3 h. The reaction was monitored by TLC; after completion of the reaction, the reaction mixture was diluted with water (30 mL) and extracted with $CH_2Cl_2$ (2×60 mL). The combined organic extracts were dried over sodium sulfate, filtered and concentrated in vacuo to obtain the crude, which was purified through silica gel column chromatography using 20% EtOAc/hexanes to afford compound 230 (1.9 g, 76%) as an off-white solid. TLC: 40% EtOAc/hexanes ($R_f$ 0.7); $^1$H-NMR (DMSO-$d_6$, 400 MHz): δ 7.38-7.32 (m, 5H), 7.02 (s, 1H), 5.11 (s, 2H), 3.72-3.62 (m, 4H), 3.58-3.47 (m, 4H).

Synthesis of benzyl 4-(2-(4-(tert-butoxycarbonyl) piperazin-1-yl)-6-chloropyrimidin-4-yl) piperazine-1-carboxylate (231)

To a stirred solution of compound 230 (1.8 g, 4.90 mmol) in n-butanol (15 mL) under argon atmosphere were added tert-butyl piperazine-1-carboxylate 4 (1.37 g, 7.35 mmol) and diisopropylethylamine (1.7 mL, 9.80 mmol) in sealed tube at RT; heated to 80° C. and stirred for 16 h. The reaction was monitored by TLC; after completion of the reaction, the volatiles were removed in vacuo, the residue was diluted with water (30 mL) and extracted with EtOAc (2×60 mL). The combined organic extracts were dried over sodium sulfate, filtered and concentrated in vacuo to obtain the crude. The crude was purified through silica gel column chromatography using 25% EtOAc/hexanes to afford compound 231 (1.6 g, 63%) as an off-white solid. TLC: 30% EtOAc/hexanes ($R_f$ 0.8); $^1$H-NMR (DMSO-$d_6$, 400 MHz): δ 7.38-7.32 (m, 5H), 6.18 (s, 1H), 5.10 (s, 2H), 3.63-3.61 (m, 8H), 3.46-3.45 (m, 4H), 3.36-3.33 (m, 4H), 1.41 (s, 9H).

Synthesis of benzyl 4-(2-(4-(tert-butoxycarbonyl) piperazin-1-yl)-6-(p-tolylamino) pyrimidin-4-yl) piperazine-1-carboxylate (232)

To a stirred solution of compound 231 (1 g, 1.93 mmol) in 1, 4-dioxane (10 mL) under argon atmosphere were added p-toluidine (248 mg, 2.32 mmol) and cesium carbonate (943 mg, 2.90 mmol) in sealed tube at RT and degassed under argon for 20 min. To this were added $Pd_2(dba)_3$ (89 mg, 0.10 mmol) and Xantphos (78.3 mg, 0.13 mmol) at RT and degassed under argon for 5 min; heated to 100° C. and stirred for 16 h. The reaction was monitored by TLC; after completion of the reaction, the volatiles were removed in vacuo, the residue was diluted with water (50 mL) and extracted with EtOAc (2×60 mL). The combined organic extracts were dried over sodium sulfate, filtered and concentrated in vacuo to obtain the crude. The crude was purified through silica gel column chromatography using 20% EtOAc/hexanes to afford compound 232 (500 mg, 44%) as an off-white solid. TLC: 30% EtOAc/hexanes ($R_f$ 0.5); $^1$H-NMR (DMSO-$d_6$, 500 MHz): δ 8.73 (s, 1H), 7.42-7.33 (m, 7H), 7.06 (d, J=8.0 Hz, 2H), 5.36 (s, 1H), 5.11 (s, 2H), 3.64-3.62 (m, 4H), 3.49-3.41 (m, 8H), 3.39-3.34 (m, 4H), 2.23 (s, 3H), 1.42 (s, 9H).

Synthesis of benzyl 4-(2-(piperazin-1-yl)-6-(p-tolylamino) pyrimidin-4-yl) piperazine-1-carboxylate (233)

To a stirred solution of compound 232 (500 mg, 0.85 mmol) in $CH_2Cl_2$ (10 mL) under argon atmosphere was added 4 N HCl in 1, 4-dioxane (5 mL) at 0° C.; warmed to RT and stirred for 6 h. The reaction was monitored by TLC; after completion of the reaction, the volatiles were removed in vacuo, the residue was diluted with water (20 mL) and basified with 10% aqueous $NaHCO_3$ solution (20 mL) and extracted with EtOAc (2×50 mL). The combined organic extracts were dried over sodium sulfate, filtered and concentrated in vacuo to obtain the crude compound 233 (220 mg, 53%) as an off-white solid. TLC: 40% EtOAc/hexanes ($R_f$ 0.1); $^1$H-NMR (DMSO-$d_6$, 500 MHz): δ 8.68 (s, 1H), 7.43-7.32 (m, 7H), 7.05 (d, J=8.0 Hz, 2H), 5.32 (s, 1H), 5.10 (s, 2H), 3.56-3.55 (m, 4H), 3.47-3.41 (m, 8H), 2.70-2.68 (m, 4H), 2.21 (s, 3H).

Synthesis of benzyl 4-(2-(4-((4-methoxyphenyl) sulfonyl) piperazin-1-yl)-6-(p-tolylamino) pyrimidin-4-yl) piperazine-1-carboxylate (234)

To a stirred solution of compound 233 (50 mg, 0.10 mmol) in $CH_2Cl_2$ (4 mL) under argon atmosphere were added 4-methoxybenzenesulfonyl chloride (23 mg, 0.11 mmol) and pyridine (0.04 mL, 0.51 mmol) at 0° C.; warmed to RT and stirred for 6 h. The reaction was monitored by TLC; after completion of the reaction, the reaction mixture was diluted with water (20 mL) and extracted with $CH_2Cl_2$ (2×30 mL). The combined organic extracts were washed with 1 N HCl (20 mL), 10% aqueous $NaHCO_3$ solution (10 mL) and brine (30 mL). The organic layer was dried over sodium sulfate, filtered and concentrated in vacuo to obtain the crude. The crude was purified through silica gel column chromatography using 35% EtOAc/hexanes to afford compound 234 (60 mg, 89%) as an off-white solid. TLC: 40% EtOAc/hexanes ($R_f$ 0.6); $^1$H-NMR (DMSO-$d_6$, 400 MHz): δ 8.69 (s, 1H), 7.67 (d, J=8.8 Hz, 2H), 7.37-7.32 (m, 7H), 7.12 (d, J=9.2 Hz, 2H), 7.04 (d, J=8.4 Hz, 2H), 5.31 (s, 1H), 5.09 (s, 2H), 3.82 (s, 3H), 3.74-3.73 (m, 4H), 3.46-3.41 (m, 8H), 2.87-2.86 (m, 4H), 2.22 (s, 3H).

Synthesis of 2-(4-((4-methoxyphenyl) sulfonyl) piperazin-1-yl)-6-(piperazin-1-yl)-N-(p-tolyl) pyrimidin-4-amine (1202)

To a stirred solution of compound 234 (60 mg, 0.09 mmol) in ethyl acetate (5 mL) was added 10% Pd/C (20 mg), conc. HCl (0.1 mL) at RT and stirred under hydrogen atmosphere (balloon pressure) for 6 h at RT. The reaction was monitored by TLC; after completion of the reaction, the reaction mixture was filtered through a pad of celite. The filtrate was concentrated under reduced pressure, the residue was diluted with water (20 mL) and basified with 10% aqueous NaHCO$_3$ solution (10 mL) and extracted with EtOAc (2×20 mL). The combined organic extracts were dried over sodium sulfate, filtered and concentrated in vacuo to obtain the crude, which was triturated with 20% EtOAc/hexanes to afford 1202 (20 mg, 42%) as an off-white solid. TLC: 40% EtOAc/hexanes ($R_f$ 0.1); $^1$H-NMR (DMSO-$d_6$, 400 MHz): δ 8.61 (s, 1H), 7.67 (d, J=8.4 Hz, 2H), 7.34 (d, J=8.0 Hz, 2H), 7.13 (d, J=8.8 Hz, 2H), 7.04 (d, J=8.0 Hz, 2H), 5.28 (s, 1H), 3.83 (s, 3H), 3.75-3.68 (m, 4H), 3.36-3.32 (m, 4H), 2.89-2.82 (m, 4H), 2.73-2.64 (m, 4H), 2.32-2.30 (1H), 2.22 (s, 3H); LC-MS: 96.94%; 524.6 (M$^+$+1); (column; X-select CSH C-18 (50×3.0 mm, 3.5 μm); RT 3.86 min. 5.0 mM NH$_4$OAc:ACN; 0.8 mL/min); UPLC (purity): 93.11%; (column: Acquity BEH C-18 (50×2.1 mm, 1.7μ); RT 1.86 min. ACN: 0.025% TFA (Aq); 0.5 mL/min).

Example 37: Synthesis of 1273

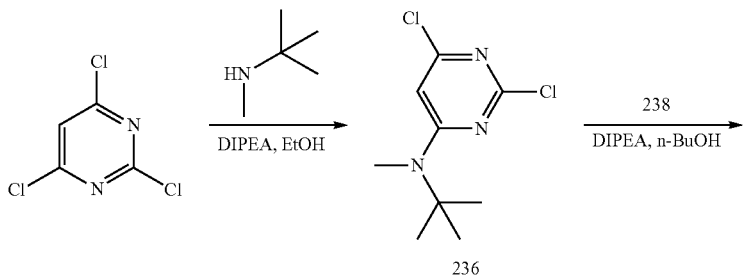

236

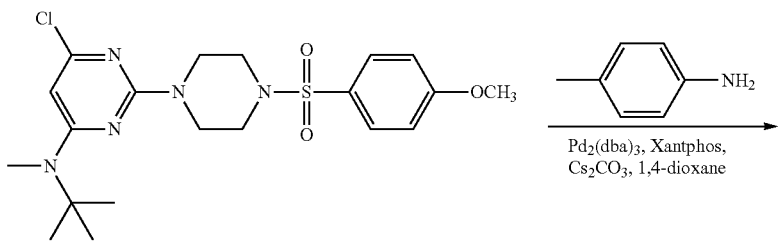

239

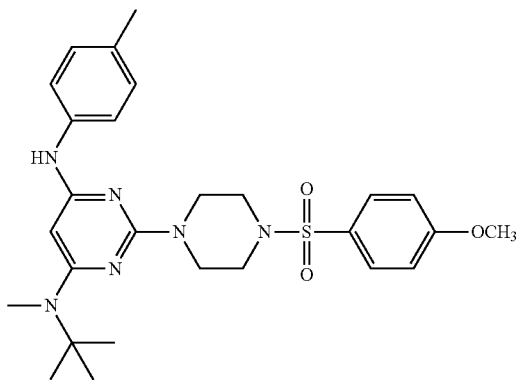

1273

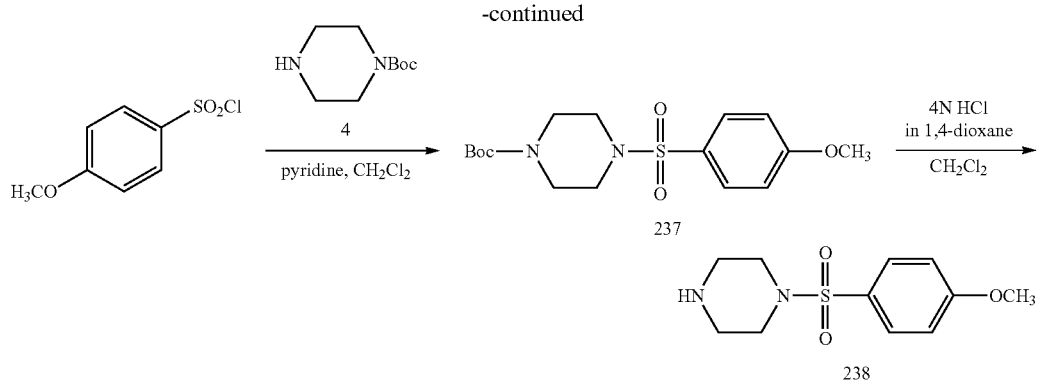

Synthesis of N-(tert-butyl)-2, 6-dichloro-N-methyl-pyrimidin-4-amine (236)

To a stirred solution of 2, 4, 6-trichloropyrimidine (2 g, 10.90 mmol) in ethanol (20 mL) under argon atmosphere were added N, 2-dimethylpropan-2-amine (1.04 g, 11.99 mmol) and diisopropylethylamine (2.8 mL, 16.35 mmol) at RT and stirred for 16 h. The reaction was monitored by TLC; after completion of the reaction, the reaction mixture was diluted with water (50 mL) and extracted with EtOAc (2×60 mL). The combined organic extracts were dried over sodium sulfate, filtered and concentrated in vacuo to obtain the crude. The crude was purified through silica gel column chromatography using 10% EtOAc/hexanes to afford compound 236 (660 mg, 26%) as colorless syrup. TLC: 10% EtOAc/hexanes ($R_f$ 0.3); $^1$H-NMR (DMSO-$d_6$, 500 MHz): δ 6.82 (s, 1H), 3.00 (m, 3H), 1.48 (s, 9H).

Synthesis of tert-butyl-4-((4-methoxyphenyl) sulfonyl) piperazine-1-carboxylate (237)

To a stirred solution of 4-methoxybenzenesulfonyl chloride (500 mg, 2.42 mmol) in $CH_2Cl_2$ (5 mL) under argon atmosphere were added tert-butyl piperazine-1-carboxylate 4 (541 mg, 2.90 mmol) and pyridine (0.98 mL, 12.10 mmol) at 0° C.; warmed to RT and stirred for 16 h. The reaction was monitored by TLC; after completion of the reaction, the reaction mixture was diluted with water (30 mL) and extracted with $CH_2Cl_2$ (2×50 mL). The organic layer was washed with 1 N HCl (20 mL), aqueous saturated $NaHCO_3$ solution (30 mL) and brine (30 mL). The organic layer was dried over sodium sulfate, filtered and concentrated in vacuo to obtain the crude, which was triturated with 20% EtOAc/hexanes to afford compound 237 (750 mg, 87%) as yellow solid. TLC: 30% EtOAc/hexanes ($R_f$ 0.6); $^1$H-NMR (DMSO-$d_6$, 500 MHz): δ 7.67 (d, J=9.0 Hz, 2H), 7.16 (d, J=8.5 Hz, 2H), 3.86 (s, 3H), 3.41-3.37 (m, 4H), 2.82-2.80 (m, 4H), 1.34 (s, 9H).

Synthesis of 1-((4-methoxyphenyl) sulfonyl) piperazine (238)

To a stirred solution of compound 237 (750 mg, 2.10 mmol) in $CH_2Cl_2$ (10 mL) under argon atmosphere was added 4 N HCl in 1, 4-dioxane (1.5 mL) at 0° C.; warmed to RT and stirred for 4 h. The reaction was monitored by TLC; after completion of the reaction, the volatiles were removed in vacuo. The residue was diluted with water (20 mL), neutralized with aqueous saturated $NaHCO_3$ solution (25 mL) and extracted with EtOAc (2×60 mL). The combined organic extracts were dried over sodium sulfate, filtered and concentrated in vacuo to obtain the crude compound 238 (400 mg, 74%) as white solid. TLC: 30% EtOAc/hexanes ($R_f$ 0.1); $^1$H-NMR (DMSO-$d_6$, 500 MHz): δ 7.65 (d, J=9.0 Hz, 2H), 7.16 (d, J=8.5 Hz, 2H), 3.86 (s, 3H), 2.74-2.70 (m, 8H), 2.25 (br s, 1H).

Synthesis of N-(tert-butyl)-6-chloro-2-(4-((4-methoxyphenyl) sulfonyl) piperazin-1-yl)-N-methyl-pyrimidin-4-amine (239)

To a stirred solution of compound 236 (365 mg, 1.56 mmol) in n-butanol (10 mL) under argon atmosphere were added compound 238 (400 mg, 1.56 mmol) and diisopropylethylamine (0.54 mL, 3.12 mmol) in sealed tube at RT; heated to 140° C. and stirred for 24 h. The reaction was monitored by TLC; after completion of the reaction, the volatiles were removed in vacuo to obtain the crude. The crude was purified through silica gel column chromatography using 35% EtOAc/hexanes to afford compound 239 (250 mg, 35%) as an off-white solid. TLC: 20% EtOAc/hexanes ($R_f$ 0.3); $^1$H-NMR (DMSO-$d_6$, 500 MHz): δ 7.68 (d, J=9.0 Hz, 2H), 7.14 (d, J=8.5 Hz, 2H), 6.00 (s, 1H), 3.84 (s, 3H), 3.73-3.72 (m, 4H), 2.92-2.84 (m, 7H), 1.43 (s, 9H).

Synthesis of $N^4$-(tert-butyl)-2-(4-((4-methoxyphenyl) sulfonyl) piperazin-1-yl)-$N^4$-methyl-$N^6$-(p-tolyl) pyrimidine-4, 6-diamine (1273)

To a stirred solution of compound 239 (100 mg, 0.22 mmol) in 1, 4-dioxane (6 mL) under argon atmosphere were added p-toluidine 2 (28.3 mg, 0.26 mmol) and cesium carbonate (107 mg, 0.33 mmol) in sealed tube at RT and degassed under argon for 15 min. To this were added $Pd_2(dba)_3$ (10 mg, 0.01 mmol) and Xantphos (9 mg, 0.01 mmol) at RT and degassed under argon for 10 min; heated to 120° C. and stirred for 16 h. The reaction was monitored by TLC; after completion of the reaction, the volatiles were removed in vacuo, the residue was diluted with water (30 mL) and extracted with EtOAc (2×50 mL). The combined organic extracts were dried over sodium sulfate, filtered and concentrated in vacuo to obtain the crude. The crude was purified through silica gel column chromatography using 30% EtOAc/hexanes to afford 1273 (30 mg, 26%) as white solid. TLC: 35% EtOAc/hexanes ($R_f$ 0.4); $^1$H-NMR (DMSO-$d_6$, 400 MHz): δ 8.57 (s, 1H), 7.67 (d, J=9.2 Hz, 2H), 7.34 (d, J=8.4 Hz, 2H), 7.12 (d, J=9.2 Hz, 2H), 7.03 (d, J=8.4 Hz, 2H), 5.30 (s, 1H), 3.82 (s, 3H), 3.73 (t, J=4.8 Hz, 4H), 2.87 (t, J=4.8 Hz, 4H), 2.84 (s, 3H), 2.21 (s, 3H), 1.41 (s, 9H); LC-MS: 99.30%; 525.7 ($M^+$+1); (column; X-select CSH C-18 (50×3.0 mm, 3.5 µm); RT 4.11 min. 0.05% TFA (Aq): ACN; 0.8 mL/min); UPLC (purity): 98.49%; (column: Acquity UPLC BEH C-18 {2.1×50 mm, 1.7µ}; RT 2.53 min. ACN: 0.025% TFA (Aq); 0.5 mL/min).

Example 38: Assay Measuring Activity of Test Compounds on Viral Production From AD38 Cells AD38 cells grown in a 175 cm flask with Growth Medium (DMEM/F12 (1:1) (cat #SH30023.01, Hyclone, 1× Pen/step (cat #: 30-002-CL, Mediatech, Inc), 10% FBS (cat #: 101, Tissue Culture Biologics), 250 µg/mL G418 (cat #: 30-234-CR, Mediatech, Inc), 1 µg/mL Tetracycline (cat #: T3325, Teknova)) were detached with 0.25% trypsin. Tetracycline-free treatment medium (15 mL DMEM/F12 (1:1) (cat #SH30023.01, Hyclone, 1× Pen/step (cat #: 30-002-CL, Mediatech, Inc), with 2% FBS, Tet-system approved (cat #: 631106, Clontech) were then added to mix and spun at 1300 rpm for 5 min. Pelleted cells were then re-suspended/washed with 50 mL of 1×PBS 2 times and 10 mL treatment medium one time. AD38 cells were then re-suspended with 10 mL of treatment medium and counted. Wells of a collagen coated 96-well NUNC microtiter plate were seeded at 50,000/well in 180 µL of treatment medium, and 20 µL of either 10% DMSO (Control) or a 10× solution of test compound in 10% DMSO in treatment media was added for a final compound concentration 1, 3, or 10 µM (1.0% final [DMSO]) and plates were incubated for 6 days at 37° C.

Subsequently viral load production was assayed by quantitative PCR of the core sequence. Briefly, 5 µL of clarified supernatant was added to a PCR reaction mixture that contained forward primers HBV-f 5'-CTGTGCCT-TGGGTGGCTTT-3', Reverse primers HBV-r 5'-AAGGAAAGAAGTCAGAAGGCAAAA-3' and Fluorescent TaqMan™ Probes HBV-probe 5'-FAM/AGCTC-CAAA/ZEN/TTCTTTATAAGGGTCGATGTCCATG/3IABkFQ-3' in Quanta Biosciences PerfeCTa® qPCR Toughmix®, and was subsequently on an Applied Biosystems VIIA7 in a final volume of 20 µL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate). Results are shown in Table 6 below.

TABLE 6

| Compound No. | AD38 Viral Load (CpAM/DMSO %) at 10 µM | AD38 Viability Normalized Result (CPAM/DMSO %) at 10 µM |
|---|---|---|
| 1133 | 35 | 108 |
| 1134 | 32 | 123 |
| 1135 | 16 | 107 |
| 1136 | 24 | 113 |
| 1143 | 8 | 107 |
| 1144 | 12 | 100 |
| 1146 | 15 | 106 |
| 1150 | 4 | 89 |
| 1151 | 1 | 73 |
| 1152 | 20 | 107 |
| 1153 | 21 | 109 |
| 1157 | 35 | 96 |
| 1158 | 51 | 92 |
| 1159 | 81 | 95 |
| 1160 | 60 | 110 |
| 1167 | 36 | 108 |
| 1168 | 51 | 100 |
| 1172 | 21 | 107 |
| 1173 | 9 | 105 |
| 1179 | 45 | 103 |
| 1186 | 76 | 106 |
| 1188 | 52 | 105 |
| 1190 | 72 | 83 |
| 1194 | 64 | 109 |
| 1200 | 81 | 98 |
| 1201 | 90 | 101 |
| 1202 | 51 | 106 |
| 1207 | 83 | 0 |
| 1212 | 77 | 94 |
| 1213 | 40 | 94 |
| 1215 | 93 | 89 |
| 1229 | 13 | 92 |
| 1230 | 0 | 95 |
| 1231 | 45 | 94 |
| 1232 | 83 | 96 |
| 1329 | 1 | |
| 1233 | 87 | 95 |
| 1234 | 82 | 101 |
| 1238 | 26 | 102 |
| 1240 | 46 | 102 |
| 1241 | 65 | 98 |
| 1242 | 30 | 103 |
| 1243 | 32 | 109 |
| 1245 | 70 | 99 |
| 1247 | 6 | 98 |
| 1248 | 8 | 33 |
| 1249 | 31 | 65 |
| 1250 | 56 | 101 |
| 1251 | 60 | 56 |
| 1258 | 50 | 105 |
| 1260 | 78 | 98 |
| 1261 | 87 | 98 |
| 1265 | 13 | 102 |
| 1273 | 16 | 98 |
| 1274 | 19 | 92 |
| 1282 | 22 | 99 |
| 1286 | 2 | 86 |
| 1287 | 77 | 98 |
| 1288 | 102 | 105 |
| 1289 | 55 | 105 |
| 1290 | 62 | 105 |
| 1295 | 84 | 101 |
| 1296 | 102 | 103 |
| 1297 | 59 | 103 |
| 1298 | 100 | 97 |
| 1299 | 54 | 112 |
| 1301 | 63 | 102 |
| 1302 | 52 | 112 |
| 1303 | 14 | 35 |
| 1304 | 48 | 113 |
| 1305 | 4 | 6 |
| 1306 | 22 | 103 |
| 1307 | 84 | 94 |
| 1308 | 63 | 88 |
| 1309 | 26 | 67 |
| 1310 | 50 | 81 |
| 1311 | 66 | 86 |
| 1312 | 31 | 96 |
| 1313 | 47 | 93 |
| 1314 | 36 | 94 |
| 1315 | 89 | 98 |
| 1316 | 25 | |
| 1319 | 5 | |
| 1320 | 18 | |
| 1321 | 1 | |
| 1322 | 35 | |
| 1324 | 1 | |
| 1325 | 1 | |
| 1326 | 2 | |
| 1327 | 1 | |
| 1328 | 9 | |

205

Example 39: Synthesis of N-(4-fluorophenyl)-6-methyl-2-(piperazin-1-yl) pyrimidin-4-amine (106): A Common Intermediate

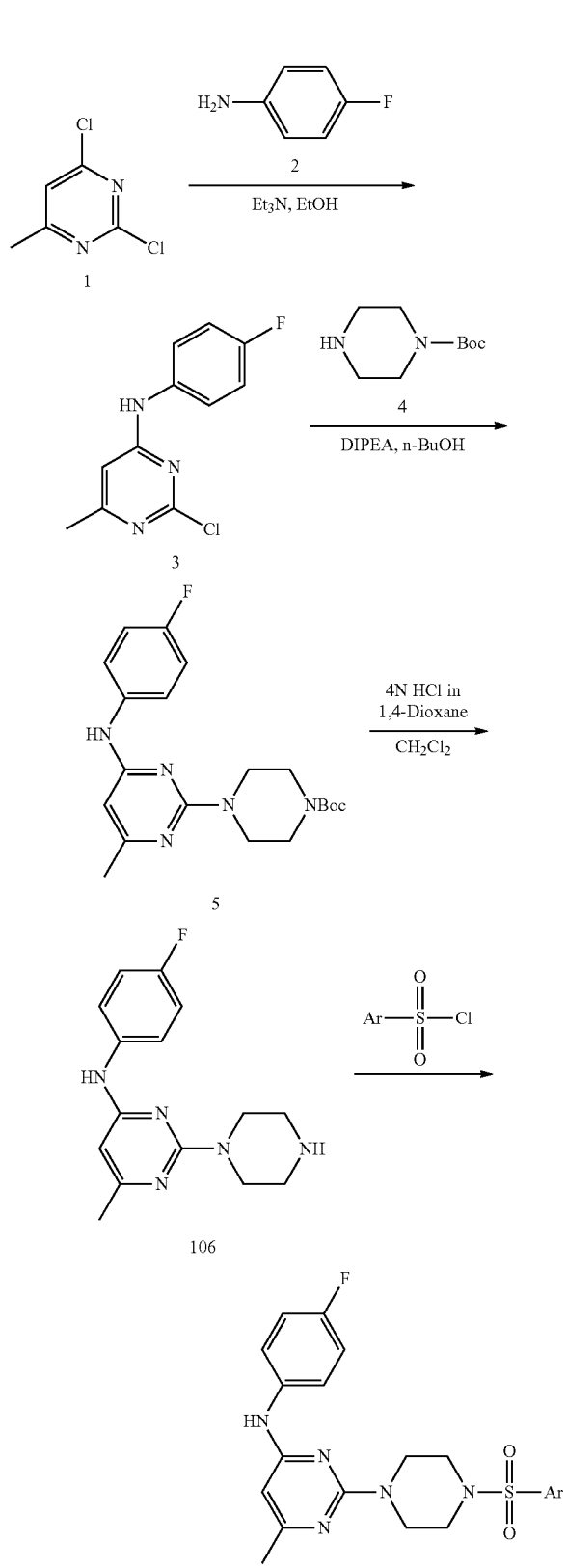

206

Synthesis of 2-chloro-N-(4-fluorophenyl)-6-methyl-pyrimidin-4-amine (3)

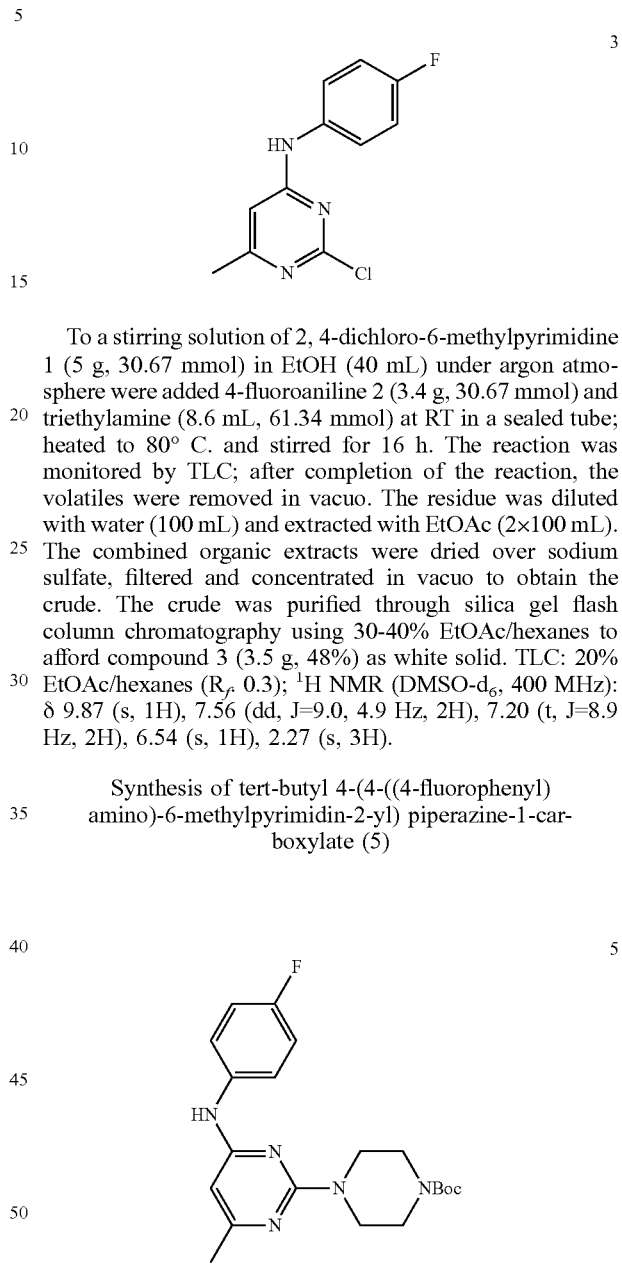

To a stirring solution of 2, 4-dichloro-6-methylpyrimidine 1 (5 g, 30.67 mmol) in EtOH (40 mL) under argon atmosphere were added 4-fluoroaniline 2 (3.4 g, 30.67 mmol) and triethylamine (8.6 mL, 61.34 mmol) at RT in a sealed tube; heated to 80° C. and stirred for 16 h. The reaction was monitored by TLC; after completion of the reaction, the volatiles were removed in vacuo. The residue was diluted with water (100 mL) and extracted with EtOAc (2×100 mL). The combined organic extracts were dried over sodium sulfate, filtered and concentrated in vacuo to obtain the crude. The crude was purified through silica gel flash column chromatography using 30-40% EtOAc/hexanes to afford compound 3 (3.5 g, 48%) as white solid. TLC: 20% EtOAc/hexanes ($R_f$ 0.3); $^1$H NMR (DMSO-$d_6$, 400 MHz): δ 9.87 (s, 1H), 7.56 (dd, J=9.0, 4.9 Hz, 2H), 7.20 (t, J=8.9 Hz, 2H), 6.54 (s, 1H), 2.27 (s, 3H).

Synthesis of tert-butyl 4-(4-((4-fluorophenyl)amino)-6-methylpyrimidin-2-yl) piperazine-1-carboxylate (5)

To a stirring solution of compound 3 (3 g, 12.65 mmol) in n-butanol (30 mL) under argon atmosphere were added tert-butyl piperazine-1-carboxylate 4 (3.06 g, 16.45 mmol) and diisopropylethylamine (4.36 mL, 25.31 mmol) at RT in a sealed tube; heated to 100° C. and stirred for 24 h. The reaction was monitored by TLC; after completion of the reaction, the volatiles were removed in vacuo to obtain the crude. The crude was purified through silica gel flash column chromatography using 25-30% EtOAc/hexanes to afford compound 5 (4 g, 82%) as white solid. TLC: 40% EtOAc/hexanes ($R_f$ 0.5); $^1$H NMR (DMSO-$d_6$, 400 MHz): δ 9.14 (s, 1H), 7.59 (dd, J=9.1, 5.0 Hz, 2H), 7.14 (t, J=8.9 Hz, 2H), 5.89 (s, 1H), 3.72-3.67 (m, 4H), 3.41-3.35 (m, 4H), 2.14 (s, 3H), 1.42 (s, 9H).

Synthesis of N-(4-fluorophenyl)-6-methyl-2-(piperazin-1-yl) pyrimidin-4-amine (106)

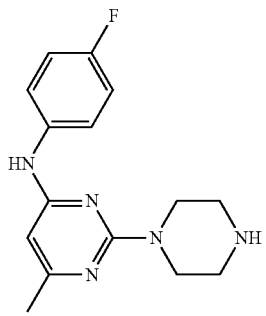

106

To a stirring solution of compound 5 (4 g, 10.33 mmol) in CH$_2$Cl$_2$ (20 mL) was added 4 N HCl in 1, 4-dioxane (20 mL) under argon atmosphere at 10° C.; warmed to RT and stirred for 2 h. The reaction was monitored by TLC; after completion of the reaction, the volatiles were removed in vacuo. The residue was diluted with water (50 mL) and neutralized with saturated NaHCO$_3$ solution (50 mL) and extracted with EtOAc (2×150 mL). The combined organic extracts were dried over sodium sulfate, filtered and concentrated in vacuo to afford compound 6 (2.80 g, 95%) as white solid. TLC: 40% EtOAc/hexanes (R$_f$ 0.1); $^1$H NMR (DMSO-d$_6$, 400 MHz): δ 9.06 (s, 1H), 7.58 (dd, J=9.1, 5.0 Hz, 2H), 7.11 (t, J=8.9 Hz, 2H), 5.84 (s, 1H), 3.61-3.56 (m, 4H), 2.72-2.67 (m, 4H), 2.32 (br s, 1H), 2.11 (s, 3H).

Example 40: Synthesis of N-(4-fluorophenyl)-6-methyl-2-(3-methylpiperazin-1-yl) pyrimidin-4-amine (8): A Common Intermediate

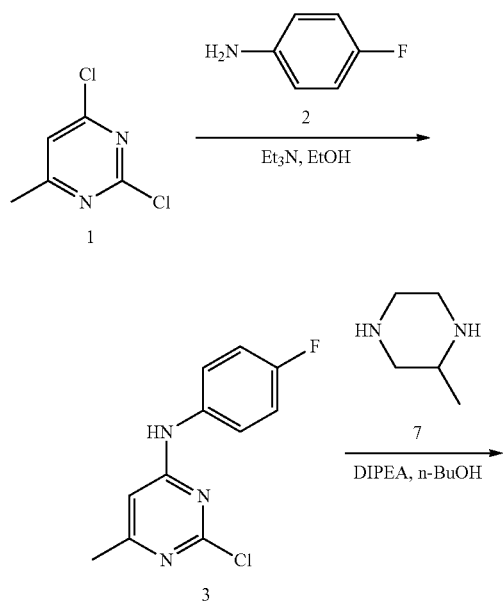

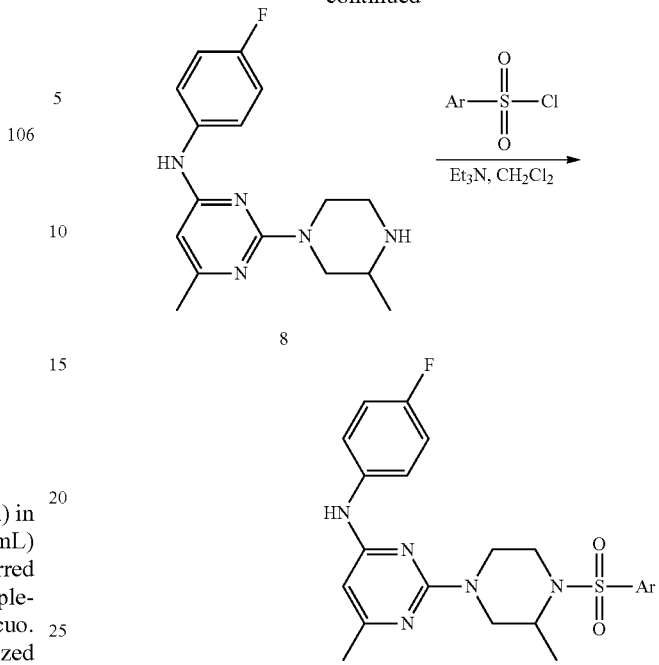

Synthesis of N-(4-fluorophenyl)-6-methyl-2-(3-methylpiperazin-1-yl) pyrimidin-4-amine (8)

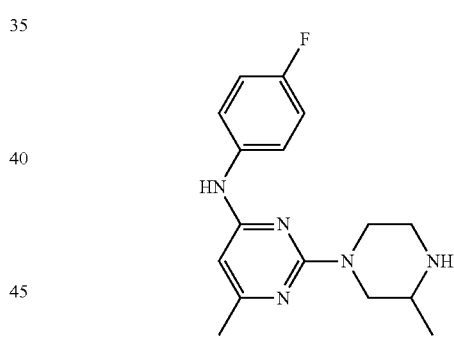

8

To a stirring solution of 2-chloro-N-(4-fluorophenyl)-6-methylpyrimidin-4-amine 3 (300 mg, 1.26 mmol) in n-butanol (10 mL) under argon atmosphere were added 2-methylpiperazine 7 (126 mg, 1.26 mmol) and diisopropylethylamine (0.44 mL, 2.53 mmol) at RT; heated to 100° C. and stirred for 30 h. The reaction was monitored by TLC; after completion of the reaction, the volatiles were removed in vacuo. The residue was diluted with water (30 mL) and extracted with EtOAc (2×40 mL). The combined organic extracts were dried over sodium sulfate, filtered and concentrated in vacuo to obtain the crude. The crude was triturated using 30% EtOAc/hexanes (2×10 mL) to afford compound 8 (300 mg, 79%) as white solid. TLC: 5% MeOH/CH$_2$Cl$_2$ (R$_f$ 0.2); $^1$H NMR (DMSO-d$_6$, 400 MHz): δ 9.32 (s, 1H), 7.58 (dd, J=9.1, 5.0 Hz, 2H), 7.14 (t, J=8.9 Hz, 2H), 5.97 (s, 1H), 4.58-4.52 (m, 2H), 3.34-3.29 (m, 1H), 3.28-3.19 (m, 3H), 3.04-2.93 (m, 2H), 2.16 (s, 3H), 1.28 (d, J=6.5 Hz, 3H).

Example 41: Synthesis of N-(4-fluorophenyl)-6-methyl-2-(2-methylpiperazin-1-yl) pyrimidin-4-amine hydrochloride (11): A Common Intermediate

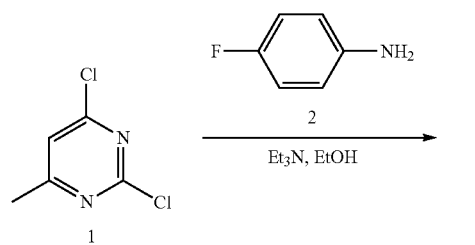

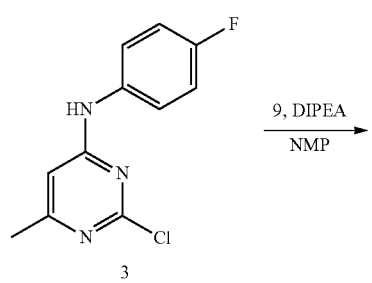

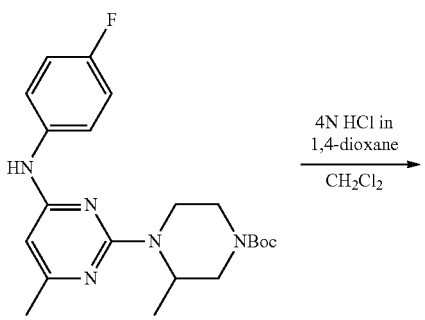

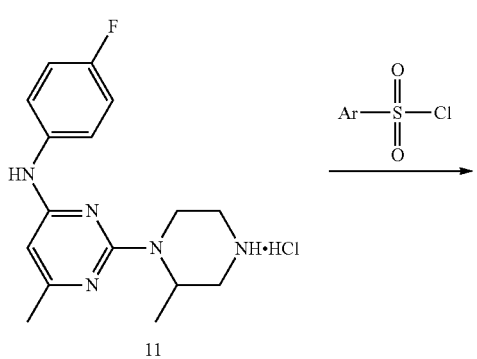

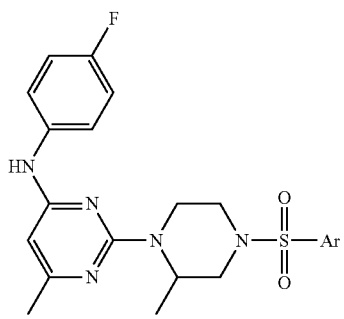

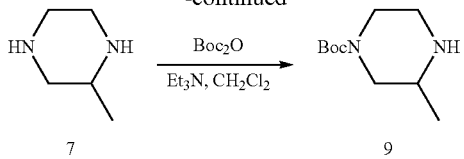

Synthesis of tert-butyl 3-methylpiperazine-1-carboxylate (9)

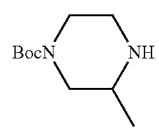

To a stirring solution of 2-methylpiperazine 7 (3 g, 30.00 mmol) in CH$_2$Cl$_2$ (100 mL) under argon atmosphere were added triethylamine (9 mL, 90.00 mmol) and Boc-anhydride (7.2 mL, 33.00 mmol) at 0° C.; warmed to RT and stirred for 16 h. The reaction was monitored by TLC; after completion of the reaction, the volatiles were removed in vacuo. The crude was washed with n-pentane (2×20 mL) and dried in vacuo to afford compound 9 (5 g, 83%) as off-white solid. TLC: 5% MeOH/CH$_2$Cl$_2$ (R$_f$ 0.4); $^1$H-NMR (DMSO-d$_6$, 400 MHz): δ 3.80-3.62 (m, 2H), 3.27-3.09 (m, 2H), 2.83-2.71 (m, 2H), 2.37-2.17 (m, 1H), 1.39 (s, 9H), 0.92 (d, J=6.3 Hz, 3H).

Synthesis of tert-butyl 4-(4-((4-fluorophenyl)amino)-6-methylpyrimidin-2-yl)-3-methylpiperazine-1-carboxylate (10)

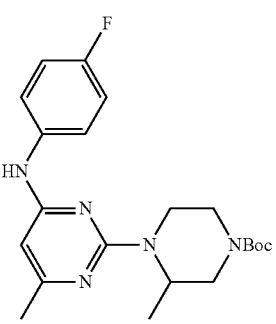

To a stirring solution of compound 3 (500 mg, 2.10 mmol) in N-methyl-2-pyrrolidone (10 mL) under argon atmosphere in a sealed tube were added compound 9 (633 mg, 3.16 mmol), diisopropylethylamine (1.82 mL, 10.54 mmol) and the reaction mixture was heated to 160° C. for 30 h. The reaction was monitored by TLC; after completion of the reaction, the reaction mixture was diluted with water (30 mL) and extracted with EtOAc (2×50 mL). The combined organic extracts were dried over sodium sulfate, filtered and concentrated in vacuo to obtain the crude. The crude was purified through silica gel flash column chromatography using 30-50% EtOAc/hexanes and to afford compound 10 (200 mg, 24%) as an off-white solid. TLC: 40% EtOAc/ hexanes (R$_f$ 0.5); $^1$H-NMR (DMSO-d$_6$, 500 MHz): δ 9.13 (s, 1H), 7.60 (dd, J=9.0, 4.9 Hz, 2H), 7.13 (t, J=8.2 Hz, 2H), 5.89 (s, 1H), 4.79-4.72 (m, 1H), 4.36-4.31 (m, 1H), 3.99-3.88 (m, 1H), 3.83-3.78 (m, 1H), 3.12-2.97 (m, 2H), 2.81 (br s, 1H), 2.14 (s, 3H), 1.43 (s, 9H), 1.07 (d, J=6.7 Hz, 3H).

Synthesis of N-(4-fluorophenyl)-6-methyl-2-(2-methylpiperazin-1-yl) pyrimidin-4-amine hydrochloride (11)

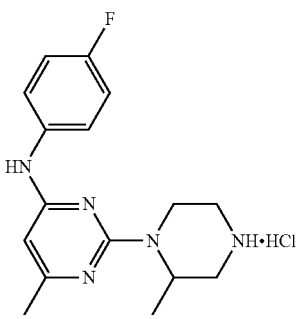

To a stirring solution of compound 10 (200 mg, 0.49 mmol) in CH$_2$Cl$_2$ (5 mL) was added 4 N HCl in 1, 4-dioxane (1 mL) under argon atmosphere at 0° C.; warmed to RT and stirred for 2 h. The reaction was monitored by TLC; after completion of the reaction, the volatiles were removed in vacuo. The crude was triturated using diethyl ether (2×10 mL) and dried in vacuo to afford compound 11 (150 mg, 89%) as an off-white solid. TLC: 40% EtOAc/hexanes (R$_f$ 0.2); LC-MS: 99.27%; 301.9 (M$^+$+1); (column; Ascentis Express C18, (50×3.0 mm, 2.7 μm); RT 1.41 min. 0.025% Aq. TFA+5% ACN: ACN+5% 0.025% Aq. TFA, 1.2 mL/min).

Example 42: Synthesis of 2-(3, 3-dimethylpiperazin-1-yl)-N-(4-fluorophenyl)-6-methylpyrimidin-4-amine (13): A Common Intermediate

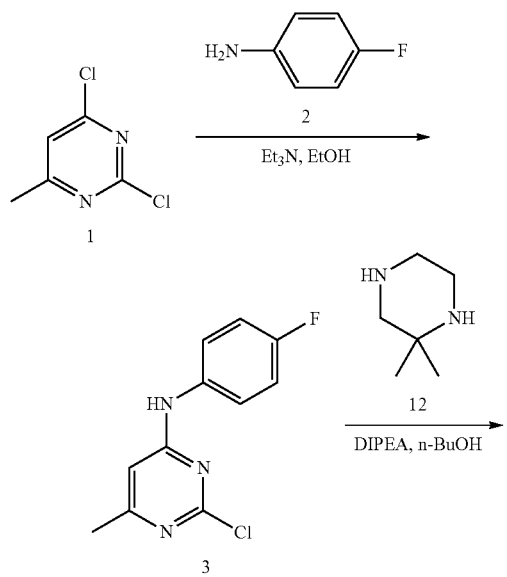

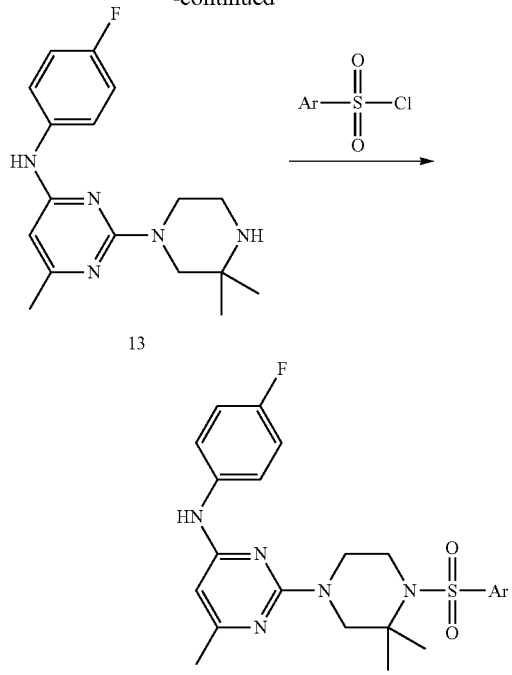

Synthesis of 2-(3, 3-dimethylpiperazin-1-yl)-N-(4-fluorophenyl)-6-methylpyrimidin-4-amine (13)

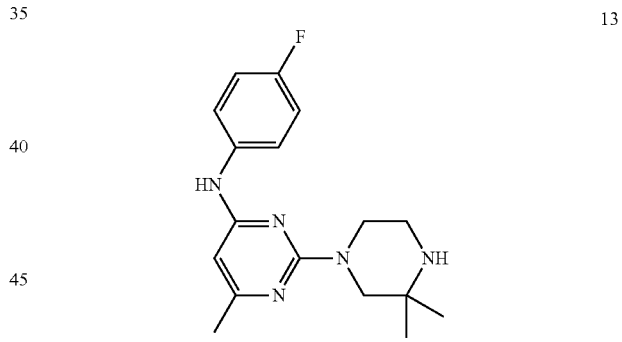

To a stirring solution of 2-chloro-N-(4-fluorophenyl)-6-methylpyrimidin-4-amine 3 (100 mg, 0.42 mmol) in n-butanol (0.5 mL) under argon atmosphere were added 2, 2-dimethylpiperazine 12 (52.8 mg, 0.46 mmol) and diisopropylethylamine (0.18 mL, 1.26 mmol) at RT; heated to 180° C. and stirred for 16 h. The reaction was monitored by TLC; after completion of the reaction, the volatiles were removed in vacuo. The residue was diluted with water (30 mL) and extracted with 5% MeOH/CH$_2$Cl$_2$ (2×40 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 13 (122 mg, 92%) as white solid. TLC: 20% EtOAc/hexanes (R$_f$ 0.3); $^1$H NMR (DMSO-d$_6$, 400 MHz): δ 9.27 (s, 1H), 7.57 (dd, J=9.1, 4.9 Hz, 2H), 7.15 (t, J=8.9 Hz, 2H), 5.95 (s, 1H), 4.10-4.04 (m, 1H), 3.94-3.83 (m, 2H), 3.74 (s, 2H), 3.66-3.56 (m, 1H), 2.16 (s, 3H), 1.32 (s, 6H).

Example 43: Synthesis of 4-((6-methyl-2-(2-ox-opiperazin-1-yl) pyrimidin-4-yl) amino) benzonitrile hydrochloride (19): A Common Intermediate

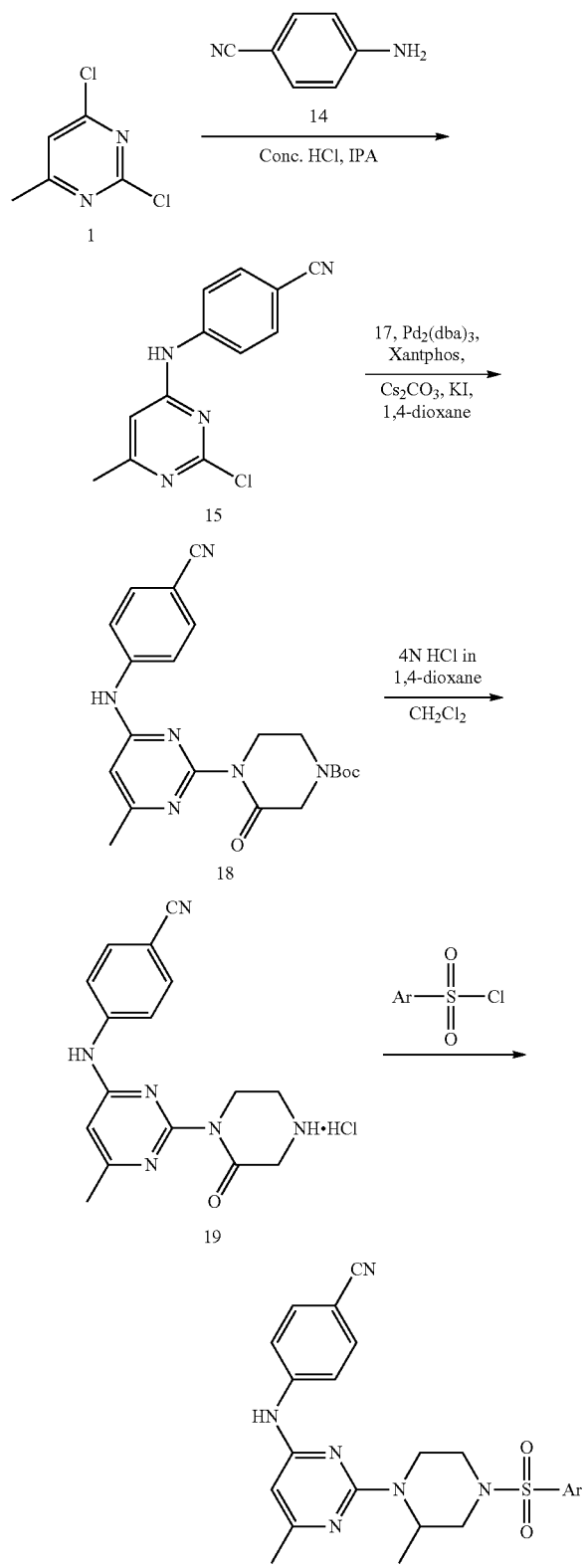

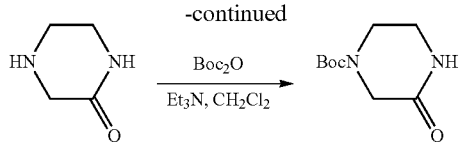

Synthesis of 4-((2-chloro-6-methylpyrimidin-4-yl) amino) benzonitrile (15)

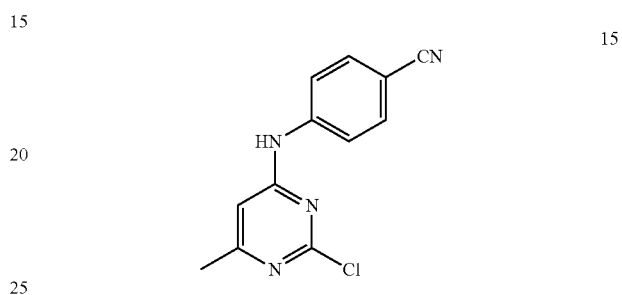

To a stirring solution of 2, 4-dichloro-6-methylpyrimidine 1 (5 g, 30.67 mmol) in isopropyl alcohol (60 mL) under argon atmosphere were added 4-aminobenzonitrile 14 (3.62 g, 30.67 mmol) and concentrated HCl (3 mL, 30.67 mmol) in sealed tube at 0° C.; warmed to RT and stirred for 120 h. The reaction was monitored by TLC; after completion of the reaction, the volatiles were removed in vacuo. The residue was diluted with water (100 mL) and pH was adjusted to ~8 with saturated NaHCO$_3$ solution (30 mL), extracted with EtOAc (3×100 mL). The combined organic extracts were washed with brine (100 mL), dried over sodium sulfate, filtered and concentrated in vacuo to obtain the crude. The crude was purified through combiflash chromatography (80 g column with 40-60 µm silica gel) using 30-40% EtOAc/hexanes to afford compound 15 (2.5 g, 33%) as white solid. TLC: 30% EtOAc/hexanes (R$_f$ 0.5); $^1$H NMR (DMSO-d$_6$, 400 MHz): δ 10.33 (s, 1H), 7.82-7.79 (m, 4H), 6.71 (s, 1H), 2.34 (s, 3H).

Synthesis of tert-butyl 3-oxopiperazine-1-carboxylate (17)

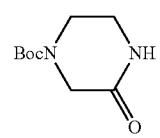

To a stirring solution of piperazin-2-one 16 (500 mg, 5.00 mmol) in CH$_2$Cl$_2$ (5 mL) under argon atmosphere were added triethylamine (1.5 mL, 10.00 mmol) and Boc-anhydride (1.3 mL, 6.00 mmol) at 0° C.; warmed to RT and stirred for 18 h. The reaction was monitored by TLC; after completion of the reaction, the volatiles were removed in vacuo. The crude was purified through silica gel flash column chromatography using 2% MeOH/CH$_2$Cl$_2$ to afford compound 17 (450 mg, 45%) as pale yellow solid. TLC: 10% MeOH/CH$_2$Cl$_2$ (R$_f$ 0.6); $^1$H-NMR (DMSO-d$_6$, 400

MHz): δ 8.02 (br s, 1H), 3.81 (s, 2H), 3.48-3.45 (m, 2H), 3.19-3.14 (m, 2H), 1.41 (s, 9H).

Synthesis of tert-butyl 4-(4-((4-cyanophenyl)amino)-6-methylpyrimidin-2-yl)-3-oxopiperazine-1-carboxylate (18)

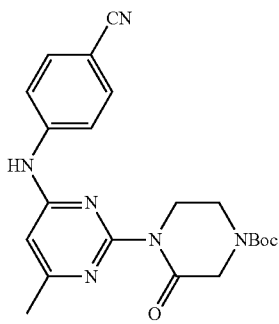

18

To a stirring solution of compound 15 (700 mg, 2.86 mmol) in 1, 4-dioxane (10 mL) under argon atmosphere were added compound 17 (573 mg, 2.86 mmol), cesium carbonate (1.86 g, 5.73 mmol) and potassium iodide (476 mg, 2.86 mmol) at RT, purged under argon for 5 min in a microwave vessel. To this were added Pd$_2$(dba)$_3$ (131 mg, 0.14 mmol) and xantphos (116 mg, 0.20 mmol) at RT and heated to 100° C. and stirred for 1.5 h. The reaction was monitored by TLC; after completion of the reaction, the reaction mixture was filtered through celite pad washed with CH$_2$Cl$_2$ (2×100 mL). The filtrate was removed in vacuo to obtain the crude. The crude was purified through silica gel flash column chromatography using 2% MeOH/CH$_2$Cl$_2$ and further purified through preparative HPLC purification to afford compound 18 (200 mg, 14%) as an off-white solid. TLC: 5% MeOH/CH$_2$Cl$_2$ (R$_f$ 0.3); $^1$H-NMR (DMSO-d$_6$, 400 MHz): δ 10.09 (s, 1H), 7.97 (d, J=8.9 Hz, 2H), 7.71 (d, J=8.9 Hz, 2H), 6.56 (s, 1H), 4.14 (s, 2H), 4.01-3.96 (m, 2H), 3.65-3.60 (m, 2H), 2.34 (s, 3H), 1.44 (s, 9H); LC-MS: 99.67%; 409.3 (M$^+$+1); (column; X-select CSH C18, (50× 3.0 mm, 2.5 μm); RT 3.65 min. 5 mM Aq. NH4OAc: ACN, 0.8 mL/min); HPLC (purity): 99.67%; (column; X Select CSH C18 (150×4.6 mm, 3.5 μm); RT 9.68 min. ACN: 0.05% TFA (Aq); 1.0 mL/min).

Synthesis of 4-((6-methyl-2-(2-oxopiperazin-1-yl)pyrimidin-4-yl)amino)benzonitrile hydrochloride (19)

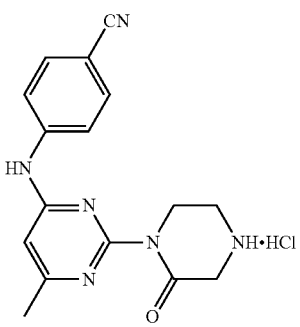

19

To a stirring solution of compound 18 (150 mg, 0.36 mmol) in CH$_2$Cl$_2$ (5 mL) was added 4 N HCl in 1, 4-dioxane (5 mL) under argon atmosphere at 0° C.; warmed to RT and stirred for 2 h. The reaction was monitored by TLC; after completion of the reaction, the volatiles were removed in vacuo. The crude was triturated with diethylether (2×5 mL) and dried in vacuo to afford 19 (140 mg, Quantitative) as an off-white solid. TLC: 5% MeOH/CH$_2$Cl$_2$ (R$_f$ 0.2); $^1$H NMR (DMSO-d$_6$, 400 MHz): δ 10.55 (br s, 1H), 9.82 (br s, 2H), 7.99 (d, J=8.8 Hz, 2H), 7.72 (d, J=8.8 Hz, 2H), 6.70 (s, 1H), 4.13-4.08 (m, 2H), 3.97-3.95 (m, 2H), 3.58-3.50 (m, 2H), 2.37 (s, 3H).

Example 44: Synthesis of 4-((6-methyl-2-(2-methylpiperazin-1-yl)pyrimidin-4-yl)amino)benzonitrile hydrochloride (21): A Common Intermediate

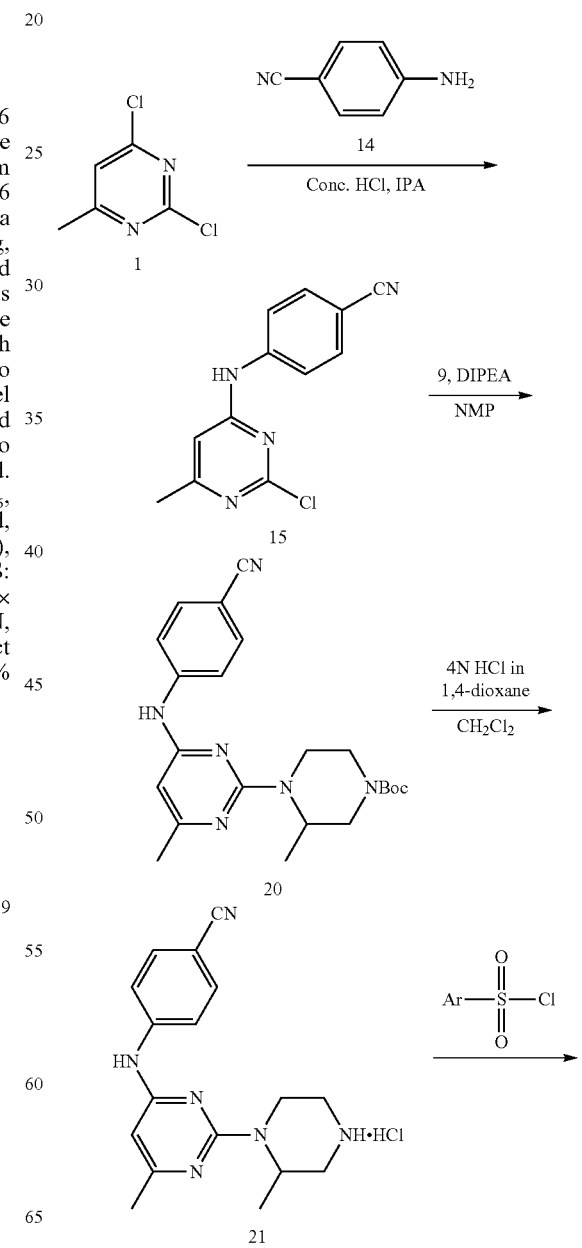

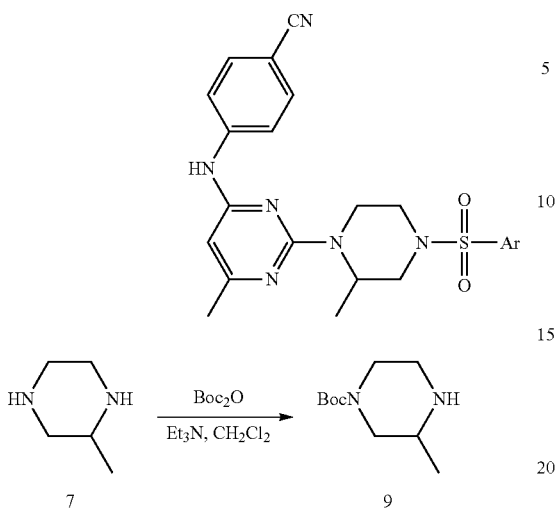

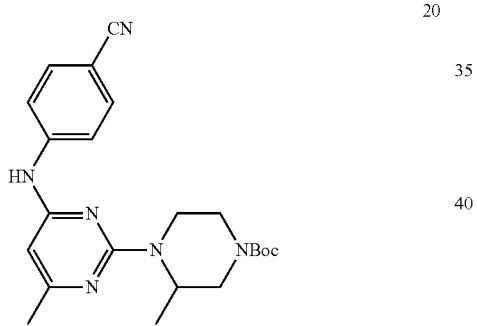

Synthesis of tert-butyl 4-(4-((4-cyanophenyl)amino)-6-methylpyrimidin-2-yl)-3-methylpiperazine-1-carboxylate (20)

To a stirring solution of 4-((2-chloro-6-methylpyrimidin-4-yl) amino) benzonitrile 15 (500 mg, 2.04 mmol) in N-methyl-2-pyrrolidone (15 mL) under argon atmosphere in a sealed tube were added tert-butyl 3-methylpiperazine-1-carboxylate 9 (450 mg, 2.28 mmol), diisopropylethylamine (1.5 mL, 10.24 mmol) and the reaction mixture was heated to 170° C. for 24 h. The reaction was monitored by TLC and LC-MS; after completion of the reaction, the reaction mixture was diluted with ice-cold water (20 mL) and extracted with diethylether (2×50 mL). The combined organic extracts were dried over sodium sulfate, filtered and concentrated in vacuo to obtain the crude. The crude was purified through silica gel column chromatography using 25% EtOAc/hexanes and to afford compound 20 (180 mg, 21%) as an off-white solid. TLC: 40% EtOAc/hexanes ($R_f$ 0.7); $^1$H-NMR (DMSO-$d_6$, 500 MHz): δ 9.65 (s, 1H), 7.82 (d, J=8.3 Hz, 2H), 7.73 (d, J=8.8 Hz, 2H), 6.01 (s, 1H), 4.78-4.74 (m, 1H), 4.37-4.31 (m, 1H), 3.86-3.80 (m, 1H), 3.13-3.03 (m, 2H), 2.92-2.80 (m, 2H), 2.19 (s, 3H), 1.43 (s, 9H), 1.10 (d, J=6.3 Hz, 3H).

Synthesis of 4-((6-methyl-2-(2-methylpiperazin-1-yl) pyrimidin-4-yl) amino) benzonitrile hydrochloride (21)

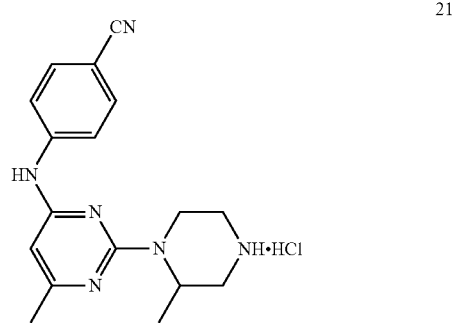

To a stirring solution of compound 20 (180 mg, 0.44 mmol) in CH$_2$Cl$_2$ (5 mL) was added 4 N HCl in 1, 4-dioxane (1.5 mL) under argon atmosphere at 0° C.; warmed to RT and stirred for 3 h. The reaction was monitored by TLC; after completion of the reaction, the volatiles were removed in vacuo. The crude was washed with diethylether (2×5 mL) and dried in vacuo to afford compound 21 (100 mg, 74%) as an off-white solid. TLC: 40% EtOAc/hexanes ($R_f$ 0.2); $^1$H-NMR (DMSO-$d_6$, 500 MHz): δ 9.58 (s, 1H), 7.82 (d, J=8.9 Hz, 2H), 7.70 (d, J=8.8 Hz, 2H), 5.96 (s, 1H), 4.67-4.60 (m, 1H), 4.31-4.24 (m, 1H), 2.99-2.89 (m, 2H), 2.78-2.75 (m, 2H), 2.56-2.54 (m, 1H), 2.17 (s, 3H), 1.18 (d, J=6.7 Hz, 3H).

Synthesis of 4-((2-(3, 3-dimethylpiperazin-1-yl)-6-methylpyrimidin-4-yl) amino) benzonitrile (22): A Common Intermediate

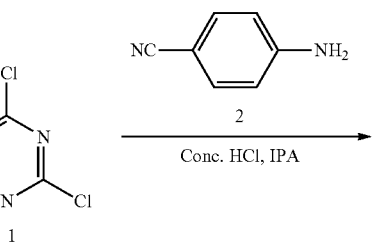

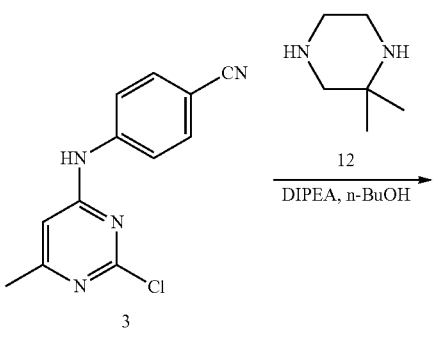

-continued

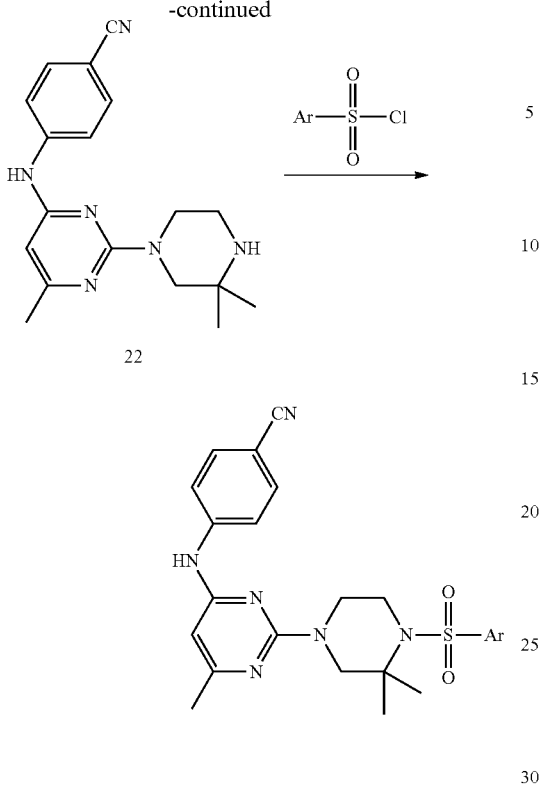

Synthesis of 4-((2-(3, 3-dimethylpiperazin-1-yl)-6-methylpyrimidin-4-yl) amino) benzonitrile (22)

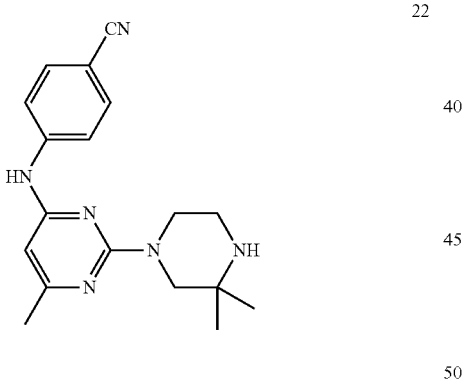

To a stirring solution of 4-((2-chloro-6-methylpyrimidin-4-yl) amino) benzonitrile 15 (50 mg, 0.20 mmol) in n-butanol (0.5 mL) under argon atmosphere were added 2, 2-dimethylpiperazine 12 (23 mg, 0.20 mmol) and diisopropylethylamine (0.052 mL, 0.40 mmol) in a sealed tube at RT; heated to 180° C. and stirred for 16 h. The reaction was monitored by TLC; after completion of the reaction, the volatiles were removed in vacuo to obtain the crude. The crude was purified through silica gel column chromatography using 5% MeOH/CH$_2$Cl$_2$ to afford compound 22 (40 mg, 61%) as an off-white solid. TLC: 10% MeOH/CH$_2$Cl$_2$ (R$_f$, 0.2); $^1$H NMR (DMSO-d$_6$, 400 MHz): δ 9.76 (s, 1H), 8.89 (br s, 1H), 7.80 (d, J=8.8 Hz, 2H), 7.74 (d, J=8.6 Hz, 2H), 6.07 (s, 1H), 3.93-3.90 (m, 2H), 3.74-3.72 (m, 2H), 3.17-3.13 (m, 2H), 2.20 (s, 3H), 1.30 (s, 6H).

Example 45: Synthesis of N-(4-fluorophenyl)-2-(piperazin-1-yl)-6-(trifluoromethyl) pyrimidin-4-amine (26): A Common Intermediate

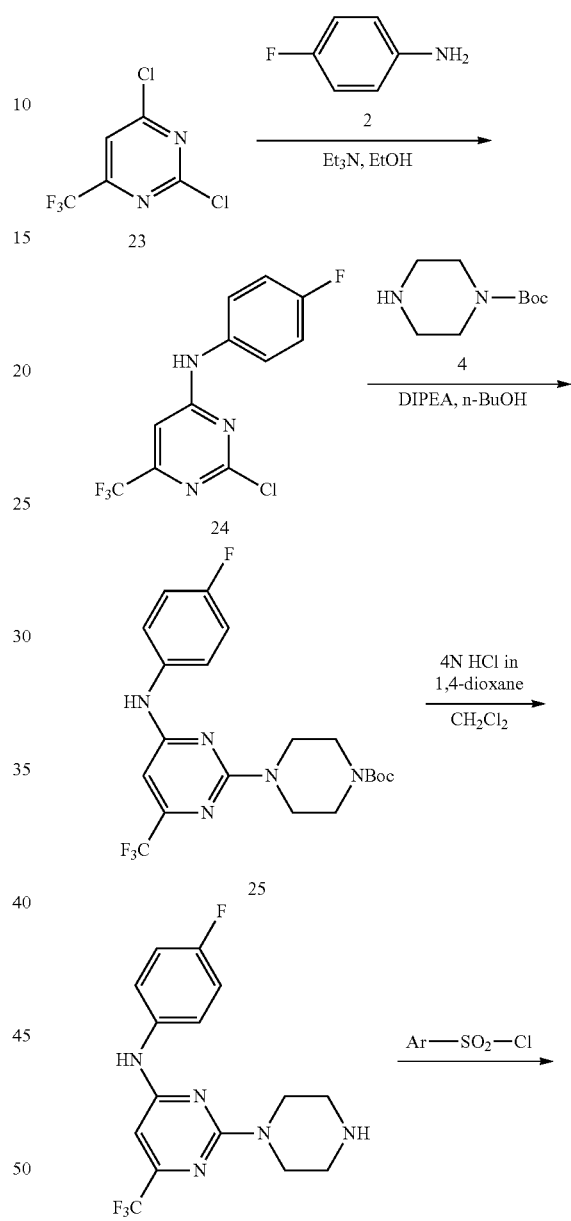

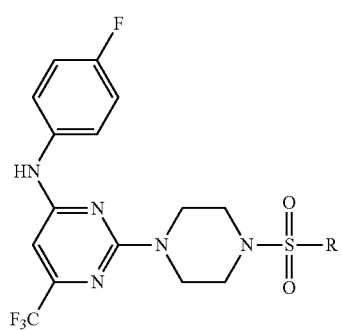

Synthesis of 2-chloro-N-(4-fluorophenyl)-6-(trifluoromethyl) pyrimidin-4-amine (24)

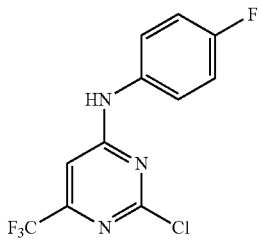

24

To a stirring solution of 2, 4-dichloro-6-(trifluoromethyl) pyrimidine 23 (2 g, 9.25 mmol) in EtOH (100 mL) under argon atmosphere were added 4-fluoroaniline 2 (1.02 g, 9.25 mmol) and triethylamine (2 mL, 13.88 mmol) in a sealed tube at RT; heated to 90° C. and stirred for 16 h. The reaction was monitored by TLC; after completion of the reaction, the volatiles were removed in vacuo. The residue was diluted with EtOAc (200 mL) and washed with 2 N HCl (2×100 mL). The organic extract was dried over sodium sulfate, filtered and concentrated in vacuo to obtain the crude. The obtained solid was triturated with 3% EtOAc/hexanes (50 mL) and dried in vacuo to afford compound 24 (2.0 g, 74%) as an off-white solid. TLC: 20% EtOAc/hexanes ($R_f$ 0.4); $^1$H NMR (DMSO-$d_6$, 400 MHz): δ 10.60 (s, 1H), 7.69-7.57 (m, 2H), 7.26 (t, J=8.9 Hz, 2H), 7.07 (br s, 1H).

Synthesis of tert-butyl 4-(4-((4-fluorophenyl)amino)-6-(trifluoromethyl) pyrimidin-2-yl) piperazine-1-carboxylate (25)

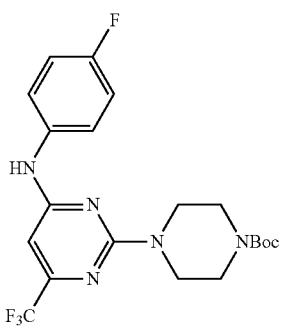

25

To a stirring solution of compound 24 (2.5 g, 8.59 mmol) in n-butanol (60 mL) under argon atmosphere were added tert-butyl piperazine-1-carboxylate 4 (2.36 g, 12.88 mmol) and diisopropylethylamine (2.37 mL, 12.88 mmol) at RT; heated to 100° C. and stirred for 16 h. The reaction was monitored by TLC; after completion of the reaction, the volatiles were removed in vacuo. The residue was diluted with CH$_2$Cl$_2$ (200 mL), and washed with water (100 mL). The organic extract was dried over sodium sulfate, filtered and concentrated in vacuo to obtain the crude. The crude was purified through silica gel column chromatography using 30% EtOAc/hexanes to afford compound 25 (2.80 g, 74%) as white solid. TLC: 30% EtOAc/hexanes ($R_f$ 0.8); $^1$H NMR (DMSO-$d_6$, 400 MHz): δ 9.77 (s, 1H), 7.63 (dd, J=8.9, 4.9 Hz, 2H), 7.20 (t, J=8.9 Hz, 2H), 6.37 (s, 1H), 3.73-3.67 (m, 4H), 3.43-3.38 (m, 4H), 1.42 (s, 9H).

Synthesis of N-(4-fluorophenyl)-2-(piperazin-1-yl)-6-(trifluoromethyl) pyrimidin-4-amine (1026)

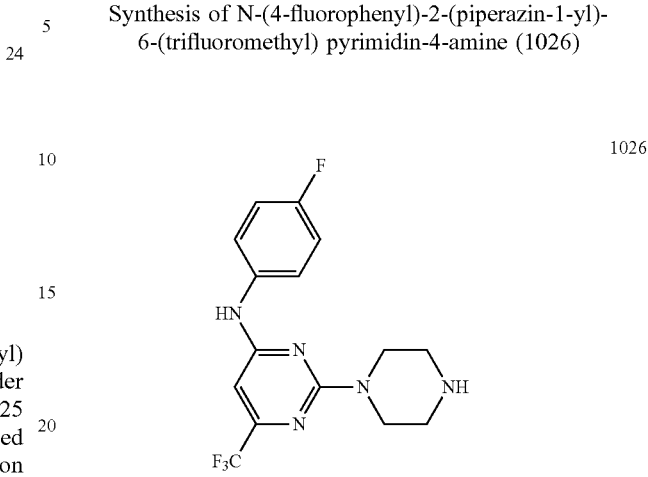

1026

To a stirring solution of compound 25 (2.8 g, 6.34 mmol) in CH$_2$Cl$_2$ (25 mL) was added 4 N HCl in 1, 4-dioxane (15.8 mL) under argon atmosphere at 0° C.; warmed to RT and stirred for 2 h. The reaction was monitored by TLC; after completion of the reaction, the volatiles were removed in vacuo. The residue was diluted with water (20 mL) and neutralized with 10% aqueous NaHCO$_3$ solution (30 mL) and extracted with CH$_2$Cl$_2$ (3×200 mL). The combined organic extracts were dried over sodium sulfate, filtered and concentrated in vacuo to obtain the crude which was triturated with 10% EtOAc/hexanes to afford compound 26 (1.80 g, 83%) as white solid. TLC: 10% MeOH/CH$_2$Cl$_2$ ($R_f$ 0.3); $^1$H NMR (DMSO-$d_6$, 400 MHz): δ 9.70 (s, 1H), 7.62 (dd, J=8.9, 5.0 Hz, 2H), 7.19 (t, J=8.9 Hz, 2H), 6.31 (s, 1H), 3.65-3.61 (m, 4H), 2.75-2.70 (m, 4H), 2.37 (br s, 1H).

Example 46: Synthesis of 4-((2-(piperazin-1-yl)-6-(trifluoromethyl) pyrimidin-4-yl) amino) benzonitrile (29): A Common Intermediate

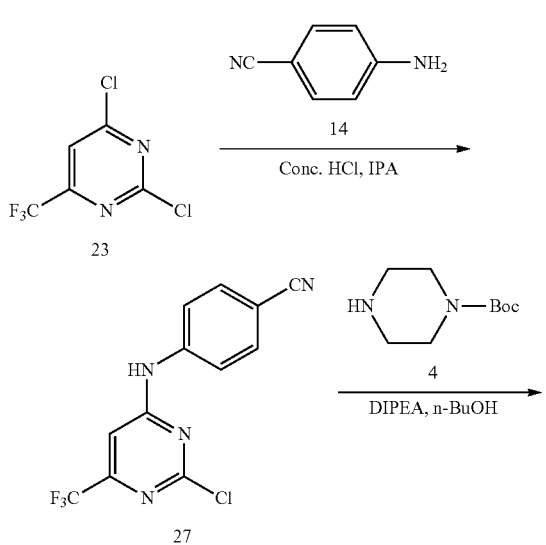

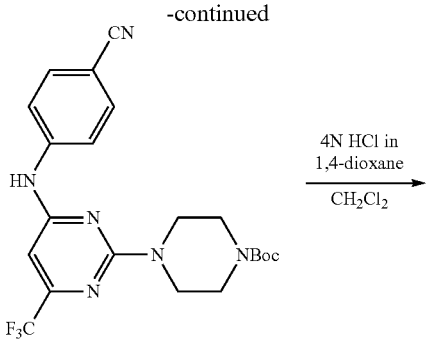

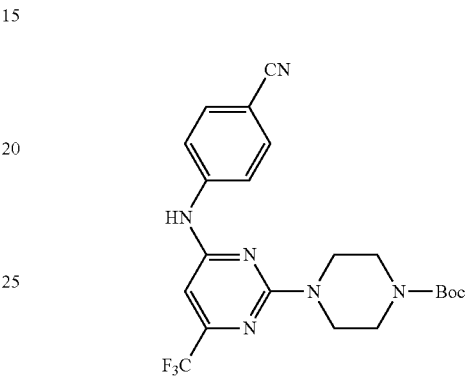

washed with 10% aqueous NaHCO₃ solution (150 mL). The organic extract was dried over sodium sulfate, filtered and concentrated in vacuo to obtain the crude, which was purified through silica gel column chromatography using 15% EtOAc/hexanes to afford compound 27 (800 mg, 23%) as white solid. TLC: 30% EtOAc/hexanes (R$_f$ 0.5); $^1$H NMR (DMSO-d$_6$, 400 MHz): δ 10.93 (s, 1H), 7.91-7.83 (m, 4H), 7.21 (s, 1H).

Synthesis of tert-butyl 4-(4-((4-cyanophenyl)amino)-6-(trifluoromethyl) pyrimidin-2-yl) piperazine-1-carboxylate (28)

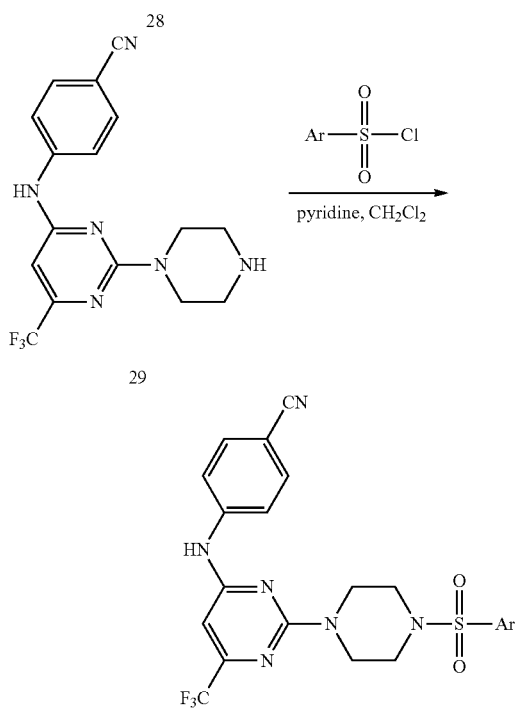

To a stirring solution of compound 27 (800 mg, 2.68 mmol) in n-butanol (15 mL) under argon atmosphere were added tert-butyl piperazine-1-carboxylate 4 (748 mg, 4.02 mmol) and diisopropylethylamine (1.48 mL, 8.05 mmol) at RT; heated to 110-120° C. and stirred for 16 h. The reaction was monitored by TLC; after completion of the reaction, the volatiles were removed in vacuo to obtain the crude. The crude was purified through silica gel column chromatography using 20% EtOAc/hexanes to afford compound 28 (890 mg, 71%) as white solid. TLC: 30% EtOAc/hexanes (R$_f$ 0.8); $^1$H NMR (DMSO-d$_6$, 400 MHz): δ 10.20 (s, 1H), 7.87-7.76 (m, 4H), 6.47 (s, 1H), 3.74-3.72 (m, 4H), 3.47-3.41 (m, 4H), 1.43 (s, 9H).

Synthesis of 4-((2-(piperazin-1-yl)-6-(trifluoromethyl) pyrimidin-4-yl) amino) benzonitrile (29)

Synthesis of 4-((2-chloro-6-(trifluoromethyl) pyrimidin-4-yl) amino) benzonitrile (27)

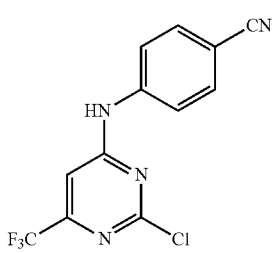

To a stirring solution of 2, 4-dichloro-6-(trifluoromethyl) pyrimidine 23 (2.5 g, 11.57 mmol) in isopropyl alcohol (50 mL) under argon atmosphere were added 4-aminobenzonitrile 14 (1.36 g, 11.57 mmol) and concentrated HCl (1.17 mL, 11.57 mmol) in sealed tube at RT; heated to 80-90° C. and stirred for 24 h. The reaction was monitored by TLC; after completion of the reaction, the volatiles were removed in vacuo, the residue was diluted with EtOAc (200 mL),

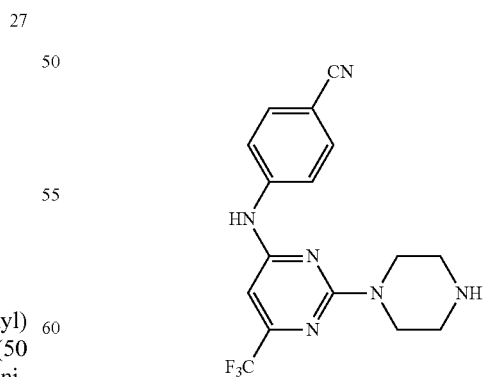

To a stirring solution of compound 28 (850 mg, 1.89 mmol) in CH₂Cl₂ (10 mL) was added 4 N HCl in 1, 4-dioxane (5 mL) under argon atmosphere at 0° C.; warmed to RT and stirred for 2 h. The reaction was monitored by TLC; after completion of the reaction, the pH of the reaction mixture was neutralized with 10% aqueous NaHCO₃ solution and extracted with 5% MeOH/CH₂Cl₂ (2×100 mL). The combined organic extracts were dried over sodium sulfate, filtered and concentrated in vacuo to afford compound 29 (500 mg, 76%) as white solid. TLC: 7% MeOH/CH₂Cl₂ ($R_f$ 0.2); ¹H NMR (DMSO-$d_6$, 400 MHz): δ 10.52 (br s, 1H), 7.89-7.84 (m, 2H), 7.81-7.75 (m, 2H), 6.50 (s, 1H), 3.68-3.59 (m, 4H), 2.78-2.72 (m, 4H).

Example 47: Synthesis of N-(4-fluorophenyl)-2-(piperazin-1-yl)-6-(thiazol-2-yl) pyrimidin-4-amine (36): A Common Intermediate

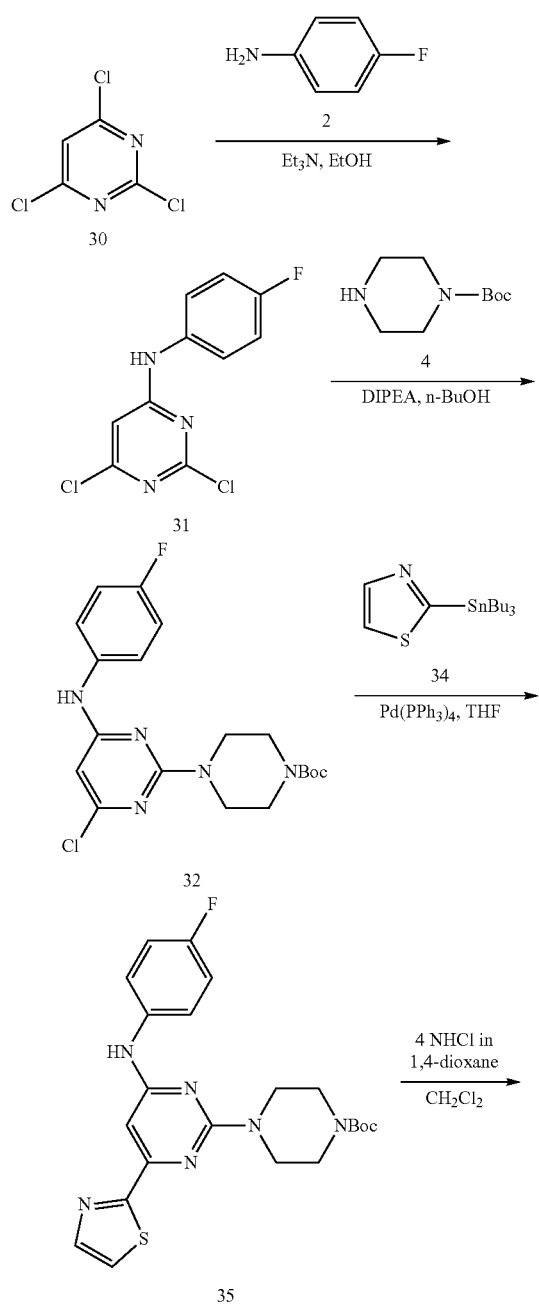

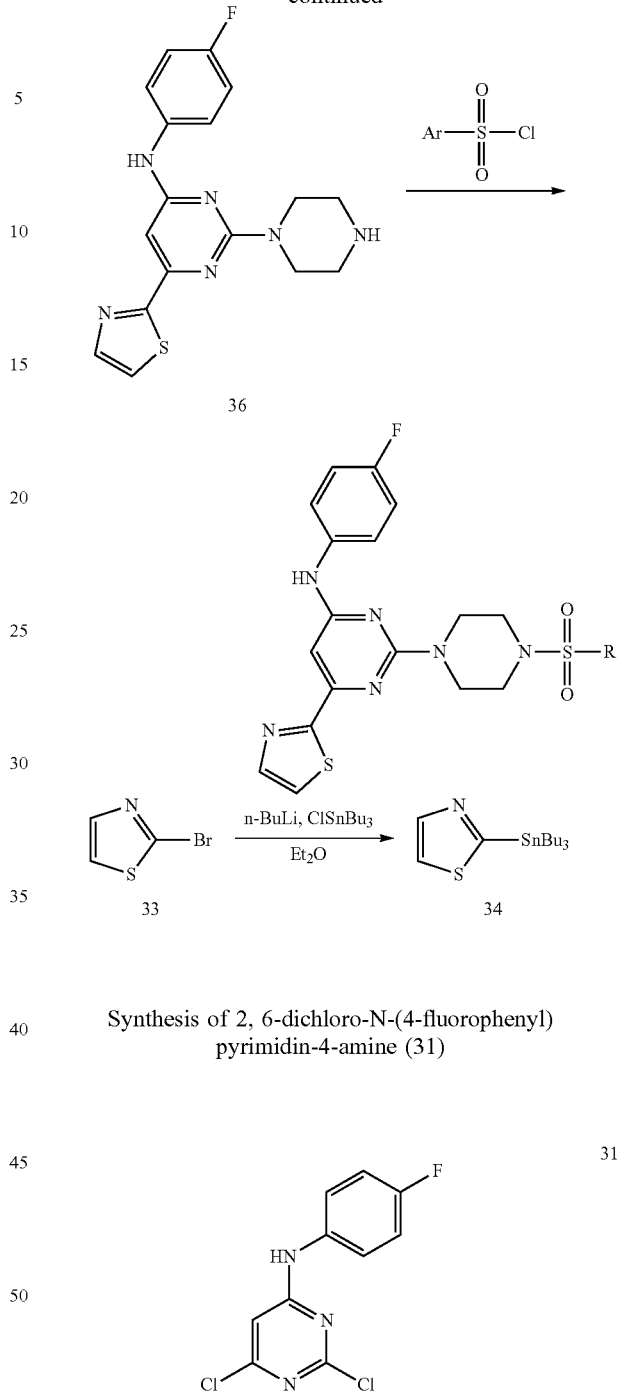

Synthesis of 2, 6-dichloro-N-(4-fluorophenyl) pyrimidin-4-amine (31)

To a stirring solution of 2, 4, 6-trichloropyrimidine 30 (10 g, 54.52 mmol) in ethanol (100 mL) were added triethylamine (11.39 mL, 81.77 mmol) and 4-fluoroaniline 2 (6.05 g, 54.52 mmol) at 0° C. under argon atmosphere; warmed to RT and stirred for 16 h. The reaction was monitored by TLC; after completion of the reaction, the volatiles were removed in vacuo to obtain the crude. The crude was purified through silica gel column chromatography using 10% EtOAc/hexanes to afford compound 31 (11 g, 78%) as white solid. TLC: 10% EtOAc/hexanes ($R_f$ 0.1); ¹H-NMR (DMSO-$d_6$, 500 MHz): δ 10.26 (br s, 1H), 7.56-7.52 (m, 2H), 7.23 (t, J=8.3 Hz, 2H), 6.71 (s, 1H).

Synthesis of tert-butyl 4-(4-chloro-6-((4-fluorophenyl) amino) pyrimidin-2-yl) piperazine-1-carboxylate (32)

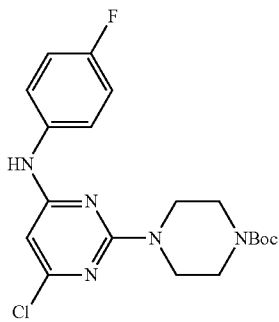

To a stirring solution of compound 31 (5.5 g, 21.4 mmol) in n-butanol (20 mL) were added tert-butyl piperazine-1-carboxylate 4 (3.98 g, 21.4 mmol) and diisopropylethylamine (4.47 mL, 25.68 mmol) in sealed tube at RT under argon atmosphere; heated to 80° C. and stirred for 24 h. The reaction was monitored by TLC; after completion of the reaction, the volatiles were removed in vacuo to obtain the crude. The crude was purified through silica gel column chromatography using 10% EtOAc/hexanes to afford compound 32 (3.5 g, 40%) as white solid. TLC: 30% EtOAc/hexanes ($R_f$ 0.6); $^1$H-NMR (DMSO-$d_6$, 500 MHz): δ 9.50 (s, 1H), 7.64-7.53 (m, 2H), 7.17 (t, J=8.9 Hz, 2H), 6.02 (s, 1H), 3.66-3.64 (m, 4H), 3.40-3.38 (m, 4H), 1.42 (s, 9H).

Synthesis of 2-(tributylstannyl) thiazole (34)

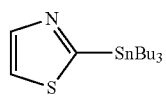

To a stirring solution of 2-bromothiazole 33 (5 g, 30.48 mmol) in diethyl ether (50 mL) under inert atmosphere was added n-butyl lithium (12.2 mL, 33.53 mmol, 2.5 M solution in hexane) dropwise for 15 min at −70° C. and stirred for 30 min. To this a solution of tributyltin chloride (10 mL, 30.48 mmol) in diethyl ether (15 mL) was added dropwise for 10 min at −70° C. and stirred at the same temperature for 4 h. The reaction was monitored by TLC; after completion of the reaction, the reaction mixture was diluted with water (50 mL) and extracted with diethylether (3×50 mL), washed with saturated potassium fluoride solution (50 mL). The combined organic extracts were dried over sodium sulfate, filtered and concentrated in vacuo to afford crude compound 34 (11 g) as brown color syrup. The crude was carried forward for next step without further purification. TLC: 30% EtOAc/hexanes ($R_f$ 0.2); $^1$H NMR (CDCl$_3$, 400 MHz): δ 8.17 (d, J=3.0 Hz, 1H), 7.54 (d, J=3.0 Hz, 1H), 1.58-1.50 (m, 6H), 1.34-1.27 (m, 6H), 1.16-1.10 (m, 6H), 0.89-0.83 (m, 9H) (NMR shows excess of tin reagent as impurity in the aliphatic region).

Synthesis of tert-butyl 4-(4-((4-fluorophenyl) amino)-6-(thiazol-2-yl) pyrimidin-2-yl) piperazine-1-carboxylate (35)

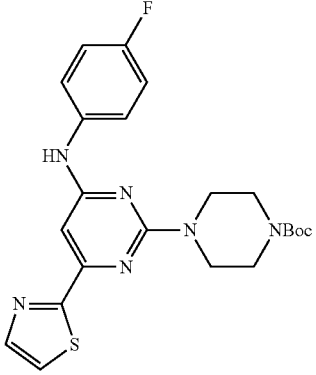

To a stirring solution of compound 32 (2 g, 4.90 mmol) in THF (30 mL) was added Pd(PPh$_3$)$_4$ (566 mg, 0.49 mmol) at RT and purged under argon atmosphere for 10 min. To this was added compound 34 (5.51 g, 14.70 mmol) at RT and heated to 80° C. and stirred for 16 h. The reaction was monitored by TLC; after completion of the reaction, the reaction mixture was diluted with water (100 mL) and extracted with EtOAc (2×100 mL). The combined organic extracts were dried over sodium sulfate, filtered and concentrated in vacuo to obtain the crude. The crude was purified through silica gel flash column chromatography using 30-35% EtOAc/hexanes to afford compound 35 (1.4 g, 63%) as an off-white solid. TLC: 40% EtOAc/hexanes ($R_f$ 0.4); $^1$H-NMR (DMSO-$d_6$, 400 MHz): δ 9.59 (s, 1H), 8.00 (d, J=3.1 Hz, 1H), 7.88 (d, J=3.1 Hz, 1H), 7.65 (dd, J=8.9, 5.0 Hz, 2H), 7.19 (t, J=8.9 Hz, 2H), 6.81 (s, 1H), 3.78-3.72 (m, 4H), 3.48-3.41 (m, 4H), 1.44 (s, 9H).

Synthesis of N-(4-fluorophenyl)-2-(piperazin-1-yl)-6-(thiazol-2-yl) pyrimidin-4-amine (36)

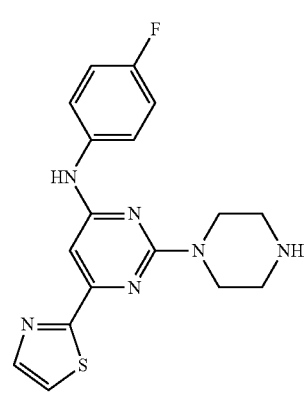

To a stirring solution of compound 35 (1.4 g, 3.07 mmol) in CH$_2$Cl$_2$ (15 mL) was added 4 N HCl in 1, 4-dioxane (15 mL) under argon atmosphere at 0° C.; warmed to RT and stirred for 2 h. The reaction was monitored by TLC; after completion of the reaction, the volatiles were removed in vacuo. The residue was dissolved in water (100 mL) and the pH was adjusted to ~7 with saturated NaHCO₃ solution and stirred for 30 min. The precipitated solid was filtered and dried in vacuo to afford compound 36 (900 mg, 83%) as an off-white solid. TLC: 5% MeOH/CH$_2$Cl$_2$ (R$_f$ 0.1); $^1$H NMR (DMSO-d$_6$, 500 MHz): δ 9.54 (s, 1H), 7.99 (d, J=3.2 Hz, 1H), 7.87 (d, J=3.2 Hz, 1H), 7.65 (dd, J=8.7, 4.9 Hz, 2H), 7.18 (t, J=8.8 Hz, 2H), 6.76 (s, 1H), 3.70-3.66 (m, 4H), 2.79-2.73 (m, 4H).

Example 48: Synthesis of N-(4-fluorophenyl)-2-(piperazin-1-yl)-6-(thiazol-5-yl) pyrimidin-4-amine hydrochloride (39): A Common Intermediate

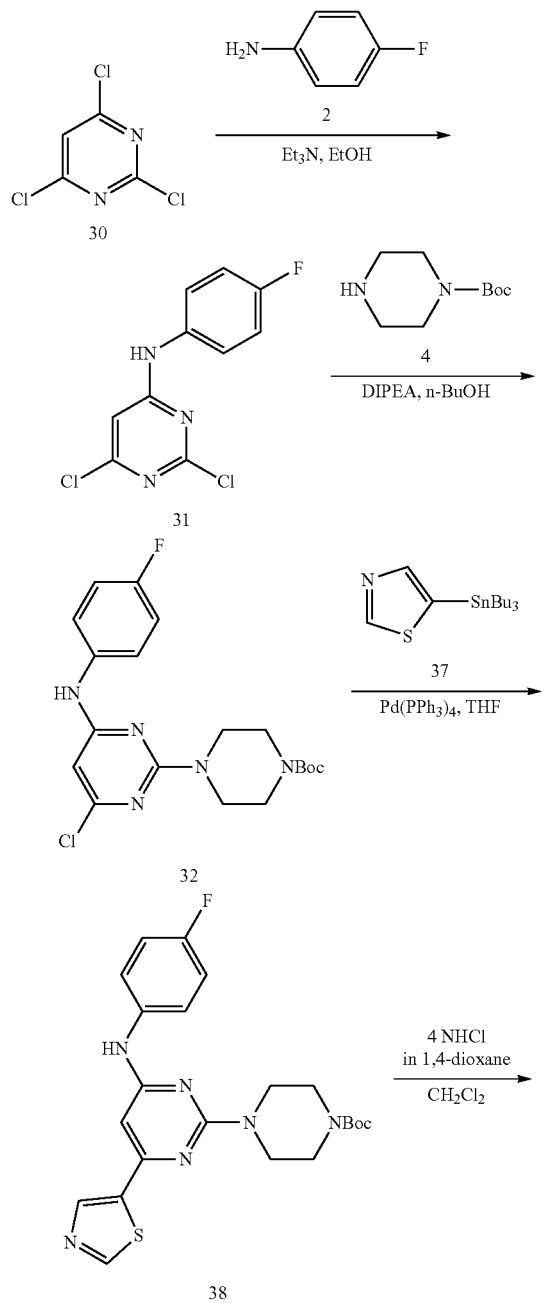

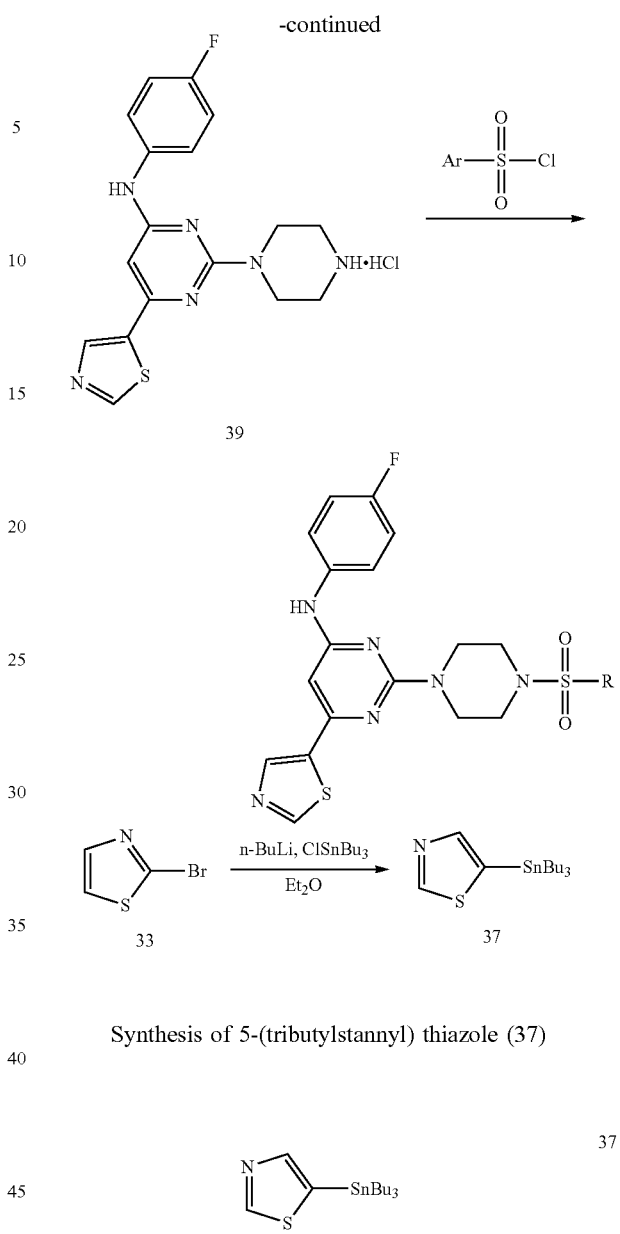

Synthesis of 5-(tributylstannyl) thiazole (37)

To a stirring solution of 2-bromothiazole 33 (5 g, 30.48 mmol) in diethyl ether (35 mL) under inert atmosphere was added n-butyl lithium (12.2 mL, 33.53 mmol, 2.5 M solution in hexane) at −70° C. and stirred for 30 min. To this was added a solution of tributyltin chloride (10 mL, 30.48 mmol) in diethyl ether (15 mL) dropwise for 10 min at −70° C. and stirred at the same temperature for 4 h; warmed to RT and stirred for 2 h. The reaction was monitored by TLC; after completion of the reaction, the reaction mixture was diluted with water (100 mL) and extracted with diethylether (3×50 mL) and washed with saturated potassium fluoride solution (50 mL). The combined organic extracts were dried over sodium sulfate, filtered and concentrated in vacuo to obtain the crude. The crude was purified through column chromatography using 25-30% EtOAc/hexanes to afford compound 37 (3.5 g, 31%) as white solid. TLC: 30% EtOAc/hexanes (R$_f$ 0.4); $^1$H NMR (DMSO-d$_6$, 400 MHz): δ 9.35 (s, 1H), 7.89 (s, 1H), 1.58-1.47 (m, 6H), 1.34-1.24 (m, 6H), 1.13 (t, J=8.0 Hz, 6H), 0.85 (t, J=7.3 Hz, 9H).

Synthesis of tert-butyl 4-(4-((4-fluorophenyl)amino)-6-(thiazol-5-yl) pyrimidin-2-yl) piperazine-1-carboxylate (38)

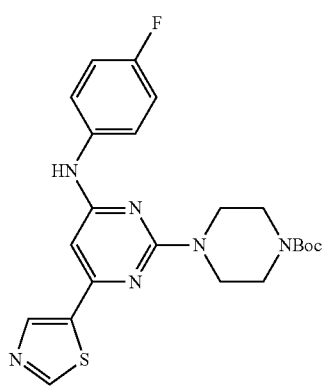

38

To a stirring solution of tert-butyl 4-(4-chloro-6-((4-fluorophenyl) amino) pyrimidin-2-yl) piperazine-1-carboxylate 32 (500 mg, 1.22 mmol) in THF (10 mL) under inert atmosphere was added Pd(PPh$_3$)$_4$ (142 mg, 0.12 mmol) at RT and purged under argon for 10 min. To this was added compound 37 (689 mg, 1.83 mmol) at RT and heated to 80° C. and stirred for 16 h. The reaction was monitored by TLC; after completion of the reaction, the reaction mixture was diluted with water (50 mL) and extracted with EtOAc (2×70 mL). The combined organic extracts were dried over sodium sulfate, filtered and concentrated in vacuo to obtain the crude. The crude was purified through silica gel flash column chromatography using 40-50% EtOAc/hexanes to afford compound 38 (300 mg, 54%) as an off-white solid. TLC: 50% EtOAc/hexanes (R$_f$ 0.2); $^1$H-NMR (DMSO-d$_6$, 400 MHz): δ 9.48 (s, 1H), 9.16 (s, 1H), 8.46 (s, 1H), 7.64 (dd, J=9.1, 5.0 Hz, 2H), 7.17 (t, J=8.9 Hz, 2H), 6.47 (s, 1H), 3.75-3.70 (m, 4H), 3.45-3.40 (m, 4H), 1.43 (s, 9H).

Synthesis of N-(4-fluorophenyl)-2-(piperazin-1-yl)-6-(thiazol-5-yl) pyrimidin-4-amine hydrochloride (39)

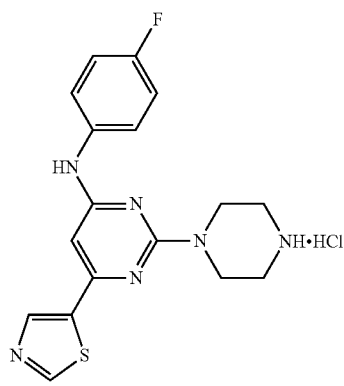

39

To a stirring solution of compound 38 (300 mg, 0.67 mmol) in CH$_2$Cl$_2$ (3 mL) was added 4 N HCl in 1, 4-dioxane (3 mL) under argon atmosphere at 0° C.; warmed to RT and stirred for 2 h. The reaction was monitored by TLC; after completion of the reaction, the volatiles were removed in vacuo. The residue was washed with diethyl ether (2×10 mL) and dried in vacuo to afford compound 39 (240 mg, 93%; HCl salt) as an off-white solid. TLC: 5% MeOH/CH$_2$Cl$_2$ (R$_f$ 0.1); $^1$H NMR (DMSO-d$_6$, 400 MHz): δ 9.71 (s, 1H), 9.32 (br s, 2H), 9.19 (s, 1H), 8.49 (s, 1H), 7.64 (dd, J=9.1, 5.0 Hz, 2H), 7.16 (t, J=8.9 Hz, 2H), 6.58 (s, 1H), 3.99-3.94 (m, 4H), 3.20-3.15 (m 4H).

Example 49: Synthesis of 4-((2-(piperazin-1-yl)-6-(thiazol-2-yl) pyrimidin-4-yl) amino) benzonitrile (43): A Common Intermediate

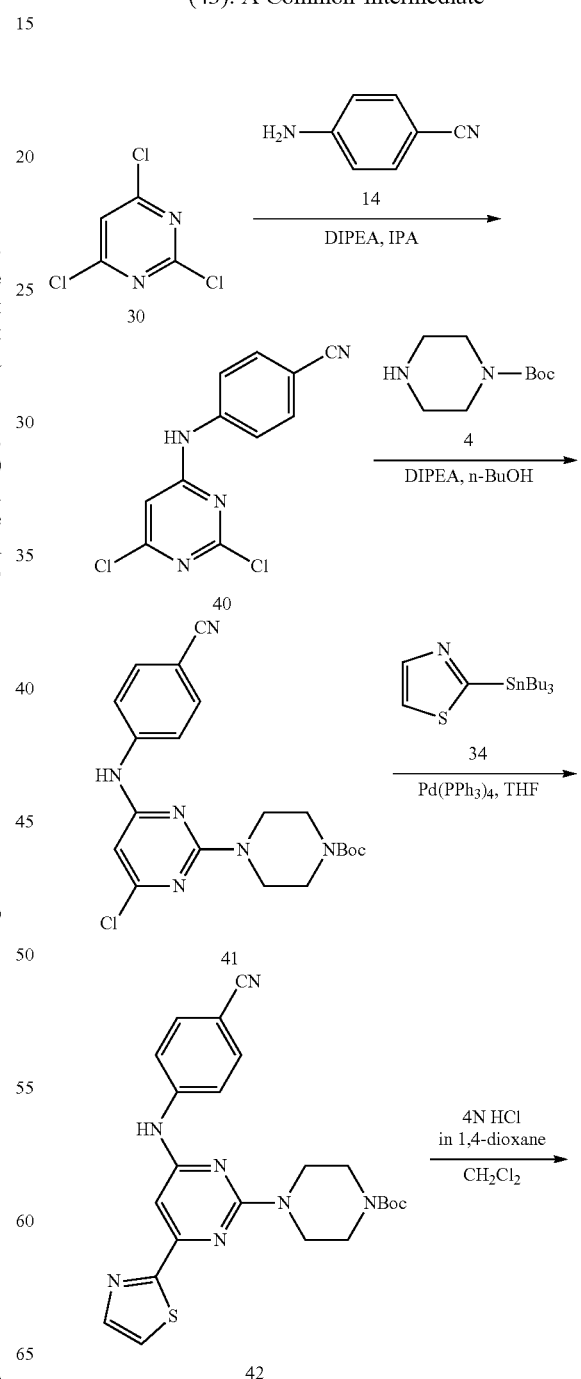

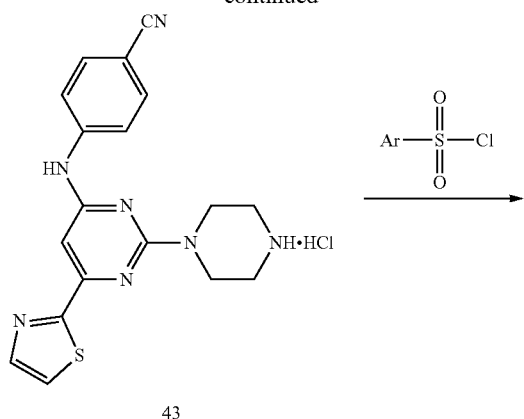

43

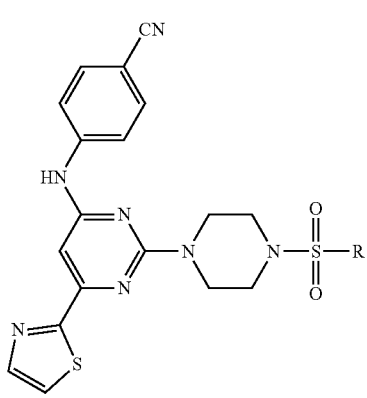

Synthesis of 4-((2, 6-dichloropyrimidin-4-yl) amino) benzonitrile (40)

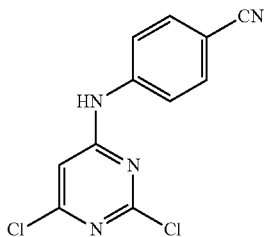

To a stirring solution of 2, 4, 6-trichloropyrimidine 30 (10 g, 54.52 mmol) in isopropyl alcohol (80 mL) were added diisopropylethylamine (14.6 mL, 81.78 mmol) and 4-aminobenzonitrile 14 (5.80 g, 49.07 mmol) at 0° C. in a sealed tube under argon atmosphere; heated to 70° C. and stirred for 48 h. The reaction was monitored by TLC; after completion of the reaction, the reaction mixture was diluted with water (300 mL). The precipitated solid was filtered, washed with 10% EtOAc/diethylether (2×100 mL) and dried in vacuo to afford compound 40 (8 g, 56%) as an off-white solid. TLC: 20% EtOAc/hexanes ($R_f$ 0.1); $^1$H-NMR (DMSO-$d_6$, 400 MHz): δ 10.63 (s, 1H), 7.90-7.73 (m, 4H), 6.89 (s, 1H).

Synthesis of tert-butyl 4-(4-chloro-6-((4-cyanophenyl) amino) pyrimidin-2-yl) piperazine-1-carboxylate (41)

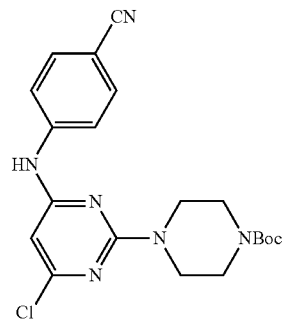

To a stirring solution of compound 40 (5 g, 18.93 mmol) in n-butanol (100 mL) under argon atmosphere were added tert-butyl piperazine-1-carboxylate 4 (3.5 g, 18.93 mmol) and diisopropylethylamine (5.08 mL, 28.40 mmol) in a sealed tube at RT; heated to 100° C. and stirred for 16 h. The reaction was monitored by TLC; after completion of the reaction, the volatiles were removed in vacuo. The residue was diluted with EtOAc (300 mL) and washed with water (100 mL). The organic extract was dried over sodium sulfate, filtered and concentrated in vacuo to obtain the crude which triturated with 10% diethyl ether/n-pentane (2×30 mL) to afford compound 41 (5.7 g, crude) as off-white solid. TLC: 30% EtOAc/hexanes ($R_f$ 0.2); $^1$H NMR (DMSO-$d_6$, 400 MHz): δ 9.95 (s, 1H), 7.81-7.74 (m, 4H), 6.14 (s, 1H), 3.72-3.62 (m, 4H), 3.45-3.40 (m, 4H), 1.43 (s, 9H). LC-MS: 66.87%; 414.9 (M$^+$+1); (column; Ascentis Express C18, (50×3.0 mm, 2.7 μm); RT 3.02 min. 2.5 mM Aq. NH$_4$OOCH+5% ACN: ACN+5% 2.5 mM Aq. NH$_4$OOCH, 0.8 mL/min).

Synthesis of tert-butyl 4-(4-((4-cyanophenyl) amino)-6-(thiazol-2-yl) pyrimidin-2-yl) piperazine-1-carboxylate (42)

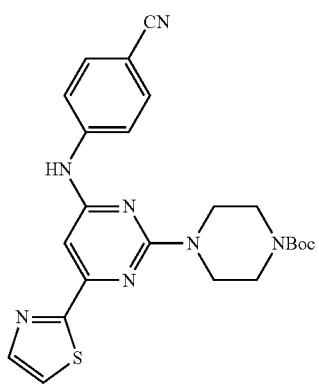

To a stirring solution of compound 41 (4.7 g, 11.35 mmol) in THF (40 mL) under argon atmosphere was added Pd(PPh$_3$)$_4$ (142 mg, 0.12 mmol) at RT and purged under argon for 10 min; to this was added compound 34 (12.77 mg, 17.02 mmol) at RT and heated to 60° C. and stirred for 16 h. The reaction was monitored by TLC; after completion of the reaction, the reaction mixture was filtered through celite. The filtrate was diluted with EtOAc (250 mL) and washed with water (100 mL). The organic extract was dried over sodium sulfate, filtered and concentrated in vacuo to obtain the crude. The crude was purified through silica gel flash column chromatography using 40% EtOAc/hexanes to afford compound 42 (1.5 g, 29%) as an off-white solid. TLC: 40% EtOAc/hexanes ($R_f$ 0.2); $^1$H-NMR (DMSO-$d_6$, 400 MHz): δ 10.06 (s, 1H), 8.02 (d, J=3.1 Hz, 1H), 7.91 (d, J=3.1 Hz, 1H), 7.86 (d, J=9.2 Hz, 2H), 7.78 (d, J=8.9 Hz, 2H), 6.92 (s, 1H), 3.80-3.75 (m, 4H), 3.49-3.45 (m, 4H), 1.44 (s, 9H).

Synthesis of 4-((2-(piperazin-1-yl)-6-(thiazol-2-yl) pyrimidin-4-yl) amino) benzonitrile hydrochloride (43)

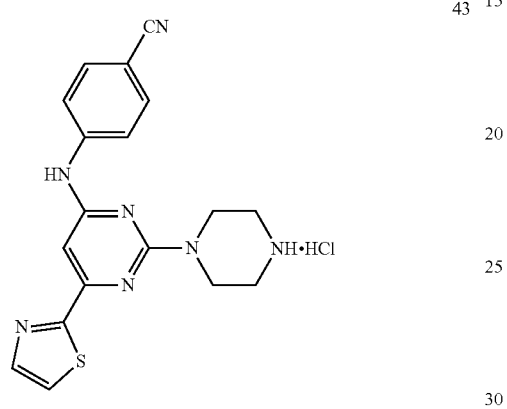

43

To a stirring solution of compound 42 (1.5 g, 3.23 mmol) in CH$_2$Cl$_2$ (15 mL) was added 4 N HCl in 1, 4-dioxane (2 mL) under argon atmosphere at 0° C.; warmed to RT and stirred for 4 h. The reaction was monitored by TLC; after completion of the reaction, the volatiles were removed in vacuo to obtain the crude, which was triturated with diethyl ether (2×5 mL) and dried in vacuo to afford compound 43 (1.3 g, HCl salt) as yellow solid. TLC: 40% EtOAc/hexanes ($R_f$ 0.1); $^1$H NMR (DMSO-$d_6$, 500 MHz): δ 10.32 (s, 1H), 9.25 (br s, 2H), 8.03 (d, J=3.2 Hz, 1H), 7.93 (d, J=3.2 Hz, 1H), 7.86 (d, J=9.0 Hz, 2H), 7.76 (d, J=8.7 Hz, 2H), 7.01 (s, 1H), 4.04-3.94 (m, 4H), 3.24-3.19 (m, 4H).

Example 50: Synthesis of 4-((2-(piperazin-1-yl)-6-(thiazol-5-yl) pyrimidin-4-yl) amino) benzonitrile hydrochloride (45): A Common Intermediate

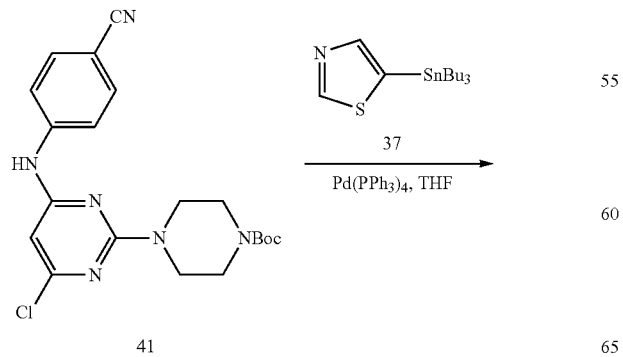

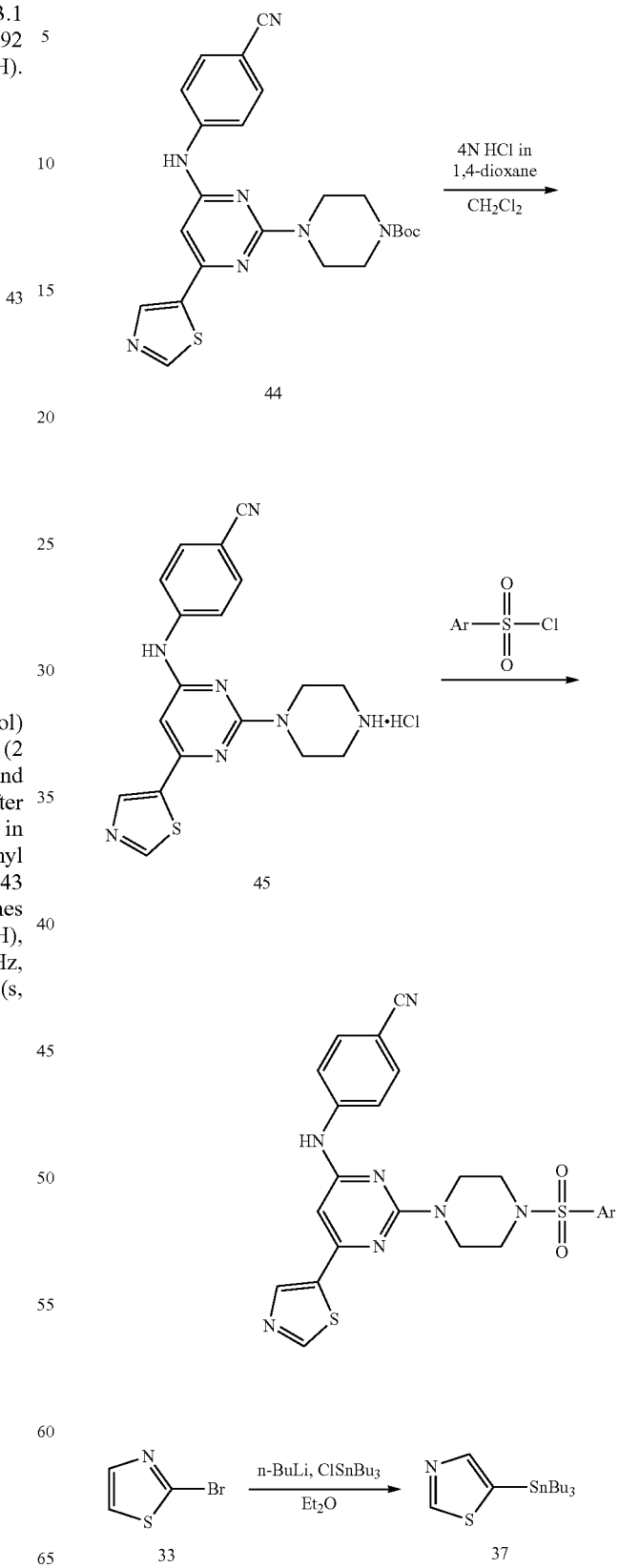

Synthesis of tert-butyl 4-(4-((4-cyanophenyl)amino)-6-(thiazol-5-yl) pyrimidin-2-yl) piperazine-1-carboxylate (44)

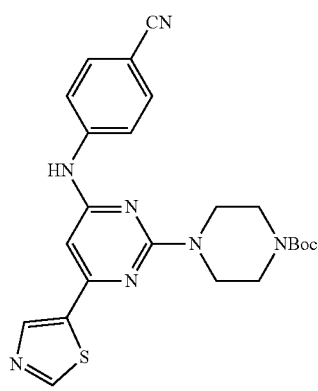

To a stirring solution of tert-butyl 4-(4-chloro-6-((4-cyanophenyl) amino) pyrimidin-2-yl) piperazine-1-carboxylate 41 (1.7 g, 4.10 mmol) in THF (25 mL) under inert atmosphere was added compound 37 (2.3 g, 6.15 mmol) and Pd(PPh$_3$)$_4$ (473 mg, 0.41 mmol) at RT and purged under argon atmosphere for 20 min; heated to 60° C. and stirred for 16 h. The reaction was monitored by TLC; after completion of the reaction, the reaction mixture was filtered through celite. The filtrate was diluted with EtOAc (250 mL) and washed with water (100 mL). The organic extract was dried over sodium sulfate, filtered and concentrated in vacuo to obtain the crude. The crude was purified through silica gel column chromatography using 70% EtOAc/hexanes to afford compound 44 (600 mg, 32%) as yellow solid. TLC: 50% EtOAc/hexanes (R$_f$, 0.2); $^1$H-NMR (DMSO-d$_6$, 500 MHz): δ 9.96 (s, 1H), 9.18 (s, 1H), 8.49 (s, 1H), 7.84 (d, J=8.7 Hz, 2H), 7.76 (d, J=8.7 Hz, 2H), 6.57 (s, 1H), 3.75-3.73 (m, 4H), 3.46-3.42 (m, 4H), 1.42 (s, 9H).

Synthesis of 4-((2-(piperazin-1-yl)-6-(thiazol-5-yl) pyrimidin-4-yl) amino) benzonitrile hydrochloride (45)

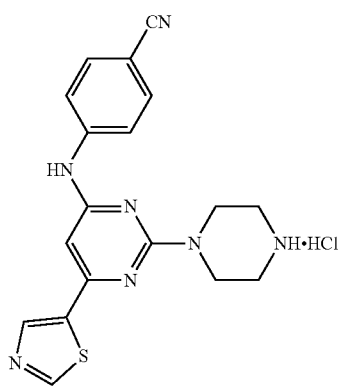

To a stirring solution of compound 44 (600 mg, 1.29 mmol) in CH$_2$Cl$_2$ (10 mL) under argon atmosphere was added 4 N HCl in 1, 4-dioxane (2 mL) at 0° C.; warmed to RT and stirred for 4 h. The reaction was monitored by TLC; after completion of the reaction, the volatiles were removed in vacuo to obtain the crude. The crude was triturated with CH$_2$Cl$_2$ (2×5 mL) and dried in vacuo to afford compound 45 (390 mg, HCl salt) as yellow solid. TLC: 40% EtOAc/hexanes (R$_f$, 0.1); $^1$H NMR (DMSO-d$_6$, 500 MHz): δ 10.36 (s, 1H), 9.50 (br s, 2H), 9.22 (s, 1H), 8.50 (s, 1H), 7.86 (d, J=8.7 Hz, 2H), 7.73 (d, J=8.7 Hz, 2H), 6.73 (s, 1H), 4.03-3.95 (m, 4H), 3.21-3.13 (m, 4H).

Example 51: Synthesis of N-(4-fluorophenyl)-2-(imidazolidin-1-yl)-6-(trifluoromethyl) pyrimidin-4-amine hydrochloride (51): A Common Intermediate

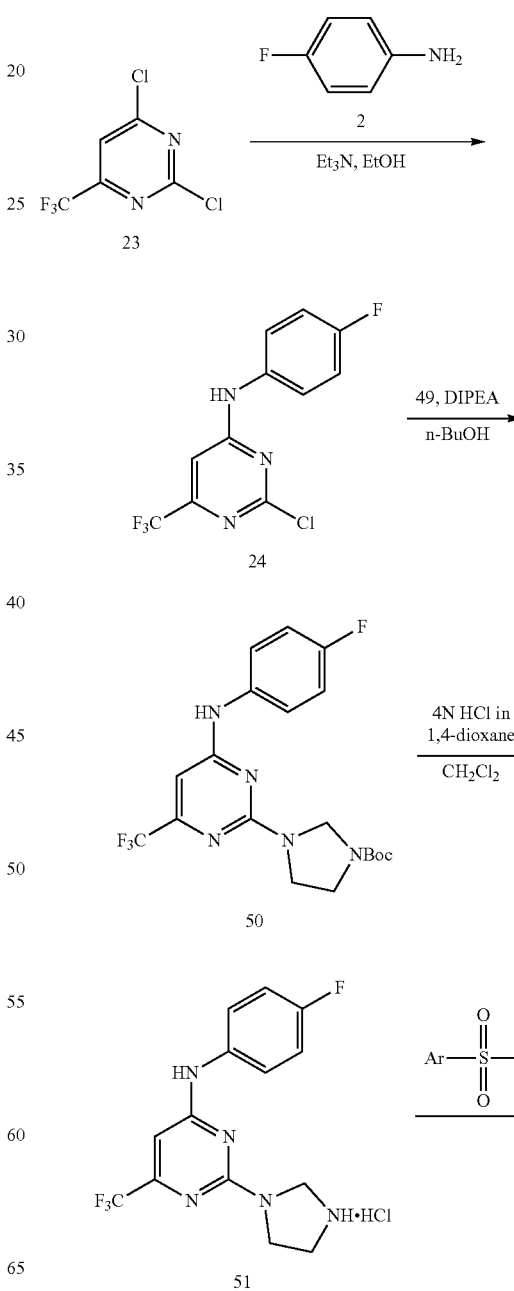

δ 7.33-7.30 (m, 4H), 7.28-7.23 (m, 1H), 3.83-3.80 (m, 2H), 3.60 (s, 2H), 3.27-3.25 (m, 2H), 2.80-2.73 (m, 2H), 1.37 (d, J=9.3 Hz, 9H).

Synthesis of tert-butyl imidazolidine-1-carboxylate (49)

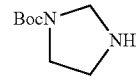

49

To a stirring solution of compound 48 (200 mg, 0.76 mmol) in MeOH (5 mL) under inert atmosphere were added 10% Pd/C (20 mg) at RT and stirred under $H_2$ (balloon pressure) for 6 h. The reaction was monitored by TLC; after completion of the reaction, the reaction mixture was filtered through celite. The filtrate was concentrated in vacuo to afford compound 49 (115 mg, 87%) as colorless thick syrup. TLC: 5% MeOH/$CH_2Cl_2$ ($R_f$, 0.2); $^1$H-NMR (DMSO-$d_6$, 400 MHz): δ 3.99 (s, 2H), 3.26 (br s, 1H), 3.11-3.03 (m, 2H), 2.96-2.89 (m, 2H), 1.40 (s, 9H).

Synthesis of tert-butyl 3-(4-((4-fluorophenyl)amino)-6-(trifluoromethyl) pyrimidin-2-yl) imidazolidine-1-carboxylate (50)

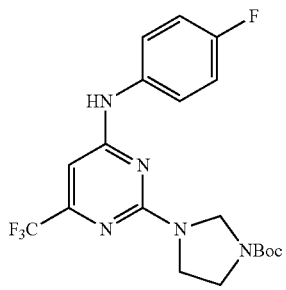

50

To a stirring solution of compound 24 (150 mg, 0.51 mmol) in n-butanol (5 mL) under inert atmosphere were added compound 49 (106 mg, 9.25 mmol) and diisopropylethylamine (0.284 mL, 1.54 mmol) in a sealed tube at RT; heated to 120° C. and stirred for 16 h. The reaction was monitored by TLC; after completion of the reaction, the volatiles were removed in vacuo to obtain the crude which was purified by column chromatography using 5% EtOAc/hexanes to afford compound 50 (75 mg, 34%) as white solid. TLC: 10% EtOAc/hexanes ($R_f$, 0.7); $^1$H NMR (DMSO-$d_6$, 400 MHz): δ 9.85 (s, 1H), 7.73-7.67 (m, 2H), 7.17 (t, J=7.6 Hz, 2H), 6.44 (s, 1H), 4.76 (br s, 2H), 3.77-3.72 (m, 2H), 3.66-3.55 (m, 2H), 1.45 (s, 9H).

Synthesis of N-(4-fluorophenyl)-2-(imidazolidin-1-yl)-6-(trifluoromethyl) pyrimidin-4-amine hydrochloride (51)

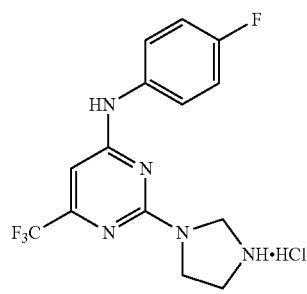

51

---

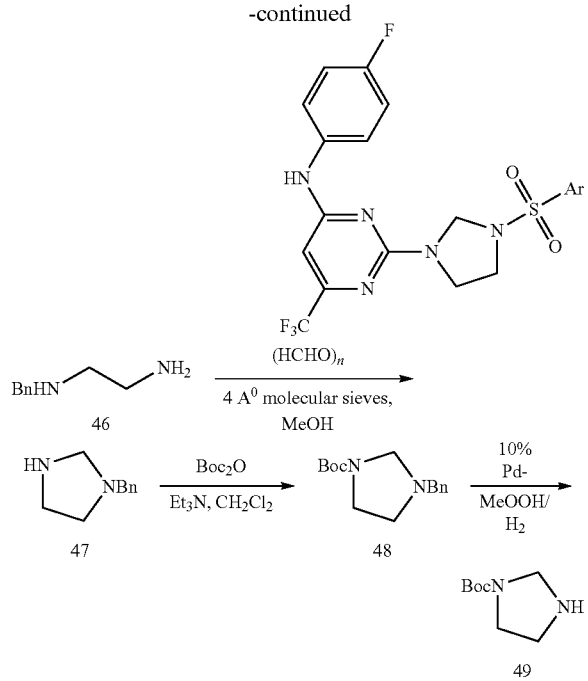

Synthesis of 1-benzylimidazolidine (47)

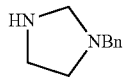

47

To a stirring solution of $N^1$-benzylethane-1, 2-diamine 46 (1 g, 6.66 mmol) in MeOH (25 mL) under inert atmosphere were added paraformaldehyde (300 mg, 9.99 mmol) and molecular sieves (4 A°) (2 g) at RT and stirred for 36 h. The reaction was monitored by TLC; after completion of the reaction, the precipitated solid was filtered and the filtrate was removed in vacuo to obtain the crude. The crude was purified through silica gel flash column chromatography using 3% MeOH/$CH_2Cl_2$ to afford compound 47 (800 mg, crude) as colorless liquid. TLC: 5% MeOH/$CH_2Cl_2$ ($R_f$, 0.2); LC-MS: 86.29%; 162.9 (M$^+$+1); (column; Ascentis Express C18, (50×3.0 mm, 2.7 μm); RT 2.05 min. 2.5 mM Aq. $NH_4OOCH$+5% ACN: ACN+5% 2.5 mM Aq. $NH_4OOCH$, 0.8 mL/min).

Synthesis of tert-butyl 3-benzylimidazolidine-1-carboxylate (48)

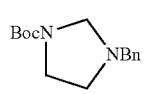

48

To a stirring solution of compound 47 (800 mg, 4.93 mmol) in $CH_2Cl_2$ (20 mL) under argon atmosphere were added triethylamine (1.06 mL, 7.40 mmol) and Boc-anhydride (1.3 mL, 5.92 mmol) at 0° C.; warmed to RT and stirred for 6 h. The reaction was monitored by TLC; after completion of the reaction, the volatiles were removed in vacuo. The crude was purified through silica gel flash column chromatography using 3% MeOH/$CH_2Cl_2$ to afford compound 48 (400 mg, 31%) as yellow liquid. TLC: 40% EtOAc/hexanes ($R_f$, 0.8); $^1$H-NMR (DMSO-$d_6$, 500 MHz):

To a stirring solution of compound 50 (70 mg, 0.16 mmol) in CH$_2$Cl$_2$ (5 mL) was added 4 N HCl in 1, 4-dioxane (0.4 mL, 1.63 mmol) under inert atmosphere at 0° C.; warmed to RT and stirred for 2 h. The reaction was monitored by TLC; after completion of the reaction, the volatiles were removed in vacuo. The obtained solid was washed with ether (2×15 mL) and concentrated in vacuo to afford compound 51 (50 mg, 84%) as white solid. TLC: 10% MeOH/CH$_2$Cl$_2$ (R$_f$ 0.2); $^1$H-NMR (DMSO-d$_6$, 400 MHz): δ 10.20 (s, 1H), 10.02 (br s, 2H), 7.72 (dd, J=8.3, 4.8 Hz, 2H), 7.19 (t, J=8.9 Hz, 2H), 6.60 (s, 1H), 4.72 (br s, 2H), 3.79-3.74 (m, 2H), 3.60-3.53 (s, 2H).

Example 52: Synthesis of 2-(1, 4-diazepan-1-yl)-N-(4-fluorophenyl)-6-(trifluoromethyl) pyrimidin-4-amine hydrochloride (54): A Common Intermediate

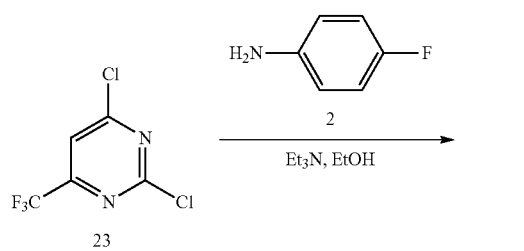

23

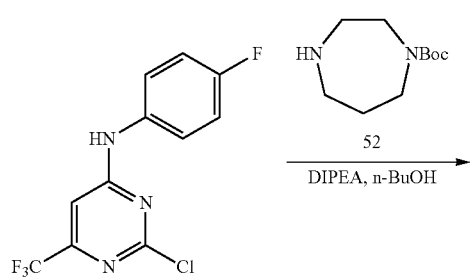

24

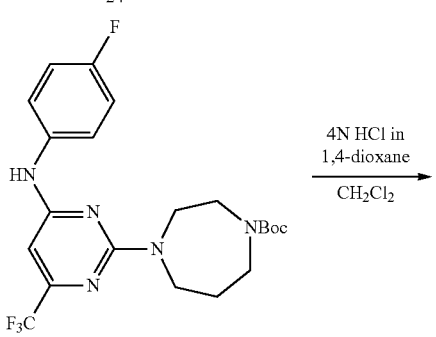

53

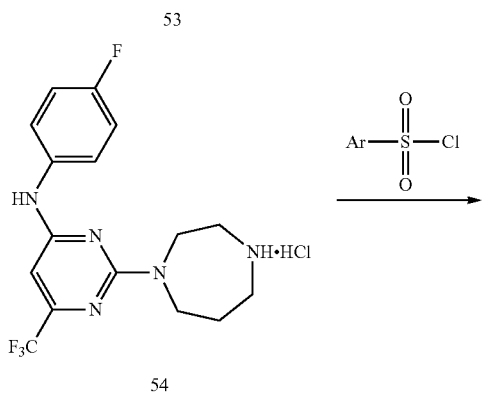

54

Synthesis of tert-butyl 4-(4-((4-fluorophenyl)amino)-6-(trifluoromethyl) pyrimidin-2-yl)-1, 4-diazepane-1-carboxylate (53)

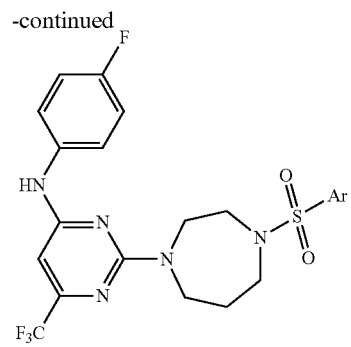

53

To a stirring solution of 2-chloro-N-(4-fluorophenyl)-6-(trifluoromethyl) pyrimidin-4-amine 24 (200 mg, 0.68 mmol) in n-butanol (5 mL) under inert atmosphere were added compound 52 (164 mg, 0.82 mmol) and diisopropylethylamine (0.25 mL, 1.37 mmol) in a sealed tube at RT; heated to 130° C. and stirred for 16 h. The reaction was monitored by TLC; after completion of the reaction, the volatiles were removed in vacuo to obtain the crude which was purified by column chromatography using 5% EtOAc/hexanes to afford compound 53 (260 mg, 85%) as white solid. TLC: 10% EtOAc/hexanes (R$_f$ 0.6); $^1$H NMR (DMSO-d$_6$, 500 MHz): δ 9.77-9.65 (m, 1H), 7.67 (dd, J=7.2, 4.9 Hz, 2H), 7.18 (t, J=8.7 Hz, 2H), 6.33 (s, 1H), 3.84-3.77 (m, 2H), 3.72-3.66 (m, 2H), 3.60-3.50 (m, 2H), 3.28-3.23 (m, 2H), 1.90-1.65 (m, 2H), 1.35-1.20 (m, 9H).

Synthesis of 2-(1, 4-diazepan-1-yl)-N-(4-fluorophenyl)-6-(trifluoromethyl) pyrimidin-4-amine hydrochloride (54)

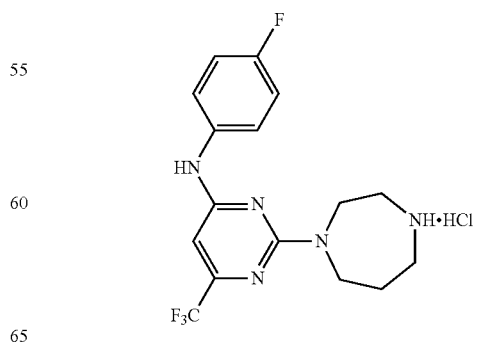

54

To a stirring solution of compound 53 (320 mg, 0.70 mmol) in CH$_2$Cl$_2$ (10 mL) under inert atmosphere was added 4 N HCl in 1, 4-dioxane (10 mL) under inert atmosphere at 0° C.; warmed to RT and stirred for 1 h. The reaction was monitored by TLC; after completion of the reaction, the volatiles were removed in vacuo to afford compound 54 (230 mg, 92%) as an off-white solid. TLC: 5% MeOH/CH$_2$Cl$_2$ (R$_f$, 0.2); $^1$H-NMR (DMSO-d$_6$, 500 MHz): δ 9.96 (s, 1H), 8.99 (br s, 1H), 7.70-7.64 (m, 2H), 7.20 (t, J=8.8 Hz, 2H), 6.46 (s, 1H), 3.96-3.93 (m, 3H), 3.81 (t, J=6.1 Hz, 2H), 3.30-3.25 (m, 2H), 3.19-3.14 (m, 2H), 2.08-2.02 (m, 2H).

Example 53: Synthesis of 2-(piperazin-1-yl)-N-(pyridin-2-yl)-6-(trifluoromethyl) pyrimidin-4-amine hydrochloride (58): A Common Intermediate

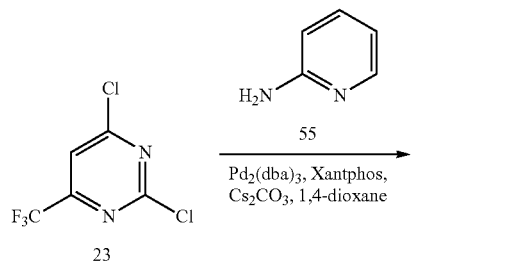

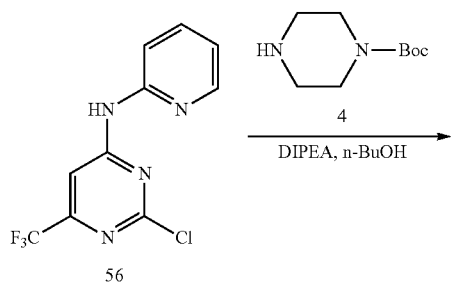

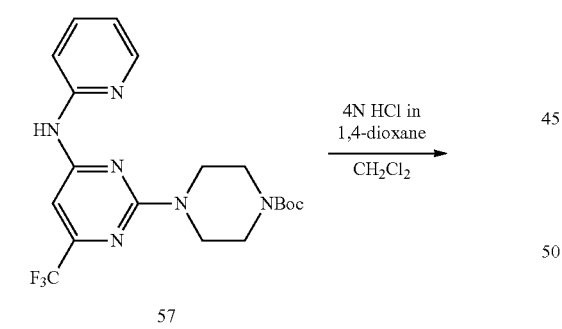

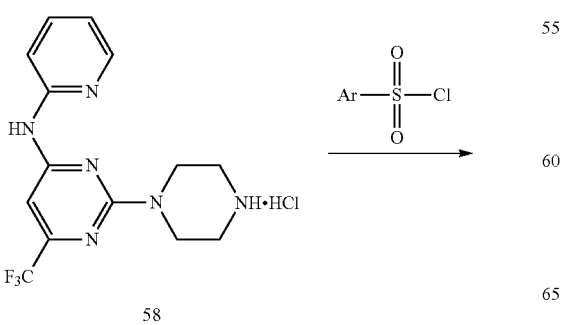

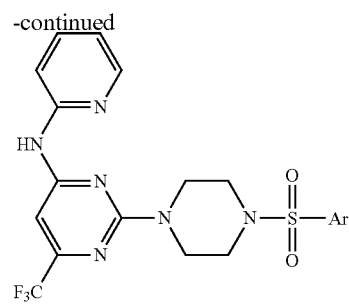

Synthesis of 2-chloro-N-(pyridin-2-yl)-6-(trifluoromethyl) pyrimidin-4-amine (56)

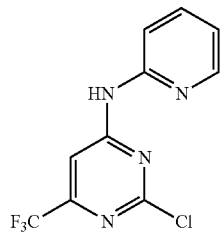

To a stirring solution of 2, 4-dichloro-6-(trifluoromethyl) pyrimidine 23 (1 g, 4.60 mmol) in 1, 4-dioxane (20 mL) under argon atmosphere were added pyridin-2-amine 55 (390 mg, 4.14 mmol), cesium carbonate (1.8 g, 1.2 mmol) at RT and purged under argon for 15 min. To this were added Pd$_2$(dba)$_3$ (211 mg, 0.23 mmol), xantphos (187 mg, 0.32 mmol) at RT and purged under argon for 15 min, heated to 100° C. and stirred for 3 h. The reaction was monitored by TLC; after completion of the reaction, the reaction mixture was filtered through celite pad washed with CH$_2$Cl$_2$ (2×60 mL). The filtrate was removed in vacuo to obtain the crude. The crude was purified through silica gel flash column chromatography using 5-10% EtOAc/hexanes to afford compound 56 (400 mg, 21%) as an off-white solid. TLC: 15% EtOAc/hexanes (R$_f$, 0.5); $^1$H-NMR (DMSO-d$_6$, 500 MHz): δ 11.25 (br s, 1H), 8.43-8.38 (m, 1H), 8.26 (br s, 1H), 7.89-7.83 (m, 1H), 7.59 (br s, 1H), 7.16 (dd, J=7.1, 5.4 Hz, 1H).

Synthesis of tert-butyl 4-(4-(pyridin-2-ylamino)-6-(trifluoromethyl) pyrimidin-2-yl) piperazine-1-carboxylate (57)

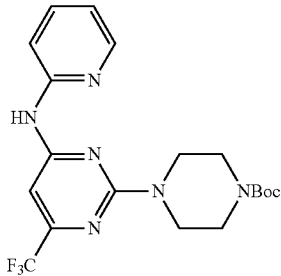

To a stirring solution of compound 56 (400 mg, 1.45 mmol) in n-butanol (10 mL) under inert atmosphere were added tert-butyl piperazine-1-carboxylate 4 (407 mg, 2.18 mmol), diisopropylethyl amine (0.5 mL, 2.91 mmol) at RT; heated to 100° C. and stirred for 16 h. The reaction was monitored by TLC; after completion of the reaction, the volatiles were removed in vacuo. The residue was dissolved in water (30 mL) and extracted with EtOAc (2×60 mL). The combined organic extracts were dried over sodium sulfate, filtered and concentrated in vacuo to obtain the crude which was triturated using diethyl ether (2×20 mL) to afford compound 57 (550 mg, 89%) TLC: 20% EtOAc/hexanes ($R_f$ 0.6); $^1$H NMR (DMSO-$d_6$, 500 MHz): δ 10.30 (s, 1H), 8.32 (d, J=4.3 Hz, 1H), 7.89-7.84 (m, 1H), 7.83-7.78 (m, 1H), 7.20-7.12 (m, 1H), 7.07-7.03 (m, 1H), 3.77-3.71 (m, 4H), 3.46-3.41 (m, 4H), 1.43 (s, 9H).

Synthesis of 2-(piperazin-1-yl)-N-(pyridin-2-yl)-6-(trifluoromethyl) pyrimidin-4-amine hydrochloride (58)

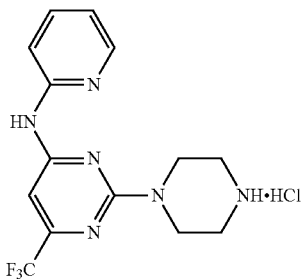

58

To a stirring solution of compound 57 (550 mg, 1.29 mmol) in $CH_2Cl_2$ (5 mL) was added 4 N HCl in 1, 4-dioxane (5 mL) under inert atmosphere at 0° C.; warmed to RT and stirred for 2 h. The reaction was monitored by TLC; after completion of the reaction, the volatiles were removed in vacuo. The residue was triturated with diethylether (2×20 mL) to afford compound 58 (400 mg, 86%; HCl salt) as white solid. TLC: 20% EtOAc/hexanes ($R_f$ 0.1); $^1$H NMR (DMSO-$d_6$, 500 MHz): δ 10.56 (s, 1H), 9.30 (br s, 2H), 8.35 (d, J=4.9 Hz, 1H), 7.86-7.82 (m, 2H), 7.23 (br s, 1H), 7.12-7.08 (m, 1H), 4.01-3.95 (m, 4H), 3.22-3.19 (m, 4H).

Amines similar to compound 106, 8, 11, 13, 19, 21, 22, 26, 29, 36, 39, 43, 45, 51, 54, 58 were synthesized as mentioned and converted to final products using commercially available sulfonyl chlorides employing typical procedure A and the results are captured in the Table 7:

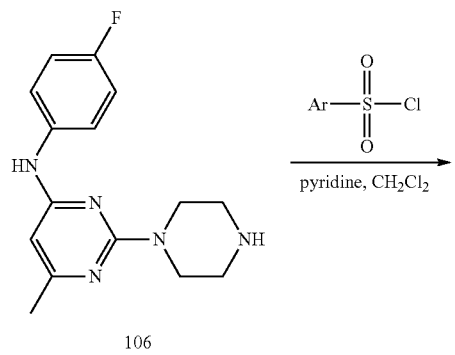

106

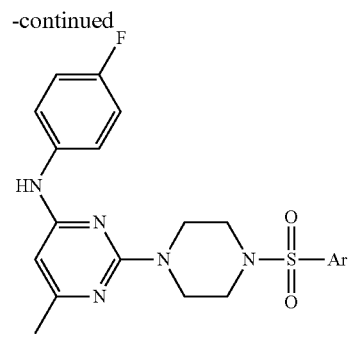

Typical Procedure A: To a stirring solution of compound 106 (100 mg, 0.34 mmol) in $CH_2Cl_2$ (5 mL) under argon atmosphere were added pyridine (0.137 mL, 1.70 mmol) and 4-ethoxybenzenesulfonyl chloride 60 (92 mg, 0.41 mmol) at 0° C.; warmed to RT and stirred for 16 h. The reaction was monitored by TLC; after completion of the reaction, the reaction mixture was diluted with EtOAc (100 mL) and washed with 10% aqueous $NaHCO_3$ solution (50 mL). The organic layer was dried over sodium sulfate, filtered and concentrated in vacuo to obtain the crude. The crude material was either directly dried in vacuo or triturated or purified by column chromatography to afford the desired compound.

Commercially Available Sulfonyl Chlorides Used for Test Compounds

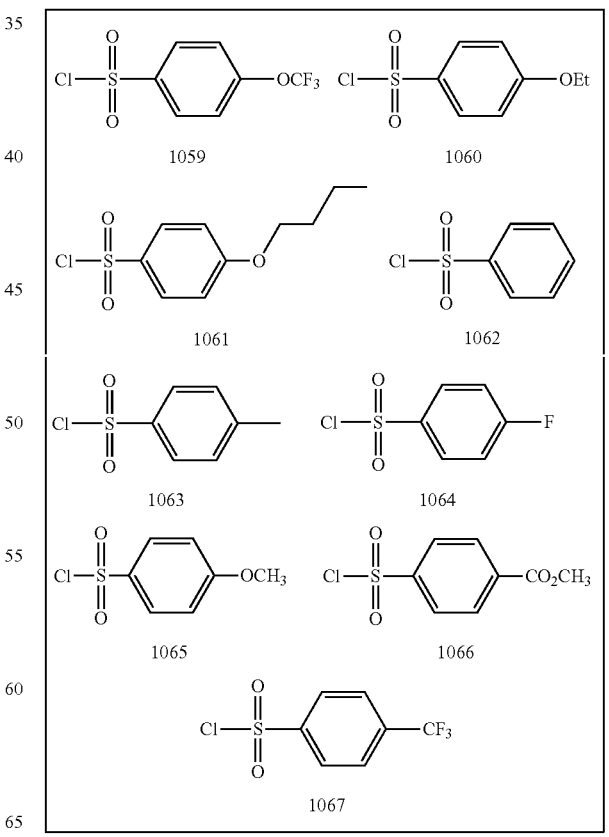

TABLE 7

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1336 | 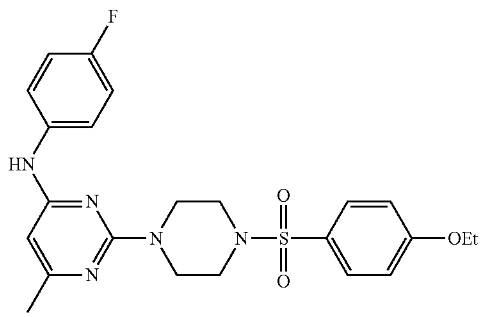 [SMILES: CCOc1ccc(S(=O)(=O)N2CCN(c3nc(C)cc(Nc4ccc(F)cc4)n3)CC2)cc1] | A, 6, 1060 | 73 | 472.0 (M$^+$ + 1) | 471.17 for $C_{23}H_{26}FN_5O_3S$ | $^1$H NMR (DMSO-d$_6$, 400 MHz): δ 9.14 (s, 1H), 7.65 (d, J = 8.9 Hz, 2H), 7.54 (dd, J = 9.1, 4.9 Hz, 2H), 7.15-7.09 (m, 4H), 5.87 (s, 1H), 4.10 (q, J = 6.9 Hz, 2H), 3.80-3.74 (m, 4H), 2.89-2.87 (m, 4H), 2.10 (s, 3H), 1.32 (t, J = 7.0 Hz, 3H); |
| 1337 | 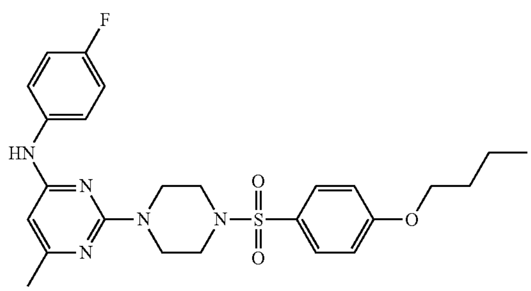 [SMILES: CCCCOc1ccc(S(=O)(=O)N2CCN(c3nc(C)cc(Nc4ccc(F)cc4)n3)CC2)cc1] | A, 6, 1061 | 64 | 500.0 (M$^+$ + 1) | 499.21 for $C_{25}H_{30}FN_5O_3S$ | $^1$H NMR (DMSO-d$_6$, 400 MHz): δ 9.14 (s, 1H), 7.65 (d, J = 8.9 Hz, 2H), 7.54 (dd, J = 9.0, 5.0 Hz, 2H), 7.14-7.08 (m, 4H), 5.87 (s, 1H), 4.04 (t, J = 6.4 Hz, 2H), 3.80-3.74 (m, 4H), 2.89-2.87 (m, 4H), 2.10 (s, 3H), 1.73-1.65 (m, 2H), 1.46-1.37 (m, 2H), 0.91 (t, J = 7.4 Hz, 3H); |
| 1339 | 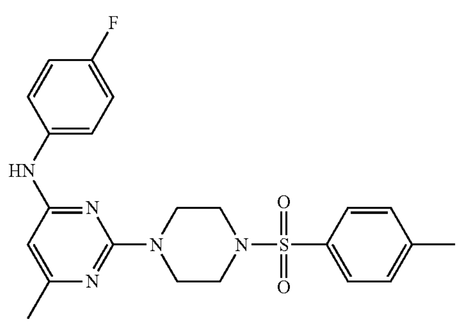 [SMILES: Cc1ccc(S(=O)(=O)N2CCN(c3nc(C)cc(Nc4ccc(F)cc4)n3)CC2)cc1] | A, 6, 1063 | 78 | 442.0 (M$^+$ + 1) | 441.16 for $C_{22}H_{24}FN_5O_2S$ | $^1$H NMR (DMSO-d$_6$, 400 MHz): δ 9.14 (s, 1H), 7.62 (d, J = 8.2 Hz, 2H), 7.54 (dd, J = 9.0, 5.0 Hz, 2H), 7.42 (d, J = 8.0 Hz, 2H), 7.12 (t, J = 8.8 Hz, 2H), 5.87 (s, 1H), 3.80-3.74 (m, 4H), 2.90-2.87 (m, 4H), 2.38 (s, 3H), 2.10 (s, 3H); |
| 1347 | 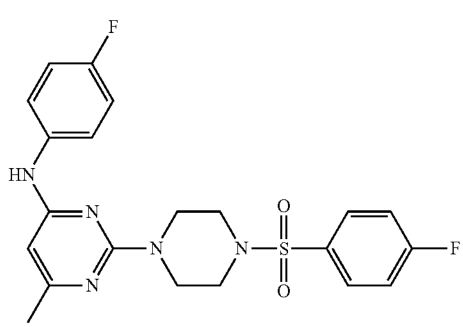 [SMILES: Cc1cc(Nc2ccc(F)cc2)nc(N2CCN(S(=O)(=O)c3ccc(F)cc3)CC2)n1] | A, 6, 1064 | 77 | 446.0 (M$^+$ + 1) | 445.14 for $C_{21}H_{21}F_2N_5O_2S$ | $^1$H NMR (DMSO-d$_6$, 400 MHz): δ 9.14 (s, 1H), 7.82 (dd, J = 8.8, 5.1 Hz, 2H), 7.54 (dd, J = 9.0, 5.0 Hz, 2H), 7.47 (t, J = 8.8 Hz, 2H), 7.12 (t, J = 8.8 Hz, 2H), 5.87 (s, 1H), 3.81-3.75 (m, 4H), 2.95-2.93 (m, 4H), 2.10 (s, 3H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | 1H-NMR |
|---|---|---|---|---|---|---|
| 1348 | 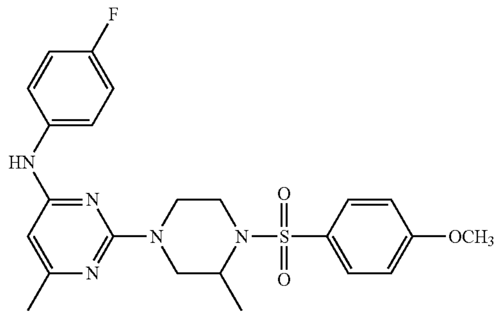 [SMILES: COc1ccc(S(=O)(=O)N2CCN(c3nc(C)cc(Nc4ccc(F)cc4)n3)CC2C)cc1] | A*a*, 8, 1065 | 19 | 472.0 (M+ + 1) | 471.17 for C23H26FN5O3S | 1H NMR (DMSO-d6, 400 MHz): δ 9.12 (s, 1H), 7.76 (d, J = 8.9 Hz, 2H), 7.55 (dd, J = 9.1, 5.0 Hz, 2H), 7.15-7.09 (m, 4H), 5.86 (s, 1H), 4.45-4.40 (m, 1H), 4.32-4.26 (m, 1H), 4.12-4.05 (m, 1H), 3.82 (s, 3H), 3.64-3.58 (m, 1H), 3.14-3.12 (m 1H), 2.99-2.92 (m, 1H), 2.87-2.77 (m, 1H), 2.11 (s, 3H), 0.95 (d, J = 6.7 Hz, 3H); |
| 1371 | 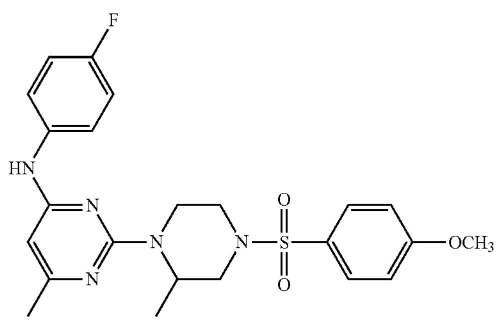 [SMILES: COc1ccc(S(=O)(=O)N2CCN(c3nc(C)cc(Nc4ccc(F)cc4)n3)C(C)C2)cc1] | A*a*, 11, 1065 | 18 | 472.0 (M+ + 1) | 471.17 for C23H26FN5O3S | 1H NMR (DMSO-d6, 500 MHz): δ 9.11 (s, 1H), 7.65 (d, J = 9.0 Hz, 2H), 7.53 (dd, J = 8.7, 4.9 Hz, 2H), 7.15-7.07 (m, 4H), 5.85 (s, 1H), 4.90-4.84 (m, 1H), 4.48-4.44 (m, 1H), 3.82 (s, 3H), 3.64-3.62 (m, 1H), 3.47-3.45 (m, 1H), 3.13-3.05 (m, 1H), 2.31-2.14 (m, 1H), 2.16-2.11(m, 1H), 2.09 (s, 3H), 1.17 (d, J = 6.7 Hz, 3H); |
| 1370 | 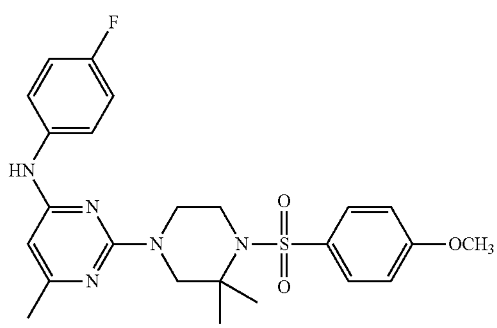 [SMILES: COc1ccc(S(=O)(=O)N2CCN(c3nc(C)cc(Nc4ccc(F)cc4)n3)CC2(C)C)cc1] | A*b*, 13, 1065 | 26 | 486.0 (M+ + 1) | 485.19 for C24H28FN5O3S | 1H NMR (DMSO-d6, 500 MHz): δ 9.12 (s, 1H), 7.75 (d, J = 9.0 Hz, 2H), 7.55 (dd, J = 8.7, 4.9 Hz, 2H), 7.14-7.07 (m, 4H), 5.86 (s, 1H), 3.82 (s, 3H), 3.73-3.66 (m, 2H), 3.58 (s, 2H), 3.53-3.49 (m, 2H), 2.11 (s, 3H), 1.20 (s, 6H); |
| 1352 | 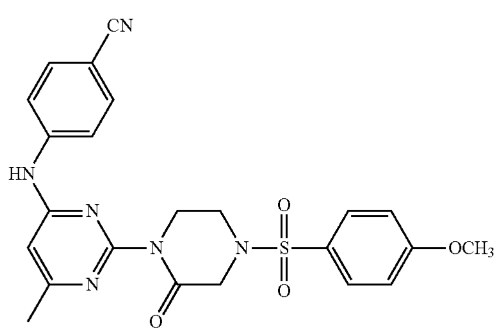 [SMILES: COc1ccc(S(=O)(=O)N2CCN(c3nc(C)cc(Nc4ccc(C#N)cc4)n3)C(=O)C2)cc1] | A*c*, 19, 1065 | 48 | 477.2 (M − 1)+ | 478.14 for C23H22N6O4S | 1H NMR (DMSO-d6, 500 MHz): δ 10.08 (s, 1H), 7.91 (d, J = 8.8 Hz, 2H), 7.79 (d, J = 9.0 Hz, 2H), 7.70 (d, J = 8.8 Hz, 2H), 7.15 (d, J = 9.0 Hz, 2H), 6.55 (s, 1H), 3.91 (t, J = 5.5 Hz, 2H), 3.82 (s, 5H), 3.44-3.39 (m, 2H), 2.32 (s, 3H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1363 | 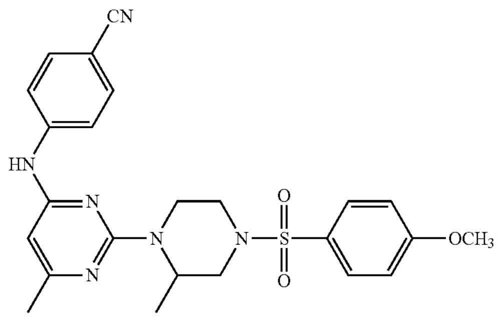 [SMILES: COc1ccc(S(=O)(=O)N2CCN(c3nc(C)cc(Nc4ccc(C#N)cc4)n3)C(C)C2)cc1] | $A^d$, 21, 1065 | 39 | 479.0 ($M^+ + 1$) | 478.18 for $C_{24}H_{26}N_6O_3S$ | $^1$H NMR (DMSO-$d_6$, 400 MHz): δ 9.64 (s, 1H), 7.77 (d, J = 8.8 Hz, 2H), 7.72-7.66 (m, 4H), 7.14 (d, J = 8.9 Hz, 2H), 5.99 (s, 1H), 4.90-4.85 (m, 1H), 4.51-4.45 (m, Hz, 1H), 3.83 (s, 3H), 3.71-3.65 (m, 1H), 3.52-3.48 (m, 1H), 3.19-3.11 (m, 1H), 2.38-2.31 (m, 1H), 2.24-2.18 (m, 1H), 2.16 (s, 3H), 1.20 (d, J = 6.7 Hz, 3H); |
| 1376 | 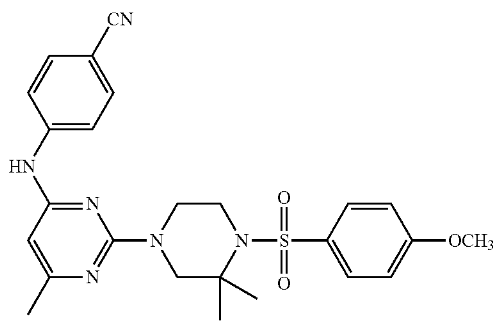 [SMILES: COc1ccc(S(=O)(=O)N2CCN(c3nc(C)cc(Nc4ccc(C#N)cc4)n3)CC2(C)C)cc1] | $A^b$, 22, 1065 | 39 | 493.1 ($M^+ + 1$) | 492.19 for $C_{25}H_{28}N_6O_3S$ | $^1$H NMR (DMSO-$d_6$, 500 MHz): δ 9.65 (s, 1H), 7.80-7.75 (m, 4H), 7.71 (d, J = 8.7 Hz, 2H), 7.10 (d, J = 9.0 Hz, 2H), 5.98 (s, 1H), 3.82 (s, 3H), 3.75-3.71 (m, 2H), 3.62-3.59 (s, 2H), 3.56-3.52 (m, 2H), 2.16 (s, 3H), 1.23 (s, 6H); |
| 1332 | 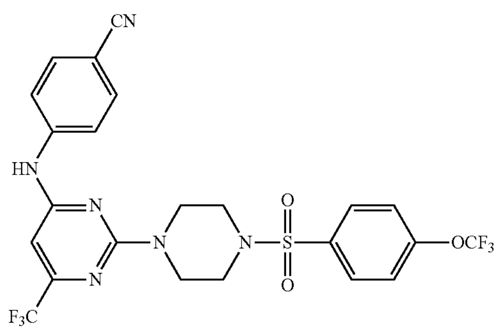 | A, 29, 1059 | 46 | 573.0 ($M^+ + 1$) | 572.11 for $C_{23}H_{18}F_6N_6O_3S$ | $^1$H NMR (DMSO-$d_6$, 400 MHz): δ 10.20 (s, 1H), 7.90 (d, J = 8.8 Hz, 2H), 7.79-7.77 (m, 4H), 7.62 (d, J = 8.3 Hz, 2H), 6.45 (s, 1H), 3.87-3.83 (m, 4H), 3.08-3.05 (m 4H); |
| 1333 | 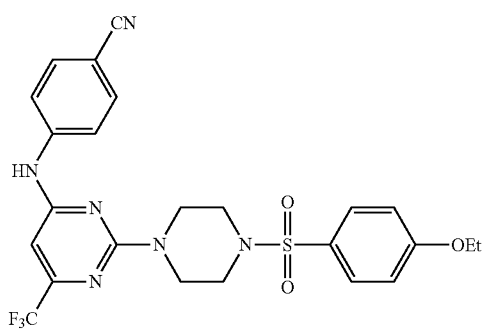 | A, 29, 1060 | 30 | 533.0 ($M^+ + 1$) | 532.15 for $C_{24}H_{23}F_3N_6O_3S$ | $^1$H NMR (DMSO-$d_6$, 400 MHz): δ 10.19 (s, 1H), 7.79-7.77 (m, 4H), 7.66 (d, J = 8.9 Hz, 2H), 7.12 (d, J = 8.9 Hz, 2H), 6.44 (s, 1H), 4.10 (q, J = 6.9 Hz, 2H), 3.87-3.80 (m, 4H), 2.98-2.94 (m, 4H), 1.33 (t, J = 7.0 Hz, 3H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1334 | 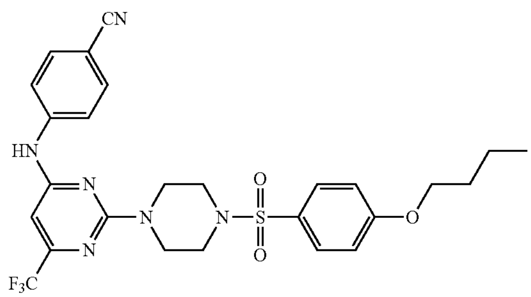 [SMILES: CCCCOc1ccc(S(=O)(=O)N2CCN(c3nc(Nc4ccc(C#N)cc4)cc(C(F)(F)F)n3)CC2)cc1] | A, 29, 1061 | 42 | 561.0 (M$^+$ + 1) | 560.18 for $C_{26}H_{27}F_3N_6O_3S$ | $^1$H NMR (DMSO-d$_6$, 400 MHz): δ 10.19 (s, 1H), 7.79-7.77 (m, 4H), 7.66 (d, J = 8.9 Hz, 2H), 7.13 (d, J = 9.0 Hz, 2H), 6.44 (s, 1H), 4.04 (t, J = 6.5 Hz, 2H), 3.85-3.80 (m, 4H), 2.97-2.94 (m, 4H), 1.74-1.65 (m, 2H), 1.37-1.46 (m, 2H), 0.91 (t, J = 7.4 Hz, 3H); |
| 1340 | 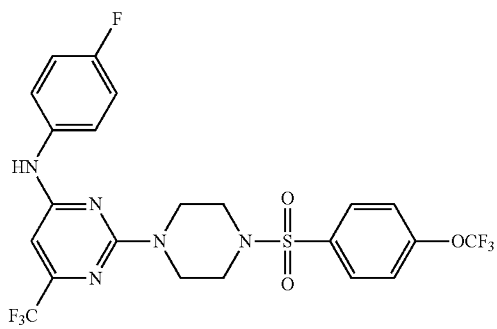 [SMILES: O=S(=O)(c1ccc(OC(F)(F)F)cc1)N1CCN(c2nc(Nc3ccc(F)cc3)cc(C(F)(F)F)n2)CC1] | A, 26, 1059 | 33 | 566.0 (M$^+$ + 1) | 565.10 for $C_{22}H_{18}F_7N_5O_3S$ | $^1$H NMR (DMSO-d$_6$, 400 MHz): δ 9.77 (s, 1H), 7.89 (d, J = 8.8 Hz, 2H), 7.64-7.55 (m, 4H), 7.18 (t, J = 8.9 Hz, 2H), 6.34 (s, 1H), 3.85-3.78 (m, 4H), 3.04-3.00 (m, 4H); |
| 1341 | 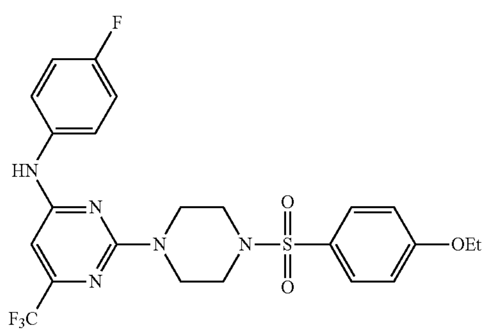 | A$^e$, 26, 1060 | 72 | 526.0 (M$^+$ + 1) | 525.15 for $C_{23}H_{23}F_4N_5O_3S$ | $^1$H NMR (DMSO-d$_6$, 400 MHz): δ 9.77 (s, 1H), 7.66 (d, J = 8.9 Hz, 2H), 7.58 (dd, J = 8.9, 4.9 Hz, 2H), 7.18 (t, J = 8.9 Hz, 2H), 7.12 (d, J = 9.0 Hz, 2H), 6.33 (s, 1H), 4.10 (q, J = 7.0 Hz, 2H), 3.82-3.77 (m, 4H), 2.95-2.90 (m, 4H), 1.33 (t, J = 7.0 Hz, 3H); |
| 1342 | 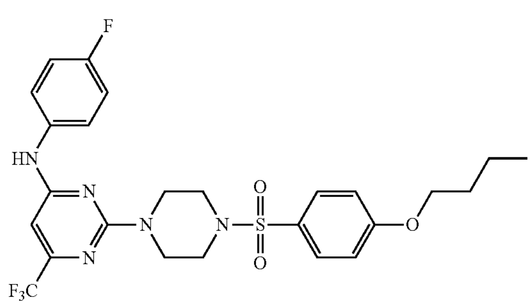 [SMILES: CCCCOc1ccc(S(=O)(=O)N2CCN(c3nc(Nc4ccc(F)cc4)cc(C(F)(F)F)n3)CC2)cc1] | A, 26, 1061 | 59 | 554.0 (M$^+$ + 1) | 553.18 for $C_{25}H_{27}F_4N_5O_3S$ | $^1$H NMR (DMSO-d$_6$, 400 MHz): δ 9.77 (s, 1H), 7.66 (d, J = 8.9 Hz, 2H), 7.58 (dd, J = 8.9, 4.9 Hz, 2H), 7.18 (t, J = 8.9 Hz, 2H), 7.12 (d, J = 8.9 Hz, 2H), 6.33 (s, 1H), 4.04 (t, J = 6.4 Hz, 2H), 3.82-3.77 (m, 4H), 2.95-2.91 (m, 4H), 1.77-1.64 (m, 2H), 1.47-1.36 (m, 2H), 0.91 (t, J = 7.4 Hz, 3H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1343 | 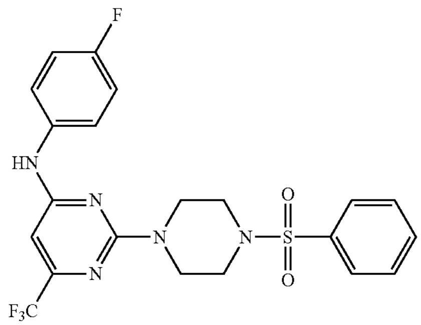 [SMILES: O=S(=O)(c1ccccc1)N1CCN(c2nc(Nc3ccc(F)cc3)cc(C(F)(F)F)n2)CC1] | A, 26, 1062 | 53 | 482.0 (M$^+$ + 1) | 481.12 for $C_{21}H_{19}F_4N_5O_2S$ | $^1$H NMR (DMSO-d$_6$, 400 MHz): δ 9.77 (s, 1H), 7.79-7.69 (m, 3H), 7.67-7.61 (m, 2H), 7.57 (dd, J = 8.8, 5.0 Hz, 2H), 7.18 (t, J = 8.9 Hz, 2H), 6.33 (s, 1H), 3.83-3.77 (m, 4H), 3.00-2.95 (m, 4H); |
| 1344 | 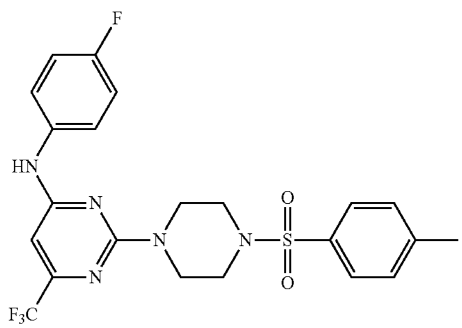 [SMILES: Cc1ccc(S(=O)(=O)N2CCN(c3nc(Nc4ccc(F)cc4)cc(C(F)(F)F)n3)CC2)cc1] | A, 26, 1063 | 53 | 496.1 (M$^+$ + 1) | 495.14 for $C_{22}H_{21}F_4N_5O_2S$ | $^1$H NMR (DMSO-d$_6$, 400 MHz): δ 9.77 (s, 1H), 7.63 (d, J = 8.4 Hz, 2H), 7.57 (dd, J = 9.0, 4.9 Hz, 2H), 7.43 (d, J = 8.0 Hz, 2H), 7.18 (t, J = 8.9 Hz, 2H), 6.33 (s, 1H), 3.83-3.77 (m, 4H), 2.96-2.92 (m, 4H), 2.38 (s, 3H); |
| 1345 | 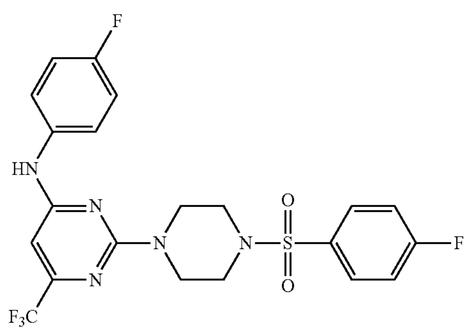 [SMILES: O=S(=O)(c1ccc(F)cc1)N1CCN(c2nc(Nc3ccc(F)cc3)cc(C(F)(F)F)n2)CC1] | A, 26, 1064 | 51 | 500.1 (M$^+$ + 1) | 499.11 for $C_{21}H_{18}F_5N_5O_2S$ | $^1$H NMR (DMSO-d$_6$, 400 MHz): δ 9.78 (s, 1H), 7.83 (dd, J = 8.8, 5.1 Hz, 2H), 7.58 (dd, J = 8.8, 4.9 Hz, 2H), 7.47 (t, J = 8.8 Hz, 2H), 7.18 (t, J = 8.8 Hz, 2H), 6.34 (s, 1H), 3.84-3.78 (m, 4H), 3.01-2.97 (m, 4H); |
| 1386 | 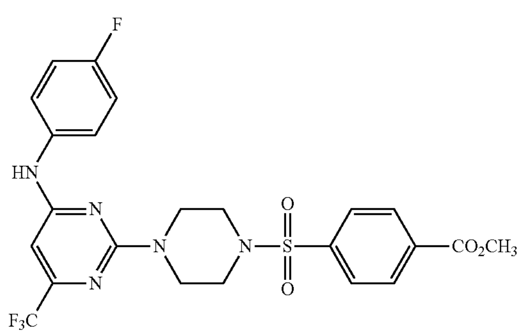 [SMILES: COC(=O)c1ccc(S(=O)(=O)N2CCN(c3nc(Nc4ccc(F)cc4)cc(C(F)(F)F)n3)CC2)cc1] | A$^c$, 26, 1066 | 83 | 540.1 (M$^+$ + 1) | 539.13 for $C_{23}H_{21}F_4N_5O_4S$ | $^1$H NMR (DMSO-d$_6$, 500 MHz): δ 9.77 (s, 1H), 8.16 (d, J = 8.4 Hz, 2H), 7.89 (d, J = 8.4 Hz, 2H), 7.57 (dd, J = 8.7, 4.9 Hz, 2H), 7.18 (t, J = 8.8 Hz, 2H), 6.33 (s, 1H), 3.88 (s, 3H), 3.82-3.78 (m, 4H), 3.05-3.01 (m, 4H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1391 | 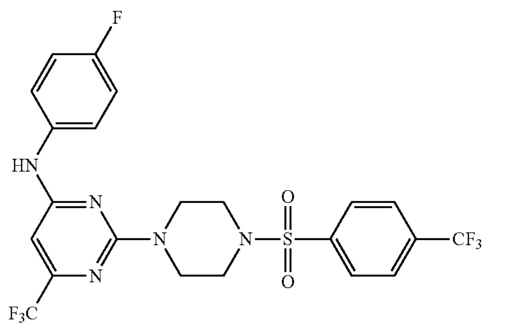 [SMILES: O=S(=O)(c1ccc(C(F)(F)F)cc1)N1CCN(c2nc(Nc3ccc(F)cc3)cc(C(F)(F)F)n2)CC1] | A$^b$, 26, 1067 | 37 | 549.9 (M$^+$ + 1) | 549.11 for $C_{22}H_{18}F_7N_5O_2S$ | $^1$H NMR (DMSO-d$_6$, 400 MHz): 9.77 (s, 1H), 8.03-7.95 (m, 4H), 7.57 (dd, J = 8.4, 4.9 Hz, 2H), 7.18 (t, J = 8.8 Hz, 2H), 6.33 (s, 1H), 3.83-3.80 (m, 4H), 3.07-3.03 (m, 4H); |
| 1357 | 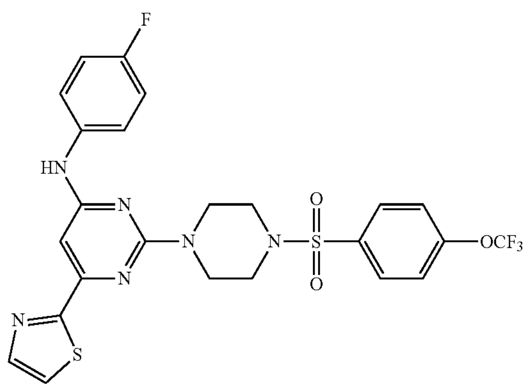 [SMILES: O=S(=O)(c1ccc(OC(F)(F)F)cc1)N1CCN(c2nc(Nc3ccc(F)cc3)cc(-c3nccs3)n2)CC1] | A, 36, 1059 | 25 | 580.9 (M$^+$ + 1) | 580.10 for $C_{24}H_{20}F_4N_6O_3S_2$ | $^1$H NMR (DMSO-d$_6$, 400 MHz): δ 9.59 (s, 1H), 7.98 (d, J = 3.2 Hz, 1H), 7.91 (d, J = 8.9 Hz, 2H), 7.87 (d, J = 3.2 Hz, 1H), 7.64-7.58 (m, 4H), 7.17 (t, J = 8.8 Hz, 2H), 6.78 (s, 1H), 3.89-3.85 (m, 4H), 3.07-3.03 (m, 4H); |
| 1358 | 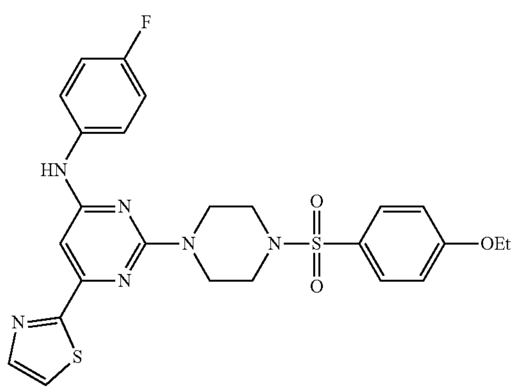 [SMILES: CCOc1ccc(S(=O)(=O)N2CCN(c3nc(Nc4ccc(F)cc4)cc(-c4nccs4)n3)CC2)cc1] | A$^c$, 36, 1060 | 55 | 541.0 (M$^+$ + 1) | 540.14 for $C_{25}H_{25}FN_6O_3S_2$ | $^1$H NMR (DMSO-d$_6$, 400 MHz): 9.59 (s, 1H), 7.98 (d, J = 3.1 Hz, 1H), 7.87 (d, J = 3.1 Hz, 1H), 7.68 (d, J = 8.7 Hz, 2H), 7.60 (dd, J = 8.7, 5.0 Hz, 2H), 7.17 (t, J = 8.8 Hz, 2H), 7.11 (d, J = 8.8 Hz, 2H), 6.78 (s, 1H), 4.10 (q, J = 7.0 Hz, 2H), 3.87-3.84 (m, 4H), 2.97-2.94 (m, 4H), 1.32 (t, J = 6.9 Hz, 3H); |
| 1359 | 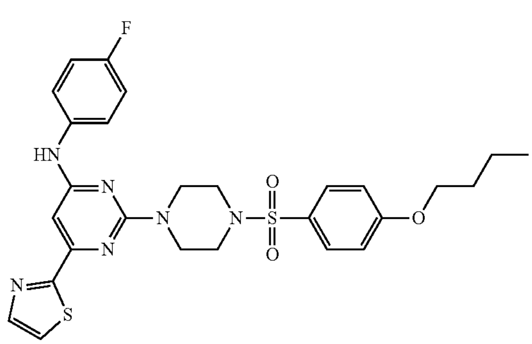 | A, 36, 1061 | 53 | 569.0 (M$^+$ + 1) | 568.17 for $C_{27}H_{29}FN_6O_3S_2$ | $^1$H NMR (DMSO-d$_6$, 400 MHz): δ 9.58 (s, 1H), 7.98 (d, J = 3.2 Hz, 1H), 7.87 (d, J = 3.1 Hz, 1H), 7.67 (d, J = 8.9 Hz, 2H), 7.60 (dd, J = 9.0, 5.0 Hz, 2H), 7.17 (t, J = 8.9 Hz, 2H), 7.11 (d, J = 9.0 Hz, 2H), 6.78 (s, 1H), 4.03 (t, J = 6.4 Hz, 2H), 3.89-3.82 (m, 4H), 2.97-2.94 (m, 4H), 1.72-1.64 (m, 2H), 1.45-1.36 (m, 2H), 0.90 (t, J = 7.4 Hz, 3H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1360 | 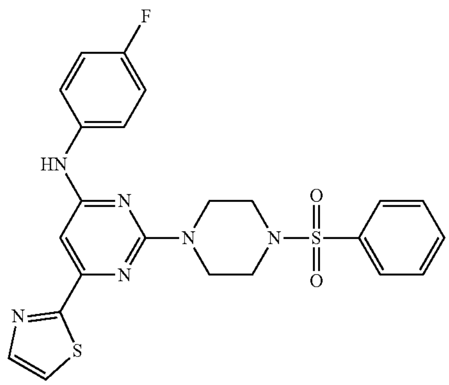 [SMILES: O=S(=O)(c1ccccc1)N1CCN(c2nc(Nc3ccc(F)cc3)cc(-c3nccs3)n2)CC1] | A, 36, 1062 | 58 | 497.3 (M$^+$ + 1) | 496.12 for $C_{23}H_{21}FN_6O_2S_2$ | $^1$H NMR (DMSO-d$_6$, 400 MHz): δ 9.58 (s, 1H), 7.98 (d, J = 3.1 Hz, 1H), 7.86 (d, J = 3.1 Hz, 1H), 7.80-7.75 (m, 2H), 6.78 (s, 1H), 7.74-7.68 (m, 1H), 7.65 (d, J = 7.7 Hz, 2H), 7.62-7.57 (m, 2H), 7.17 (t, J = 8.9 Hz, 2H), 3.88-3.84 (m, 4H), 3.03-2.99 (m, 4H); |
| 1361 | 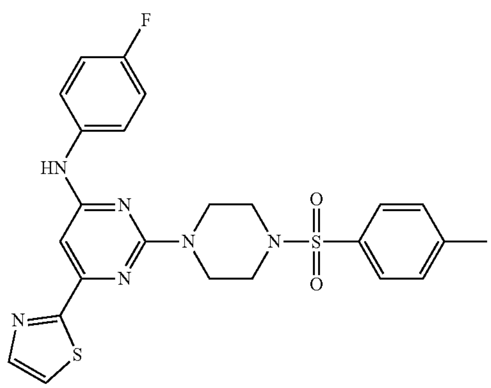 [SMILES: Cc1ccc(S(=O)(=O)N2CCN(c3nc(Nc4ccc(F)cc4)cc(-c4nccs4)n3)CC2)cc1] | A, 36, 1063 | 71 | 511.0 (M$^+$ + 1) | 510.13 for $C_{24}H_{23}FN_6O_2S_2$ | $^1$H NMR (DMSO-d$_6$, 400 MHz): δ 9.56 (s, 1H), 7.98 (d, J = 3.1 Hz, 1H), 7.86 (d, J = 3.1 Hz, 1H), 7.65 (d, J = 8.3 Hz, 2H), 7.59 (dd, J = 9.1, 4.9 Hz, 2H), 7.43 (d, J = 7.9 Hz, 2H), 7.17 (t, J = 8.9 Hz, 2H), 6.78 (s, 1H), 3.88-3.82 (m, 4H), 2.99-2.96 (m, 4H), 2.37 (s, 3H); |
| 1362 | 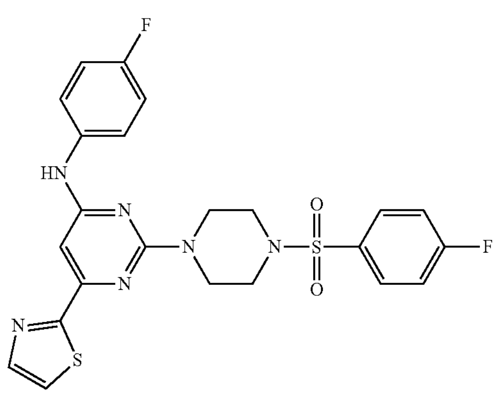 | A, 36, 1064 | 58 | 515.0 (M$^+$ + 1) | 514.11 for $C_{23}H_{20}F_2N_6O_2S_2$ | $^1$H NMR (DMSO-d$_6$, 400 MHz): δ 9.58 (s, 1H), 7.98 (d, J = 3.1 Hz, 1H), 7.86 (d, J = 3.2 Hz, 1H), 7.86-7.81 (m, 2H), 7.60 (dd, J = 9.1, 4.9 Hz, 2H), 7.46 (t, J = 8.8 Hz, 2H), 7.17 (t, J = 8.9 Hz, 2H), 6.78 (s, 1H), 3.89-3.84 (m, 4H), 3.04-3.00 (m, 4H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1367 | 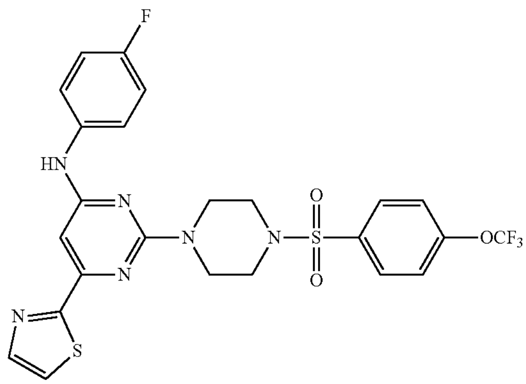 [SMILES: O=S(=O)(c1ccc(OC(F)(F)F)cc1)N1CCN(c2nc(Nc3ccc(F)cc3)cc(-c3nccs3)n2)CC1] | A, 39, 1059 | 31 | 581.0 (M$^+$ + 1) | 580.10 for $C_{24}H_{20}F_4N_6O_3S_2$ | $^1$H NMR (DMSO-d$_6$, 400 MHz): δ 9.43 (br s, 1H), 9.14 (s, 1H), 8.43 (s, 1H), 7.91 (d, J = 8.9 Hz, 2H), 7.65-7.55 (m, 4H), 7.14 (t, J = 8.9 Hz, 2H), 6.45 (s, 1H), 3.88-3.81 (m, 4H), 3.06-3.03 (m, 4H); |
| 1368 | 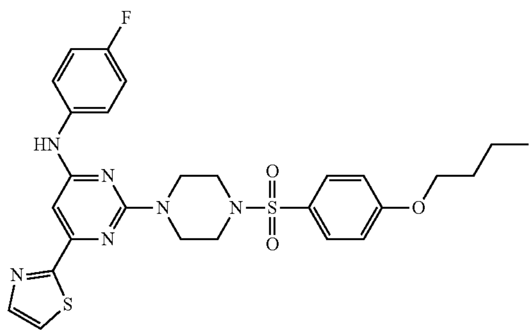 [SMILES: CCCCOc1ccc(S(=O)(=O)N2CCN(c3nc(Nc4ccc(F)cc4)cc(-c4nccs4)n3)CC2)cc1] | A, 39, 1061 | 47 | 569.0 (M$^+$ + 1) | 568.17 for $C_{27}H_{29}FN_6O_3S_2$ | $^1$H NMR (DMSO-d$_6$, 400 MHz): 9.44 (s, 1H), 9.14 (s, 1H), 8.42 (s, 1H), 7.67 (d, J = 8.9 Hz, 2H), 7.59 (dd, J = 9.1, 4.9 Hz, 2H), 7.19-7.08 (m, 4H), 6.44 (s, 1H), 4.04 (t, J = 6.5 Hz, 2H), 3.85-3.81 (m, 4H), 2.97-2.92 (m, 4H), 1.73-1.64 (m, 2H), 1.46-1.36 (m, 2H), 0.91 (t, J = 7.4 Hz, 3H); |
| 1375 | 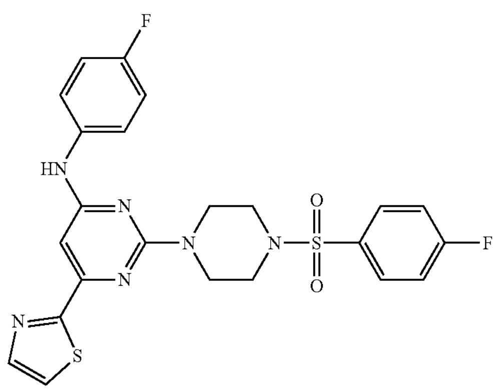 [SMILES: O=S(=O)(c1ccc(F)cc1)N1CCN(c2nc(Nc3ccc(F)cc3)cc(-c3nccs3)n2)CC1] | A, 39, 1064 | 61 | 514.9 (M$^+$ + 1) | 514.11 for $C_{23}H_{20}F_2N_6O_2S_2$ | $^1$H NMR (DMSO-d$_6$, 500 MHz): δ 9.46 (s, 1H), 9.13 (s, 1H), 8.42 (s, 1H), 7.82 (dd, J = 8.7, 5.2 Hz, 2H), 7.57 (dd, J = 9.0, 4.9 Hz, 2H), 7.45 (t, J = 8.7 Hz, 2H), 7.13 (t, J = 9.0 Hz, 2H), 6.43 (s, 1H), 3.85-3.81 (m, 4H), 3.00-2.96 (m, 4H); |
| 1364 | 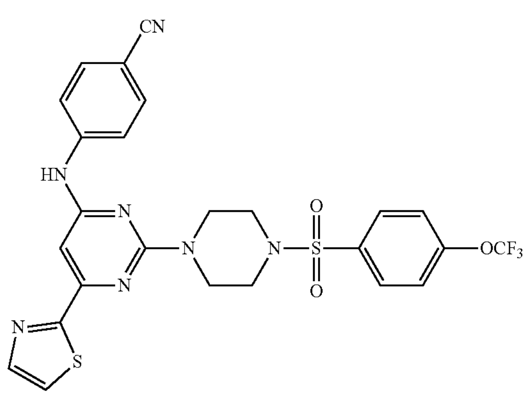 [SMILES: N#Cc1ccc(Nc2cc(-c3nccs3)nc(N3CCN(S(=O)(=O)c4ccc(OC(F)(F)F)cc4)CC3)n2)cc1] | A$^j$, 43, 1059 | 47 | 587.9 (M$^+$ + 1) | 587.10 for $C_{25}H_{20}F_3N_7O_3S_2$ | $^1$H NMR (DMSO-d$_6$, 500 MHz): δ 10.05 (s, 1H), 8.00 (d, J = 3.2 Hz, 1H), 7.92-7.88 (m, 3H), 7.80 (d, J = 9.0 Hz, 2H), 7.75 (d J = 9.0 Hz, 2H), 7.61 (d, J = 8.4 Hz, 2H), 6.89 (s, 1H), 3.90-3.87 (m, 4H), 3.08-3.06 (m, 4H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1353 | 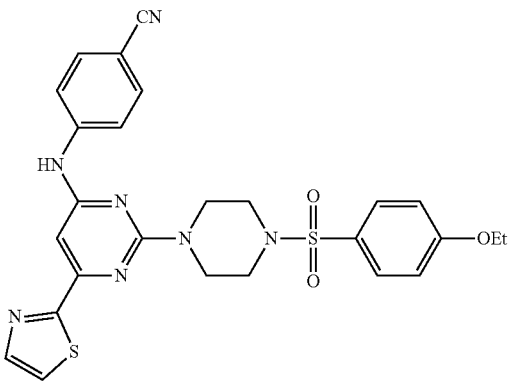 [SMILES: CCOc1ccc(S(=O)(=O)N2CCN(c3nc(Nc4ccc(C#N)cc4)cc(-c4nccs4)n3)CC2)cc1] | A$^f$, 43, 1060 | 42 | 548.0 (M$^+$ + 1) | 547.15 for C$_{26}$H$_{25}$N$_7$O$_3$S$_2$ | $^1$H NMR (DMSO-d$_6$, 400 MHz): δ 10.04 (s, 1H), 8.01 (d, J = 3.1 Hz, 1H), 7.90 (d, J = 3.1 Hz, 1H), 7.81 (d, J = 8.8 Hz, 2H), 7.76 (d, J = 8.9 Hz, 2H), 7.68 (d, J = 8.9 Hz, 2H), 7.11 (d, J = 8.9 Hz, 2H), 6.89 (s, 1H), 4.09 (q, J = 7.0 Hz, 2H), 3.91-3.85 (m, 4H), 3.00-2.98 (m, 4H), 1.32 (t, J = 7.0 Hz, 3H); |
| 1354 | 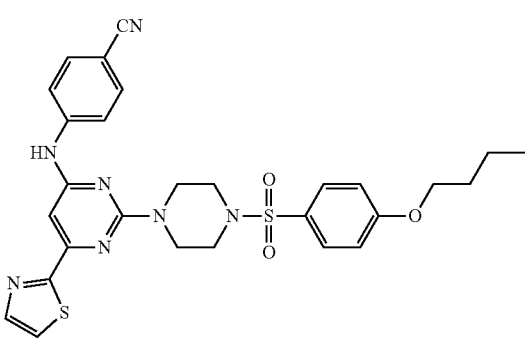 [SMILES: CCCCOc1ccc(S(=O)(=O)N2CCN(c3nc(Nc4ccc(C#N)cc4)cc(-c4nccs4)n3)CC2)cc1] | A$^f$, 43, 1061 | 40 | 576.0 (M$^+$ + 1) | 575.18 for C$_{28}$H$_{29}$N$_7$O$_3$S$_2$ | $^1$H NMR (DMSO-d$_6$, 400 MHz): δ 10.04 (s, 1H), 8.00 (d, J = 3.1 Hz, 1H), 7.89 (d, J = 3.1 Hz, 1H), 7.80 (d, J = 9.3 Hz, 2H), 7.74 (d, J = 8.5 Hz, 2H), 7.66 (d, J = 8.9 Hz, 2H), 7.11 (d, J = 8.9 Hz, 2H), 6.88 (s, 1H), 4.02 (t, J = 6.4 Hz, 2H), 3.89-3.84 (m, 4H), 2.98-2.94 (m, 4H), 1.73-1.61 (m, 2H), 1.44-1.34 (m, 2H), 0.89 (t, J = 7.4 Hz, 3H); |
| 1355 | 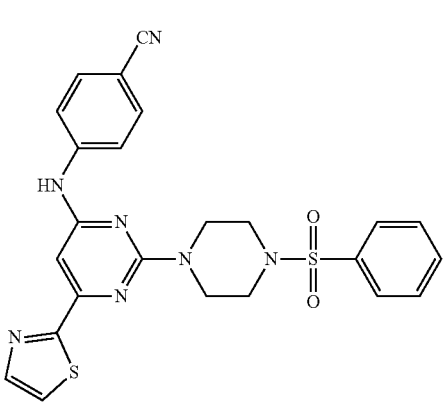 [SMILES: N#Cc1ccc(Nc2cc(-c3nccs3)nc(N3CCN(S(=O)(=O)c4ccccc4)CC3)n2)cc1] | A$^f$, 43, 1062 | 63 | 503.9 (M$^+$ + 1) | 503.12 for C$_{24}$H$_{21}$N$_7$O$_2$S$_2$ | $^1$H NMR (DMSO-d$_6$, 400 MHz): δ 10.06 (s, 1H), 8.01 (d, J = 3.1 Hz, 1H), 7.90 (d, J = 3.1 Hz, 1H), 7.83-7.69 (m, 7H), 7.67-7.61 (m, 2H), 6.89 (s, 1H), 3.91-3.86 (m, 4H), 3.05-3.02 (m, 4H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1356 | 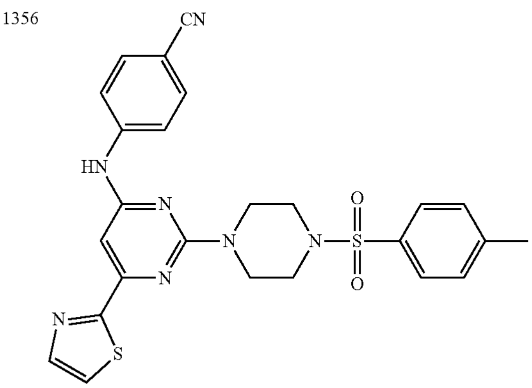 | A$^f$, 43, 1063 | 66 | 518.1 (M$^+$ + 1) | 517.14 for C$_{25}$H$_{23}$N$_7$O$_2$S$_2$ | $^1$H NMR (DMSO-d$_6$, 400 MHz): δ 10.05 (s, 1H), 8.01 (d, J = 3.1 Hz, 1H), 7.90 (d, J = 3.1 Hz, 1H), 7.81 (d, J = 8.9 Hz, 2H), 7.76 (d, J = 8.9 Hz, 2H), 7.65 (d, J = 8.3 Hz, 2H), 7.43 (d, J = 7.9 Hz, 2H), 6.89 (s, 1H), 3.91-3.85 (m, 4H), 3.01-2.98 (m, 4H), 2.37 (s, 3H); |
| 1365 | 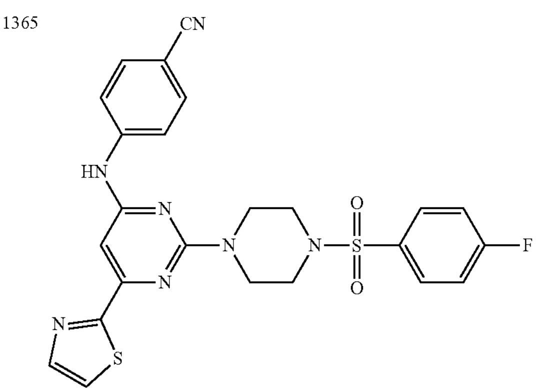 | A$^f$, 43, 1064 | 39 | 522.0 (M$^+$ + 1) | 521.11 for C$_{24}$H$_{20}$FN$_7$O$_2$S$_2$ | $^1$H NMR (DMSO-d$_6$, 400 MHz): δ 10.05 (s, 1H), 8.01 (d, J = 3.1 Hz, 1H), 7.90 (d, J = 3.1 Hz, 1H), 7.87-7.79 (m, 4H), 7.77-7.74 (m, 2H), 7.47 (t, J = 8.8 Hz, 2H), 6.90 (s, 1H), 3.95-3.85 (m, 4H), 3.06-3.04 (m, 4H); |
| 1372 | 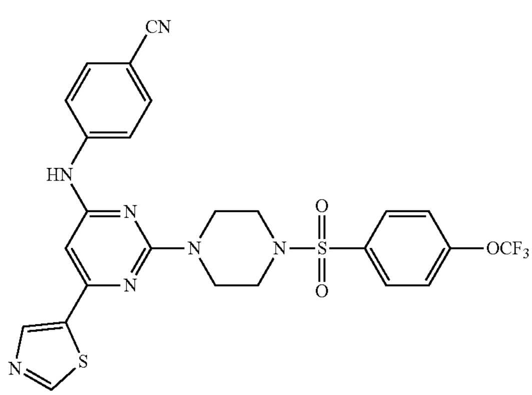 [SMILES: N#Cc1ccc(Nc2cc(-c3cncs3)nc(N3CCN(S(=O)(=O)c4ccc(OC(F)(F)F)cc4)CC3)n2)cc1] | A$^f$, 45, 1059 | 36 | 588.0 (M$^+$ + 1) | 587.10 for C$_{25}$H$_{20}$F$_3$N$_7$O$_3$S$_2$ | $^1$H NMR (DMSO-d$_6$, 500 MHz): δ 9.94 (s, 1H), 9.16 (s, 1H), 8.46 (s, 1H), 7.89 (d, J = 8.7 Hz, 2H), 7.78 (d, J = 8.4 Hz, 2H), 7.72 (d, J = 8.7 Hz, 2H), 7.60 (d, J = 8.4 Hz, 2H), 6.54 (s, 1H), 3.88-3.83 (m, 4H), 3.06-3.02 (m, 4H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1373 | 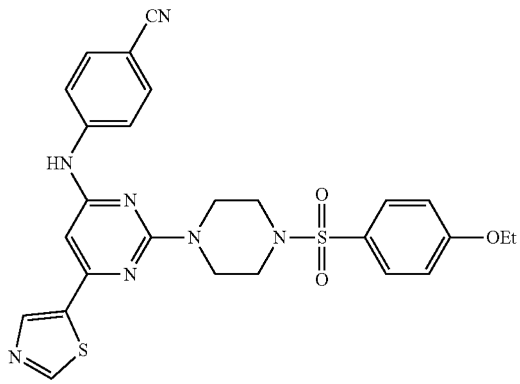 [SMILES: CCOc1ccc(S(=O)(=O)N2CCN(c3nc(Nc4ccc(C#N)cc4)cc(-c4cncs4)n3)CC2)cc1] | A$^f$, 45, 1060 | 15 | 547.9 (M$^+$ + 1) | 547.15 for $C_{26}H_{25}N_7O_3S_2$ | $^1$H NMR (DMSO-d$_6$, 500 MHz): δ 9.95 (s, 1H), 9.17 (s, 1H), 8.47 (s, 1H), 7.78 (d, J = 9.3 Hz, 2H), 7.73 (d, J = 9.3 Hz, 2H), 7.67 (d, J = 9.0 Hz, 2H), 7.10 (d, J = 9.0 Hz, 2H), 6.54 (s, 1H), 4.08 (q, J = 6.9 Hz, 2H), 3.87-3.83 (m, 4H), 2.97-2.93 (m, 4H), 1.30 (t, J = 6.9 Hz, 3H); |
| 1369 | 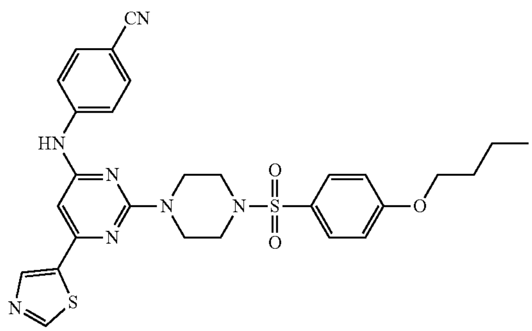 [SMILES: CCCCOc1ccc(S(=O)(=O)N2CCN(c3nc(Nc4ccc(C#N)cc4)cc(-c4cncs4)n3)CC2)cc1] | A$^f$, 45, 1061 | 37 | 576.1 (M$^+$ + 1) | 575.18 for $C_{28}H_{29}N_7O_3S_2$ | $^1$H NMR (DMSO-d$_6$, 500 MHz): δ 9.94 (s, 1H), 9.16 (s, 1H), 8.46 (s, 1H), 7.78 (d, J = 8.7 Hz, 2H), 7.73 (d, J = 9.0 Hz, 2H), 7.65 (d, J = 8.7 Hz, 2H), 7.10 (d, J = 9.0 Hz, 2H), 6.53 (s, 1H), 4.03-4.00 (m, 2H), 2.95-2.93 (m, 4H), 2.95-2.93 (m, 4H), 1.70-1.63 (m, 2H), 1.42-1.34 (m, 2H), 0.88 (t, J = 7.4 Hz, 3H); |
| 1374 | 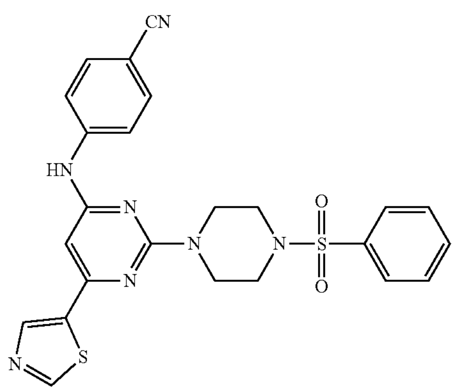 [SMILES: N#Cc1ccc(Nc2cc(-c3cncs3)nc(N3CCN(S(=O)(=O)c4ccccc4)CC3)n2)cc1] | A$^f$, 45, 1062 | 29 | 504.0 (M$^+$ + 1) | 503.12 for $C_{24}H_{21}N_7O_2S_2$ | $^1$H NMR (DMSO-d$_6$, 500 MHz): δ 9.95 (s, 1H), 9.17 (s, 1H), 8.46 (s, 1H), 7.80-7.68 (m, 7H), 7.65-7.61 (m, 2H), 6.54 (s, 1H), 3.87-3.83 (m, 4H), 3.01-2.98 (m, 4H); |
| 1379 | 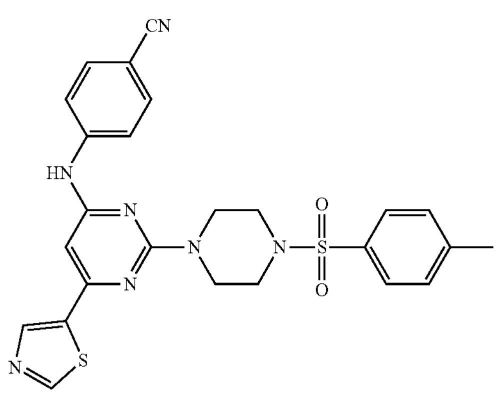 [SMILES: Cc1ccc(S(=O)(=O)N2CCN(c3nc(Nc4ccc(C#N)cc4)cc(-c4cncs4)n3)CC2)cc1] | A$^f$, 45, 1063 | 29 | 518.0 (M$^+$ + 1) | 517.14 for $C_{25}H_{23}N_7O_2S_2$ | $^1$H NMR (DMSO-d$_6$, 500 MHz): δ 9.96 (s, 1H), 9.18 (s, 1H), 8.48 (s, 1H), 7.79 (d, J = 8.4 Hz, 2H), 7.74 (d, J = 9.0 Hz, 2H), 7.65 (d, J = 8.1 Hz, 2H), 7.43 (d, J = 8.1 Hz, 2H), 6.55 (s, 1H), 3.87-3.84 (m, 4H), 2.98-2.96 (m, 4H), 2.37 (s, 3H); |

TABLE 7-continued

Synthesis of test compounds from compounds 106, 8, 11, 13, 19, 21, 22, 26, 29, 36, 39, 43, 45, 51, 54, 58 and various sulfonyl chlorides

| No | Structure | Procedure, Intermediate | Rx. Yield (%) | Mass Spec. Found | Mass Spec. Calculated | $^1$H-NMR |
|---|---|---|---|---|---|---|
| 1380 | 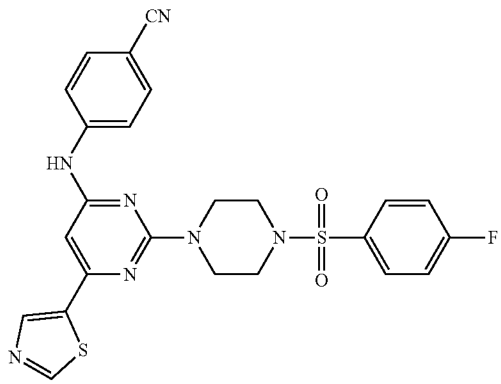 [SMILES: N#Cc1ccc(Nc2cc(-c3cncs3)nc(N3CCN(S(=O)(=O)c4ccc(F)cc4)CC3)n2)cc1] | A$^f$, 45, 1064 | 19 | 522.0 (M$^+$ + 1) | 521.11 for $C_{24}H_{20}FN_7O_2S_2$ | $^1$H NMR (DMSO-d$_6$, 500 MHz): δ 9.96 (s, 1H), 9.18 (s, 1H), 8.48 (s, 1H), 7.84 (dd, J = 8.7, 5.2 Hz, 2H), 7.80 (d, J = 8.1 Hz, 2H), 7.74 (d, J = 8.4 Hz, 2H), 7.47 (t, J = 8.7 Hz, 2H), 6.56 (s, 1H), 3.88-3.85 (m, 4H), 3.03-3.01 (m, 4H); |
| 1420 | 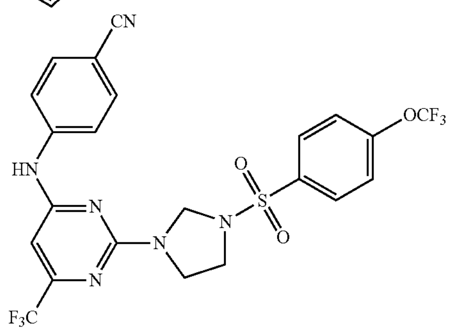 | A$^g$, 51, 1059 | 40 | 552.0 (M$^+$ + 1) | 551.09 for $C_{21}H_{16}F_7N_5O_3S$ | $^1$H-NMR (DMSO-d$_6$, 400 MHz): δ 9.82 (s, 1H), 7.93 (d, J = 8.5 Hz, 2H), 7.64-7.56 (m, 2H), 7.43 (d, J = 8.4 Hz, 2H), 7.24-7.14 (m, 2H), 6.39 (s, 1H), 4.88 (s, 2H), 3.80-3.74 (m, 2H), 3.31-3.30 (m, 2H); |
| 1419 | 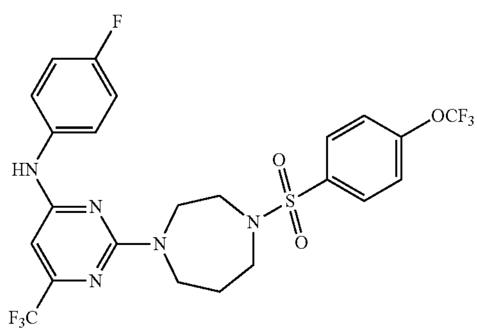 [SMILES: O=S(=O)(c1ccc(OC(F)(F)F)cc1)N1CCCN(c2nc(Nc3ccc(F)cc3)cc(C(F)(F)F)n2)CC1] | A$^b$, 54, 1059 | 18 | 580.1 (M$^+$ + 1) | 579.12 for $C_{23}H_{20}F_7N_5O_3S$ | $^1$H-NMR (DMSO-d$_6$, 400 MHz): δ 9.73 (br s, 1H), 7.87-7.79 (m, 2H), 7.62 (dd, J = 9.0, 5.0 Hz, 2H), 7.44 (d, J = 8.0 Hz, 2H), 7.24-7.14 (m, 2H), 6.33 (s, 1H), 3.82 (t, J = 5.6 Hz, 2H), 3.71 (t, J = 5.7 Hz, 2H), 3.48-3.44 (m, 2H), 3.40-3.34 (m, 2H), 1.83-1.74 (m, 2H); |
| 1415 | 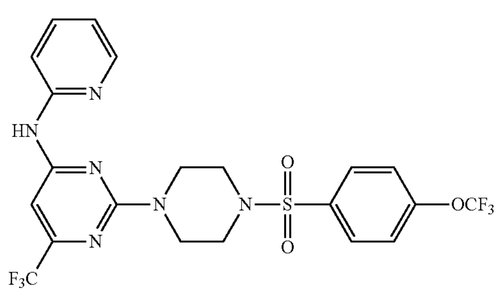 [SMILES: O=S(=O)(c1ccc(OC(F)(F)F)cc1)N1CCN(c2nc(Nc3ccccn3)cc(C(F)(F)F)n2)CC1] | A$^h$, 58, 1059 | 78 | 548.9 (M$^+$ + 1) | 548.11 for $C_{21}H_{18}F_6N_6O_3S$ | $^1$H NMR (DMSO-d$_6$, 400 MHz): δ 10.30 (s, 1H), 8.31 (d, J = 4.6 Hz, 1H), 7.90 (d, J = 8.7 Hz, 2H), 7.78 (d, J = 5.5 Hz, 2H), 7.62 (d, J = 8.4 Hz, 2H), 7.16 (br s, 1H), 7.08-7.03 (m, 1H), 3.88-3.86 (m, 4H), 3.07-3.03 (m, 4H); |

$^a$Et$_3$N (10 equiv);
$^b$Et$_3$N (3 equiv);
$^c$Et$_3$N (5 equiv);
$^d$pyridine (3 equiv);
$^e$Et$_3$N (10 equiv), sulfonyl chloride (2 equiv);
$^f$DIPEA (3 equiv), sulfonyl chloride (1.1 equiv);
$^g$Et$_3$N (5 equiv), RT, 1 h;
$^h$Et$_3$N (10 equiv), RT, 2 h

Example 54: Synthesis of 1366

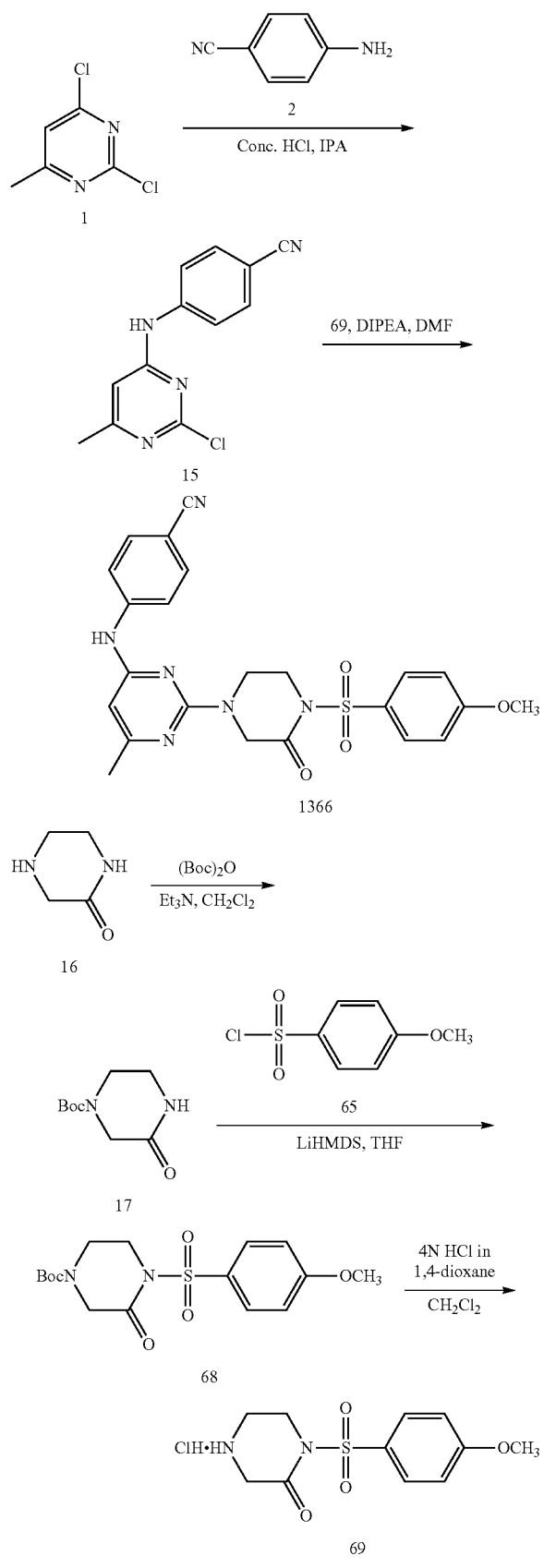

Synthesis of tert-butyl 4-((4-methoxyphenyl) sulfonyl)-3-oxopiperazine-1-carboxylate (68)

To a stirring solution of tert-butyl 3-oxopiperazine-1-carboxylate 17 (2 g, 10.00 mmol) in THF (50 mL) under argon atmosphere were added LiHMDS (15 mL, 15.00 mmol, 1.0 M solution in THF) dropwise for 15 min at −78° C. and stirred for 1 h. To this was added 4-methoxy benzenesulfonyl chloride 1065 (4.2 g, 20.00 mmol) in THF (5 mL) dropwise for 10 min at −78° C. and stirred for 1 h. The reaction was monitored by TLC; after completion the reaction, the reaction mixture was diluted with EtOAc (100 mL) washed with saturated ammonium chloride solution (100 mL). The organic extract was dried over sodium sulfate, filtered and concentrated in vacuo to obtain crude. The crude was purified through silica gel column chromatography using 20-30% EtOAc/hexanes to afford compound 68 (1.1 g, 30%) as pale yellow solid. TLC: 10% MeOH/CH$_2$Cl$_2$ (R$_f$ 0.4); $^1$H-NMR (DMSO-d$_6$, 500 MHz): δ 7.90 (d, J=9.0 Hz, 2H), 7.12 (d, J=9.0 Hz, 2H), 3.98 (br s, 2H), 3.95-3.92 (m, 2H), 3.84 (s, 3H), 3.61-3.57 (m, 2H), 1.37 (s, 9H).

Synthesis of 1-((4-methoxyphenyl) sulfonyl) piperazin-2-one (69)

To a stirring solution of compound 68 (1.1 g, 2.97 mmol) in CH$_2$Cl$_2$ (10 mL) was added 4 N HCl in 1, 4-dioxane (10 mL) under argon atmosphere at 0° C.; warmed to RT and stirred for 4 h. The reaction was monitored by TLC; after completion of the reaction, the volatiles were removed in vacuo to obtain the crude which was triturated with diethylether (2×10 mL) to afford compound 69 (650 mg, 72%) as an off-white solid. TLC: 30% EtOAc/hexanes (R$_f$ 0.2); $^1$H NMR (DMSO-d$_6$, 500 MHz): δ 9.67 (br s, 2H), 7.93 (d, J=9.0 Hz, 2H), 7.16 (d, J=8.7 Hz, 2H), 4.08-4.04 (m, 2H), 3.85-3.82 (m, 5H), 3.51-3.46 (m, 2H).

Synthesis of 4-((2-(4-((4-methoxyphenyl) sulfonyl)-3-oxopiperazin-1-yl)-6-methylpyrimidin-4-yl) amino) benzonitrile (1366)

To a stirring solution of compound 15 (200 mg, 0.82 mmol) in NMP (2 mL) under argon atmosphere were added diisopropylethylamine (0.8 mL, 4.09 mmol) and compound 69 (250 mg, 0.82 mmol) in a sealed tube and heated 180° C. and stirred for 18 h. The reaction was monitored by TLC; after completion the reaction, the reaction mixture was diluted with EtOAc (100 mL), washed with saturated ammonium chloride solution (100 mL). The organic extract was dried over sodium sulfate, filtered and concentrated in vacuo to obtain crude. The crude was purified through silica gel column chromatography using 20-30% EtOAc/hexanes, further purified using preparative HPLC purification to afford compound 1366 (80 mg, 20%) as pale yellow solid. TLC: 10% MeOH/CH$_2$Cl$_2$ (R$_f$ 0.4); $^1$H-NMR (DMSO-d$_6$, 500 MHz): δ 9.73 (s, 1H), 7.92 (d, J=9.0 Hz, 2H), 7.78 (d, J=8.7 Hz, 2H), 7.71 (d, J=8.4 Hz, 2H), 7.11 (d, J=9.0 Hz, 2H), 6.06 (s, 1H), 4.35 (s, 2H), 4.07-4.03 (m, 2H), 4.01-3.96 (m, 2H), 3.84 (s, 3H), 2.19 (s, 3H); LC-MS: 92.70%; 479.0 (M$^+$+1); (column; Ascentis Express C18, (50×3.0 mm, 2.7 μm); RT 2.04 min. 0.025% Aq. TFA+5% ACN: ACN+5% 0.025% Aq. TFA, 1.2 mL/min); HPLC (purity): 91.26%; (column; Zorbax-SB-C-18 (150×4.6 mm, 5 μm); RT 7.66 min. ACN: 0.05% TFA (Aq); 1.0 mL/min).

Example 55: Synthesis of 1418

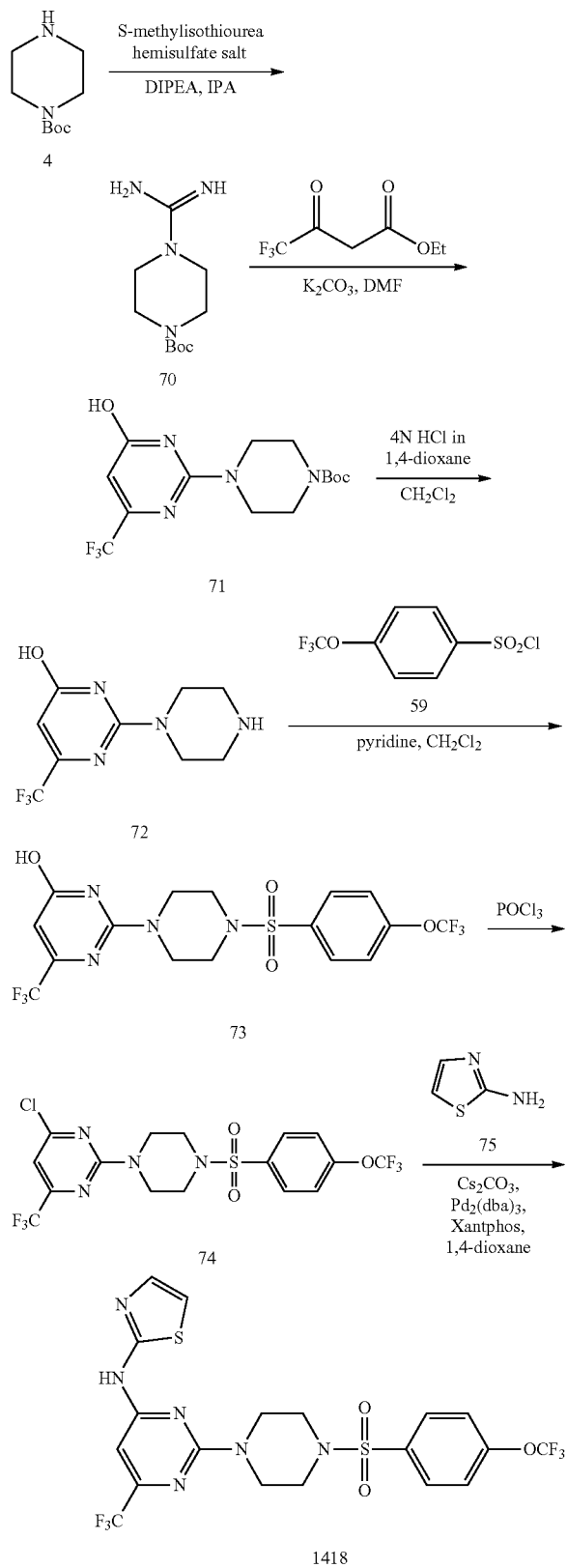

Synthesis of tert-butyl 4-carbamimidoylpiperazine-1-carboxylate (70)

To a stirring solution of tert-butyl piperazine-1-carboxylate 4 (10 g, 53.76 mmol) in isopropyl alcohol (150 mL) under inert atmosphere were added S-methylisothiourea hemisulfate salt (6 g, 21.50 mmol), diisopropylethylamine (25 mL, 134.4 mmol) at RT; heated to 100° C. and stirred for 24 h. The reaction was monitored by TLC; after completion of the reaction, the volatiles were removed in vacuo to obtain the crude. The crude was triturated with $CH_3CN$ (100 mL) to afford compound 70 (10 g, crude) as white solid. TLC: 10% $MeOH/CH_2Cl_2$ ($R_f$ 0.3). LC-MS: 58.28%; 228.9 ($M^-+1$); (column; Ascentis Express C18, (50×3.0 mm, 2.7 µm); RT 1.59 min. 0.025% Aq. TFA+5% ACN: ACN+5% 0.025% Aq. TFA, 1.2 mL/min).

Synthesis of tert-butyl 4-(4-hydroxy-6-(trifluoromethyl) pyrimidin-2-yl) piperazine-1-carboxylate (71)

To a stirring solution of compound 70 (5 g, crude) in DMF (100 mL) under inert atmosphere were added potassium carbonate (4.5 g, 32.89 mmol) and ethyl 4, 4, 4-trifluoro-3-oxobutanoate (4 g, 21.92 mmol) at RT and heated to 120° C. and stirred for 16 h. The reaction was monitored by TLC; after completion of the reaction, the reaction mixture was diluted with ice-cold water (600 mL) and extracted with EtOAc (2×500 mL). The combined organic extracts were dried over sodium sulfate, filtered and concentrated in vacuo to obtain the crude. The crude was purified through silica gel flash column chromatography using 35-40% EtOAc/hexanes and the obtained compound was triturated with hexanes (2×10 mL) to afford compound 71 (500 mg, 33%) as white solid. TLC: 50% EtOAc/hexanes ($R_f$ 0.7); $^1$H NMR (DMSO-$d_6$, 400 MHz): δ 11.71 (br s, 1H), 6.05 (br s, 1H), 3.67-3.62 (m, 4H), 3.42-3.37 (m, 4H), 1.42 (s, 9H).

Synthesis of 2-(piperazin-1-yl)-6-(trifluoromethyl) pyrimidin-4-ol (72)

To a stirring solution of compound 71 (500 mg, 1.44 mmol) in $CH_2Cl_2$ (5 mL) was added 4 N HCl in 1, 4-dioxane (5 mL) under inert atmosphere at 0° C.; warmed to RT and stirred for 2 h. The reaction was monitored by TLC; after completion of the reaction, the volatiles were removed in vacuo. The residue was triturated with diethylether (2×20 mL) to afford compound 72 (350 mg, 86%) as white solid. TLC: 50% EtOAc/hexanes ($R_f$ 0.1); $^1$H NMR (DMSO-$d_6$, 400 MHz): δ 12.70-11.53 (m, 1H), 9.23 (br s, 1H), 6.19 (br s, 1H), 3.92-3.87 (m, 4H), 3.19-3.15 (m, 4H).

Synthesis of 2-(4-((4-(trifluoromethoxy) phenyl) sulfonyl) piperazin-1-yl)-6-(trifluoromethyl) pyrimidin-4-ol (73)

To a stirring solution of compound 72 (350 mg, 1.41 mmol) in $CH_2Cl_2$ (10 mL) under argon atmosphere were added pyridine (1.14 mL, 14.11 mmol) and 4-(trifluoromethoxy) benzenesulfonyl chloride 1059 (404 mg, 1.55 mmol) at 0° C.; warmed to RT and stirred for 16 h. The reaction was monitored by TLC; after completion of the reaction, the reaction mixture was diluted with water (50 mL) and extracted with $CH_2Cl_2$ (2×60 mL). The combined organic extracts were dried over sodium sulfate, filtered and concentrated in vacuo to obtain the crude. The crude was purified through silica gel flash column chromatography using 2% $MeOH/CH_2Cl_2$ to afford 73 (400 mg, 69%) as white solid. TLC: 5% MeOH/CH$_2$Cl$_2$ (R$_f$ 0.6); $^1$H NMR (DMSO-d$_6$, 500 MHz): δ 11.68 (br s, 1H), 7.90 (d, J=8.7 Hz, 2H), 7.63 (d, J=8.4 Hz, 2H), 6.03 (br s, 1H), 3.83-3.72 (m, 4H), 3.05-3.01 (m, 4H).

Synthesis of 4-chloro-2-(4-((4-(trifluoromethoxy) phenyl) sulfonyl) piperazin-1-yl)-6-(trifluoromethyl) pyrimidine (74)

To compound 73 (400 mg, 0.84 mmol) was added phosphorous oxychloride (10 mL) under argon atmosphere at 0° C.; heated to 90° C. for 16 h. The reaction was monitored by TLC; after completion of the reaction, the volatiles were removed in vacuo. The residue was poured into ice-cold water (50 mL) and extracted with EtOAc (2×50 mL). The combined organic extracts were dried over sodium sulfate, filtered and concentrated in vacuo to obtain the crude. The crude was purified through silica gel flash column chromatography using 10-15% EtOAc/hexanes to afford compound 74 (300 mg, 72%) as white solid. TLC: 30% EtOAc/hexanes (R$_f$ 0.8); $^1$H NMR (DMSO-d$_6$, 500 MHz): δ 7.89 (d, J=8.7 Hz, 2H), 7.62 (d, J=8.4 Hz, 2H), 7.22 (s, 1H), 3.88-3.84 (m, 4H), 3.08-3.06 (m, 4H).

Synthesis of N-(2-(4-((4-(trifluoromethoxy) phenyl) sulfonyl) piperazin-1-yl)-6-(trifluoromethyl) pyrimidin-4-yl) thiazol-2-amine (1418)

To a stirring solution of compound 74 (100 mg, 0.20 mmol) in 1, 4-dioxane (5 mL) under inert atmosphere were added thiazol-2-amine 75 (24.5 mg, 0.24 mmol), cesium carbonate (99 mg, 0.30 mmol) at RT, purged under argon for 15 min. To this were added Pd$_2$(dba)$_3$ (10 mg, 0.01 mmol), xantphos (8.5 mg, 0.014 mmol), heated to 100° C. and stirred for 16 h. The reaction was monitored by TLC; after completion of the reaction, the reaction mixture was filtered through celite pad, washed with CH$_2$Cl$_2$ (2×20 mL). The filtrate was removed in vacuo to obtain the crude. The crude was purified through silica gel flash column chromatography using 10-15% EtOAc/hexanes and the obtained compound was triturated using diethyl ether (2×5 mL) to afford 1418 (65 mg, 58%) as white solid. TLC: 30% EtOAc/hexanes (R$_f$ 0.4); $^1$H NMR (DMSO-d$_6$, 400 MHz): δ 11.89 (s, 1H), 7.90 (d, J=8.9 Hz, 2H), 7.61 (dd, J=8.0, 1.0 Hz, 2H), 7.49 (d, J=3.6 Hz, 1H), 7.25 (d, J=3.6 Hz, 1H), 6.58 (s, 1H), 4.01-3.93 (m, 4H), 3.10-3.06 (m, 4H); LC-MS: 96.56%; 554.9 (M$^+$+1); (column; Ascentis Express C18, (50×3.0 mm, 2.7 µm); RT 2.97 min. 0.025% Aq. TFA+5% ACN: ACN+ 5% 0.025% Aq. TFA, 1.2 mL/min); HPLC (purity): 98.13%; (column; Zorbax-SB-C-18 (150×4.6 mm, 3.5 µm); RT 11.39 min. ACN: 0.05% TFA (Aq); 1.0 mL/min).

Example 56: Synthesis of 1378

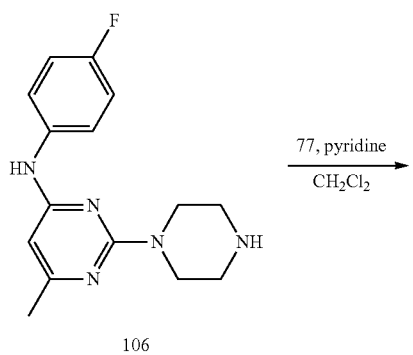

106

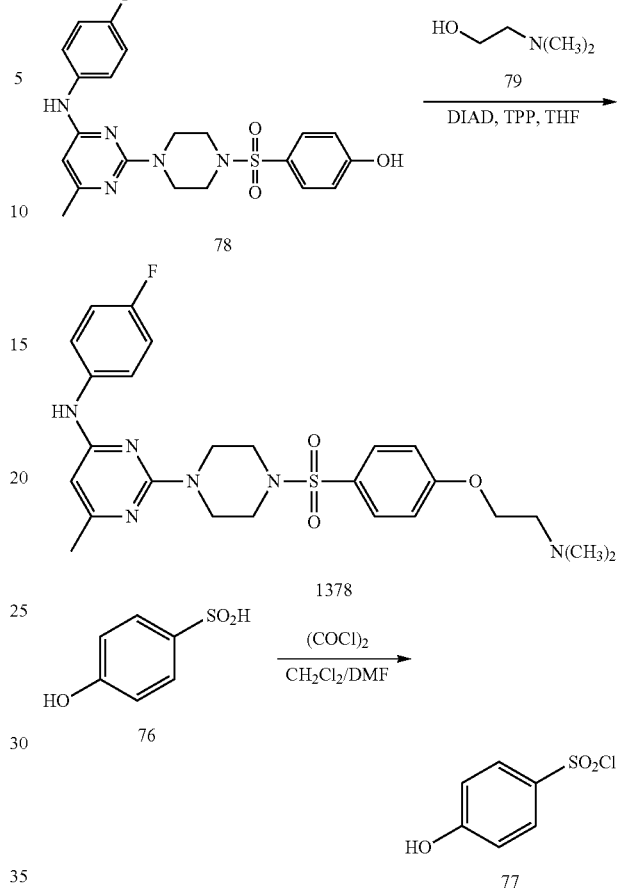

Synthesis of 4-hydroxybenzenesulfonyl chloride (77)

To a stirring solution of 4-hydroxybenzenesulfinic acid 76 (2 g, 9.52 mmol) in CH$_2$Cl$_2$ (30 mL) were added oxalyl chloride (5.45 mL, 57.14 mmol), DMF (10 mL) under argon atmosphere at −30° C.; warmed to RT and stirred for 18 h. The reaction was monitored by TLC; after completion the reaction, the reaction mixture was diluted with ice cold water (30 mL) and extracted with CH$_2$Cl$_2$ (2×50 mL). The combined organic extracts were dried over sodium sulfate, filtered and concentrated in vacuo to obtain the crude compound 77 (2.8 g) as light brown syrup. The crude was carried to the next step without further purification. TLC: 5% MeOH/CH$_2$Cl$_2$ (R$_f$ 0.8); $^1$H-NMR (DMSO-d$_6$, 400 MHz): δ 10.88 (br s, 1H), 7.43 (d, J=8.4 Hz, 2H), 6.70 (d, J=8.4 Hz, 2H).

Synthesis of 4-((4-(4-((4-fluorophenyl) amino)-6-methylpyrimidin-2-yl) piperazin-1-yl) sulfonyl) phenol (78)

To a stirring solution of N-(4-fluorophenyl)-6-methyl-2-(piperazin-1-yl) pyrimidin-4-amine 6 (500 mg, 1.74 mmol) in CH$_2$Cl$_2$ (10 mL) under inert atmosphere were added pyridine (0.70 mL, 8.71 mmol) and 4-hydroxybenzenesulfonyl chloride 77 (503 mg, 2.61 mmol) at 0° C.; warmed to RT and stirred for 16 h. The reaction was monitored by TLC; after completion of the reaction, the reaction mixture was diluted with water (60 mL) and extracted with CH$_2$Cl$_2$ (2×80 mL). The combined organic extracts were dried over sodium sulfate, filtered and concentrated in vacuo to obtain the crude. The crude material was purified through silica gel flash column chromatography using 50-60% EtOAc/hexanes to afford compound 78 (320 mg, 42%) as white solid. TLC: 5% MeOH/CH$_2$Cl$_2$ (R$_f$, 0.6); $^1$H-NMR (DMSO-d$_6$, 500 MHz): δ 10.51 (s, 1H), 9.12 (s, 1H), 7.57-7.51 (m, 4H), 7.10 (t, J=9.0 Hz, 2H), 6.92 (d, J=8.7 Hz, 2H), 5.86 (s, 1H), 3.79-3.71 (m, 4H), 2.88-2.84 (m, 4H), 2.09 (s, 3H).

Synthesis of 2-(4-((4-(2-(dimethylamino) ethoxy) phenyl) sulfonyl) piperazin-1-yl)-N-(4-fluorophenyl)-6-methylpyrimidin-4-amine (1378)

To a stirring solution of compound 78 (100 mg, 0.22 mmol) in THF (5 mL) under inert atmosphere were added diisopropyl azodicarboxylate (137 mg, 0.67 mmol), triphenyl phosphine (177.6 mg, 0.67 mmol) and 2-(dimethylamino) ethan-1-ol 79 (30 mg, 0.33 mmol) at 0° C.; warmed to RT and stirred for 16 h. The reaction was monitored by TLC; after completion of the reaction, the volatiles were removed in vacuo. The residue was diluted with water (30 mL) and extracted with EtOAc (2×40 mL). The combined organic extracts were dried over sodium sulfate, filtered and concentrated in vacuo to obtain the crude. The crude was purified through silica gel flash column chromatography using 5% MeOH/CH$_2$Cl$_2$ to afford 1378 (85 mg, 49%) as white solid. TLC: 5% MeOH/CH$_2$Cl$_2$ (R$_f$, 0.4); $^1$H-NMR (DMSO-d$_6$, 500 MHz): δ 9.14 (s, 1H), 7.67 (d, J=8.7 Hz, 2H), 7.54 (dd, J=8.8, 5.1 Hz, 2H), 7.17-7.09 (m, 4H), 5.87 (s, 1H), 4.17 (t, J=5.4 Hz, 2H), 3.79-3.75 (m, 4H), 2.90-2.87 (m, 4H), 2.80-2.74 (m, 2H), 2.30 (br s, 6H), 2.10 (s, 3H); LC-MS: 99.13%; 515.1 (M$^+$+1); (column; Ascentis Express C18, (50×3.0 mm, 2.7 μm); RT 1.81 min. 0.025% Aq. TFA+5% ACN: ACN+5% 0.025% Aq. TFA, 1.2 mL/min); HPLC (purity): 97.56%; (column; Zorbax SB C-18 (150×4.6 mm, 5 μm); RT 6.60 min. ACN+5% 0.05% TFA (Aq): 0.05% TFA (Aq)+5% ACN; 1.0 mL/min; Diluent: ACN: water).

Example 57: Synthesis of 1394 & 1387

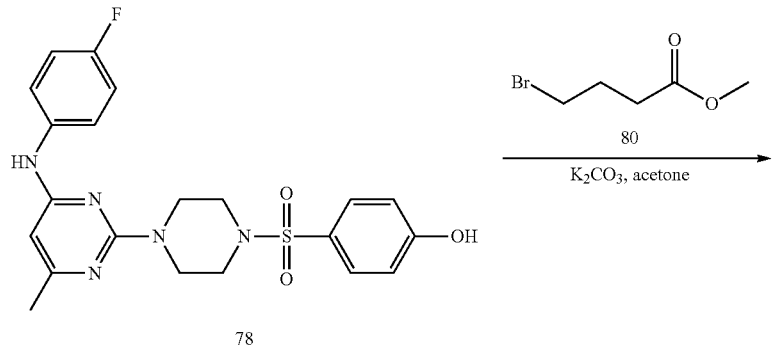

78

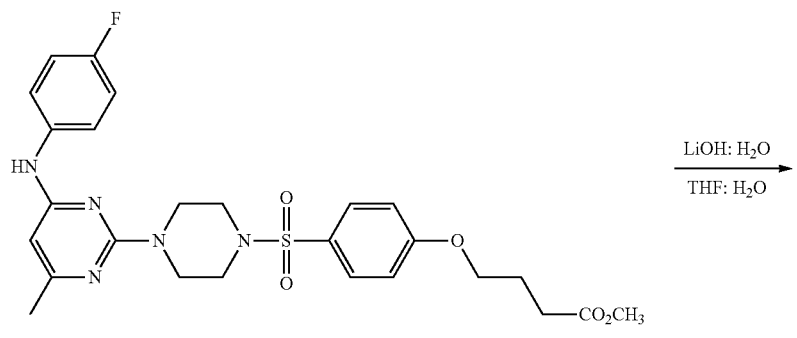

1387

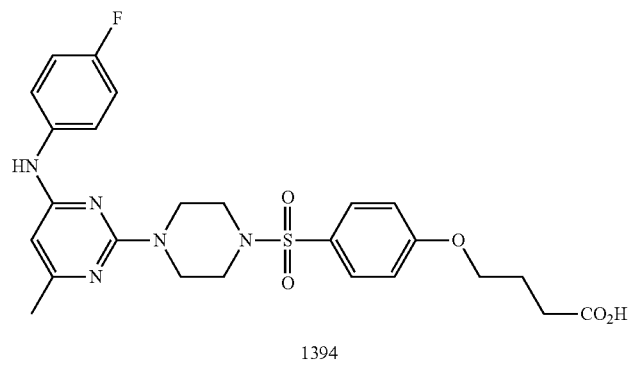

1394

Synthesis of methyl 4-(4-((4-(4-((4-fluorophenyl) amino)-6-methylpyrimidin-2-yl) piperazin-1-yl) sulfonyl) phenoxy) butanoate (1387)

To a stirring solution of compound 78 (200 mg, 0.45 mmol) in acetone (10 mL) under argon atmosphere were added potassium carbonate (124 mg, 0.90 mmol) methyl 4-bromobutanoate 80 (100 mg, 0.54 mmol) at RT; heated to 50° C. and stirred for 16 h. The reaction was monitored by TLC; after completion of the reaction, the volatiles were removed in vacuo. The residue was diluted with water (30 mL) and extracted with $CH_2Cl_2$ (2×25 mL). The combined organic extracts were dried over sodium sulfate, filtered and concentrated in vacuo to obtain the crude. The crude was purified through silica gel column chromatography using 3% MeOH/$CH_2Cl_2$ and the obtained solid was triturated using diethylether (2×5 mL), 20% EtOAc/hexanes (5 mL) and dried in vacuo to afford 1387 (150 mg, 62%) as white solid. TLC: 3% MeOH/$CH_2Cl_2$ ($R_f$, 0.7); $^1$H-NMR (DMSO-$d_6$, 500 MHz): δ 9.14 (s, 1H), 7.66 (d, J=8.9 Hz, 2H), 7.53 (dd, J=9.1, 5.0 Hz, 2H), 7.14-7.09 (m, 4H), 5.86 (s, 1H), 4.07 (t, J=6.3 Hz, 2H), 3.79-3.75 (m, 4H), 3.58 (s, 3H), 2.90-2.86 (m, 4H), 2.46 (t, J=7.3 Hz, 2H), 2.10 (s, 3H), 2.02-1.93 (m, 2H); LC-MS: 94.71%; 544.0 (M$^+$+1); (column; Ascentis Express C18, (50×3.0 mm, 2.7 µm); RT 2.21 min. 0.025% Aq. TFA+5% ACN: ACN+5% 0.025% Aq. TFA, 1.2 mL/min); HPLC (purity): 94.26%; (column; Zorbax SB C-18 (150×4.6 mm, 3.5 µm); RT 8.02 min. ACN: 5% 0.05% TFA (Aq): 0.05% TFA (Aq)+5% ACN 1.0 mL/min; Diluent: ACN: water).

Synthesis of 4-(4-((4-(4-((4-fluorophenyl) amino)-6-methylpyrimidin-2-yl) piperazin-1-yl) sulfonyl) phenoxy) butanoic acid (1394)

To a stirring solution of 1387 (90 mg, 0.16 mmol) in THF:$H_2O$ (4:1, 6 mL) was added lithium hydroxide monohydrate (17 mg, 0.41 mmol) at 0° C.; warmed to RT and stirred for 6 h. The reaction was monitored by TLC; after completion of the reaction, the volatiles were removed in vacuo. The residue was diluted with ice-cold water (10 mL) and the pH was adjusted to ~2 with 2 N HCl. The precipitated solid was filtered, triturated with diethylether (2×5 mL), n-pentane (10 mL) and dried in vacuo to afford 1394 (60 mg, 70%) as an off-white solid. TLC: 10% MeOH/$CH_2Cl_2$ ($R_f$, 0.2); $^1$H-NMR (DMSO-$d_6$, 500 MHz): δ 12.10 (br s, 1H), 10.63 (br s, 1H), 7.67 (d, J=8.7 Hz, 2H), 7.61-7.54 (m, 2H), 7.21 (t, J=8.0 Hz, 2H), 7.14 (d, J=8.7 Hz, 2H), 6.11 (br s, 1H), 4.06 (t, J=6.1 Hz, 2H), 3.87-3.82 (m, 4H), 3.00-2.96 (m, 4H), 2.37 (t, J=7.1 Hz, 2H), 2.27 (br s, 3H), 1.94 (t, J=6.7 Hz, 2H); LC-MS: 96.86%; 530.0 (M$^+$+1); (column; Ascentis Express C18, (50×3.0 mm, 2.7 µm); RT 2.07 min. 0.025% Aq. TFA+5% ACN: ACN+5% 0.025% Aq. TFA, 1.2 mL/min); HPLC (purity): 96.21%; (column; Zorbax SB C-18 (150×4.6 mm, 3.5 µm); RT 7.30 min. ACN: 5% 0.05% TFA (Aq): 0.05% TFA (Aq)+5% ACN 1.0 mL/min; Diluent:ACN:water).

Example 58: Synthesis of 1383

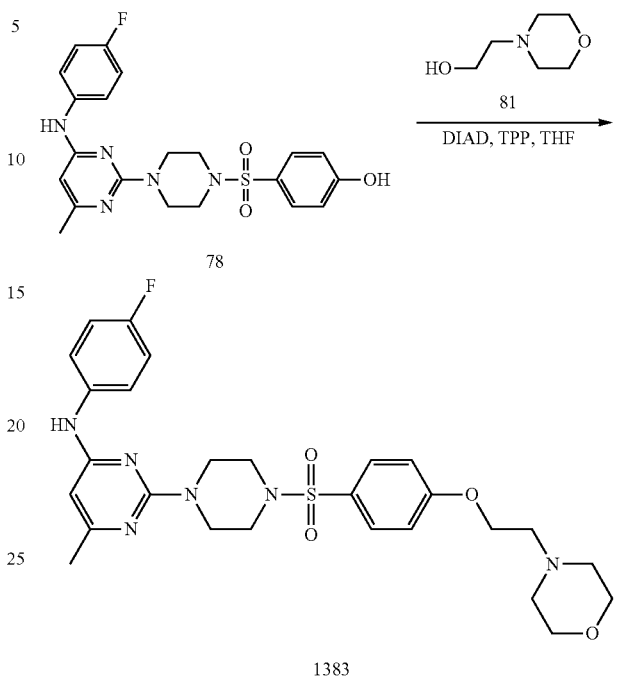

Synthesis of N-(4-fluorophenyl)-6-methyl-2-(4-((4-(2-morpholinoethoxy) phenyl) sulfonyl) piperazin-1-yl) pyrimidin-4-amine (1383)

Using the Mistunobu conditions as described in the preparation of 1378 the title compound was obtained in 52% yield as a white solid. TLC: 5% MeOH/$CH_2Cl_2$ ($R_f$, 0.4); $^1$H-NMR (DMSO-$d_6$, 500 MHz): δ 9.14 (s, 1H), 7.66 (d, J=8.9 Hz, 2H), 7.56-7.51 (m, 2H), 7.17-7.08 (m, 4H), 5.86 (s, 1H), 4.16 (t, J=5.5 Hz, 2H), 3.79-3.75 (m, 4H), 3.57-3.52 (m, 4H), 2.90-2.86 (m, 4H), 2.68 (t, J=5.6 Hz, 2H), 2.90-2.86 (m, 4H), 2.10 (s, 3H); LC-MS: 97.11%; 557.1 (M$^+$+1); (column; Ascentis Express C18, (50×3.0 mm, 2.7 µm); RT 1.74 min. 0.025% Aq. TFA+5% ACN: ACN+5% 0.025% Aq. TFA, 1.2 mL/min); HPLC (purity): 99.22%; (column; Zorbax SB C-18 (150×4.6 mm, 3.5 µm); RT 6.51 min. ACN+5% 0.05% TFA (Aq): 0.05% TFA (Aq)+5% ACN; 1.0 mL/min; Diluent:ACN:water).

Example 59: Synthesis of 1395

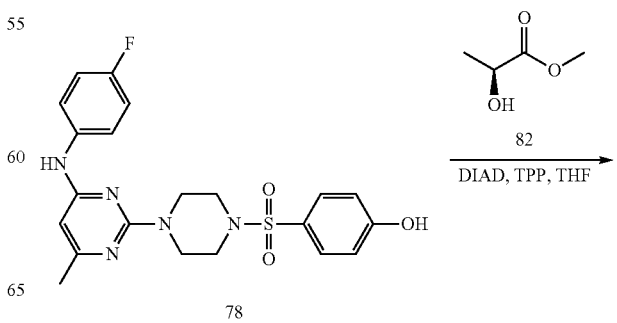

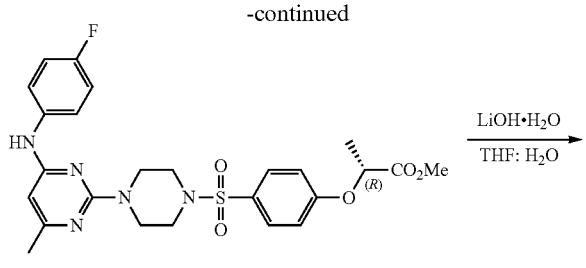

Synthesis of methyl (R)-2-(4-((4-(4-((4-fluorophenyl) amino)-6-methylpyrimidin-2-yl) piperazin-1-yl) sulfonyl) phenoxy) propanoate (83)

To a stirring solution of 4-((4-(4-((4-fluorophenyl) amino)-6-methylpyrimidin-2-yl) piperazin-1-yl) sulfonyl) phenol 78 (150 mg, 0.33 mmol) in THF (10 mL) under inert atmosphere were added diisopropyl azodicarboxylate (205 mg, 1.01 mmol), triphenyl phosphine (266 mg, 1.01 mmol) and methyl (S)-2-hydroxypropanoate 82 (53 mg, 0.50 mmol) at 0° C.; warmed to RT and stirred for 16 h. The reaction was monitored by TLC; after completion of the reaction, the volatiles were removed in vacuo. The residue was diluted with water (30 mL) and extracted with EtOAc (2×30 mL). The combined organic extracts were dried over sodium sulfate, filtered and concentrated in vacuo to obtain the crude. The crude was purified through silica gel flash column chromatography using 30-35% EtOAc/hexanes to afford compound 83 (120 mg, 50%) as white solid. TLC: 50% EtOAc/hexanes ($R_f$ 0.5); $^1$H-NMR (DMSO-$d_6$, 500 MHz): δ 9.14 (s, 1H), 7.67 (d, J=8.7 Hz, 2H), 7.54 (dd, J=8.8, 5.1 Hz, 2H), 7.14-7.07 (m, 4H), 5.87 (s, 1H), 5.14 (q, J=6.7 Hz, 1H), 3.78-3.75 (m, 4H), 3.67 (s, 3H), 2.91-2.88 (m, 4H), 2.10 (s, 3H), 1.52 (d, J=6.7 Hz, 3H).

Synthesis of (R)-2-(4-((4-(4-((4-fluorophenyl) amino)-6-methylpyrimidin-2-yl) piperazin-1-yl) sulfonyl) phenoxy) propanoic acid (1395)

To a stirring solution of compound 83 (90 mg, 0.17 mmol) in THF:H$_2$O (4:1, 5 mL) was added lithium hydroxide monohydrate (8 mg, 0.34 mmol) at RT and stirred for 2 h. The reaction was monitored by TLC; after completion of the reaction, the volatiles were removed in vacuo. The residue was diluted with water (10 mL), washed with diethylether (2×20 mL). The pH of the aqueous layer was acidified with 2 N HCl to ~5-6. The precipitated solid was filtered and dried in vacuo to afford 1395 (70 mg, 80%) as white solid. TLC: 40% EtOAc/hexanes ($R_f$ 0.2); $^1$H-NMR (DMSO-$d_6$, 500 MHz): δ 13.13 (br s, 1H), 11.86 (br s, 1H), 7.66 (d, J=8.7 Hz, 2H), 7.56-7.50 (m, 2H), 7.19-7.13 (m, 2H), 7.06 (d, J=9.0 Hz, 2H), 5.97 (br s, 1H), 4.96 (q, J=6.7 Hz, 1H), 3.80-3.76 (m, 4H), 2.98-2.90 (m, 4H), 2.18 (br s, 3H), 1.50 (d, J=6.9 Hz, 3H); LC-MS: 97.99%; 516.0 (M$^+$+1); (column; Ascentis Express C18, (50×3.0 mm, 2.7 μm); RT 1.99 min. 0.025% Aq. TFA+5% ACN: ACN+5% 0.025% Aq. TFA, 1.2 mL/min); HPLC (purity): 96.35%; (column; Zorbax SB C-18 (150×4.6 mm, 3.5 μm); RT 7.21 min. ACN: 0.05% TFA (Aq); 1.0 mL/min; Diluent:ACN:water).

Example 60: Synthesis of 1396

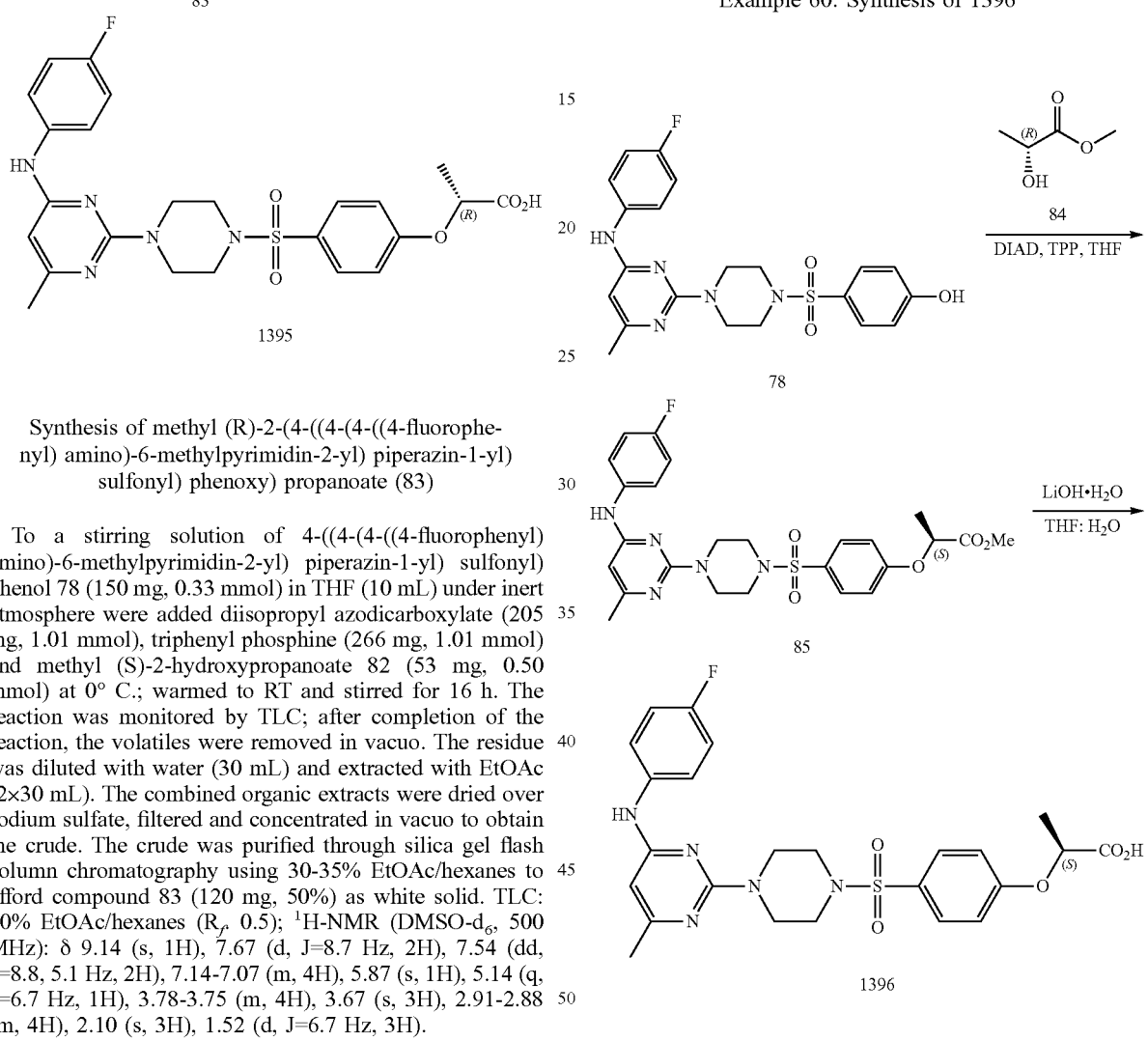

Synthesis of methyl (S)-2-(4-((4-(4-((4-fluorophenyl) amino)-6-methylpyrimidin-2-yl) piperazin-1-yl) sulfonyl) phenoxy) propanoate (85)

To a stirring solution of 4-((4-(4-((4-fluorophenyl) amino)-6-methylpyrimidin-2-yl) piperazin-1-yl) sulfonyl) phenol 78 (150 mg, 0.33 mmol) in THF (10 mL) under inert atmosphere were added diisopropyl azodicarboxylate (205 mg, 1.01 mmol), triphenyl phosphine (266 mg, 1.01 mmol) and methyl (R)-2-hydroxypropanoate 84 (53 mg, 0.50 mmol) at 0° C.; warmed to RT and stirred for 16 h. The reaction was monitored by TLC; after completion of the reaction, the volatiles were removed in vacuo. The residue was diluted with water (30 mL) and extracted with EtOAc (2×30 mL). The combined organic extracts were dried over sodium sulfate, filtered and concentrated in vacuo to obtain the crude. The crude was purified through silica gel flash column chromatography using 30-35% EtOAc/hexanes to afford compound 85 (150 mg, 63%) as white solid. TLC: 50% EtOAc/hexanes ($R_f$ 0.5); $^1$H-NMR (DMSO-$d_6$, 500 MHz): δ 9.14 (s, 1H), 7.67 (d, J=9.0 Hz, 2H), 7.54 (dd, J=9.0, 4.9 Hz, 2H), 7.14-7.06 (m, 4H), 5.87 (s, 1H), 5.14 (q, J=6.7 Hz, 1H), 3.78-3.75 (m, 4H), 3.67 (s, 3H), 2.91-2.88 (m, 4H), 2.10 (s, 3H), 1.52 (d, J=6.7 Hz, 3H).

Synthesis of (S)-2-(4-((4-(4-((4-fluorophenyl) amino)-6-methylpyrimidin-2-yl) piperazin-1-yl) sulfonyl) phenoxy) propanoic acid (1396)

To a stirring solution of compound 85 (120 mg, 0.22 mmol) in THF:H$_2$O (4:1, 5 mL) was added lithium hydroxide monohydrate (11 mg, 0.45 mmol) at RT and stirred for 2 h. The reaction was monitored by TLC; after completion of the reaction, the volatiles were removed in vacuo. The residue was diluted with water (15 mL), washed with diethylether (2×20 mL). The pH of the aqueous layer was acidified with 2 N HCl to ~5-6. The precipitated solid was filtered and dried in vacuo to afford 1396 (110 mg, 95%) as white solid. TLC: 40% EtOAc/hexanes ($R_f$ 0.2); $^1$H-NMR (DMSO-$d_6$, 500 MHz): δ 13.14 (br s, 1H), 11.91 (br s, 1H), 7.66 (d, J=8.7 Hz, 2H), 7.57-7.50 (m, 2H), 7.19-7.13 (m, 2H), 7.06 (d, J=8.7 Hz, 2H), 5.98 (br s, 1H), 4.96 (q, J=6.7 Hz, 1H), 3.81-3.77 (m, 4H), 2.97-2.91 (m, 4H), 2.18 (br s, 3H), 1.50 (d, J=6.7 Hz, 3H); LC-MS: 97.48%; 516.0 (M$^+$+1); (column; Ascentis Express C18, (50×3.0 mm, 2.7 μm); RT 1.98 min. 0.025% Aq. TFA+5% ACN: ACN+5% 0.025% Aq. TFA, 1.2 mL/min); HPLC (purity): 94.17%; (column; Zorbax SB C-18 (150×4.6 mm, 3.5 μm); RT 7.21 min. ACN: 0.05% TFA (Aq); 1.0 mL/min; Diluent:ACN:water).

Example 61: Synthesis of 1384 & 1385

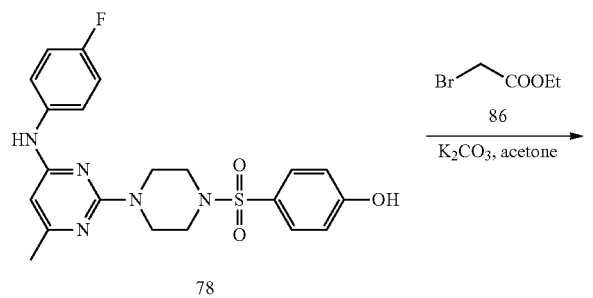

78

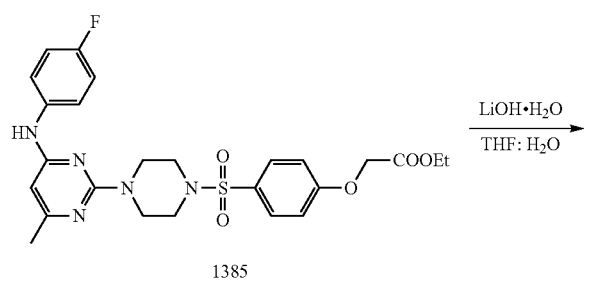

1385

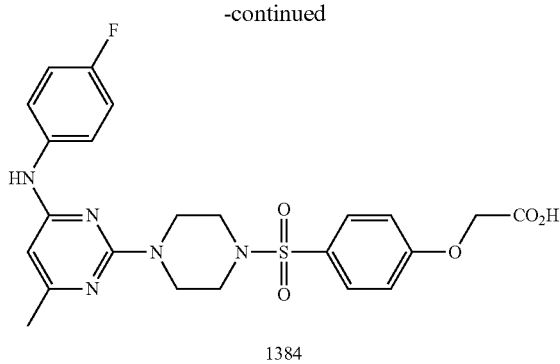

1384

Synthesis of ethyl 2-(4-((4-(4-((4-fluorophenyl) amino)-6-methylpyrimidin-2-yl) piperazin-1-yl) sulfonyl) phenoxy) acetate (1385)

To a stirring solution of 4-((4-(4-((4-fluorophenyl) amino)-6-methylpyrimidin-2-yl) piperazin-1-yl) sulfonyl) phenol 78 (50 mg, 0.11 mmol) in acetone (5 mL) under inert atmosphere were added potassium carbonate (47 mg, 0.33 mmol) and ethyl 2-bromoacetate 86 (22.6 mg, 0.13 mmol) at 0° C.; heated to 70° C. and stirred for 16 h. The reaction was monitored by TLC; after completion of the reaction, the volatiles were removed in vacuo. The residue was diluted with water (30 mL) and extracted with EtOAc (2×30 mL). The combined organic extracts were dried over sodium sulfate, filtered and concentrated in vacuo to obtain the crude. The crude was purified through silica gel flash column chromatography using 30-40% EtOAc/hexanes to afford 1385 (100 mg, 84%) as white solid. TLC: 50% EtOAc/hexanes ($R_f$ 0.6); $^1$H-NMR (DMSO-$d_6$, 400 MHz): δ 9.14 (s, 1H), 7.68 (d, J=8.9 Hz, 2H), 7.57-7.50 (m, 2H), 7.17-7.09 (m, 4H), 5.86 (s, 1H), 4.89 (s, 2H), 4.15 (q, J=7.1 Hz, 2H), 3.79-3.75 (m, 4H), 2.91-2.87 (m, 4H), 2.10 (s, 3H), 1.18 (t, J=7.1 Hz, 3H); LC-MS: 98.01%; 530.0 (M$^-$+1); (column; Ascentis Express C18, (50×3.0 mm, 2.7 μm); RT 2.15 min. 0.025% Aq. TFA+5% ACN: ACN+5% 0.025% Aq. TFA, 1.2 mL/min); HPLC (purity): 97.05%; (column; Zorbax SB C-18 (150×4.6 mm, 3.5 μm); RT 7.90 min. ACN: 0.05% TFA (Aq); 1.0 mL/min; Diluent:ACN:water).

Synthesis of 2-(4-((4-(4-((4-fluorophenyl) amino)-6-methylpyrimidin-2-yl) piperazin-1-yl) sulfonyl) phenoxy) acetic acid (1384)

To a stirring solution of 1385 (80 mg, 0.15 mmol) in THF:H$_2$O (4:1, 5 mL) was added lithium hydroxide monohydrate (6 mg, 0.22 mmol) at RT and stirred for 2 h. The reaction was monitored by TLC; after completion of the reaction, the volatiles were removed in vacuo. The residue was diluted with water (15 mL) and acidified with 2 N HCl to pH~2. The precipitated solid was filtered. The solid was diluted with water (15 mL), stirred for 2 h, filtered and dried in vacuo to afford 1384 (56 mg, 74%) as white solid. TLC: 50% EtOAc/hexanes ($R_f$ 0.2); $^1$H-NMR (DMSO-$d_6$, 400 MHz): δ 13.09 (br s, 1H), 9.13 (br s, 1H), 7.68 (d, J=8.9 Hz, 2H), 7.54 (dd, J=9.0, 5.0 Hz, 2H), 7.14-7.09 (m, 4H), 5.87 (s, 1H), 4.79 (s, 2H), 3.80-3.75 (m, 4H), 2.92-2.88 (m, 4H), 2.10 (s, 3H); LC-MS: 99.48%; 502.0 (M$^+$+1); (column; Ascentis Express C18, (50×3.0 mm, 2.7 μm); RT 2.04 min. 0.025% Aq. TFA+5% ACN: ACN+5% 0.025% Aq. TFA, 1.2 mL/min); HPLC (purity): 99.01%; (column; Zorbax SB C-18 (150×4.6 mm, 3.5 μm); RT 6.18 min. ACN: 0.05% TFA (Aq); 1.0 mL/min; Diluent:ACN:water).

Example 62: Synthesis of 1403 and 1404

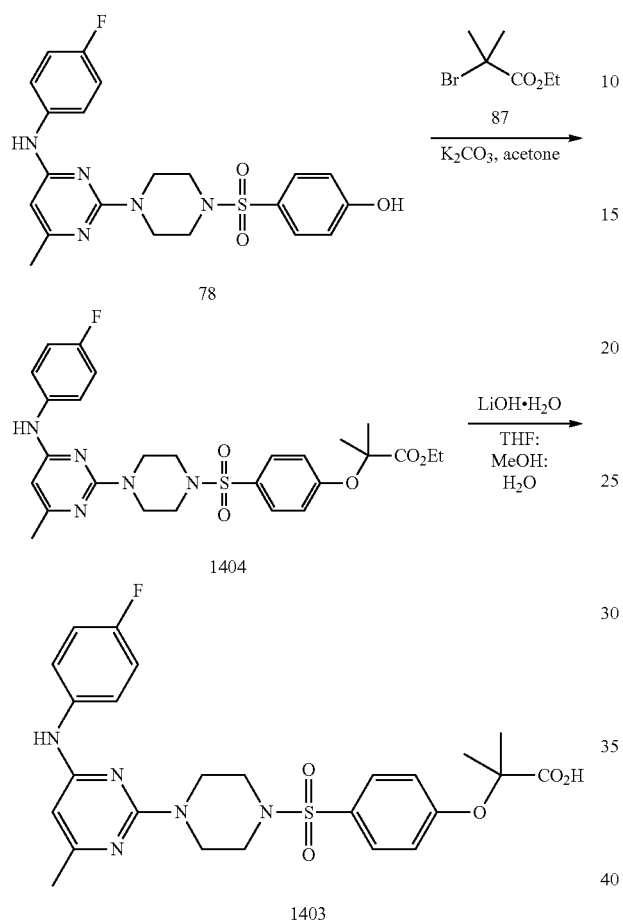

Synthesis of ethyl 2-(4-((4-(4-((4-fluorophenyl) amino)-6-methylpyrimidin-2-yl) piperazin-1-yl) sulfonyl) phenoxy)-2-methylpropanoate (1404)

To a stirring solution of 4-((4-(4-((4-fluorophenyl) amino)-6-methylpyrimidin-2-yl) piperazin-1-yl) sulfonyl) phenol 78 (200 mg, 0.45 mmol) in acetone (5 mL) under inert atmosphere were added potassium carbonate (124 mg, 0.90 mmol) and ethyl 2-bromo-2-methylpropanoate 87 (88 mg, 0.45 mmol) at RT; heated to reflux and stirred for 32 h. The reaction was monitored by TLC; after completion of the reaction, the reaction mixture was filtered through celite, washed with EtOAc (2×30 mL) and the filtrate was concentrated in vacuo to obtain the crude. The crude was purified through silica gel column chromatography using 20-35% EtOAc/hexanes to afford HVBS-284-A (95 mg, 38%) as an off-white solid. TLC: 50% EtOAc/hexanes ($R_f$ 0.5); $^1$H-NMR (DMSO-$d_6$, 500 MHz): δ 9.14 (s, 1H), 7.65 (d, J=9.0 Hz, 2H), 7.54 (dd, J=8.8, 5.1 Hz, 2H), 7.11 (t, J=9.0 Hz, 2H), 6.95 (d, J=8.7 Hz, 2H), 5.87 (s, 1H), 4.12 (q, J=6.9 Hz, 2H), 3.78-3.75 (m, 4H), 2.91-2.88 (m, 4H), 2.10 (s, 3H), 1.58 (s, 6H), 1.06 (t, J=7.1 Hz, 3H); LC-MS: 96.44%; 558.1 (M$^+$+1); (column; X-Select CSH C-18, (50×3.0 mm, 2.5 μm); RT 3.81 min. 2.5 mM Aq. NH$_4$OOCH+5% ACN: ACN+5% 2.5 mM Aq. NH$_4$OOCH, 0.8 mL/min); HPLC (purity): 97.24%; (column; Zorbax SB C-18 (150×4.6 mm, 3.5 μm); RT 8.79 min. ACN+5% 0.05% TFA (Aq): 0.05% TFA (Aq)+5% ACN; 1.0 mL/min; Diluent:ACN:water).

Synthesis of 2-(4-((4-(4-((4-fluorophenyl) amino)-6-methylpyrimidin-2-yl) piperazin-1-yl) sulfonyl) phenoxy)-2-methylpropanoic acid (1403)

To a stirring solution of 1404 (70 mg, 0.12 mmol) in THF:MeOH:H$_2$O (3:1:1, 5 mL) was added lithium hydroxide monohydrate (10.55 mg, 0.24 mmol) at RT and stirred for 32 h. The reaction was monitored by TLC; after completion of the reaction, the volatiles were removed in vacuo. The residue was diluted with water (10 mL) and acidified with 2 N HCl to ~3. The precipitated solid was filtered washed with water (10 mL) and dried in vacuo to afford 1403 (56 mg, 84%) as white solid. TLC: 50% EtOAc/hexanes ($R_f$ 0.2); $^1$H-NMR (DMSO-$d_6$, 500 MHz): δ 13.24 (br s, 1H), 9.18 (br s, 1H), 7.67 (d, J=8.7 Hz, 2H), 7.57-7.53 (m, 2H), 7.19-7.12 (m, 2H), 6.97 (d, J=9.0 Hz, 2H), 5.93 (br s, 1H), 3.82-3.77 (m, 4H), 2.98-2.91 (m, 4H), 2.16 (br s, 3H), 1.56 (s, 6H); LC-MS: 99.27%; 530.0 (M$^+$+1); (column; Ascentis Express C18, (50×3.0 mm, 2.7 μm); RT 2.12 min. 0.025% Aq. TFA+5% ACN: ACN+5% 0.025% Aq. TFA, 1.2 mL/min); HPLC (purity): 99.53%; (column; Zorbax SB C-18 (150×4.6 mm, 3.5 μm); RT 7.89 min. ACN+0.05% TFA (Aq): 0.5% TFA (Aq)+5% ACN; 1.0 mL/min; Diluent: ACN:water).

Example 63: Synthesis of 1377

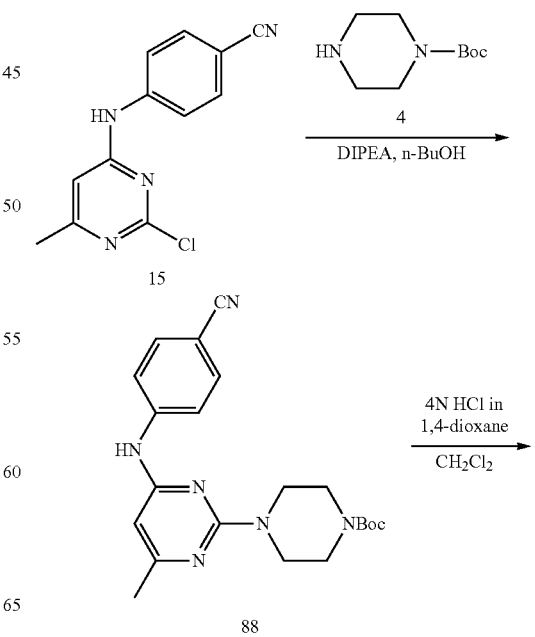

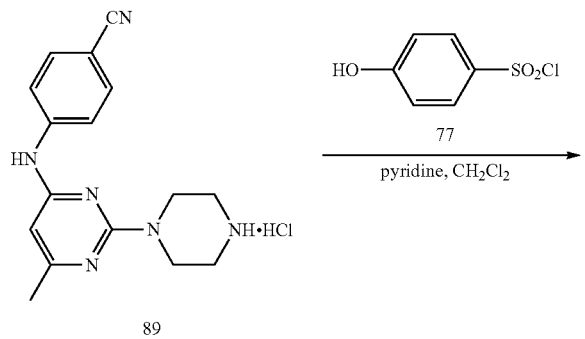

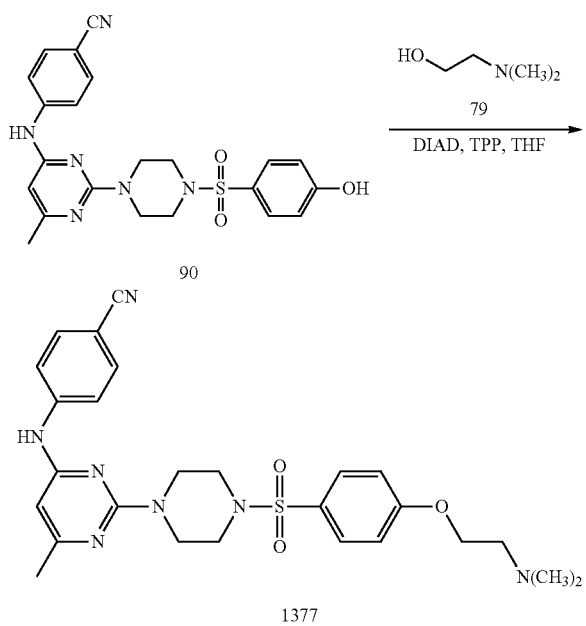

h. The reaction was monitored by TLC; after completion of the reaction, the volatiles were removed in vacuo. The crude was triturated using diethylether (2×30 mL) and dried in vacuo to afford compound 89 (1.2 g, 96%) as an off-white solid. TLC: 40% EtOAc/hexanes ($R_f$, 0.2); $^1$H NMR (DMSO-$d_6$, 400 MHz): δ 10.96 (br s, 1H), 9.42 (br s, 2H), 7.86-7.78 (m, 4H), 6.32 (br s, 1H), 4.05-4.01 (m, 4H), 3.24-3.19 (m, 4H), 2.36 (s, 3H).

Synthesis of 4-((2-(4-((4-hydroxyphenyl) sulfonyl) piperazin-1-yl)-6-methylpyrimidin-4-yl) amino) benzonitrile (90)

To a stirring solution of compound 89 (1 g, 3.03 mmol) in $CH_2Cl_2$ (10 mL) under inert atmosphere were added pyridine (1.23 mL, 15.15 mmol) and 4-hydroxybenzenesulfonyl chloride 77 (875 mg, 4.54 mmol) at 0° C.; warmed to RT and stirred for 16 h. The reaction was monitored by TLC; after completion of the reaction, the reaction mixture was quenched with ice-cold water (60 mL) and extracted with $CH_2Cl_2$ (2×60 mL). The combined organic extracts were dried over sodium sulfate, filtered and concentrated in vacuo to obtain the crude. The crude material was purified through silica gel flash column chromatography using 2-3% MeOH/$CH_2Cl_2$ to afford compound 90 (600 mg, 44%) as an off-white solid. TLC: 5% MeOH/$CH_2Cl_2$ ($R_f$: 0.8); $^1$H-NMR (DMSO-$d_6$, 500 MHz): δ 10.52 (s, 1H), 9.68 (s, 1H), 7.82-7.69 (m, 4H), 7.57 (d, J=8.7 Hz, 2H), 6.93 (d, J=8.7 Hz, 2H), 5.99 (s, 1H), 3.80-3.77 (m, 4H), 2.91-2.88 (m, 4H), 2.15 (s, 3H).

Synthesis of 4-((2-(4-((4-(2-(dimethylamino) ethoxy) phenyl) sulfonyl) piperazin-1-yl)-6-methyl-pyrimidin-4-yl) amino) benzonitrile (1377)

To a stirring solution of compound 90 (100 mg, 0.22 mmol) in THF (5 mL) under inert atmosphere were added diisopropyl azodicarboxylate (135 mg, 0.66 mmol), triphenyl phosphine (173 mg, 0.66 mmol) and 2-(dimethylamino) ethan-1-ol 79 (30 mg, 0.33 mmol) at 0° C.; warmed to RT and stirred for 16 h. The reaction was monitored by TLC; after completion of the reaction, the reaction mixture was diluted water (30 mL) and extracted with EtOAc (2×50 mL). The combined organic extracts were dried over sodium sulfate, filtered and concentrated in vacuo to obtain the crude. The crude was purified through silica gel flash column chromatography using 5% MeOH/$CH_2Cl_2$ to afford 1377 (70 mg, 40%) as an off-white solid. TLC: 5% % MeOH/$CH_2Cl_2$ ($R_f$, 0.2); $^1$H-NMR (DMSO-$d_6$, 500 MHz): δ 9.68 (s, 1H), 7.76 (d, J=9.3 Hz, 2H), 7.71 (d, J=8.7, 2H), 7.68 (d, J=9.0 Hz, 2H), 7.16 (d, J=8.7 Hz, 2H), 5.99 (s, 1H), 4.20 (t, J=5.4 Hz, 2H), 3.82-3.78 (m, 4H), 2.94-2.90 (m, 4H), 2.88-2.84 (m, 2H), 2.37 (br s, 6H), 2.15 (s, 3H); LC-MS: 97.67%; 522.1 (M$^+$+1); (column; Ascentis Express C18, (50×3.0 mm, 2.7 μm); RT 1.82 min. 0.025% Aq. TFA+5% ACN: ACN+5% 0.025% Aq. TFA, 1.2 mL/min); HPLC (purity): 95.68%; (column; Zorbax SB C-18 (150×4.6 mm, 3.5 μm); RT 6.51 min. ACN+5% 0.05% TFA (Aq): 0.05% TFA (Aq)+5% ACN; 1.0 mL/min; Diluent:ACN: water).

Synthesis of tert-butyl 4-(4-((4-cyanophenyl) amino)-6-methylpyrimidin-2-yl) piperazine-1-carboxylate (88)

To a stirring solution of 4-((2-chloro-6-methylpyrimidin-4-yl) amino) benzonitrile 15 (2 g, 8.19 mmol) in n-butanol (20 mL) under argon atmosphere were added tert-butyl piperazine-1-carboxylate 4 (2.29 g, 12.29 mmol) and diisopropylethylamine (2.8 mL, 16.39 mmol) at RT; heated to 100° C. and stirred for 30 h. The reaction was monitored by TLC; after completion of the reaction, the volatiles were removed in vacuo to obtain the crude. The crude was purified through flash column chromatography using 20-25% EtOAc/hexanes to afford compound 88 (2.45 g, 76%) as white solid. TLC: 50% EtOAc/hexanes ($R_f$, 0.8); $^1$H NMR (DMSO-$d_6$, 400 MHz): δ 9.65 (s, 1H), 7.81 (d, J=8.8 Hz, 2H), 7.72 (d, J=9.0 Hz, 2H), 6.01 (s, 1H), 3.72-3.67 (m, 4H), 3.40-3.38 (m, 4H), 2.19 (s, 3H), 1.43 (s, 9H).

Synthesis of 4-((6-methyl-2-(piperazin-1-yl) pyrimidin-4-yl) amino) benzonitrile hydrochloride (89)

To a stirring solution of 88 (1.5 g, 3.80 mmol) in $CH_2Cl_2$ (15 mL) was added 4 N HCl in 1, 4-dioxane (7.5 mL) under argon atmosphere at 0° C.; warmed to RT and stirred for 2

Example 64: Synthesis of 4 4-((4-(4-((4-fluorophenyl) amino)-6-(trifluoromethyl) pyrimidin-2-yl) piperazin-1-yl) sulfonyl) phenol (1091): A Common Intermediate

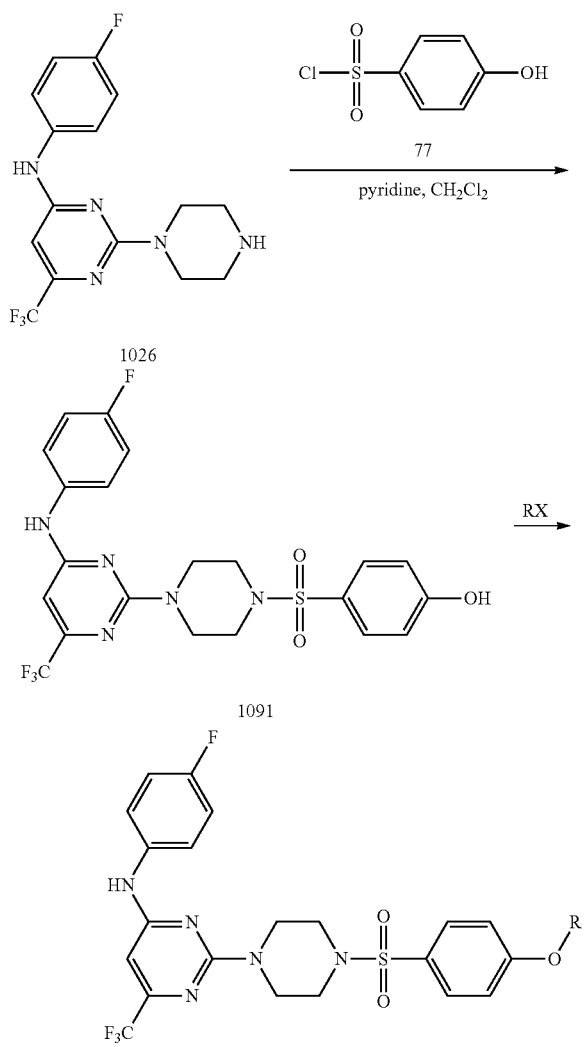

Synthesis of 4 4-((4-(4-((4-fluorophenyl) amino)-6-(trifluoromethyl) pyrimidin-2-yl) piperazin-1-yl) sulfonyl) phenol (1091)

To a stirring solution of N-(4-fluorophenyl)-2-(piperazin-1-yl)-6-(trifluoromethyl) pyrimidin-4-amine 1026 (2 g, 5.86 mmol) in $CH_2Cl_2$ (150 mL) under inert atmosphere were added pyridine (4.8 mL, 58.6 mmol) and 4-hydroxybenzenesulfonyl chloride 77 (1.7 g, 8.79 mmol) at 0° C.; warmed to RT and stirred for 20 min. The reaction was monitored by TLC; after completion of the reaction, the reaction mixture was quenched with ice-cold water, extracted with $CH_2Cl_2$ (2×200 mL), The combined organic extracts were dried over sodium sulfate, filtered and concentrated in vacuo to obtain the crude. The crude material was purified through silica gel column chromatography using 2% $MeOH/CH_2Cl_2$ and titurated with mixture of diethylether:n-pentane (2:1, 50 mL) to afford compound 1091 (2.9 g, 70%) as an off-white solid.

TLC: 5% $MeOH/CH_2Cl_2$ ($R_f$ 0.8); $^1$H-NMR (DMSO-$d_6$, 500 MHz): δ 10.51 (br s, 1H), 9.75 (s, 1H), 7.54 (d, J=8.7 Hz, 4H), 7.16 (t, J=9.0 Hz, 2H), 6.32 (s, 1H), 6.91 (d, J=8.7 Hz, 2H), 3.79-3.75 (m, 4H), 2.91-2.86 (m, 4H); LC-MS: 80.10%; 498.0 ($M^+$+1); (column; Ascentis Express C18, (50×3.0 mm, 2.7 μm); RT 2.78 min. 0.025% Aq. TFA+5% ACN: ACN+5% 0.025% Aq. TFA, 1.2 mL/min);

Compound 1091 was synthesized as mentioned above and converted to final products using commercially available bromo compounds employing typical procedure B and the results are captured in the Table 8:

Commercially Available Alkyl Bromide Used for the Synthesis of Test Compounds

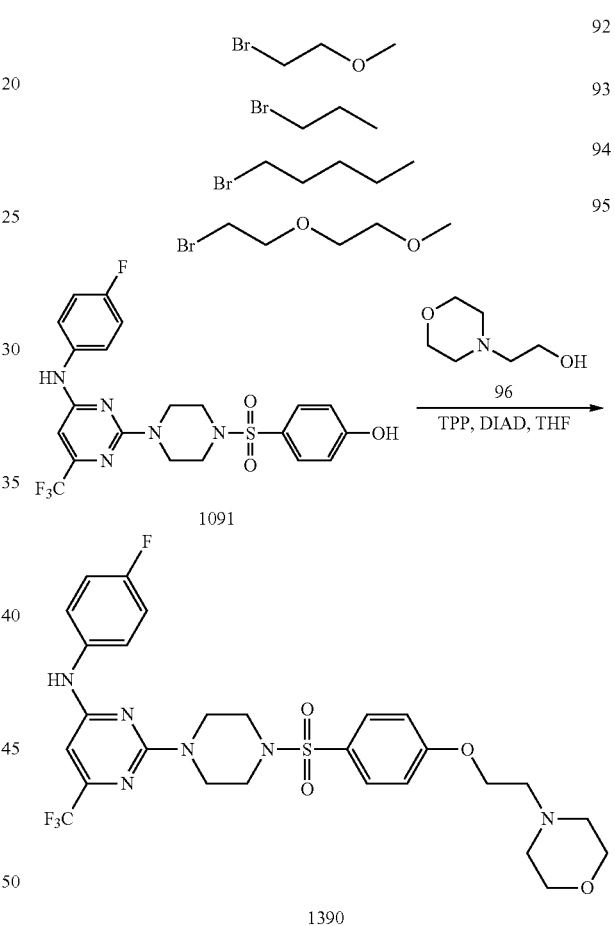

Typical Procedure B:

To a stirring solution of compound 1091 (100 mg, 0.20 mmol) in acetone (10 mL) under inert atmosphere were added potassium carbonate (55 mg, 0.40 mmol) and 1-bromo-2-methoxyethane 92 (22 mg, 0.16 mmol) at 0-5° C.; heated to reflux and stirred for 16 h. The reaction was monitored by TLC; after completion of the reaction, the reaction mixture was extracted with EtOAc (2×30 mL) or $CH_2Cl_2$ or filtered through celite. The combined organic extracts or the filtrate were dried over sodium sulfate, filtered and concentrated in vacuo to obtain the crude. The crude material was either directly dried in vacuo or triturated or purified through silica gel flash column chromatography to afford the desired compound.

TABLE 8

Synthesis of test compounds from compounds 1091 and commercially available alkyl bromo compounds

| No | Structure | Procedure, Intermediate, alkyl bromide | Rx. Yield (%) | Mass Spec. Found | Mass Spec. Calculated | ¹H-NMR |
|----|-----------|----------------------------------------|---------------|------------------|-----------------------|--------|
| 1407 | 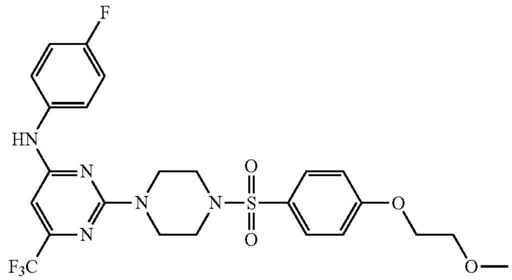 [SMILES: COCCOc1ccc(S(=O)(=O)N2CCN(c3nc(Nc4ccc(F)cc4)cc(C(F)(F)F)n3)CC2)cc1] | B, 1091, 92 | 22 | 556.0 (M$^+$ + 1) | 555.16 for C$_{24}$H$_{25}$F$_4$N$_5$O$_4$S | ¹H NMR (DMSO-d$_6$, 500 MHz): 9.76 (s, 1H), 7.66 (d, J = 9.0 Hz, 2H), 7.57 (dd, J = 8.4, 4.9 Hz, 2H), 7.21-7.13 (m, 4H), 6.33 (s, 1H), 4.19-4.16 (m, 2H), 3.81-3.77 (m, 4H), 3.67-3.64 (m, 2H), 3.28 (s, 3H), 2.94-2.90 (m, 4H); |
| 1400 | 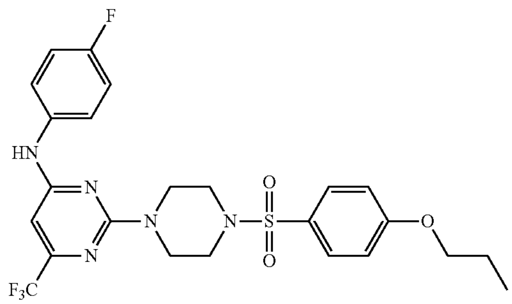 [SMILES: CCCOc1ccc(S(=O)(=O)N2CCN(c3nc(Nc4ccc(F)cc4)cc(C(F)(F)F)n3)CC2)cc1] | B$^a$, 1091, 93 | 51 | 540.2 (M$^+$ + 1) | 539.16 for C$_{24}$H$_{25}$F$_4$N$_5$O$_3$S | ¹H NMR (DMSO-d$_6$, 500 MHz): δ 9.77 (s, 1H), 7.66 (d, J = 8.7 Hz, 2H), 7.58 (dd, J = 8.7, 4.9 Hz, 2H), 7.18 (t, J = 8.8 Hz, 2H), 7.12 (d, J = 9.0 Hz, 2H), 6.33 (s, 1H), 4.00 (t, J = 6.5 Hz, 2H), 3.81-3.78 (m, 4H), 2.95-2.91 (m, 4H), 1.77-1.68 (m, 2H), 0.96 (t, J = 7.4 Hz, 3H); |
| 1401 | 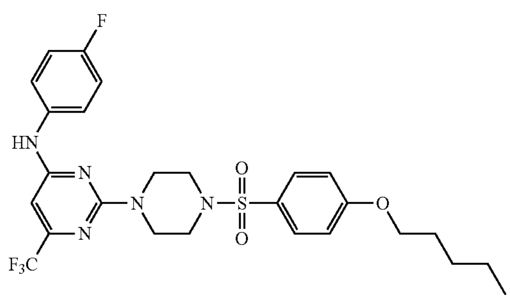 [SMILES: CCCCCOc1ccc(S(=O)(=O)N2CCN(c3nc(Nc4ccc(F)cc4)cc(C(F)(F)F)n3)CC2)cc1] | B$^b$, 1091, 94 | 44 | 568.1 (M$^+$ + 1) | 567.19 for C$_{26}$H$_{29}$F$_4$N$_5$O$_3$S | ¹H NMR (DMSO-d$_6$, 500 MHz): δ 9.75 (s, 1H), 7.64 (d, J = 9.0 Hz, 2H), 7.56 (dd, J = 8.5, 5.1 Hz, 2H), 7.16 (t, J = 8.8 Hz, 2H), 7.10 (d, J = 9.0 Hz, 2H), 6.32 (s, 1H), 4.01 (t, J = 6.5 Hz, 2H), 3.80-3.76 (m, 4H), 2.93-2.89 (m, 4H), 1.73-1.65 (m, 2H), 1.39-1.26 (m, 4H), 0.85 (t, J = 7.1 Hz, 3H); |
| 1402 | 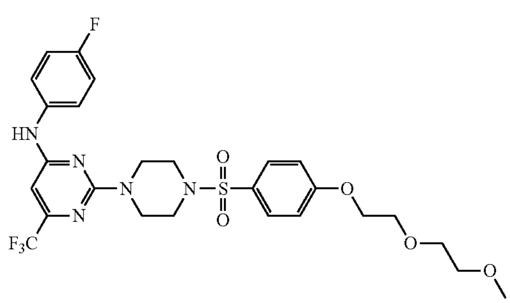 [SMILES: COCCOCCOc1ccc(S(=O)(=O)N2CCN(c3nc(Nc4ccc(F)cc4)cc(C(F)(F)F)n3)CC2)cc1] | B$^c$, 1091, 95 | 21 | 600.0 (M$^+$ + 1) | 599.18 for C$_{26}$H$_{29}$F$_4$N$_5$O$_5$S | ¹H NMR (DMSO-d$_6$, 500 MHz): 9.75 (s, 1H), 7.65 (d, J = 9.0 Hz, 2H), 7.56 (dd, J = 8.1, 4.9 Hz, 2H), 7.21-7.11 (m, 4H), 6.32 (s, 1H), 4.18-4.15 (m, 2H), 3.80-3.77 (m, 4H), 3.74-3.70 (m, 2H), 3.55 (t, J = 4.6 Hz, 2H), 3.43-3.40 (m, 2H), 3.20 (s, 3H), 2.94-2.89 (m, 4H); |

$^a$1-bromopropane 93 (1.1 equiv), RT, 24 h;
$^b$16 h RT, 1-bromopentane 94 (1.1 equiv), RT, 16 h;
$^c$K$_2$CO$_3$ (3 equiv), 1-bromo-2-(2-methoxyethoxy) ethane 95 (1.2 equiv)

Example 65: Synthesis of 1389

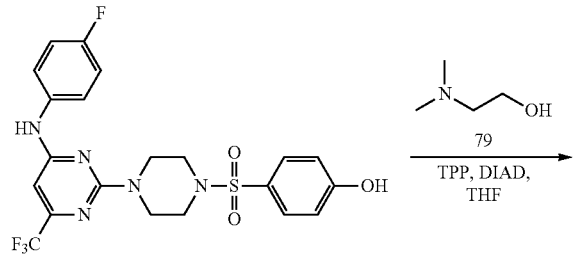

91

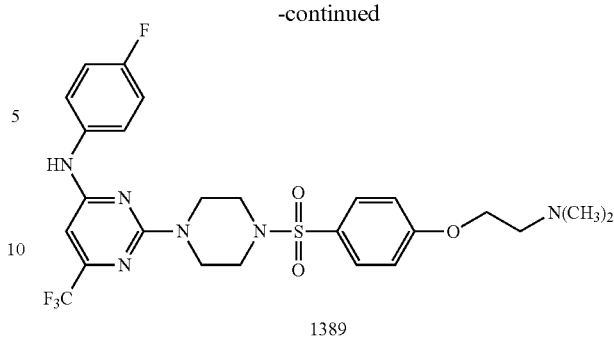

1389

Synthesis of 2-(4-((4-(2-(dimethylamino) ethoxy) phenyl) sulfonyl) piperazin-1-yl)-N-(4-fluorophenyl)-6-(trifluoromethyl) pyrimidin-4-amine (1389)

To a mixture of 4-((4-(4-((4-fluorophenyl) amino)-6-(trifluoromethyl) pyrimidin-2-yl) piperazin-1-yl) sulfonyl) phenol 1091 (150 mg, 0.30 mmol) and 2-(dimethylamino) ethan-1-ol 79 (0.05 mL, 0.45 mmol) in THF (5 mL) under inert atmosphere were added triphenyl phosphine (237 mg, 0.90 mmol) and diisopropyl azodicarboxylate (183 mg, 0.90 mmol) was added dropwise for 5 min at 0° C.; warmed to RT and stirred for 16 h. The reaction was monitored by TLC; after completion of the reaction, the reaction mixture was diluted with EtOAc (50 mL), washed with water (30 mL) and brine (30 mL). The combined organic extracts were dried over sodium sulfate, filtered and concentrated in vacuo to obtain the crude. The crude was purified through silica gel column chromatography using 4-5% MeOH/CH$_2$Cl$_2$ and triturated with 2% EtOAc/hexanes to afford 1389 (70 mg, 41%) as an off-white solid. TLC: 10% MeOH/CH$_2$Cl$_2$ (R$_f$ 0.3); $^1$H-NMR (DMSO-d$_6$, 500 MHz): δ 9.77 (br s, 1H), 7.66 (d, J=8.4 Hz, 2H), 7.60-7.58 (m, 2H), 7.21-7.12 (m, 4H), 6.33 (s, 1H), 4.12 (t J=4.9 Hz, 2H), 3.81-2.91 (m, 4H), 2.95-2.91 (m, 4H), 2.67-2.62 (m, 2H), 2.21 (s, 6H); LC-MS: 96.01%; 569.0 (M$^+$+1); (column; Ascentis Express C18, (50×3.0 mm, 2.7 μm); RT 2.29 min. 0.025% Aq. TFA+5% ACN: ACN+5% 0.025% Aq. TFA, 1.2 mL/min); HPLC (purity): 95.26%; (column; Zorbax SB C-18 (150×4.6 mm, 3.5 μm); RT 8.78 min. ACN+5% 0.05% TFA (Aq): 0.05% TFA (Aq)+5% ACN; 1.0 mL/min; Diluent:ACN:water).

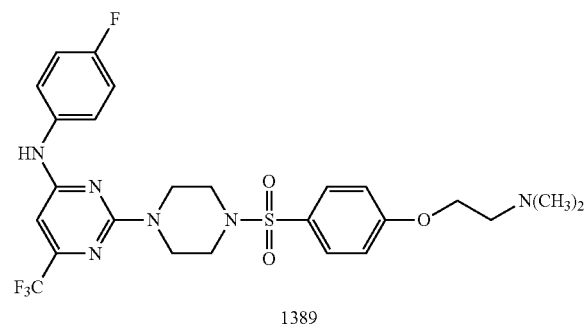

1389

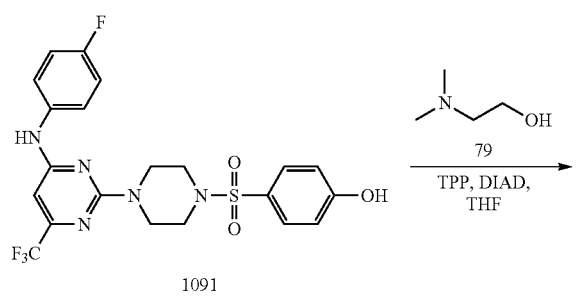

1091

Example 66: Synthesis of 1390

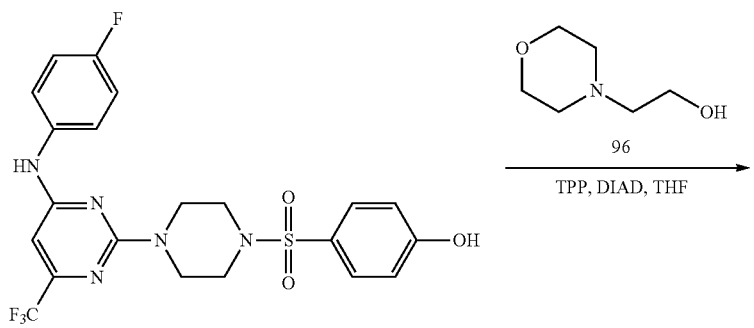

1091

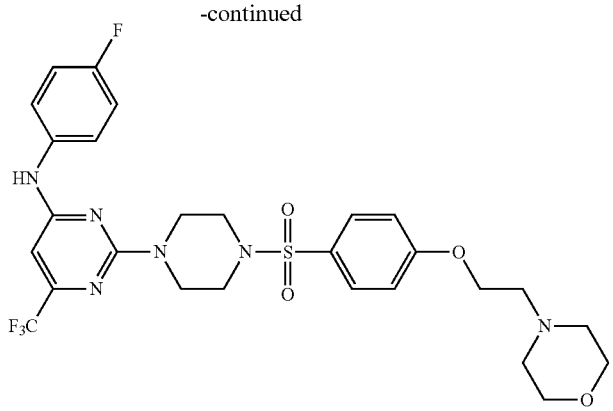

1390

Synthesis of N-(4-fluorophenyl)-2-(4-((4-(2-morpholinoethoxy) phenyl) sulfonyl) piperazin-1-yl)-6-(trifluoromethyl) pyrimidin-4-amine (1390)

To a stirring solution of 4-((4-(4-((4-fluorophenyl) amino)-6-(trifluoromethyl) pyrimidin-2-yl) piperazin-1-yl) sulfonyl) phenol 1091 (100 mg, 0.20 mmol) in THF (5 mL) under inert atmosphere were added diisopropyl azodicarboxylate (0.12 mL, 0.60 mmol), triphenyl phosphine (158 mg, 0.60 mmol) and 2-morpholinoethan-1-ol 96 (0.04 mL, 0.30 mmol) at 0° C.; warmed to RT and stirred for 16 h. The reaction was monitored by TLC and LC-MS; after completion of the reaction, the volatiles were removed in vacuo. The residue was diluted with water (25 mL) and extracted with EtOAc (2×25 mL). The combined organic extracts were dried over sodium sulfate, filtered and concentrated in vacuo to obtain the crude. The crude was purified through silica gel column chromatography using 10-50% EtOH/hexanes to afford compound 1390 (50 mg, 41%) as an off-white solid. TLC: 50% EtOAc/hexanes ($R_f$ 0.5); $^1$H NMR (DMSO-$d_6$, 500 MHz): δ 9.75 (s, 1H), 7.64 (d, J=8.7 Hz, 2H), 7.56 (dd, J=8.4, 4.9 Hz, 2H), 7.16 (t, J=8.8 Hz, 2H), 7.12 (d, J=9.0 Hz, 2H), 6.31 (s, 1H), 4.14 (t, J=5.5 Hz, 2H), 3.79-3.76 (m, 4H), 3.54-3.50 (m, 4H), 2.92-2.89 (m, 4H), 2.66 (t, J=5.6 Hz, 2H), 2.44-2.41 (m, 4H); LC-MS: 98.43%; 611.0 (M$^+$+1); (column; Ascentis Express C18, (50×3.0 mm, 2.7 μm); RT 2.29 min. 0.025% Aq. TFA+5% ACN: ACN+5% 0.025% Aq. TFA, 1.2 mL/min); HPLC (purity): 97.75%; (column; Zorbax SB C-18 (150×4.6 mm, 3.5 μm); RT 8.48 min. ACN+5% 0.05% TFA (Aq): 0.05% TFA (Aq)+5% ACN; 1.0 mL/min; Diluent:ACN:water).

Example 67: Synthesis of 1397 & 1398

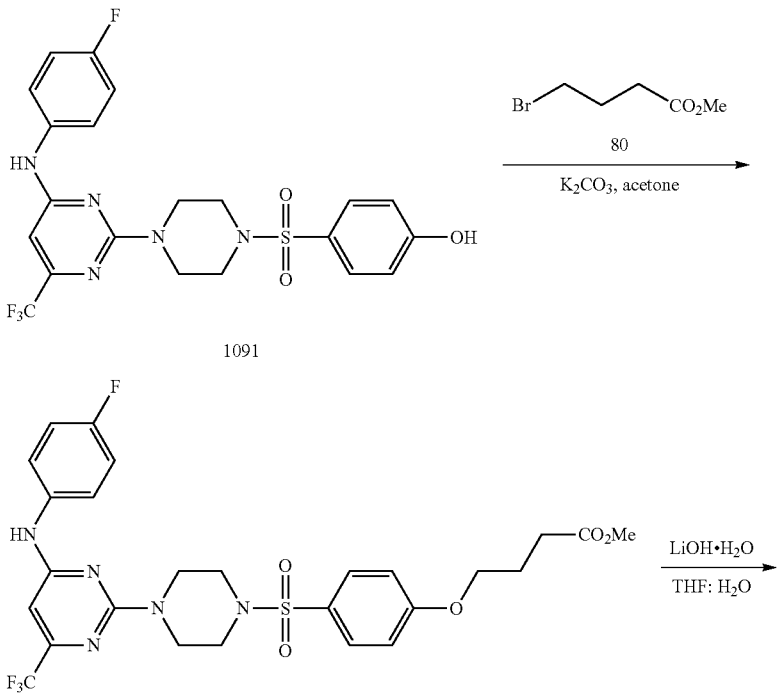

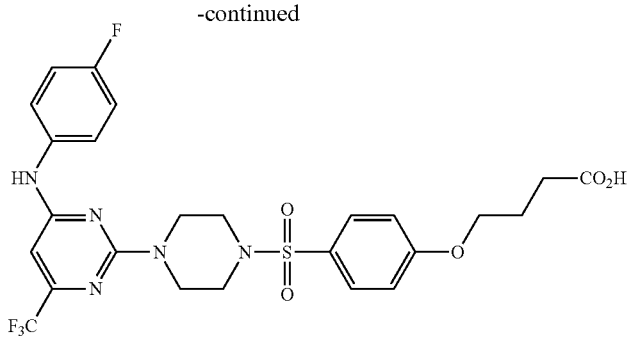

1398

Synthesis of methyl 4-(4-((4-(4-((4-fluorophenyl) amino)-6-(trifluoromethyl) pyrimidin-2-yl) piperazin-1-yl) sulfonyl) phenoxy) butanoate (1397)

To a stirring solution of 4-((4-(4-((4-fluorophenyl) amino)-6-(trifluoromethyl) pyrimidin-2-yl) piperazin-1-yl) sulfonyl) phenol 1091 (160 mg, 0.32 mmol) in acetone (5 mL) under inert atmosphere were added potassium carbonate (61 mg, 0.64 mmol) and methyl 4-bromobutanoate 80 (64 mg, 0.35 mmol) at RT; heated to 40° C. and stirred for 16 h. The reaction was monitored by TLC; after completion of the reaction, the volatiles were removed in vacuo. The residue was diluted with water (100 mL) extracted with $CH_2Cl_2$ (2×30 mL). The combined organic extracts were dried over sodium sulfate, filtered and concentrated in vacuo to obtain the crude. The crude was purified through silica gel column chromatography using 30% EtOAc/hexanes to afford compound 1397 (120 mg, 63%) as an off-white solid. TLC: 30% EtOAc/hexanes ($R_f$ 0.5); $^1$H NMR (DMSO-$d_6$, 500 MHz): 9.77 (s, 1H), 7.66 (d, J=9.0 Hz, 2H), 7.58 (dd, J=8.7, 4.9 Hz, 2H), 7.18 (t, J=8.8 Hz, 2H), 7.12 (d, J=8.7 Hz, 2H), 6.33 (s, 1H), 4.07 (t, J=6.4 Hz, 2H), 3.82-3.77 (m, 4H), 3.58 (s, 3H), 2.95-2.91 (m, 4H), 2.46 (t, J=7.2 Hz, 2H), 2.01-1.94 (m, 2H); LC-MS: 98.27%; 598.1 (M$^+$+1); (column; Ascentis Express C18, (50×3.0 mm, 2.7 µm); RT 3.07 min. 0.025% Aq. TFA+5% ACN: ACN+5% 0.025% Aq. TFA, 1.2 mL/min); HPLC (purity): 99.49%; (column; Zorbax SB C-18 (150×4.6 mm, 3.5 µm); RT 11.96 min. ACN: 0.05% TFA (Aq); 1.0 mL/min; Diluent:ACN:water).

Synthesis of 4-(4-((4-(4-((4-fluorophenyl) amino)-6-(trifluoromethyl) pyrimidin-2-yl) piperazin-1-yl) sulfonyl) phenoxy) butanoic acid (1398)

To a stirring solution of 1397 (80 mg, 0.13 mmol) in THF:H$_2$O (3:1, 8 mL) was added lithium hydroxide monohydrate (17 mg, 0.40 mmol) at 0° C. warmed to RT and stirred for 6 h. The reaction was monitored by TLC; after completion of the reaction, the volatiles were removed in vacuo. The residue was diluted with ice-cold water (10 mL) and pH was adjusted to ~3 with 3 N HCl. The precipitated solid was filtered, washed with water (30 mL) and triturated with diethylether:n-pentane (3:2, 10 mL) and dried in vacuo to afford 1398 (48 mg, 62%) as an off-white solid. TLC: 40% EtOAc/hexanes ($R_f$ 0.2); $^1$H-NMR (DMSO-$d_6$, 500 MHz): 12.15 (br s, 1H), 9.77 (s, 1H), 7.66 (d, J=9.0 Hz, 2H), 7.58 (dd, J=8.4, 4.9 Hz, 2H), 7.18 (t, J=8.8 Hz, 2H), 7.13 (d, J=9.0 Hz, 2H), 6.33 (s, 1H), 4.06 (t, J=6.2 Hz, 2H), 3.82-3.78 (m, 4H), 2.95-2.91 (m, 4H), 2.36 (t, J=7.4 Hz, 2H), 1.98-1.90 (m, 2H); LC-MS: 99.00%; 584.0 (M$^+$+1); (column; Ascentis Express C18, (50×3.0 mm, 2.7 µm); RT 2.81 min. 0.025% Aq. TFA+5% ACN: ACN+5% 0.025% Aq. TFA, 1.2 mL/min); HPLC (purity): 99.41%; (column; Zorbax SB C-18 (150×4.6 mm, 3.5 µm); RT 10.78 min. ACN+5% 0.05% TFA (Aq): 0.05% TFA (Aq)+5% ACN; 1.0 mL/min; Diluent:ACN:water).

Example 68: Synthesis of 1409

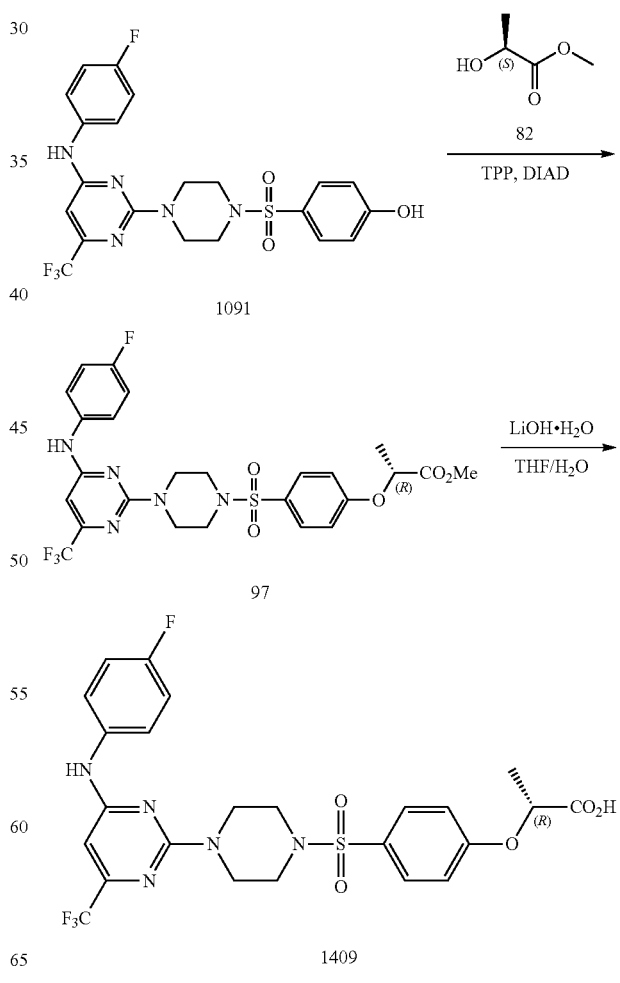

Synthesis of methyl (R)-2-(4-((4-(4-((4-fluorophenyl) amino)-6-(trifluoromethyl) pyrimidin-2-yl) piperazin-1-yl) sulfonyl) phenoxy) propanoate (97)

To a stirring solution of 4-((4-(4-((4-fluorophenyl) amino)-6-(trifluoromethyl) pyrimidin-2-yl) piperazin-1-yl) sulfonyl) phenol 1091 (150 mg, 0.30 mmol) in THF (10 mL) under inert atmosphere were added diisopropyl azodicarboxylate (183 mg, 0.90 mmol), triphenyl phosphine (237 mg, 0.90 mmol) and methyl (S)-2-hydroxypropanoate 82 (47 mg, 0.45 mmol) at 0° C.; warmed to RT and stirred for 16 h. The reaction was monitored by TLC; after completion of the reaction, the volatiles were removed in vacuo. The residue was diluted with water (30 mL) and extracted with EtOAc (2×40 mL). The combined organic extracts were dried over sodium sulfate, filtered and concentrated in vacuo to obtain the crude. The crude was purified through combiflash column chromatography (24 g of 40-60 mesh silica gel) using 20% EtOAc/hexanes to afford compound 97 (80 mg, 45%) as white solid. TLC: 40% EtOAc/hexanes ($R_f$ 0.7); $^1$H NMR (DMSO-$d_6$, 400 MHz): δ 9.77 (s, 1H), 7.67 (d, J=9.0 Hz, 2H), 7.58 (dd, J=8.1, 4.9 Hz, 2H), 7.18 (t, J=8.8 Hz, 2H), 7.09 (d, J=8.7 Hz, 2H), 6.34 (s, 1H), 4.88-4.83 (m, 1H), 3.81-3.78 (m, 4H), 3.67 (s, 3H), 2.96-2.92 (m, 4H), 1.52 (d, J=6.7 Hz, 3H).

Synthesis of (R)-2-(4-((4-(4-((4-fluorophenyl) amino)-6-(trifluoromethyl) pyrimidin-2-yl) piperazin-1-yl) sulfonyl) phenoxy) propanoic acid (1409)

To a stirring solution of compound 97 (150 mg, 0.25 mmol) in THF:H$_2$O (4:1, 10 mL) was added lithium hydroxide monohydrate (22 mg, 0.51 mmol) at RT and stirred for 2 h. The reaction was monitored by TLC; after completion of the reaction, the volatiles were removed in vacuo. The residue was diluted with water (15 mL) and washed with diethyl ether (2×20 mL). The pH of the aqueous layer was adjusted to ~5 with 2 N HCl. The precipitated solid was filtered and dried in vacuo to afford 1409 (120 mg, 82%) as white solid. TLC: 30% EtOAc/hexanes ($R_f$ 0.2); $^1$H-NMR (DMSO-$d_6$, 500 MHz): δ 9.80 (s, 1H), 7.65 (d, J=8.7 Hz, 2H), 7.61-7.56 (m, 2H), 7.18 (t, J=8.7 Hz, 2H), 7.04 (d, J=8.4 Hz, 2H), 6.34 (s, 1H), 5.14 (q, J=6.7 Hz, 1H), 3.81-3.77 (m, 4H), 2.95-2.91 (m, 4H), 1.47 (d, J=6.4 Hz, 3H); LC-MS: 97.85%; 569.9 (M$^+$+1); (column; Ascentis Express C18, (50×3.0 mm, 2.7 μm); RT 2.83 min. 0.025% Aq. TFA+5% ACN: ACN+5% 0.025% Aq. TFA, 1.2 mL/min); HPLC (purity): 97.62%; (column; Zorbax SB C-18 (150×4.6 mm, 3.5 μm); RT 10.90 min. ACN+5% 0.05% TFA (Aq): 0.05% TFA (Aq)+5% ACN; 1.0 mL/min; Diluent:ACN:water)

Example 69: Synthesis of 1410

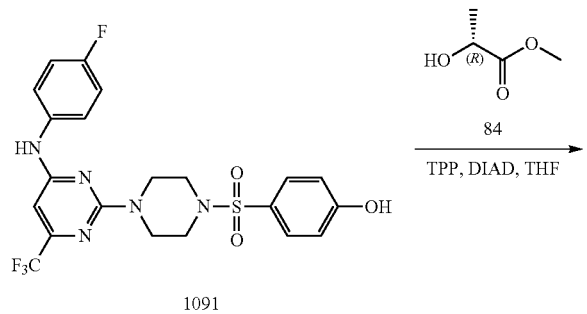

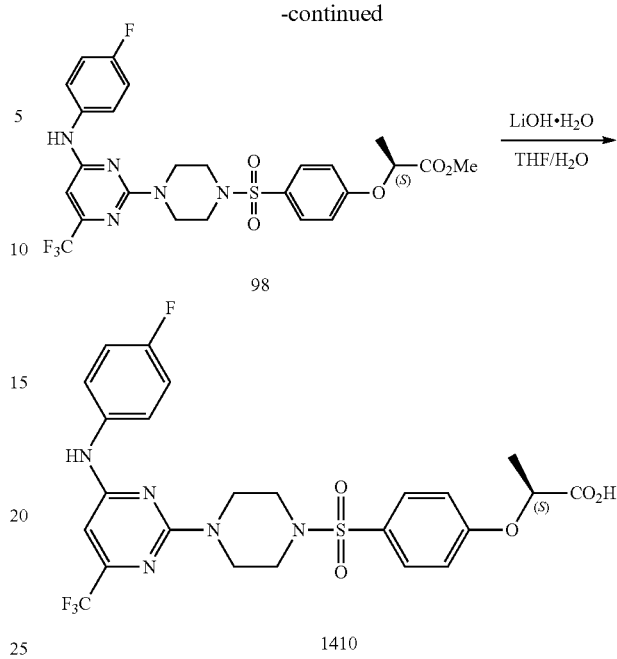

Synthesis of methyl (S)-2-(4-((4-(4-((4-fluorophenyl)amino)-6-(trifluoromethyl) pyrimidin-2-yl) piperazin-1-yl) sulfonyl) phenoxy) propanoate (98)

To a stirring solution of 4-((4-(4-((4-fluorophenyl) amino)-6-(trifluoromethyl) pyrimidin-2-yl) piperazin-1-yl) sulfonyl) phenol 1091 (150 mg, 0.30 mmol) in THF (10 mL) under inert atmosphere were added diisopropyl azodicarboxylate (183 mg, 0.90 mmol), triphenyl phosphine (237 mg, 0.90 mmol) and methyl (R)-2-hydroxypropanoate 84 (47 mg, 0.45 mmol) at 0° C.; warmed to RT and stirred for 16 h. The reaction was monitored by TLC; after completion of the reaction, the volatiles were removed in vacuo. The residue was diluted with water (30 mL) and extracted with EtOAc (2×40 mL). The combined organic extracts were dried over sodium sulfate, filtered and concentrated in vacuo to obtain the crude. The crude was purified through silica gel column chromatography using 20% EtOAc/hexanes to afford compound 98 (80 mg, 46%) as white solid. TLC: 40% EtOAc/hexanes ($R_f$ 0.7); $^1$H NMR (DMSO-$d_6$, 500 MHz): δ 9.77 (s, 1H), 7.67 (d, J=8.7 Hz, 2H), 7.58 (dd, J=8.0, 5.1 Hz, 2H), 7.18 (t, J=8.7 Hz, 2H), 7.09 (d, J=8.7 Hz, 2H), 6.34 (s, 1H), 5.14 (q, J=6.7 Hz, 1H), 3.81-3.78 (m, 4H), 3.67 (s, 3H), 2.96-2.94 (m, 4H), 1.52 (d, J=6.7 Hz, 3H).

Synthesis of (S)-2-(4-((4-(4-((4-fluorophenyl) amino)-6-(trifluoromethyl) pyrimidin-2-yl) piperazin-1-yl) sulfonyl) phenoxy) propanoic acid (1410)

To a stirring solution of compound 98 (80 mg, 0.13 mmol) in THF:H$_2$O (4:1, 7.5 mL) was added lithium hydroxide monohydrate (11.5 mg, 0.27 mmol) at RT and stirred for 2 h. The reaction was monitored by TLC; after completion of the reaction, the volatiles were removed in vacuo. The residue was diluted with water (15 mL) and washed with diethyl ether (2×20 mL). The pH of the aqueous layer was adjusted to ~5 with 2 N HCl. The precipitated solid was filtered and dried in vacuo to afford 1410 (60 mg, 77%) as white solid. TLC: 30% EtOAc/hexanes ($R_f$ 0.2); $^1$H-NMR (DMSO-d$_6$, 500 MHz): δ 13.21 (br s, 1H), 9.78 (s, 1H), 7.66 (d, J=9.0 Hz, 2H), 7.58 (dd, J=8.5, 4.8 Hz, 2H), 7.18 (t, J=8.8 Hz, 2H), 7.05 (d, J=8.7 Hz, 2H), 6.34 (s, 1H), 4.94-4.88 (m, 1H), 3.81-3.78 (m, 4H), 2.95-2.91 (m, 4H), 1.49 (d, J=6.7 Hz, 3H); LC-MS: 98.29%; 570.0 (M$^+$+1); (column; Ascentis Express C18, (50×3.0 mm, 2.7 µm); RT 2.83 min. 0.025% Aq. TFA+5% ACN: ACN+5% 0.025% Aq. TFA, 1.2 mL/min); HPLC (purity): 98.78%; (column; Zorbax SB C-18 (150×4.6 mm, 3.5 µm); RT 10.90 min. ACN+5% 0.05% TFA (Aq): 0.05% TFA (Aq)+5% ACN; 1.0 mL/min; Diluent:ACN:water).

Example 70: Synthesis of 1399

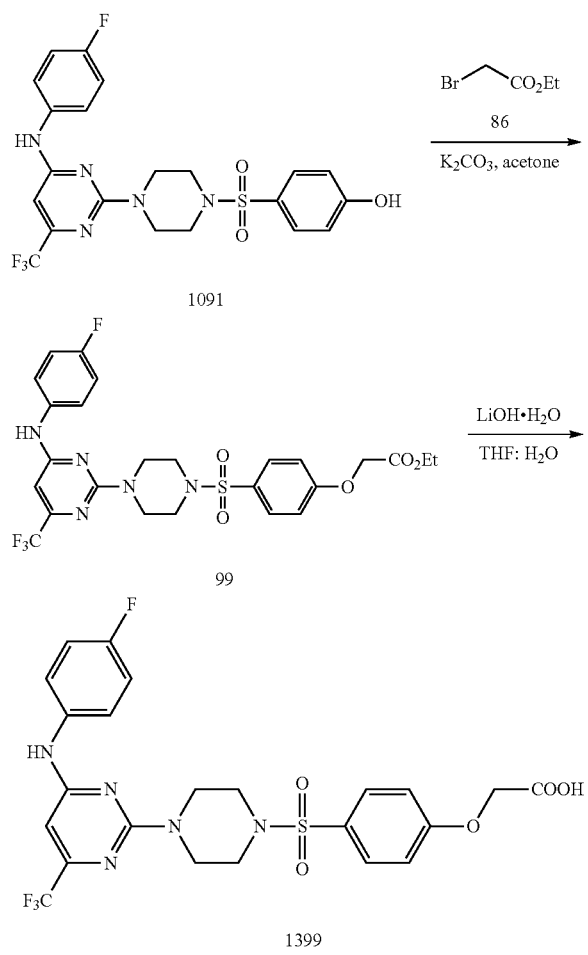

Synthesis of ethyl 2-(4-((4-(4-((4-fluorophenyl) amino)-6-(trifluoromethyl) pyrimidin-2-yl) piperazin-1-yl) sulfonyl) phenoxy) acetate (99)

To a stirring solution of 4-((4-(4-((4-fluorophenyl) amino)-6-(trifluoromethyl) pyrimidin-2-yl) piperazin-1-yl) sulfonyl) phenol 1091 (100 mg, 0.20 mmol) in acetone (10 mL) under inert atmosphere were added potassium carbonate (55 mg, 0.40 mmol) and ethyl 2-bromoacetate 86 (27 mg, 0.16 mmol) at RT and stirred for 16 h. The reaction was monitored by TLC; after completion of the reaction, the reaction mixture was diluted with ice-cold water (50 mL) and extracted with EtOAc (2×30 mL). The combined organic extracts were dried over sodium sulfate, filtered and concentrated in vacuo to obtain the crude. The crude was purified through silica gel column chromatography using 40% EtOAc/hexanes to afford compound 99 (90 mg, 78%) as an off-white solid. TLC: 70% EtOAc/hexanes (R$_f$, 0.5); $^1$H NMR (DMSO-d$_6$, 500 MHz): δ 9.77 (s, 1H), 7.68 (d, J=9.0 Hz, 2H), 7.58 (dd, J=8.5, 5.8 Hz, 2H), 7.18 (t, J=8.8 Hz, 2H), 7.14 (d, J=9.0 Hz, 2H), 6.33 (s, 1H), 4.89 (s, 2H), 4.15 (q, J=6.9 Hz, 2H), 3.82-3.78 (m, 4H), 2.96-2.98 (m, 4H), 1.18 (t, J=7.2 Hz, 3H).

Synthesis of 2-(4-((4-(4-((4-fluorophenyl) amino)-6-(trifluoromethyl) pyrimidin-2-yl) piperazin-1-yl) sulfonyl) phenoxy) acetic acid (1399)

To a stirring solution of compound 99 (70 mg, 0.12 mmol) in THF:H$_2$O (4:1, 5 mL) was added lithium hydroxide monohydrate (13 mg, 0.40 mmol) at 0-5° C. warmed to RT and stirred for 3.5 h. The reaction was monitored by TLC; after completion of the reaction, the volatiles were removed in vacuo. The residue was diluted with ice-cold water (10 mL) and pH was adjusted to ~6 with 3 N HCl. The precipitated solid was filtered washed with water (30 mL), n-pentane (10 mL) and dried in vacuo to afford 1399 (60 mg, 90%) as an off-white solid. TLC: 40% EtOAc/hexanes (R$_f$, 0.2); $^1$H-NMR (DMSO-d$_6$, 500 MHz): δ 9.78 (s, 1H), 7.65 (d, J=8.7 Hz, 2H), 7.57 (dd, J=8.1, 4.9 Hz, 2H), 7.17 (t, J=8.8 Hz, 2H), 7.08 (d, J=9.0 Hz, 2H), 6.33 (s, 1H), 4.68 (s, 2H), 3.80-3.77 (m, 4H), 2.94-2.91 (m, 4H); LC-MS: 98.16%; 555.9 (M$^+$+1); (column; Ascentis Express C18, (50×3.0 mm, 2.7 µm); RT 2.73 min. 0.025% Aq. TFA+5% ACN: ACN+5% 0.025% Aq. TFA, 1.2 mL/min); HPLC (purity): 98.41%; (column; Zorbax SB C-18 (150×4.6 mm, 3.5 µm); RT 10.42 min. ACN+5% 0.05% TFA (Aq): 0.05% TFA (Aq)+5% ACN; 1.0 mL/min; Diluent:ACN:water).

Example 71: Synthesis of 1405 & 1406

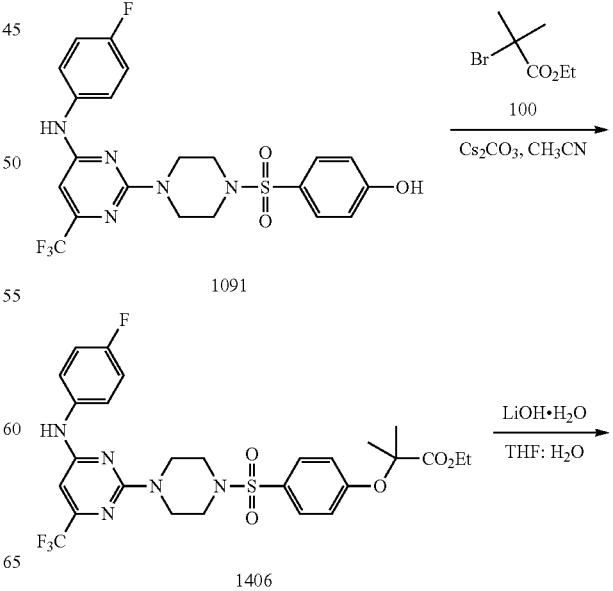

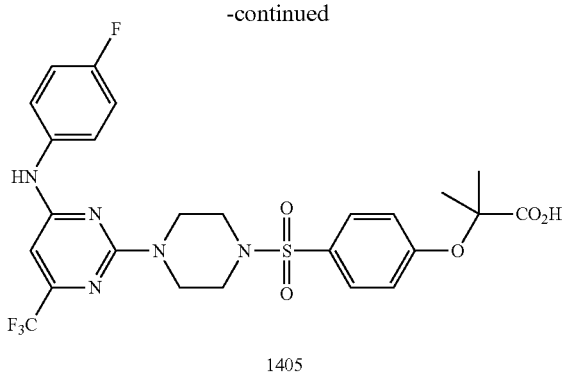

1405

Synthesis of ethyl 2-(4-((4-(4-((4-fluorophenyl) amino)-6-(trifluoromethyl) pyrimidin-2-yl) piperazin-1-yl) sulfonyl) phenoxy)-2-methylpropanoate (1406)

To a stirring solution of 4-((4-(4-((4-fluorophenyl) amino)-6-(trifluoromethyl) pyrimidin-2-yl) piperazin-1-yl) sulfonyl) phenol 1091 (100 mg, 0.20 mmol) in acetonitrile (5 mL) under inert atmosphere were added cesium carbonate (98 mg, 0.20 mmol) and ethyl 2-bromo-2-methylpropanoate 100 (39 mg, 0.20 mmol) at 0° C.; heated to 80° C. and stirred for 8 h. The reaction was monitored by TLC; after completion of the reaction, the reaction mixture was diluted with water (50 mL) and extracted with EtOAc (2×30 mL). The combined organic extracts was dried over sodium sulfate, filtered and concentrated in vacuo to obtain the crude. The crude was purified through silica gel column chromatography using 15% EtOAc/hexanes to afford 1406 (75 mg, 61%) as an off-white solid. TLC: 30% EtOAc/hexanes ($R_f$ 0.5); $^1$H-NMR (DMSO-$d_6$, 500 MHz): δ 9.77 (s, 1H), 7.66 (d, J=9.0 Hz, 2H), 7.58 (d, J=6.6 Hz, 2H), 7.18 (t, J=8.8 Hz, 2H), 6.95 (d, J=9.0 Hz, 2H), 6.34 (s, 1H), 4.13 (q, J=7.1 Hz, 2H), 3.81-3.78 (m, 4H), 2.96-2.92 (m, 4H), 1.58 (s, 6H), 1.06 (t, J=7.1 Hz, 3H); LC-MS: 98.65%; 612.1 (M$^-$+1); (column; Ascentis Express C18, (50×3.0 mm, 2.7 μm); RT 3.21 min. 0.025% Aq. TFA+5% ACN: ACN+5% 0.025% Aq. TFA, 1.2 mL/min); HPLC (purity): 97.53%; (column; Zorbax SB C-18 (150×4.6 mm, 3.5 μm); RT 12.75 min. ACN+5% 0.05% TFA (Aq): 0.05% TFA (Aq)+5% ACN; 1.0 mL/min; Diluent:ACN:water).

Synthesis of 2-(4-((4-(4-((4-fluorophenyl) amino)-6-(trifluoromethyl) pyrimidin-2-yl) piperazin-1-yl) sulfonyl) phenoxy)-2-methylpropanoic acid (1405)

To a stirring solution of 1406 (75 mg, 0.12 mmol) in THF:H$_2$O (3:1, 10 mL) was added lithium hydroxide monohydrate (15 mg, 0.36 mmol) at 5° C. warmed to RT and stirred for 5 h. The reaction was monitored by TLC; after completion of the reaction, the volatiles were removed in vacuo. The pH of the residue was adjusted to ~2 with 3 N HCl. The precipitated solid was filtered washed with water (30 mL), n-pentane (10 mL) and dried in vacuo to afford 1405 (40 mg, 56%) as an off-white solid. TLC: 10% MeOH/CH$_2$Cl$_2$ ($R_f$ 0.2); $^1$H-NMR (DMSO-$d_6$, 500 MHz): δ 9.77 (s, 1H), 7.66 (d, J=9.0 Hz, 2H), 7.58 (dd, J=8.4, 4.9 Hz, 2H), 7.18 (t, J=8.8 Hz, 2H), 6.95 (d, J=9.0 Hz, 2H), 6.34 (s, 1H), 4.13 (q, J=7.1 Hz, 2H), 3.81-3.78 (m, 4H), 2.96-2.92 (m, 4H), 1.58 (s, 6H), 1.06 (t, J=7.1 Hz, 3H); LC-MS: 96.62%; 584.1 (M$^+$+1); (column; X-Select CSH C-18, (50×3.0 mm, 2.5 μm); RT 2.99 min. 2.5 mM Aq. NH$_4$OOCH+5% ACN: ACN+5% 2.5 mM Aq. NH$_4$OOCH, 0.8 mL/min); HPLC (purity): 96.35%; (column; Zorbax SB C-18 (150×4.6 mm, 3.5 μm); RT 11.49 min. ACN+5% 0.05% TFA (Aq): 0.05% TFA (Aq)+5% ACN; 1.0 mL/min; Diluent:ACN: water).

Example 72: Synthesis of 1388

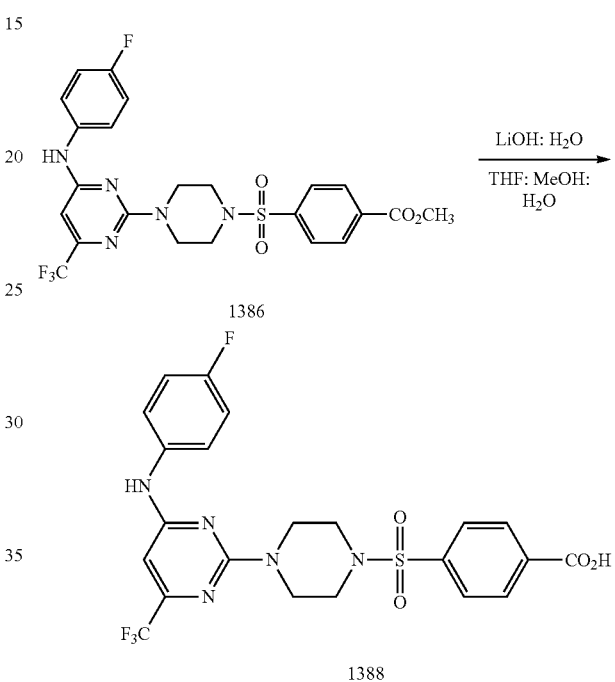

Synthesis of 4-((4-(4-((4-fluorophenyl) amino)-6-(trifluoromethyl) pyrimidin-2-yl) piperazin-1-yl) sulfonyl) benzoic acid (1388)

To a stirring solution of 1386 (150 mg, 0.27 mmol) in THF:MeOH:H$_2$O (3:3:1, 14 mL) was added lithium hydroxide monohydrate (35 mg, 0.83 mmol) at RT and stirred for 5 h. The reaction was monitored by TLC; after completion of the reaction, the volatiles were removed in vacuo. The pH of the residue was acidified at 0° C. with 3 N HCl to ~3. The precipitated solid was filtered washed with water (30 mL), diethylether (20 mL) and dried in vacuo to afford 1388 (125 mg, 85%) as an off-white solid. TLC: 10% MeOH/CH$_2$Cl$_2$ ($R_f$ 0.2); $^1$H-NMR (DMSO-$d_6$, 500 MHz): δ 13.62 (br s, 2H), 9.79 (s, 1H), 8.11 (d, J=8.4 Hz, 2H), 7.81 (d, J=8.4 Hz, 2H), 7.57 (dd, J=8.7, 4.9 Hz, 2H), 7.17 (t, J=8.8 Hz, 2H), 6.33 (s, 1H), 3.82-3.80 (m, 4H), 3.02-2.79 (m, 4H); LC-MS: 99.78%; 525.9 (M$^+$+1); (column; Ascentis Express C18, (50×3.0 mm, 2.7 μm); RT 2.79 min. 0.025% Aq. TFA+5% ACN: ACN+5% 0.025% Aq. TFA, 1.2 mL/min); HPLC (purity): 99.52%; (column; Zorbax SB C-18 (150×4.6 mm, 3.5 μm); RT 9.80 min. ACN: 0.05% TFA (Aq); 1.0 mL/min; Diluent:ACN:water).

Example 73: Synthesis of 1408 & 2001

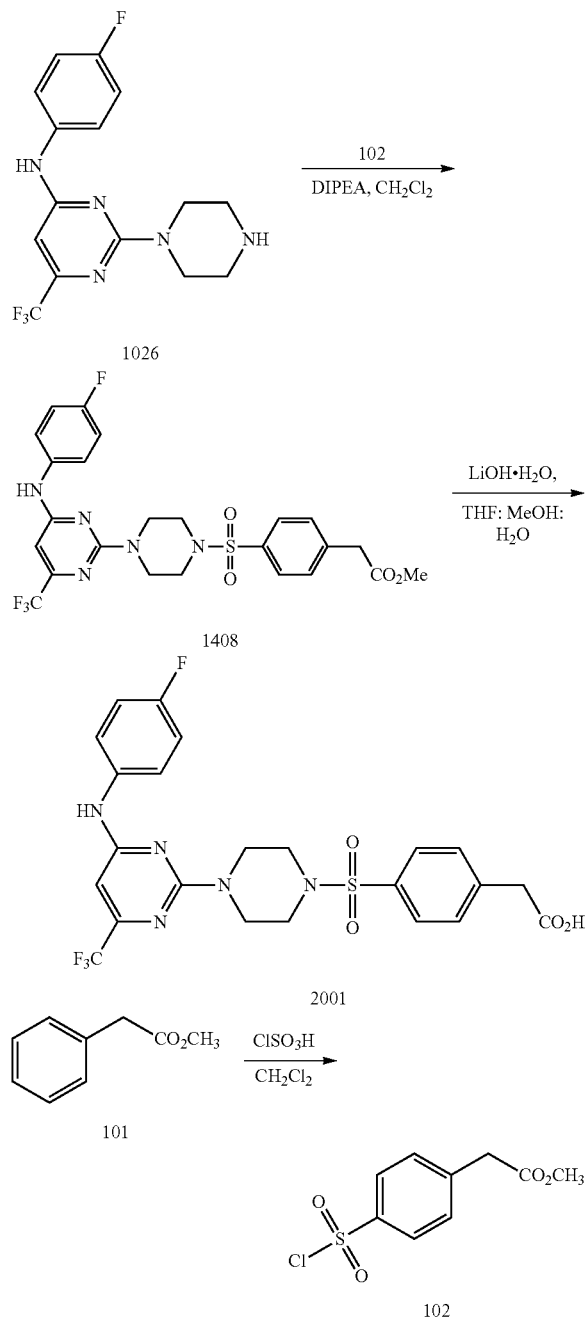

Synthesis of methyl 2-(4-(chlorosulfonyl) phenyl) acetate (102)

To a stirring solution of methyl 2-phenylacetate 101 (5 g, 33.3 mmol) in $CH_2Cl_2$ (5 mL) under inert atmosphere was added chlorosulfonic acid (30 mL) dropwise for 20 min at 0° C.; warmed to RT and stirred for 3 h. The reaction was monitored by TLC; after completion of the reaction, the reaction mixture was poured into ice-cold water and extracted with $CH_2Cl_2$ (2×100 mL). The combined organic extracts were dried over sodium sulfate, filtered and concentrated in vacuo to afford crude compound 102 (6.8 g) along with its meta isomer as colorless thick syrup. TLC: 10% EtOAc/hexanes ($R_f$ 0.3); $^1H$ NMR ($CDCl_3$, 500 MHz): δ 8.00 (d, J=8.4 Hz, 2H), 7.98-7.95 (m, 1H), 7.68 (d, J=7.8 Hz, 0.5H), 7.60 (d, J=8.1 Hz, 0.5H), 7.54 (d, J=8.4 Hz, 2H), 3.80 (s, 0.5H), 3.76 (s, 3H), 3.74-3.73 (m, 4H).

Synthesis of methyl 2-(4-((4-(4-((4-fluorophenyl) amino)-6-(trifluoromethyl) pyrimidin-2-yl) piperazin-1-yl) sulfonyl) phenyl) acetate (1408)

To a stirring solution of N-(4-fluorophenyl)-2-(piperazin-1-yl)-6-(trifluoromethyl) pyrimidin-4-amine 1026 (500 mg, 1.46 mmol) in $CH_2Cl_2$ (20 mL) under inert atmosphere were added diisopropylethylamine (0.78 mL, 4.39 mmol) and compound 102 (728 mg, crude) at 0° C.; warmed to RT and stirred for 16 h. The reaction was monitored by TLC; after completion of the reaction, the reaction mixture was diluted with $CH_2Cl_2$ (20 mL) and washed with water (50 mL). The organic extract was dried over sodium sulfate, filtered and concentrated in vacuo to obtain the crude. The crude was purified through silica gel column chromatography using 30% EtOAc/hexanes. The title compound was separated from its region isomer by preparative HPLC purification to afford compound 1408 (140 mg, 17%) as an off-white solid. TLC: 30% EtOAc/hexanes ($R_f$ 0.4); $^1H$ NMR (DMSO-$d_6$, 500 MHz): δ 9.77 (s, 1H), 7.71 (d, J=8.4 Hz, 2H), 7.58 (dd, J=8.8, 4.8 Hz, 2H), 7.53 (d, J=8.4 Hz, 2H), 7.18 (t, J=9.0 Hz, 2H), 6.34 (s, 1H), 3.82 (s, 2H), 3.81-3.78 (m, 4H), 3.61 (s, 3H), 2.99-2.95 (m, 4H); LC-MS: 97.87%; 554.0 ($M^+$+1); (column; Ascentis Express C18, (50×3.0 mm, 2.7 μm); RT 3.11 min. 0.025% Aq. TFA+5% ACN: ACN+5% 0.025% Aq. TFA, 1.2 mL/min); HPLC (purity): 99.89%; (column; Zorbax SB C-18 (150×4.6 mm, 3.5 μm); RT 11.79 min. ACN: 0.05% TFA (Aq); 1.0 mL/min; Diluent:ACN:water).

Synthesis of 2-(4-((4-(4-((4-fluorophenyl) amino)-6-(trifluoromethyl) pyrimidin-2-yl) piperazin-1-yl) sulfonyl) phenyl) acetic acid (2001)

To a stirring solution of 1408 (100 mg, 0.18 mmol) in THF:MeOH:$H_2O$ (3:3:1, 7 mL) was added lithium hydroxide monohydrate (23 mg, 0.54 mmol) at RT and stirred for 3 h. The reaction was monitored by TLC; after completion of the reaction, the volatiles were removed in vacuo. The pH of the residue was acidified at 0° C. with 1 N HCl to ~2. The precipitated solid was filtered, washed with water (30 mL), triturated with EtOAc (5 mL) and dried in vacuo to afford 2001 (75 mg, 78%) as an off-white solid. TLC: 30% EtOAc/hexanes ($R_f$ 0.1); $^1H$-NMR (DMSO-$d_6$, 400 MHz): δ 12.50 (br s, 1H), 9.80 (s, 1H), 7.70 (d, J=8.3 Hz, 2H), 7.58 (dd, J=9.0, 4.9 Hz, 2H), 7.52 (d, J=8.3 Hz, 2H), 7.18 (t, J=8.9 Hz, 2H), 6.34 (s, 1H), 3.83-3.77 (m, 4H), 3.71 (s, 2H), 2.99-2.95 (m, 4H); LC-MS: 99.53%; 540.0 ($M^+$+1); (column; Ascentis Express C18, (50×3.0 mm, 2.7 μm); RT 2.78 min. 0.025% Aq. TFA+5% ACN: ACN+5% 0.025% Aq. TFA, 1.2 mL/min); HPLC (purity): 98.06%; (column; X Select CSH-18 (150×4.6 mm, 3.5 μm); RT 10.89 min. ACN: 0.05% TFA (Aq); 1.0 mL/min; Diluent:ACN:water).

Example 74: Synthesis of 1381 & 1382

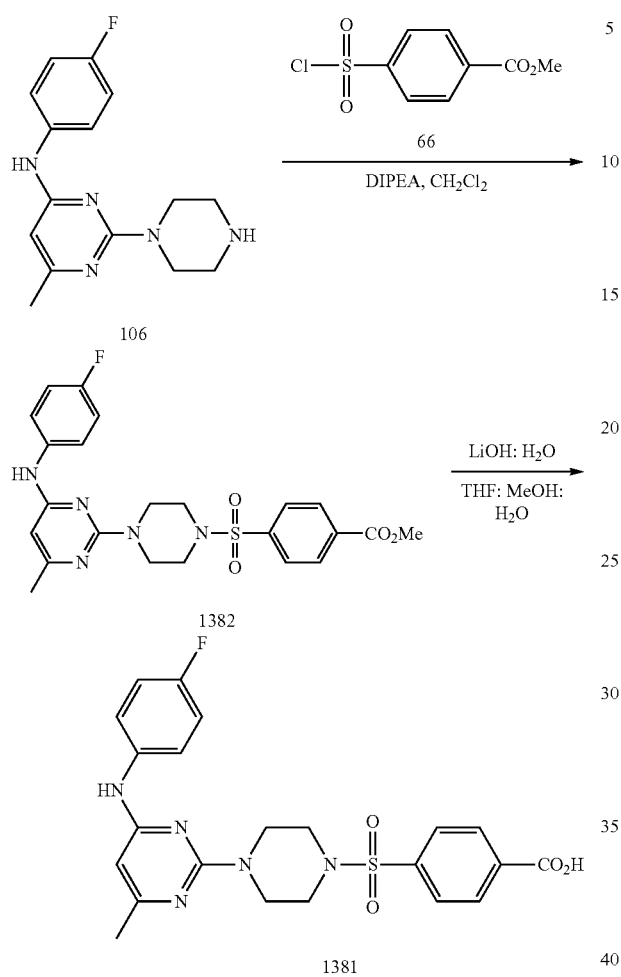

Synthesis of methyl 4-((4-(4-((4-fluorophenyl)amino)-6-methylpyrimidin-2-yl) piperazin-1-yl) sulfonyl) benzoate (1382)

To a stirring solution of N-(4-fluorophenyl)-6-methyl-2-(piperazin-1-yl) pyrimidin-4-amine 106 (300 mg, 1.04 mmol) in CH$_2$Cl$_2$ (20 mL) under argon atmosphere were added diisopropylethylamine (0.56 mL, 3.13 mmol), methyl 4-(chlorosulfonyl) benzoate 66 (291 g, 1.25 mmol) at 0° C.; warmed to RT and stirred for 16 h. The reaction was monitored by TLC; after completion of the reaction, the volatiles were removed in vacuo. The residue was diluted with CH$_2$Cl$_2$ (100 mL), washed with water (2×50 mL). The combined organic extracts were dried over sodium sulfate, filtered and concentrated in vacuo to obtain the crude. The crude material was purified through silica gel column chromatography using 30% EtOAc/hexanes to afford compound 1382 (200 mg, 39%) as white solid. TLC: 50% EtOAc/hexanes (R$_f$ 0.5); $^1$H-NMR (DMSO-d$_6$, 400 MHz): δ 9.14 (s, 1H), 8.16 (d, J=8.5 Hz, 2H), 7.89 (d, J=8.5 Hz, 2H), 7.53 (dd, J=9.1, 5.0 Hz, 2H), 7.11 (t, J=8.9 Hz, 2H), 5.86 (s, 1H), 3.88 (s, 3H), 3.80-3.75 (m, 4H), 3.00-2.95 (m, 4H), 2.09 (s, 3H); LC-MS: 99.18%; 486.0 (M$^+$+1); (column; Ascentis Express C18, (50×3.0 mm, 2.7 μm); RT 2.20 min. 0.025% Aq. TFA+5% ACN: ACN+5% 0.025% Aq. TFA, 1.2 mL/min); HPLC (purity): 99.75%; (column; Zorbax SB C-18 (150×4.6 mm, 3.5 μm); RT 7.90 min. ACN+0.05% TFA (Aq); 1.0 mL/min; Diluent:ACN:water).

Synthesis of 4-((4-(4-((4-fluorophenyl) amino)-6-methylpyrimidin-2-yl) piperazin-1-yl) sulfonyl) benzoic acid (1381)

To a stirring solution of 1382 (100 mg, 0.20 mmol) in THF:MeOH:H$_2$O (3:3:1, 7 mL) was added lithium hydroxide monohydrate (26 mg, 0.61 mmol) at 0° C.; warmed to RT and stirred for 3 h. The reaction was monitored by TLC; after completion of the reaction, the volatiles were removed in vacuo. The pH of the residue was acidified with 1 N HCl to ~2. The precipitated solid was filtered, triturated with diethylether (2×10 mL) and dried in vacuo to afford 1381 (90 mg, 93%) as white solid. TLC: 50% EtOAc/hexanes (R$_f$ 0.2); $^1$H-NMR (DMSO-d$_6$, 500 MHz): δ 13.48 (br s, 1H), 9.45 (br s, 1H), 8.15 (d, J=8.5 Hz, 2H), 7.87 (d, J=8.5 Hz, 2H), 7.54 (dd, J=8.3, 4.9 Hz, 2H), 7.15 (t, J=8.6 Hz, 2H), 5.95 (br s, 1H), 3.82-3.78 (m, 4H), 3.03-3.00 (m, 4H), 2.16 (br s, 3H); LC-MS: 96.45%; 472.0 (M$^+$+1); (column; Ascentis Express C18, (50×3.0 mm, 2.7 μm); RT 2.00 min. 0.025% Aq. TFA+5% ACN: ACN+5% 0.025% Aq. TFA, 1.2 mL/min); HPLC (purity): 99.79%; (column; Zorbax SB C-18 (150×4.6 mm, 5 μm); RT 7.60 min. ACN: 0.05% TFA (Aq); 1.0 mL/min; Diluent:ACN:water).

Example 75: Synthesis of 1393 & 1392

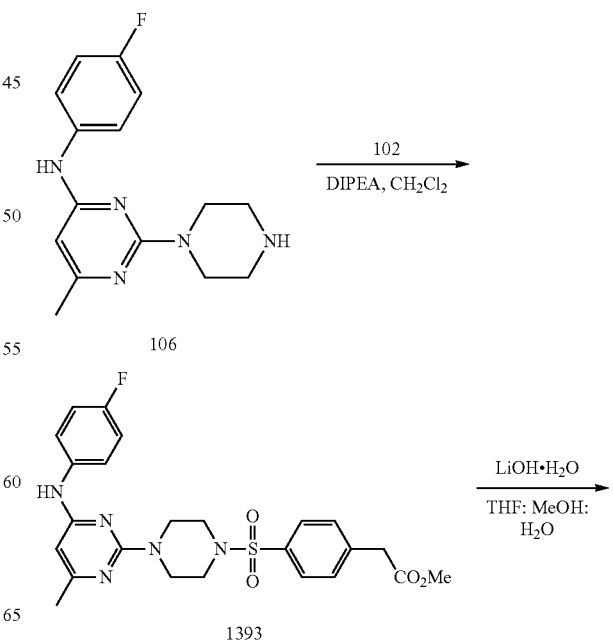

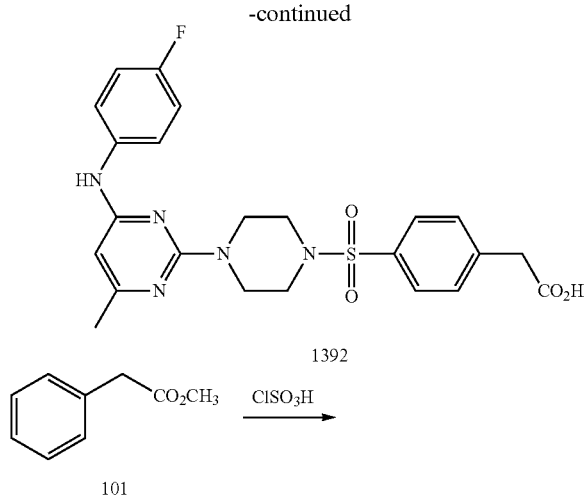

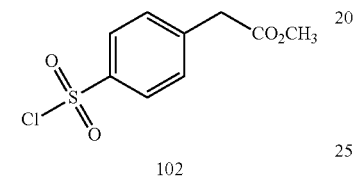

Synthesis of methyl 2-(4-((4-(4-((4-fluorophenyl) amino)-6-methylpyrimidin-2-yl) piperazin-1-yl) sulfonyl) phenyl) acetate (1393)

To a stirring solution of N-(4-fluorophenyl)-6-methyl-2-(piperazin-1-yl) pyrimidin-4-amine 106 (500 mg, 1.74 mmol) in CH$_2$Cl$_2$ (25 mL) under inert atmosphere were added diisopropylethylamine (0.93 mL, 5.22 mmol), compound 102 (865 mg, crude) at 0° C.; warmed to RT and stirred for 16 h. The reaction was monitored by TLC; after completion of the reaction, the reaction mixture was diluted with CH$_2$Cl$_2$ (20 mL), washed with water (50 mL). The organic extract was dried over sodium sulfate, filtered and concentrated in vacuo to obtain the crude. The crude material was purified through silica gel column chromatography using 70% EtOAc/hexanes. The title compound was separated from its regio isomers by preparative HPLC purification to afford 1393 (170 mg) as white solid. TLC: 50% EtOAc/hexanes (R$_f$: 0.4). $^1$H-NMR (DMSO-d$_6$, 500 MHz): δ 9.12 (s, 1H), 7.69 (d, J=8.1 Hz, 2H), 7.55-7.49 (m, 4H), 7.10 (t, J=8.8 Hz, 2H), 5.85 (s, 1H), 3.80 (s, 2H), 3.77-3.73 (m, 4H), 3.59 (s, 3H), 2.92-2.88 (m, 4H), 2.08 (s, 3H); LC-MS: 99.02%; 500.1 (M$^+$+1); (column; Ascentis Express C18, (50×3.0 mm, 2.7 μm); RT 2.09 min. 0.025% Aq. TFA+5% ACN: ACN+5% 0.025% Aq. TFA, 1.2 mL/min); HPLC (purity): 98.68%; (column; Zorbax SB C-18 (150×4.6 mm, 5 μm); RT 7.49 min. ACN: 0.05% TFA (Aq); 1.0 mL/min; Diluent:ACN:water).

Synthesis of 2-(4-((4-(4-((4-fluorophenyl) amino)-6-methylpyrimidin-2-yl) piperazin-1-yl) sulfonyl) phenyl) acetic acid (1392)

To a stirring solution of 1393 (110 mg, 0.22 mmol) in THF:MeOH:H$_2$O (2:2:1, 10 mL) was added lithium hydroxide monohydrate (28 mg, 0.66 mmol) at 0° C.; warmed to RT and stirred for 3 h. The reaction was monitored by TLC; after completion of the reaction, the volatiles were removed in vacuo and the pH of the residue was acidified with 1 N HCl to ~2. The precipitated solid was filtered, washed with EtOAc (10 mL) and dried in vacuo to afford 1392 (75 mg, 70%) as white solid. TLC: 50% EtOAc/hexanes (R$_f$: 0.1); $^1$H-NMR (DMSO-d$_6$, 500 MHz): δ 12.10 (br s, 1H), 10.84 (br s, 1H), 7.72 (d, J=8.4 Hz, 2H), 7.63-7.57 (m, 2H), 7.54 (d, J=8.4 Hz, 2H), 7.23 (t, J=8.7 Hz, 2H), 6.17 (br s, 1H), 3.89-3.87 (m, 4H), 3.72 (s, 2H), 3.07-3.03 (m, 4H), 2.30 (s, 3H); LC-MS: 99.38%; 486.0 (M$^+$+1); (column; Ascentis Express C18, (50×3.0 mm, 2.7 μm); RT 1.96 min. 0.025% Aq. TFA+5% ACN: ACN+5% 0.025% Aq. TFA, 1.2 mL/min); HPLC (purity): 99.23%; (column; Zorbax SB C-18 (150×4.6 mm, 3.5 μm); RT 6.73 min. ACN+5% 0.05% TFA (Aq): 0.05% TFA (Aq)+5% ACN; 1.0 mL/min; Diluent: ACN:water).

Example 76: Synthesis of 1411, 1412

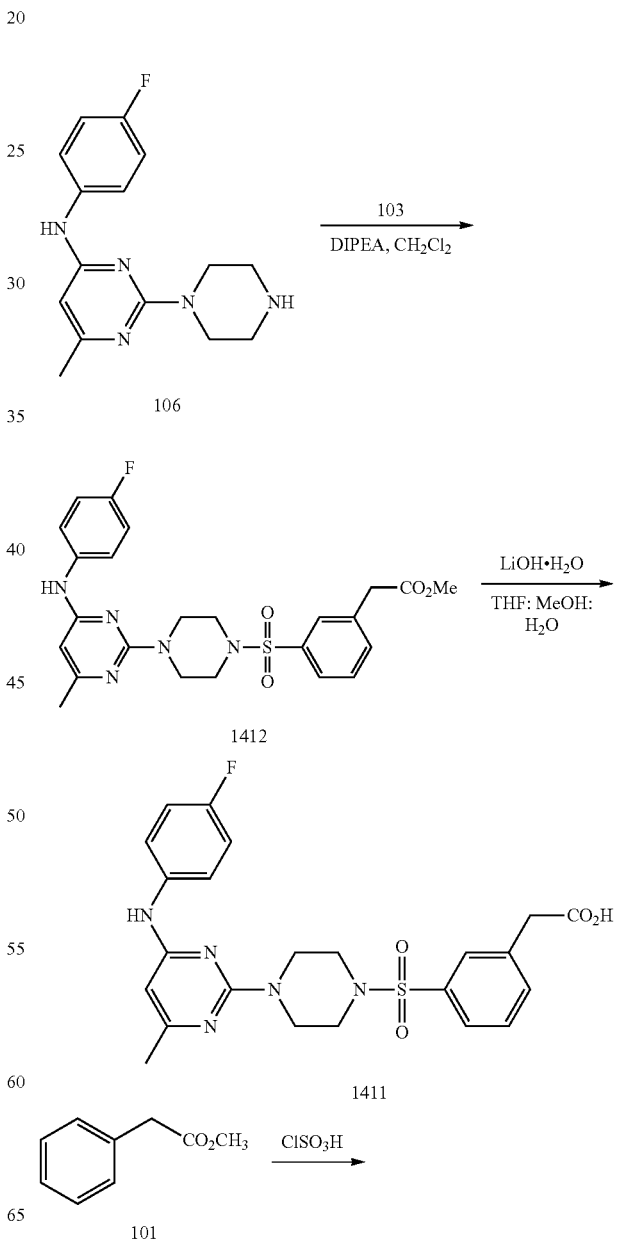

-continued

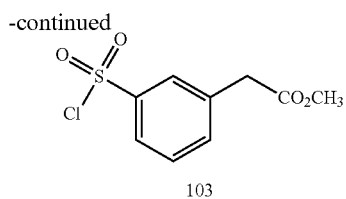

103

Synthesis of methyl 2-(3-(chlorosulfonyl) phenyl) acetate (103)

To a stirring solution of methyl 2-phenylacetate 101 (5 g, 33.3 mmol) in CH$_2$Cl$_2$ (5 mL) under inert atmosphere was added chlorosulfonic acid (30 mL) dropwise for 20 min at 0° C.; warmed to RT and stirred for 3 h. The reaction was monitored by TLC; after completion of the reaction, the reaction mixture was poured into ice-cold water and extracted with CH$_2$Cl$_2$ (2×100 mL). The combined organic extracts were dried over sodium sulfate, filtered and concentrated in vacuo to afford crude compound 103 (6.8 g) along with its regio isomer as colorless thick syrup. TLC: 10% EtOAc/hexanes (R$_f$ 0.3); $^1$H NMR (CDCl$_3$, 500 MHz): δ 8.00 (d, J=8.4 Hz, 2H), 7.98-7.95 (m, 1H), 7.68 (d, J=7.8 Hz, 0.5H), 7.60 (d, J=8.1 Hz, 0.5H), 7.54 (d, J=8.4 Hz, 2H), 3.80 (s, 0.5H), 3.76 (s, 3H), 3.74-3.73 (m, 4H).

Synthesis of methyl 2-(3-((4-(4-((4-fluorophenyl) amino)-6-methylpyrimidin-2-yl) piperazin-1-yl) sulfonyl) phenyl) acetate (1412)

To a stirring solution of N-(4-fluorophenyl)-6-methyl-2-(piperazin-1-yl) pyrimidin-4-amine 106 (500 mg, 1.74 mmol) in CH$_2$Cl$_2$ (25 mL) under inert atmosphere were added diisopropylethylamine (0.93 mL, 5.22 mmol), compound 103 (865 mg, crude) at 0° C.; warmed to RT and stirred for 16 h. The reaction was monitored by TLC; after completion of the reaction, the reaction mixture was diluted with CH$_2$Cl$_2$ (20 mL), washed with water (50 mL). The organic extract was dried over sodium sulfate, filtered and concentrated in vacuo to obtain the crude. The crude material was purified through silica gel column chromatography using 70% EtOAc/hexanes. The title compound was separated from its regio isomer by preparative HPLC purification to afford 1412 (140 mg) as white solids. TLC: 50% EtOAc/hexanes (R$_f$ 0.4). $^1$H-NMR (DMSO-d$_6$, 500 MHz): δ 9.12 (s, 1H), 7.66 (s, 1H), 7.63 (dt, J=6.4, 2.0 Hz, 1H), 7.58-7.56 (m, 2H), 7.51 (dd, J=9.0, 4.9 Hz, 2H), 7.10 (t, J=8.8 Hz, 2H), 5.85 (s, 1H), 3.83 (s, 2H), 3.77-3.75 (m, 4H), 3.57 (s, 3H), 2.93-2.89 (m, 4H), 2.08 (s, 3H); LC-MS: 99.17%; 500.2 (M$^+$+1); (column; Ascentis Express C18, (50×3.0 mm, 2.7 μm); RT 2.11 min. 0.025% Aq. TFA+5% ACN: ACN+5% 0.025% Aq. TFA, 1.2 mL/min); HPLC (purity): 99.70%; (column; Zorbax SB C-18 (150×4.6 mm, 3.5 μm); RT 7.53 min. ACN: 0.05% TFA (Aq); 1.0 mL/min; Diluent:ACN: water).

Synthesis of 2-(3-((4-(4-((4-fluorophenyl) amino)-6-methylpyrimidin-2-yl) piperazin-1-yl) sulfonyl) phenyl) acetic acid (1411)

To a stirring solution of 1412 (90 mg, 0.18 mmol) in THF:MeOH:H$_2$O (2:2:1, 5 mL) was added lithium hydroxide monohydrate (23 mg, 0.54 mmol) at 0° C.; warmed to RT and stirred for 3 h. The reaction was monitored by TLC; after completion of the reaction, the volatiles were removed in vacuo and the pH of the residue was acidified with 1 N HCl to ~2. The precipitated solid was filtered, washed with EtOAc (10 mL) and dried in vacuo to afford 1411 (65 mg, 75%) as an off-white solid. TLC: 50% EtOAc/hexanes (R$_f$ 0.1); $^1$H-NMR (DMSO-d$_6$, 500 MHz): δ 12.31 (br s, 1H), 11.07 (br s, 1H), 7.70 (s, 1H), 7.67-7.57 (m, 5H), 7.23 (t, J=8.7 Hz, 2H), 6.25 (br s, 1H), 3.91-3.87 (m, 4H), 3.60 (br s, 2H), 3.08-3.05 (m, 4H), 2.34 (s, 3H); LC-MS: 98.93%; 486.0 (M$^+$+1); (column; Ascentis Express C18, (50×3.0 mm, 2.7 μm); RT 1.96 min. 0.025% Aq. TFA+5% ACN: ACN+5% 0.025% Aq. TFA, 1.2 mL/min); HPLC (purity): 99.35%; (column; Zorbax SB C-18 (150×4.6 mm, 3.5 μm); RT 7.41 min. ACN: 0.05% TFA (Aq); 1.0 mL/min; Diluent:ACN: water).

Example 77: Assay Measuring Activity of Test Compounds on Viral Production From AD38 Cells AD38 cells grown in a 175 cm flask with Growth Medium (DMEM/F12 (1:1) (cat #SH30023.01, Hyclone, 1× Pen/step (cat #: 30-002-CL, Mediatech, Inc), 10% FBS (cat #: 101, Tissue Culture Biologics), 250 μg/mL G418 (cat #: 30-234-CR, Mediatech, Inc), 1 μg/mL Tetracycline (cat #: T3325, Teknova)) were detached with 0.25% trypsin. Tetracycline-free treatment medium (15 mL DMEM/F12 (1:1) (cat #SH30023.01, Hyclone, 1× Pen/step (cat #: 30-002-CL, Mediatech, Inc), with 2% FBS, Tet-system approved (cat #: 631106, Clontech) were then added to mix and spun at 1300 rpm for 5 min. Pelleted cells were then re-suspended/washed with 50 mL of 1×PBS 2 times and 10 mL treatment medium one time. AD38 cells were then re-suspended with 10 mL of treatment medium and counted. Wells of a collagen coated 96-well NUNC microtiter plate were seeded at 50,000/well in 180 μL of treatment medium, and 20 μL of either 10% DMSO (Control) or a 10× solution of test compound in 10% DMSO in treatment media was added for a final compound concentration 1, 3, or 10 μM (1.0% final [DMSO]) and plates were incubated for 6 days at 37° C.

Subsequently viral load production was assayed by quantitative PCR of the core sequence. Briefly, 5 μL of clarified supernatant was added to a PCR reaction mixture that contained forward primers HBV-f 5'-CTGTGCCT-TGGGTGGCTTT-3', Reverse primers HBV-r 5'-AAGGAAAGAAGTCAGAAGGCAAAA-3' and Fluorescent TaqMan™ Probes HBV-probe 5'-FAM/AGCTC-CAAA/ZEN/TTCTTTATAAGGGTCGATGTCCATG/ 3IABkFQ-3' in Quanta Biosciences PerfeCTa® qPCR Toughmix®, and was subsequently on an Applied Biosystems VIIA7 in a final volume of 20 μL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate). Results are shown in Table 9 below.

TABLE 9

| Compound No. | AD38 Viral Load (CpAM/DMSO %) at 10 μM | AD38 Viability Normalized Result (CPAM/DMSO %) at 10 μM |
|---|---|---|
| 1332 | 13 | 85 |
| 1333 | 2 | 85 |
| 1334 | 2 | 102 |
| 1336 | 59 | 103 |
| 1337 | 34 | 93 |

TABLE 9-continued

| Compound No. | AD38 Viral Load (CpAM/DMSO %) at 10 μM | AD38 Viability Normalized Result (CPAM/DMSO %) at 10 μM |
|---|---|---|
| 1339 | 50 | 93 |
| 1340 | 1 | 88 |
| 1341 | 1 | 95 |
| 1342 | 17 | 107 |
| 1343 | 6 | 31 |
| 1344 | 2 | 0 |
| 1345 | 14 | 77 |
| 1347 | 2 | 7 |
| 1348 | 5 | 102 |
| 1352 | 89 | 96 |
| 1353 | 7 | 107 |
| 1354 | 24 | 97 |
| 1355 | 5 | 103 |
| 1356 | 6 | 97 |
| 1357 | 67 | 95 |
| 1358 | 77 | 99 |
| 1359 | 60 | 97 |
| 1360 | 28 | 94 |
| 1361 | 25 | 95 |
| 1362 | 54 | 88 |
| 1363 | 1 | 93 |
| 1364 | 62 | 100 |
| 1365 | 53 | 98 |
| 1366 | 41 | 108 |
| 1367 | 44 | 105 |
| 1368 | 147 | 94 |
| 1369 | 56 | 96 |
| 1370 | 12 | 114 |
| 1371 | 29 | 111 |
| 1372 | 21 | 109 |
| 1373 | 8 | 109 |
| 1374 | 7 | 107 |
| 1375 | 43 | 104 |
| 1376 | 20 | 121 |
| 1377 | 1 | 15 |
| 1378 | 13 | 1 |
| 1379 | 6 | 110 |
| 1380 | 10 | 108 |
| 1381 | 46 | 107 |
| 1382 | 34 | 107 |
| 1383 | 14 | 94 |
| 1384 | 122 | 91 |
| 1385 | 105 | 94 |
| 1386 | 23 | 118 |
| 1387 | 19 | 107 |
| 1388 | 15 | 106 |
| 1389 | 2 | 0 |
| 1390 | 1 | 104 |
| 1391 | 16 | 88 |
| 1392 | 69 | 99 |
| 1393 | 79 | 102 |
| 1394 | 32 | 79 |
| 1395 | 42 | 98 |
| 1396 | 70 | 100 |
| 1397 | 5 | 33 |
| 1398 | 4 | 0 |
| 1399 | 43 | 93 |
| 1400 | 73 | 93 |
| 1401 | 42 | 97 |
| 1402 | 12 | 97 |
| 1403 | 83 | 100 |
| 1404 | 90 | 96 |
| 1405 | 28 | 84 |
| 1406 | 63 | 98 |
| 1407 | 12 | 91 |
| 1408 | 8 | 107 |
| 1409 | 59 | 108 |
| 1410 | 14 | 58 |
| 1411 | 117 | 102 |
| 1412 | 61 | 109 |
| 1415 | 120 | 101 |
| 1418 | 120 | 100 |
| 1419 | 11 | 93 |
| 1420 | 17 | 16 |

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

We claim:

1. A pharmaceutical composition comprising: (i) a compound of Formula 1 having the structure:

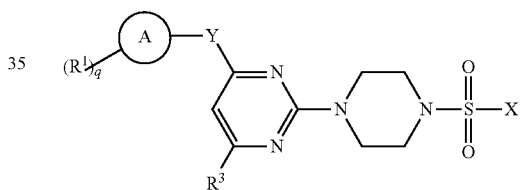

Formula 1 or a pharmaceutically acceptable salt or stereoisomer thereof, wherein:

is selected from the group consisting of

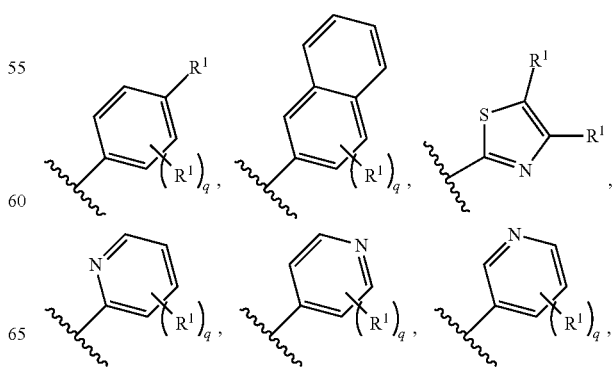

-continued

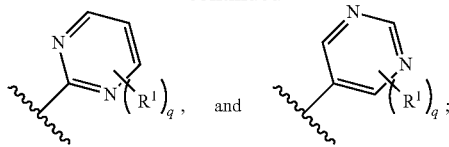

Y is selected from the group consisting of a bond, —O—, —S(O)$_w$, and —N(R')—;
X is selected from the group consisting of phenyl, naphthyl, and heteroaryl; wherein X is optionally substituted with one, two, three, or four R$^2$ groups;
provided that at least one of

or X is a heteroaryl;
R$^1$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —N(R')S(O)$_w$—C$_1$-C$_6$alkyl, and —S(O)$_w$—N(R')(R");
q is 0, 1, 2, 3 or 4;
w is 0, 1 or 2;
R' is independently for each occurrence selected from the group consisting of —H and —C$_1$-C$_6$alkyl;
R" is independently for each occurrence selected from the group consisting of —H and —C$_1$-C$_6$alkyl; or
R' and R" are taken together with the nitrogen atom to which they are attached to form a 4-7 membered heterocyclic or heteroaryl ring, each of which is optionally substituted with an oxo group;
R$^2$ is independently for each occurrence selected from the group consisting of —H, —C$_1$-C$_6$alkyl, —C$_1$-C$_6$alkoxy, —C$_1$-C$_6$alkyl-O—C$_1$-C$_6$alkyl, halogen, oxo, cyano, —OH, —C(O)H, —CO$_2$R', —C(O)N(R')(R"), —C(O)C$_1$-C$_6$alkyl, —N(R')(R"), —NO$_2$, —N(R')C(O)C$_1$-C$_6$alkyl, —S(O)$_w$—C$_1$-C$_6$alkyl, —N(R')S(O)$_w$—C$_1$-C$_6$alkyl, and —S(O)$_w$—N(R')(R"); and
R$^3$ is selected from the group consisting of —H, —C$_1$-C$_6$alkyl, —N(R')(R"), —N(R')C$_1$-C$_6$alkyl-N(R')(R"), —N(R)—C$_1$-C$_6$alkyl-OR', —OH, —C$_1$-C$_6$alkoxy, —O—C$_1$-C$_6$alkyl-OR', —O-heterocyclyl, —O-heteroaryl, —O—C$_1$-C$_6$alkyl-heteroaryl, —C$_1$-C$_6$alkyl-heteroaryl, heterocyclyl, and heteroaryl, wherein heterocyclyl and heteroaryl are optionally substituted with one or two C$_1$-C$_6$alkyl or halogen;
wherein C$_1$-C$_6$alkyl or C$_1$-C$_6$alkoxy may be independently for each occurrence optionally substituted with one, two, or three halogens; and
(ii) optionally, a pharmaceutically acceptable excipient.

2. The pharmaceutical composition of claim 1, wherein

is phenyl.

3. The pharmaceutical composition of claim 1, wherein X is selected from the group consisting of

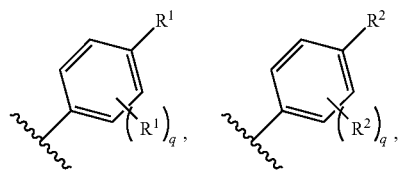

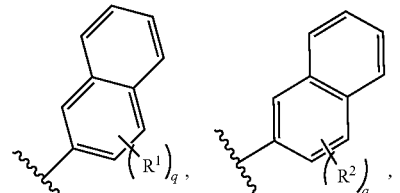

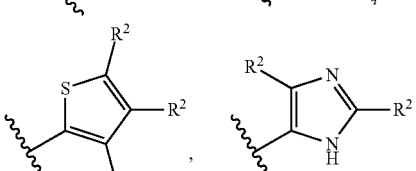

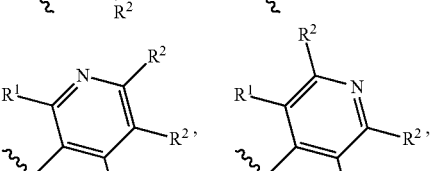

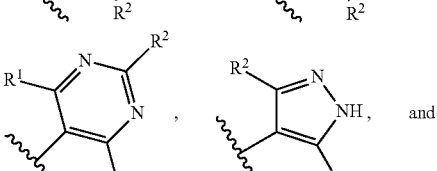

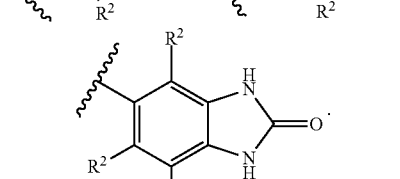

and

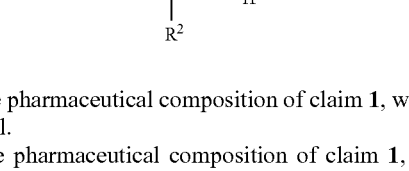

4. The pharmaceutical composition of claim 1, wherein X is phenyl.

5. The pharmaceutical composition of claim 1, wherein R$^1$ is independently for each occurrence selected from the group consisting of —C$_1$-C$_6$alkyl, —C$_1$-C$_6$alkoxy, halogen, cyano, —OH, —CO$_2$R', and —N(R')(R").

6. The pharmaceutical composition of claim 1, wherein R$^1$ is independently for each occurrence selected from the group consisting of —CH$_3$, —Et, i-Pr, —CF$_3$, —OMe, —OCF$_3$, F, Cl, Br, —NH$_2$, —NHMe, and —NMe$_2$.

7. The pharmaceutical composition of claim 1, wherein q is 1, 2, or 3.

8. The pharmaceutical composition of claim 1, wherein R$^2$ is independently for each occurrence selected from the group consisting of —C$_1$-C$_6$alkyl, —C$_1$-C$_6$alkoxy, halogen, oxo, cyano, —OH, —CO$_2$R', and —N(R')(R").

9. The pharmaceutical composition of claim 1, wherein R$^2$ is independently for each occurrence selected from the group consisting of —CH$_3$, —Et, i-Pr, —CF$_3$, oxo, —OMe, —OCF$_3$, F, Cl, Br, —NH$_2$, —NHMe, and —NMe$_2$.

10. The pharmaceutical composition of claim 1, wherein X is optionally substituted with one, two, or three R$^2$ groups.

11. The pharmaceutical composition of claim 1, wherein R³ is independently for each occurrence selected from the group consisting of —H, —N(R')(R"), —NH—C₁-C₆alkyl-N(C₁-C₆alkyl)₂, —NH—C₁-C₆-alkyl-OR', —OH, —C₁-C₆alkoxy, —O—C₁-C₆alkyl-OR', heterocyclyl, and heteroaryl, wherein heterocyclyl and heteroaryl are optionally substituted with one or two C₁-C₆alkyl or halogen.

12. The pharmaceutical composition of claim 1, wherein R³ is independently for each occurrence selected from the group consisting of —H, —CH₃, —Et, i-Pr, —N(CH₃)₂, —NH(i-Pr), —NH(t-Bu), —N(CH₃)(t-Bu), —NH(CH₃), —NH(CH₂CH₂OH), —NH—CH₂CH₂—N(CH₃)₂, —OMe, —OCH₂CH₂OH,

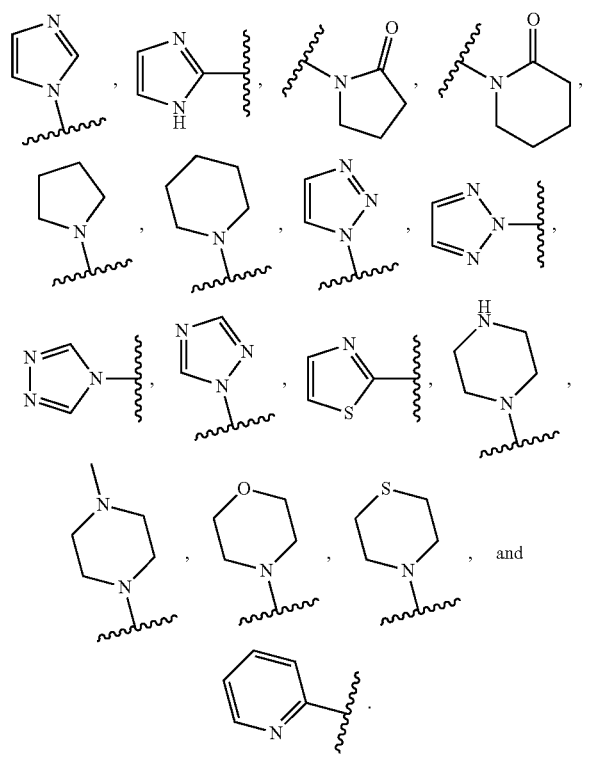

13. A pharmaceutical composition comprising: (i) a compound of Formula 1-A having the structure:

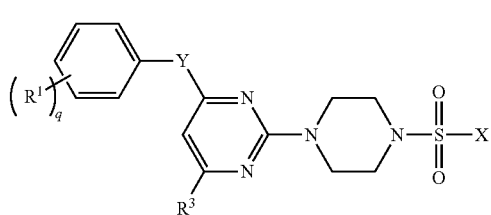

or a pharmaceutically acceptable salt or stereoisomer thereof, wherein:
Y is selected from the group consisting of a bond, —O—, —S(O)_w—, and —N(R')—;
X is heteroaryl optionally substituted with one, two, three, or four R² groups;
R¹ is independently for each occurrence selected from the group consisting of —H, —C₁-C₆alkyl, —C₁-C₆alkoxy, —C₁-C₆alkyl-O—C₁-C₆alkyl, halogen, cyano, —OH, —C(O)H, —CO₂R', —C(O)N(R')(R"), —C(O)C₁-C₆alkyl, —N(R')(R"), —NO₂, —N(R')C(O)C₁-C₆alkyl, —N(R')S(O)_w—C₁-C₆alkyl, and —S(O)_w—N(R')(R");
q is 0, 1, 2, 3 or 4;
w is 0, 1 or 2;
R' is independently for each occurrence selected from the group consisting of —H and —C₁-C₆alkyl;
R" is independently for each occurrence selected from the group consisting of —H and —C₁-C₆alkyl; or
R' and R" are taken together with the nitrogen atom to which they are attached to form a 4-7 membered heterocyclic or heteroaryl ring, each of which is optionally substituted with an oxo group;
R² is independently for each occurrence selected from the group consisting of —H, —C₁-C₆alkyl, —C₁-C₆alkoxy, —C₁-C₆alkyl-O—C₁-C₆alkyl, halogen, oxo, cyano, —OH, —C(O)H, —CO₂R', —C(O)N(R')(R"), —C(O)C₁-C₆alkyl, —N(R')(R"), —NO₂, —N(R')C(O)C₁-C₆alkyl, —N(R')S(O)_w—C₁-C₆alkyl, and —S(O)_w—N(R')(R"); and
R³ is selected from the group consisting of —H, —C₁-C₆alkyl, —N(R')(R"), —N(R')C₁-C₆alkyl-N(R')(R"), —N(R)—C₁-C₆alkyl-OR', —OH, —C₁-C₆alkoxy, —O—C₁-C₆alkyl-OR', —O-heterocyclyl, —O-heteroaryl, —O—C₁-C₆alkyl-heteroaryl, —C₁-C₆alkyl-heteroaryl, heterocyclyl, and heteroaryl, wherein heterocyclyl and heteroaryl are optionally substituted with one or two C₁-C₆alkyl or halogen;
wherein C₁-C₆alkyl or C₁-C₆alkoxy may be independently for each occurrence optionally substituted with one, two, or three halogens; and
(ii) optionally, a pharmaceutically acceptable excipient.

14. A pharmaceutical composition comprising: (i) a compound of Formula 1 having the structure:

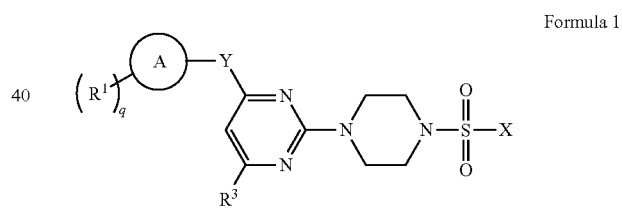

Formula 1 or a pharmaceutically acceptable salt or stereoisomer thereof, wherein:

is selected from the group consisting of phenyl, naphthyl, and heteroaryl;
Y is —NH—;
X is selected from the group consisting of phenyl, naphthyl, and heteroaryl; wherein X is optionally substituted with one, two, three, or four R² groups;
provided that at least one of

or X is a heteroaryl;

$R^1$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —N(R')S(O)$_w$—$C_1$-$C_6$alkyl, and —S(O)$_w$—N(R')(R");

q is 0, 1, 2, 3 or 4;

w is 0, 1 or 2;

R' is independently for each occurrence selected from the group consisting of —H and —$C_1$-$C_6$alkyl;

R" is independently for each occurrence selected from the group consisting of —H and —$C_1$-$C_6$alkyl; or R' and R" are taken together with the nitrogen atom to which they are attached to form a 4-7 membered heterocyclic or heteroaryl ring, each of which is optionally substituted with an oxo group;

$R^2$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, oxo, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R"); and $R^3$ is selected from the group consisting of —H, —$C_1$-$C_6$alkyl, —N(R')(R"), —N(R')$C_1$-$C_6$alkyl-N(R')(R"), —N(R)—$C_1$-$C_6$alkyl-OR', —OH, —$C_1$-$C_6$alkoxy, —O—$C_1$-$C_6$alkyl-OR', —O-heterocyclyl, —O-heteroaryl, —O—$C_1$-$C_6$alkyl-heteroaryl, —$C_1$-$C_6$alkyl-heteroaryl, heterocyclyl, and heteroaryl, wherein heterocyclyl and heteroaryl are optionally substituted with one or two $C_1$-$C_6$alkyl or halogen;

wherein $C_1$-$C_6$alkyl or $C_1$-$C_6$alkoxy may be independently for each occurrence optionally substituted with one, two, or three halogens; and (ii) optionally, a pharmaceutically acceptable excipient.

15. A method of treating or ameliorating a hepatitis B viral infection in an individual, the method comprising administering to the individual a pharmaceutical composition according to claim 1.

* * * * *